(12) United States Patent
Bandic et al.

(10) Patent No.: US 10,085,643 B2
(45) Date of Patent: Oct. 2, 2018

(54) ANALYTIC METHODS OF TISSUE EVALUATION

(76) Inventors: Jadran Bandic, Pancevo (RS); Djuro Koruga, Belgrade (RS); Sava Marinkovich, Jersey City, NJ (US); Rahul Mehendale, Jersey City, NJ (US)

( * ) Notice: Subject to any disclaimer, the term of this patent is extended or adjusted under 35 U.S.C. 154(b) by 2185 days.

(21) Appl. No.: 13/036,783

(22) Filed: Feb. 28, 2011

(65) Prior Publication Data

US 2011/0301441 A1    Dec. 8, 2011

Related U.S. Application Data

(63) Continuation-in-part of application No. 12/690,749, filed on Jan. 20, 2010, now abandoned, and a
(Continued)

(51) Int. Cl.
*A61B 5/00* (2006.01)
*A61B 5/053* (2006.01)
(Continued)

(52) U.S. Cl.
CPC .......... *A61B 5/0059* (2013.01); *A61B 5/0088* (2013.01); *A61B 5/0531* (2013.01);
(Continued)

(58) Field of Classification Search
CPC .................................. A61B 5/441; A61B 5/443
(Continued)

(56) References Cited

U.S. PATENT DOCUMENTS

| 4,170,987 A | 10/1979 | Anselmo et al. |
| 4,398,541 A | 8/1983 | Pugliese |

(Continued)

FOREIGN PATENT DOCUMENTS

| AU | 2009204227 A1 | 7/2009 |
| AU | 2009204227 B2 | 3/2012 |

(Continued)

OTHER PUBLICATIONS

Beckmann et al. Monitoring change of body fluids during physical exercise using Bioimpedance Spectroscopy.31st Annual Internation Conference of the IEEE EMBS. 2009.*
(Continued)

*Primary Examiner* — Christian Jang

(57) ABSTRACT

The present invention generally relates to methods and systems for (i) skin assessment based on the utilization of bioimpedance and fractional calculus and implementation of methods for skin hydration assessment based on the utilization of bioimpedance and fractional calculus and systems thereof, (ii) an Opto-Magnetic method based on RGB and gray images data as "cone-rods" principles with enhanced qualitative and quantitative parameters for analyzing water based on Opto-Magnetic properties of light-matter interaction and systems thereof, and (iii) imaging and analyzing skin based on the interaction between matter and electro-magnetic radiation and implementation of an Opto-Magnetic method with enhanced qualitative and quantitative parameters for imaging and analyzing skin based on Opto-Magnetic properties of light-matter interaction and systems thereof.

8 Claims, 217 Drawing Sheets

Related U.S. Application Data continuation-in-part of application No. 11/970,448, filed on Jan. 7, 2008, now abandoned, said application No. 12/690,749 is a continuation-in-part of application No. 12/350,164, filed on Jan. 7, 2009, now abandoned.

(60) Provisional application No. 61/308,704, filed on Feb. 26, 2010, provisional application No. 61/310,287, filed on Mar. 4, 2010, provisional application No. 61/332,413, filed on May 7, 2010, provisional application No. 61/380,003, filed on Sep. 3, 2010, provisional application No. 61/386,962, filed on Sep. 27, 2010, provisional application No. 61/407,454, filed on Oct. 28, 2010, provisional application No. 61/431,926, filed on Jan. 12, 2011, provisional application No. 61/145,756, filed on Jan. 20, 2009, provisional application No. 61/150,010, filed on Feb. 5, 2009, provisional application No. 61/149,025, filed on Feb. 2, 2009, provisional application No. 61/149,027, filed on Feb. 2, 2009, provisional application No. 61/150,053, filed on Feb. 5, 2009, provisional application No. 61/150,331, filed on Feb. 6, 2009, provisional application No. 61/169,316, filed on Apr. 15, 2009, provisional application No. 61/235,362, filed on Aug. 20, 2009, provisional application No. 61/254,214, filed on Oct. 23, 2009, provisional application No. 60/883,769, filed on Jan. 5, 2007, provisional application No. 60/883,764, filed on Jan. 5, 2007, provisional application No. 60/883,768, filed on Jan. 5, 2007, provisional application No. 61/019,440, filed on Jan. 7, 2008, provisional application No. 61/061,852, filed on Jun. 16, 2008, provisional application No. 61/380,155, filed on Sep. 3, 2010.

(51) Int. Cl.

| | | |
|---|---|---|
| *A61B 5/103* | (2006.01) | |
| *G06T 7/00* | (2017.01) | |
| *G16H 50/20* | (2018.01) | |
| *G01J 3/50* | (2006.01) | |
| *G06F 19/00* | (2018.01) | |
| *G16H 50/70* | (2018.01) | |
| *G16H 15/00* | (2018.01) | |

(52) U.S. Cl.
CPC .......... *A61B 5/0534* (2013.01); *A61B 5/0537* (2013.01); *A61B 5/1032* (2013.01); *A61B 5/442* (2013.01); *A61B 5/4869* (2013.01); *A61B 5/4875* (2013.01); *G01J 3/508* (2013.01); *G06F 19/00* (2013.01); *G06T 7/0016* (2013.01); *G16H 50/20* (2018.01); *A61B 5/411* (2013.01); *A61B 5/415* (2013.01); *A61B 5/443* (2013.01); *A61B 5/444* (2013.01); *A61B 5/445* (2013.01); *A61B 5/4547* (2013.01); *A61B 5/7257* (2013.01); *G01J 3/50* (2013.01); *G06F 19/321* (2013.01); *G06F 19/3418* (2013.01); *G06T 2200/24* (2013.01); *G06T 2207/10152* (2013.01); *G06T 2207/30036* (2013.01); *G06T 2207/30088* (2013.01); *G16H 15/00* (2018.01); *G16H 50/70* (2018.01)

(58) Field of Classification Search
USPC ....................................................... 600/306
See application file for complete search history.

(56) References Cited

U.S. PATENT DOCUMENTS

| | | |
|---|---|---|
| 4,655,225 A | 4/1987 | Dahne et al. |
| 5,016,173 A | 5/1991 | Kenet et al. |
| 6,032,071 A | 2/2000 | Binder |
| 6,081,612 A | 6/2000 | Gutkowicz-Krusin |
| 6,177,984 B1 | 1/2001 | Jacques |
| 6,215,893 B1 | 4/2001 | Leshem |
| 6,373,568 B1 | 4/2002 | Miller et al. |
| 6,445,818 B1 | 9/2002 | Kim et al. |
| 6,462,835 B1 | 10/2002 | Loushin et al. |
| 6,567,682 B1 | 5/2003 | Osterweil |
| 6,622,033 B2 | 9/2003 | Messerschmidt et al. |
| 6,692,032 B2 | 2/2004 | Christy |
| 6,916,288 B2 | 7/2005 | Nakata |
| 6,993,167 B1 | 1/2006 | Skladnev et al. |
| 7,027,153 B2 | 4/2006 | Mullani |
| 7,289,211 B1 | 10/2007 | Walsh, Jr. et al. |
| 2002/0007123 A1 | 1/2002 | Balas |
| 2002/0065468 A1 | 5/2002 | Utzinger et al. |
| 2002/0084417 A1 | 7/2002 | Khalil et al. |
| 2002/0161664 A1 | 10/2002 | Shaya et al. |
| 2003/0065523 A1 | 4/2003 | Pruche et al. |
| 2004/0092824 A1 | 5/2004 | Stamnes et al. |
| 2004/0097812 A1 | 5/2004 | Angilella |
| 2004/0122299 A1 | 6/2004 | Nakata |
| 2004/0125996 A1 | 7/2004 | Eddowes et al. |
| 2005/0154382 A1 | 7/2005 | Altshuler et al. |
| 2005/0195316 A1 | 9/2005 | Kollias |
| 2006/0092418 A1 | 5/2006 | Xu et al. |
| 2006/0224057 A1 | 10/2006 | Burd et al. |
| 2006/0227137 A1 | 10/2006 | Weyrich et al. |
| 2006/0241495 A1 | 10/2006 | Kurtz |
| 2006/0281068 A1 | 12/2006 | Maier et al. |
| 2007/0178067 A1 | 8/2007 | Maier et al. |
| 2007/0249913 A1 | 10/2007 | Freeman et al. |
| 2008/0194928 A1 | 8/2008 | Bandic et al. |
| 2008/0294012 A1 | 11/2008 | Kurtz et al. |
| 2009/0185163 A1 | 7/2009 | Shimazu et al. |
| 2009/0245603 A1 | 10/2009 | Koruga et al. |
| 2010/0185064 A1 | 7/2010 | Bandic et al. |
| 2012/0321759 A1 | 12/2012 | Marinkovich et al. |

FOREIGN PATENT DOCUMENTS

| | | |
|---|---|---|
| CA | 2711519 A1 | 7/2009 |
| CN | 101198290 A | 6/2008 |
| EP | 2389573 A2 | 11/2011 |
| GB | 2396504 | 6/2004 |
| GB | 2429385 A | 2/2007 |
| JP | 483302 | 7/1992 |
| JP | 7075629 | 3/1995 |
| JP | 835928 A | 2/1996 |
| JP | 8035928 | 2/1996 |
| JP | 11308496 | 11/1999 |
| JP | 2002200050 A | 7/2002 |
| JP | 2003275179 | 9/2003 |
| JP | 2003275179 A | 9/2003 |
| JP | 2004283357 | 10/2004 |
| JP | 2005221266 A | 8/2005 |
| JP | 2005-345191 A | 12/2005 |
| JP | 2006133856 | 5/2006 |
| JP | 2006516338 A | 6/2006 |
| JP | 2010515489 A | 5/2010 |
| KR | 20090097904 | 9/2009 |
| WO | 2006/073450 A2 | 7/2006 |
| WO | 2007031946 A2 | 3/2007 |
| WO | 2008086311 A2 | 7/2008 |
| WO | 2008086311 A3 | 11/2008 |
| WO | 2009089292 A1 | 7/2009 |
| WO | 2010093503 A2 | 8/2010 |
| WO | 2010093503 A3 | 12/2010 |
| WO | 2010093503 A9 | 3/2011 |
| WO | 2011106792 A2 | 9/2011 |

(56) References Cited

FOREIGN PATENT DOCUMENTS

WO    2011106792 A3    3/2012
WO    2012159012 A1    11/2012

OTHER PUBLICATIONS

Ward et al. Assessment of Body Composition of Rats by Bioimpedance Spectroscopy: Validation Against Dual-Energy X-Ray Absorptiometry. Scand. J. Lab. Anim. Sci. 2009.*
Papic-Obradovic. Opto-Magnetic Method for Epstein-Barr Virus and Cytomegalovirus Detection in Blood Plasma Samples. Acta Physica Polonica A. 2010.*
Atanackovic, T. M., "On a fractional distributed-order oscillator", J. Phys. A: Math. Gen., vol. 38, 2005, pp. 6703-6713.
Bouwstra, J. A. et al., "Phase behavior of lipid mixtures based on human ceramides: coexistence of crystalline and liquid phases", Journal of Lipid Research, vol. 42, 2001, pp. 1759-1770.
Cole, Kenneth S., "Permeability and Impermeability of Cell Membranes for Ions", Cold Spring Harb Symp Quant Biol, vol. 8, 1940, pp. 110-122.
Fereira, D. M. et al., "Electrical impedance model for evaluation of skin irritation in rabbits and humans", Skin Research and Technology, vol. 13, 2007, pp. 259-267.
Gilchrest, Barbara A., "Skin aging and photoaging: An overview", J. Am. Acad. Dermatol., vol. 21, 1989, pp. 610-613.
Grimnes, Sverre et al., "Chapter 8—Data and Models in", Bioimpedance and Bioelectricity Basics, Second Edition, Elsevier Ltd, 2008, pp. 283-332.
Haschka, Markus et al., "A Direct Approximation of Fractional Cole-Cole Systems by Ordinary First-Order Processes", Advances in Fractional Calculus: Theoretical Developments and Applications in Physics and Engineering, J. Sabatier et al. (eds.), Springer, 2007, pp. 257-270.
Kang, K., "Low-complexity Cole-Cole expression for modeling human biological tissues in (FD)^ 2TD method", Electronics Letters, vol. 43, Feb. 1, 2007, 3 pages.
Koruga, D., "Epidermal Layers Characterisation by Opto-Magnetic Spectroscopy Based on Digital Image of Skin", Acta Physica Polonica A, vol. 121, No. 3, 2012, pp. 1111-1115.
Koruga, D., "Water Hydrogen Bonds Study by Opto-Magnetic Fingerprint Technique", Acta Physica Polonica A, vol. 117, No. 5, 2010, pp. 777-781.
Koruga, D. J., "Gibbson: Peptide Plain as a Unique Biological Nanostructure", Materials Science Forum, vol. 518, 2006, pp. 491-496.
Martinsen, O. G. et al., "On Using Single Frequency Electrical Measurements for Skin Hydration Assessment", Innov. Techn. Biol. Med., vol. 19, No. 5, 1998, pp. 395-299.
McGarvey, James et al., "Sensitivity and specificity of clinical signs for assessment of dehydration in endurance athletes", Br. J. Sports Med., vol. 44, 2010, pp. 716-719.
Norlen, Lars, "Skin Barrier Structure and Function: The Single Gel Phase Model", J. Invest. Dermatol., vol. 117, 2001, pp. 830-836.

Ortigueira, Coito et al., "Initial Conditions: What Are We Talking About?", Proceedings of the 3rd FAC Workshop on Fractional Differentiation and its Applications, Ankara, Turkey, (abstract only), Nov. 5-7, 2008, 1 page.
Prokhorov, E. F. et al., "In vivo electrical characteristics of human skin including at biological active points", Med. Biol. Eng. Comput., vol. 38, 2000, pp. 507-511.
Stamenkovic, Dragomir et al., "Physical Properties of Contact Lenses Characterized by Scanning Probe Microscopy and Optomagnetic Fingerprint", International Journal of Modern Physics B, vol. 24, No. 6 & 7, 2010, pp. 825-834.
Int'l Search Report, PCT/US08/50438, dated Sep. 10, 2008, 3 pages.
Int'l Search Report, PCT/US09/30347, dated Jun. 25, 2009, 3 pages.
Int'l Search Report, PCT/US10/21529, dated Oct 13, 2010, 3 pages.
European Supplemental Search Report, dated Nov. 29, 2011, 7 pages.
09701382.5, European Application Serial No. 09701382.5 Extended European Search Report dated Sep. 11, 2012, 6 pages.
Ikeuchi, K et al., "Separating reflection components of textured surfaces using a single image", IEEE Transactions on Pattern Analysis and Machine Intelligence, IEEE Service Center;Los Alamitos, CA, US, vol. 27(2), Feb. 1, 2005, 178-193.
Papic-Obradovic, M et al., "Opto-Magnetic Method for Epstein Barr Virus and Cytomegalovirus Detection in Blood Plasma Samples", 11th Annual Conference of the Materials Research Society of Serbia,, Proceedings Supplement [1899-2358], vol. 117, No. 5 (2010)., Dec. 31, 2010, pp. 782-785.
PCT/US2008/50438, International Application Serial No. PCT/US2008/50438, International Preliminary Report on Patentability dated Jul. 7, 2009, 7 pages.
PCT/US2009/030347, International Application Serial No. PCT/US2009/030347, International Preliminary Report on Patentability dated Jul. 13, 2010, dated Jul. 13, 2010, 6 pages.
PCT/US2010/021529, International Application Serial No. PCT/US2010/021529, International Preliminary Report on Patentability dated Aug. 4, 2011, dated Aug. 4, 2011, 8 pages.
PCT/US2011/026548, International Application Serial No. PCT/US2011/026548, International Preliminary Report on Patentability dated Aug. 28, 2012, 14 pages.
PCT/US2011/026548, International Application Serial No. PCT/US2011/026548, International Search Report dated Jan. 25, 2012, 4 pages.
PCT/US2012/038534, International Application Serial No. PCT/US2012/038534, International Search Report and Written Opinion dated Oct. 10, 2012, 11 pages.
PCT/US2010/021529, International Application Serial No. PCT/US2010/021529, International Search Report dated Oct. 13, 2010.
10741554.9, "European Application Serial No. 10741554.9, Extended European Search Report dated Jun. 17, 2013", Myskin, Inc, 6 pages.
PCT/US2012/038534, "International Application Serial No. PCT/US2012/038534, International Preliminary Report on Patentability and Written Opinion dated Nov. 28, 2013", Myskin, Inc., 7 pages.

* cited by examiner

Myskin address your skin concern from the convenience and privacy of your home

Welcome, Milena | Log out

MySkin Home

You are Main User, and you have 2 Family Users.

MySkin Info:

- Select User: Milena
- Relationship: Self
- First Name: Milena
- Second Name: Milovanovic
- Sex: Female
- Occupation: Student
- Birth Date: 08/08/1975
- ID: 1234567
- Home Address: Kraljice Marije 16/5
  Belgrade, Serbia
- Phone Number: +381 11 1234567
- Fax Number:
- E-mail: milena@srd.com ( Update MySkin Info )

( Regiser a New Family Member )

Skin History

| Lesion ID ↕ | Skin Area ↕ | Report Status ↕ |
|---|---|---|
| 08-08-2006-001 | Upper Left Arm | Analysis Complete |
| 08-08-2006-002 | Face | Analysis Complete |
| 22-08-2006-003 | Upper Left Arm | Analysis Complete |
| 01-09-2006-004 | Right Leg | In-Progress |
| 01-09-2006-005 | Skin Health Test - Face | Week 4 to 6 |

1 | 2 | Show All

Currently showing last 5 submitted lesions.

( Skin Health Test )

( Submit a New Skin Concern )

( Forward Analysis )

( Ask an Expert )

( Payment Info/History )

Myskin

Welcome, Milena — address your skin concern from the convenience and privacy of your home | Log out

Skin Health Test

Basic Info

Select User: Milena ▲▼

Skin type:

Skin Analysis

Email Notification?
Email:
SMS Notification?
Mobile Phone:

Test Purpose

For your Skin Health Test, where do/will you use the product.
☐ Face
☐ Hands
☐ Neck
☐ Legs
☐ Torso Why are you using your product?
(Select all that apply)
☐ To protect
☐ To repair Why are /will you be using your product?
(Select all that apply)
☐ Reduce Wrinkles / Fine Lines
☐ Increase Shine / Luminosity
☐ Increase Softness / Elasticity You are Main User, and you have 2 Family Users.

Current Usage

How long have been using your product?
☐ Never - just purchased
☐ 0-2 weeks
☐ <1 month
☐ 1-4 months
☐ >6 months How often do you apply your Product?
(Check all theat apply)
☐ Daily
☐ In the Morning
☐ During the day
☐ At Nighttime When do you apply your product?
(Check all that apply)
☐ As needed
☐ In the Morning
☐ During the day
☐ At Nighttime
☐ After washing hands

[ Submit and Begin Scan ]

[ Cancel ]

Myskin

Welcome, Milena — address your skin concern from the convenience and privacy of your home You are Main User, and you have 2 Family Users.    Log out

Skin Health Test

Completed 1 of 6 Samples

Last Picture: Today

Next Picture: in 7 days

Congratulations, you have completed your first baseline assessment!

Continue to use your product in according to your regimen and rescan your skin in the next 7 days

| Skin Category | Measure | Description | |
|---|---|---|---|
| Wrinkles | 12 wsx | Wrinkle Defination ...xalskjfblaksjdbfikajsbifkj your wrinkle level is below average for someone your age. Wrinkles are caused x,y,z,.... | More Info |
| Elasticity | .7 esx | Elasticity Defination ...asdasjhdlkajshdlakjsdhlkajshd your elasticity is above average for your age | More Info |
| Luminosity | 233 lsx | Description of how your skin level compares to healthy skin at your age level... | More Info |
| Firmness | 1.5 fsx | Description of how your skin level compares to healthy skin at your age level... | More Info |
| Tightness | 4 tsx | Description of how your skin level compares to healthy skin at your age level... | More Info |

Take Next Picture

MySkin Record

Cancel

Myskin address your skin concern from the convenience and privacy of your home

Welcome, Milena | Log out

You are Main User, and you have 2 Family Users.

Skin Health Test

Elasticity
Objective

- Congratulations, your regimen has improved elasticity

[Bar chart with bars labeled B, 1, 2, 3, 4, F]

Your Product / Regimen

- Congratulations, your regimen has improved elasticity

Other products to Consider

- you want a product that can ..XXXX.Xxx.xxx.
- With the following ingredients ..XXXX.Xxx.xxx.

Top Products used by other users for this objective

- Giselle by L'Oreal
- 2069 users

- Clarins Day Cream
- 2069 users

More Products

Next Indicator
Return to Summary

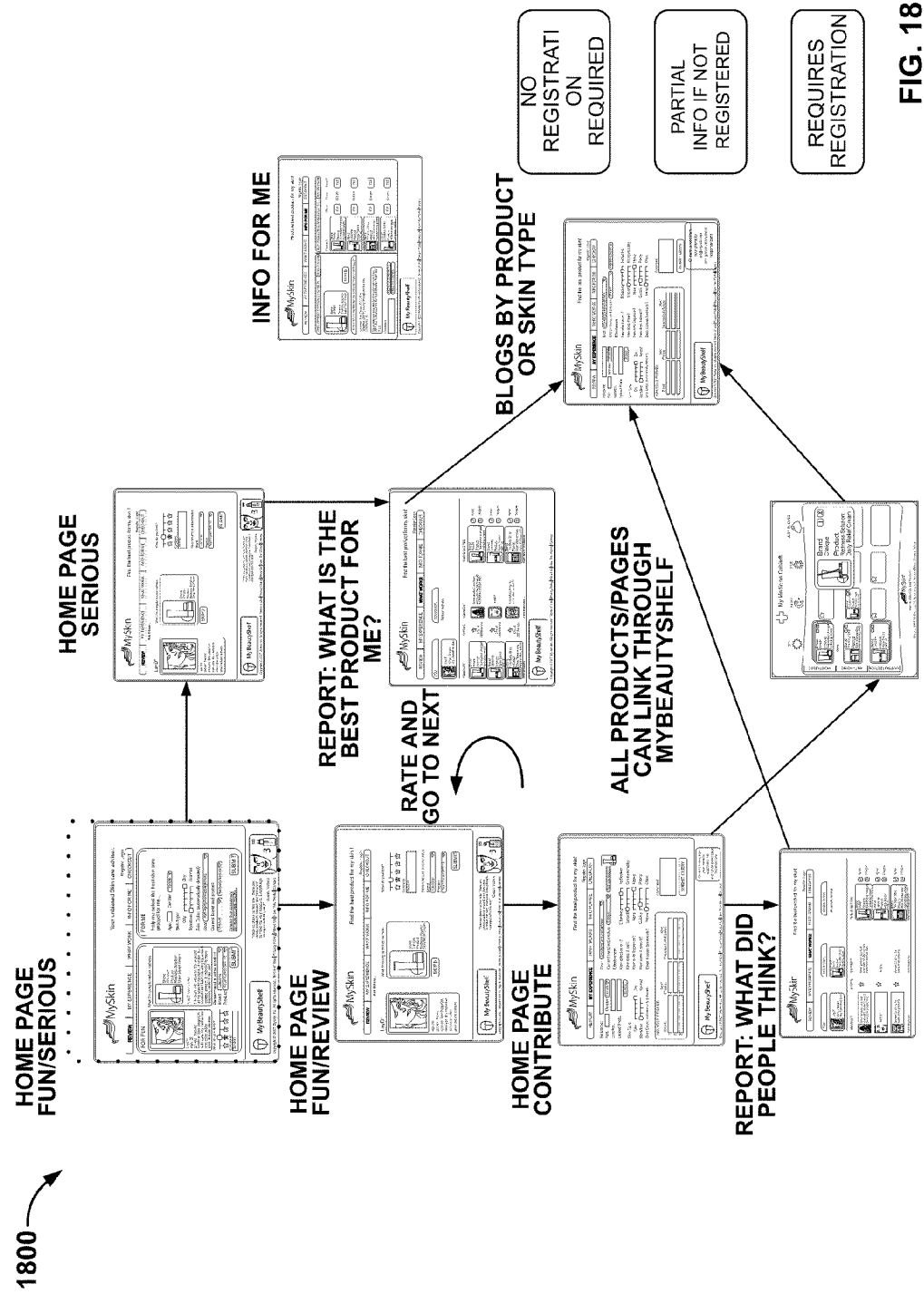

FIG. 19

MySkin

Your unbiased Skin care adviser.

Register Login

| REVIEW | MY EXPERIENCE | WHAT WORK | INFO FOR ME | CHECKOUT |

FOR FUN

What I'm using to reduce redness

LayD*
age: 32
gender: female
location: San Diego CA
skin type: dry / sensitive
skin color: white
goal: reduce redness Brand
Clinique Product
Redness Solution:
Daily Relief Cream LayD' comments:
I brought this because it's targeted at my specific problem. It works, but sometimes I feel mild stinging since I started using it. Is this ok? Is there anything better I can use?

Recommend a better product
Brand [Lancome ▽]
Product [Aqua Fusion SPF 15 ▽]

[SUBMIT]

What do you think?
☆ ☆ ☆ ☆ ☆
Comment:
[Terrible!]

FOR ME

Help me select the best skin care product for me....

Age: [    ]  Gender: [Female ▽]

Skin Type:
Oily [□——————] Dry
Sensitive [□——————] Normal

Skin Color: (automatically detected)

Goal: [Anti-Aging/wrinkles/tightness ▽]

Current Brand and product:
[Clinique ▽]  [Redness Solution ▽]

Detailed Skin Assessment
(for more accurate results)...

[SUBMIT]

My BeautyShelf

3

"I feel so drawn to this site. There are many products around and that used to make me very insecure. Everything's changed with this site!"

Queen, Victoria

Copyright © 2007 Myskin Inc. All rights reserved. Terms of Use | Privacy Policy | About Us | How This Works | Contact

MySkin

Find the best product for my skin!

Register Login

| REVIEW | MY EXPERIENCE | WHAT WORK | INFO FOR ME | CHECKOUT |

Ask Others...

LayD* age: 32
gender: female
location: San Diego CA
skin type: dry / sensitive
skin color: white
goal: reduce redness What I'm using to reduce redness Brand: Clinique
Product: Redness Solution Daily Relief Cream

SKIP ▷

What do you think?

☆ ☆ ☆ ☆ ☆

Comment:
Terrible!

Recommend a better product
Brand: Lancome ▽
Product: Aqua Fusion SPF 15 ▽

SUBMIT

My BeautyShelf

3

"I feel so drawn to this site. There are many products around and that used to make me very insecure. Everything's changed with this site!"
— Queen, Victoria Copyright © 2007 Myskin Inc. All rights reserved. Terms of Use | Privacy Policy | About Us | How This Works | Contact

MySkin

Find the best product for my skin!

Register Login

| REVIEW | MY EXPERIENCE | WHAT WORKS | INFO FOR ME | CHECKOUT |

Nickname: _____
Age: Gender: [Female ▽]
Location: _____
Upload Photo: [Browse...]
Skin Type:
 Oily □——— Dry
 Sensitive □——— Normal
Skin Color: (automatically detected)

Goal: [Anti-Aging/wrinkles/tightness ▽]
Current brand and product: [Clinique ▽] [Redness Solution ▽]
Effectiveness:
How effective is it? Effective □——— Ineffective
How does it feel? Smooth □——— Grainy/scrubby
How is its fragrance? None □——— Heavy
How does it absorb? Quickly □——— Poorly
Does it cause breakouts? Never □——— Often Comment: [_____]

[SUBMIT QUERY]

ASK YOUR FRIENDS
 Email: *New!* iPhone: *New!* Facebook/MySpace:
1 [____] [____] [____]
2 [____] [____] [____]
3 [____] [____] [____]

My BeautyShelf

Or send a mms from your phone to all@myskin.net and get an anonymous response bank Copyright © 2007 Myskin Inc. All rights reserved. Terms of Use | Privacy Policy | About Us | How This Works | Contact

| Page ID | 1.6 | Page Title | Registration |
|---|---|---|---|
| Date | 8 Aug 07 | Version | 1.0 |

MySkin
Your Trusted Skincare Advisor

Enabling Personalized Skin Care

[Register] [Sign In]

Spas    Salons    Doctors    My samples

Your Info

Email Address:
Password:
Screen name:
Age: [Prefilled]
Sex [ Prefilled]
Zip: [Prefilled]

Security Code to register

☐ Opt-In to MySkin Alerts
☐ Notify Me of New Samples for Products that benefit me
☐ Add to Facebook
☐ Add to Yelp
☐ Add to RSS

Your Goals
(Check all that apply)

Your Skin concerns
(Check all that apply)

Your Skin Type

(Link: Take Questionnaire)

Free Sample Registration

Address Info

Notify of new samples for
-Skin Type
-Product Launches
- Free offers

| Page ID | 1.7 | Page Title | Product Analytics for My Skin Type |
|---|---|---|---|
| Date | 8 Aug 07 | Version | 1.0 |

MySkin
Your Trusted Skincare Advisor

Enabling Personalized Skin Care

Register | Sign In

| Spas | Salons | Doctors | My samples |
|---|---|---|---|

Tag bar— shows what your personalization info is (Age, SkinType, SkinTone, etc) - constant over pages once you've logged in or given initial information

People in your Category

Sex: Women: 1,203,200
Age group [20 - 25]: 500,302
Skin Type [Oily, Complex] 100,000
Skin Concerns [Acne, Blemish] 50,000

MyBeautyShelf
(1.5)

| Your Goals | Most Popular | Most new Buzz | Blogs |
|---|---|---|---|
| Moisturize | L'oreal etecetc | | |
| Sunscreen | L'oreal etcetc | | |
| Protect | L'oreal etc | | |
| Glow | L'oreal etc | | |

MySkinMobl - Home Page
Scan a Product...
Help me find something...
SunCheck
[Incoming Alert]
Options | Return

MySkin – SunCheck

Location: Budva, CG
Current UV Rating: 4/10
MySkin Sun Impact: HIGH
Advice: Stay covered
[More]
Max Exposure:
Current time in sun: 10:00
(Start/Stop/Clear)

MySkin – UV advice

Best is to stay covered during this weather. Based on your skin type, you have a high propensity to burn.

Max recommended time is: 10 minutes

Dr. Sun Doctor says....

MySkin – Dr Sun Doctor says....

Video.....

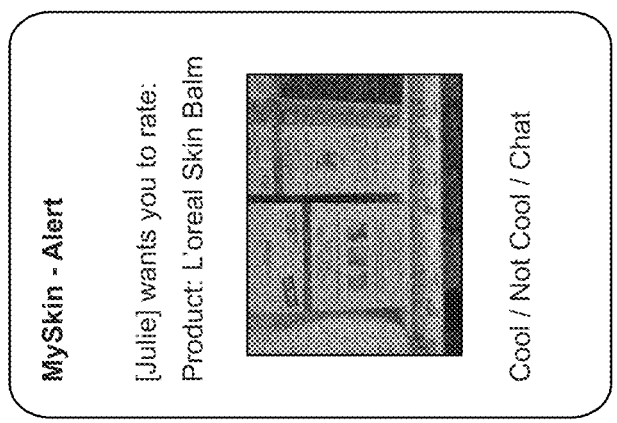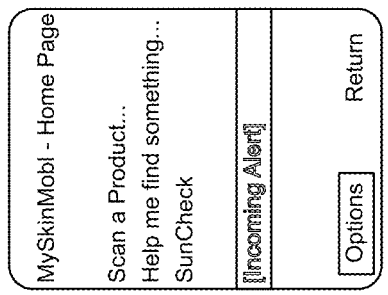
FIG. 33

5800

Flowchart Illustrating a Process for, in Accordance with an Aspect of the Present Technique.

5810
Capturing the Image

5820
Image Analysis in Pixel by Pixel Manner

5830
Conversion of Obtained Colors from Device Dependent RBG to Device Independent sRGB Color System 5840
Storing Standard R, G, and B Values in their Range of Values between 0 and 225

5850
Approximate of Color Using Gaussian Normal Distributions

5860
Generation of Estimated Values of Mathematical Expectation and Standard Deviation 5870
Above Parameters are Equated to Fitzpatrick Notation Using the Decision Tree for Determination of Skin Phototype

FIG. 58

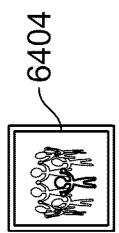
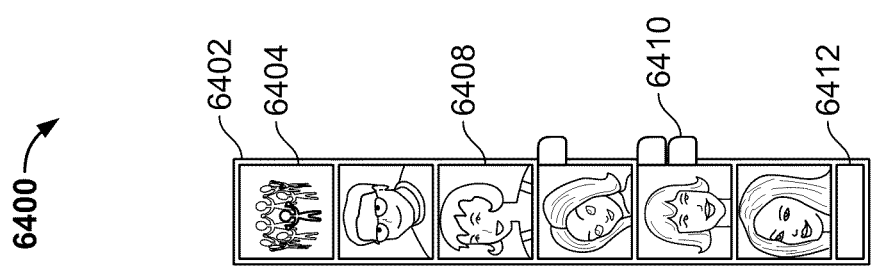
FIG. 64

FIG. 67

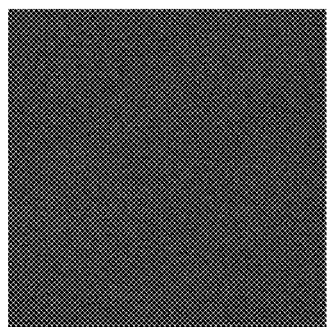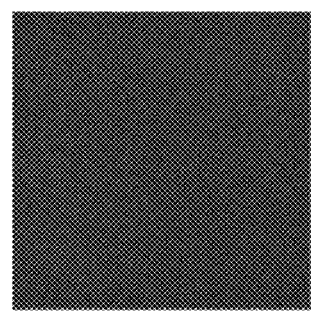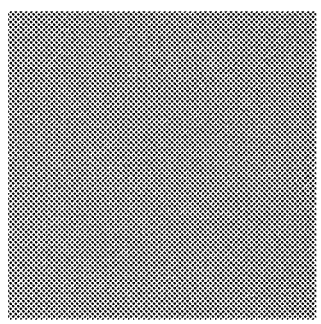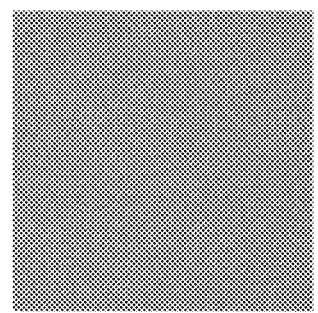
FIG. 76A
FIG. 76B

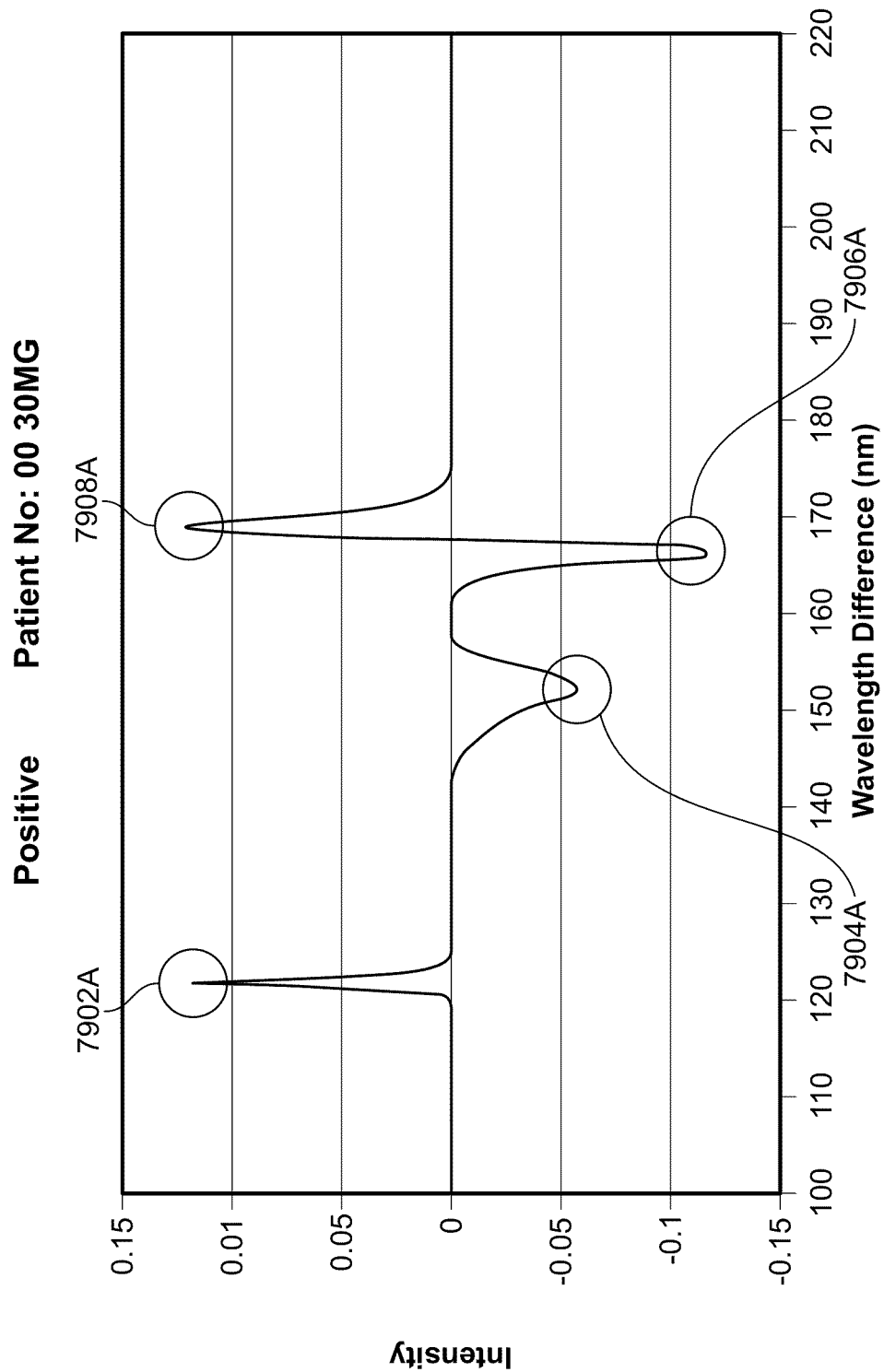

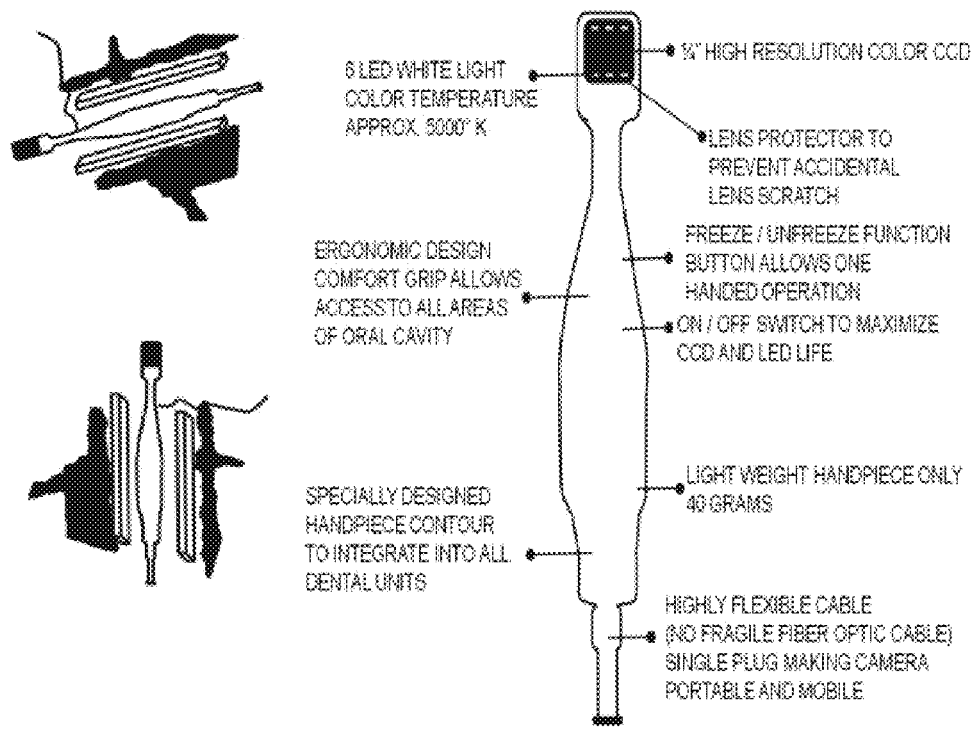

SPECIFICATION INTRAORAL CAMERA

|  | NTSC | PAL |
| --- | --- | --- |
| Pick Up Element | ¼" Color CCD | |
| Number of Total Pixels | 270K | 320K |
| Resolution | 350TV Line | |
| Electronic Shutter | Automatic, 1/60 (1/50) ~1/100,000 sec. | |
| Gain Control | Automatic | |
| Video Out | 1.0Vp-p Composite / 75 Ohm | |
| Power Supply | DC5V | |
| Dimension | L185 X W25 X H20 mm | |
| Weight | 40g | |

VIDEO FREEZE PROCESS UNIT

| TV System | NTSC or PAL |
| --- | --- |
| Video In | 1.0Vp-p, 75 Ohm Impedance |
| Video Out | 1.0Vp-p, 75 Ohm Impedance |
| Digital Resolution | 8 bit 256 Grad, 512 X 1024 pixels |
| Digital I/O | 16 bits |
| Signal | 52dB |
| Power Source | DC9V |
| Freeze Mode | Frame |
| Dimension | L110 X W82 X H37 mm |
| Weight | 310g |

Figure 105B

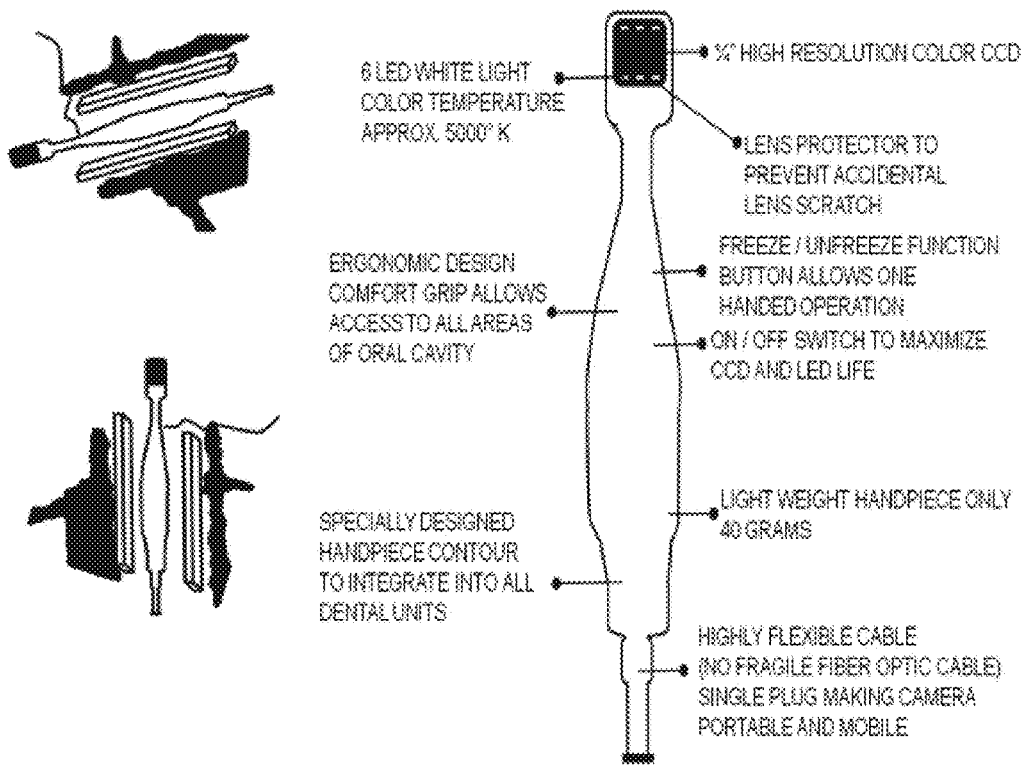

SPECIFICATION INTRAORAL CAMERA     VIDEO FREEZE PROCESS UNIT

|  | NTSC | PAL |
|---|---|---|
| Pick Up Element | ¼" Color CCD | |
| Number of Total Pixels | 270K | 320K |
| Resolution | 350TV Line | |
| Electronic Shutter | Automatic, 1/60 (1/50) ~1/100,000 sec. | |
| Gain Control | Automatic | |
| Video Out | 1.0Vp-p Composite / 75 Ohm | |
| Power Supply | DC5V | |
| Dimension | L185 X W25 X H20 mm | |
| Weight | 40g | |

| TV System | NTSC or PAL |
|---|---|
| Video In | 1.0Vp-p,75 Ohm Impedance |
| Video Out | 1.0Vp-p,75 Ohm Impedance |
| Digital Resolution | 8 bit 256 Grad, 512 X 1024 pixels |
| Digital I/O | 16 bits |
| Signal | 52dB |
| Power Source | DC9V |
| Freeze Mode | Frame |
| Dimension | L110 X W82 X H37 mm |
| Weight | 310g |

Figure 111B

ENAMEL – HEALTHY.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 105.8 degrees. This is a characteristic of healthy enamel.
Lower Right: We see OMF diagram of the same tissue, showing characteristic distribution of peaks with respect to wavelengths and intensities. We note here that intensity range is between -32.74 and +31.71 n.a.u.

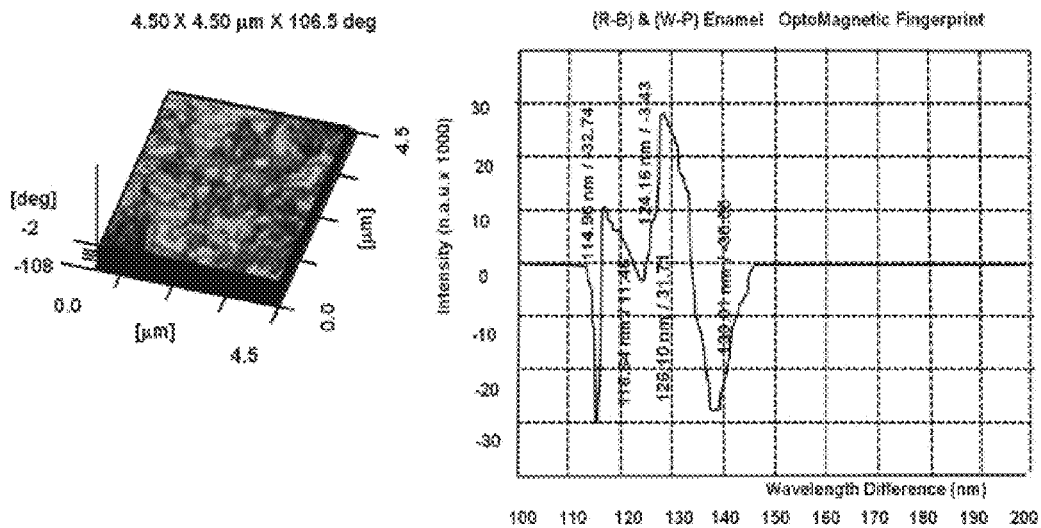

Figure 118A

ENAMEL – CARIES.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 86.9 degrees, which is lower compared to healthy enamel.
Lower Right: We see OMF diagram of the same tissue, showing characteristic distribution of peaks with respect to wavelengths and intensities. We note here that intensity range is between -15.38 and +25.13 n.a.u, which is narrower than the range for healthy enamel, showing correspondence with results of MFM.

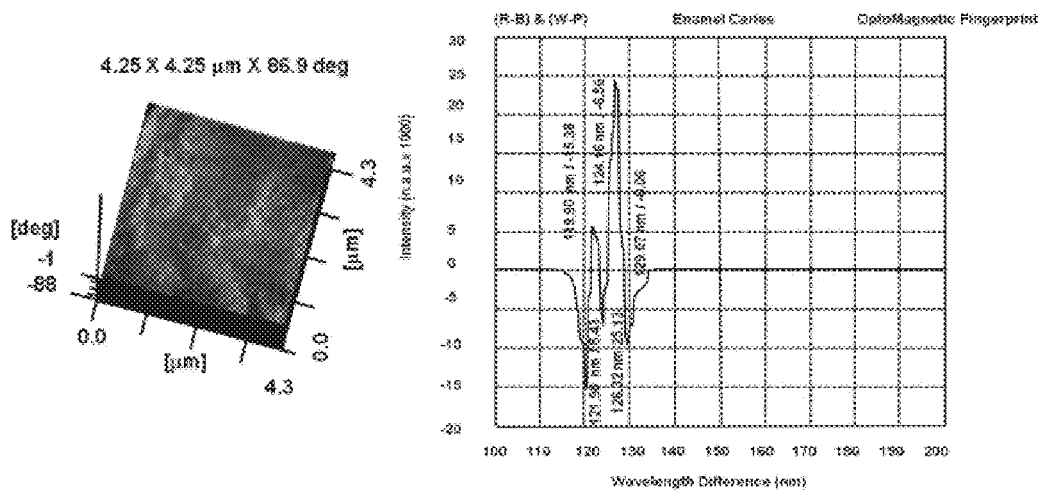

Figure 118B

DENTIN – HEALTHY.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 30.5 degrees. This is a characteristic of healthy dentin.
Lower Right: We see OMF diagram of the same tissue, showing characteristic distribution of peaks with respect to wavelengths and intensities. We note here that intensity range is between -6.73 and +7.59 n.a.u.

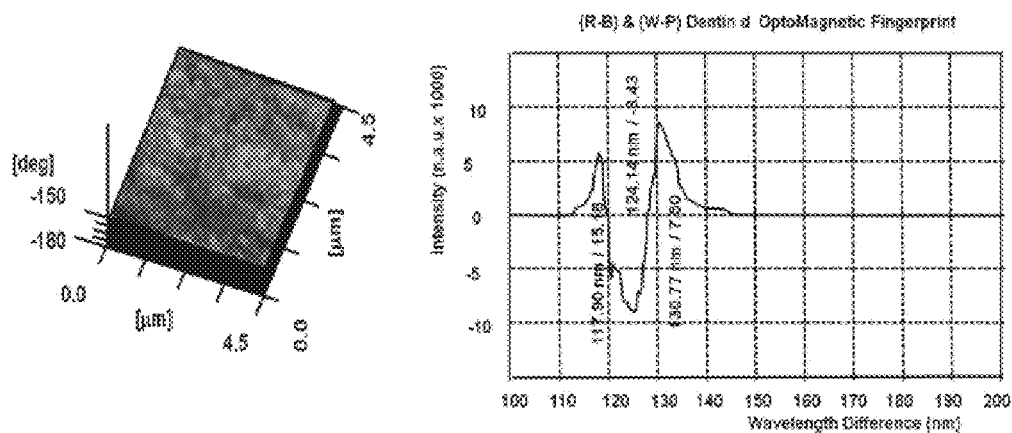

Figure 118C

DENTIN – CARIES.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 32.7 degrees, which is higher compared to healthy dentin.
Lower Right: We see OMF diagram of the same tissue, showing characteristic distribution of peaks with respect to wavelengths and intensities. We note here that intensity range is between -16.93 and +10.47 n.a.u, which is broader than the range for healthy dentin, showing correspondence with results of MFM.

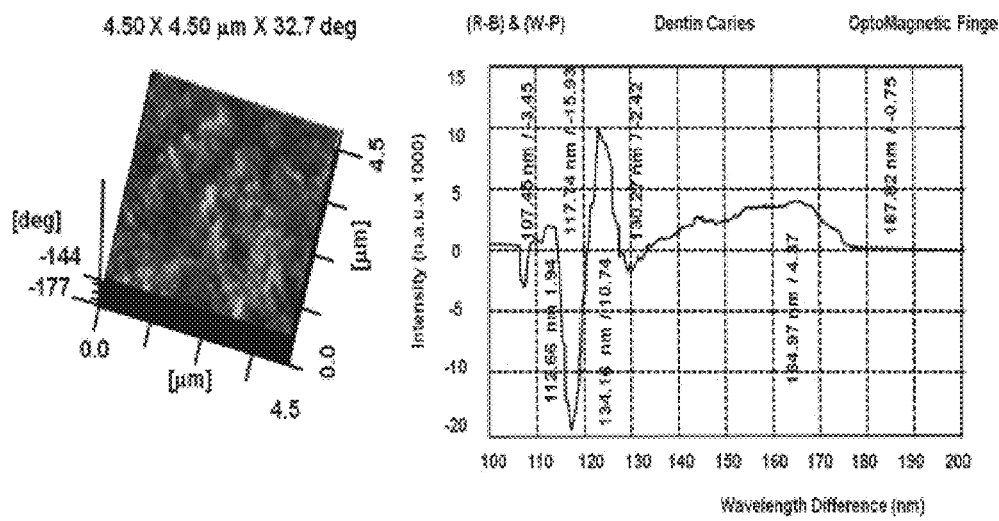

Figure 118D

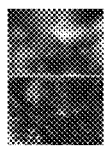

CEMENT – HEALTHY.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 95.7 degrees. This is a characteristic of healthy enamel.
Lower Right: We see OMF diagram of the same tissue, showing characteristic distribution of peaks with respect to wavelengths and intensities. We note here that intensity range is between -12.89 and +14.09 n.a.u.

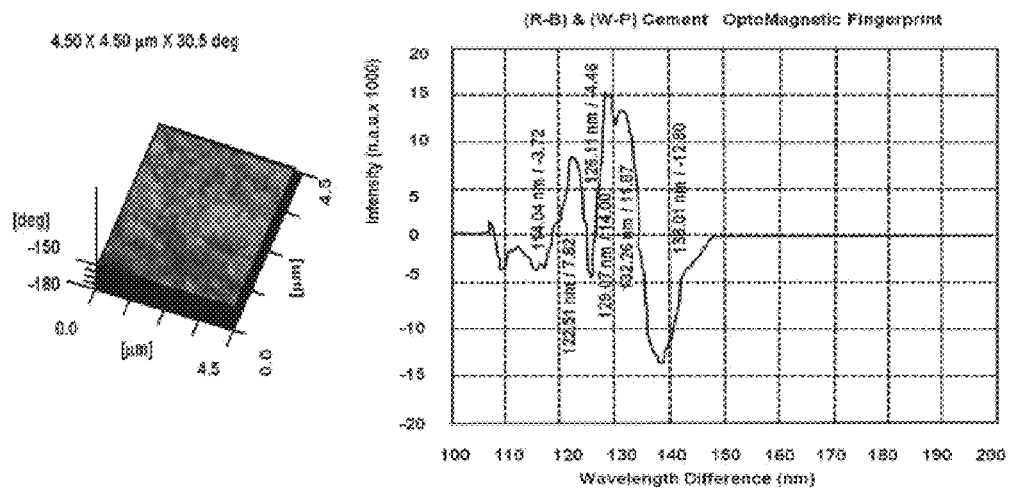

Figure 118E

DENTIN – CARIES.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 32.7 degrees, which is higher compared to healthy dentin.
Lower Right: We see OMF diagram of the same tissue, showing characteristic distribution of peaks with respect to wavelengths and intensities. We note here that intensity range is between -16.93 and +10.47 n.a.u, which is broader than the range for healthy dentin, showing correspondence with results of MFM.

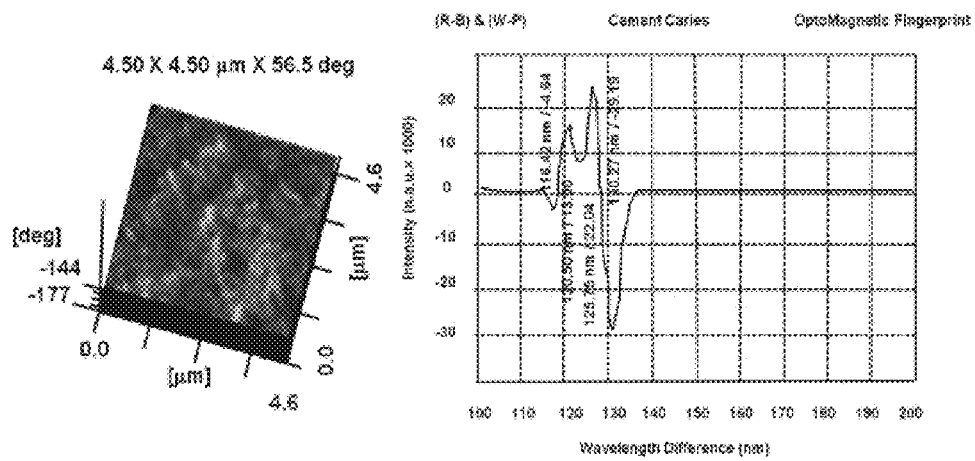

Figure 118F

ENAMEL – HEALTHY.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 105.8 degrees. This is a characteristic of healthy enamel.
Lower Right: We see OMF diagram of the same tissue, showing characteristic distribution of peaks with respect to wavelengths and intensities. We note here that intensity range is between -32.74 and +31.71 n.a.u.

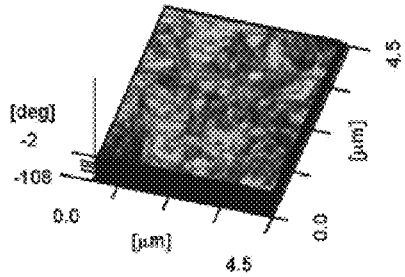

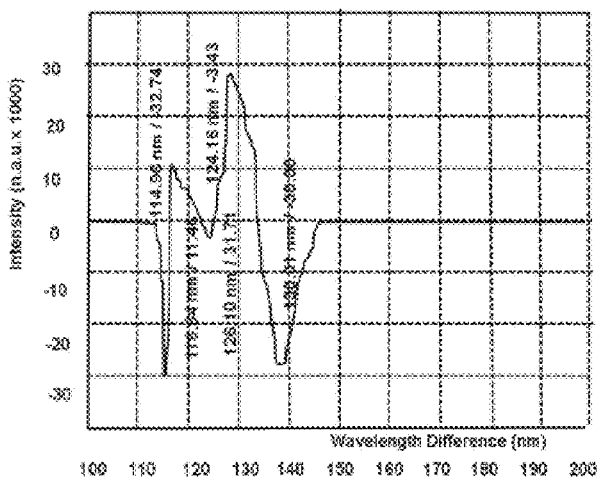

Figure 119A

ENAMEL – CARIES.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 86.9 degrees, which is lower compared to healthy enamel.
Lower Right: We see OMF diagram of the same tissue, showing characteristic distribution of peaks with respect to wavelengths and intensities. We note here that intensity range is between -15.38 and +25.13 n.a.u, which is narrower than the range for healthy enamel, showing correspondence with results of MFM.

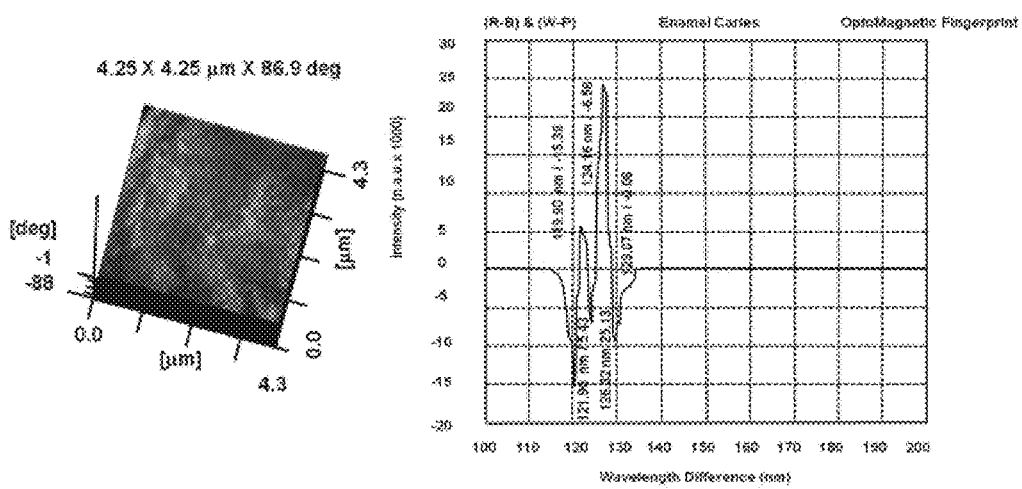

Figure 119B

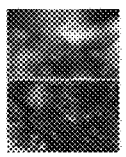

DENTIN – HEALTHY.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 30.5 degrees. This is a characteristic of healthy dentin.
Lower Right: We see OMF diagram of the same tissue, showing characteristic distribution of peaks with respect to wavelengths and intensities. We note here that intensity range is between -6.73 and +7.59 n.a.u.

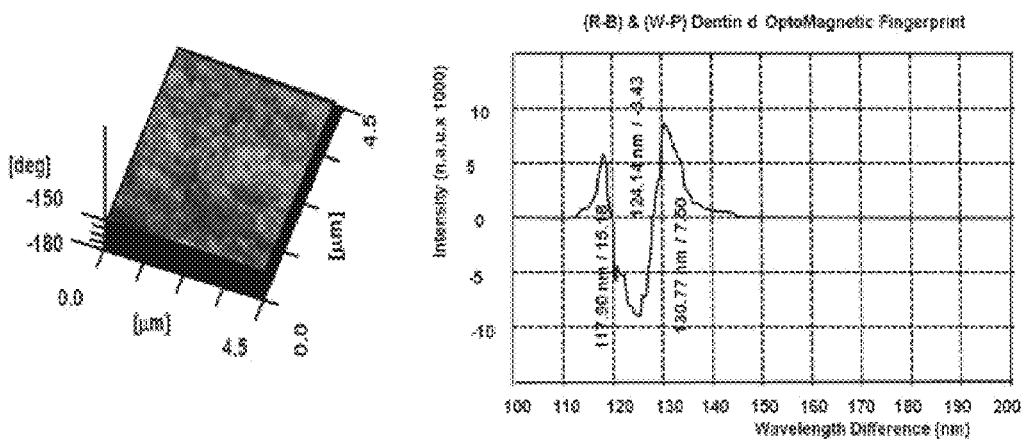

Figure 119C

DENTIN – CARIES.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 32.7 degrees, which is higher compared to healthy dentin.
Lower Right: We see OMF diagram of the same tissue, showing characteristic distribution of peaks with respect to wavelengths and intensities. We note here that intensity range is between -16.93 and +10.47 n.a.u, which is broader than the range for healthy dentin, showing correspondence with results of MFM.

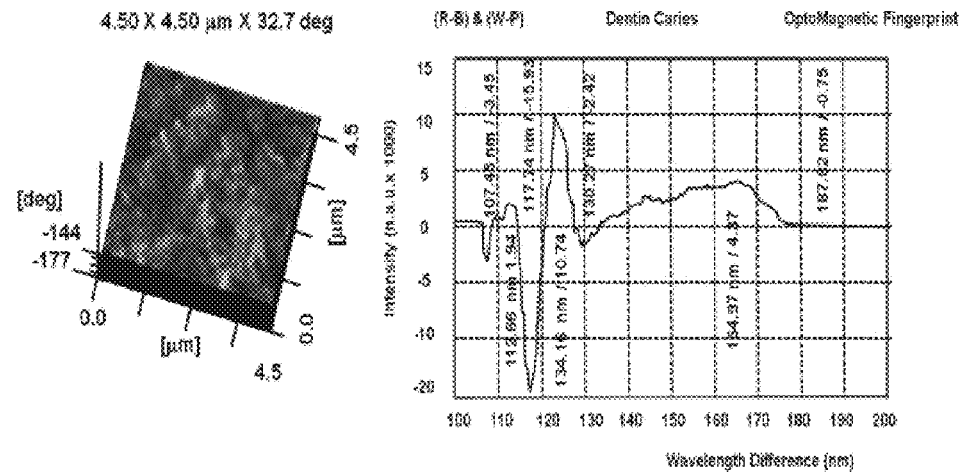

Figure 119D

CEMENT – HEALTHY.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 95.7 degrees. This is a characteristic of healthy enamel.
Lower Right: We see OMF diagram of the same tissue, showing characteristic distribution of peaks with respect to wavelengths and intensities. We note here that intensity range is between -12.89 and +14.09 n.a.u.

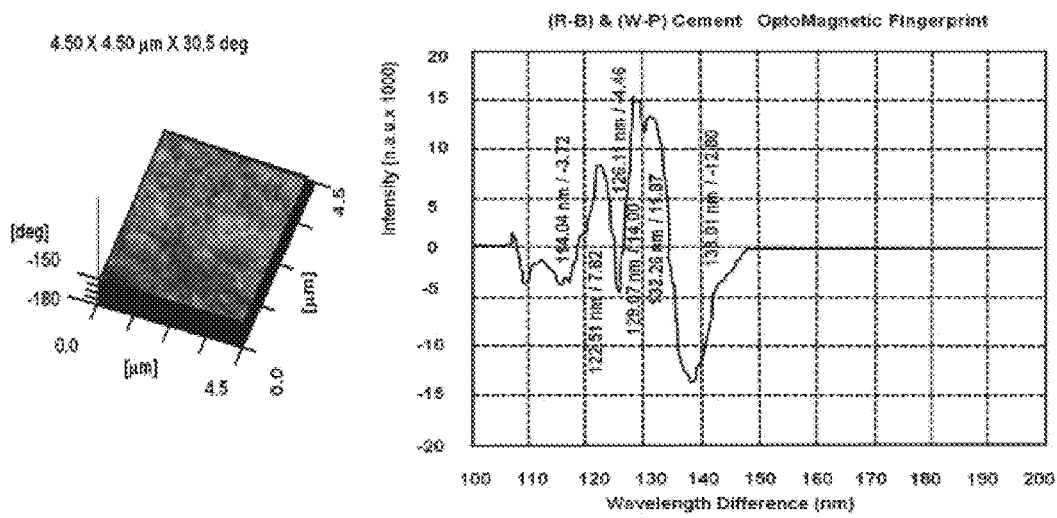

Figure 119E

DENTIN – CARIES.
Left: AFM/MFM images of enamel surface.
Lower Left: 3D display of MFM image showing the distribution of magnetic force gradient. The gradient is expressed as angle with ranges shown in degrees. We see that the difference between maximum (paramagnetic) and minimum (diamagnetic) values of gradients is 32.7 degrees, which is higher compared to healthy dentin.
Lower Right: We see OMF diagram of the same tissue, showing characteristic distribution of peaks with respect to wavelengths and intensities. We note here that intensity range is between -16.93 and +10.47 n.a.u, which is broader than the range for healthy dentin, showing correspondence with results of MFM.

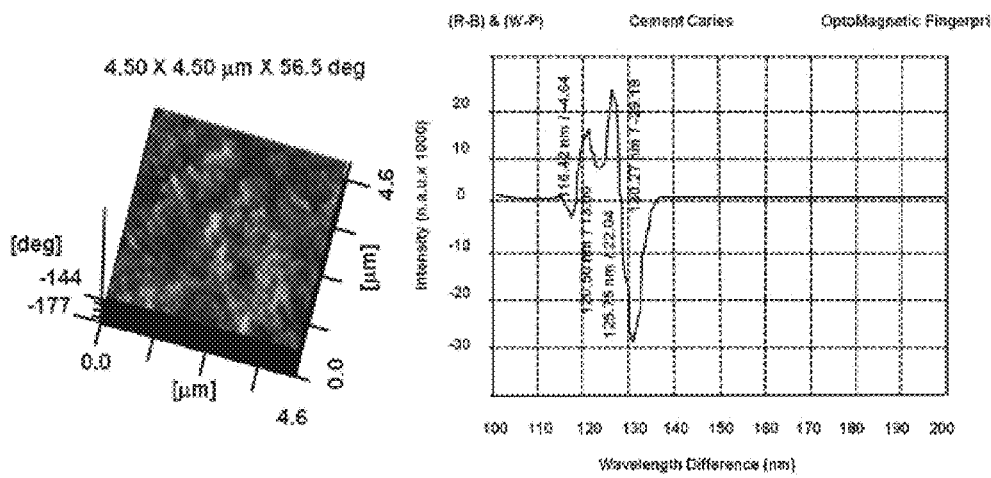

Figure 119F

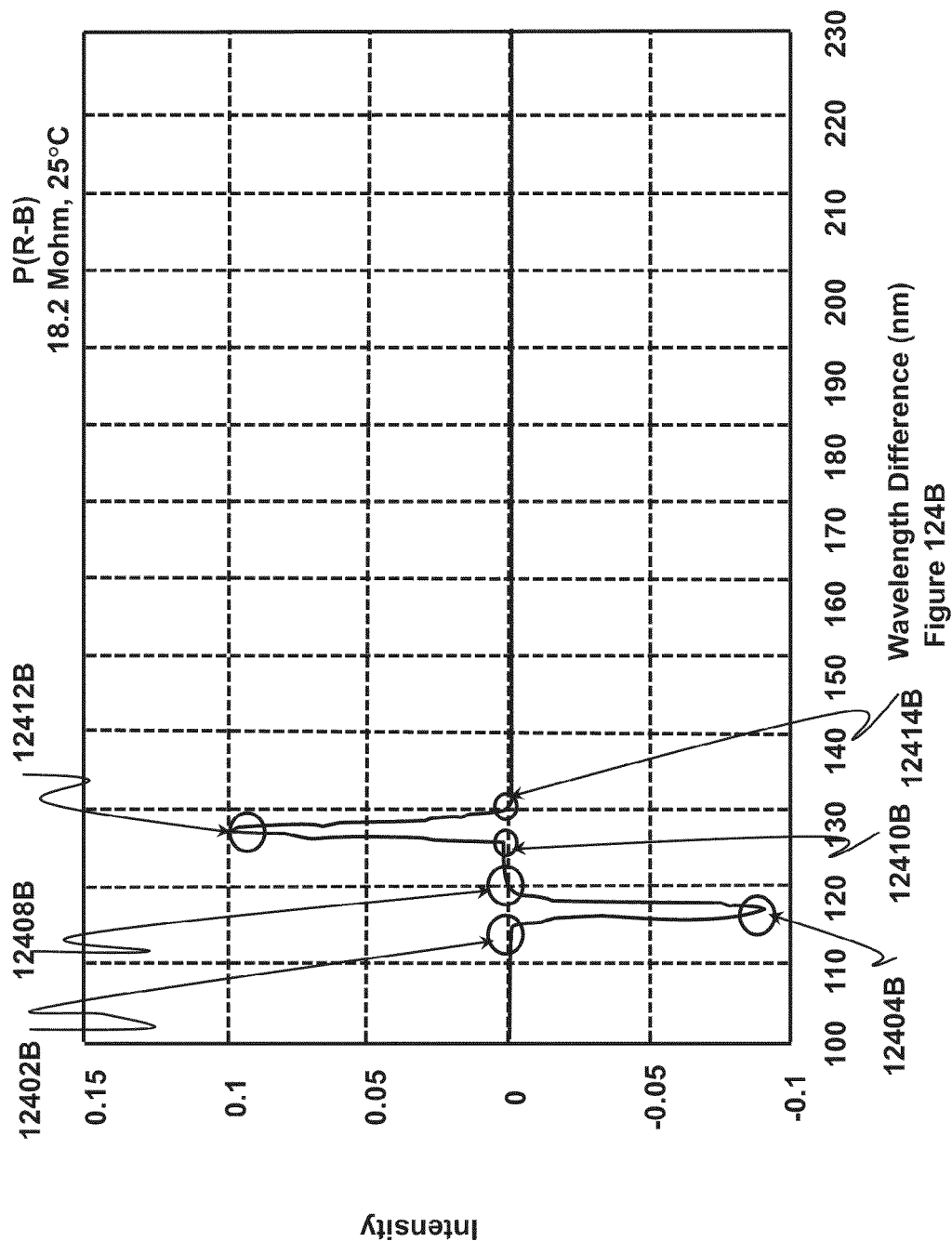

Section D-D

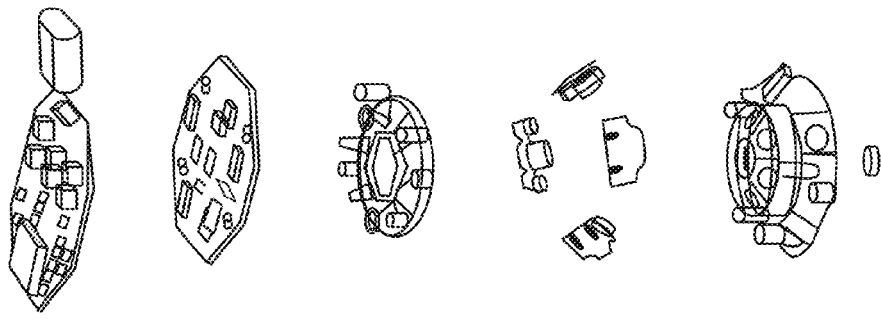
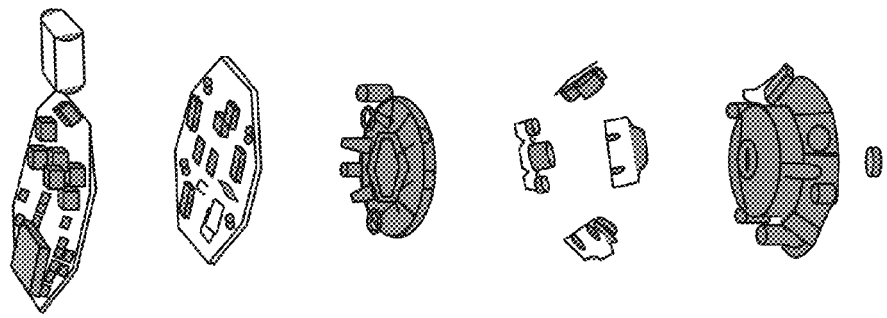
Figure 130D
Assembly: Optoelectronics

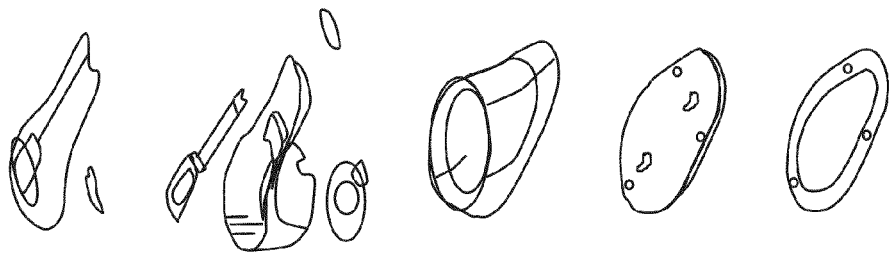
Figure 130E
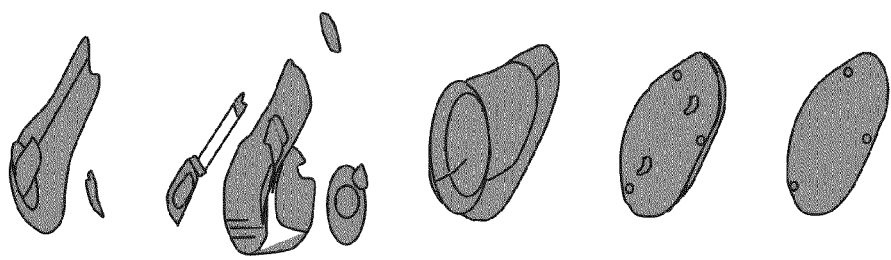
Assembly: Handle and Cradle

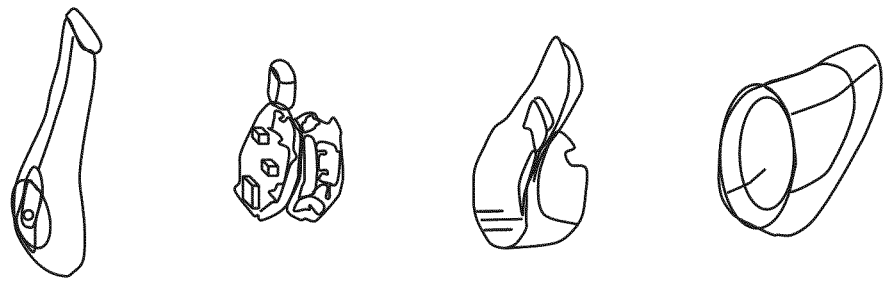
Figure 130F
Assembly: Optoelectronics into Handle
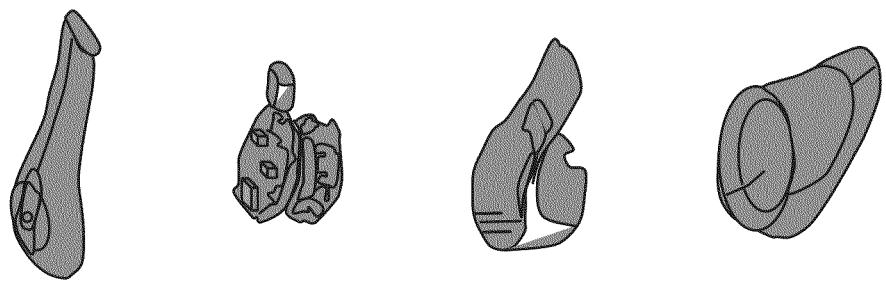

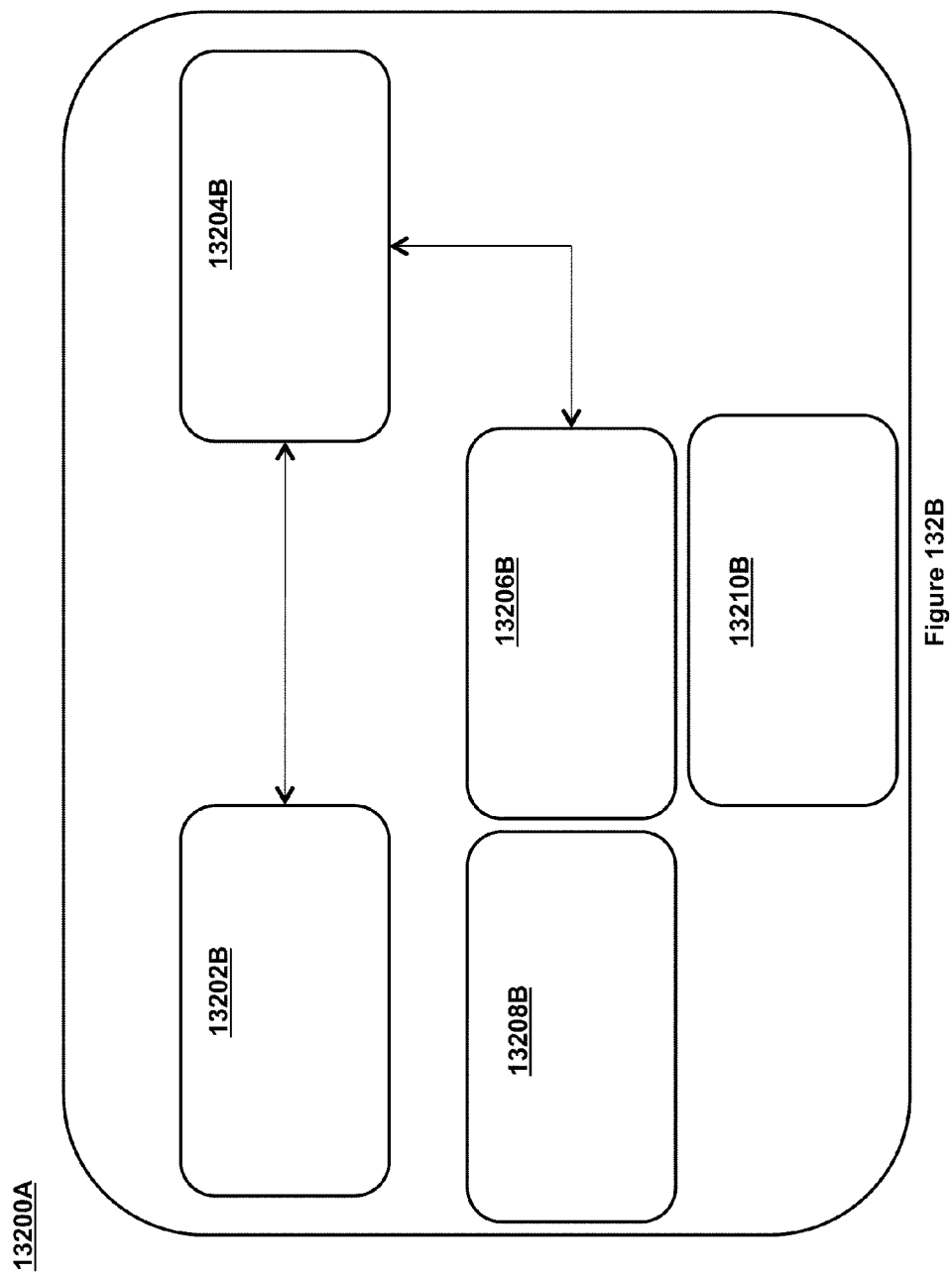

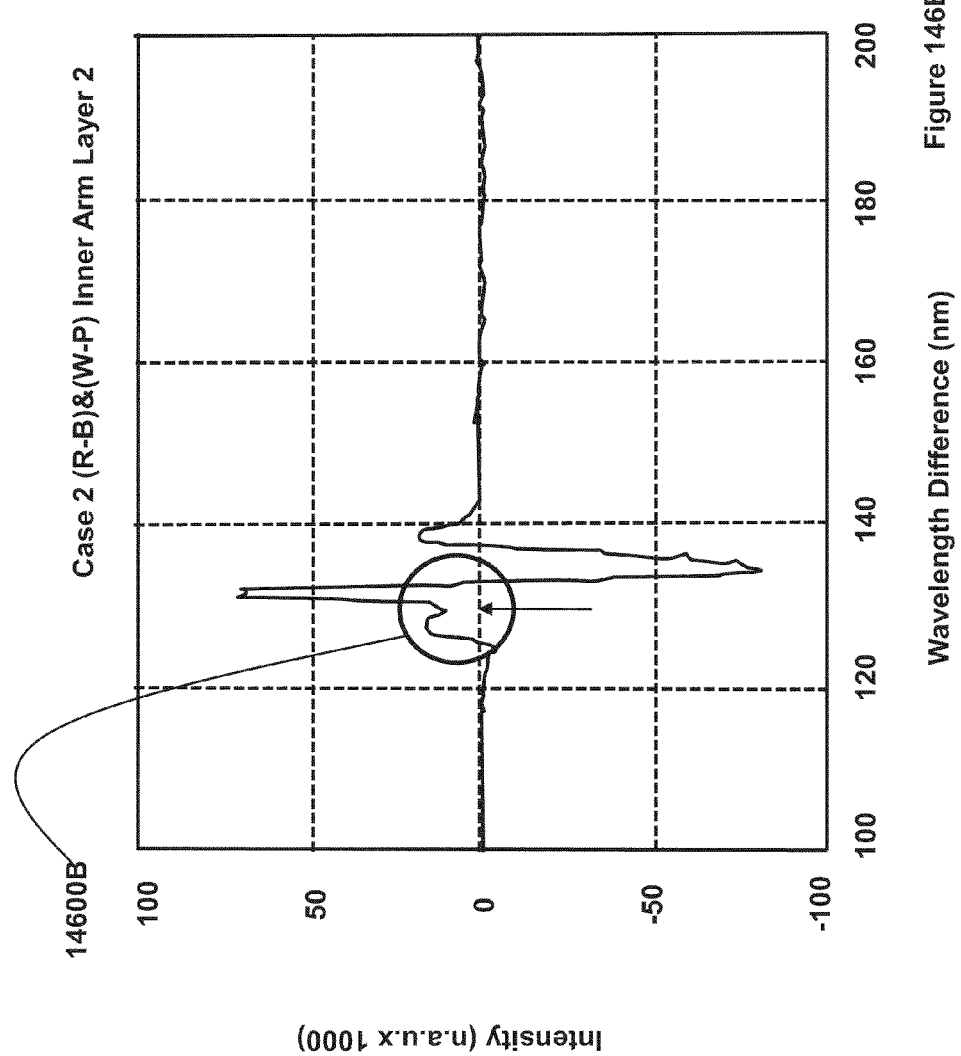

ANALYTIC METHODS OF TISSUE EVALUATION

CROSS-REFERENCE TO RELATED APPLICATIONS

This application claims priority to the following provisional applications, each of which is hereby incorporated by reference in its entirety: U.S. Provisional Patent Application No. 61/310,287, filed Mar. 4, 2010; U.S. Provisional Patent Application No. 61/308,704 filed Feb. 26, 2010; U.S. Provisional Patent Application No. 61/332,413 filed May 7, 2010; U.S. Provisional Patent Application No. 61/380,003 filed Sep. 3, 2010; U.S. Provisional Patent Application No. 61/386,962 filed Sep. 27, 2010; U.S. Provisional Patent Application No. 61/407,454 filed Oct. 28, 2010; U.S. Provisional Patent Application No. 61/380,155 filed Sep. 3, 2010; and U.S. Provisional Patent Application No. 61/431,926 filed Jan. 12, 2011.

This application is a continuation-in-part of U.S. application Ser. No. 12/690,749, filed Jan. 20, 2010, which is incorporated herein by reference in its entirety and which claims the benefit of the following provisional applications, each of which is hereby incorporated by reference in its entirety: U.S. Provisional Patent Application No. 61/145,756, filed Jan. 20, 2009; U.S. Provisional Patent Application No. 61/150,010, filed Feb. 5, 2009; U.S. Provisional Patent Application No. 61/149,025, filed Feb. 2, 2009; U.S. Provisional Patent Application No. 61/149,027, filed Feb. 2, 2009; U.S. Provisional Patent Application No. 61/150,053, filed Feb. 5, 2009; U.S. Provisional Patent Application No. 61/150,331, filed Feb. 6, 2009; U.S. Provisional Patent Application No. 61/169,316, filed Apr. 15, 2009; U.S. Provisional Patent Application No. 61/235,362, filed Aug. 20, 2009; and U.S. Provisional Patent Application No. 61/254,214, filed Oct. 23, 2009.

This application is a continuation-in-part application of the following U.S. patent application, which is hereby incorporated by reference in its entirety: U.S. patent application Ser. No. 11/970,448, filed Jan. 7, 2008, which claims the benefit of the following provisional applications, each of which is hereby incorporated by reference in their entirety: U.S. Patent Application Ser. No. 60/883,769, filed Jan. 5, 2007; U.S. Patent Application Ser. No. 60/883,764, filed Jan. 5, 2007; and U.S. Patent Application Ser. No. 60/883,768, filed Jan. 5, 2007.

This application is a continuation-in-part application of the following U.S. patent application, which is hereby incorporated by reference in its entirety: U.S. patent application Ser. No. 12/350,164, filed Jan. 7, 2009, which claims the benefit of the following provisional applications, each of which is hereby incorporated by reference in their entirety: U.S. Patent Application Ser. No. 61/019,440, filed Jan. 7, 2008 and U.S. Provisional Patent Application No. 61/061,852, filed Jun. 16, 2008.

BACKGROUND OF THE INVENTION

Field of the Invention

The invention relates to methods and apparatus for enabling the collection of dermal and non-dermal images using a non-invasive imaging device, the development of a skin state based at least in part on analysis of such images, and the monitoring of the skin state by, at least, a collection and analysis of subsequent images. The invention further pertains to the field of skin care devices and systems capable of facilitating skin care decisions, more specifically the field of devices for skin condition assessment, skin care regimen recommendation, and skin care regimen effectiveness tracking.

The present invention also relates to an image processing technique. More particularly, the present invention relates to determining a skin photo type of a captured image in a Red Green Blue (RGB) color imaging system and is also applicable in classification of other skin characteristics (e.g. elasticity, melanin, oil concentration etc.), melanoma, skin related tumors and skin related disorders.

Description of the Related Art

Opto-Magnetic Dental Analysis.

In general, teeth comprise of the following parts, namely enamel, dentin, cementum and pulp. Specifically, tooth enamel is the hardest and most highly mineralized substance of the body. Tooth enamel with dentin, cementum and dental pulp is one of the four major tissues, which make up the tooth in vertebrates. Ninety-six percent of enamel consists of mineral whereas the remaining four percent of enamel is composed of water and organic material. Normally, the color of enamel varies from light yellow to grayish white. However, at the edges of teeth the color of enamel sometimes has a slightly blue tone because there is no dentin underlying the enamel. Since enamel is semi translucent, the color of dentin and any restorative dental material underneath the enamel strongly affects the appearance of a tooth. Enamel varies in thickness over the surface of the tooth and is often thickest at the cusp, up to 2.5 mm, and thinnest at its border, which is seen clinically as the Cementoenamel Junction (or CEJ).

Likewise, dentin is covered by enamel on the crown and cementum on the root and surrounds the entire pulp. By weight, seventy percent of dentin consists of the mineral hydroxylapatite, twenty percent is organic material and ten percent is water. Yellow in appearance, it greatly affects the color of a tooth due to the translucency of enamel. Dentin, which is less mineralized and less brittle than enamel, is necessary for the support of enamel. There are three types of dentin, primary, secondary and tertiary. Primary dentin is the outermost layer of dentin and borders the enamel. Secondary dentin is a layer of dentin produced after the root of the tooth is completely formed. Tertiary dentin is created in response to a stimulus, such as a carious attack.

Mineralized tissues are biological materials that incorporate minerals into soft matrices to get the stiffness needed for a protective shield or structural support in most cases. For example, mineralized tissues are found in bone, mollusc shells, deep sea sponge *Euplectella* species, radiolarians, diatoms, antler bone, tendon, cartilage, tooth enamel and dentin. These tissues have been finely tuned to enhance their mechanical capabilities over millions of years of evolution. Thus, mineralized tissues have been the subject of many studies since there is a lot to learn from nature as seen from the growing field of biomimetics. The remarkable structural organization and engineering properties makes these tissues desirable candidates for duplication by artificial means. Mineralized tissues inspire miniaturization, adaptability and multifunctionality. While natural materials are made up of a limited number of components, a larger variety of material chemistries can be used to simulate the same properties in engineering applications. However, the success of biomimetics lies in fully grasping the performance and mechanics of these biological hard tissues before swapping the natural components with artificial materials for engineering design.

Mineralized tissues combine stiffness, low weight, strength and toughness due to the presence of minerals (the inorganic portion) in soft protein networks and tissues (the organic part). There are approximately 60 different minerals generated through biological processes, but the most common ones are calcium carbonate found in seashells and hydroxyapatite present in teeth and bones. Two types of biological tissues have been the target of extensive investigation, namely nacre from seashells and bone that are both high performance natural composites. Many mechanical and imaging techniques, such as nanoindentation and Atomic Force Microscopy (or AFM), are used to characterize these tissues. One of the studies involving mineralized tissues in dentistry is on the mineral phase of dentin in order to understand its alteration with aging. These alterations lead to "transparent" dentin, which is also called sclerotic. It was shown that a "dissolution and reprecipitation" mechanism reigns the formation of transparent dentin. The causes and cures of these conditions can possibly be decoded from further studies on the role of the mineralized tissues involved.

Further, the increasing knowledge on the properties of mineralized tissues, hierarchical structure and role of the different components could not have been made possible without the emergence of imaging techniques and mechanical testing methods. Examples of such techniques and methods are air-abrasive, AFM, Fluorescent staining, infrared spectroscopic imaging, Scanning Electron Microscopy (or SEM) and Energy Dispersive Spectroscopy (or EDS), Transmission Electron Microscopy (or TEM), small angle x-ray scattering and Notch sensitivity. Although, there are many techniques available to characterize mineralized tissues but the best techniques are the ones matched with the objective of an experiment as they emit different information to different accuracies and resolution. Therefore, before choosing a method for evaluation of mineralized tissues, the desired information parameters must first be identified and each method carefully studied to see whether it can satisfy the goal of the study.

One major problem is dental caries, also known as tooth decay or cavity, a disease wherein bacterial processes damage hard tooth structure, i.e. enamel, dentin, and cementum. These tissues progressively break down, producing dental caries (or cavities, holes in the teeth). Two groups of bacteria are responsible for initiating caries: *Streptococcus Mutans* and *Lactobacillus*. If left untreated, the disease can lead to pain, tooth loss, infection, and, in severe cases, death. Today, caries remains one of the most common diseases throughout the world. Cariology is the study of dental caries.

Caries (tooth decay) is the most common human disease, and there is currently no sensitive or accurate means for detecting it in its early stages, when tissue damage can be minimized or even reversed. The inadequacies of existing clinical tools are compounded by the fact that some dentists do not regularly assess patients for caries with x-rays owing to fears associated with exposure to ionizing radiation. These fears are even more acute when assessing children.

Dental caries and dental erosion are endemic in most of the world's population. Caries is a sub-surface disease until the surface breaks down (cavitates) to produce an actual cavity in a tooth. Prior to surface cavitation, the carious lesion has the potential to be arrested or even remineralised. Dental erosion (i.e. the progressive loss of tooth substance from the surface) is a growing problem, largely owing to an increased consumption of acid-containing beverages. There is currently no detection or diagnostic tool capable of measuring small amounts of tooth erosion in the mouth, and current methods to identify caries lesions are insensitive, relatively inaccurate, and highly susceptible to subjective opinions. In recent years dental researchers have begun to look at technologies that might assist dentists in identifying and measuring dental caries and erosion.

In certain applications, primary diagnosis involves inspection of all visible tooth surfaces using a good light source, dental mirror and explorer. In certain other applications, dental radiographs (X-rays) may show dental caries before it is otherwise visible, particularly caries between the teeth. Large dental caries are often apparent to the naked eye, but smaller lesions can be difficult to identify. Visual and tactile inspections along with radiographs are employed frequently among dentists, particularly to diagnose pit and fissure caries. Early, uncavitated caries is often diagnosed by blowing air across the suspect surface, which removes moisture and changes the optical properties of the unmineralized enamel.

However, some dental researchers caution against the use of dental explorers to find caries. For example, if small areas of tooth begin demineralizing but have not yet cavitated, the pressure from the dental explorer could cause a cavity. Since the carious process is reversible before a cavity is present, it may be possible to arrest the caries with fluoride and remineralize the tooth surface. When a cavity is present, a restoration will be needed to replace the lost tooth structure. Still, however, at times pit and fissure caries may be difficult to detect. Bacteria can penetrate the enamel to reach dentin, but then the outer surface may remineralize, especially if fluoride is present. These caries, sometimes referred to as "hidden caries", may still be visible on x-ray radiographs, but visual examination of the tooth would show the enamel intact or minimally perforated.

Accordingly, there is a need in the art for methods for overall management of dental or oral health based on the interaction between matter and electromagnetic radiation and systems and apparatuses facilitating implementation of such methods. More specifically, there is a need for the design and implementation of an Opto-Magnetic method with enhanced qualitative and quantitative parameters for analysis of teeth based on Opto-Magnetic properties of light-matter interaction and systems and apparatuses thereof. Still more specifically, there is a need for the design and implementation of an Opto-Magnetic method with enhanced qualitative and quantitative parameters, such as novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for analysis of teeth based on Opto-Magnetic properties of light-matter interaction and systems and apparatuses thereof.

Opto-Magnetic Methods of Cancer Detection.

Typically, hydrogen bonds are the attractive interaction of hydrogen atoms with electronegative atoms. Specifically, the hydrogen atom must be covalently bonded to another electronegative atom, such as nitrogen, oxygen or fluorine, to create the bond. Hydrogen bonds occur in both inorganic molecules, such as water and organic molecules, such as DNA.

In certain contexts, hydrogen bonds are often described as electrostatic dipole-dipole interactions. Specifically, as per advanced theory, hydrogen bonds are viewed as metric-dependent electrostatic scalar field between two or more intermolecular bonds. In certain specific contexts related to natural sciences, from the standpoint of quantum mechanics intermolecular interactions are considered as intermolecular forces of attraction between two molecules or atoms. They occur from either momentary interactions between molecules, such as the London dispersion force or permanent electrostatic attractions between dipoles. However, they are also explained using a simple logical approach as in intermolecular forces, or using a quantum mechanical approach.

Using quantum mechanics, it is possible to calculate the electronic structure, energy levels, bond angles, bond distances, dipole moments, and electromagnetic spectra of simple molecules with a high degree of accuracy. Bond distances and angles can be calculated as accurately as they can be measured (distances to a few pm and bond angles to a few degrees). For small molecules, calculations are sufficiently accurate to be useful for determining thermodynamic heats of formation and kinetic activation energy barriers.

Hydrogen bonds have dual property, such as classical (i.e. electrostatic interaction based on Coulomb's law) and quantum (i.e. wave function based on Schrödinger equation).

Thus, hydrogen bond and its nature have engaged the attention of scientific community from the time when the intra and intermolecular bonds were described as non-covalent bonds. However, hydrogen bond became common term when Pauling gave systematic concept of the hydrogen bond. Despite Pauling's proposal that hydrogen bond in water is not merely classical electrical attraction between a positively charged hydrogen atom and a negatively charged oxygen atom, but is also affected by the sigma bonds, the proposal was not considered seriously until it was experimentally shown that hydrogen bond posses covalence and has both classical and quantum properties.

On the basis of data obtained from neutron diffraction experiments it is obvious that product of distance between center of hydrogen and oxygen atoms in a covalent bond d (O—H) of different structures is between 95 picometer (pm) and 120 pm, while distance of center of hydrogen and oxygen atoms in non-covalent bond d (OxxxH) is between 120 pm and 200 pm. However, for each type of matter product value d (O—H) d (OxxxH) is about 162 pm. Systematic investigation and quantitative analysis of bond lengths of O—HxxxO showed that bond-valence parameters of hydrogen bonds follow Golden ratio rule, whose value is around 1.62 pm.

In general, water is matter that is most abundant with hydrogen bonds. These hydrogen bonds have both classical and quantum properties and may be organized in molecular networks. Thus, water via hydrogen bonds may play a significant role in molecular and biomolecular recognition. In particular, two major fundamental problems exist in modern pharmacy, namely (1) understanding mechanism for molecular recognition in water solution, and (2) water structure for drug design. Thus, water structure for drug design is important. This is because modeling ligand-receptor interaction has to include specific geometry, which relates to water structure. In addition, it is well known that hydrogen bonds are a link between two nucleotide chains in DNA and support existence of secondary, ternary and quaternary structure of proteins.

In addition, Deoxyribonucleic acid (or DNA) research indicates that both classical and quantum mechanical approach give same phenomenological results for those structures. The reason for similar result is simple. For stationary quantum state Hamiltonian H is a sum of kinetic T and potential V energy, while Lagrangian is a difference between them when system is in equilibrium with external forces. From the energy viewpoint, a pair of similar pictures, one classical and another quantum, of same object with similar results exist. Thus, the goal is to detect how hydrogen bonds participate in water to be more or less at least one of classical and quantum entity.

Accordingly, there is a need in the art for methods for detection of cancer based on the interaction between matter and electromagnetic radiation and systems and apparatuses facilitating implementation of such methods. More specifically, there is a need for the design and implementation of an Opto-Magnetic method with enhanced qualitative and quantitative parameters for detection of cervical and endometrial cancer in samples based on Opto-Magnetic properties of light-matter interaction and systems and apparatuses thereof. Still more specifically, there is a need for the design and implementation of an Opto-Magnetic method with enhanced qualitative and quantitative parameters, such as novel, enhanced and easy interpretability, enhanced and easy detectability, enhanced sensitivity, enhanced specificity, enhanced efficiency, greater accuracy, easily operable, rapid, economical, precise, timely and minute variation sensitive, for analysis of water samples based on Opto-Magnetic properties of light-matter interaction and systems and apparatuses thereof.

Bioimpedance and Skin Hydration Analysis.

Typically, the skin hydration and desquamation are uninterrupted processes in stratum corneum to keep it healthy. Stratum corneum is the outermost layer of epidermis, which in turn is the outermost part of the skin. Particularly, constant hydration of the stratum corneum and constant desquamation of dead skin cells is necessary to keep the skin elastic and even. More particularly, any damage to the processes of hydration and desquamation results in many problems and diseases.

In general, the problem of skin hydration and its evaluation is among the most debated by specialists. Specifically, the measurement (or assessment) of stratum corneum hydration is an important and interesting field of research. Unfortunately, it is also a field where one or more obsolete theories and information still exist.

In general, in biomedical engineering, bioimpedance is the response of a living organism to an externally applied electric current. Bioimpedance is a measure of the opposition to the flow of the electric current through the tissues, which is the opposite of electrical conductivity. This measurement of the bioimpedance (or bioelectrical impedance) of the humans and animals has proved useful as a non-invasive method for the computation of one or more physiological parameters, such as blood flow (often referred to as Bioimpedance Plethysmography) and body composition (known as Bioelectrical Impedance Analysis or BIA).

Still, in general, the impedance of skin is dominated by the stratum corneum at low frequencies. For example, it is commonly stated that skin impedance is determined mainly by the stratum corneum at frequencies below 10 kHz whereas by the viable skin at higher frequencies. Skin impedance may certainly be dependent on one or more factors, such as skin hydration, dimensional and geometrical specifications of electrodes used thereof, and the like, but may nevertheless function as a rough guideline. The Cole-Cole (Cole) equation has been found suitable for modeling most electrical measurements on biological tissue, including skin. However, the impact of the skin hydration by layers to bioelectrical properties is not fully tested.

Bioelectro-physical properties of human skin tissue, like most other soft tissues, exhibit electroviscoelastic behavior. However, in order to acquire complete information about the electroviscoelastic behavior of human skin, it is also obligatory to capture and maintain (i.e. manage) experimental data over a wide range of time scales.

Bio-impedance can be measured by applying electricity from an external source outside the living organism. In order to analyze the skin impedance effectively, it is desirable to introduce the skin impedance model. Additionally, the complex modulus concept is a powerful and widely used tool for characterizing the electroviscoelastic behavior of materials in the frequency domain. In this case, according to the proposed concept, bioimpedance moduli can be regarded as complex quantities.

As per the Bioelectrical Impedance Spectroscopy (or BIS) technique, impedance measurements are done at each frequency, which are subsequently plotted, thereby forming a circular arc. Further, using the electrical engineering modeling mathematics the points on a circular arc can be transformed into an equivalent electrical model, where the values correspond to specific compositional elements. Still further, from the mathematical viewpoint, the fractional integro-differential operators (i.e. fractional calculus) are a generalization of integration and derivation to non-integer order (fractional) operators.

On the other hand, a memory function equation, scaling relationships and structural-fractal behavior of biomaterials and, here, mathematical model based on fractional calculus, were used for the physical interpretation of the Cole-Cole exponents. It must be noted that, three expressions for the impedance, namely Cole-Cole function, Cole-Davidson function and Havriliak-Negami function, allow description of a wide range of experimental data.

Accordingly, there is a need in the art for methods for skin hydration assessment based on the utilization of bioimpedance and fractional calculus and systems and apparatuses facilitating implementation of such methods. More specifically, there is a need for the design and implementation of a method for skin hydration assessment based on the utilization of bioimpedance and fractional calculus with enhanced qualitative and quantitative parameters and systems and apparatuses thereof. Still more specifically, there is a need for the design and implementation of a method for skin hydration assessment based on the utilization of bioimpedance and fractional calculus with enhanced qualitative and quantitative parameters, such as novel, enhanced and easy interpretability, enhanced and easy detectability, enhanced sensitivity, enhanced specificity, enhanced efficiency, greater accuracy, easily operable, rapid, economical, precise, timely and minute variation sensitive, and systems and apparatuses thereof.

Opto-Magnetic Skin Imaging.

Typically, ageing or aging is the accumulation of changes in an organism or object over time. Specifically, ageing in humans refers to a multidimensional process of physical, psychological, and social change. Some dimensions of ageing grow and expand over time, while others decline. Reaction time, for example, may slow with age, while knowledge of world events and wisdom may expand. Research shows that even late in life potential exists for physical, mental, and social growth and development. Ageing is an important part of all human societies reflecting the biological changes that occur, but also reflecting cultural and societal conventions.

More specifically, "physiological aging," "senescence" or "biological aging" is the combination of processes of deterioration, which follow the period of development of an organism. Stated differently, "physiological aging," "senescence" or "biological aging" is the change in the biology of an organism as it ages after its maturity. Such changes range from those affecting its cells and their function to that of the whole organism. There are a number of theories why senescence occurs including those that it is programmed by gene expression changes and that it is the accumulative damage of biological processes. Organismal senescence is the aging of whole organisms.

One possible treatment for skin senescence is Blepharoplasty. Blepharoplasty is a surgical procedure that can restore a youthful appearance to the eye area. The upper and lower eyelids are lifted and loose or excess skin and fat tissue are removed from the eye area. The procedure is limited to the eyelids and may be combined with methods to improve other areas of the face. Brow lifts, which raise the eyebrows or keep them from sagging over the eyes, may be recommended to help improve the upper third of the face.

However, this is an invasive procedure and results in post-operative effects and possible complications. For example, a "too tight" or uneven appearance can be caused by the removal of too much skin or uneven amounts of fat. Additional surgeries may be usually required to reverse this problem. On certain occasions, bleeding can occur in the socket.

Similarly, Botulinum Toxin Therapy is another solution. Before treatment, the dermatologist obtains the patient's medical history, including any medications taken. Treatment involves injecting very small amounts of Botulinum toxin directly into the underlying facial muscles to relax them. A tiny needle is used; the procedure is well tolerated and takes just a few minutes with no "down time" or prolonged recovery period.

However, this therapy is intrusive and Botulinum toxin takes effect about 3 to 7 days after treatment. The improvement generally lasts about 3 to 4 months; the effect gradually fades as muscle action returns. Patients require re-injection at various intervals. With repeated treatments, atrophy (thinning) of the muscle may occur.

Accordingly, there is a need in the art for methods for analysis of skin based on the interaction between matter and electromagnetic radiation and systems and apparatuses facilitating implementation of such methods. More specifically, there is a need for the design and implementation of an Opto-Magnetic method with enhanced qualitative and quantitative parameters for analysis of skin based on Opto-Magnetic properties of light-matter interaction and systems and apparatuses thereof. Still more specifically, there is a need for the design and implementation of an Opto-Magnetic method with enhanced qualitative and quantitative parameters, such as novel, enhanced and easy interpretability, enhanced and easy detectability, enhanced sensitivity, enhanced specificity, enhanced efficiency, greater accuracy, easily operable, rapid, highly interactive, fuzzy logic knowledge-based, artificial neural network knowledge-based, economical, precise, timely and minute variation sensitive, for analysis of skin based on Opto-Magnetic properties of light-matter interaction and systems and apparatuses thereof.

Further, there is a need in the art for methods for imaging and analysis of skin based on the interaction between matter and electromagnetic radiation and systems and apparatuses facilitating implementation of such methods. More specifically, there is a need for the design and implementation of an Opto-Magnetic method with enhanced qualitative and quantitative parameters for imaging and analysis of skin based on Opto-Magnetic properties of light-matter interaction and systems and apparatuses thereof. Still more specifically, there is a need for the design and implementation of an Opto-Magnetic method with enhanced qualitative and quantitative parameters, such as novel, enhanced and easy interpretability, enhanced and easy detectability, enhanced sensitivity, enhanced specificity, enhanced efficiency, greater accuracy, easily operable, rapid, highly interactive, fuzzy logic knowledge-based, artificial neural network knowledge-based, economical, precise, timely and minute variation sensitive single handed operability, motion tolerant, skin-based inductive chargeability, lens-independent (or -free), reduced complexity or simplicity, economical, disease diagnosability, rapid drug screenability or high throughput screenability, easy integrability or couplability to portable communication devices and slim configuration, for imaging and analysis of skin based on Opto-Magnetic properties of light-matter interaction and systems and apparatuses thereof.

Opto-Magnetic Methods for Skin Characterization.

Broadly, skin is made up of three main different skin layers, namely epidermis, dermis and subcutis. The epidermis is tightly connected to the dermis by a basement membrane. The basement membrane is very thin layer between the epidermis and dermis. The basement membrane structurally and energetically separates the epidermis and the dermis. These layers exhibit different types of light propagation owing to the fact that they are composed of different types of cellular and extracellular molecules.

On average, the thickness of epidermis is approximately 200 µm. However, the thickness of epidermis varies and is up to approximately 2 mm, depending on the location on the body. Still, however, the thickness of the epidermis varies according to the volume of the water held thereof.

Anatomically, the epidermis is divided into five sub layers, namely stratum corneum (or horny cell layer), stratum lucidum (or clear layer), stratum *granulosum* (or granular layer), stratum spinosum (or prickle cell layer) and stratum basale (or basal cell layer). Metabolically, the epidermis is an active tissue. Specifically, one type of epidermal cells, keratinocytes, moves upward to the outer surface. This process is called turn-over, and takes a minimum of approximately 28 days to a maximum of approximately 72 days. During this process keratinocytes change their structure and physiological function.

More specifically, keratinocytes are produced in the stratum basale, which holds approximately 10% of the epidermal water. With aging, this layer becomes thinner and losses the ability to retain water. Basal cells, through the process of turn-over, make their shape somewhat flatter and form stratum spinosum layer with about 20 layers that lie on the top of the basal cell layer. The thickness of the stratum spinosum layer ranges from a minimum of approximately 60 µm to a maximum of approximately 150 µm, and holds about 35% of epidermal water. In the next turnover process organelles, such as nuclei and mitochondria, start to resolve. Cells are increasingly filled with keratin fibers and contain less intracellular water than basal and spinosum cells. However, this layer called stratum *granulosum*, is about 5 µm thick and has very well ordered lipid-water layers, from 5 to 20, depending on the skin condition. Water layers are thin from 20 to 50 nm.

Based on a common standpoint disclosed in one or more literature, the skin is usually observed as a simple structure with equivalent electrical model, which includes general properties of epidermis, basal membrane and dermis. Further, there are numerous conventional approaches to skin characterization. However, the emerging technologies have been mainly focused on non-invasive methods in order to limit pain to patients. Lines of investigations cover aspect related to dermatology or dermocosmetic science by exploiting characteristic measurements related to one or more properties of the skin, such as mechanical, electrical, thermal, optical, acoustic, piezoelectric and morphological.

Previous studies have focused on correlating the skin mechanical properties with age, gender, anatomical site, and hydration. However, age-related studies have reached disparate conclusions. Despite the many devices that have been developed in the last twenty years, a lot still remains to be accomplished in terms of comparability of the measures and standardization of the results. In fact, even when dealing with the same parameters, different devices could yield different values. Finally, methods relying only on mechanical properties cannot assess topography measurements of the skin.

Accordingly, there is a need in the art for methods for characterization of skin based on the interaction between matter and electromagnetic radiation and systems and apparatuses facilitating implementation of such methods. More specifically, there is a need for the design and implementation of an Opto-Magnetic method with enhanced qualitative and quantitative parameters for characterization of skin samples based on Opto-Magnetic properties of light-matter interaction and systems and apparatuses thereof. Still more specifically, there is a need for the design and implementation of an Opto-Magnetic method with enhanced qualitative and quantitative parameters, such as novel, easily operable, rapid, economical, precise, timely and minute variation sensitive, complex analytical capability, nanomaterials detectability and analyzability and dual process approach, for characterization of skin samples based on Opto-Magnetic properties of light-matter interaction and systems and apparatuses thereof.

SUMMARY OF THE INVENTION

Real-time analysis of digitally captured skin characteristics facilitates timely skin condition assessment, skin regimen recommendation, and skin regimen effectiveness tracking.

The problem of generating a skin condition assessment in real-time is solved by having a skin condition analysis module capable of doing real-time analysis of digital skin data, acquired partly using diffused reflectance spectroscopy and/or detecting the red-green-blue components of re-emitted white light.

In an aspect of the invention, a skin care device may include an electromagnetic radiation source capable of directing incident electromagnetic radiation to a location on the skin of a user, a radiation detector for measuring various parameters of radiation re-emitted from the location, and a skin condition analysis module coupled to the detector, the analysis module capable of generating a skin condition assessment in real-time, based partly on at least one of RGB analysis and diffused reflectance analysis of the radiation parameters. In the device, the incident electromagnetic radiation may include radiation in at least one of the visible, near-infrared, and near-ultraviolet spectrum. The incident radiation may include white light. In the device, the radiation parameters may include at least the degree of polarization of the re-emitted radiation. In the device, the radiation source may be a set of light emitting diodes. In the device, the skin condition assessment may also be partly based on analysis of a photographic image of a skin region surrounding the location. In the device, the device may be a miniature device. Miniature may mean that no dimension of the detector exceeds six inches. The device may further comprise a memory module for storing the skin condition assessment. The device may further comprise a user interface. The user interface may be operated using voice commands. In the device, skin assessment data of locations may be overlaid on an image of a larger skin region and displayed on the display surface. The device may further comprise an access restriction module used for restricting access to authorized users only. The access restriction module may be based on biometric access control. The device may be capable of generating alerts about abnormal skin conditions in real-time. The device may further comprise a skin care regimen recommendation module that generates a displayable skin care regimen recommendation. The skin care regimen recommendation may be based at least partly on determination of a skin profile of the user and use of skin care regimen recommendations of persons with a similar profile. The skin care regimen recommendation module may be linked to a product database. The product database may include products available in a point-of-sale location. The availability of a specific product recommended by the skin care regimen recommendation module may be indicated by an audio-visual signal. The device may further comprise a skin care regimen effectiveness module that generates a displayable skin care regimen effectiveness report. The device may further comprise a communication module for communicating with a remote computer. The communication may occur wirelessly. The communication may occur over an internet. The remote computer may be operable by a physician. The device may be wand-shaped. The device may be wearable by the user.

In an aspect of the invention, the skin care device may include an electromagnetic radiation source capable of directing incident electromagnetic radiation to a location on the skin of a user, a detector for measuring various parameters of radiation re-emitted from the location, a skin condition analysis module coupled to the detector, the analysis module capable of generating a skin condition assessment in real-time, based partly on at least one of RGB analysis and diffused reflectance analysis of the radiation parameters, and a display panel for reflecting the image of the user. In the device, the display panel may be touch-sensitive such that touching the location in a skin region image displayed in the display panel triggers display of a magnified image of the location. The device may further comprise a camera. The camera may be integral with the display panel. The camera may be wirelessly linked to the display panel. In the device, the display panel may be a mirror. In the device, a stored image of the user is used to automatically identify the person. The device may further comprise a user interface for controlling the skin care device. The user interface may be operated using voice commands. The device may further comprise a skin care regimen recommendation module capable of generating a displayable skin care regimen recommendation. The skin care regimen recommendation may be based at least partly on determination of a skin profile of the user and use of skin care regimen recommendations of persons with a similar profile. The device may further comprise a skin care regimen effectiveness module capable of generating a displayable skin care regimen effectiveness report.

In aspects of the invention, an imaging device permits a user to take high magnification pictures of the skin in the vicinity of an area of concern and submit those pictures, optionally along with textual and data responses, for medical, non-medical, and cosmetic analysis, diagnosis and treatment recommendation and fallow-up.

In an aspect of the invention, a method and system of a non-invasive imaging device may comprise an illumination source comprising an incident light source to direct light upon skin; and a detector for detecting the degree of polarization of light reflected from the skin. In the method and system, the illumination source may be positioned to direct light at a selected angle alpha. Varying alpha may vary the depth of the measurement of the layers in the skin. Each depth may have a specific angle which produces a full polarized reflection. In the method and system, the incident light source may be an unpolarized light source. The unpolarized light may be white light, multiple selected wavelengths, or a single wavelength. The method and system may further comprise a sensor for capturing an image of the reflected or re-emitted light. The method and system may further comprise an optical facility for detecting reflected or re-emitted light from the skin. The method may determine both reflected or re-emitted light, and newly emitted light, through the process of absorption and re-emission. The method and system may further comprise a communication facility for transmitting the detected information. The method and system may further comprise a storage facility for storing information collected by the device.

In an aspect of the invention, a method and system for determining a skin state may comprise illuminating skin with an incident light source, detecting the degree of polarization of light reflected from the skin, and determining a skin state based on an aspect of the polarization of the reflected or re-emitted light. In the method and system, the incident light may be directed at a selected angle alpha. Varying alpha may vary the depth of the measurement of the layers in the skin. Each depth may have a specific angle which produces a full polarized reflection. In the method and system, the incident light source may be an unpolarized light source. The unpolarized light may be white light, multiple selected wavelengths, or a single wavelength. In the method of claim, the aspect of the polarization may be at least one of an orientation, an amplitude, a phase, an angle, a shape, a degree, an amount, and the like. In the method and system, determining may be done using an algorithm. The algorithm may involve artificial neural networks, non-linear regression, genetic algorithms, fuzzy logic, fractal and multifractal analysis, and the like. The methods and systems may further comprise filtering the reflected or re-emitted light to obtain polarized light of at least one wavelength defined by the filter output. The algorithmic analysis may be performed on the filtered image. In the method and system, determining may involve creating an image from the difference between the reflected diffusion light and the reflected polarized light. In the method and system, determining may involve comparing the aspect of the polarization of the reflected or re-emitted light to a calibration signal. In the method and system, determining may further comprise considering at least one of user input and a visual analysis.

In an aspect of the invention, a non-invasive imaging device may comprise an illumination source comprising an incident light source to direct light upon an area of concern and a detector for detecting the degree of polarization of light reflected from the area of concern. In the method and system, the illumination source may be positioned to direct light at a selected angle alpha. Varying alpha may vary the depth of the measurement of the layers in the skin. Each depth may have a specific angle which produces a full polarized reflection. In the method and system, the incident light source may be an unpolarized light source. The unpolarized light may be white light, multiple selected wavelengths, or a single wavelength. The method and system may further comprise a sensor for capturing an image of the reflected or re-emitted light. The method and system may further comprise an optical facility for detecting reflected or re-emitted light from the skin. The method and system may further comprise a communication facility for transmitting the detected information. The method and system may further comprise a storage facility for storing information collected by the device.

In an aspect of the invention, a method of determining moisture levels in the skin may comprise emitting incident light towards a skin structure, detecting a degree of polarization of the light induced by the skin structure, and determining a moisture level based on the amount of polarized and reflected or re-emitted light. The method and system may further comprise combining the assessment of moisture level with skin color measurements to determine luminosity. In the method and system, the incident light may be unpolarized light. The unpolarized light may be white light, light of multiple selected wavelengths, or of a single wavelength, or one or more monochromatic lights. In the method and system, determining may involve use of an algorithm. In the method and system, determining a moisture level may be based on the ratio of polarized and reflected or re-emitted light.

In an aspect of the invention, a method and system of determining elasticity of the skin may comprise emitting incident light towards a skin structure, detecting an aspect of polarization of the light reflected by the skin structure, correlating the aspect of polarization with a concentration of elastin, and determining elasticity level based on the elastin status. In the method and system, determining may involve use of an algorithm. In the method and system, the incident light may be unpolarized light. The unpolarized light may be white light, light of multiple selected wavelengths, or a single wavelength of light.

In an aspect of the invention, a method and system of determining firmness of the skin may comprise emitting incident light towards a skin structure, detecting an aspect of polarization of the light reflected by the skin structure, correlating the aspect of polarization with the status of at least one of an elastin, a collagen, and an activity of a sebaceous gland, and determining firmness based on the concentration of at least one of elastin and collagen and sebaceous gland activity. In the method and system, the sebaceous gland activity may be indicated by at least one of a number of glands, percent of glands open/closed, and level of clog/fill. In the method and system, correlating may involve use of an algorithm.

In an aspect of the invention, a method and system for obtaining dermal biophysical properties may comprise performing a spectral analysis of image data acquired from the degree of polarization of reflections and absorption and re-emission of incident light from skin structures, wherein the property is at least one of a structure, form, status, number, size, state, and stage of at least one of a: melanocyte, melanin, hemoglobin, porphyrin, triptofan, NADH, FAD, keratin, carotene, collagen, elastin, sebum, sebaceous gland activity, pore (sweat and sebaceous), moisture level, elasticity, luminosity, firmness, fine line, wrinkle count and stage, pore size, percent of open pores, skin elasticity, skin tension line, spot, skin color, psoriasis, allergy, red area, general skin disorder or infection, tumor, sunburn, rash, scratch, pimple, acne, strias, insect bite, itch, bleeding, injury, inflammation, photodamage, pigmentation, tone, tattoo, percent burn/burn classification, mole (naevi, nevus), aspect of a skin lesion (structure, color, dimensions/asymmetry), melanoma, automated follow-up of pigmented skin lesions, dermally observed disorder, cutaneous lesion, cellulite, boil, blistering disease, congenital dermal syndrome, (sub)-cutaneous mycoses, melasma, vascular condition, rosacea, spider vein, texture, skin ulcer, wound healing, post-operative tracking, melanocytic lesion, non-melanocytic lesion, basal cell carcinoma, seborrhoic keratosis, sebum (oiliness), nail- and/or hair-related concern, and the like.

In an aspect of the invention, a system and method may comprise providing an interface that includes a social networking domain or rating-and-ranking system and at least one of a skin state determination facility and a recommendation engine, and enabling users, either all or a selected few, of the interface to perform a skin state determination within the interface. In the method and system, the skin state determination facility may comprise capturing images with a non-invasive imaging device comprising an illumination source comprising an incident light source to direct light upon skin, and a detector for detecting the degree of polarization of light reflected from the skin, and determining a skin state based on an aspect of the polarization of the reflected or re-emitted light. The method and system may further comprise receiving product and regimen recommendations from the recommendation engine based on what other users with similar skin states are using as well as data regarding ingredients, effectiveness, safety, and the like. The method and system may further comprise comparing skin states, products, regimens, and recommended products or regimens with peers within the social networking domain of the interface. Comparing may comprise an analysis of similarity based on the spectral analysis of the degree of polarization of reflected or re-emitted light from users' skin. In the method and system, the interface may comprise a regimen tracker. The regimen tracker may be populated using a drag-and-drop or click-to-add functionality. In the method and system, the interface may comprise a rating facility or a product information facility. The product information facility may enable a user to obtain product information by search. Search may be a search of product identifiers, product ratings, drag-and-drop items, images, barcode scans, skin states, and profiles.

In an aspect of the invention, a method and system for determining a skin state may comprise obtaining the answers to a series of subjective questions regarding the skin, obtaining an objective skin analysis using a dermal imaging device, and combining the subjective and objective results algorithmically to obtain a skin state.

In an aspect of the invention, a system and method for providing recommendations for skin care based on a skin state and a skin care goal may comprise obtaining a skin state of an individual, categorizing the individual by skin state, and recommending products and regimens that are effective for other individuals of the category in achieving the skin care goal. In the method and system, the system may be operable over a network. In the method and system, the skin state may be determined based on analysis of the degree of polarization of light reflected from the skin of the individual.

In an aspect of the invention, a method for tracking the effectiveness of a skin care product or regimen may comprise obtaining a baseline skin state assessment, recommending a monitoring interval based on at least one of the skin care goal, product, and regimen, obtaining a second skin state assessment, comparing the second assessment to the baseline assessment to determine progress towards a skin care goal, and optionally, optimizing the regimen or product in order to improve a skin state. In the method and system, the skin assessment may be based on analysis of the degree of polarization of light reflected from the skin of the individual.

In an aspect of the invention, a personalized skin condition analysis system and related methods may comprise an imaging device, comprising an illumination source comprising an incident light source to direct light upon skin, and a detector for detecting the degree of polarization of light reflected from the skin, and a user interface for controlling the device. In the methods and system, the device may be adapted to interact with a physical interface to download image data to update a record of at least one of a practitioner, a spa, a salon, cosmetic sales, a cosmetics manufacturer, a clinical trials database, and a third party database. In the method and system, the illumination source may be positioned to direct light at a selected angle alpha. Varying alpha may vary the depth of the measurement of the layers in the skin. Each depth may have a specific angle which produces a full polarized reflection. In the method and system, the incident light source may be an unpolarized light source. The unpolarized light may be white light, multiple selected wavelengths, or a single wavelength. The method and system may further comprise a sensor for capturing an image of the reflected or re-emitted light. The method and system may further comprise an optical facility for detecting reflected or re-emitted light from the skin. The method and system may further comprise a communication facility for transmitting the detected information. The method and system may further comprise a storage facility for storing information collected by the device.

In an aspect of the invention, a non-invasive imaging device may comprise an illumination source comprising an incident light source to direct light upon skin; and a detector for detecting a characteristic of the light reflected from the skin. In the device, the illumination source may be positioned to direct light at a selected angle alpha. Varying alpha may vary the depth of the measurement of the layers in the skin. Each depth may have a specific angle which produces a full polarized reflection. In the device, the incident light source may be a polarized light source or unpolarized light source. The unpolarized light may be at least one of white light, light of a single wavelength, and light of multiple single wavelengths. The device may further comprise a sensor for capturing an image of the reflected or re-emitted light. The device may further comprise an optical facility for detecting reflected or re-emitted light from the skin. The device may further comprise a communication facility for transmitting the detected information. The device may further comprise a storage facility for storing information collected by the device. In the device, the reflected or re-emitted light may be at least one of polarized light and unpolarized light.

In an aspect of the invention, a method and system for determining a skin state may comprise illuminating skin with an incident light source; detecting a characteristic of the light reflected from the skin; and determining a skin state based on at least one characteristic of the reflected or re-emitted light. In the method and system, the incident light may be directed at a selected angle alpha. Varying alpha may vary the depth of the measurement of the layers in the skin. Each depth may have a specific angle which produces a full polarized reflection. In the method and system, the incident light may be unpolarized or polarized light. The unpolarized light may be at least one of white light, light of a single wavelength, and light of multiple single wavelengths. In the method and system, the reflected or re-emitted light may be at least one of polarized light and unpolarized light. In the method and system, the characteristic may be at least one of light source, light intensity, wavelength of light, angle of light, electrical and magnetic properties of the light, and polarization state of the light. An aspect of the polarization may be at least one of an orientation, an amplitude, a phase, an angle, a shape, a degree, and an amount. In the method and system, determining may be done using an algorithm. The algorithm may involve artificial neural networks, non-linear regression, genetic algorithms, fuzzy logic, or fractal and multi-fractal analysis. The method and system may further comprise filtering the reflected or re-emitted light to obtain light of a wavelength defined by the filter output. The analysis may be performed on the filtered image. In the method and system, determining may involve creating an image of the difference between reflected diffusion light and reflected polarized light. In the method and system, determining may involve comparing the aspect of the polarization of the reflected or re-emitted light to a calibration signal. In the method and system, determining may further comprise considering at least one of user input and a visual analysis.

In an aspect of the invention, a non-invasive imaging device may comprise an illumination source comprising an incident light source to direct light upon an area of concern; and a detector for detecting a characteristic of the light reflected from the area of concern. In the device, the illumination source may be positioned to direct light at a selected angle alpha. Varying alpha may vary the depth of the measurement of the layers in the skin. Each depth may have a specific angle which produces a full polarized reflection. In the device, the incident light source may be a polarized light source or unpolarized light source. The unpolarized light may be at least one of white light, light of a single wavelength, and light of multiple single wavelengths. The device may further comprise a sensor for capturing an image of the reflected or re-emitted light. The device may further comprise an optical facility for detecting reflected or re-emitted light from the skin. The device may further comprise a communication facility for transmitting the detected information. The device may further comprise a storage facility for storing information collected by the device. In the device, the reflected or re-emitted light may be at least one of polarized light and unpolarized light.

In an aspect the invention, a system and method may be used to determine healthy and melanocytic skin. The first, reflected spectrum and/or emission spectrum from sample which is skin malformation (SM), subtract reflected spectrum from normal healthy skin (SN). The second, from obtained resulting spectral plots (SM−SN) subtract reflected spectrum from adequate comparing screen, which represents spectral plot of the light source (SO). In that path appeared pure characteristics of change generated by skin. For differentiation between melanoma, other malignant or benign nevus and healthy skin can be used data on maxima, minima and zero positions, in wavelength scale and data on maxima and minima intensities.

In an aspect of the invention, a system and method may comprise capturing an image of a material illuminated with incident non-angled white light and angled white light, generating a normalized red and blue color channel histogram for each image, correlating the normalized red and blue color channel histograms to a wavelength scale to obtain red and blue color channel spectral plots, and convoluting the spectral plots by subtracting the spectral plot for angled light from the spectral plot for non-angled light for each color channel to generate red and blue normalized, composite color channel spectral plots, and subtracting the normalized, composite blue channel spectral plot from the normalized, composite red channel spectral plot to generate a spectral signature for the material. In the system and method, the illumination source may be positioned to direct light at a selected angle alpha. Varying alpha varies the depth of the measurement in the material. In the system and method, the unit scale on the spectral signature may be a difference of wavelength. In the system and method, the material is inorganic and/or organic matter. In the system and method, the spectral signature may be analyzed for at least one of number of peaks and troughs, amplitude and shape of peaks and intermediate structures and patterns. In the system and method, the spectral signature may be analyzed for metal composition, identification, purity, and strength. In the system and method, the spectral signature may be analyzed for water quality, composition, and purity. In the system and method, elements of the spectral signature may be tagged and tracked over time in order to track changes in the characteristics of the material. In the system and method, the spectral signature may be analyzed to measure, track or monitor a skin state. In the system and method, the spectral signature may be useful for the counterfeit analysis of money. In the system and method, the spectral signature may be analyzed for at least one of sweat gland activity and anti-perspirant effectiveness. In the system and method, the spectral signature may be analyzed for Mad Cow disease. In the system, the spectral signature may be analyzed for food, all epidermal diseases, melanoma and skin cancers, rheumatoid diseases, and all diseases that show on the skin. In the system and method, the spectral signature may be useful for monitoring post-operative cosmetic concerns. In the system and method, the spectral signature may be useful for predicting and monitoring secretion from the mammary glands of lactating women. In the system and method, the spectral signature may be fed into a recommendation engine to provide feedback and modifications to aspects of a regimen. In the system and method, the wavelength position of ideal blue in Maxwell's color triangle is aligned with the wavelength position of ideal red in Maxwell's color triangle when convoluting the composite spectral plots to obtain the spectral signature.

A method and a system are disclosed for determining skin characteristics and cosmetic features. A minimal error output is generated. In accordance with exemplary embodiments of the present invention, according to a first aspect of the present invention, a method for determining skin characteristics and cosmetic features using color analysis may include a step of analyzing color of skin images in a pixel by pixel manner in a Red Green Blue (RGB) color system for an acquired digital image. The step of analyzing color of skin images in a pixel by pixel manner in a RGB color system for an acquired digital image may include analyzing a picture of a part of a person's skin by generating a table of most frequent colors appearing in the picture.

According to the first aspect, a method for determining skin characteristics and cosmetic features using color analysis includes a step of generating a sample of most frequent standard RGB (sRGB) colors responsive to analyzing color of skin images in a pixel by pixel manner in the RGB color system for the acquired digital image after converting colors obtained in device dependent RGB color system into device independent standard RGB color system (sRGB). The step of generating a sample of most frequent sRGB colors responsive to analyzing color of skin images in the sRGB color system for the acquired digital image may include preserving a plurality of sRGB color values.

In this embodiment of the invention, the sRGB color system may be used for image analysis. Determination of other skin characteristics, melanoma, skin related tumors and skin related disorders require image analysis based on other color systems such as YIQ, YCbCr, L*a*b*, L*u*v* and HSL/HSV. The enhancement of the current algorithm may include at least one of these color systems and its/their correlation with presented sRGB analysis.

According to the first aspect, a method for determining skin characteristics and cosmetic features using color analysis includes a step of modeling the R, G and B component color distribution with Gaussian probabilistic distribution with estimated parameters (expected value and standard deviation) on the generated sRGB color sample for the acquired digital image further including approximating colors on the generated sRGB color samples by a Gaussian normal distribution. In accordance with an exemplary embodiment of the present invention the step of approximating colors on the generated sRGB color samples by a Gaussian normal distribution comprises approximating colors on the generated sRGB color samples by a superposition of a plurality of Gaussian normal distributions.

According to the first aspect, a method for determining skin characteristics and cosmetic features using color analysis includes a step of generating a phototype of the skin through a decision tree unit responsive to the estimated distribution model parameters colors. The phototype of the skin may be generated according to a corrected Fitzpatrick classification. In accordance with an exemplary embodiment of the present invention, the step of generating phototype of the skin according to corrected Fitzpatrick classification includes generating phototype of the skin according to a skin type scale which ranges from very fair skin to very dark skin. This method may be measured both on the most exposed region and relate to the current level of phototype based on level of tan on the skin.

According to a second aspect, a system for skin phototype determination using photograph analysis may be disclosed. The system may include an image capturing device for capturing digital images of a skin. The image capturing device may include a digital camera unit.

According to the second aspect, the system for skin phototype determination using photograph analysis may include an analyzer coupled to the image capturing device for performing a pixel by pixel analysis of a picture of a part of a person's skin. The analyzer may include a quantization device for generating a look-up table of most frequent colors appearing on the picture of the part of the person's skin.

According to the second aspect, the system for skin phototype determination using photograph analysis may include a sampling device coupled to the image capturing device for generating standard Red Green Blue (sRGB) color samples for the captured digital image of the skin.

According to the second aspect, the system for skin phototype determination using photograph analysis may include an approximating device coupled to the sampling device for approximating the color distribution parameters on the generated sRGB color samples using the estimates of expected value and standard deviation for the captured digital image of the skin. The approximating device may include at least one Gaussian normal distribution unit.

According to the second aspect, the system for skin phototype determination using photograph analysis may include a decision tree unit coupled to the approximating device for generating a phototype of the skin using Red and Blue components of the approximated colors. The decision tree unit may include a Fitzpatrick scaling unit for categorizing a skin phototype in accordance with a skin type scale which ranges from very fair skin to very dark skin.

According to the second aspect, an exemplary embodiment of the present invention discloses a scaled Gaussian normal distribution unit for approximating colors on the generated sRGB color samples using estimates of expected value and standard deviation for the captured digital image of the skin.

According to the second aspect of the present invention, the system for skin phototype determination using photograph analysis may include a subsystem for determination of cosmetic features for a human element and a veterinary element. The cosmetic features may further include features pertaining to hair, nail and skin.

In another aspect the system may include a sampling device for generating standard Red Green Blue color samples of the captured digital image of the skin, the generated samples of standard Red Green Blue are in the range of values between 0 and 255 and they are preserved for further processing.

In another aspect the system may include an approximating device coupled to the sampling device for approximating the color distribution parameters on the generated sRGB color samples in the range of values between 0 and 255 by Gaussian normal distribution using the estimates of expected value and standard deviation for the captured digital image of the skin.

In another aspect the system may further include a decision tree unit coupled to the approximating device for generating a phototype of the skin using standard Red and Blue components of the approximated colors, the decision tree unit with an algorithm equates estimates of expected values and standard deviation for the captured image of the skin to the Fitzpatrick notation of skin analysis for determination of skin phototype.

In another aspect the system may automatically adjust lighting intensity and wavelengths and angles in order to assess various factors of the skin.

In yet another aspect of the system skin phototype may be determined using photograph analysis for use in cosmetics and surgical industry.

In an aspect of the invention, a skin care device may include an electromagnetic radiation source capable of directing incident electromagnetic radiation to a location on the skin of a user, a radiation detector for measuring various parameters of radiation re-emitted from the location, and a skin condition analysis module coupled to the detector, the analysis module capable of generating a skin condition assessment in real-time, based partly on at least one of RGB analysis and diffused reflectance analysis of the radiation parameters. In the device, incident electromagnetic radiation may include radiation in at least one of the visible, near-infrared, and near-ultraviolet spectrum. The incident radiation may be white light. In the device, the radiation parameters include at least the degree of polarization of the re-emitted radiation. In the device, the radiation source may be a set of light emitting diodes. In the device, the skin condition assessment may be also partly based on analysis of a photographic image of a skin region surrounding the location. In the device, the device may be a miniature device. Miniature may mean that no dimension of the detector exceeds six inches. The device may further include a memory module for storing the skin condition assessment. The device may further include a user interface. The device may further include a display surface. The skin assessment data of locations may be overlaid on an image of a larger skin region and displayed on the display surface. The device may further include an access restriction module used for restricting access to authorized users only. The access restriction module may be based on biometric access control. The device may be capable of generating alerts about abnormal skin conditions in real-time. The user interface may be operated using voice and/or eye movement commands. The device may further include a skin care regimen recommendation module that generates a displayable skin care regimen recommendation. The skin care regimen recommendation may be based at least partly on determination of a skin profile of the user and use of skin care regimen recommendations of persons with a similar profile. The skin care regimen recommendation module may be linked to a product database. The product database may include products available in a point-of-sale location. The availability of a specific product recommended by the skin care regimen recommendation module may be indicated by an audio-visual signal. The device may further include a skin care regimen effectiveness module that generates a displayable skin care regimen effectiveness report. The device may further include a communication module for communicating with a remote computer. The communication may occur wirelessly. The communication may occur over an internet. The remote computer may be operable by a physician. The device may be wand-shaped. The device may be wearable by the user.

In an aspect of the invention, the device an electromagnetic radiation source capable of directing incident electromagnetic radiation to a location on the skin of a user, a detector for measuring various parameters of radiation re-emitted from the location, a skin condition analysis module coupled to the detector, the analysis module capable of generating a skin condition assessment in real-time, based partly on at least one of RGB analysis and diffused reflectance analysis of the radiation parameters, and a display panel for reflecting the image of the user. In the device, the display panel may be touch-sensitive such that touching the location in a skin region image displayed in the display panel triggers display of a magnified image of the location. The skin care device may further include a camera. The camera may be integral with the display panel. The camera may be wirelessly linked to the display panel. In the device, the display panel may be a mirror. In the device, a stored image of the user may be used to automatically identify the person. The device may further include a user interface for controlling the skin care device. The user interface may be operated using voice and/or eye movement commands. The device may further include a skin care regimen recommendation module capable of generating a displayable skin care regimen recommendation. The skin care regimen recommendation may be based at least partly on determination of a skin profile of the user and use of skin care regimen recommendations of persons with a similar profile. The device may further include a skin care regimen effectiveness module capable of generating a displayable skin care regimen effectiveness report.

In an aspect of the invention, a system and method for moving information objects available on a website to a receptacle to communicate with a plurality of people in a controlled access community network may include enabling movement of a plurality of information objects from a predetermined website to a web based network responsive to a regimen of a person, a routine of a person, a purpose of use of an information object of the plurality of information objects and a degree of affinity of a first person towards a second person, initiating at least one customized action from the actions including a drop down movement; a drag and drop movement for populating data; and a pop-up movement in a Graphical User Interface (GUI) responsive to enabling movement of a plurality of information objects from a predetermined healthcare website, and enabling transportation of the plurality of information objects across a plurality of websites. In the system and method, the plurality of information objects may pertain to a questionnaire on at least one of a human skin condition, product information, an article, a blog posting, an image, a video, an individual message, a forum posting, and a veterinary skin condition. In the system and method, the plurality of information objects pertains to a questionnaire on human cosmetic parameters and veterinary cosmetic parameters. The questionnaire on human cosmetic parameters and veterinary cosmetic parameters may include questions on at least one of a human nail and a veterinary nail. The questionnaire on human cosmetic parameters and veterinary cosmetic parameters may include questions on at least one of a human hair and a veterinary hair. In the system and method, the purpose of use of the information object may pertain to controlling at least one of cleansing, protection, repair, moisturizing, elasticity, firmness, glow, luminosity, anti-inflammatory properties, anti-itch properties, anti-wrinkle properties, firming, exfoliating, anti-redness properties, oil controlling, anti-aging properties and shine of a human skin. In the system and method, the degree of affinity of a first person towards a second person comprises at least one of a relationship of friendship between the first person and the second person; a genetic similarity between the first person and the second person; a similarity of lifestyle between the first person and the second person; a climatic similarity between a first residential environment and a second residential environment; and a skin type similarity between the first person and the second person. In the system and method, the step of enabling transportation of the plurality of information objects across a plurality of websites may include a sub-step of dragging an item of user interest off a website of the plurality of websites in a predetermined format and transferring through an electronic signal to affiliates of a user accessing the website. The affiliates of the user may be friends and relatives of the user or associated experts. In the system and method, the step of enabling movement of a plurality of information objects from a predetermined website to a web based network may include a sub-step of enabling drop down menus on the Graphical User Interface (GUI) responsive to a plurality of end user convenience and requirement parameters. In the system and device, the plurality of people in a web based network includes a plurality of people in an online friendship network. In the system and device, the plurality of people in a web based network includes a plurality of people in an online social network.

In an aspect of the invention, an interface including a social networking domain and at least one skin health assessment and recommendation unit for enabling users of the interface to perform a skin health assessment within the interface and to receive product and regimen recommendations from a recommendation engine based on a predetermined usage of health assessment and maintenance data may include a regimen tracker populated using a drag and drop facility, a rating unit for rating a plurality of healthcare facilities, and a product information unit for enabling a user to obtain product information by conducting a web based search of a plurality of web based drag and drop products, web based images and bar code scans. In the interface, the regimen tracker includes a diet tracking unit. In the interface, the plurality of healthcare facilities comprises at least one of skin cleansing, skin protection, skin moisture control, skin repair, skin elasticity, skin luminosity, skin firmness, skin wrinkles, pore size on skin, spots on skin, glow on skin, hair color, hair type, age and life stage further including marriage, pregnancy, dating and social life. In the interface, the product information comprises at least one of a product type, a product function, a product format, a product appropriateness level, a regimen information, product articles, product blogs, product safety, product toxicity, a product effectiveness index, a product cost information, and a product timeliness information. In the interface, the interface is a multiple language and customized interface for: web based applications; mobile phone applications; touch screen applications; and personal digital assistant applications. In the interface, the interface is seamlessly coupled with a dermal imaging device for customized web based access, control and maintenance of spectral analysis of image data acquired from a degree of polarization of reflections and re-emission of incident light from skin structures. The degree of polarization of reflections and/or re-emissions of incident light from skin structures is derived from at least one of a Red Green Blue (RGB) color analysis of a plurality of digital images; and an analysis from spectroscopic data image analysis.

In an aspect of the invention, a system and method for determining a health state may include obtaining the answers to a series of subjective questions regarding health conditions, obtaining an objective health assessment report through a dermal imaging device, and generating a combination of answers to the series of subjective questions and the objective health assessment report to thereby generate a health state output and a real skin type output. In the system and method, a real skin type output is generated based on biophysical properties generated by at least one of a person seeking skin health monitoring, a spa, and a cosmetic advisor. In the system and method, the objective health assessment report may include an objective skin health assessment report on at least one of systemic hydration, skin hydration, skin firmness, skin wrinkles, pore size on skin, spots on skin, glow on skin, melanocyte, melanin, hemoglobin, porphyrin, triptofan, NADH, FAH, keratin, carotene, collagen, elastin, sebum, sebaceous gland activity, sweat pore, sebaceous pore, moisture level, elasticity, luminosity, firmness, fine line, wrinkle count, pore size, percent of open pores, skin elasticity, skin tension line, spots, viscosity, epidermal, dermal sebum levels, skin color, psoriasis, allergy, red area, general skin disorder, infection, tumor, sunburn, rash, scratch, pimple, acne, insect bite, itch, bleeding, injury, inflammation, photodamage, pigmentation, tone, tattoo, percent burn, burn classification, mole, aspect of a skin lesion, melanoma, dermally observed disorder, cutaneous lesion, cellulite, strias, current tan level, boil, blistering disease, congenital dermal syndrome, cutaneous mycoses, melasma, vascular condition, rosacea, spider vein, texture, skin ulcer, wound healing, post-operative tracking, melanocytic lesion, nonmelanocytic lesion, basal cell carcinoma, seborrhoic keratosis, sebum hair color, hair type, nail condition, and age and life stage further including marriage, pregnancy, dating and social life. In the system and method, the objective health assessment report is sent to an end user through at least one of email, SMS, MMS, mobile phone, a graphical user interface (GUI) of an internet connected device, and a touch screen enabled personal digital assistant. The system and method may further include obtaining health assessment and maintenance data from a physiologically polarized light data. The step of obtaining health assessment and maintenance data from a physiologically polarized light data comprises obtaining health assessment and maintenance data from a Red Green Blue (RGB) color analysis device, wherein the data comprise at least one of a white light data, a blue light data, and an ultra violet light data. The step may further comprise obtaining at least one of the white light data, the blue light data, and the ultra violet light data by reading and recording conditions of at least one of the dermis and epidermis. Obtaining health assessment and maintenance data from a physiologically polarized light data comprises obtaining data pertaining to age, geography and demography for a person subjected to health monitoring.

In an aspect of the invention, a web-enabled health tracking method and system may include a camera comprising a photo guide unit for generating notes for each photograph captured, an interface coupled between the camera and a web-enabled computing system for uploading the photograph captured by the camera, a graphical user interface unit included in the web-enabled computing system for generating a frequently asked questionnaire unit further comprising a self answer guide module, a scoring module coupled to the frequently asked questionnaire unit, a comparison module coupled to the scoring module for comparing: a color parameter; a symmetry parameter; and a border parameter, an automation unit coupled to the graphical user interface for enabling a time-based synchronization of the frequently asked questionnaire unit, the scoring module, and the comparison module, and a learning unit coupled to the automation unit for activating: a user training module, an article module coupled to the user training module, a blogging unit coupled to the user training module and the article module, and a report unit including an email unit for emailing health related information. In the system and method, the camera comprises a tracking unit for tracking at least one of skin spots over time, laser treatment effectiveness, cellulite content in skin, current tan level, condition of veins and capillaries, botox treatment effectiveness, anti-aging treatment effectiveness, anti-acne treatment effectiveness, and a pictorial history of skin to be given to the doctor. The skin spots over time include at least one of blemishes, scars, rashes, lesions, and moles. In the system and method, the web-enabled computing system for uploading the photograph captured by the camera further includes a walk-through module for walking through features of a skin health record of a first time user of the system, a personal skin photo album for reviewing pictorial history of a regular user of the system, and a product quality menu for tracking product expiration dates. In the system and method, the interface for uploading the photograph further includes a reminder unit for next photo for a regular user of the system; and a cosmetic status unit coupled to the reminder unit for displaying a current usage of a cosmetic for the regular user of the system. The current usage comprises a usage of at least one of a moisturizer, an antiseptic, a toner, a laser, and a botox. The system and method may further include a photo review unit for date based reviewing of at least one of a condition of a predetermined body part, a current usage status of a cosmetic, and a recommended usage list of cosmetics. In the system and method, the report unit may further include a secure transmission unit for sending a health assessment report to a medical practitioner, an affinity unit for discussing health assessment data with a friend, and a printing unit for printing health assessment data.

In an aspect of the invention, a mobile device-based health assessment system and method may include a photograph capturing device for capturing a skin image of a mobile device user, a transmission unit coupled with the photograph capturing device for uploading the captured skin image to a network location, a global positioning device coupled to the photograph capturing device for determining a location of the photograph capturing device, and a weather estimation device coupled to the photograph capturing device to determine a weather condition at a location of the mobile device user to thereby obtain a remote diagnosis report. In the system and method, the photograph capturing device further comprises at least one of a skin photograph assessment unit, a nail photograph assessment unit, and a hair photograph assessment unit. In the system and method, the global positioning device comprises a location tracker for answering user raised questions pertaining to geographical positioning of the user. In the system and method, the location tracker includes a database pertaining to weather intensive cosmetics. The system and method may further include a phone number tracker for enabling a mobile device user to contact health assessment and cosmetic outlets.

In an aspect of the invention, a system and method for estimation of skin type and skin features to create a unique spectral signature may include convoluting data from a first image captured in incident diffuse white light, wherein the data relate to reflected and/or re-emitted polarized or white light, convoluting data from a second image captured in incident polarized light, wherein the data relate to reflected and/or re-emitted polarized light, comparing extreme positions of at least two unique convolutions generated by convoluting data from the first image and the second image, and determining a distance between minimum and maximum intensity positions in convoluted red minus blue spectral plots from the at least two unique convolutions for generating a numerical skin type output. In the system and method, the physiological white light comprises three spectral intervals including a width less than 100 nanometer. The three spectral intervals pertain to red, green, and blue (RGB) colors. The three spectral intervals provide a natural white light sensation to a human eye. In the system and method, the step of comparing extreme positions of at least two unique convolutions comprises comparing a component (R–B)(W–P) for the reflected and/or re-emitted polarized light, and a component (R–B)W for the white light. The two unique convolutions in white light and polarized light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards. The system and method may further include a spectral convolution scheme wherein multiple combinations of subtraction of blue spectrum from red, in white light and polarized white light are determined, wherein the spectral interval is expressed in a wavelength scale interval of 100 nanometers to 300 nanometers.

In an aspect of the invention, a system and method for creating a unique spectral signature of skin features may include a RGB (Red Green Blue) color channel spectral plot generated from digital images including single wavelength light matter interaction thereby generating skin type characterization output, skin moisture conductivity and skin elasticity in numerical and descriptive standards. In the system and method, the RGB (Red Green Blue) color channel spectral plots generated from digital images include multi-wavelength light matter interaction.

In an aspect of the invention, a system and method to track and store movement parameters of an imaging device moving over a subject area may include the steps of capturing an image of the subject area at a plurality of locations, identifying a direction of movement of the imaging device using an image processing technique for at least one captured frame, recognizing the direction of movement of the imaging device by comparing each frame with at least three distinct features captured to thereby triangulate a location of the imaging device, and comparing data of the captured image with a predetermined image database to store the image of the subject area and to store placement parameters of the imaging device. In the system and method, the step of capturing the image of the subject area at a plurality of locations comprises a sub step of capturing a continuous video image of the subject area. In the system and method, the step of capturing the image of the subject area at a plurality of locations comprises a sub step of capturing a frame by frame sequence of images of the subject area. In the system and method, the step of identifying a direction of movement of the imaging device using an image processing technique comprises a sub-step of a frame by frame comparison of the captured image to identify movement parameters of the imaging device. In the system and method, the step of recognizing the direction of movement of the imaging device by comparing each frame with at least three distinct features captured to triangulate a location of the imaging device comprises a sub-step of capturing a direction of movement of the imaging device by comparing three or more distinct positions across different frames.

In an aspect of the invention, an automated location tracking and data storage method and system for an imaging device may include an image capturing unit, a positioning unit coupled to the image capturing unit for positioning the imaging device on a subject area, and an image processing unit for enabling a frame by frame comparison of the captured image and for enabling the imaging device to capture three or more distinct points to triangulate a location of the imaging device to identify a direction of movement of the imaging device. In the system and method, the image capturing unit comprises a digital camera. In the system and method, the image capturing unit comprises at least one of a mobile device and a Personal Digital Assistant (PDA). In the system and method, the image processing unit comprises a comparison unit for comparing positions of three or more distinct points across different frames to capture direction of movement of the imaging device. The system and method may further include a sub-system for measuring lateral motion of the image capturing unit from a predetermined point to a new location on the subject area.

In an aspect of the invention, a system and method for determining a surgical excision margin may include illuminating a melanocytic lesion skin with an incident light source, detecting a characteristic of the light reflected and/or re-emitted from the melanocytic lesion, and determining a border between the melanocytic lesion and surrounding healthy tissue based on at least one characteristic of the reflected and/or re-emitted light. In the system and method, the incident light is directed at a selected angle alpha. In the system and method, varying alpha varies the depth of the measurement of the layers in the melanocytic lesion. Each depth has a specific angle which produces a full polarized reflection. In the system and method, the incident light is unpolarized light. The unpolarized light is at least one of white light, light of a single wavelength, and light of multiple single wavelengths. In the system and method, the incident light is polarized light. In the system and method, the reflected and/or re-emitted light is at least one of polarized light and unpolarized light. In the system and method, the characteristic is at least one of light source, light intensity, wavelength of light, angle of light, electrical and magnetic properties of the light, and polarization state of the light. An aspect of the polarization is at least one of an orientation, an amplitude, a phase, an angle, a shape, a degree, and an amount. In the system and method, determining is done using an algorithm. The algorithm involves at least one of artificial neural networks, fuzzy logic, fractal and multi-fractal analysis, non-linear regression, a genetic algorithm, white light analysis and RGB color analysis. The system and method may further include filtering the reflected and/or re-emitted light to obtain light of a wavelength defined by the filter output. Algorithmic analysis is performed on the filtered image. In the system and method, determining involves creating an image of the difference between reflected diffusion light and reflected polarized light. In the system and method, determining involves comparing the aspect of the polarization of the reflected and/or re-emitted light to a calibration signal. In the system and method, determining further comprises considering at least one of user input and a visual analysis.

In accordance certain embodiments, a handheld device for capture or acquisition of an image of an individual tooth, the gums, or the entire set of teeth. Specifically, the device can be handheld and a person can perform sweeping motion to take an image of the entire dental set. In operation, the device facilitates creation or generation of a 3D model of the teeth for analysis of pre-existing conditions thereof, facilitates measurement of the health of a tooth and determination of the health of the tooth, such as in a cautionary status or needs intervention and maintenance of photo record of the teeth.

Still, in accordance with certain embodiments, the methods and systems for overall management of dental or oral health performs one or more functions. By way of example, and in no way limiting the scope of the invention, the methods and systems for overall management of dental or oral health exhibition of degree of mineralization of enamel and ratio of minerals to water and other organic material thereof, color of enamel, comparison of enamel over time, validation of a person's hygienic routine by determining progress of enamel cleaning, thickness of enamel, health of cementoenamel junction (or CEJ), measurement of strength on a relative scale or in comparison with peers, on custom scales or on Mohs hardness scale, for example, presence of proteins called amelogenins and enamelins, determination of type of Dentin, such as primary, secondary and tertiary, porosity, verification of the health and status of a teeth enamel and other dermal structures thereof, determination of depth of enamel towards application, determination of predisposition of dental cavities and other dental problems, identification and presence of rod sheath, Striae of Retzius, neonatal line, Perikymata, Gnarled Enamel, Keratin levels, Nasmyth's membrane or enamel cuticle, acquired pellicle, food debris, presence microcracks within the tooth, degree of microcracking within the tooth, amount of Plaque, tooth decay or attrition, sensitivity of teeth, gum diseases, such as gingivitis, Peridontis, color of gums (e.g. bright-red, or purple gums) that gives indication of gum health, degree of swelling of gums, presence of mouth sores, tracking of progress of mouth sores over time, shinyness of gums, presence of pus in gums, presence of new teeth coming, status of fillings, presence of plaque/level of plaque, determination of the extent of a cavity, determination of the propensity/predisposition of developing carries or cavities, Chronic Bilirubin Encephalopathy, Enamel Hypoplasia, Erythropoietic Porphyria, Fluorosis, Celiac Disease, presence of Tetracycline, presence and status of composites and sealants, determination of health and structural integrity of crowns and veneers, amalgams and the like, track the progress of conditions like Bruxism (i.e. grinding of the teeth) and indication of attrition over time, determination of presence of amelogenins, ameloblastins, enamelins, and tuftelins.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures:

FIG. 10 depicts a questionnaire page of a skin care system.

FIG. 12 depicts a results page with bar graphs of a skin care system.

FIG. 14 depicts a summary screen of a skin care system.

FIG. 17 depicts an elasticity summary screen of a skin care system.

FIG. 18 depicts a map of a user interface for a skin care system.

FIG. 19 depicts a review page of a skin care system.

FIG. 20 depicts a review page of a skin care system.

FIG. 21 depicts a My Experience page of a skin care system.

FIG. 22 depicts a What Works page of a skin care system.

FIG. 27 depicts a registration page of a skin care system.

FIG. 28 depicts a recommendation page of a skin care system.

FIG. 32 depicts a Suncheck message flow.

FIG. 33 depicts an Alert message flow.

FIG. 58 is a flowchart illustrating a process for RGB color analysis.

FIG. 64 depicts an embodiment of a friend toolbar.

FIG. 67 depicts the drag-and-drop share functionality of the friend toolbar.

FIGS. 76A and 76B depict a dual pair of typical digital images of samples, tested positive and negative for EBV and CMV, captured with diffuse white light (W) and reflected polarized light (P), in that order;

FIGS. 79A and 79B depict a third pair of plots of typical spectral data obtained on implementation of the OMF method for processing digital images of unique samples from a third set of two different patients subjected to a third test case for confirmation of EBV, namely "Case III: EBV-IgG", designed and implemented in accordance with certain embodiments of the invention;

FIG. 11B depicts an intraoral camera specification.

FIG. 118 depicts the results of the implementation of the OMF method on 44 cross-sections on multiple locations and the high sensitivity of the OMF method in terms of wavelength and reflected light intensities;

FIG. 119A depicts images for the comparative analysis of the teeth with healthy enamel obtained using AFM/MFM and OMF methods, in accordance with the principles of the invention;

FIG. 119B depicts images for the comparative analysis of the teeth with enamel affected with caries obtained using AFM/MFM and OMF methods, in accordance with the principles of the invention;

FIG. 119C depicts images for the comparative analysis of the teeth with healthy dentin obtained using AFM/MFM and OMF methods, in accordance with the principles of the invention;

FIG. 119D depicts images for the comparative analysis of the teeth with dentin affected with caries obtained using AFM/MFM and OMF methods, in accordance with the principles of the invention;

FIG. 119E depicts images for the comparative analysis of the teeth with healthy cement obtained using AFM/MFM and OMF methods, in accordance with the principles of the invention;

FIG. 119F depicts images for the comparative analysis of the teeth with cement affected with caries obtained using AFM/MFM and OMF methods, in accordance with the principles of the invention;

FIG. 120 is a block diagrammatic view of a system facilitating implementation of an Opto-Magnetic process based on light-water interaction using digital imaging for analysis of water samples, designed and implemented in accordance with certain embodiments of the invention;

FIG. 121 is an exploded diagrammatic representation of the host computing subsystem, of the FIG. 120, comprising an Opto-Magnetic Fingerprint (or OMF) Generator sub-module designed and implemented in accordance with at least some embodiments;

FIG. 122 depicts a flow diagram delineating at least one process implemented by the system configuration of FIGS. 120 and 121 thereby facilitating estimation of water sample type and properties (or characteristics) thereof and creation of a unique spectral signature;

Figure 123A:
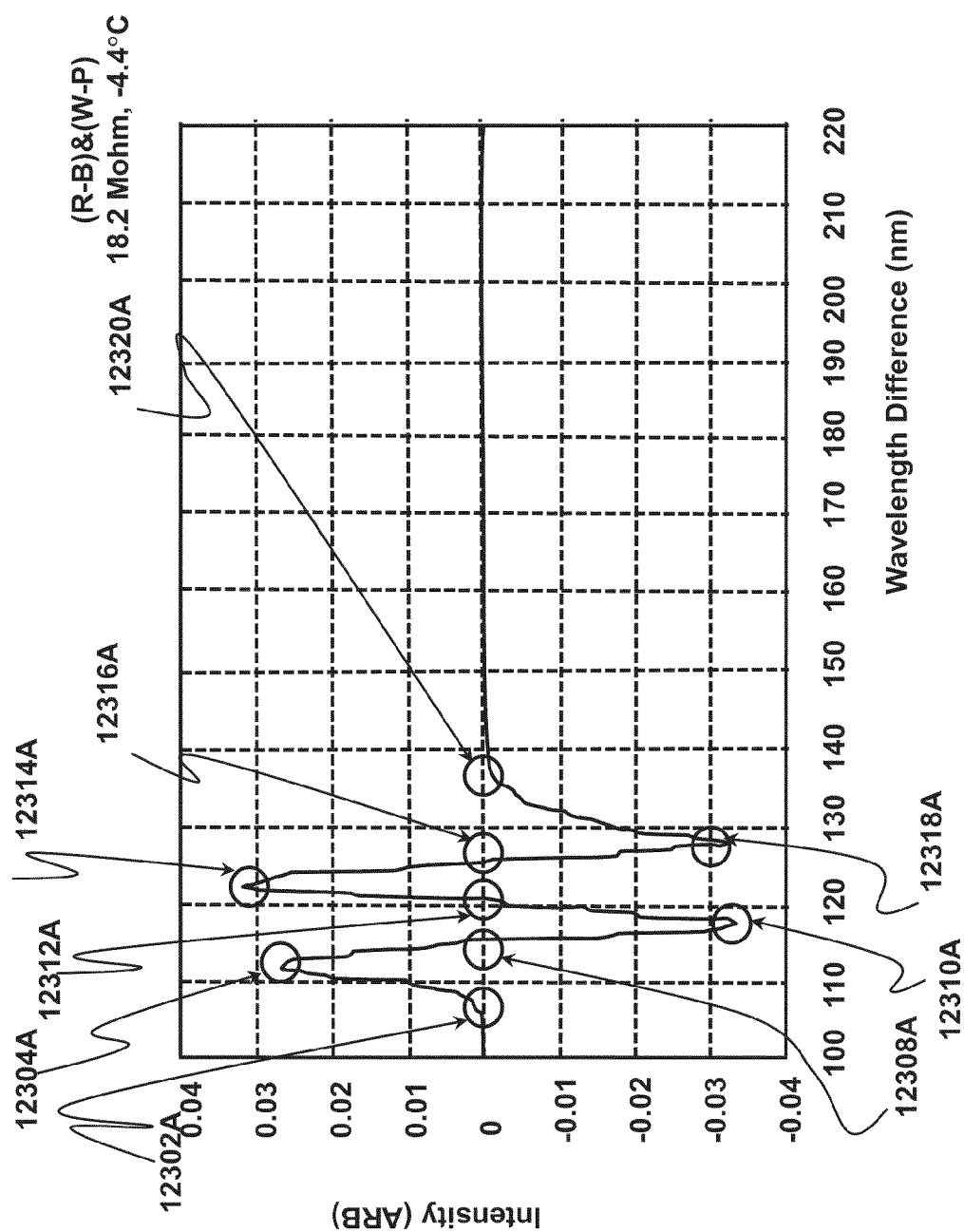
Figure 123B:
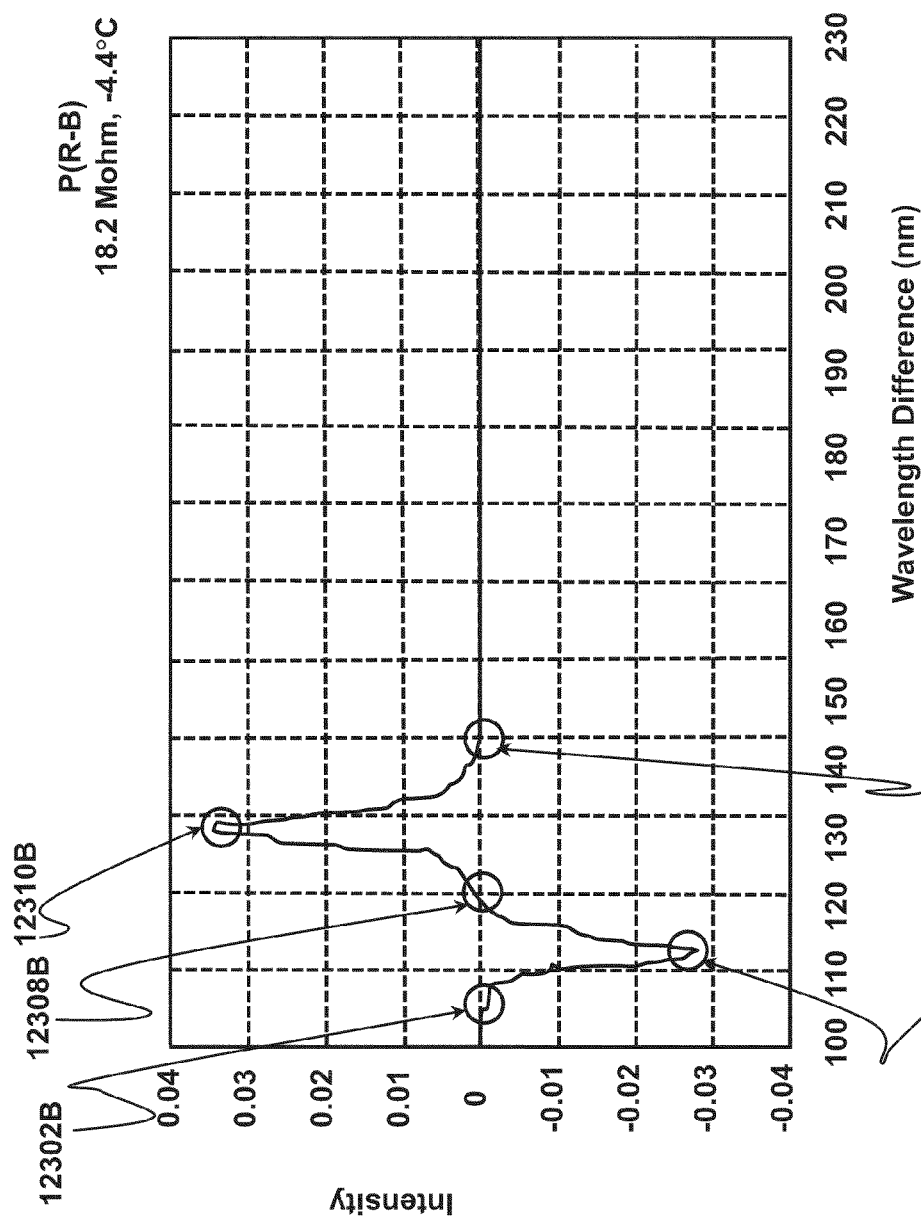
Figure 124A:
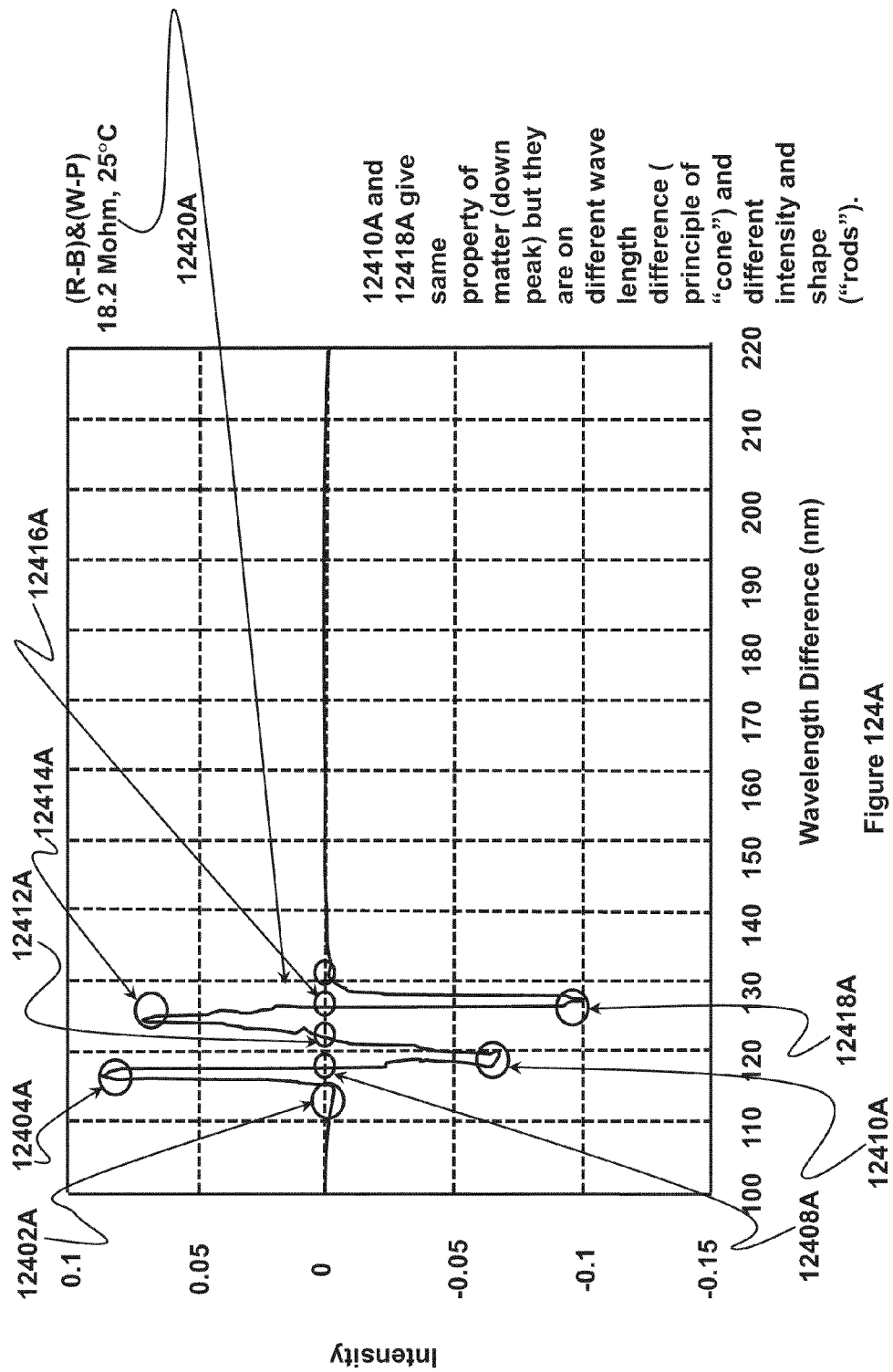
Figure 125A:
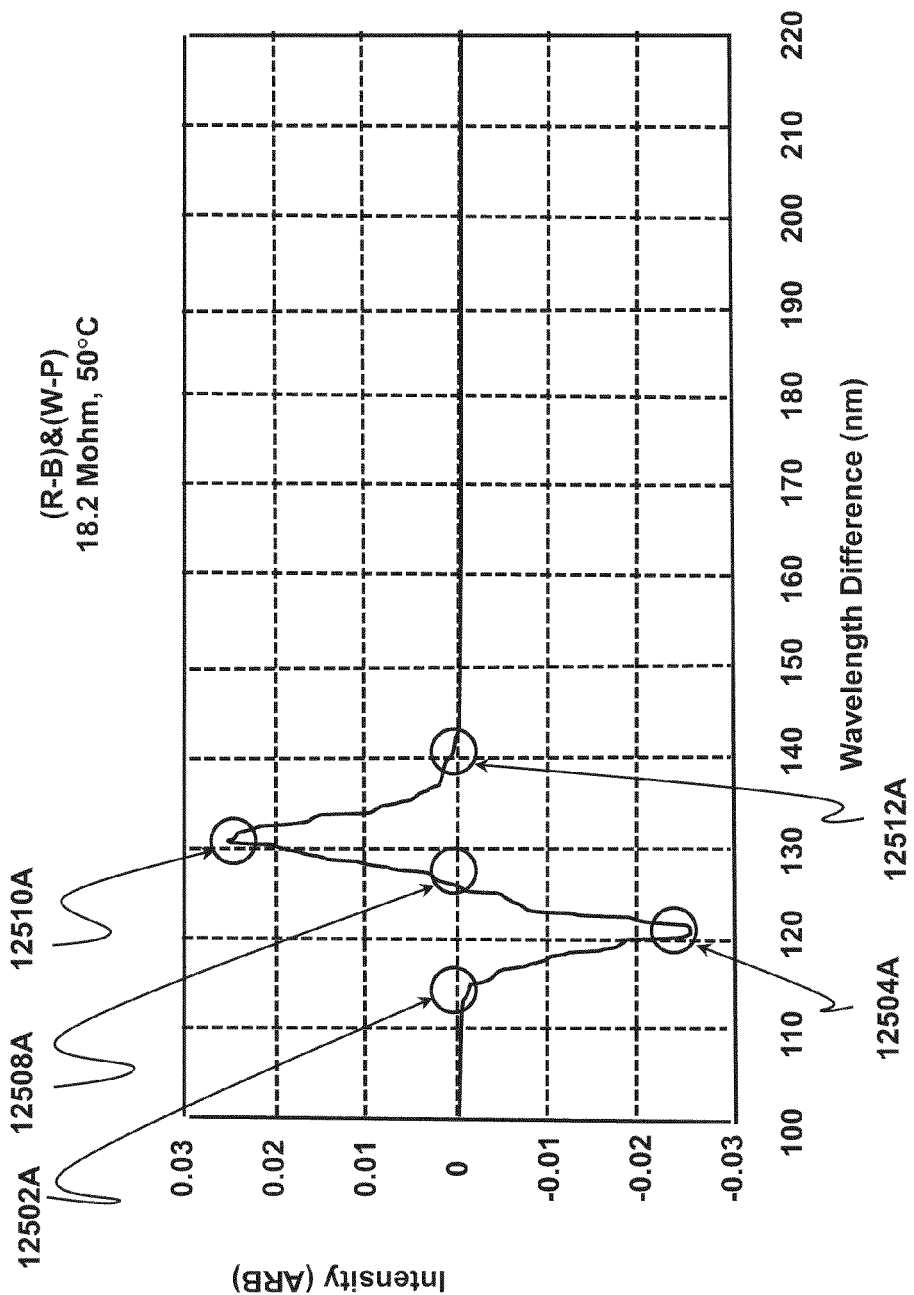
Figure 125B:
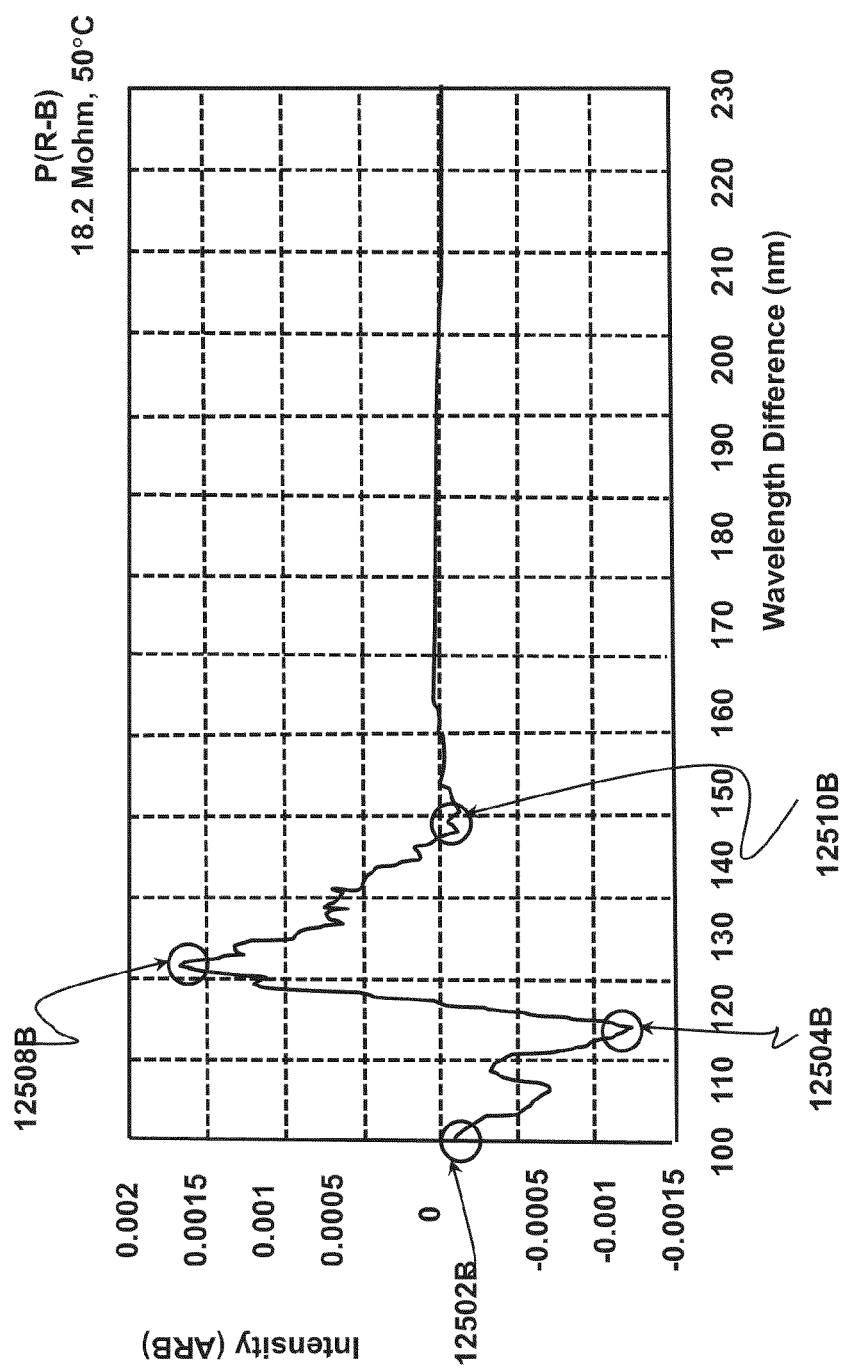
Figure 126A:
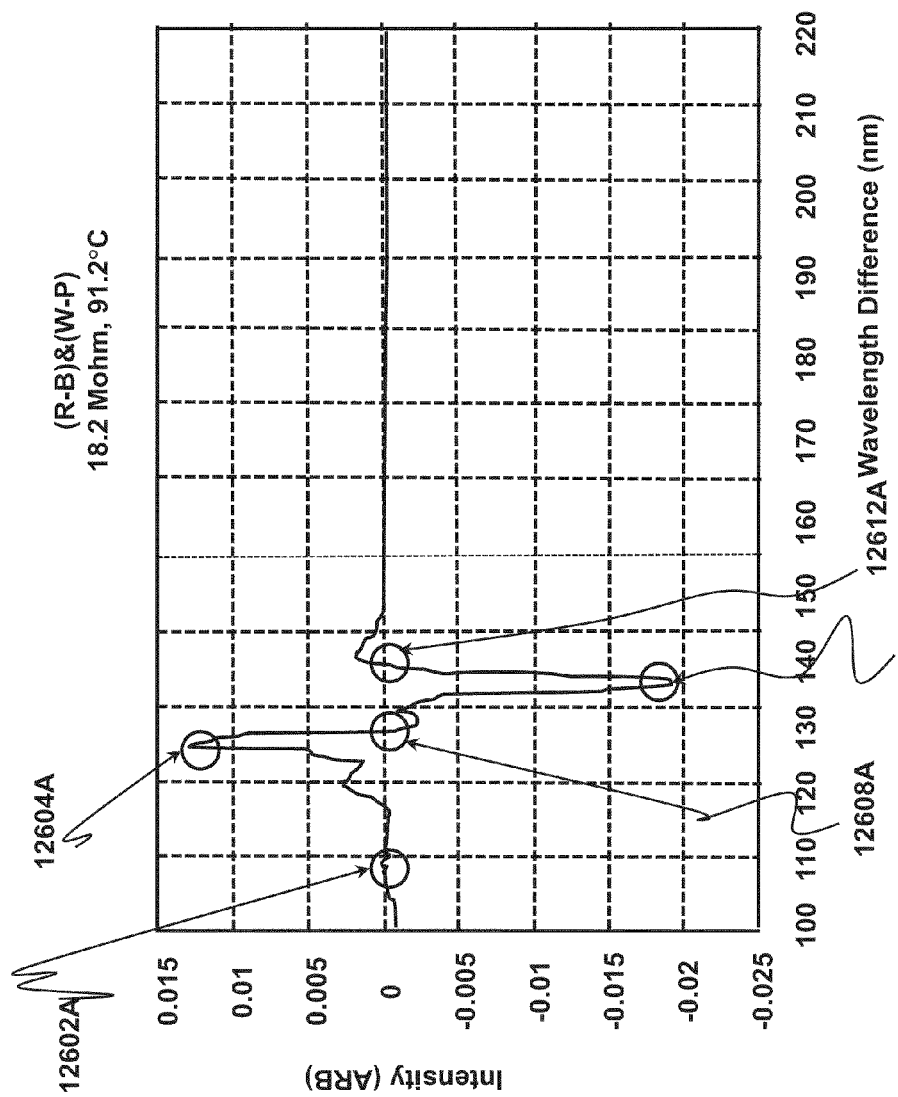
Figure 126B:
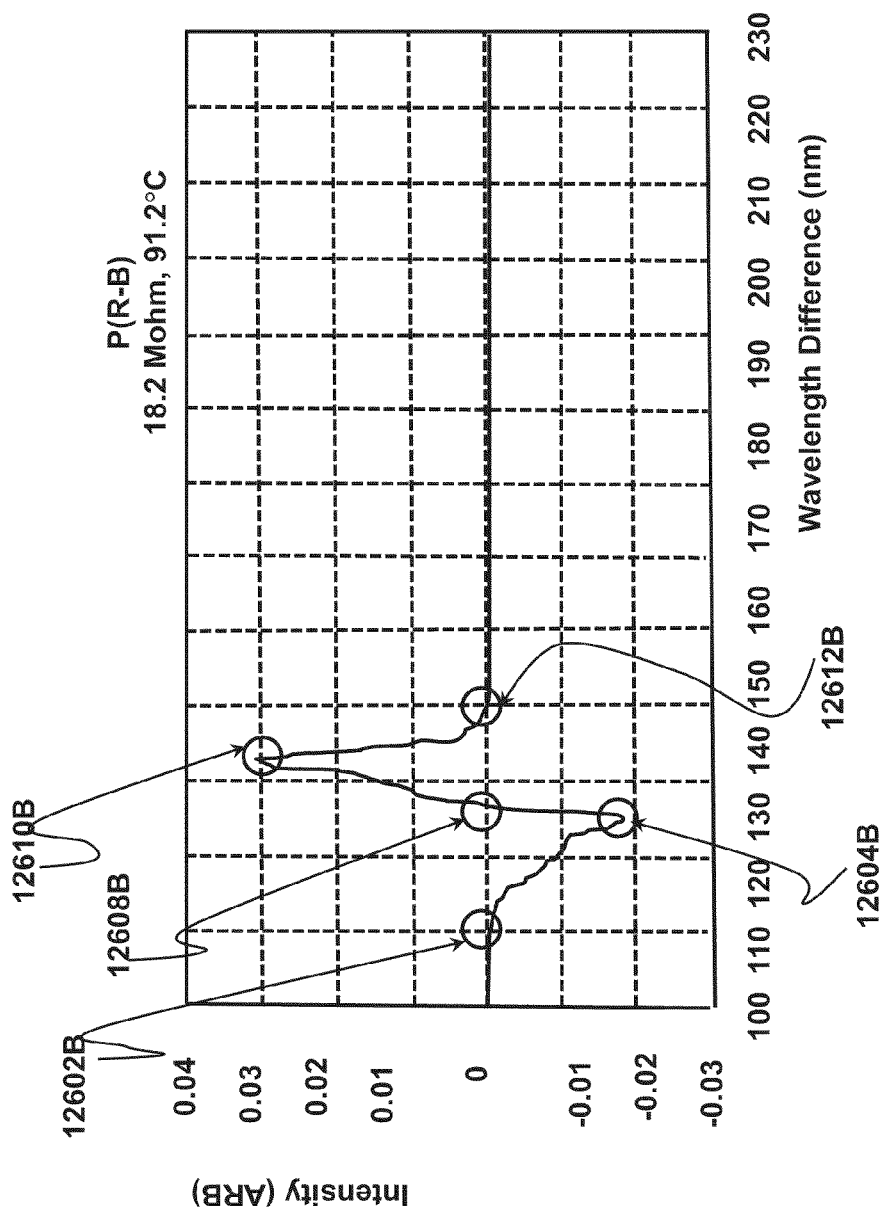
Figure 127A:
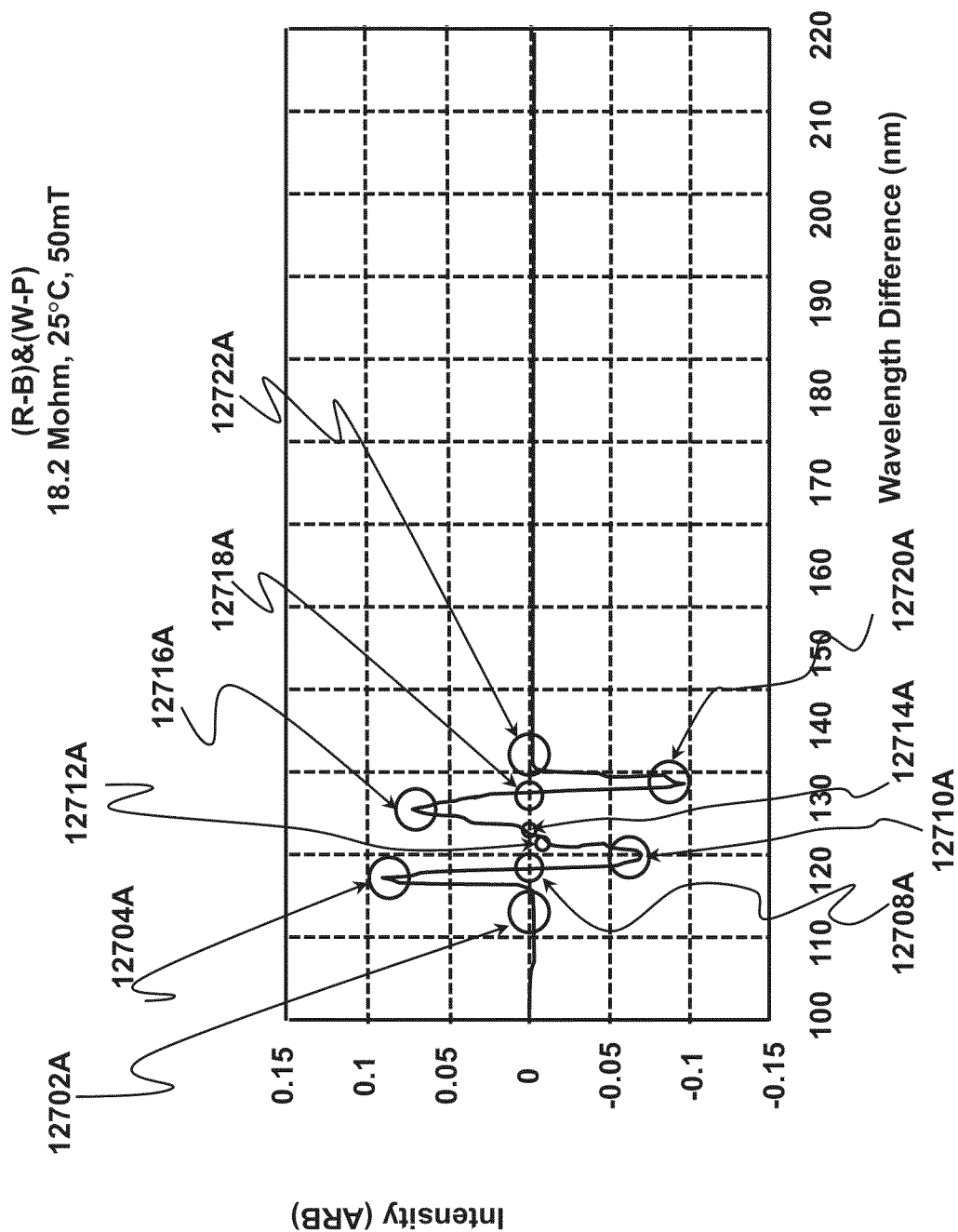
Figure 127B:
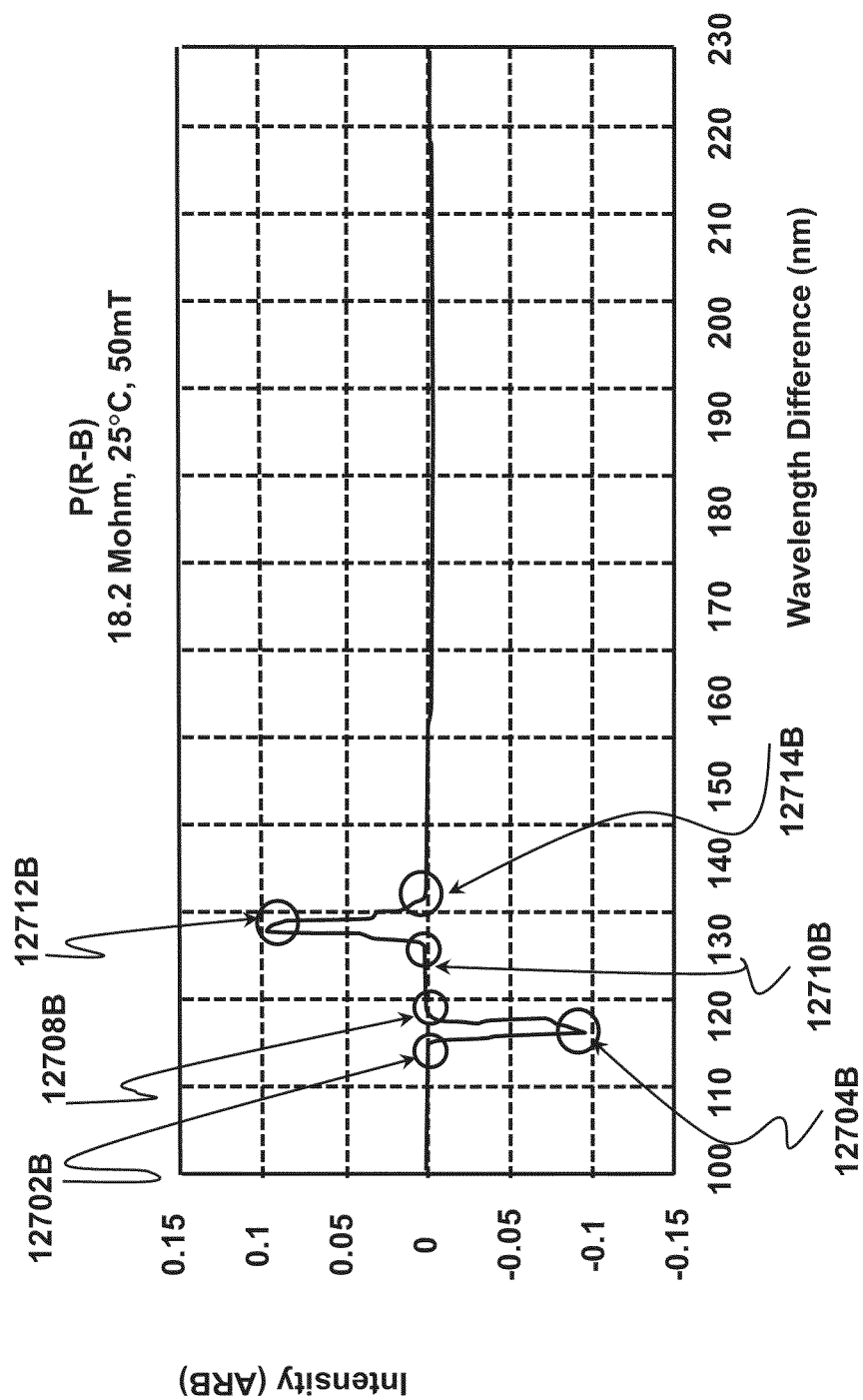
Figure 128A:
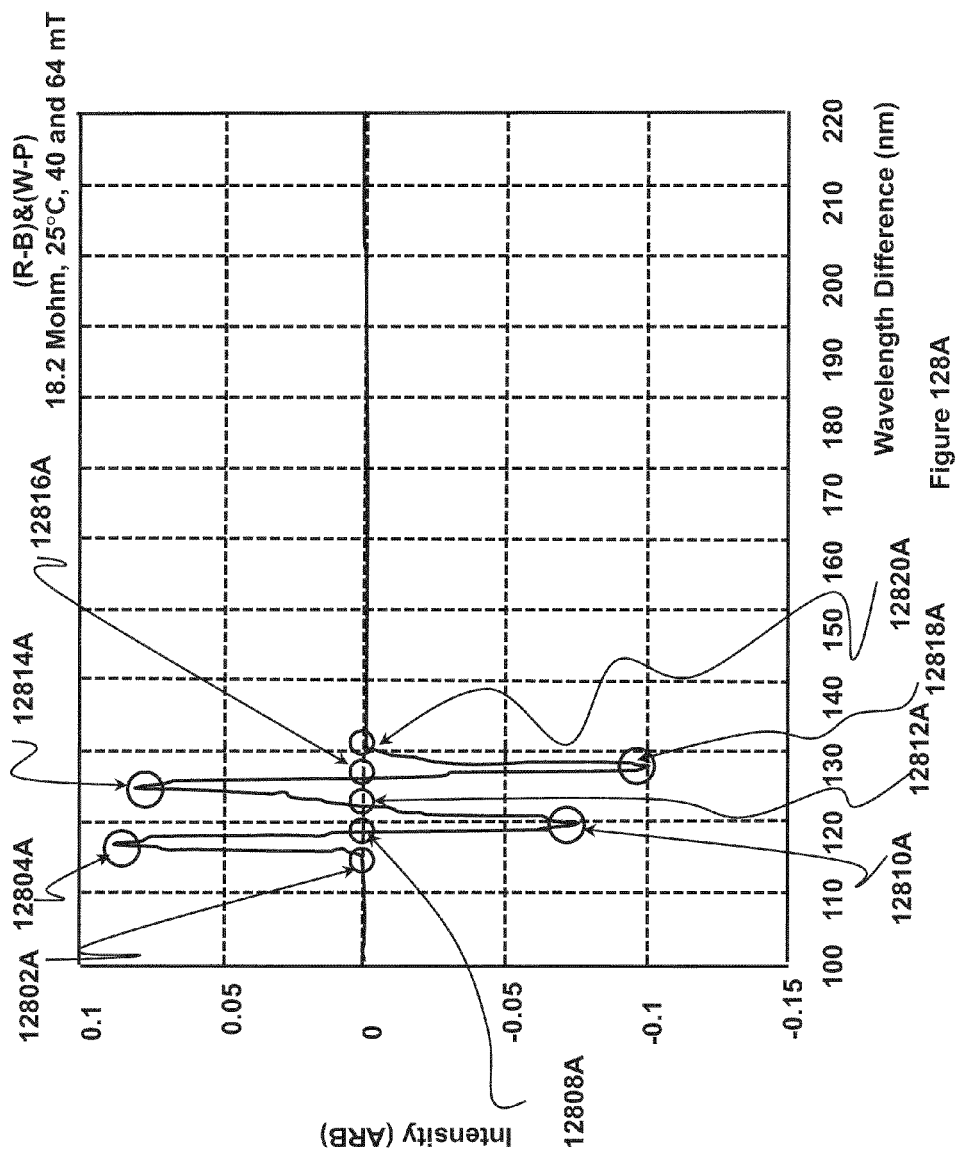
Figure 128B:
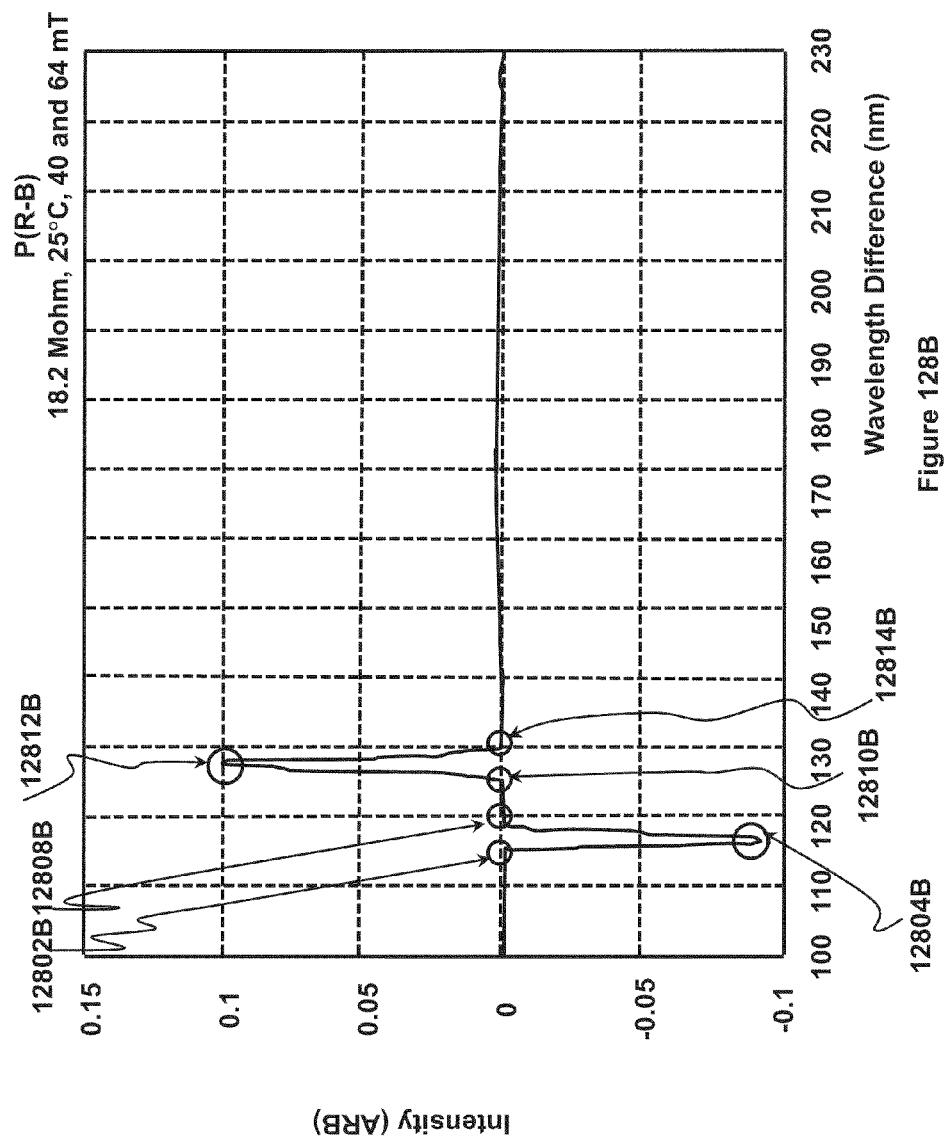
Figure 129A:
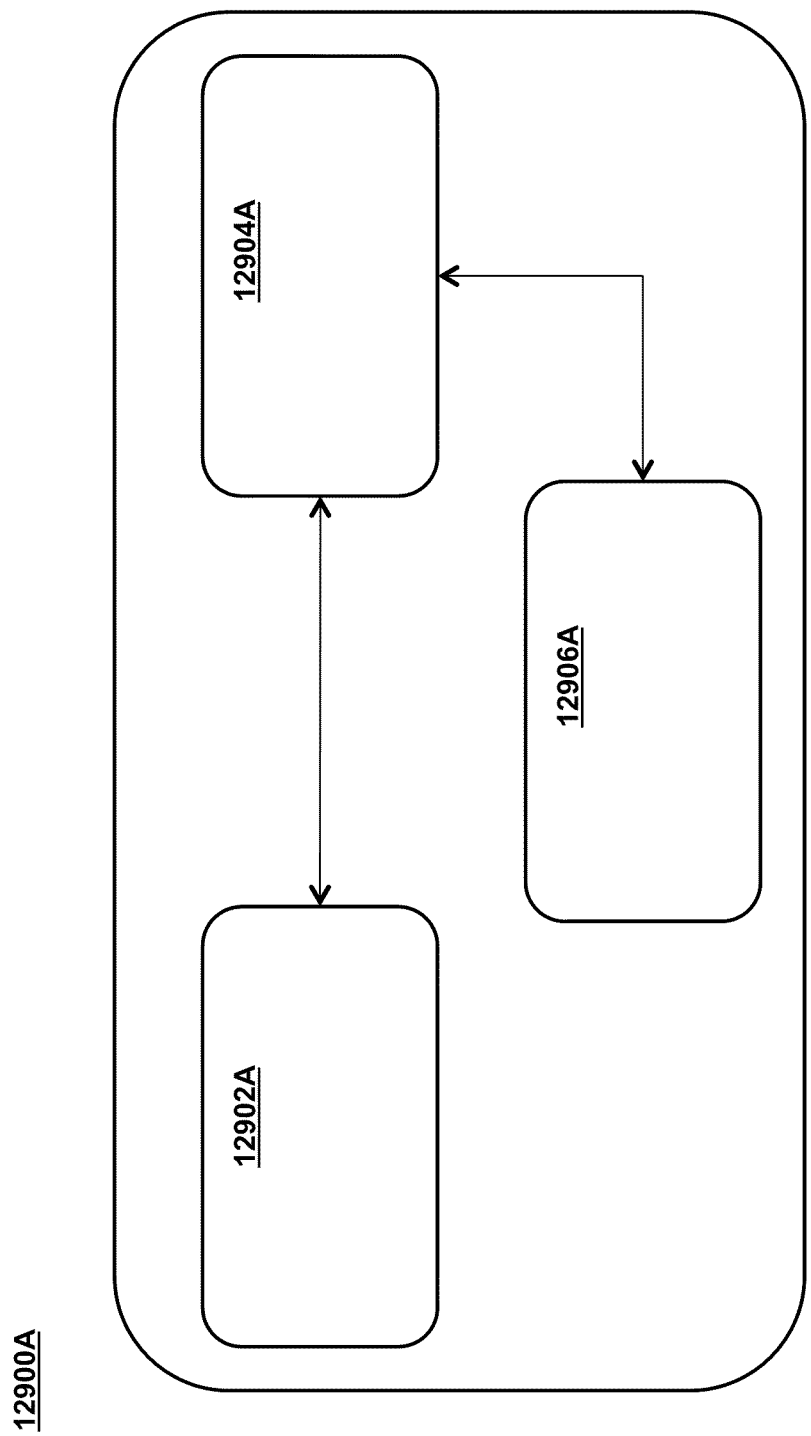
Figure 129B:
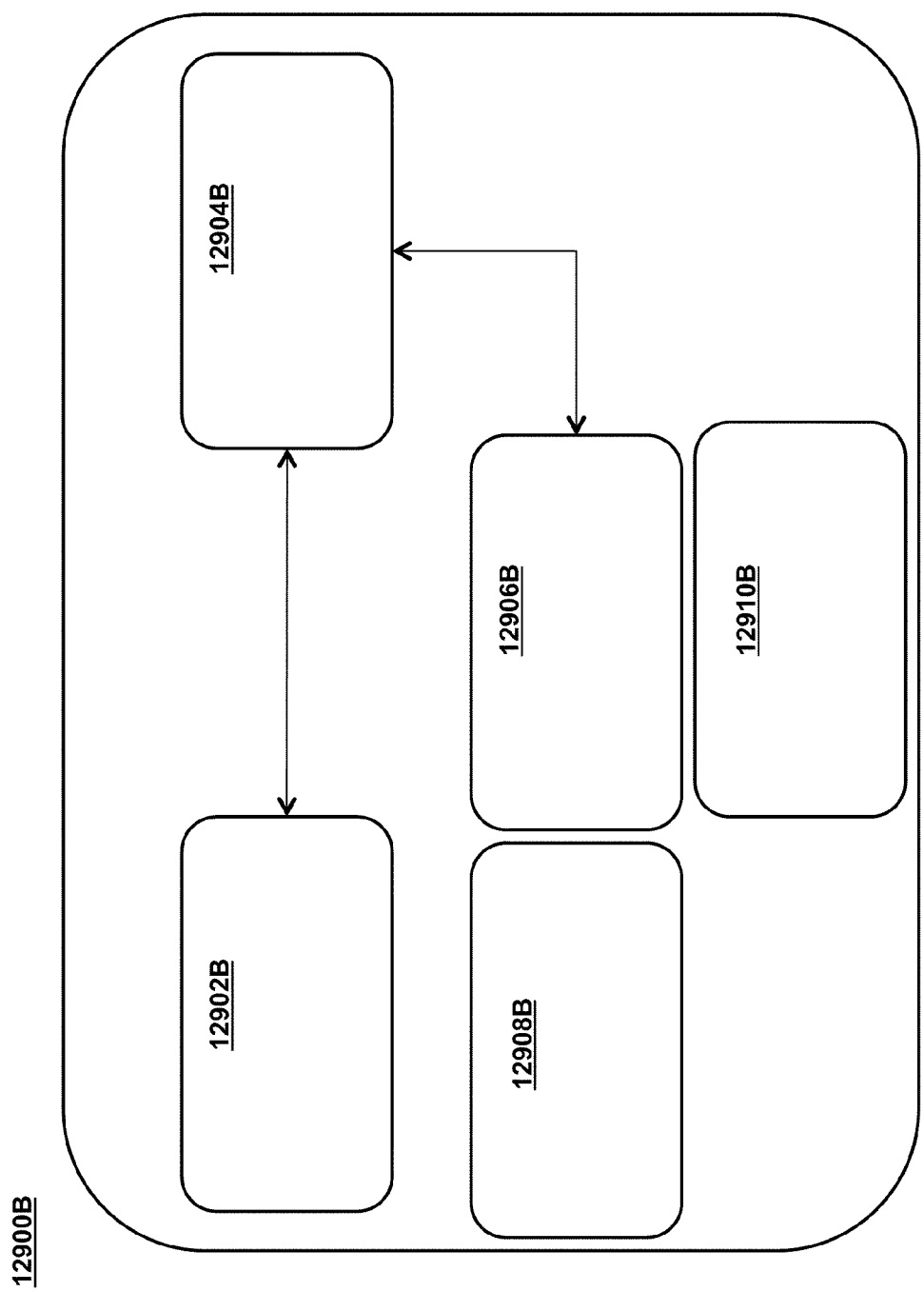
Figure 130A:
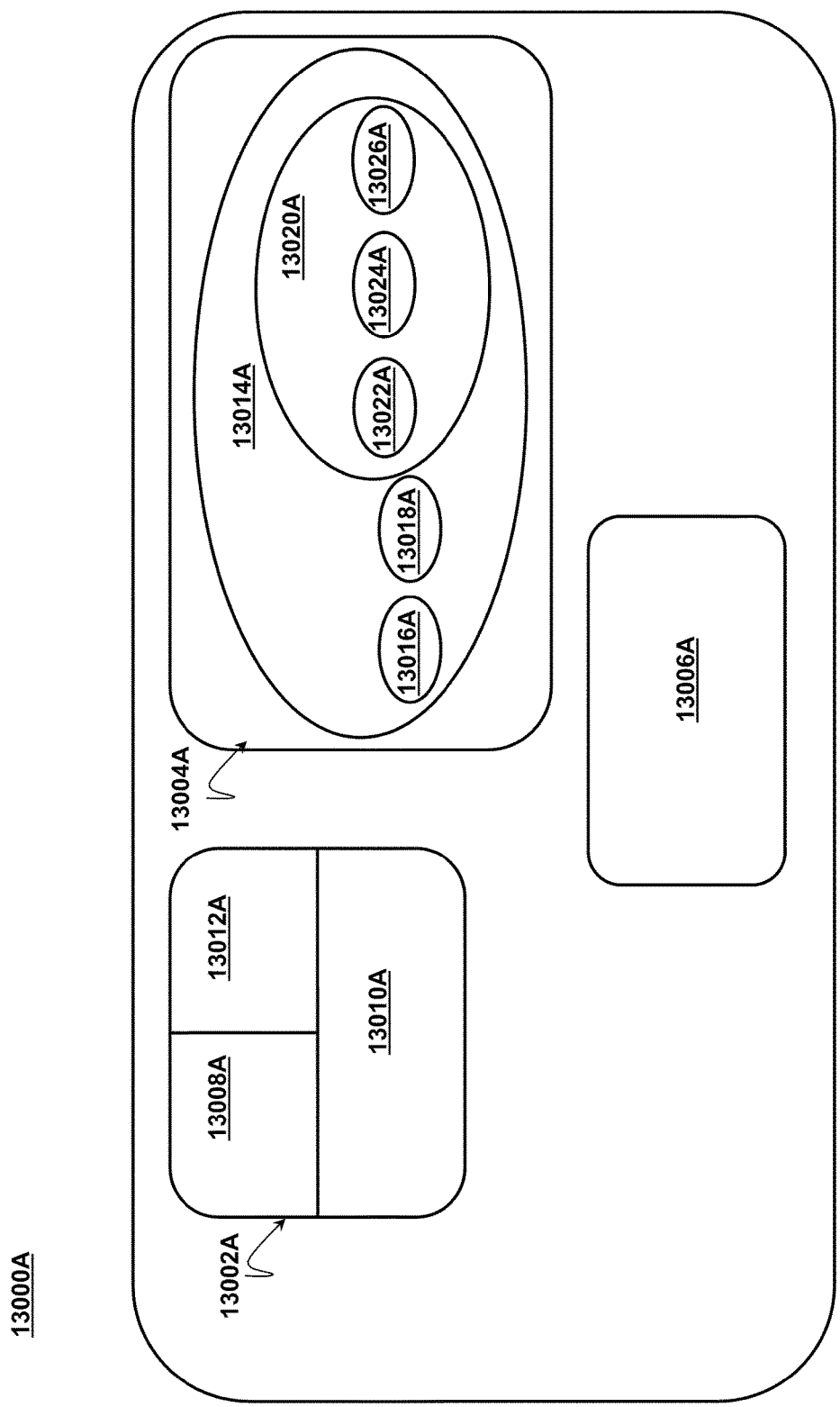
Figure 130B:
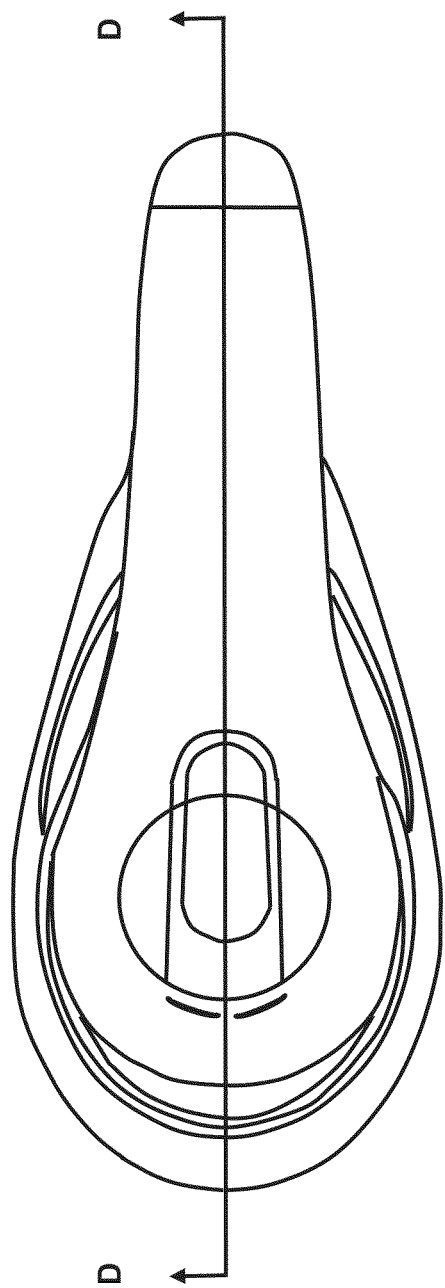
Figure 130C:
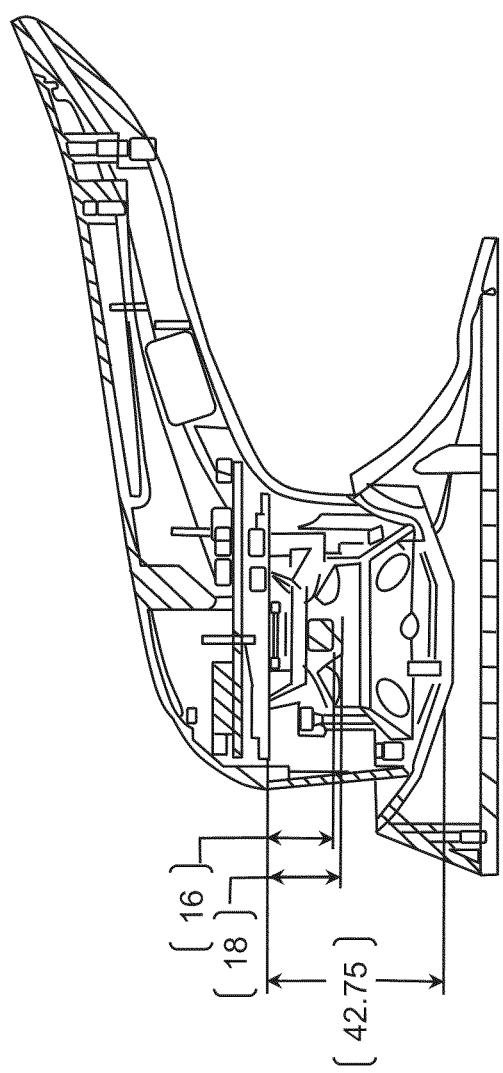
Figure 131:
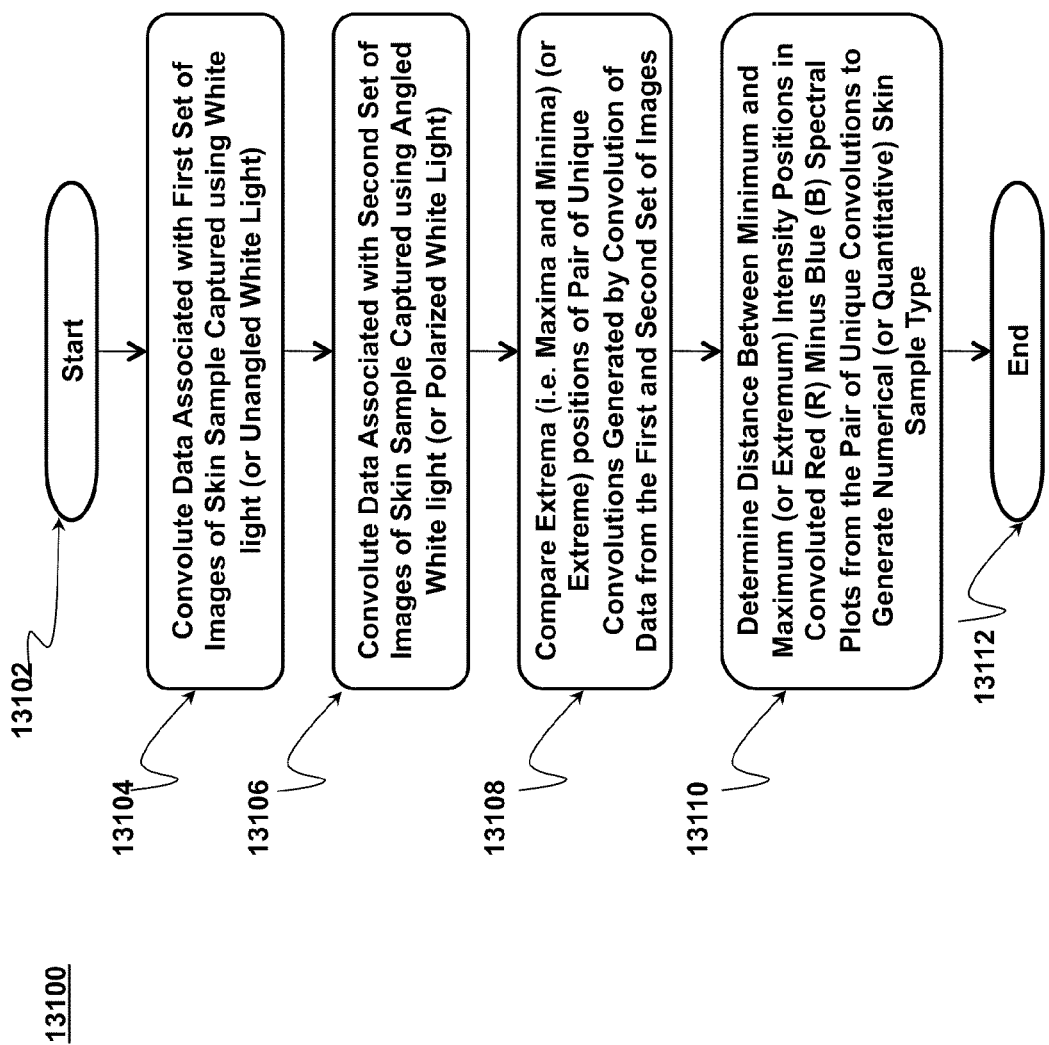
Figure 132A:
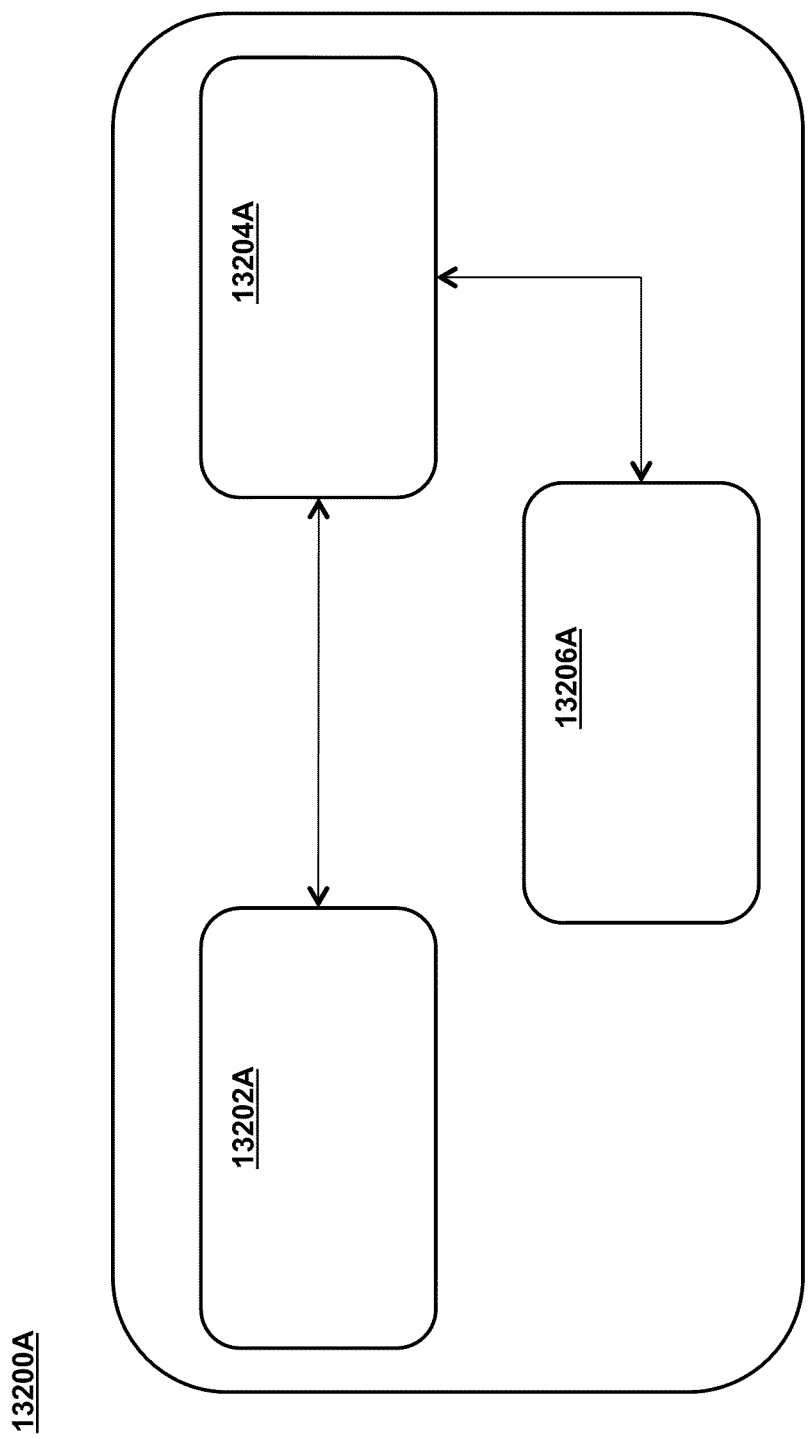
Figure 133A:
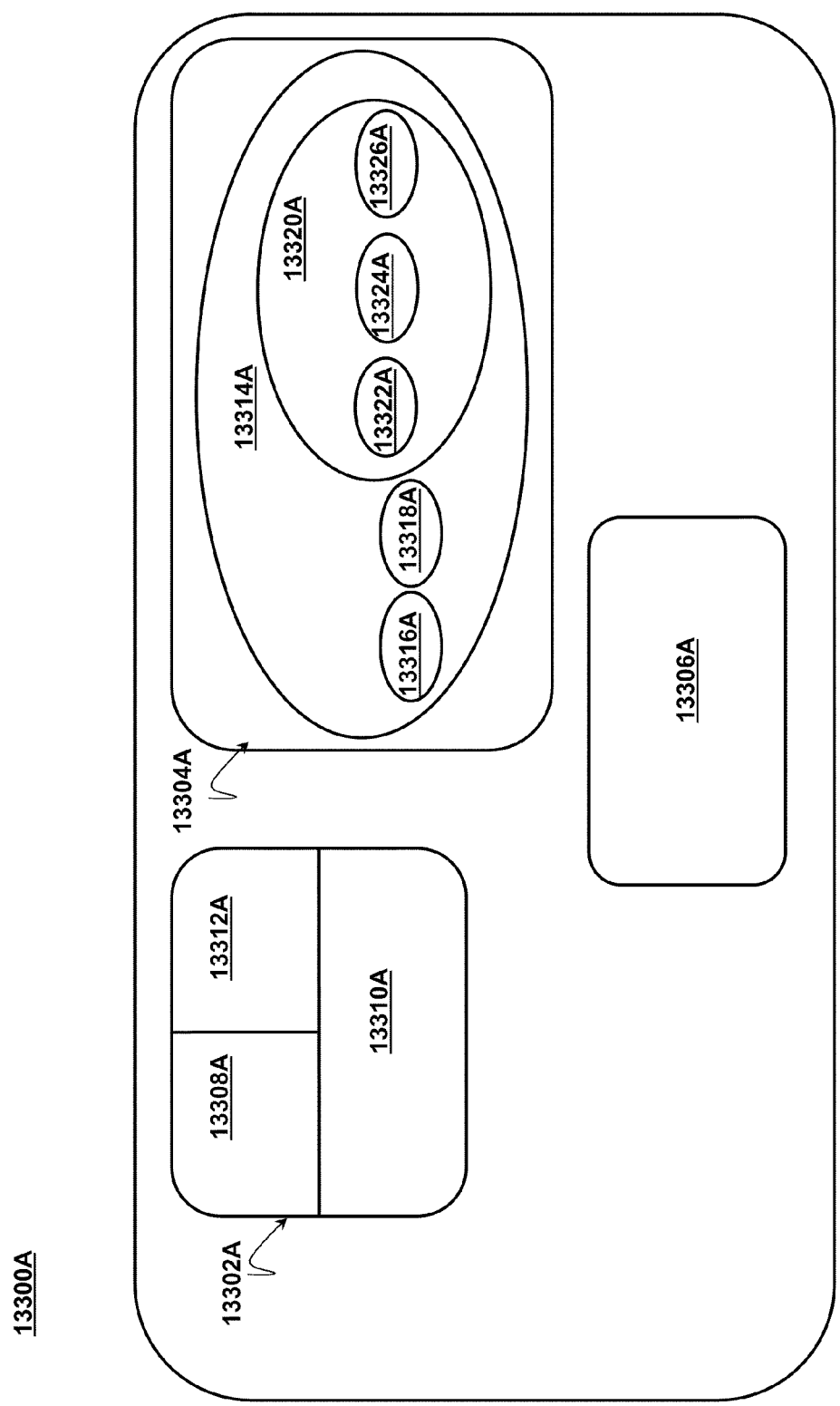
Figure 133B:
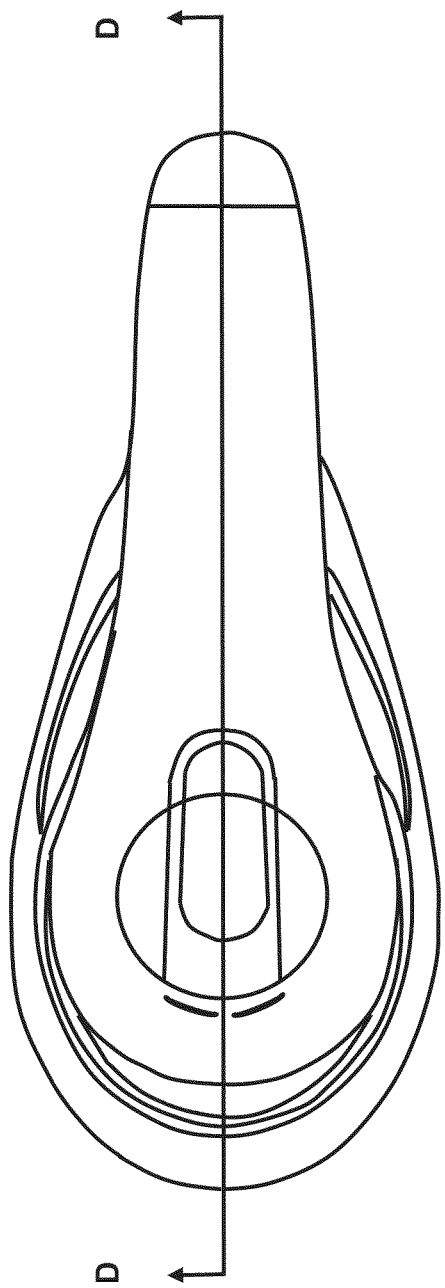
Figure 134:
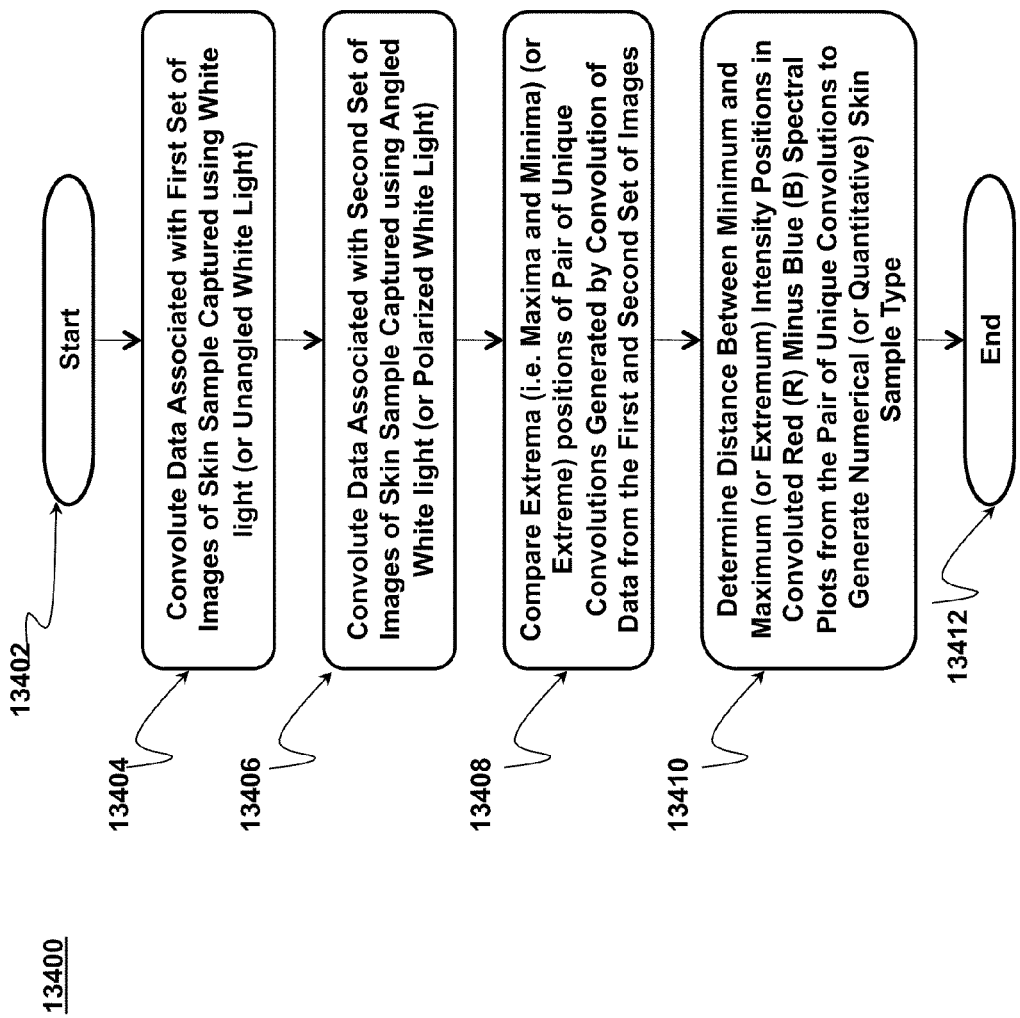
Figure 135:
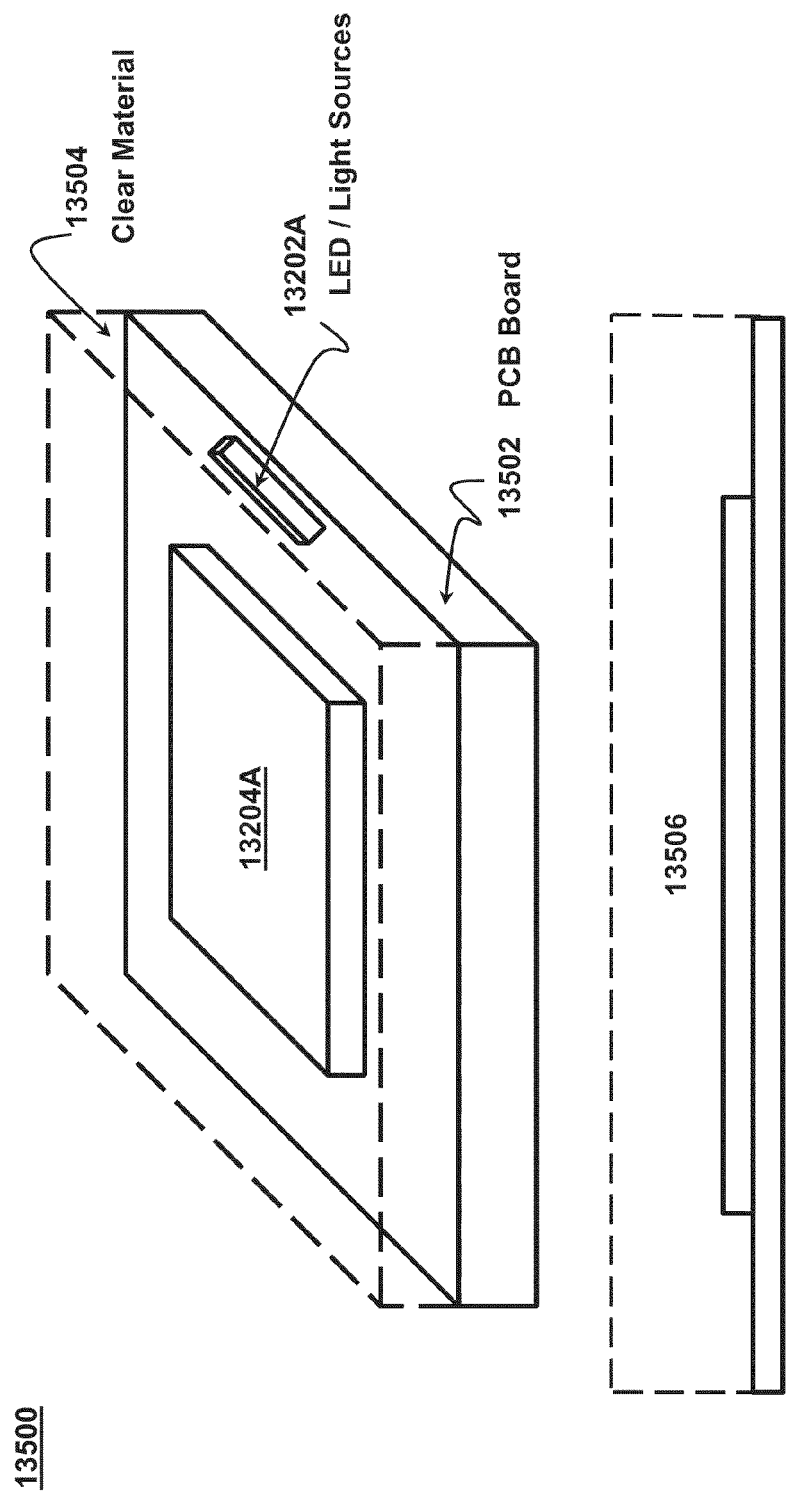
Figure 136:
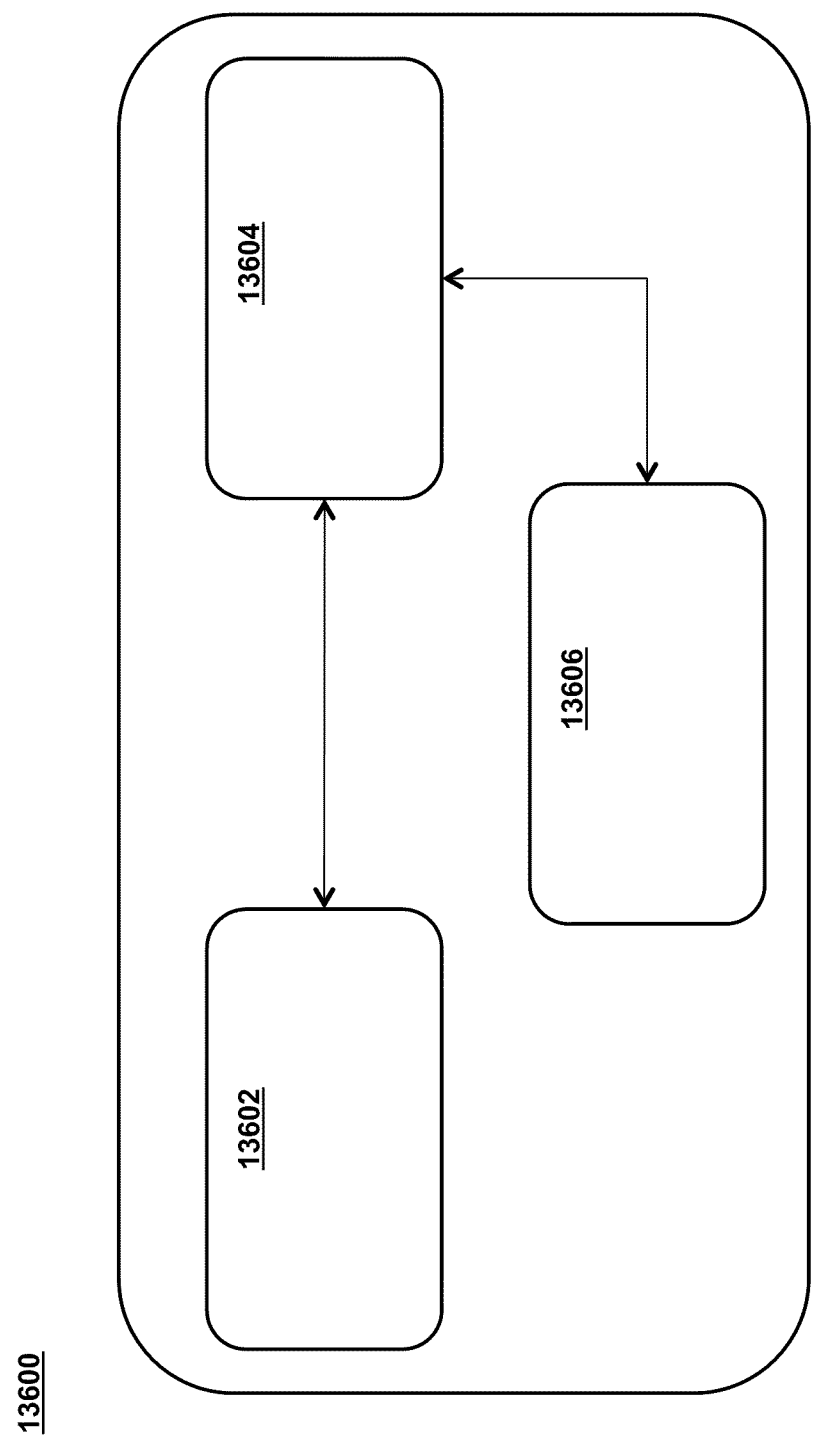
Figure 137:
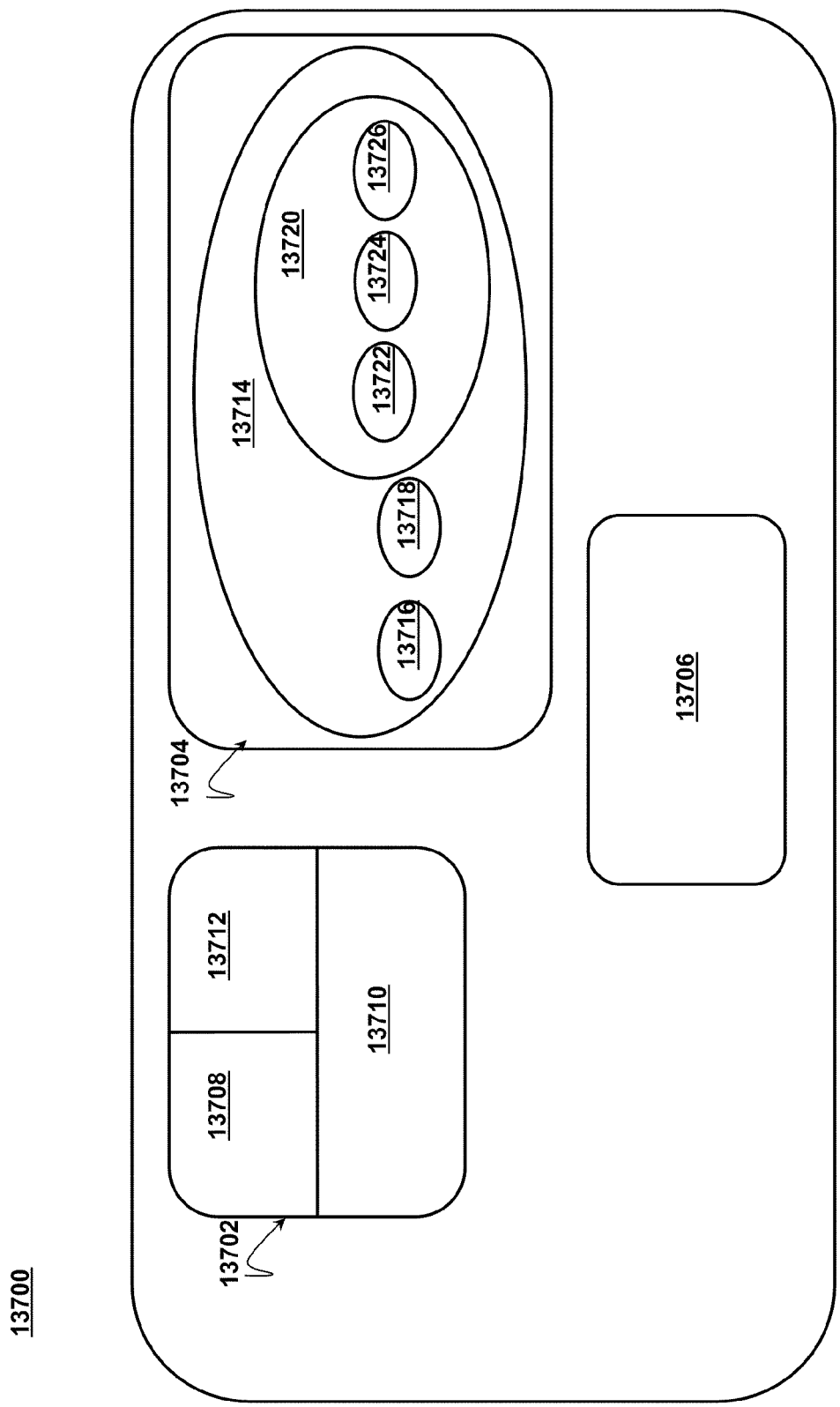
Figure 138:
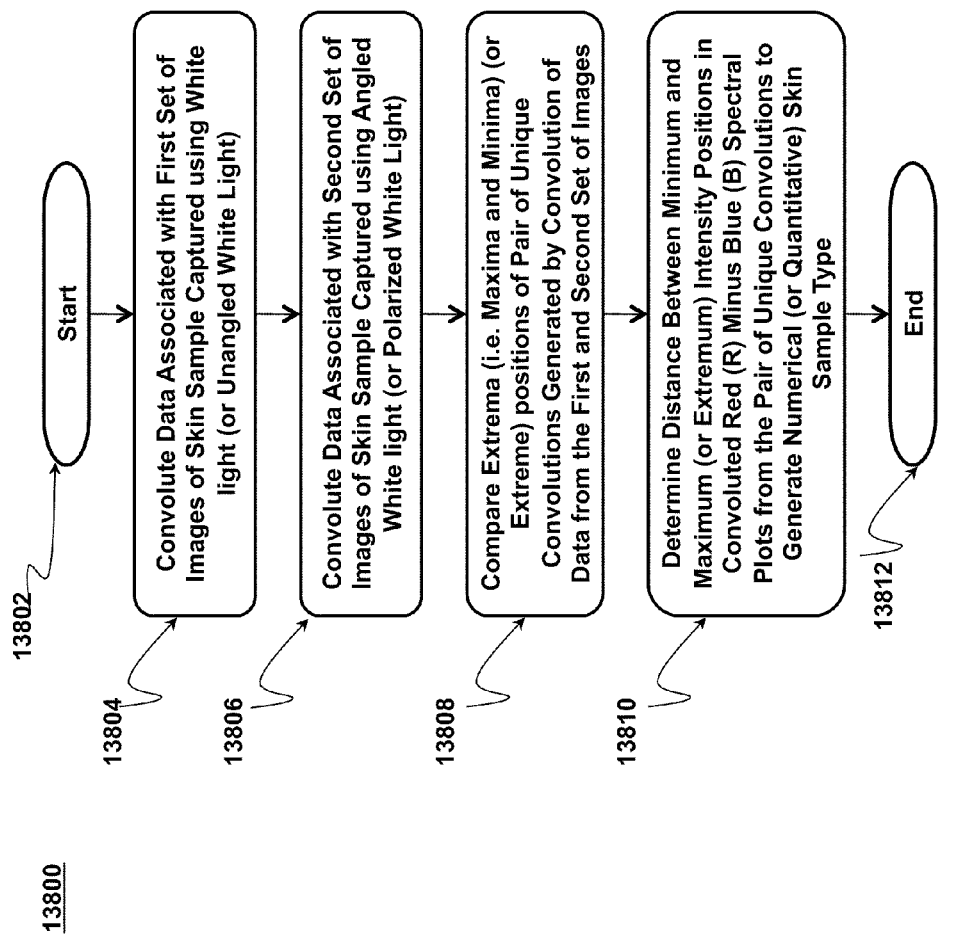
Figure 139:
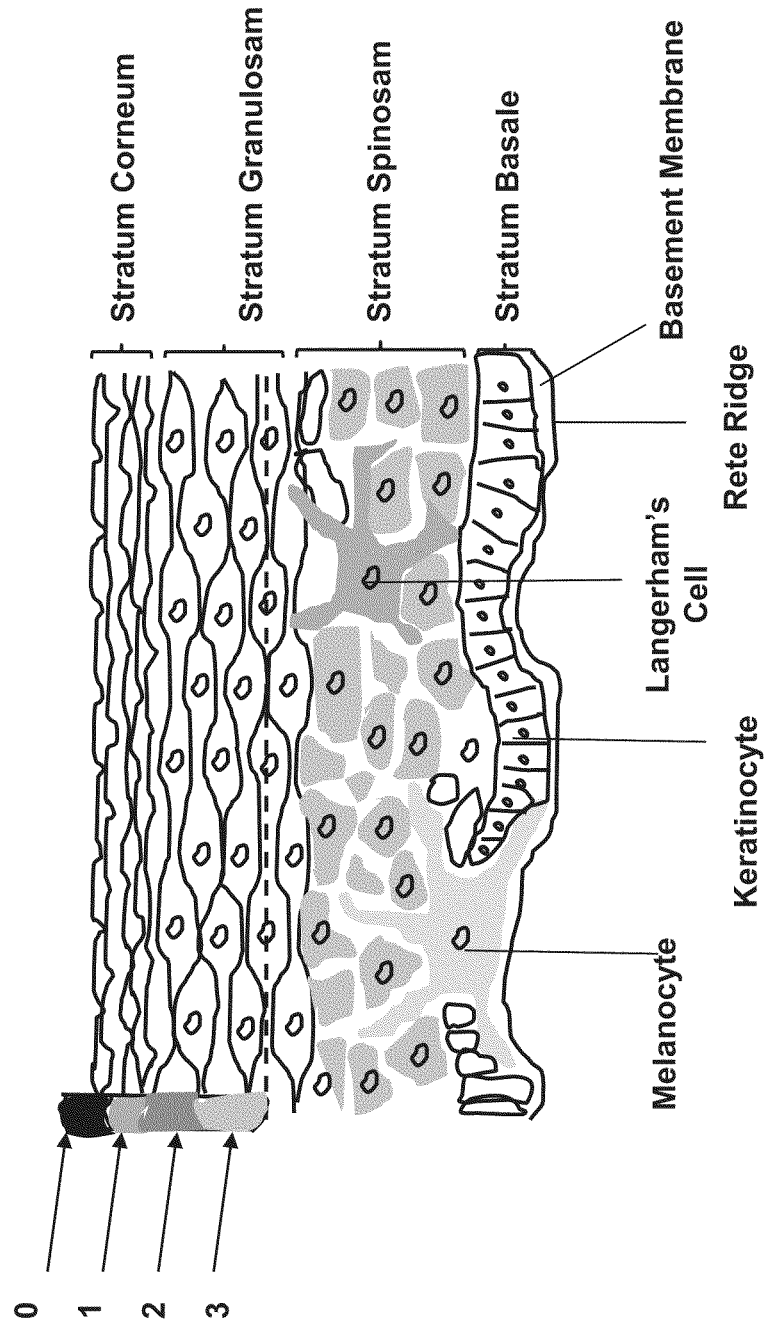
Figure 140C:
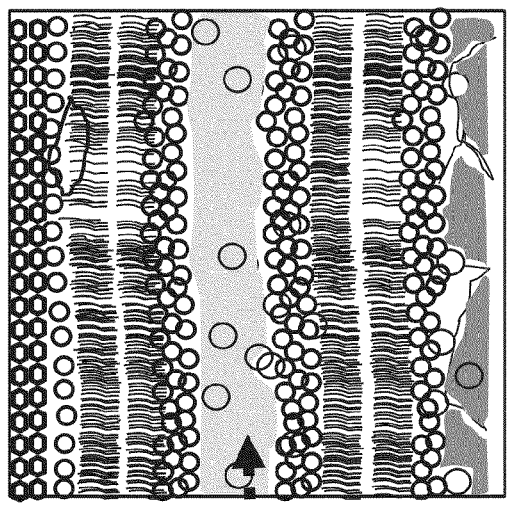
Figure 140B:
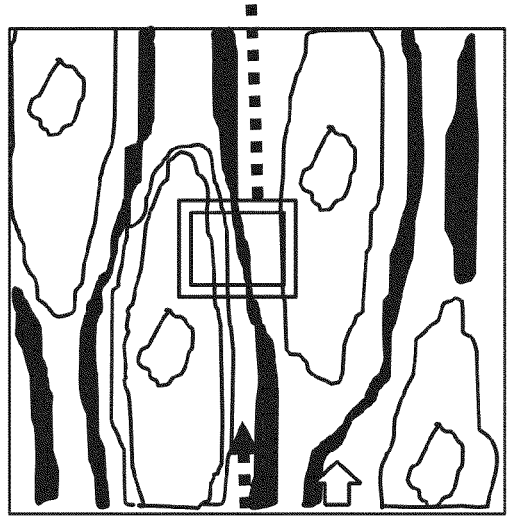
Figure 140A:
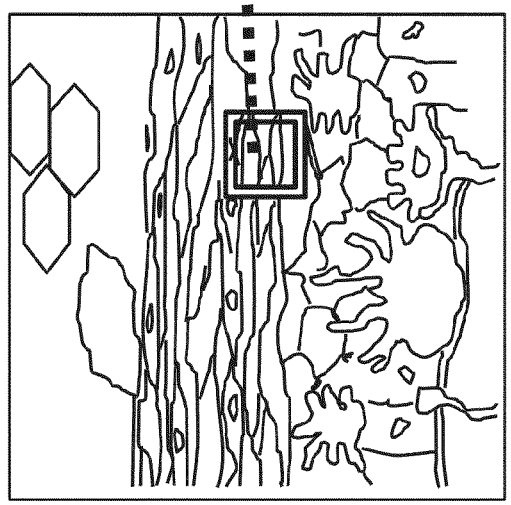
Figure 141A:
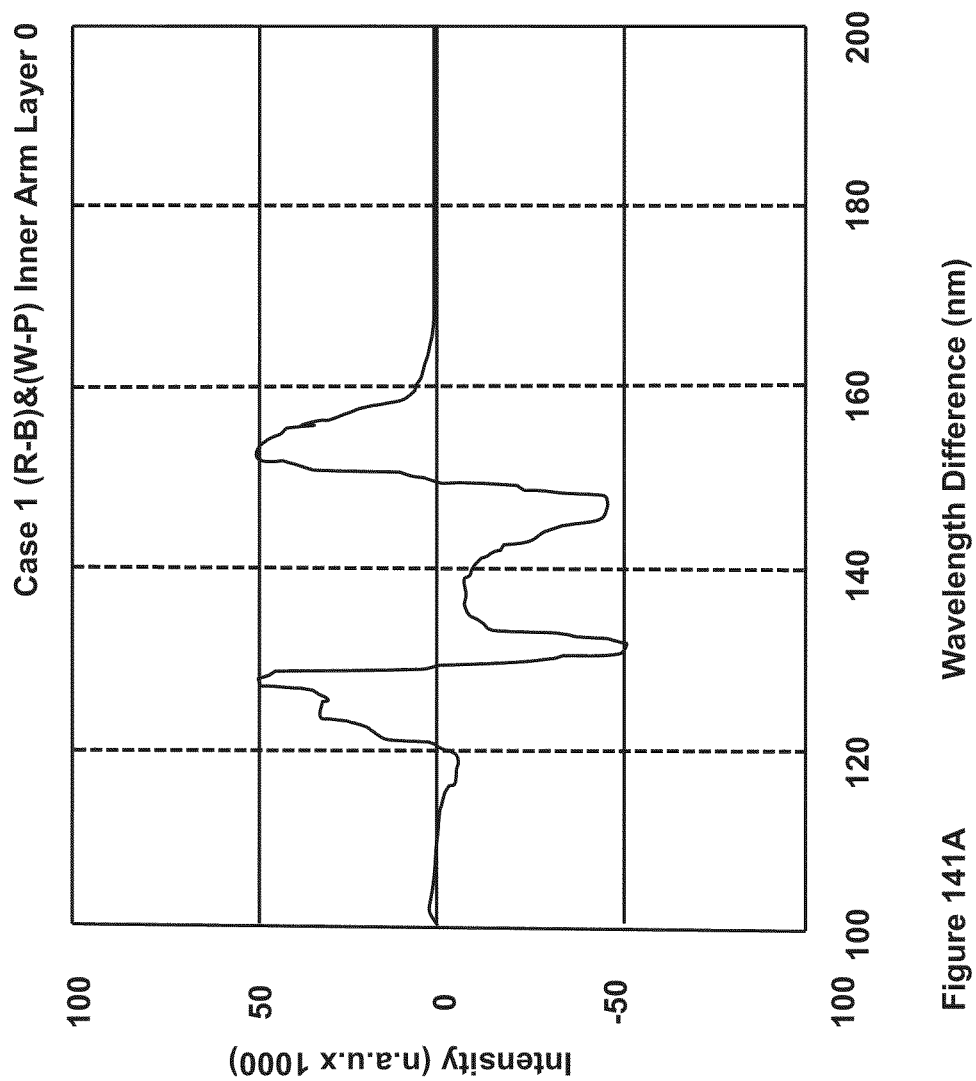
Figure 141B:
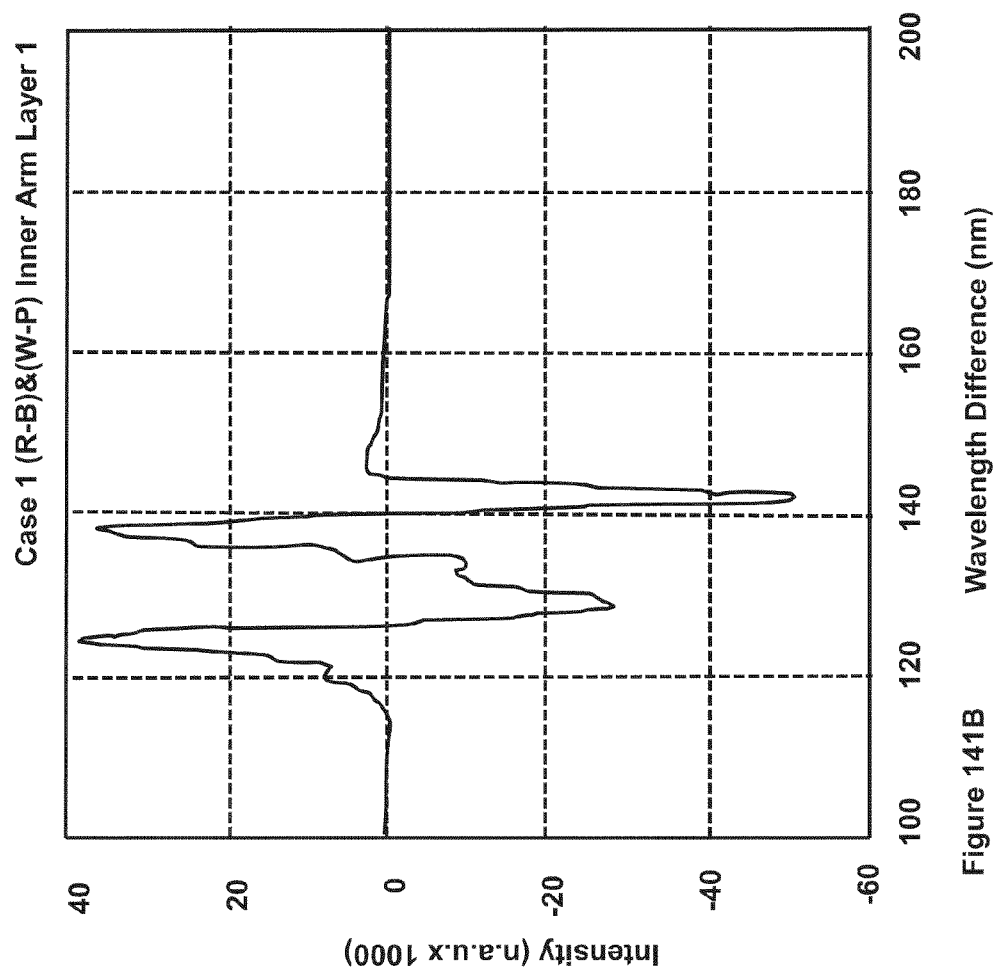
Figure 141C:
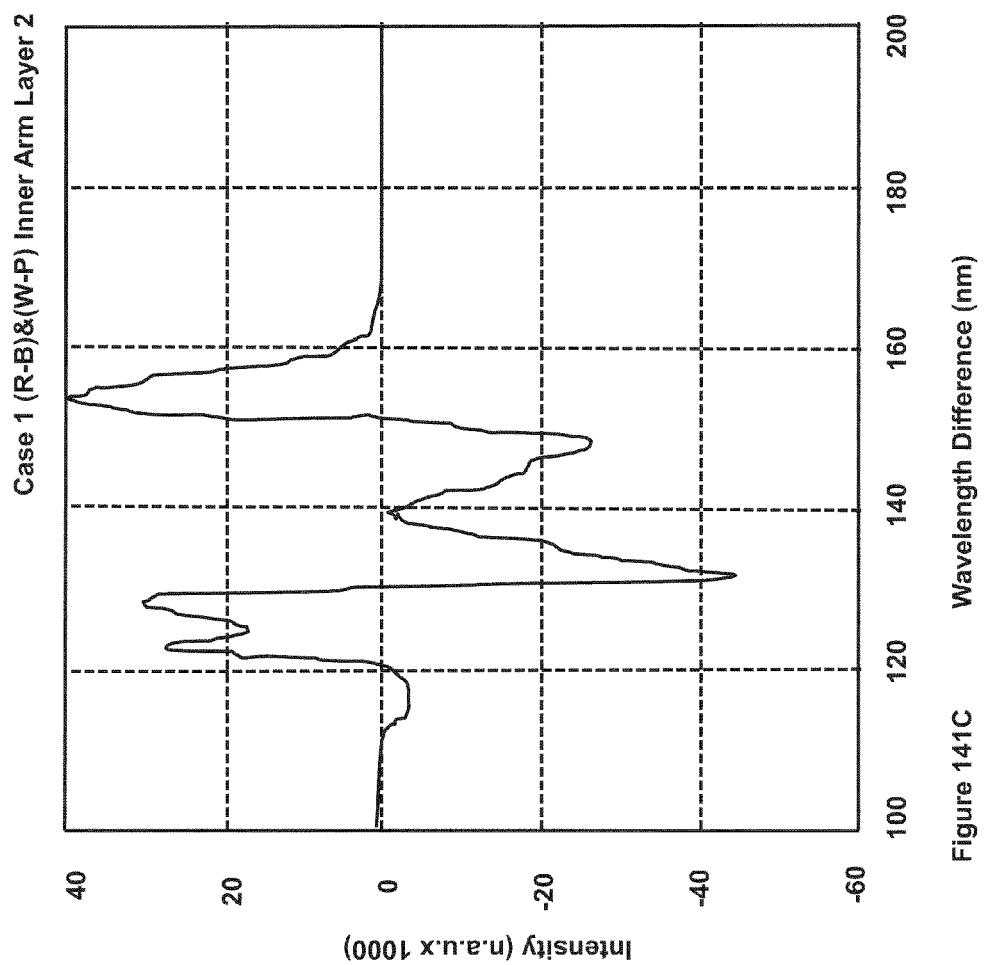
Figure 141D:
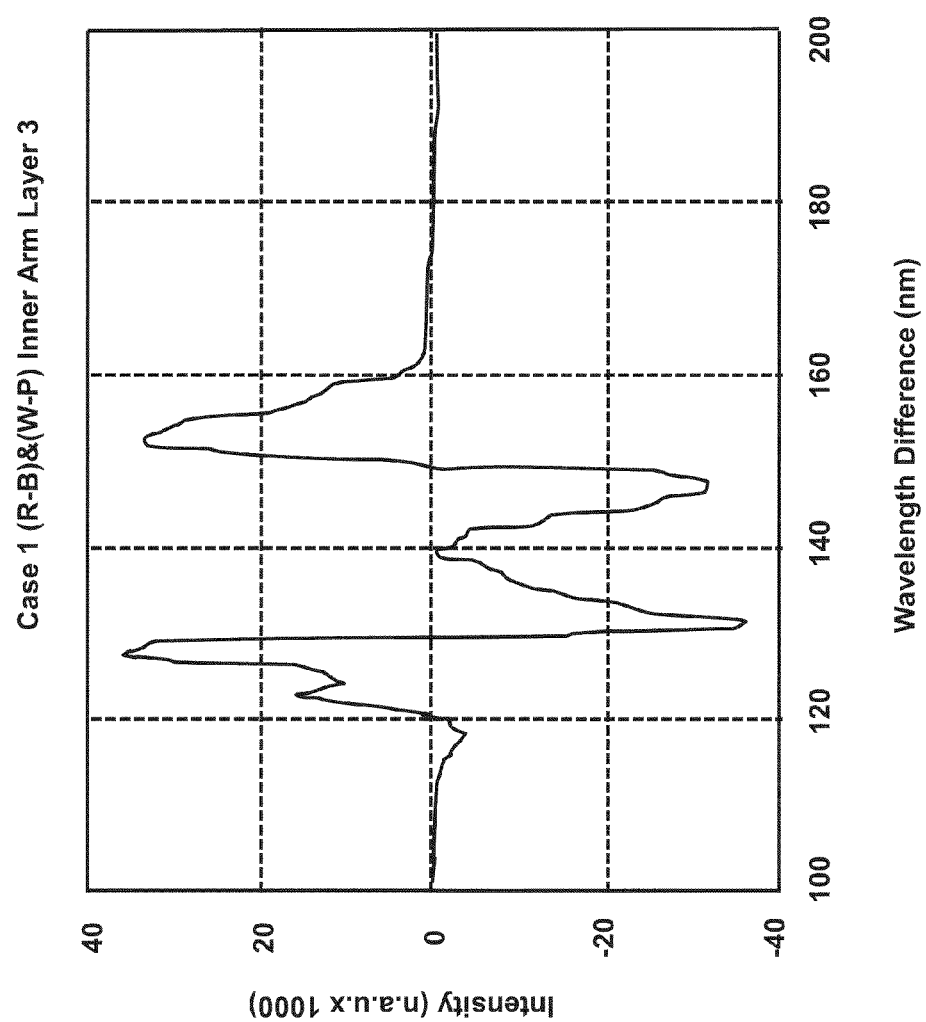
Figure 142A:
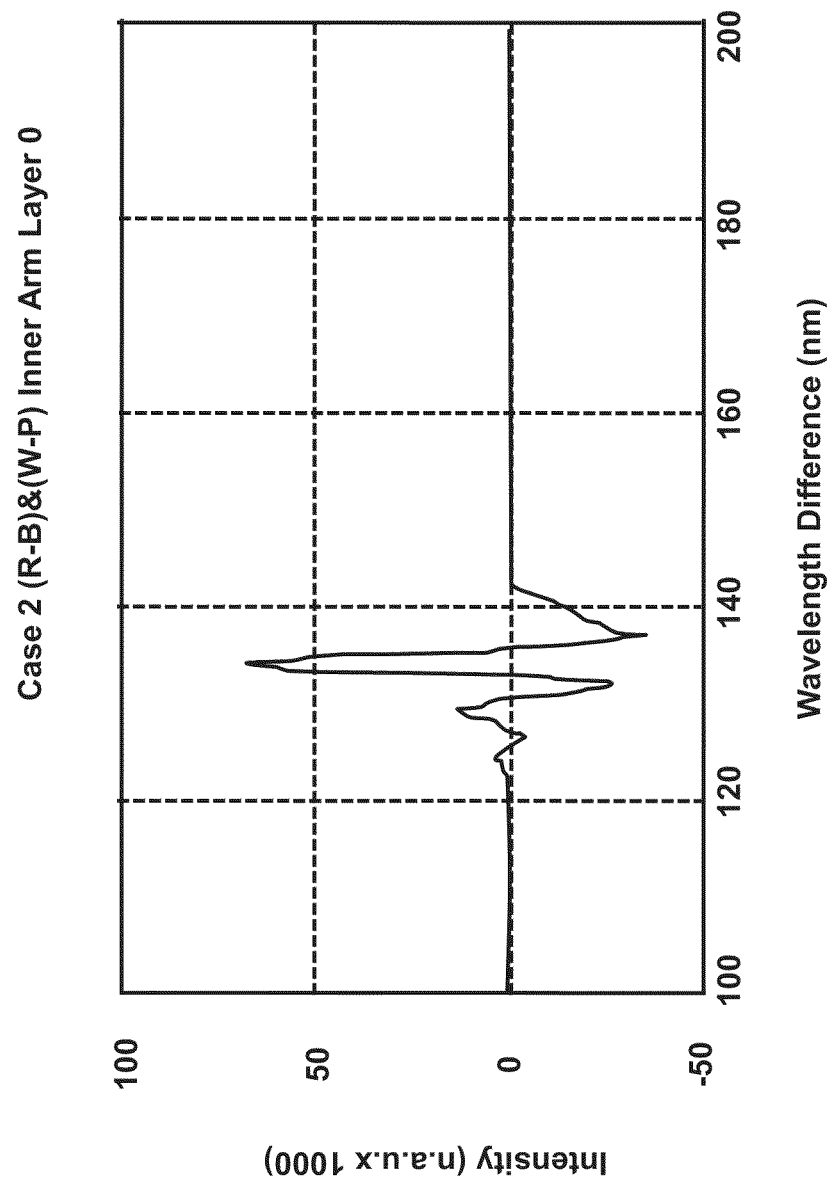
Figure 142B:
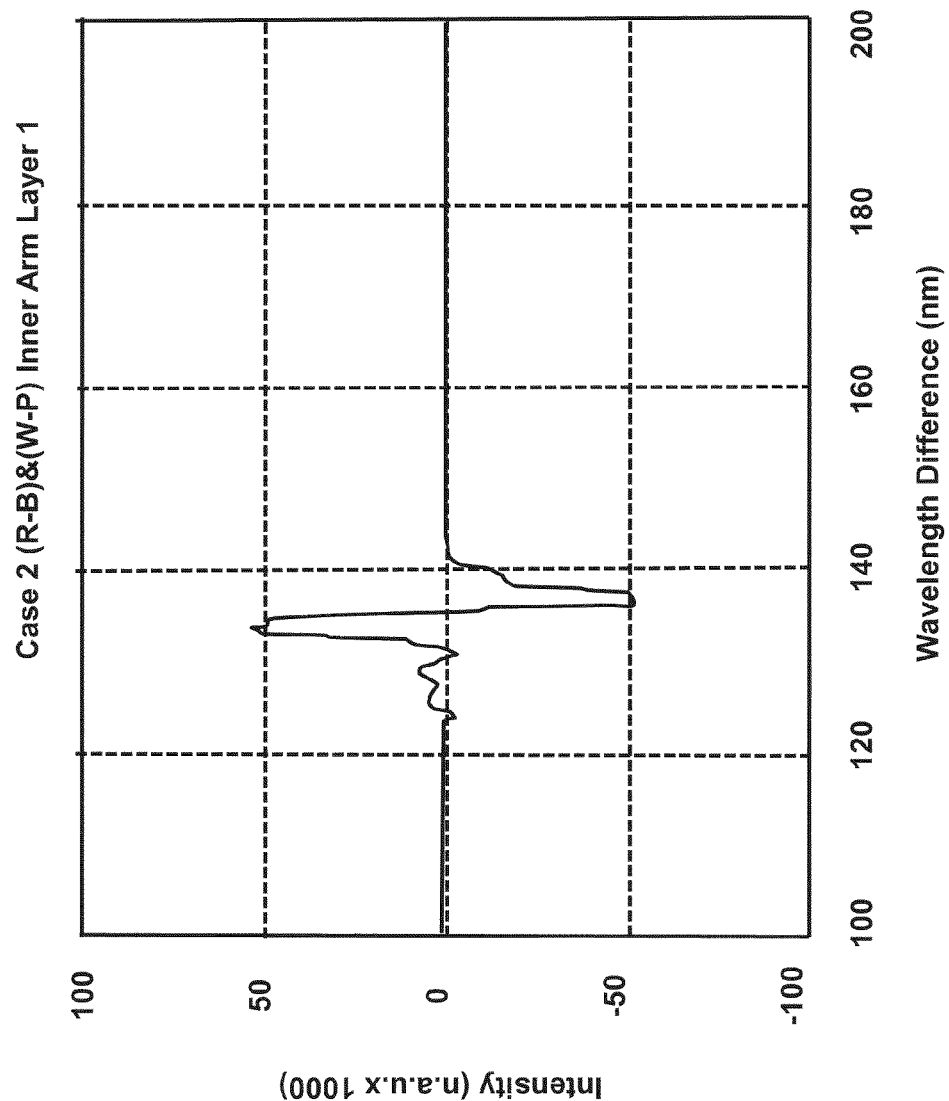
Figure 142C:
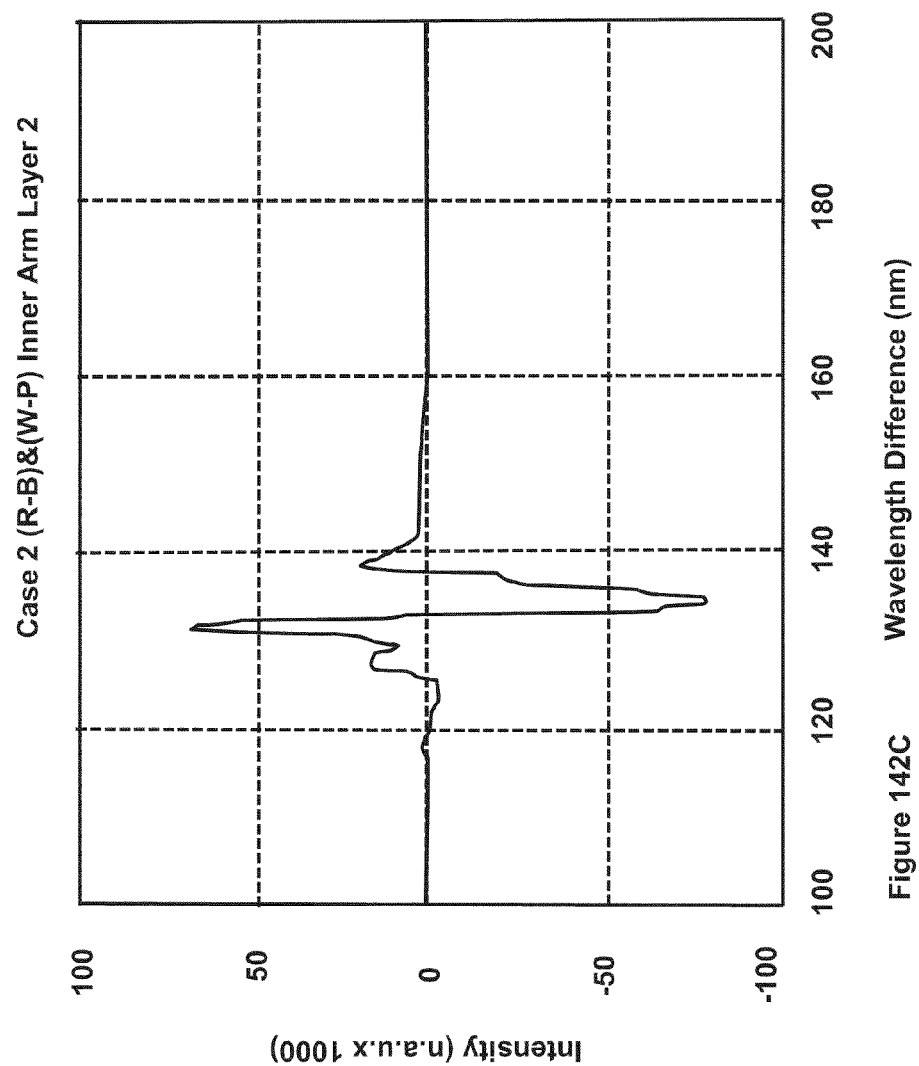
Figure 142D:
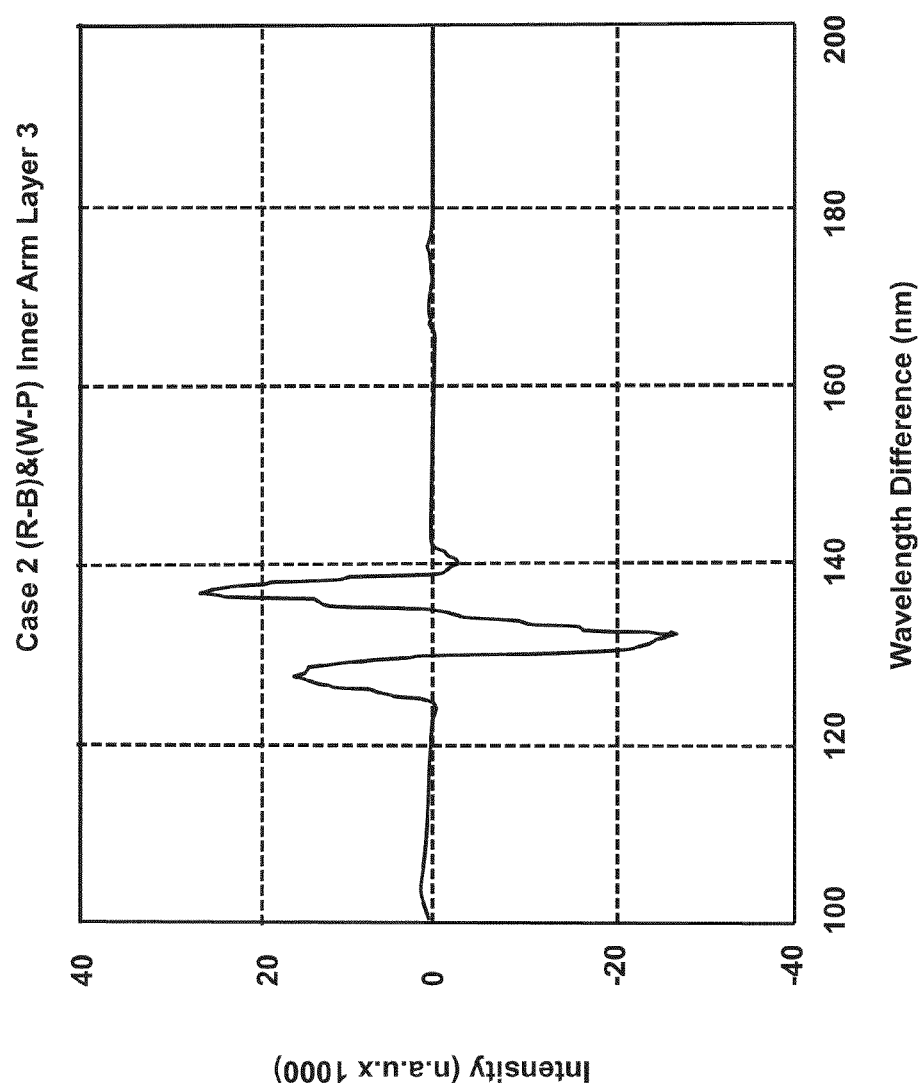
Figure 143A:
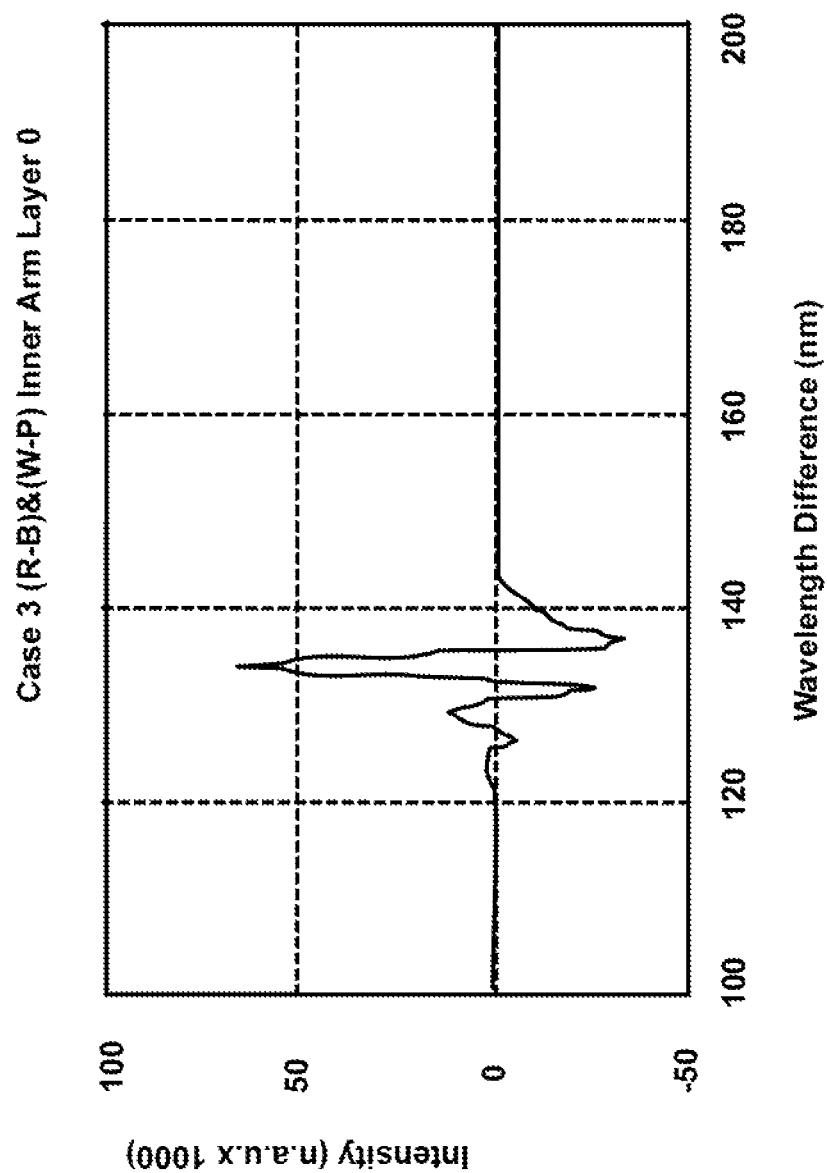
Figure 143B:
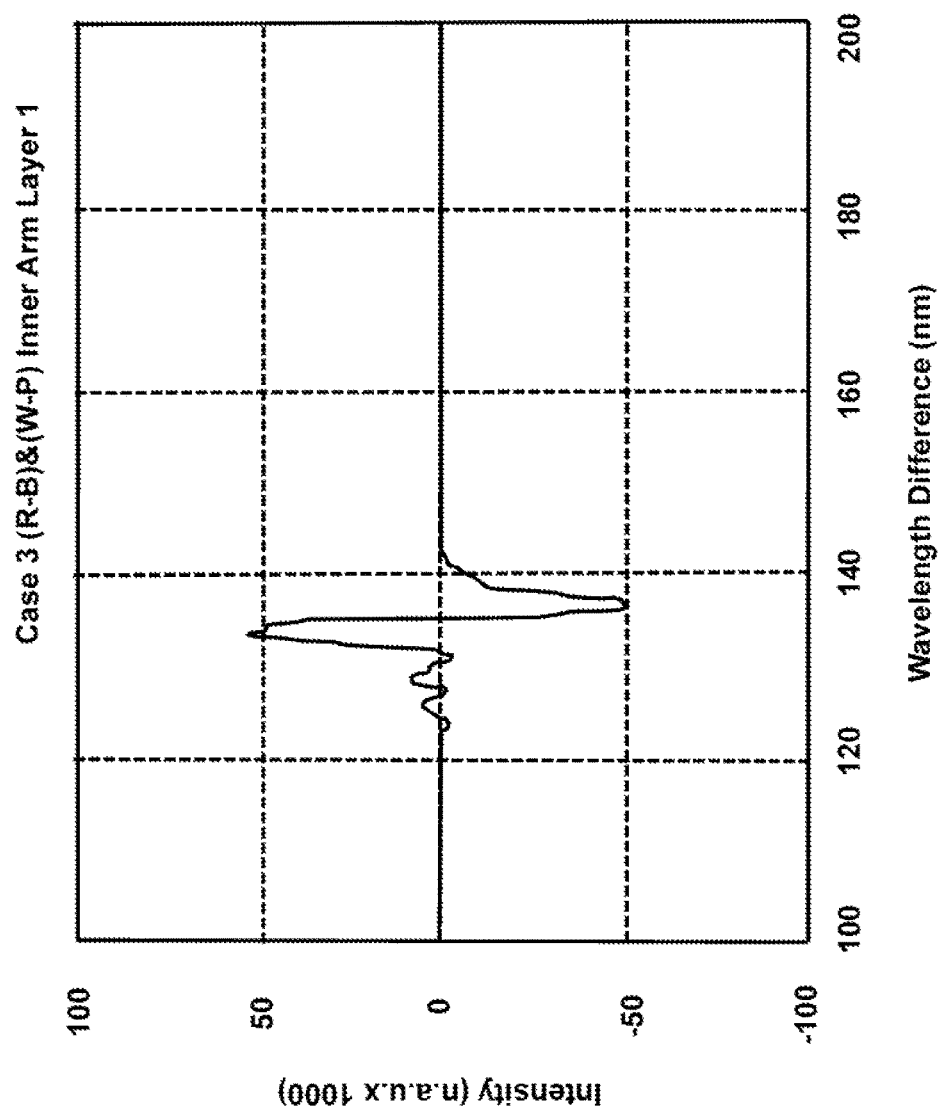
Figure 143C:
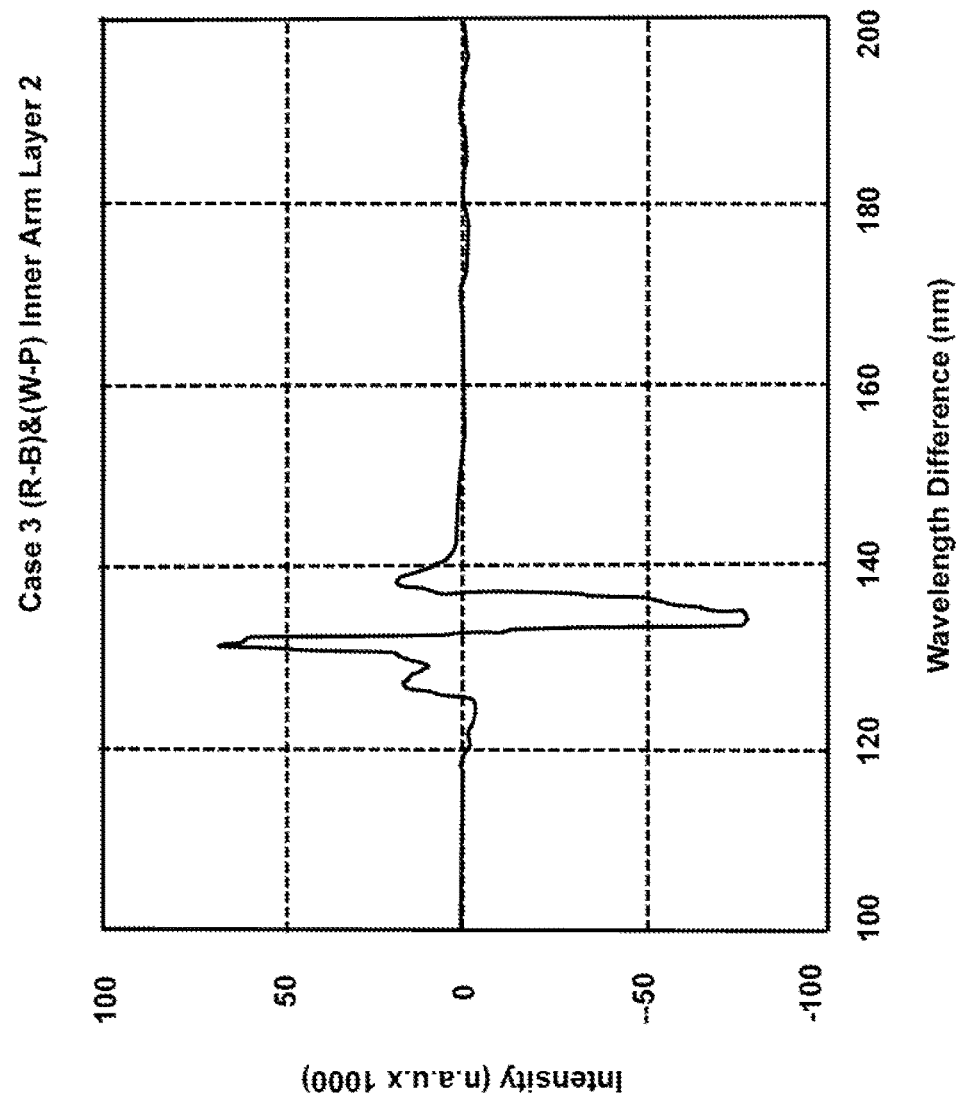
Figure 143D:
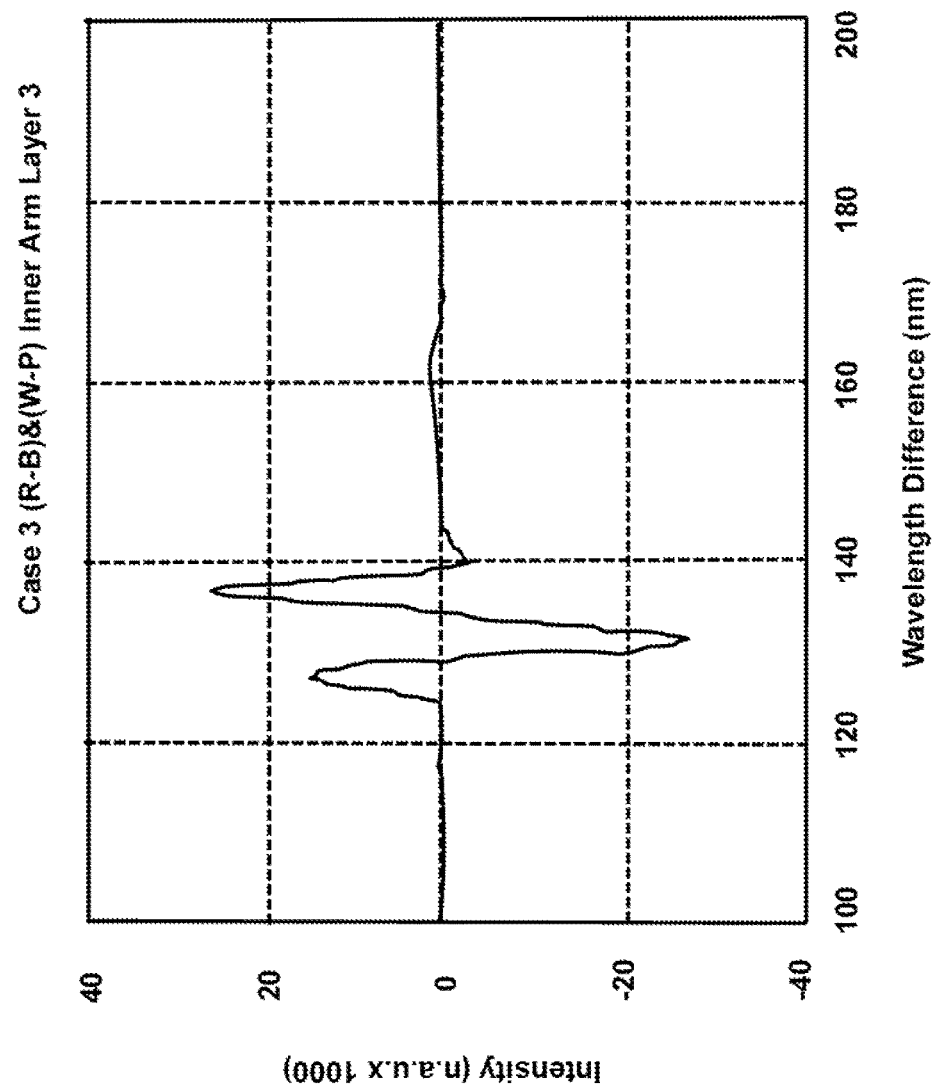
Figure 144A:
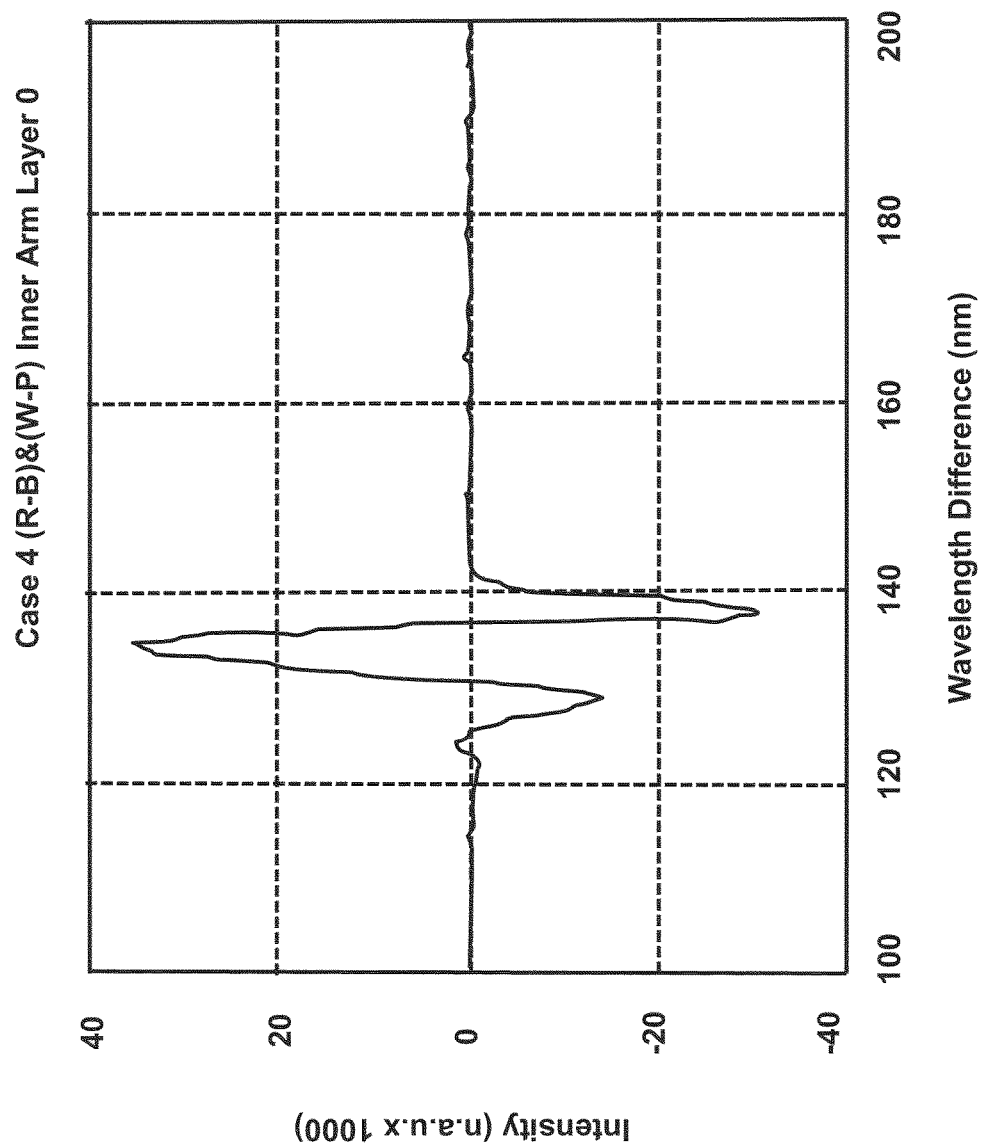
Figure 144B:
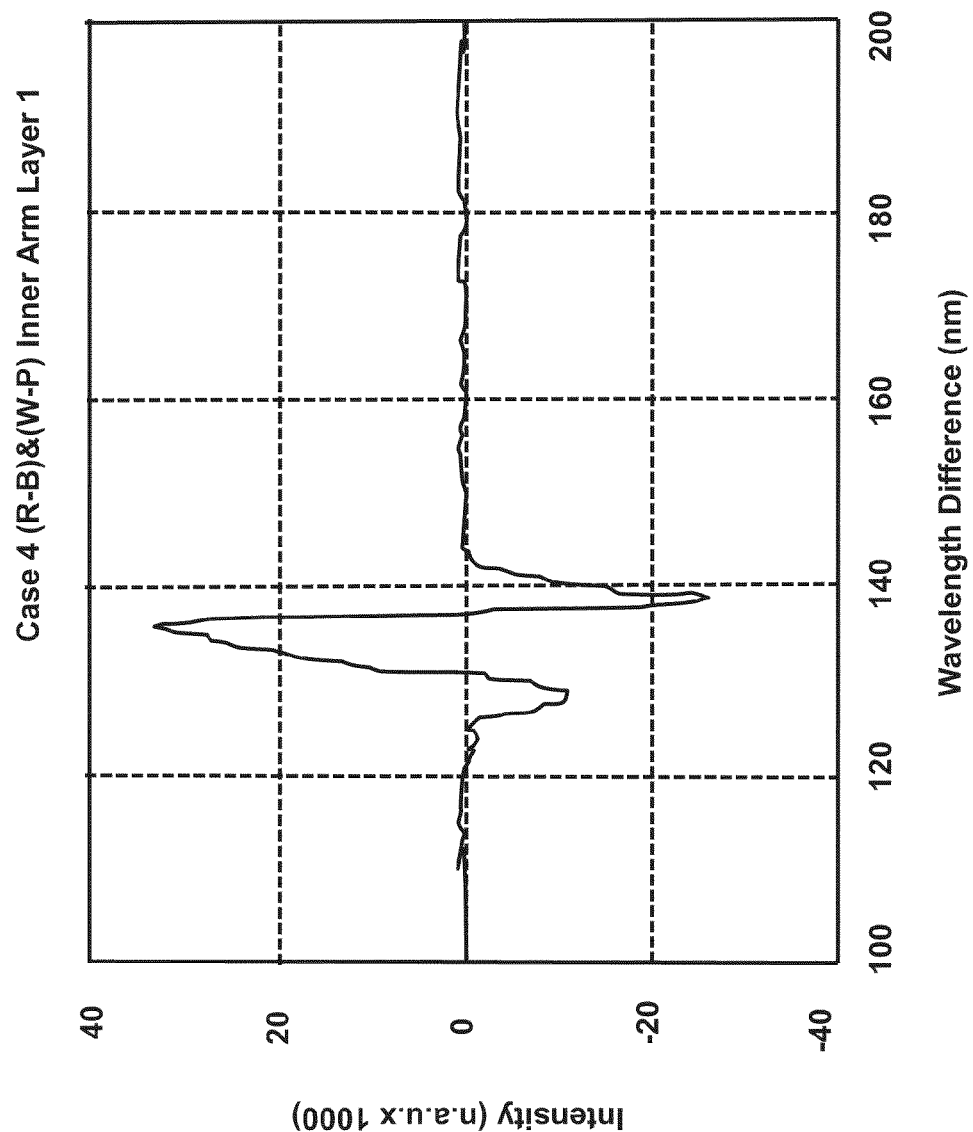
Figure 144C:
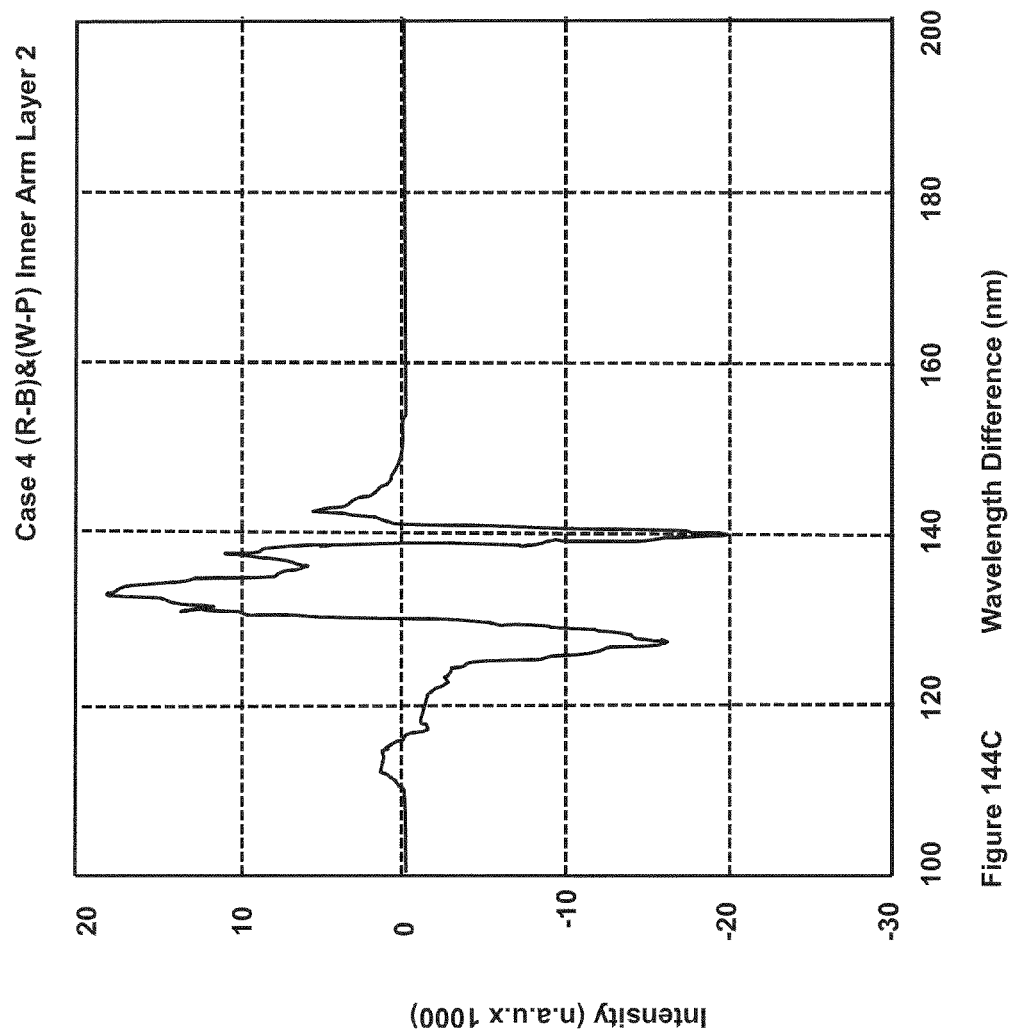
Figure 144D:
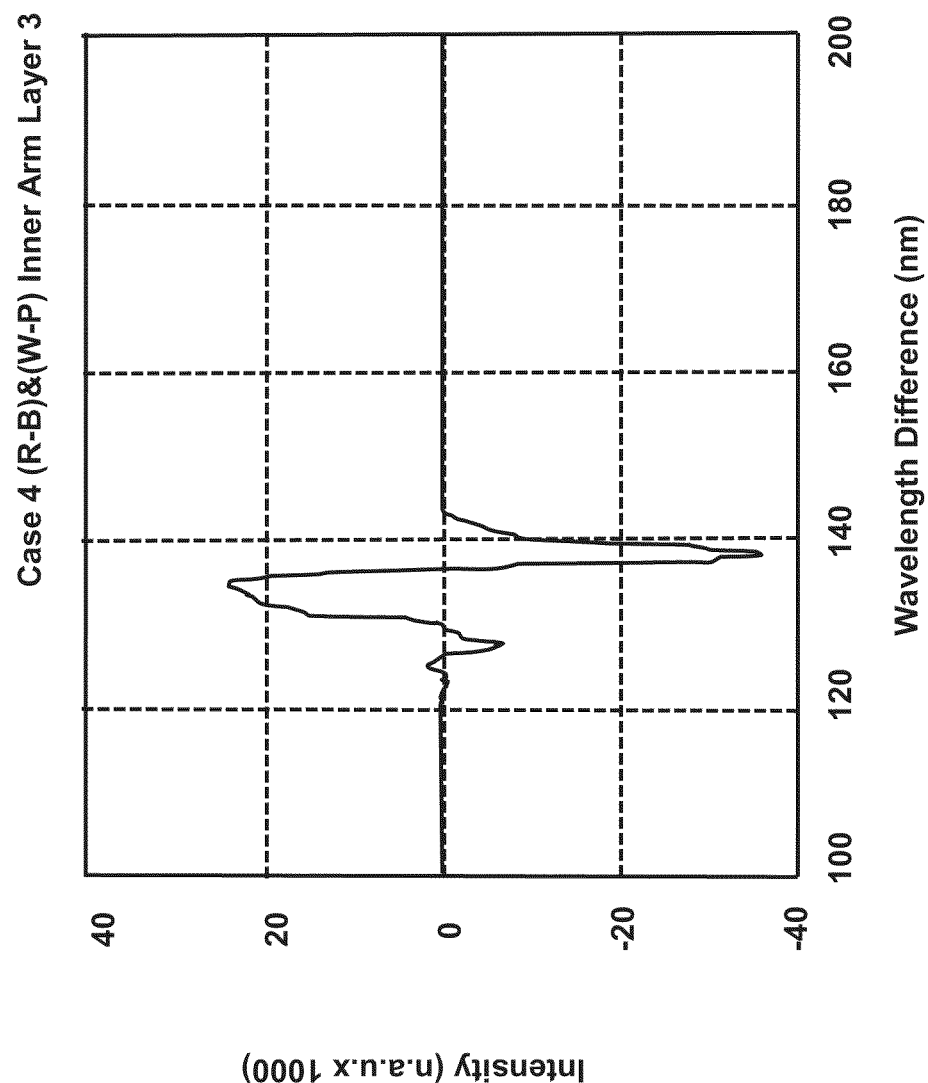
Figure 145:
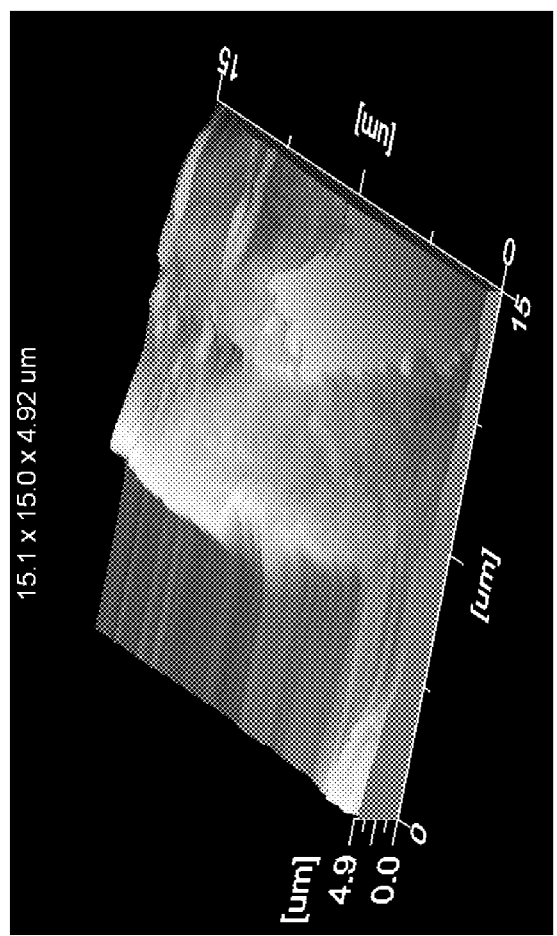
Figure 146A:
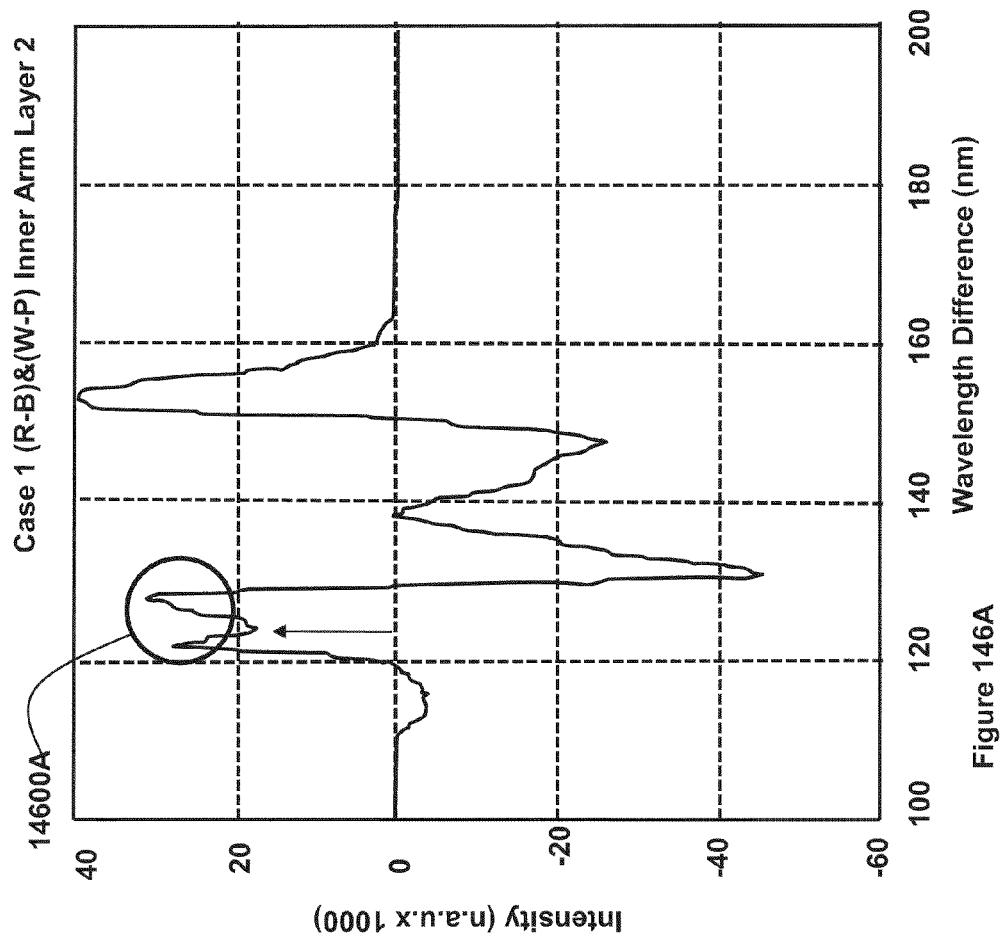
Figure 146C:
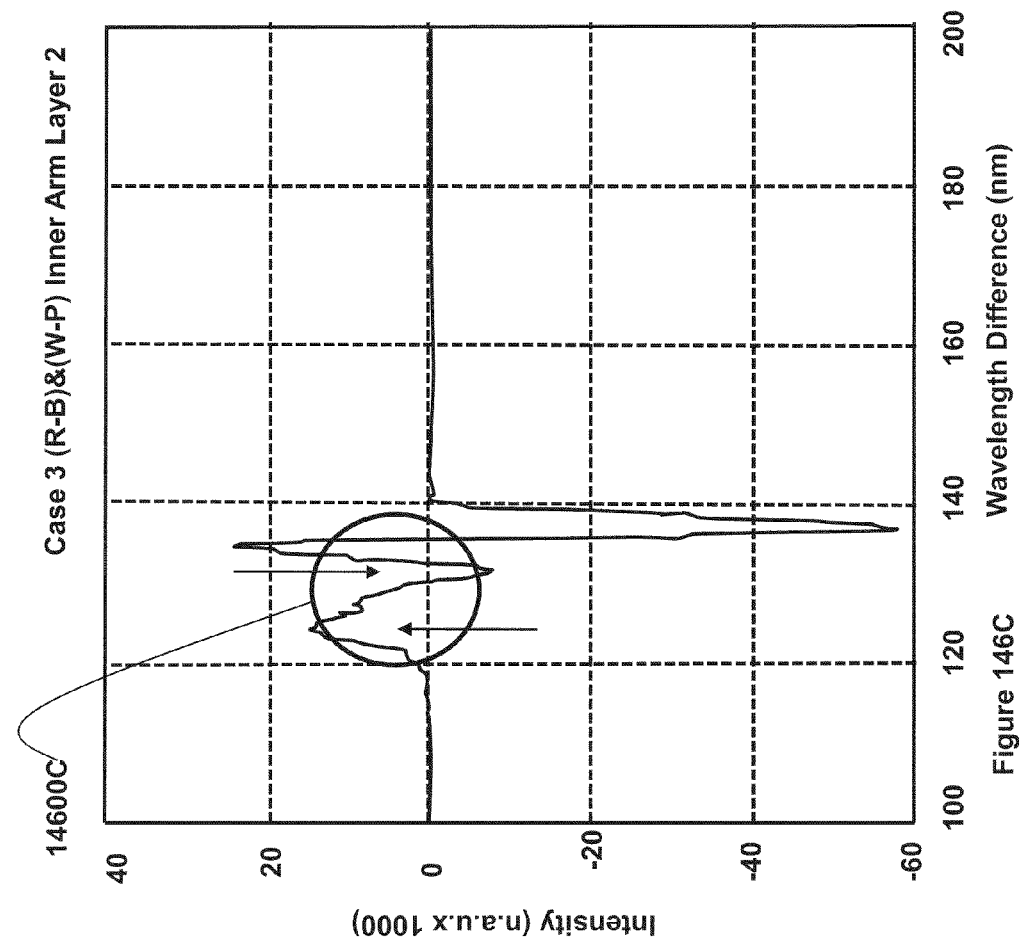
Figure 146D:
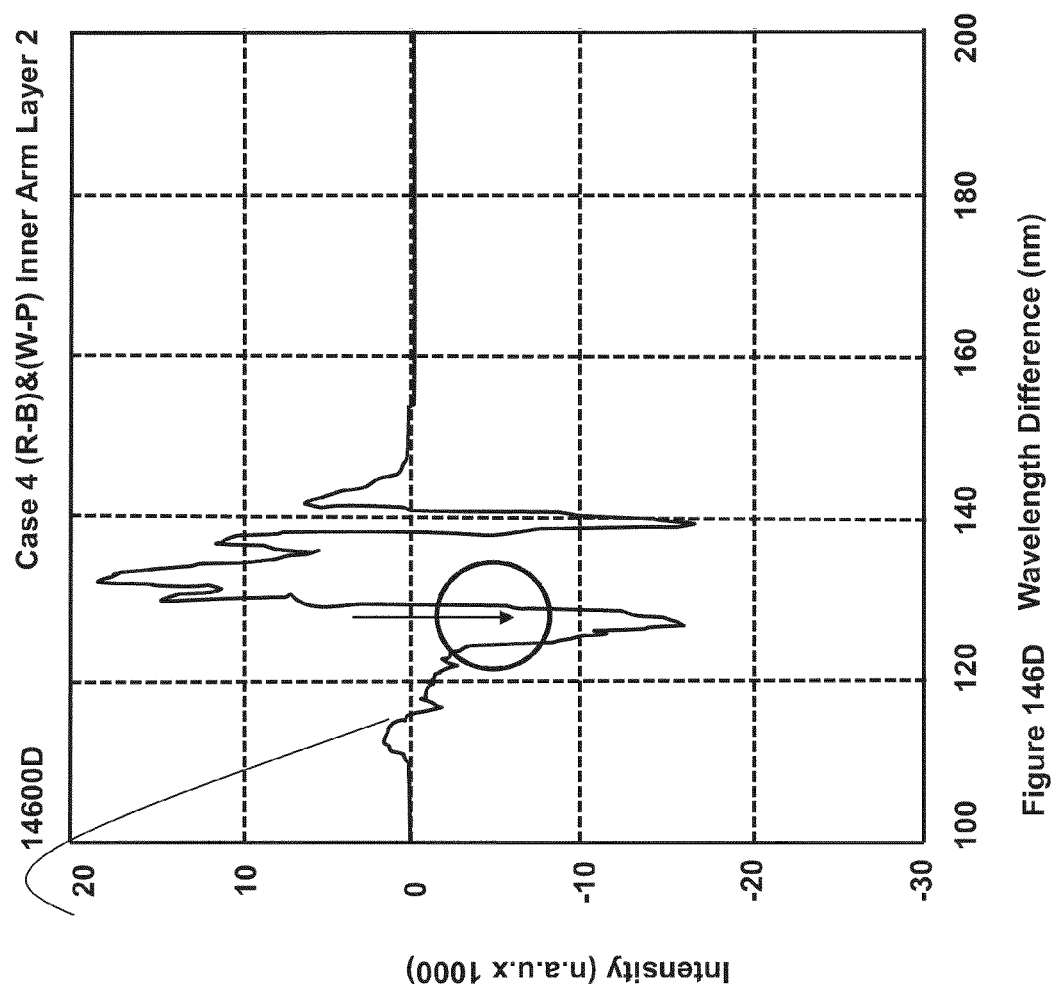
Figure 147:
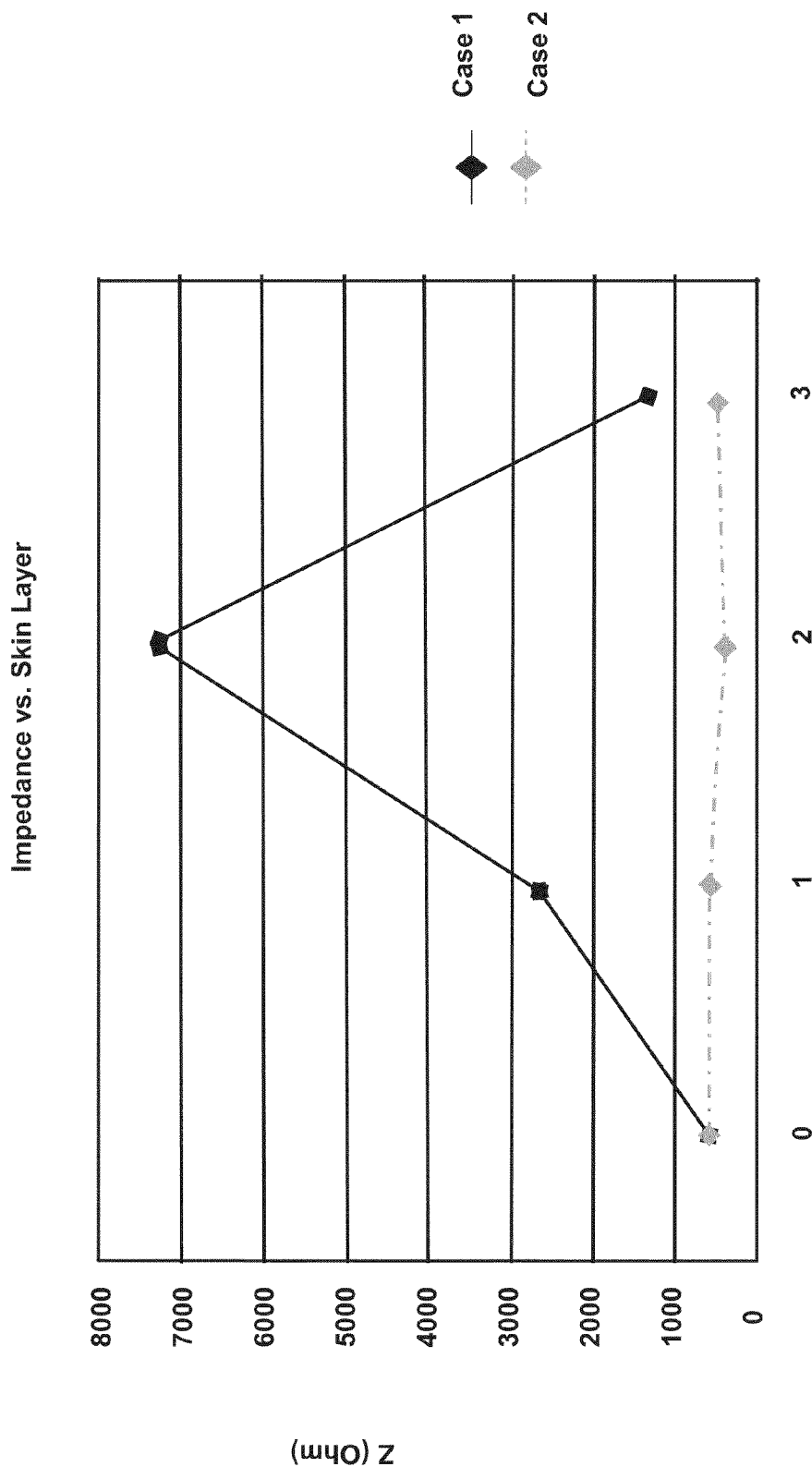
Figure 148:
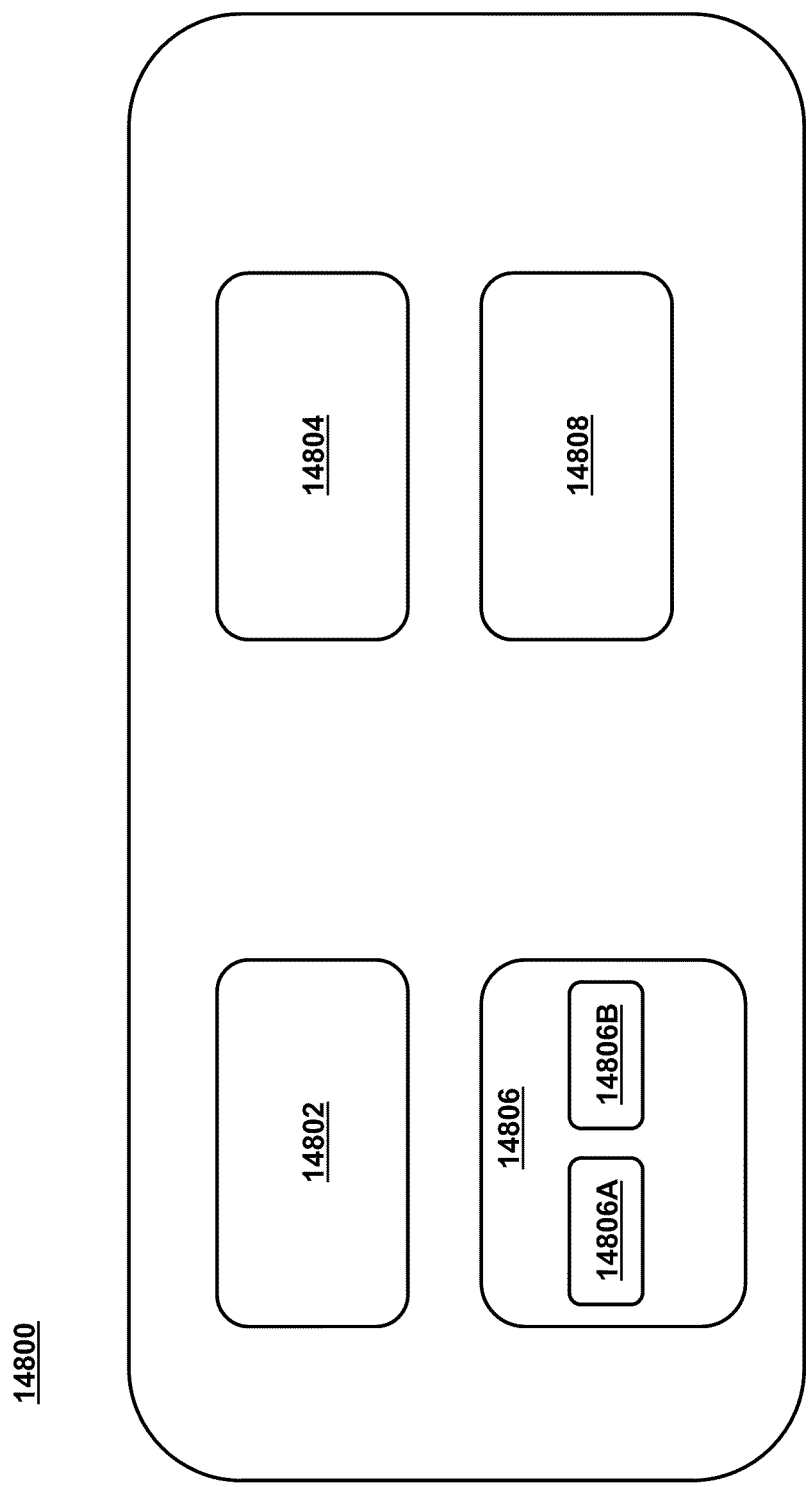
Figure 149:
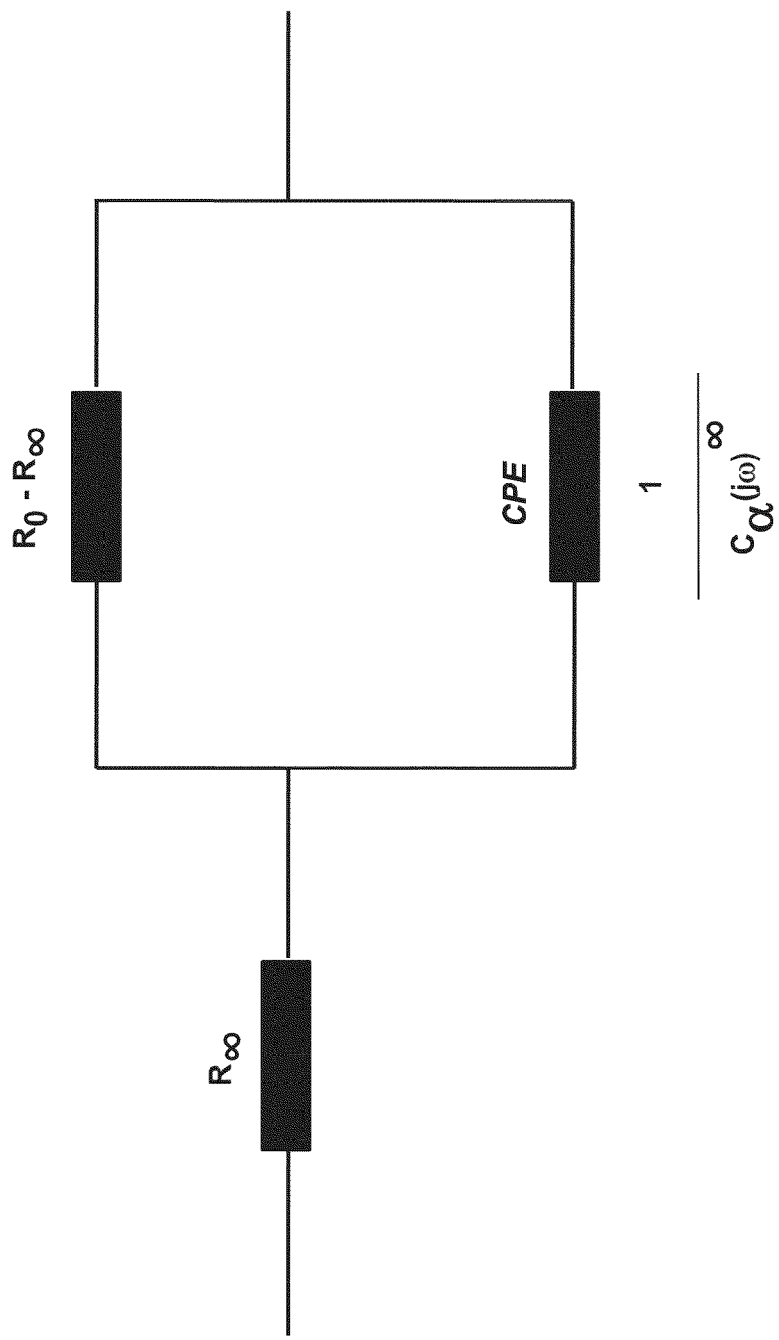
Figure 150:
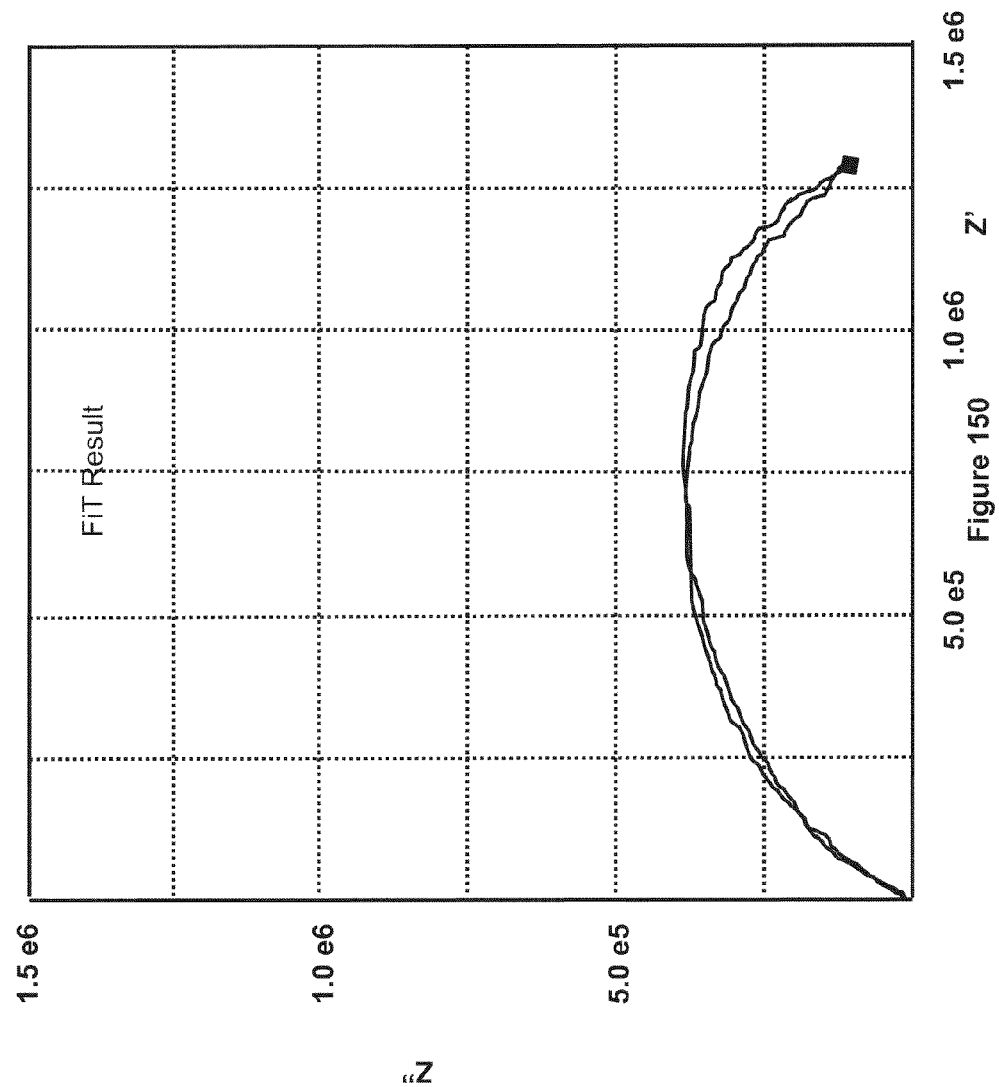
Figure 151:
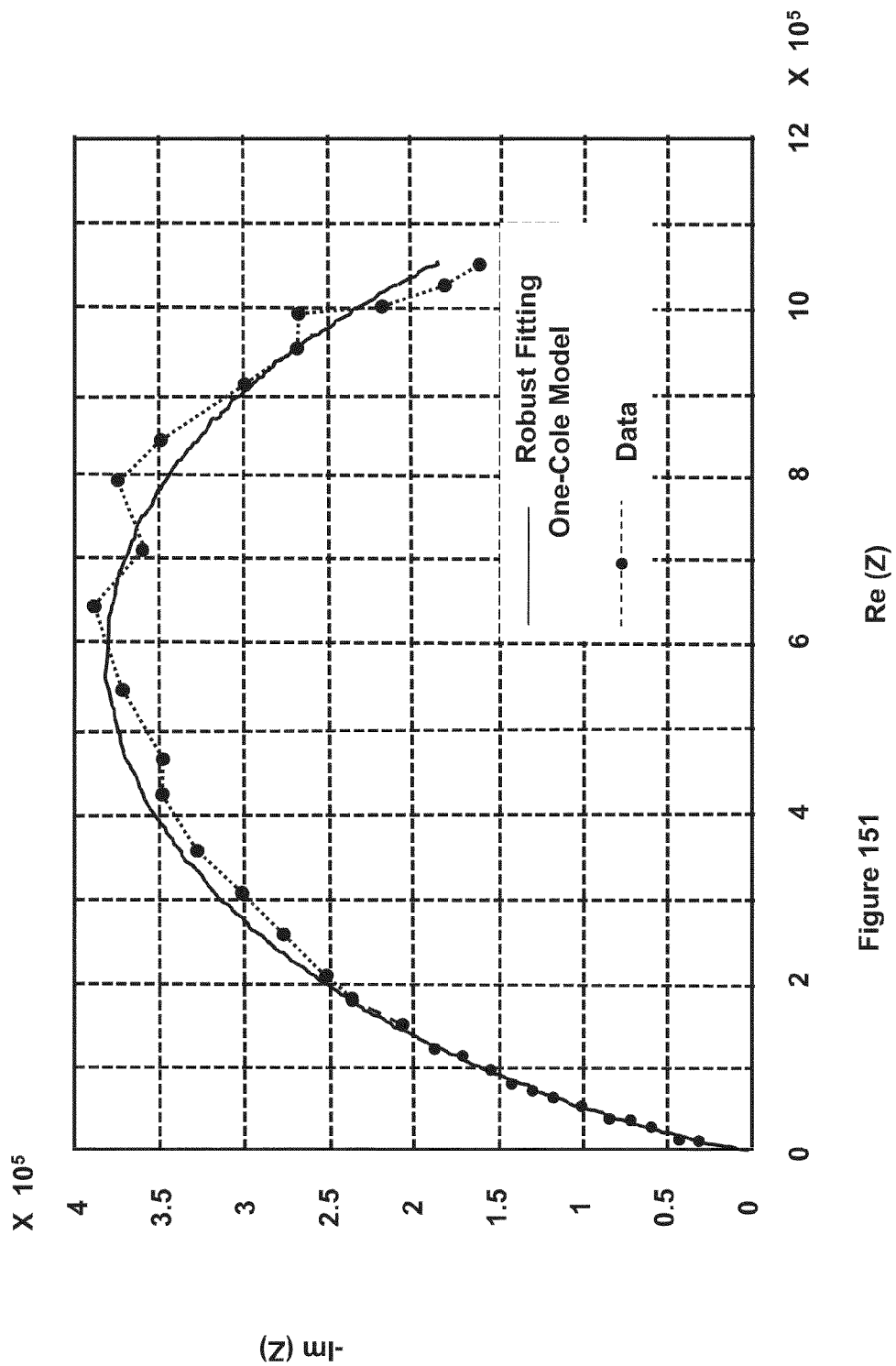
Figure 152:
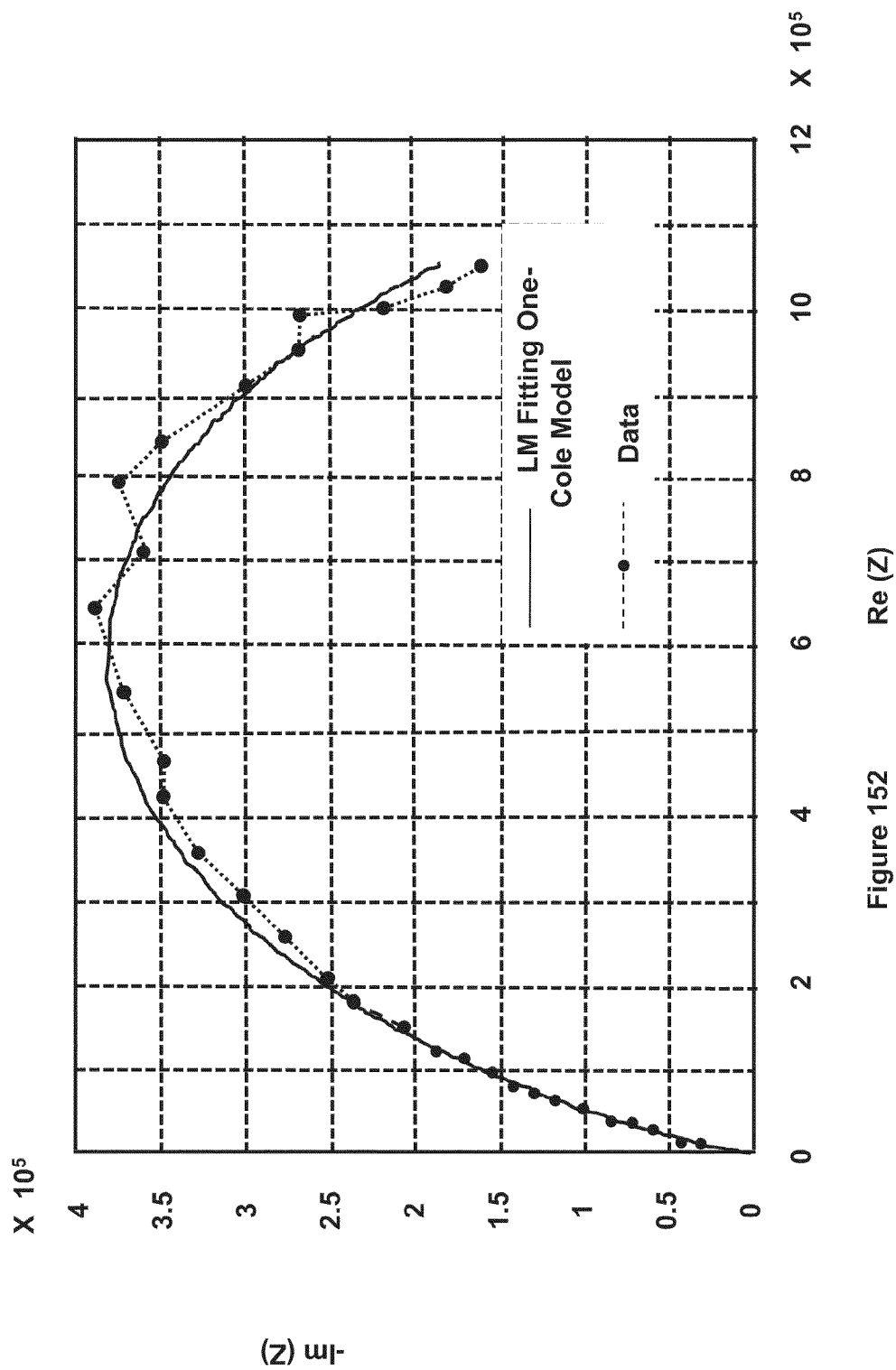
Figure 153:
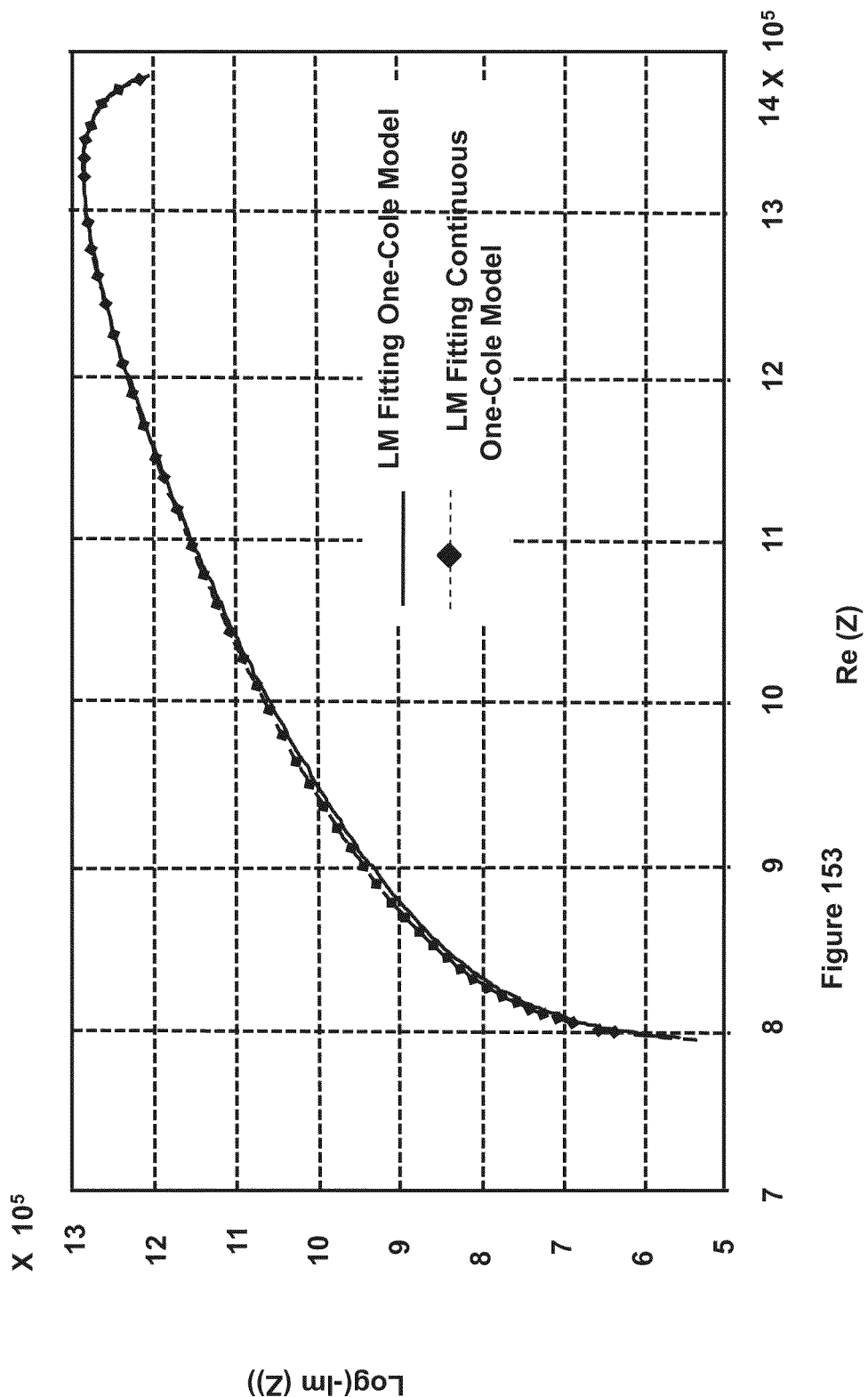
Figure 154:
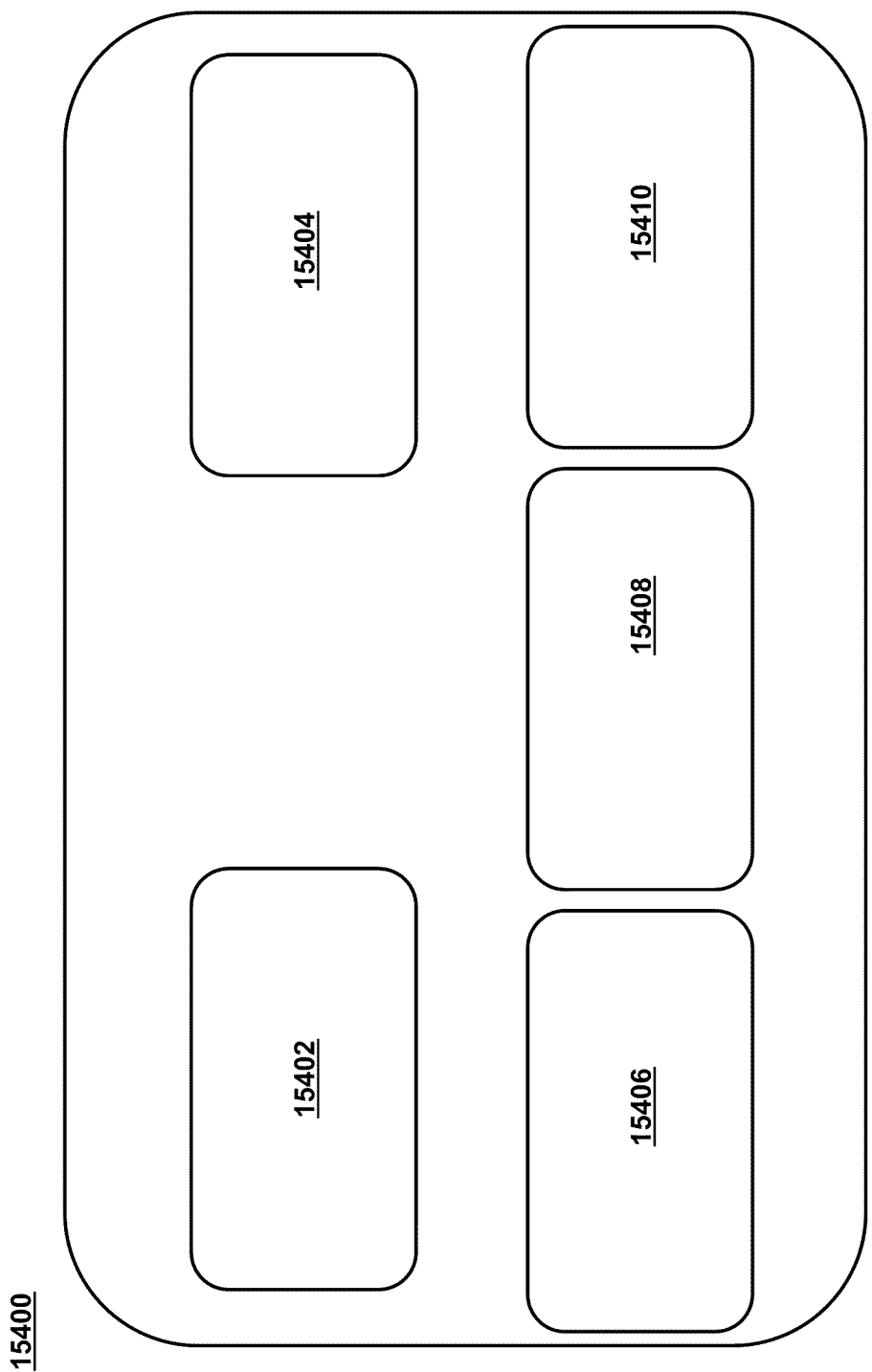

FIGS. 123A-B depict a first pair of plots for typical spectral data (or OMF diagrams) obtained by the device facilitating implementation of the OMF method on digital images of the given, selected first pair of samples at a given, selected first temperature for characterization of the same in magnetic and electric domains, in accordance with certain embodiments of the invention;

FIGS. 124A-B depict a second pair of plots for typical spectral data (or OMF diagrams) obtained by the device facilitating implementation of the OMF method on digital images of the given, selected second pair samples at a given, selected second temperature for characterization of the same in magnetic and electric domains, in accordance with certain embodiments of the invention;

FIGS. 125A-B depict plots possessing specifications and associated analytical information including Wavelength Difference Value, Intensity Value); horizontal X-axis includes a closed interval of Wavelength Difference Values in accordance with certain embodiments of the invention;

FIGS. 126A-B depict a fourth pair of plots for typical spectral data (or OMF diagrams) obtained by the device facilitating implementation of the OMF method on digital images of the given, selected fourth pair of samples at a given, selected fourth temperature for characterization of the same in magnetic and electric domains, in accordance with certain embodiments of the invention;

FIGS. 127A-B depict a fifth pair of plots for typical spectral data (or OMF diagrams) obtained by the device facilitating implementation of the OMF method on digital images of the given, selected fifth pair of samples at the given, selected second temperature and under the influence a given, selected magnetic flux density for a given, selected time duration for characterization of the samples in magnetic and electric domains, in accordance with certain embodiments of the invention;

FIGS. 128A-B depict a sixth pair of plots for typical spectral data (or OMF diagrams) obtained by the device facilitating implementation of the OMF method on digital images of the given, selected sixth pair of samples at the given, selected second temperature and under the influence a changeable (or exchangeable) magnetic flux density (or magnetic field intensity) for characterization of the samples in magnetic and electric domains, in accordance with certain embodiments of the invention;

FIG. 129A is a block diagrammatic view of a system facilitating implementation of an Opto-Magnetic process based on light-matter interaction using digital imaging for analysis of skin samples, designed and implemented in accordance with certain embodiments of the invention;

FIG. 129B is an exploded diagrammatic representation of the IS 12900 designed and implemented in accordance with at least some embodiments;

FIG. 130A is an exploded diagrammatic representation of the host computing subsystem, of the FIG. 129A, comprising an Opto-Magnetic Fingerprint (or OMF) Generator sub-module designed and implemented in accordance with at least some embodiments;

FIG. 130B is a top view of the IS 12900 assembly illustrated in conjunction with FIG. 129A;

FIG. 130C depicts a cross-sectional view of the IS 12900 along a section line D-D thereof;

FIG. 130D is an exploded view of Optoelectronics sub-assembly, constituting the IS 12900 assembly, designed and implemented in accordance with certain embodiments of the invention;

FIG. 130E is an exploded view of handle and cradle sub-assembly, constituting the constituting the IS 12900 assembly, designed and implemented in accordance with certain embodiments of the invention;

FIG. 130F is an exploded view of the Optoelectronics sub-assembly incorporated in the handle and cradle sub-assembly, designed and implemented in accordance with certain embodiments of the invention;

FIG. 131 depicts a flow diagram delineating at least one process implemented by the system configuration of FIGS. 129A-B and 130A-F thereby facilitating estimation of skin sample type and properties (or characteristics) thereof and creation of a unique spectral signature;

FIG. 132A is a block diagrammatic view of a system facilitating implementation of an Opto-Magnetic process based on light-matter interaction using digital imaging for analysis of skin samples, designed and implemented in accordance with certain embodiments of the invention;

FIG. 132B is an exploded diagrammatic representation of the IS 13200 designed and implemented in accordance with at least some embodiments;

FIG. 133A is an exploded diagrammatic representation of the host computing subsystem, of the FIGS. 132A-B, comprising an Opto-Magnetic Fingerprint (or OMF) Generator sub-module designed and implemented in accordance with at least some embodiments;

FIG. 133B depicts a sample embodiment of an optoelectronics apparatus designed and implemented in accordance with at least some embodiments;

FIG. 134 depicts a flow diagram delineating at least one process implemented by the system configuration of FIGS. 132A-B and 133A-B thereby facilitating estimation of skin sample type and properties (or characteristics) thereof and creation of a unique spectral signature;

FIG. 135 is a block diagrammatic view of an improved system facilitating implementation of an Opto-Magnetic process based on light-matter interaction using lens-free digital imaging for analysis of skin samples, designed and implemented in accordance with certain embodiments of the invention;

FIG. 136 is a block diagrammatic view of a system facilitating implementation of an Opto-Magnetic process based on light-matter interaction using digital imaging for characterization of samples of skin, designed and implemented in accordance with certain embodiments of the invention;

FIG. 137 is an exploded diagrammatic representation of the host computing subsystem, of the FIG. 136, comprising an Opto-Magnetic Fingerprint (or OMF) Generator submodule designed and implemented in accordance with at least some embodiments;

FIG. 138 depicts a flow diagram delineating at least one process implemented by the system configuration of FIGS. 136 and 137 thereby facilitating estimation of skin test sample type and properties (or characteristics) thereof and creation of a unique spectral signature;

FIG. 139 is a cross-sectional anatomical view of the epidermis with four main layers, basement membrane and other structures including, but not limited to, melanocyte, Langerhans cell, in accordance with the prior art and adapted therefrom;

FIGS. 140A-C depicts three distinct snapshots of epidermis of human skin, and layers thereof, juxtaposed to each other, in accordance with the prior art and adapted therefrom;

FIG. 141A depicts a first plot of a typical spectral data (or OMF diagram) obtained on implementation of the OMF method on digital images of skin layers, confined to the inner arm region, captured from a given, selected first sample procured from a given, selected first male subject or volunteer aged 11 years, in accordance with certain embodiments of the invention;

FIG. 141B depicts a second plot of a typical spectral data (or OMF diagram) obtained on implementation of the OMF method on digital images of the Layer "1" of skin, disclosed in conjunction with FIG. 139, and confined to the inner arm region, in which the digital images captured from a given, selected second sample procured from the given, selected first male subject or volunteer aged 11 years, in accordance with certain embodiments of the invention;

FIG. 141C depicts a third plot of a typical spectral data (or OMF diagram) obtained on implementation of the OMF method on digital images captured from of a given, selected third sample procured from a third selected layer confined to the inner arm region, of skin of the given, selected first male subject or volunteer aged 11 years, in accordance with certain embodiments of the invention;

FIG. 141D depicts a fourth plot of a typical spectral data (or OMF diagram) obtained on implementation of the OMF method on digital images captured from of a given, selected fourth sample procured from a fourth selected layer confined to the inner arm region of skin of the given, selected first male subject or volunteer aged 11 years, in accordance with certain embodiments of the invention;

FIG. 142A depicts a fifth plot of a typical spectral data (or OMF diagram) obtained on implementation of the OMF method on digital images captured from of a given, selected fifth sample procured from the given, selected first layer confined to the inner arm region of skin of the given, selected second male subject or volunteer aged 63 years, in accordance with certain embodiments of the invention;

FIG. 142B depicts a sixth plot of a typical spectral data (or OMF diagram) obtained on implementation of the OMF method on digital images captured from of a given, selected sixth sample procured from the given, selected second layer confined to the inner arm region of skin of the given, selected second male subject or volunteer aged 63 years, in accordance with certain embodiments of the invention;

FIG. 142C depicts a seventh plot of a typical spectral data (or OMF diagram) obtained on implementation of the OMF method on digital images captured from of a given, selected seventh sample procured from the given, selected third layer confined to the inner arm region of skin of the given, selected second male subject or volunteer aged 63 years, in accordance with certain embodiments of the invention;

FIG. 142D depicts an eighth plot of a typical spectral data (or OMF diagram) obtained on implementation of the OMF method on digital images captured from of a given, selected eighth sample procured from the given, selected fourth layer confined to the inner arm region of skin of the given, selected second male subject or volunteer aged 63 years, in accordance with certain embodiments of the invention;

FIG. 143A depicts a ninth plot of a typical spectral data (or OMF diagram) obtained on implementation of the OMF method on digital images captured from of a given, selected ninth sample procured from the given, selected first layer confined to the inner arm region of skin of the given, selected third male subject or volunteer aged 50 years, in accordance with certain embodiments of the invention;

FIG. 143B depicts a tenth plot of a typical spectral data (or OMF diagram) obtained on implementation of the OMF method on digital images captured from of a given, selected tenth sample procured from the given, selected second layer confined to the inner arm region of skin of the given, selected third male subject or volunteer aged 50 years, in accordance with certain embodiments of the invention;

FIG. 143C depicts an eleventh plot of a typical spectral data (or OMF diagram) obtained on implementation of the OMF method on digital images captured from of a given, selected eleventh sample procured from the given, selected third layer confined to the inner arm region of skin of the given, selected third male subject or volunteer aged 50 years, in accordance with certain embodiments of the invention;

FIG. 143D depicts a twelfth plot of a typical spectral data (or OMF diagram) obtained on implementation of the OMF method on digital images captured from of a given, selected twelfth sample procured from the given, selected fourth layer confined to the inner arm region of skin of the given, selected third male subject or volunteer aged 50 years, in accordance with certain embodiments of the invention;

FIG. 144A depicts a thirteenth plot of a typical spectral data (or OMF diagram) obtained on implementation of the OMF method on digital images captured from of a given, selected thirteenth sample procured from the given, selected first layer confined to the inner arm region of skin of the given, selected fourth male subject or volunteer aged 43 years, in accordance with certain embodiments of the invention;

FIG. 144B depicts a fourteenth plot of a typical spectral data (or OMF diagram) obtained on implementation of the OMF method on digital images captured from of a given, selected fourteenth sample procured from the given, selected second layer confined to the inner arm region of skin of the given, selected fourth male subject or volunteer aged 43 years, in accordance with certain embodiments of the invention;

FIG. 144C depicts a fifteenth plot of a typical spectral data (or OMF diagram) obtained on implementation of the OMF method on digital images captured from of a given, selected fifteenth sample procured from the given, selected third layer confined to the inner arm region of skin of the given, selected fourth male subject or volunteer aged 43 years, in accordance with certain embodiments of the invention;

FIG. 144D depicts a sixteenth plot of a typical spectral data (or OMF diagram) obtained on implementation of the OMF method on digital images captured from of a given, selected sixteenth sample procured from the given, selected fourth layer confined to the inner arm region of skin of the given, selected fourth male subject or volunteer aged 43 years, in accordance with certain embodiments of the invention;

FIG. 145 depicts a three-dimensional (or 3-D) Atomic Force Microscopy (or AFM) image of skin on removal of the Layer "3", in accordance with certain embodiments of the invention;

FIG. 146A depicts a seventeenth plot of a typical spectral data (or OMF diagram) obtained on implementation of the OMF method on digital images captured from of a given, selected seventeenth sample procured from the given, selected third layer confined to the inner arm region of skin of the given, selected first male subject or volunteer aged 11 years, in accordance with certain embodiments of the invention;

FIG. 146B depicts an eighteenth plot of a typical spectral data (or OMF diagram) obtained on implementation of the OMF method on digital images captured from of a given, selected eighteenth sample procured from the given, selected third layer confined to the inner arm region of skin of the given, selected second male subject or volunteer aged 63 years, in accordance with certain embodiments of the invention;

FIG. 146C depicts an nineteenth plot of a typical spectral data (or OMF diagram) obtained on implementation of the OMF method on digital images captured from of a given, selected nineteenth sample procured from the given, selected third layer confined to the inner arm region of skin of the given, selected third male subject or volunteer aged 50 years, in accordance with certain embodiments of the invention;

FIG. 146D depicts a twentieth plot of a typical spectral data (or OMF diagram) obtained on implementation of the OMF method on digital images captured from of a given, selected twentieth sample procured from the given, selected third layer confined to the inner arm region of skin of the given, selected fourth male subject or volunteer aged 43 years, in accordance with certain embodiments of the invention;

FIG. 147 depicts a graphical representation of bioimpedance versus skin layers obtained on implementation of bioimpedance measurements on one or more samples procured from corresponding one or more layers confined to the inner arm region of skin of the given, selected first and second male subjects aged 11 and 63 years, in accordance with certain embodiments of the invention;

FIG. 148 is a block diagrammatic view of a system facilitating implementation of a process using a pair of electrodes for measurement of skin impedance, designed and implemented in accordance with certain embodiments of the invention;

FIG. 149 depicts an equivalent circuit Cole mathematical model for calculation of the electrical impedance of the skin, partly in accordance with the prior art and adapted therefrom;

FIG. 150 depicts a plot for bioimpedance of human skin for a voltage amplitude of 0.1V and diameter of electrodes is 2 cm:

FIG. 151 depicts a plot for a robust fit one-Cole model, "bisquare"-method, designed and implemented in accordance with certain embodiments of the invention;

FIG. 152 depicts a plot for Levenberg-Marquardt nonlinear least squares fit one-Cole model, in accordance with certain embodiments of the invention;

FIG. 153 depicts a plot for Levenberg-Marquardt nonlinear least squares fit one-Cole and continuous one-Cole model for $\zeta=0.20$, "log-log"-plot; and FIG. 154 is a block diagrammatic view of a system facilitating organ (or bio) printing deployed in conjunction with the system configuration of FIGS. 129A-B and 130A-F, designed and implemented in accordance with certain embodiments of the invention.

DETAILED DESCRIPTION

Provided herein may be methods, systems, and a device for dermal and non-dermal imaging. Throughout this disclosure the phrase "such as" means "such as and without limitation". Throughout this disclosure the phrase "for example" means "for example and without limitation". Throughout this disclosure the phrase "in an example" means "in an example and without limitation". Throughout this disclosure, the term "product" refers to any medical, non-medical, cosmetic, skin, hair, or nail care product. Generally, any and all examples may be provided for the purpose of illustration and not limitation.

Real-time analysis of digitally captured skin-related and other information may facilitate real-time skin condition assessment, real-time skin regimen recommendation, and real-time evaluation of the effectiveness of a selected skin regimen. Real-time analysis of digitally captured data may be performed by using a skin care device embodying the principles of the invention disclosed herein. A skin care device embodying the principles of the invention may include, for example, an electromagnetic radiation source capable of directing incident electromagnetic radiation, a radiation detector for measuring various parameters of the re-emitted radiation, and a skin condition analysis module capable of generating a skin condition assessment in real-time.

The skin condition assessment may be cosmetic and/or medical in nature. By way of example, and in no way limiting the scope of the invention, the skin condition assessment may include any one of an acne condition assessment, a pore condition assessment, a wrinkle condition assessment, a skin elasticity assessment, a skin oiliness assessment, a skin moisture assessment, a skin luminosity assessment, a skin sebum assessment, a skin redness assessment, a skin inflammation assessment, a skin texture assessment, a skin color assessment or any combination of the listed assessments. For example, the pore condition assessment can help in determining whether the pores are clean, open and of optimal health.

Skin-condition data may be acquired, for example, by directing incident electromagnetic radiation to a location, such as a pin-point location, on the skin of a person and detecting the re-emitted radiation from the location by using a radiation detector. The effectiveness of generating high-quality, real-time skin condition assessments may be enhanced in some embodiments by using a skin condition analysis module that bases its analysis at least partly on diffused reflectance spectroscopy. The quality of real-time skin condition assessments may be further enhanced in other embodiments by using white light as the incident radiation and by detecting the red-green-blue components of the re-emitted light.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional signal and applying standard signal-processing techniques to it.

Image processing usually refers to digital image processing, but optical and analog image processing are also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Likewise, the term "digital imaging or digital image acquisition" refers to creation of digital images, typically from a physical object. The term is often assumed to imply or include the processing, compression, storage, printing and display of such images.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

Figure 1:
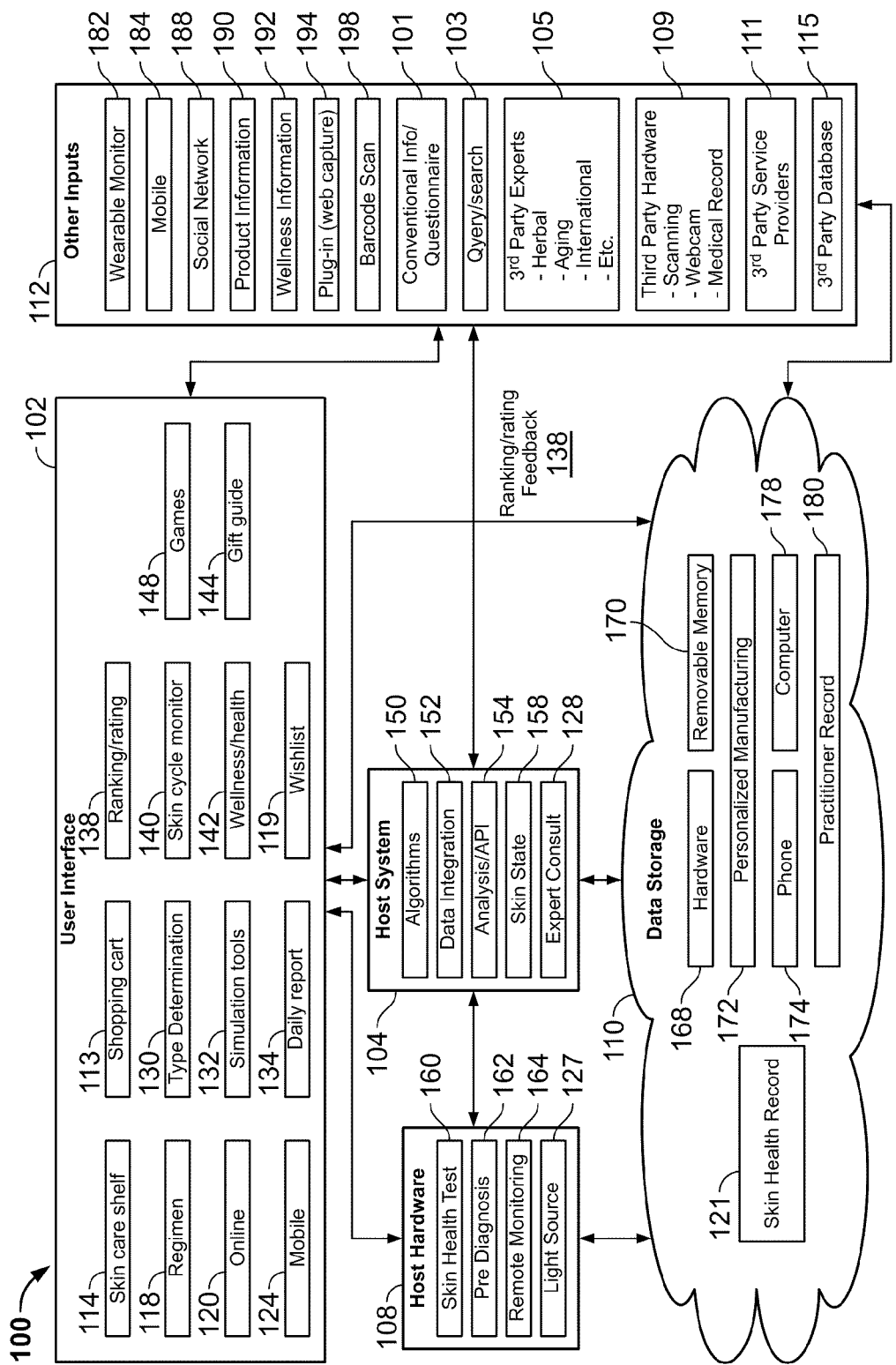
FIG. 1 depicts a skin care system for skin health analysis and monitoring, and skin care assessment and recommendation.

Referring to FIG. 1, a system for skin health analysis, monitoring, and recommendation may comprise host hardware 108, such as an imaging device 108, for capturing biophysical skin properties such as in a skin health test 160, performing pre-diagnosis 162, and performing remote monitoring 164 using a light source 127; a user interface 102 interfacing with the host hardware 108, an online platform 120, or a mobile platform 124 for capturing demographic information, additional anecdotal information on skin health, current skin care regimen 118, rankings and ratings 138 of current skin care products and regimen, populating a skin care shelf 114, and accessing a skin cycle monitor 140, health and/or wellness information 142, games 148, a gift guide 144, a wishlist 119, a Daily Report 134, simulation tools 132, a type determination engine 130, a shopping cart 113, and the like; a host system 104 for processing and analyzing captured information such as by employing an algorithm 150, obtaining an expert consultation 128, data integration 152, and analysis tools/API's 154 to define a skin state 158; other inputs 112 to the host system 104, which may be subject to ranking/rating feedback 138, for providing additional granularity in identifying, monitoring, and adjusting a skin state 158, such as a wearable monitor 182, a mobile communications device 184, a social network 188, product information 190, wellness information 192, a plug-in (web capture) 194, a barcode scan 198, conventional information/questionnaire answers 101, a query/search 103, third part experts 105, third party hardware 109, third part service providers 111, and the like; and data storage 110 for storing data from the host hardware 108, host system 104, user interface 102, and other inputs 112, such as hardware 168, removable memory 170, a wireless communication device 174, a computer 178, a practitioner record 180 such as a dermatologist, general physician, aesthetician, spa employee, salon employee, cosmetic salesperson, and the like, a personalized manufacturing record 172, and the like. While dermal embodiments are contemplated throughout this disclosure, except where context prohibits such embodiments should be understood to encompass non-dermal embodiments, such as and without limitation any hair, nail, agricultural, veterinary, internal, biological and non-biological embodiments.

An imaging device 108 may be used to capture images of skin structures to obtain biophysical skin properties such as in a skin health test 160, a pre-diagnosis 162, remote monitoring 164, and the like. The imaging device 108 may also be adapted to capture images of non-dermal structures, such as hair, nails, teeth, eyes, internal organs and structures, and the like. The imaging device 108 may use an internal or external light source 127 to provide a specific sequence of irradiation using unpolarized light, such as diffusion light, white light, monochromatic light, light of multiple single wavelengths, and the like, then polarized light in order to obtain data on skin structures. In embodiments, the incident light may be polarized or unpolarized and the reflected or re-emitted light may be polarized or unpolarized. The polarized light may result from the reflection on the skin and is not polarized from the light source. The capture and storage of the reflections enables the imaging and analysis of skin lesions, as well as all types of skin diseases, skin problems, and cosmetic concerns and indications. Analysis of polarized reflections may enable obtaining thermal, electrical, and magnetic properties of the imaged skin area. The images may be transmitted to an analysis facility 154, analyst, practitioner and the like, which may also include assessment with patient questionnaires, to determine a final analysis of skin health. The device 108 may also employ specific targeted wavelengths, such as in the red, green, and blue areas, to identify key features, based on spectroscopic and quantitative analysis of skin lesions. The device 108 may be used with diffused reflectance techniques, as well as with color imaging analysis based on indirect results from spectroscopic techniques (DR, SF, etc). In embodiment, the device 108 may be adapted to emit polarized light. The device 108 may be adapted to emit more than one type of light and may be able to switch among or combine various light sources 127. The skin health analysis may be compared with a previous user skin health analysis, other users' skin health analysis, other users' experience data, and ingredient, product, and regimen characteristics to provide a recommendation for and track the effectiveness of a product or regimen 108.

Figure 2:
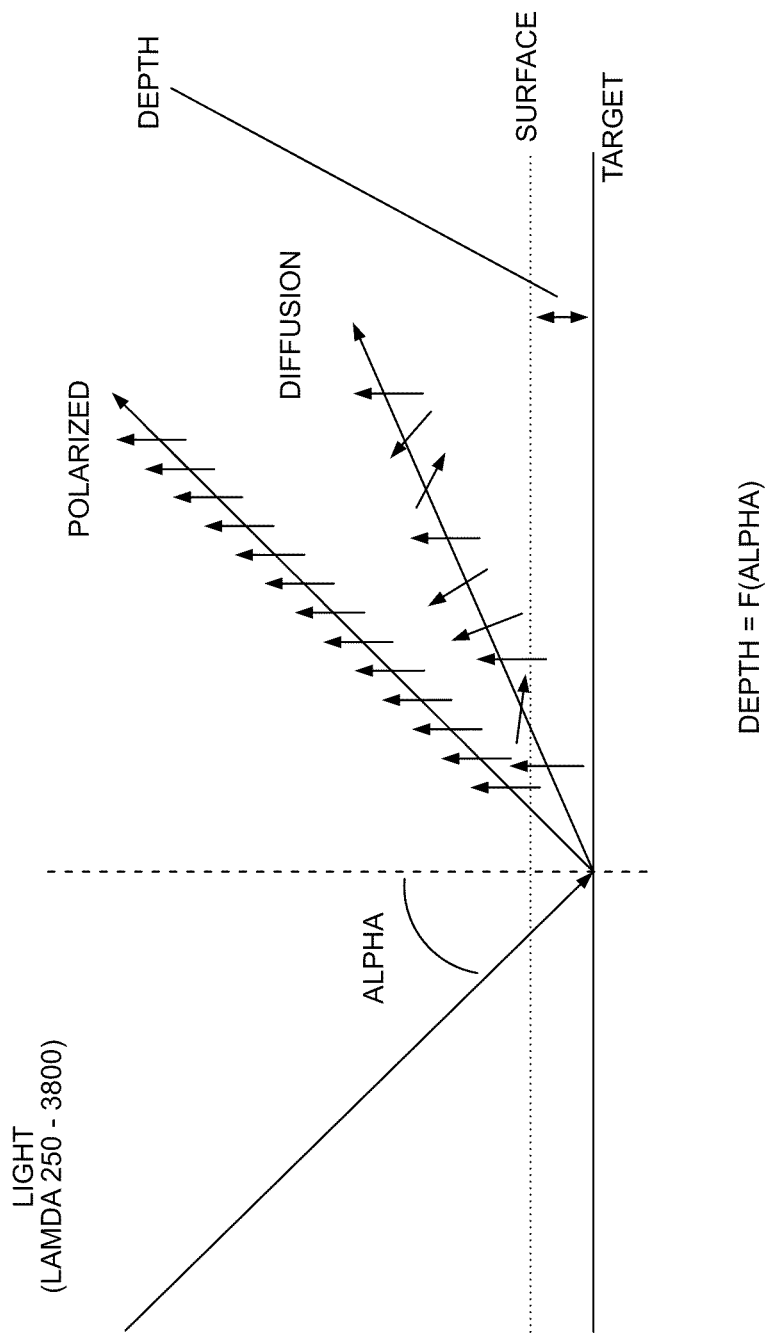
FIG. 2 depicts a mechanism for light polarization by a skin structure.

Referring now to FIG. 2, in an embodiment, the imaging device 108 may comprise an illumination source 127 to direct unpolarized light, diffusion light, white light, monochromatic light, light of multiple single wavelengths, polarized light, and the like, upon the skin at an angle alpha, a sensor for detecting reflected or re-emitted light from a skin structure, and an image storage device for storing and transmitting the captured images. A skin structure may be at least one of a cell, a molecule, a group of cells, a group of molecules, an epidermis and sublayers, a basement membrane, a dermis', a subcutis, a gland, a stratum, a follicle, a pore, a vascular component, and the like resident within the skin. In an embodiment, the light source may be white light for generating reflected or re-emitted light and diffuse emission, such as polarized light, to measure the electrical and magnetic components of the skin. White light may be emitted as a combination of wavelengths of light across the spectrum of visible light. Incident unpolarized light may be directed at its target at a defined angle 'alpha' from vertical. As the value of alpha changes, such as and without limitation over a range of 0 to 90 degrees from vertical, incident unpolarized light may interact with different structural elements of the skin since varying the angle of incidence affects the depth of penetration. The angle alpha may be changed by changing the position of the light source, either manually, through a remote control, through a user interface 102, and the like. The relationship between depth of penetration and alpha may be defined by the formula depth=f(alpha). For each skin structure which may correspond to a particular known depth within the skin, there may be a specific angle of incidence which produces a full polarized reflection. By analyzing the reflected or re-emitted light and/or diffuse emission, either polarized and/or diffusion, information on the underlying skin structures responsible for the reflection and/or re-emission may be obtained. The diffuse emission occurs because there is scattering and absorption that occurs from light bouncing around in the substructures. The polarization of the light may be due to classical/quantum effects of skin structures interacting water. That is, skin structures possess enough of a magnetic and electric field to be able to alter the polarization of light as it strikes the structures and to affect the wavelength of light as it strikes the structures. An aspect of the polarization of the reflected or re-emitted light, such as an orientation, an amplitude, a phase, an angle, a shape, a degree, an amount, and the like, may correlate with various measures associated with the particular skin structures targeted, and ultimately, a skin state 158. For example, a lesion present in a particular skin structure may cause the diffusion of a portion of the reflected or re-emitted light resulting in reflected or re-emitted light that is partially polarized and partially diffused. For example, collagen structures are one indicator of a biological difference between a benign and a malignant melanocytic skin lesion. The collagenous differences may affect the polarization state of reflected or re-emitted light, and the resultant images may indicate locations of tumor center and tumor periphery. Such images may aid a practitioner in visualizing excision margins, as will be further described herein. Because melanocytes are located at the lower part of the epidermis, the appropriate wavelength may be selected for this depth as well as for the chromophores within the various types of nevi.

If incident light is polarized, only the electrical properties of skin will be apparent but unpolarized incident light may reveal both the electrical and magnetic properties of skin. While using polarized light may generate improved induction of optical activity, the data sets generated may be of less value as compared to the data sets captured using incident unpolarized light, such as white light, a monochromatic light, light of multiple single wavelengths, and the like. By measuring the effects between 10E-34 and 10E-30 Js, one can make measurements at the border area of quantum and classical physics effects on the skin and as a difference of action of electrical and magnetic forces of valence electrons of skin's biomolecules.

In an embodiment, the wavelength and/or intensity of the incident light may be modified in order to measure the presence of specific molecules, such as collagen, elastin, cadherin, hemoglobin, and the like. Certain molecules possess the property of endogenous fluorescence. For example, if incident light is limited to a particular wavelength, such as 325 nm, collagen may be detected at an emission wavelength of 400 nm and 405 nm. Table 1 lists certain illustrative examples of excitation and emission maxima of biological molecules that exhibit endogenous fluorescence, such as amino acids, structural proteins, enzymes and coenzymes, vitamins and vitamin derivates, lipids, porphyrins, and the like. To detect the presence of specific molecules in the skin, a user may shine a light of a specified wavelength, such as and without limitation those shown in the excitation maxima column, onto the skin and collect reflected or re-emitted light to identify the presence of specific emission wavelengths in the reflections. It may be understood by one knowledgeable in the art that many different single wavelengths and combinations of wavelengths of light may be used to illuminate the skin.

| ENDOGENOUS FLUORESCENCE | | EXCITATION MAXIMA (NM) | EMISSION MAXIMA (NM) |
|---|---|---|---|
| AMINO ACIDS | TRYPTOPHAN | 280 | 350 |
| | TYROSINE | 275 | 300 |
| | PHENYLALANINE | 260 | 280 |
| STRUCTURAL PROTEINS | COLLAGEN | 325 | 400, 405 |
| | ELASTIN | 290, 325 | 340, 400 |
| ENZYMES AND COENZYMES | FAD, FLAVINS | 450 | 535 |
| | NADH | 290, 351 | 440, 460 |
| | NADPH | 336 | 464 |
| VITAMINS | VITAMIN A | 327 | 510 |
| | VITAMIN K | 335 | 480 |
| | VITAMIN D | 390 | 480 |
| VITAMIN B6 COMPOUNDS | PYRIDOXINE | 332, 340 | 400 |
| | PYRIDOXAMINE | 335 | 400 |
| | PYRIDOXAL | 330 | 385 |
| | PYRIDOXIC ACID | 315 | 425 |
| | PYRIDOXAL 50-PHOSPHATE | 330 | 400 |
| | VITAMIN B12 | 275 | 305 |
| LIPIDS | PHOSPHOLIPIDS | 436 | 540, 560 |
| | LIPOFUSCIN | 340-395 | 540, 430-460 |
| | CEROID | 340-395 | 430-460, 540 |
| PORPHYRINS | | 400-450 | 630, 690 |

FAD, flavin adenine dinucleotide; NADH, reduced nicotinamide adenine dinucleotide; AND(P)H, reduced nicotinamide adenine dinucleotide phosphate.

In an embodiment, light may be emitted at any wavelength, such as across the range from 280 nm to 3800 nm. Incident light may be blue, yellow, orange, red, or some other light.

Continuing to refer to FIG. 1, in an embodiment, the light source may be integral to the device 108 or provided from an associated source. The light source may be a light-emitting or laser diode (LED) of any wavelength, such as and without limitation 280, 340, 360, 385, 405, 395, 400, or 480 nm incident excitation wavelengths, as well as infrared and near-infrared. Wavelengths in the ultraviolet and infrared ranges may also be emitted by the device 108. The light source may be diffusion light, white light, monochromatic light, light of multiple single wavelengths, incandescent, electroluminescent, fluorescent, halogen, ultraviolet, polarized light, collimated light, light provided by a wireless communications device, light provided by a fiber optic cable, and the like. In an embodiment, the light source may comprise a diffuser to provide diffuse incident light.

In an embodiment, a sensor for detecting reflected or re-emitted light from the skin may be embodied in optics resident in a CCD camera, CMOS-based imaging system, digital camera, webcam, camera embedded in a communications device such as a cell phone or iPhone, PDA (Personal Digital Assistant), a watch or other wearable device for continuous monitoring of the skin as in a sports-type indication, a third party device, a scanner, and the like. The sensor may be adapted to absorb any wavelength of light, such as near IR or visible wavelengths. The sensor may be adapted to automatically filter out particular wavelengths. The sensor may be adapted to image any size area, such as a small portion of the skin, the full face, a complete cutaneous examination, and the like. The sensor may be adapted to operate without any intervening fluids between the device 108 and the area of concern, or may be used with an oil-like application or other reflective media to the area of concern. The sensor may be adapted to detect reflected or re-emitted light, from any distance from the area or when in contact with the area of concern, which may be used for subsequent visual and/or algorithmic analysis. The images generated from this reflected or re-emitted light may be considered both visual as well as spectroscopically resolved images or electromagnetic skin maps. The sensor may have an internal calibration scale that enables measuring the size of the region being imaged as well as the distance from the imaged area. In an embodiment, a lens may focus the reflected or re-emitted light from the detection optics onto a visible-NIR sensitive CCD, CMOS, or other sensory device. In an embodiment, the sensor may be adapted to acquire images at a high frame rate. In an embodiment, the device may possess a high magnification lens.

In an embodiment, the device 108 may store captured images for analysis and/or transmittal to an analysis facility 154. The analysis facility 154 may be a practitioner, an automated analysis tool, a practitioner employing analysis tools, and the like. Data storage 110 may occur manually when image capture is initiated, may occur automatically upon contact with the skin, may be remotely controlled, and the like. Data may be stored in an internal device memory 168 or may be stored externally in memory media 170 such as USB memory, an external hard drive, a mass storage device, and the like. The device may be able to connect externally, either through a wired connection or wirelessly, to a computer, such as a laptop, kiosk, desktop computer, central server, and the like. For example, the connection may be a direct USB connection. When the device 108 is connected to the computer, captured data may be downloaded or transmitted either automatically or upon manual initiation from the device 108 to the computer. For example, the device 108 may have a cradle in connection with a computer. When the device 108 is placed in the cradle, data may be transmitted or downloaded from the device 108. Additionally, the device 108 may receive software updates when connected to the computer, such as through the cradle. In embodiments, the device 108 may have no internal storage and may only be able to transmit or store data externally through a persistent hard-wired or wireless connection. Data transmittal and storage may be a fully automated process or may be manually operated. Data may be transmitted over a wireless network connection, a cellular connection, a wired connection, a Bluetooth connection, and the like. Data transmittal from the device 108 may enable remote assessment techniques. In an embodiment, non-image data may also be stored and/or transmitted by the device 108 as described herein, such as voice responses, text responses, video data, and the like. The device 108 may have an internal microphone to record audio, a video camera to record video, a keyboard input to record text responses, and the like. In an embodiment, the device 108 may use externally available audio and video.

In an embodiment, data storage may be in a skin health record 121. The skin health record 121 may be an object or database or repository for an individual that contains information on key medical, non-medical, and cosmetic indications related to a user's skin. This may comprise images, graphics, icons, written history, personal demographic information, levels of cosmetic conditions such as moisture, elasticity, firmness, texture, color level, or non-medical conditions such as inflammation, and the like. A user may self-populate the record 121 with data from any device 108, 109 or input 112. The record 121 may contain a history of skin concerns, comments, a user blog, and the like. In an embodiment, the skin health record 121 may auto-populate upon acquisition of an image. For example, when a user submits their first image for analysis, a record 121 may be automatically created and populated with information, which may be edited, derived from the image and its analysis.

In an embodiment, data storage 110 may occur in a practitioner record 180. A practitioner record 180 may be a repository of key health characteristics including background demographic data, personal information, information on diet, skin health record 121 and the like. It may have embedded images, links to other image data files, tracking effectiveness of personal skin products, medical products, and OTC products and the like and their historical impact on key parameters. It may also capture community data or data of selected individuals who may be similar to the patient or user and may include rankings and comments and the like In an embodiment, data storage 110 may be in a personalized manufacturing record 172. Based on the skin health measurement 160, product ingredients to obtain a desired effect to make the skin healthy may be selected. This ingredient selection may be achieved by analyzing and tracking the change of various skin health parameters through the application of various products and ingredients through using the device 108 and tracking the change of the skin health over time through a personalized manufacturing record 172. Once the selected product ingredients are identified, they may be mixed to create a product best suited for the individual's skin characteristics and/or desired goals (such as improved moisturization). Thus a personalized product may be developed for the user. Additionally, this same process could be used for creation of specific customized skin products and ingredients for medical and non-medical purposes and conditions.

In an embodiment, the form of the data captured may be compatible with any standard image processing and manipulation software and techniques, word processing software, slideshow presentation, spreadsheet applications, and the like. For example, the captured data may be in any suitable image format, such as jpeg, tiff, pict, png, bmp, gif, pdf, and the like. In an embodiment, multiple images may be captured as a movie or a movie may be constructed from combining multiple images.

In an embodiment, the device 108 may be powered by any suitable source, such as an electric power plug, a battery, solar power, USB power, and the like. A user may initiate power to the device 108 in order to begin acquiring images. Acquisition may commence automatically, may commence when the device 108 is placed against the skin, may commence when a trigger, such as a button, is actuated by a user, and the like.

The device 108 may have a display for viewing the area to be imaged. For example, a user may use the display with positioning tools to obtain exact images over time, such as a series of images taken over different days. The display may be integral to the device 108 or may be a separate display. For example, the device 108 may be connected to a monitor, such as that of a computer, using a wired connection or a wireless connection. In an embodiment, a user interface 102 to the device 108 may display a real time view of the imaging.

Figure 55:
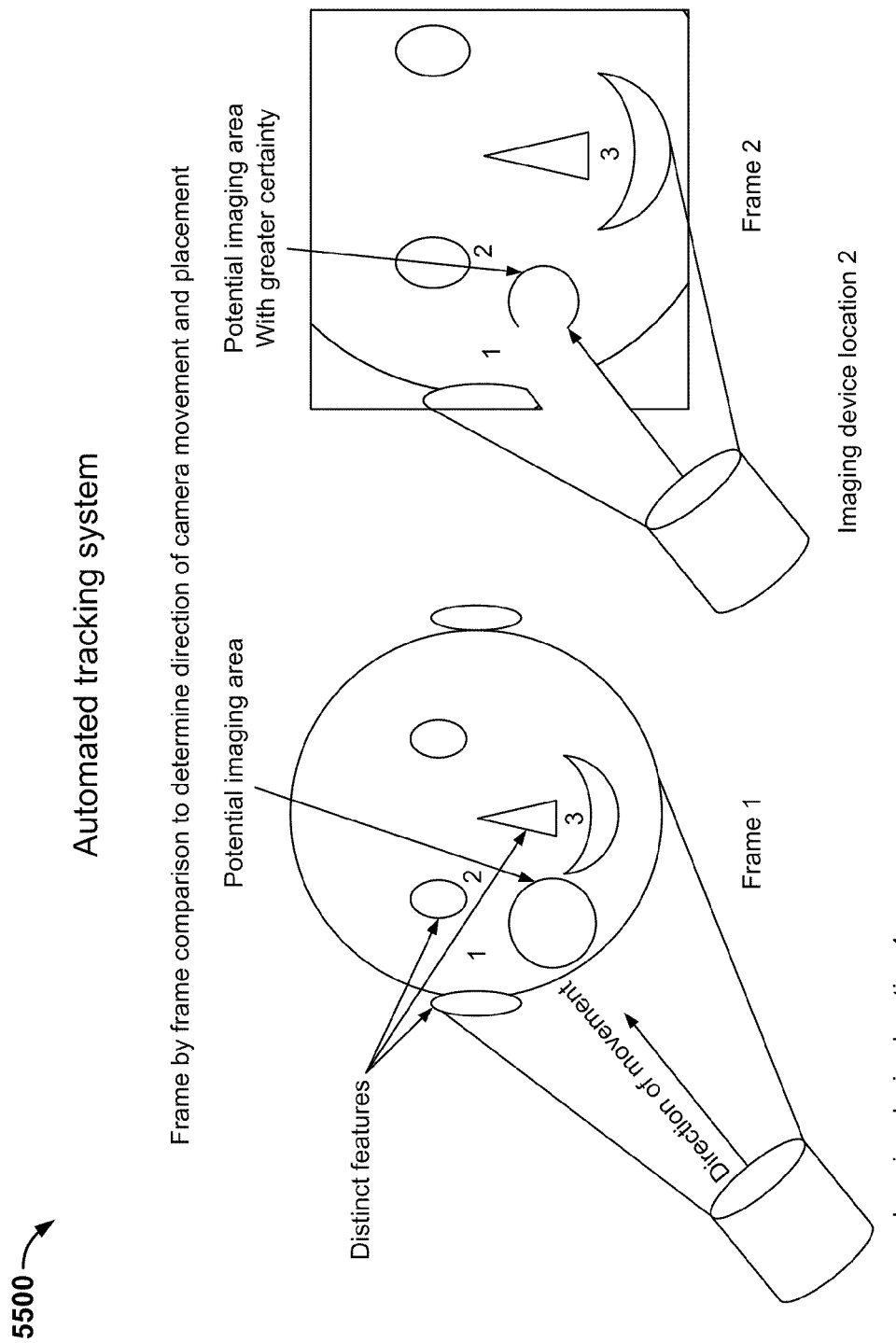
FIG. 55 depicts a system for tracking and targeting an image.

The positioning tools may enable tracking and targeting. Referring to FIG. 55, a method of tracking and targeting is depicted. The positioning tools may be used to track and store movement parameters of the imaging device 108 moving over a subject area. First, the device may capture an image of the subject area at a plurality of locations. Then, the device 108 may identify a direction of movement of the imaging device 108 using an image processing technique for at least one captured frame. The image processing technique may recognize the direction of movement of the imaging device by comparing each frame with at least three distinct features captured to thereby triangulate a location of the imaging device, as shown in FIG. 55. The data of the captured image may be compared with a predetermined image database to store the image of the subject area and to store placement parameters of the imaging device 108. If no entry exists in the database, a new entry may be made. The step of capturing the image of the subject area at a plurality of locations may include a sub-step of capturing a continuous video image of the subject area. The step of capturing the image of the subject area at a plurality of locations may include a sub-step of capturing a frame by frame sequence of images of the subject area. The step of identifying a direction of movement of the imaging device using an image processing technique may include a sub-step of a frame by frame comparison of the captured image to identify movement parameters of the imaging device. The step of recognizing the direction of movement of the imaging device by comparing each frame with at least three distinct features captured to triangulate a location of the imaging device may include a sub-step of capturing a direction of movement of the imaging device by comparing three or more distinct positions across different frames. The positioning tools may be an automated location tracking and data storage system for the imaging device 108, including an image capturing unit, a positioning unit coupled to the image capturing unit for positioning the imaging device on a subject area, and an image processing unit for enabling a frame by frame comparison of the captured image and for enabling the imaging device to capture three or more distinct points to triangulate a location of the imaging device to identify a direction of movement of the imaging device. The image capturing unit may include a digital camera. The image capturing unit may include at least one of a mobile device and a Personal Digital Assistant (PDA). The image processing unit may include a comparison unit for comparing positions of three or more distinct points across different frames to capture direction of movement of the imaging device. The automated location tracking and data storage system may further include a sub-system for measuring lateral motion of the image capturing unit from a predetermined point to a new location on the subject area.

In an embodiment, the device 108 may have security features in order to protect the privacy of user data. For example, the device 108 may have a unique MacID with encryption technology.

In an embodiment, the device 108 may be associated with peripherals or other functional attachments. For example, the device 108 may be associated with a blood pressure monitor or sensor, a heart rate monitor or sensor, and the like. For example, the device 108 may be used to perform a pre-diagnosis 162 of a skin lesion while also monitoring other endpoints such as blood pressure, heart rate, and the like in order to assess other aspects of health in addition to skin health.

In an embodiment, the device 108 may be sized to permit a user to operate the device 108 in a handheld fashion. The device 108 may sized for portability. The device 108 may adapted for single-handed operation. For example, the device may be embodied as in FIGS. 4 A & B, but it may have multiple other embodiments in any shape and/or size, such as a mirror, a large device adapted to image a large area, a PDA, a scanner, a mobile communication device, and the like. In FIG. 4 A, the illumination source is visible as a ring of LED's around a central detection area. In both images, the size, handheld nature, and portability are clearly demonstrated. The ease of operation enables even an inexperienced user, such as a home user connected to a laptop, to employ the device 108. The device 108 may be a self-contained unit and not part of a larger camera system. In an embodiment, the device 108 may be designed for one handed ergonomic holding. In an embodiment, the device 108 may be used with or without application of reflective media. In an embodiment, the device 108 may be used to capture images at a distance, close-up, in direct contact, and the like. For example, software loaded on a computer interfaced with the device 108 may prompt for near distance and far distance image capture.

In an embodiment, the device 108 may also be a stand-alone, non-hand-held version, which may be used to take images or particular body components or materials.

In some embodiments of the skin care device, the device may be a miniature one, enabling portability and hand-held use. Some embodiments of the skin care device may be in the form of a hand-held and portable wand that can be conveniently moved across a skin region to be examined. Some other embodiments of the skin care device may be so miniaturized that no dimension of the skin care device exceeds six inches. Such skin care devices may be embedded in wearable accessories, for example, bracelets, necklaces, ear-rings, and the like. Some embodiments of the skin care device may have a convenient user interface and/or a display surface. In some embodiments of the skin care device, the device may be coupled to or embedded in a vertical display panel, for example but not limited to, a mirror, an LCD screen, a plasma screen, and the like.

Figure 47:
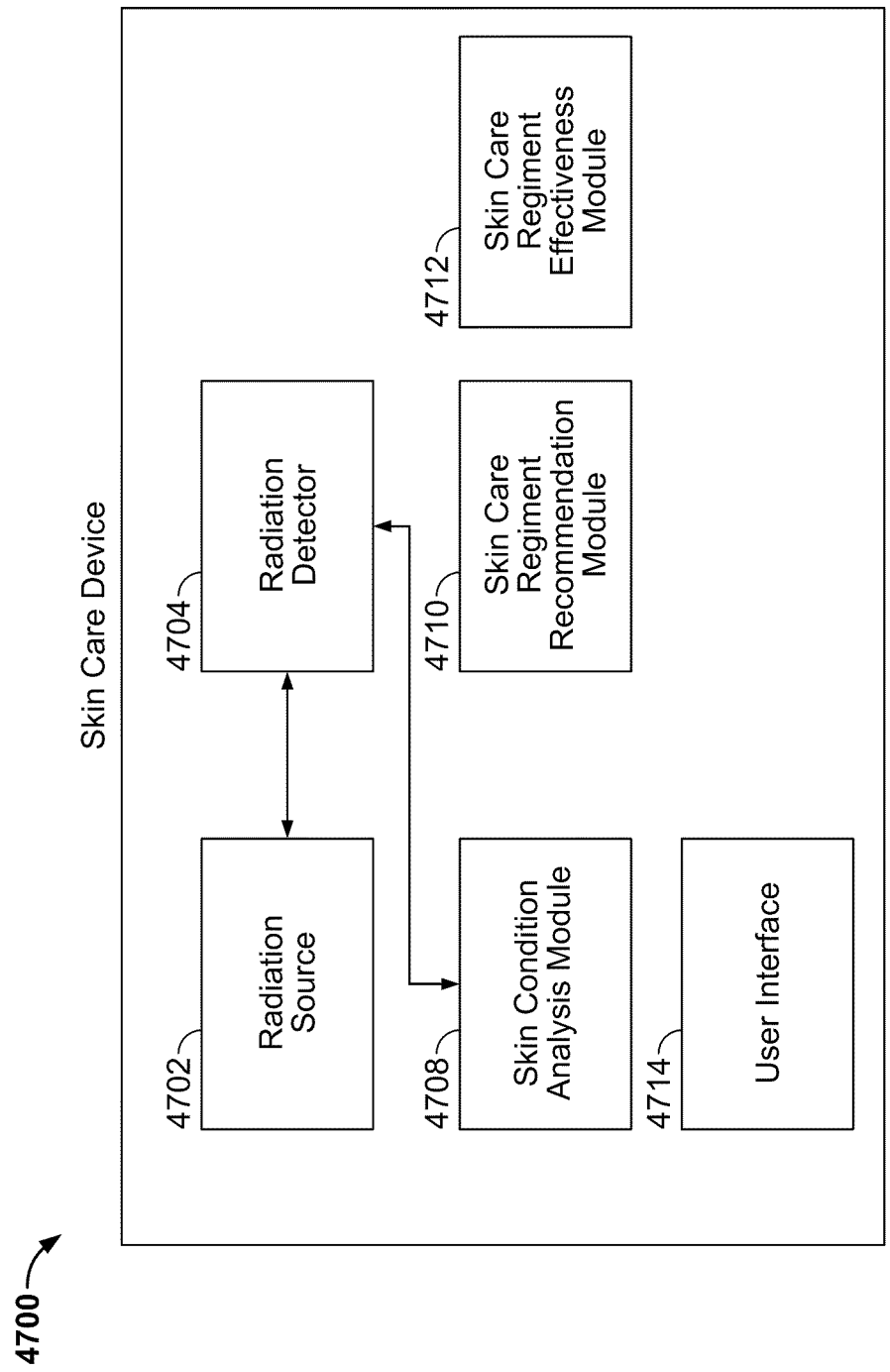
FIG. 47 depicts a block diagram of a skin care device embodiment.

Referring to FIG. 47, an exemplary skin care device 4700 embodying the principles of the invention is shown in a block diagram. The skin care device 4700 may include an electromagnetic radiation source 4702, a radiation detector 4704, and a skin condition analysis module 4708.

The electromagnetic radiation source 4702 may be capable of directing incident electromagnetic radiation to one or more locations on the skin of a person. For example, and not by way of limitation, the radiation source 4702 may be a set of light emitting diodes (LEDs). In certain embodiments, the incident radiation emitted by the radiation source 4702 may include radiation in the visible, near-infrared (NIR) and near-ultraviolet (NUV) spectrum. In certain other embodiments, the incident radiation may include white light.

As depicted in FIG. 47, the electromagnetic radiation source 4702 may be coupled to the radiation detector 4704. The radiation detector 4704 may be capable of detecting the radiation re-emitted from the location and measuring various radiation parameters of the re-emitted radiation. As shown in the FIG. 47, the radiation detector 4704 may be coupled to the skin condition analysis module 4708. A variety of radiation parameters may be detected by the radiation detector, including, for example but not limited to, degree of polarization, intensity of the radiation at different wavelengths, and the like. The electromagnetic radiation sources, radiation detectors, and the skin condition analysis module have been previously described herein.

The skin condition analysis module 4708 may be capable of analyzing the radiation parameters of the reflected radiation and other information to generate a skin condition assessment. The skin condition analysis module 4708 may be adapted to generate the skin condition assessment in real-time. In some embodiments, the radiation detector 4704 measures diffused reflectance. In some other embodiments, the incident radiation may be white light and the radiation detector 4704 may measure the red, green, and blue components of the re-emitted light.

In certain embodiments, the skin condition assessment may also be partly based on analysis of a photographic image of the skin location.

As used in the specification and the appended claims, the term "diffused reflectance" may refer to radiation, sometimes loosely referred to as light, scattered in many directions from target samples. Diffused reflectance is the complement to specular, or mirror-like, reflection. If a surface is completely non-specular, the reflected or re-emitted light will be evenly spread over the hemisphere surrounding the surface. Diffused reflectance stems from tiny irregularities on surfaces of targets and is the reflection of incident light from uneven or granular surfaces of targets such that incident light strikes the targets and is scattered over wide angles.

Some embodiments of the skin care device may have a memory module for storing the skin condition assessments and other data, such as with timestamps. Some embodiments of the skin care device may have a communication module for communicating the skin condition assessments and other data with timestamps to a remote computer. The communication of data may occur, for example, over a wire, wirelessly, using an internet, and the like. The skin condition assessments and other data may also be accessed in remote locations via mobile devices and/or computers. Such remote access may be particularly convenient for service providers, such as for example, dermatologists.

Some embodiments of the skin care device may have a user interface to enable a user to interact with the skin care device. The user interface may enable a user to give instructions to the device, for example, to analyze the available information to generate a real-time skin condition assessment of a skin location or a larger skin region. In some other embodiments, the user interface may be voice-operated providing the facility to give commands to the skin care device through speech commands. Other examples of user interfaces that may be used in the skin care device are graphical user interface (GUI), web-based user interface (WUI), command line interface, touch interface, and any combination of the above.

In certain embodiments, the user interface may also provide alerts to a user if any abnormal skin condition, such as for example, a clogged pore, is detected. The alerts may be in the form of a light signal, a beep, an email alert, an SMS alert, and the like. There may be other methods, such as a small electric tingle, a mark, a sound, and a light, a heat emitting signal, and the like, to alert users about skin conditions requiring user attention.

Some embodiments of the skin care device may have also have a display surface either for a more convenient and intuitive user interface and/or for viewing an image of a skin region and/or for viewing some useful skin-related information, for example, a skin condition assessment report, a skin regimen recommendation report, and/or a skin regimen effectiveness report. In some embodiments, the display surface and/or the user interface may be touch-sensitive to enable touch-control of the device.

In some embodiments, the skin condition assessment data of locations may be overlaid on an image of a larger skin region displayed on the display surface, providing a useful picture of the health of the entire skin region in a single view.

Some embodiments of the skin care device may also have an access restriction module restricting access to patient data to authorized users only. The access restriction module may be based on a user name and password feature and/or biometric access control, for example, fingerprint recognition, facial recognition, retina recognition, and the like.

In some embodiments, the skin condition analysis module 4708 may have access to user information like age, gender, ethnic group, and the like, and such information may be used to build a user profile and used in analysis of the skin condition.

The skin care device 4700 may be used in a user's home, a user's bathroom, a cosmetic store, a provider's office, a mobile location, and the like. The skin care device 4700 may be used at any time of the day, such as before going to bed, before or after using a cleanser on the skin, and the like.

The skin care device 4700 may have a skin care regimen recommendation module 4710 capable of generating a displayable skin care regimen recommendation. The skin care regimen recommendation may include information not only about the most appropriate skin-care products, but also information about the best way of applying the product, the timing, amount, and frequency of application, and the like. The skin care regimen recommendation module 4710 may be linked to the skin condition analysis module 4708 so that the skin care regimen recommendation is personalized to the skin condition of each person. The skin care regimen recommendation may be generated in real-time based on skin condition assessments generated by the skin condition analysis module 4708, product information, and other relevant information analyzed using algorithms, as described herein. In some embodiments, the skin care regimen recommendations generated by the skin care regimen recommendation module 4710 may be displayed to the user in real-time, for example, on a display surface attached with the skin care device 4700.

In some embodiments, it may be possible to print the skin care regimen recommendations generated by the skin care regimen recommendation module 4710.

In some embodiments, the skin care regimen recommendations generated by the skin care regimen recommendation module 4710 are based at least partly on determination of a skin profile, or skin state 158, of the user and use of skin care regimen recommendations of persons with a similar profile.

In some other embodiments, the skin care regimen recommendation module 4710 is coupled to a skin-care product database 190. If the products recommended by the skin care regimen recommendation module 4710 are available in the product database 190, the user may be informed and given an option to purchase the product immediately. In some embodiments, the user may operate the skin care device 4700 in a point-of-sale location, for example, a retail store, and the availability of a product recommended by the skin care regimen recommendation module 4710 may be indicated by an audio-visual signal, such as for example by lighting up the shelf in which the product is located.

A user practicing a specific skin care regimen, for example, use of a skin-care product in a prescribed manner, may be interested in tracking the effectiveness of the skin care regimen over a period of time. The skin care device 4700 may have a skin care regimen effectiveness module 4712. The skin care regimen effectiveness module 4712 may be coupled with the skin condition analysis module 4708. The skin condition of the user may be tracked at different points of time using the skin care device 4700 and may be displayed to the user on a display surface. The device could also help track changes by various activities—exercise, food, smoking, work, and the like.

Figure 48:
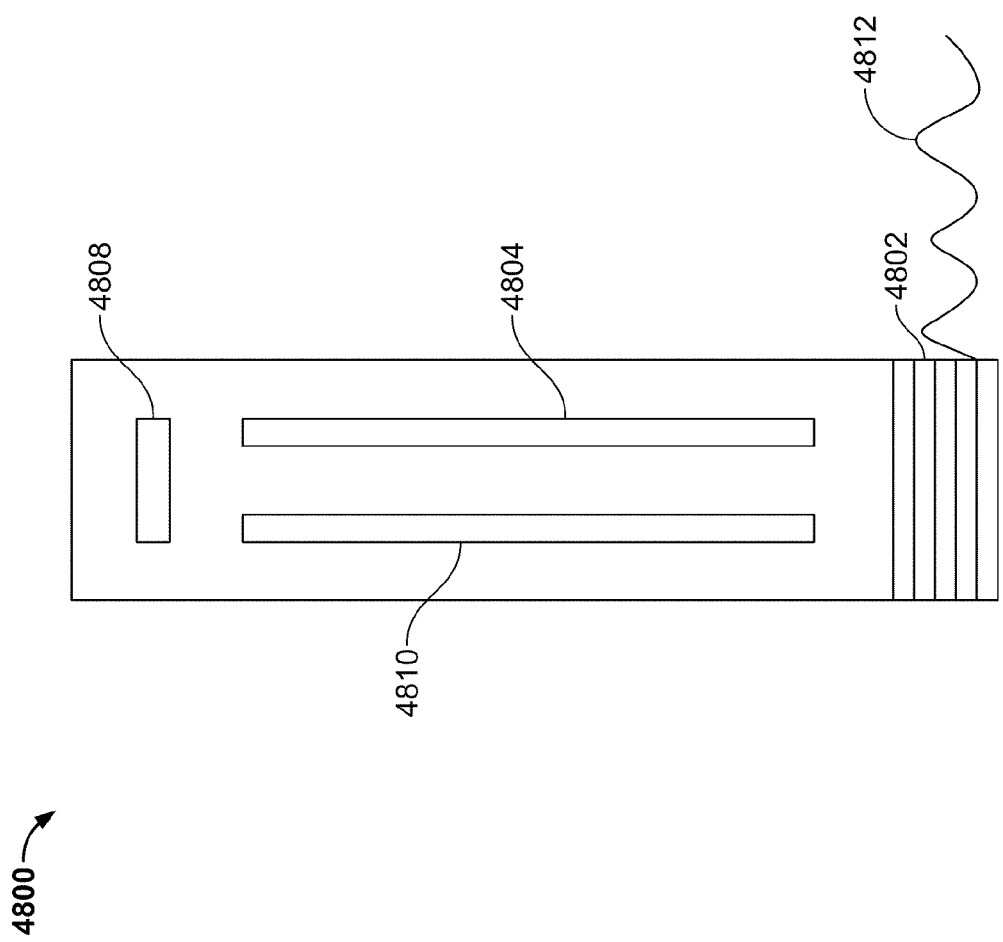
FIG. 48 depicts a wand-shaped skin care device embodiment.

FIG. 48 shows an embodiment of a skin care device 4700 in which the skin care device is wand-shaped. For example, a user may switch on the wand-shaped device 4800 and move the device over her face. The wand-shaped device may have a grip 4802, a radiation detector 4808, an indicator 4804 that may provide an indication such as with light, warmth, sound, and the like, an LED light 4810, and a power source 4812.

The wand-shaped device 4800 is functionally similar to the skin care device 4700 described earlier. The wand-shaped device 4800 may comprise an electromagnetic radiation source, a radiation detector, and a skin condition analysis module. The wand-shaped device 4800 may be miniature, hand-held, and portable.

In some embodiments of the wand-shaped device, the electromagnetic radiation source may be one or more LEDs. Each of the LEDs may have unique predetermined frequencies. In some embodiments, the one or more LEDs may be arranged in a line to form a light strip.

In some embodiments, the wand-shaped device 4800 may be powered via a USB coupled to an external power source or through built-in batteries, or other similar power source.

As the wand is moved over the skin, light is emitted from the radiation source 4702. Then, the radiation detector 4704 detects re-emitted light and sends information back to the skin condition analysis module 4708. The module 4708 employs an algorithm for skin condition analysis.

Figure 49:
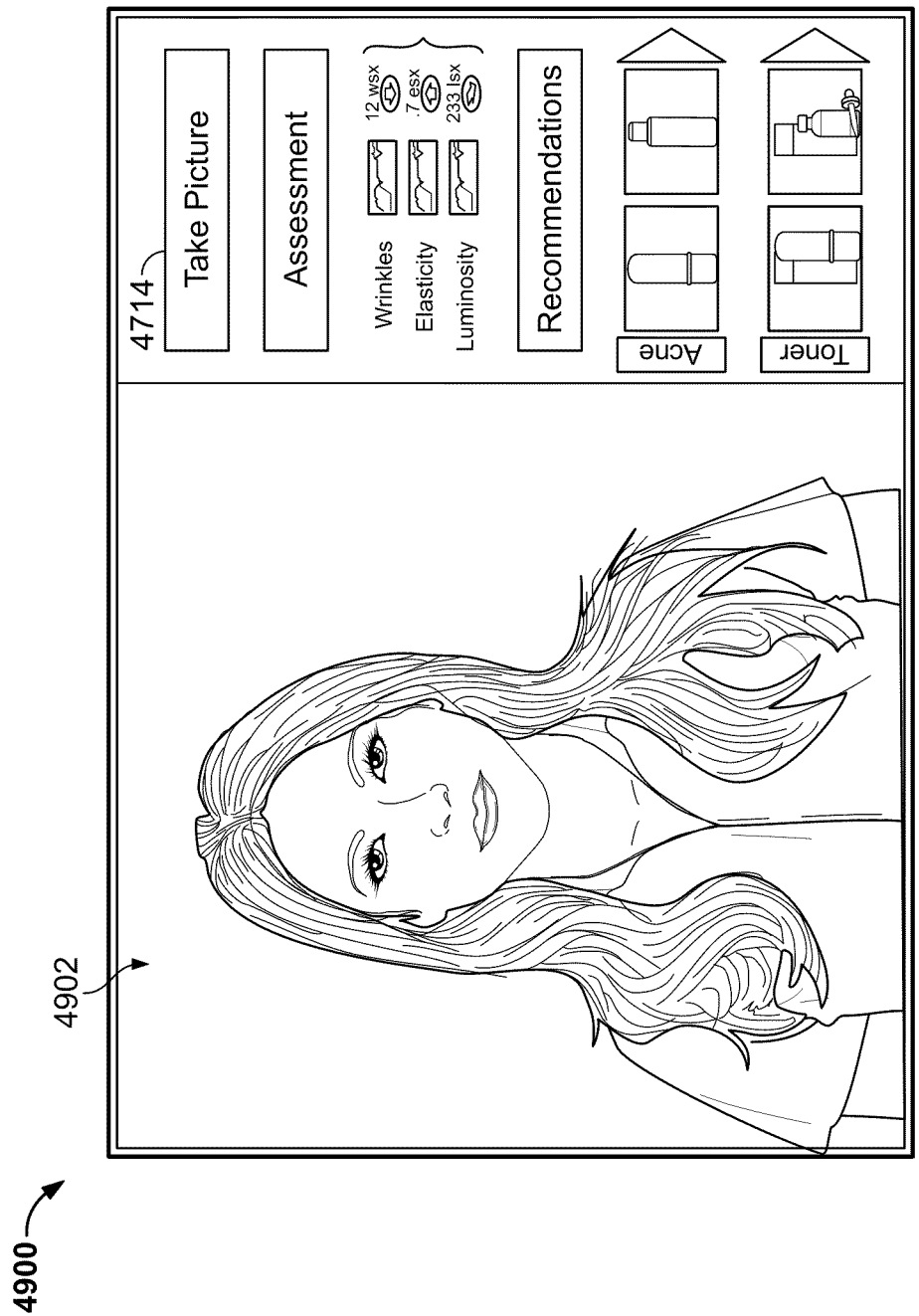
FIG. 49 depicts a vertical display panel including skin care device.

FIG. 49 shows another embodiment of a vertical panel-including skin care device 4900, in which the skin care device comprises an electromagnetic radiation source 4702, a radiation detector 4704, a skin condition analysis module 4708, a user interface 4714, and a vertical display panel 4902.

The vertical display panel 4902 may have the user interface 4714 on the sides of the vertical display panel 4902. In some embodiments, the display panel may be touch-sensitive and in such cases, the vertical panel itself may be part of the user interface. An image of a skin region may be displayed in the display panel. A user may touch a location on an image and this may trigger display of a magnified image either on the display panel or on another screen. A menu bar may show up in the user interface 4714, and the user may be able to view various reports, for example, a skin condition assessment report, a skin regimen recommendation report, a skin regimen effectiveness tracking report, and the like.

The user interface 4714 may enable a user to give instructions to the device, for example, to analyze the available information to generate a real-time skin condition assessment of a skin location or a larger skin region. In some other embodiments, the user interface may be voice-operated providing the facility to give commands to the skin care device 4900 through normal speech commands. Other examples of user interfaces that may be used in the skin care device 4900 are graphical user interface (GUI), web-based user interface (WUI), command line interface, touch interface, and any combination of the above.

The basic functioning of the vertical panel-including skin care device 4900 is similar in many respects to the skin care device 4700. The electromagnetic radiation source 4702 is capable of directing incident electromagnetic radiation to one or more locations on the skin of a person. For example, and not by way of limitation, the radiation source 4702 may be a set of light emitting diodes (LEDs). In certain embodiments, the incident radiation emitted by the radiation source 4702 may include radiation in the visible, near-infrared (NIR) and near-ultraviolet (NUV) spectrum. In certain other embodiments, the incident radiation may include white light.

As depicted in FIG. 49, the electromagnetic radiation source 4702 may be coupled to the radiation detector 4704. A variety of radiation parameters may be detected by the radiation detector 4704, including, for example but not limited to, degree of polarization, intensity of the radiation at different wave-lengths, and the like.

In certain embodiments of the vertical panel-including skin care device, the skin condition assessment may also be partly based on analysis of a photographic image of the skin location.

Some embodiments of the vertical panel-including skin care device may have a memory module for storing the skin condition assessments and other data, such as with timestamps.

Some embodiments of the vertical panel-including skin care device may have a communication module for communicating the skin condition assessments and other data with timestamps to a remote computer. The communication of data may occur, for example but not limited to, over a wire, wirelessly, using an internet, and the like. The skin condition assessments and other data may also be accessed in remote locations via mobile devices and/or computers. Such remote access may be particularly convenient for service providers, such as for example, dermatologists.

In certain embodiments, the user interface 4714 may also provide alerts to a user if any abnormal skin condition (for example, a clogged pore) is detected. The alerts may be in the form of a light signal, a beep, an email alert, an SMS alert, etc. There may be other methods e.g. a small electric tingle, a mark, a sound, and a light, a heat emitting signal, etc. to alert users about skin conditions requiring user attention.

In some embodiments, the skin condition assessment data of locations may be overlaid on an image of a larger skin region displayed on the vertical display panel 4902, providing a useful picture of the health of the entire skin region in a single view.

Some embodiments of the vertical panel-including skin care device may also have an access restriction module restricting access to private information to authorized users only. The access restriction module may be based on a user name and password feature and/or biometric access control, for example, fingerprint recognition, facial recognition, retina recognition, and the like.

In some embodiments, the skin condition analysis module 4708 may have access to user information like age, gender, ethnic group, and the like, and such information may be used to build a user profile and used in analysis of the skin condition.

The vertical panel-including skin care device 4900 may be used in a consumer's home, a consumer's bathroom, a cosmetic store, a provider's office and/or a mobile location. The vertical panel-including skin care device 4900 may be used at any time of the day, such as before going to bed, before or after using a cleanser on the skin.

In some embodiments of the vertical panel-including skin care device, the device may include or be coupled with a skin care regimen recommendation module capable of generating a displayable skin care regimen recommendation.

In some other embodiments of the vertical panel-including skin care device, the device may include or be coupled with a skin care regimen effectiveness module capable of generating a displayable skin care regimen effectiveness report.

In some embodiments of the vertical panel-including skin care device, the vertical display panel is a mirror.

In some embodiments of the vertical panel-including skin care device, the vertical display panel is an LCD panel or a plasma screen.

In some embodiments of the skin care device, the device also includes or is coupled with a camera for taking photographic images of a skin region.

In certain embodiments of the skin care device, the camera is integrally attached to the display surface or display panel. In certain other embodiments, the camera is either wired to the display surface or display panel. In other embodiments, the camera is wirelessly coupled to the display surface or display panel.

In certain embodiments of the vertical panel-including skin care device, the user interface 4714 may have one or more buttons (not shown explicitly) for doing a skin scan and/or analysis. The buttons may be of different types, for example push buttons, hard wired buttons, or a combination of both. The user may touch a button on the display panel for doing a skin scan, while she may touch another button for directing the machine to do a skin analysis.

Figure 50:
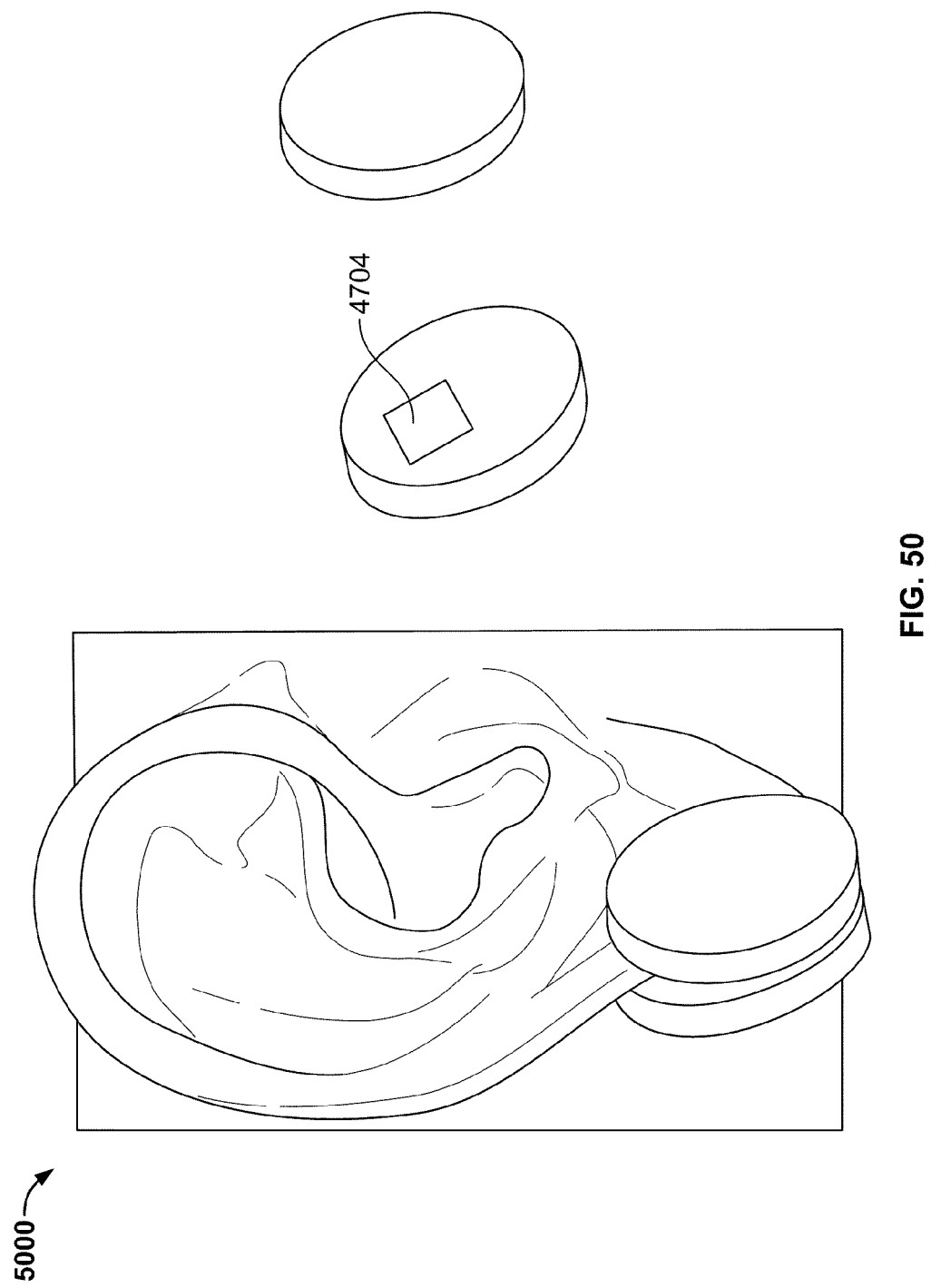
FIG. 50 depicts an embodiment of a wearable skin care device.

FIG. 50 shows an embodiment of a wearable skin care device 5000, in which the device is in the form of a wearable device. The wearable device can be worn by a user in the form of necklace, ear-rings, bracelets, a patch, or as a sensor attached to a strap, and the like. Such wearable devices can be persistent, personalized skin care monitors.

The wearable skincare device 5000 is functionally similar to the skin care device 4700 described earlier. Similar to the skin care device 4700, the wearable skincare device 5000 comprises an electromagnetic radiation source, a radiation detector, and a skin condition analysis module. Preferably, the wearable skincare device 5000 is miniature, hand-held, and portable, and no dimension of the device exceeds six inches.

In some embodiments of the wearable skincare device, the electromagnetic radiation source may be one or more LEDs. Each of the LEDs may have unique predetermined frequencies. In some embodiments, the one or more LEDs may be arranged in a line to form a light strip.

In some embodiments, the wearable skincare device 5000 may be powered via a USB coupled to an external power source or through built-in batteries, motion power, solar power, or other similar power source Embodiments of the wearable skincare device may also have sensors for measuring various body and environmental parameters. Examples of body parameters that could be measured by the wearable skincare device are body temperature, hemoglobin antioxidant level, etc. Examples of environmental parameters that could be measured by the wearable skincare device are air cleanliness, humidity, temperature, UV index, external air quality, smoke index, and the like.

In an embodiment, the device 108 may be adapted for use as a component of a minimally invasive medical device associated with laparoscopy, cytoscopy, ureteroscopy, arthroscopy, endoscopy, dermoscopy, gynecology, urology, dentistry, natural orifice insertion analysis such as through ears, mouth, anus, nose, and external breast cancer analysis through the skin, and the like. For example, the system may be able to process the data and to appear on a video monitor or other display in a surgical suite or other medical setting. A medical professional may be able to select a viewing mode, such as still image capture or video capture, and may be able to manually adjust the parameters of the light source, sensor and display to assist in observation, identification, and monitoring with the device 108. In an embodiment, the system may be pre-programmed with various protocols for the various types of medical procedures and tissues types that a medical professional may encounter such that the system may automatically handle the device 108 based on the medical professional's indication of the type of procedure and tissue being examined.

Figure 56:
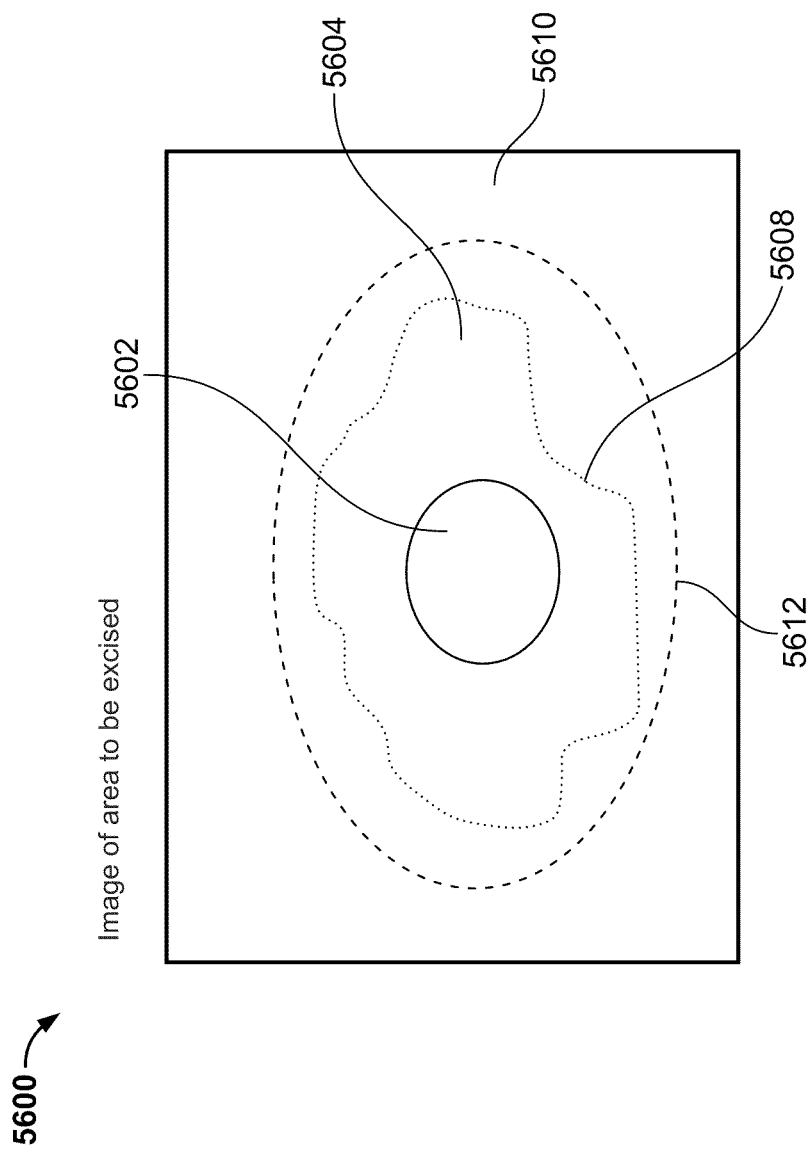
FIG. 56 depicts a system for determining an excision margin.
Figure 57:
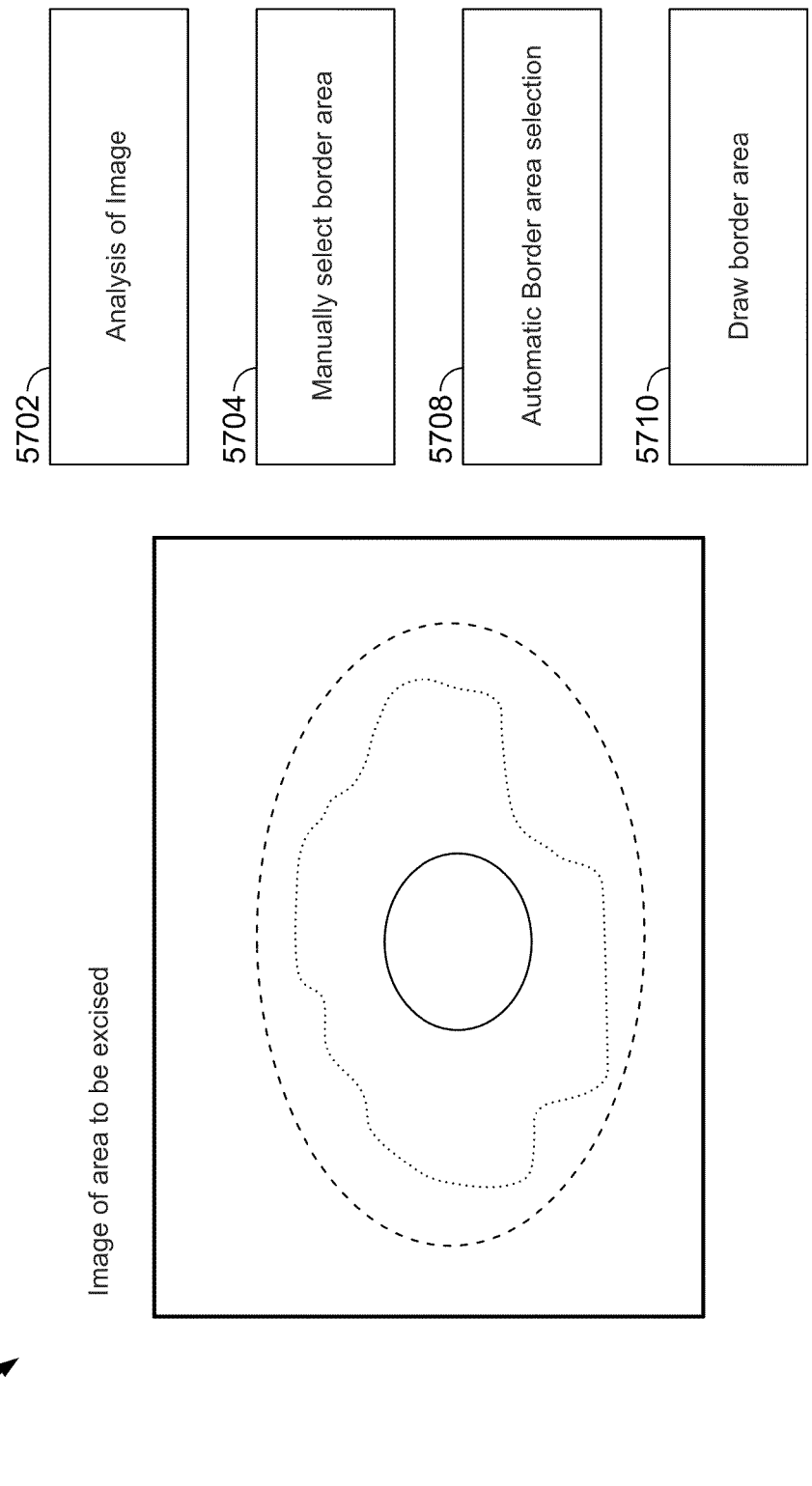
FIG. 57 depicts a system for determining an excision margin.

For example, the device 108 may be used as part of a system and method for distinguishing between healthy and suspect tissue in real or near-real time on a patient. The imaging device 108 allows a surgeon or other practitioner to precisely determine the border area around a surgical intervention for primary cutaneous melanoma, skin cancers, and other skin diseases that require excision around the skin. Generally, the surgical excision of suspect tissue, such as cutaneous melanoma, may be determined either by a surgeon's experience or through a Breslow scale and punch biopsy that determines the thickness of a melanoma and hence generally agreed-to border areas. The device 108 allows an automatic determination of the excision margin for primary cutaneous melanoma based on the optical characteristics of the surrounding skin. By precisely defining where there is healthy tissue and where there is suspect tissue, a surgeon could leave a larger amount of healthy tissue around a site, decrease recurrence and decrease micrometastasis in surrounding skin while enabling minimal surgical morbidity and improved cosmetic appearance. The device 108 and associated algorithms 150 and analysis techniques, such as the convolution technique and RGB color analysis discussed later herein, embodied in software, may be employed to image a particular site, and determine border area, suspect tissue, either before surgery, in pre-surgery, or during surgery. The software could also show post surgical analysis of affected skin tissue. Using the device 108 allows more precise determination of the border area instead of relying on subjective experience or fixed tables as noted in medical journals and other published works. The advantage of this method is better isolated suspect tissue and retaining a greater degree of healthier tissue. Referring now to FIG. 56, a melanocytic lesion is displayed. The visible melanoma 5602 or suspect tissue is surrounded by normal looking skin, but which may contain unhealthy/diseased tissue that must be excised 5604 (pseudo-normal skin 5604). The device 108 may be able to visualize the border between healthy and non healthy tissue 5608, thereby allowing the surgeon to spare healthy tissue 5610 that should remain intact. The device 108 may perform an estimation and provide an outlined area 5612 indicating where the surgeon should cut the tissue. In FIG. 57, an embodiment of a user interface for visualizing a melanocytic lesion is displayed along with access to tools for analyzing an image of the lesion 5702, manually selecting a border 5704, automatically selecting a border 5708, drawing a border area 5710, and the like.

In an embodiment, the device 108 may enable a skin health test 160. The imaging device 108 may be used to perform a skin health test 160 to learn the characteristics of the skin and to obtain a diagnosis. The hardware device may capture an image and enable analysis of the image. The imaging components within the device 108 may enable measuring various skin health characteristics like color, age, damage, collagen, elastin, pores and types, keratin, and the like. The skin health test 160 may be performed in the home, in a spa, clinic, hospital, from a mobile phone at any location, and the like. The skin health test 160 may be used in conjunction with specific background information through questionnaires, image upload, genetic testing, DNA samples, and lifestyle habits to determine a skin state 158. The test 160 would respond with specific information related to the biophysical health of the skin, a portion of which would be physical and genetic disposition to certain medical or non-medical or cosmetic problems or conditions.

In an embodiment, the device 108 may enable a pre-diagnosis 162. This is a system of pre-diagnosis where a practitioner (such as the user, a dermatologist, medical practitioner, aesthetician, and the like) may receive or request from a user to take an image and/questionnaire of a skin concern or the like and receive a pre-diagnosis based on algorithmic analysis of pre-existing conditions. The user may submit a questionnaire and image with a pre-diagnosis of conditions prior to going to see a practitioner and allow a follow-up. Images captured by the device may be submitted to obtain a preliminary diagnosis to enable effectively referring the case to the best practitioner. The pre-diagnosis 162 may be performed by software algorithms on the images, manual analysis, a combination thereof, and the like. The pre-diagnosis 162 may include the preliminary assessment as well as indicate the time required and the steps required for the final diagnosis or assessment. This pre-diagnosis 162 feature may enable effective scheduling of the practitioner. The pre-diagnosis 162 could also help screen for particular skin issues as well as identify users with certain issues.

In an embodiment, the device 108 may enable remote monitoring 164. The user may use the device in the privacy of their home, work, or any other location to perform remote monitoring 164 and submit images to track progress of their skin's health or medical conditions. A practitioner may be able to remotely guide changes in treatment or guide on prevention factors. Remote diagnosis may greatly increase efficiency of progress monitoring since users will not have to make a physician trip to the provider, and the provider could conveniently select a time during the day to observe the patients change. The monitored data may be viewed as a recording or in real time.

In an aspect of the invention, the imaging device 108 may illuminate an area of concern at a known angle of incidence with unpolarized light. To obtain a spectral diagram based on the magnetic properties of the area only, the reflected polarized light, which possesses the electrical properties of the area of concern, may be subtracted from any reflected diffusion light, which possesses electromagnetic properties of the area of concern. The distribution of pixels in the image corresponding to the diffusion light and reflected polarized light may be determined and indicated by any conventional means. For a known image sensor, a one-to-one mapping of pixel image distribution between the diffusion light image, corresponding to an electromagnetic signal, and reflected polarized light, corresponding to an electrical signal image, may be made with a distribution of the intensity of the spectroscopic data for the same area. A magnetic gradient image of the area may be made by equipment such as an AFM-MMR (Atomic Force Microscopy in Magnetic Mode Regime) and from the one-to-one correspondence, a skin state 158 may be based on the gradient image, diffusion light image, and reflected polarized light image.

In an embodiment, the device 108 may be an imaging device 108 for performing digital spectroscopic imaging of the skin. Incident unpolarized light may be delivered, either vertically or on an angle alpha from vertical, from an unpolarized light source associated with the device 108, such as a white light, diffuse light, monochromatic light, light of multiple single wavelengths, and the like, to a target skin structure. White light, which possesses both electrical and magnetic properties, when incident onto a skin structure at a particular angle interacts with the structure's components and leads to the reflected or re-emitted light having a polarized light component. In embodiments, the incident light may be polarized. Unpolarized light reflected by skin structures may become polarized, at least in part. The reflected or re-emitted light, either polarized or diffusion light, may be captured IDS/the device 108. Such multispectral skin imaging may be used to develop an electromagnetic skin topography. By measuring aspects of the polarization of the reflected or re-emitted light such as an orientation, an amplitude, a phase, an angle, a shape, a degree, and an amount, and the wavelength of the reflected or re-emitted light, the biophysical properties of skin structures may be obtained. A skin state 158 may be determined from the aggregate biophysical data obtained from one or more skin structures as well as a visual analysis of the captured images and any additional data obtained from the user anecdotally. For example, the skin state 158 may encompass data on moisture, wrinkles, pores, elasticity, luminosity, and any of a number of measures, as described herein. By varying alpha, the angle of incident white light, the depth of penetration of the light to skin structures may be varied. Each depth within the skin corresponds to different skin structures. For each skin structure or depth, there may be a specific angle which produces a full polarized reflection. For example, a certain angle of incidence may be used to obtain data for skin structures within the epidermis, however, the angle of incidence may need to be changed in order to obtain data on skin structures within the subcutis which resides at a different depth within the skin. The angle of incidence may be modified to penetrate the skin anywhere from a few microns up to a few centimeters, thus enabling the capture of reflections from other non-dermal structures. For example, the device 108 may be used as a non-invasive imaging tool, such as to image tumors, breast cancer, melanoma, and the like. In an embodiment, the area to be imaged may be any biological tissue that may have normal or pathologic variations in its structure, such as variations in the tissue's birefringent properties. For example, scars, keloids, hypertrophic scars, and stria all have organizations of collagen fibers that are different from normal skin. Since collagen is a primary determinant of cutaneous wound repair, it may be of interest to monitor changes in collagen structure and concentration. For example, the stage of healing may be determined by the size of collagen bundles which may increase as healing progresses, by the organization of collagen structures at the molecular or small-fibril level which may increase as healing progresses, by the return or increase of birefringence, and the like. Since collagen structures are polarization-sensitive, changes that occur in the structures may be monitored using a polarization-based technique during scar formation, the healing process, and treatment of scars, as has been and will be further described herein.

Being able to measure the electrical and magnetic properties of various skin structures may enable the differentiation between healthy and non-healthy skin structures. Normal or healthy skin structures exhibit a unique conformation that differs from the conformation exhibited by equivalent structures when unhealthy or abnormal. These conformational changes can be detected by differences in an aspect of the light reflected off of skin, re-emitted light, or amount of absorption in the skin, such as an aspect of the polarization of the reflected or re-emitted light. The aspect of polarization may be the wavelength of the light, an orientation, an amplitude, a phase, an angle, a shape, a degree, an amount of polarization of the light, and the like. According to Maxwell's equations, light can be described as comprising an electric field and a magnetic field which can be described as two vectors, E and B, which behave as waves. The vectors are perpendicular to the propagation direction of the light, and they are orthogonal to each other. Furthermore, given the electric field E, B can be determined via Maxwell's equations, and vice versa. Thus, by measuring the electrical component of the light reflected, re-emitted, or absorbed by the skin structures, the magnetic component or the degree of polarization/polarization state may be determined. Alternatively, the light may spread to other wavelengths that can be measured. By comparing those electrical and magnetic readings from the polarized component of reflected or re-emitted light and non-polarized white light to that of normal or healthy skin structures incident with light at the same or similar angles, changes may be detected in the skin structure and its molecular or structural conformation. Based on the amount or other aspect of both electrical and magnetic determination, specific defects such as cancer, skin diseases, cosmetic indications and the like, may be detected, since each range of measurements may correspond to a particular defective conformation. If any other molecules, cell, or structure are now incident with the same type of light at the same angle, the strength of certain wavelengths of the reflected component may enable the measurement of the intensity of the difference in conformation states of the measured component. The polarization state of the reflected or re-emitted light may be described by a number of parameters. The polarization state may be described in terms of the polarization ellipse, specifically its orientation and elongation. Parameters which may be used to describe the polarization state may include the azimuth angle ($\psi$) which is the angle between the major semi-axis of the ellipse and the x-axis, the ellipticity ($\epsilon$) which is the ratio of the two semi-axes, the ellipticity angle which is the arctangent of the ellipticity, the eccentricity, the amplitude and phase of oscillations in two components of the electric field vector in the plane of polarization, and the like. For example, an ellipticity of zero corresponds to linear polarization and an ellipticity of 1 corresponds to circular polarization. The polarization of the reflected or re-emitted light may be at least one of elliptical, linear, circular, left-circular, right-circular and any potential combinations thereof.

In an embodiment, determining a skin state 158 may comprise processing and analyzing 154 the reflected or re-emitted light to obtain images for visual and spectroscopic analysis. Analysis 154 may be facilitated by examining the wavelength and other characteristics of the reflected or re-emitted light. For example, if the incident light is white light, the reflected or re-emitted light may be filtered to examine a collection of wavelengths or a single wavelength and, ultimately, a specific skin structure fluorescence. In another example, monochromatic or semi-monochromatic light, such as provided by an LED may be used to excite targeted fluorophores and chromophores. In this example, fluorescence of deeper layers may be extracted. The reflected or re-emitted light in this example may also be filtered to isolate a specific fluorescence. In another example, varying the wavelength of the illuminating light may enable detection of biophysical properties from various depths within the skin. In addition, certain chromophores, such as the various forms of hemoglobin found in blood, have specific absorption bands; thus processing of data created with different color light may yield information about chromophore distribution that may be polarization-sensitive. The wavelength dependence may be obtained in several ways: 1) illuminate sequentially with light of a single wavelength or multiple single wavelengths and collect each resultant image separately; or 2) illuminate with white light and examine the reflected or re-emitted light for individual wavelengths or a collection of individual wavelengths either during detection or during processing. Algorithms 150 may be used to obtain information from data obtained by either method by processing and analyzing one or more wavelengths of light to form a spectroscopic, polarization-based image. In an embodiment, the combination of both techniques may enable the elimination of the reflection from the surface of the skin.

In an embodiment, filtering may be employed to filter out a range of wavelengths, such as those belonging to the ultraviolet, infrared, near infrared, visible, and the like. The filter may be a digital or an analog filter. For example, captured images may be processed by software that may be able to employ digital filter techniques to process the images for analysis. For example, using software, any digital filter parameter may be selected such as a particular cutoff wavelength, a set of single wavelengths, a sampling interval, and the like. For example and without limitation, a digital filter may be used to isolate reflections of 405, 458, 488, 532, 580, and 633 nm wavelengths. In another example, an analog filter may be employed to filter the images as they are captured, such as a filter that is integral to the optics of the device 108, or as they are stored, transmitted, manipulated, processed, and the like, such as with an external analog filter. Filtering the images may result in obtaining images of underlying structures and/or a specific pattern of polarization. Filtering the images may result in the separation of the electrical and magnetic components of the reflected or re-emitted light. Filtered images may be subjected to algorithmic analysis. Filtering may eliminate reflections due to skin surface reflections by isolating specific wavelengths of light. For example, sebaceous glands may appear as bright spots in an image when only a certain wavelength of light is isolated for analysis, while isolation of a different wavelength of light enables the visualization of all the pores in the imaged area. Thus, the fluorescence from deeper layers may be isolated. Image processing may be used to count and measure changes in the sebaceous glands and pores, including count, size, activity of gland, quantity of sebum/other materials inside the sebaceous gland, quantity of sebum/other materials inside the pore, age of the contents within the gland, age of contents within the pore, amount of inflammatory processes surrounding the gland, and the like. Multiple images from different image sources may be combined for the analysis. The analysis results in function, diagnosis, prognosis of skin health, such as disposition to acne, oiliness, shine, viscosity, and the like. The analysis may be combined with color image processing (RGB analysis, for example) to determine other skin characteristics.

In an aspect of the invention, a host system 104 may comprise algorithms 150, data integration 152, analysis tools/API's 154, a skin state 158, an expert consult 128, and the like. The skin state 158 may be a data object or characterization of skin based on tests 160, pre-diagnoses 162, and monitoring 164 performed by a device 108, user input, expert consult 128, other inputs 112, analysis 154, algorithms 150, and the like. The skin state 158 along with all of the underlying data and user information may be stored in a skin health record 121. In an embodiment, the host system 104 may comprise server architecture. The host system may be technology agnostic. The host system 104 may comprise one or more cloud computing, service-oriented architecture, distributed objects, and the like.

In an embodiment, expert consult 128 may provide analysis, recommendations, assessment advice, and the like. The skin image data collected as well as the pre-diagnosis, in addition with any other allied data such as physician's diagnosis, insurance, blood analysis, and the like may be referred to an expert either by the user or a practitioner, or by other users to obtain an analysis, recommendation or assessment advice. Experts could be located in geographically distant locations, and may have very different skills. For example, the skin image data and analysis may be shared at the request of another user with an herbal specialist in India, or the user may request the image data to be shared with an aging expert in France to learn of best suited skin care treatment from their experience. The expert's consultation analysis may be maintained on the host system 104 as part of the skin history record 121 and may be accessed by the user at their convenience, or shared with other users.

In an embodiment, the system 104 may be a home-based, in clinical or medical settings, at spas and salons, at a cosmetics counter and in cosmetics sales, and the like to perform skin analysis discretely and accurately in a low cost, rapid, and secure fashion. In embodiments, the device 108 may integrate with a user interface 102, online platform 129, mobile platform 124 and the like to perform analysis 154, skin state 158 record keeping, obtain referrals/analysis from a remote practitioner or algorithm 150, and the like. The home-based system 104 may allow a practitioner, who may be any qualified or unqualified person to give advice, to analyze cosmetic or non-cosmetic conditions that may be captured by an imaging device 108 or third party device 109 and give advice and recommendations on products, regimen, diet, lifestyle and the like based on inputs from questionnaires, uploaded images, and the like. The system may consist of a starter website that may be customizable for a personal business where the practitioner could organize clients' cosmetic skin health, track their regimens, recommend products, be their online advisor, and the like. This would leverage the analysis and device platform to allow a practitioner to analyze comments, images, questions, and/or concerns and the like and give advice, consultation on lifestyle improvement and tracking. A spa/salon based system may enable personalized skin assets. For example, the spa may own the device, the device may capture images to feed a large scale display adapted to present a skin condition, and then a practitioner may be able to simulate the effect of treatment. Users may compare a skin state 158 with peers or other spa goers and generate recommendations based on what worked for them or what they bought. Desired improvements may be correlated to ingredients and most effective products/regimens 118 for the users' skin. The regimen 118 may be a feature that enables users to learn what product sequence would work best for their skin, based on a hardware-led personalized skin care assessment 122 and/or type determination 130 for the skin and product experience sharing via ranking and rating 138 and/or comments regarding product effectiveness and experience (e.g. smell, taste, feel, texture, color, etc.) collection. The regimen 118 may be a dynamic recommendation based on users' collective inputs as well as experts' inputs on products that would best suit the user's individual needs.

The spa/salon based system 104 may generate product/service recommendations based on a skin state 158, offer one-click shopping based on recommendations and enable SKU tracking, offer wellness packages such as through a contractual relationship, provide the ability to port regimen from spa to spa, from home to spa, and the like, enable optimization of regimens/advising such as helping practitioners tailor the length of a procedure, enable development of targeted therapies, enable clear, visual communication to clients, generate effectiveness of products/services reports, and the like. Reports may be based on or comprise correlation with other users, feedback on regimen 118, modifications of a regimen 118, skin cycle monitoring, and the like. A medical practitioner based system, such as a dermatologist, general physician, metabolist, and the like, may enable pre-diagnosis, may link to the practitioner's scheduling system, may enable pre-pricing of services, may enable follow-up tracking, and the like. A cosmetic sales or retail based system 104 may enable integration with inventory of product enabling clearing of inventory. A handheld/portable device 108 may be used at a makeup counter, in a drugstore, at a home or trade makeup show/party, and the like. Users may purchase peripherals/accessories for the device, such as a holster, charger, and the like. Users may pay-per-scan or may have a subscription scanning service and the like. The system 104 may be based in health clubs, gyms, resorts, and the like. A cosmetics manufacturing/testing based system may enable skin state-based product design, targeting skin care samples to particular consumers, and the like. The system 104 may be veterinarian based to monitor veterinary dermal- and non-dermal concerns. The system 104 may be based in a hospital, ER, military setting, and the like to enable rapid assessment of medical conditions, triaging urgent skin care, and the like. The system 104 may be agriculturally based to enable application to fruits, vegetables, and other such agricultural products. The system 104 may be used in a battlefield scenario or in an austere environment, such as in space flight, air flight, underwater, submarine, and the like, to enable wound management, battlefield diagnosis and triage, and the like. The system 104 may be research based to enable comparing any materials and their specific composition. Based on using the reading of the electrical property of the light, a user may be able to determine a similarity or difference between imaged material.

In an embodiment, determining a skin state 158 may comprise employing an analysis 154. In an embodiment, the acquired data may be analyzed by a practitioner, such as a physician, dermatologist, spa employee, clinical trial practitioner, aesthetician, cosmetologist, nutritionist, cosmetic salesperson, and the like. The practitioner may analyze the data upon acquisition, visually, with the assistance of an algorithm 150, expert consult 128, database 115, and the like. In an embodiment, the practitioner may be remote from the location of data acquisition. In an embodiment, an algorithm 150 may be used to process and analyze 154 the reflected or re-emitted light to obtain spectroscopically resolved images, either automatically or under the control of a user, practitioner, and the like. For example, to obtain a spectroscopic image of the magnetic properties of the area only, an algorithm 150 may be used to generate an image of an area of concern using the difference between the reflected polarized light, which possesses the electrical properties of the area, and the reflected diffusion light, which possesses the electromagnetic properties of the area of concern. Algorithms 150 may be rules-based software and processes to 1) analyze imaging evidence to obtain skin health, 2) correlate skin health with ingredients, medicaments, and/or products that may be best suited for the determined skin health, 3) correlate skin health with peers in a skin health community, and 4) recommend and design personalized products based on skin health and/or other like users usage experience, 5) observe measurable changes in skin health, and the like. Algorithms 150 may be automated. Algorithms 150 may be used to analyze 154 medical concerns, such as degree of suspicion of cancer, rash analysis, and the like. Algorithms 150 may be used to analyze 154 non-medical concerns, such as the effectiveness of a medical, non-medical, or cosmetic regimen 118, a pimple avoidance regimen 118, a sun-protection effectiveness, an itch prevention cream, and the like. Algorithms 150 may be useful for correlating desired improvements with ingredients and most effective products for improving or maintaining the user's skin health. The algorithm 150 may utilize a calibration scale to determine the skin structures imaged based on the angle of incidence, wavelength and intensity of the light source, an aspect of the reflected or re-emitted light, filter parameters, and the like. Algorithms 150 may be useful for determining a dermascopic effect, a luminescence effect, a spectroscopic effect, and the like. For all algorithms 150, there may be an input, an output, and functional parameters to modulate the algorithm 150. In an embodiment, analysis 154 may comprise examining at least one of: physical data and/or an image of the material using diffusion white light; physical data and/or an image of material using light of a single wavelength or multiple single wavelengths; physical data and/or an image of the material using polarized, reflected or re-emitted light of a certain angle; physical data and/or an image of the material generated using the difference between diffusion white light and polarized reflected or re-emitted light of a certain angle; physical data and/or an image of the material generated using the difference between light of a single or multiple wavelengths and polarized, reflected or re-emitted light of a certain angle; and the like. Algorithms 150 may be used with data and images generated by the device 108 or third party hardware 109. Algorithms 150 may be used with data and mages captured using any image capture device or technique, employing any kind of incident light, such as unpolarized light, polarized light, monochromatic light, diffuse light, white light, multiple single wavelength light, and the like. In embodiments, any captured data or image may be subjected to algorithmic analysis, as described herein.

In an embodiment, the algorithm 150 may be based on artificial neural networks, non-linear regression, or fuzzy logic. For example, the algorithm 150 may be used in skin lesion diagnosis based on a probabilistic framework for classification. Two kinds of data may be inputs to the neural network or to non-linear regression: numerical data such as intensity, size, numbers, and the like, and descriptive data such as white, gray, dark, and the like. Fuzzy logic may directly encode structured descriptive data in a numerical framework. Based on associative memories, learning algorithms 150, and adaptive control system behavior, neural and fuzzy machine intelligence may enable correspondence between input data taken from collected images and a biophysical skin state 158.

In an embodiment, the algorithm 150 may be based on fractal and multi-fractal analysis of images based on biophysical and spatio-temporal data. Both digital image data and spectroscopic data of skin may be analyzed using Hausdorff dimensions (fractal property) and Kolmogorov's entropy (K-entropy). Then, spectroscopic data may be divided into spatio-temporal cells and analyzed as multi-fractal objects, yielding information about a level of functional disharmony of skin structures (epidermal and dermal). Structural data of these two analyses can be correlated to determinate a one-to-one correspondence between them. Once fractal correlations between digital image data and spectroscopic data of skin are established, it may be possible to obtain information about a functional state of skin structures through multi-fractal analysis of digital image data.

In an embodiment, an algorithm 150 may be for the analysis 154 of data integrity. For example, an algorithm 150 may be able to determine if the image has been captured in high enough detail to render subsequent analyses reliable.

In an embodiment, an algorithm 150 may be useful for the analysis of skin characteristics, obtaining the biophysical properties of the skin, and determining a skin state 158. The skin state 158 may capture a combination of underlying skin structure with time-based variance. Some variation may be predictable but some may be based on a transient condition like infection, sunburn, hormonal imbalance, and the like. The algorithm 150 may be able to measure aspects such as the structure, form, concentration, number, size, state, stage, and the like of melanocytes/melanin, hemoglobin, porphyrin, keratin, carotene, collagen, elastin, sebum, sebaceous gland activity, pores (sweat and sebaceous), wrinkles, moisture, elasticity, luminosity, all forms of the aforementioned, such as derivatives, salts, complexes, and the like. The algorithm 150 may be used to make a quantitative assessment of clinical, medical, non-medical, and cosmetic indications, such as moisture level, firmness, fine lines, wrinkle count and stage, pore size, percent of open pores, skin elasticity, skin tension lines, spots, skin color, psoriasis, allergies, red areas, general skin disorders and infections, or other skin related concerns for the user such as tumors, sunburns, rashes, scratches, pimples, acne, insect bites, itches, bleeding, injury, inflammation, photodamage, pigmentation, tone, tattoos, percent burn/burn classification, moles (naevi, nevus), aspects of skin lesions (structure, color, dimensions/asymmetry), melanoma, dermally observed disorders and cutaneous lesions, cellulite, boils, blistering diseases, management of congenital dermal syndromes, (sub)-cutaneous mycoses, melasma, vascular conditions, rosacea, spider veins, texture, skin ulcers, wound healing, post-operative tracking, melanocytic lesions, non-melanocytic lesions, basal cell carcinoma, seborrhoic keratosis, sebum (oiliness), nail- and/or hair-related concerns, and the like. The algorithm 150 may also be useful for the analysis of and obtaining the physical properties and composition of hair, nails, biological substances, gaseous substances, food, wine, water, liquid, metal, non-metals, plastics, polymers, and the like. Either manually or as determined by an algorithm 150, a targeted wavelength or wavelengths may be employed for specific endpoint measurements.

Either a specific wavelength or multiple wavelengths may be chosen for the incident light or a specific wavelength or wavelengths may be isolated by filtering, as described herein. An algorithm 150 may determine the presence, absence, structure, form, and the like of particular skin structures based on the properties of the reflected or re-emitted light. For example, an algorithm 150 may detect which axes/angle the light is polarized on and compare this to signature emission spectra of individual proteins/underlying skin structures. Each skin structure may have a unique signature pattern based on the electrical and magnetic contributions of molecule(s) present in the skin structure. The algorithms 150 may identify, analyze and separate the electrical and magnetic components of the unique polarization signal, as described herein. The signals may correlate with the aggregate conformation state of molecules in the skin structure. By comparing this signal to a standard calibration signal, aspects of the underlying skin structures may be determined. The standard calibration signal may be provided by a catalog of skin structures/molecules and their specific wavelength of observation. The catalog may be developed by the technique described herein or any other spectroscopic technique. For example, to determine moisture levels in the skin, an algorithm 150 may determine a ratio of the reflected polarized light and reflected diffusion light and correlate the ratio with a moisture level. Ideally, close to 100% polarized light may be generated from reflections, however if a portion of the reflected or re-emitted light is diffusion light, such as 95% polarized, 5% diffusion, the amount of diffused light may be correlated with a level of moisture. Incident unpolarized light may interact with a skin structure and lead to varying amounts of polarization of the reflected or refracted light. This polarized reflected or refracted light strength may be measured. This polarization may be as much as 100 percent, however, the reflected polarized strength may even be less than 100% in some cases. The incident angle and the imaged material would help determine the maximum strength possible for the polarization of the reflected or re-emitted light. It should be understood that there may be a maximum amount of polarization with a maximum of 100% for a particular incident angle, but any amount of polarization ranging from 0 to 100% polarized may be expected from the light reflected by any skin structure. The underlying cause for the differences in reflection may be due to the ratio of the captured and free water in the skin. To determine elasticity, an algorithm 150 may determine the concentration of elastin per area of concern. To determine luminosity, an algorithm 150 may combine moisture levels and skin color into a single, objective assessment. Objective measures may be correlated with an expert grading scale or other external measure. To determine firmness/tightness, an algorithm 150 may combine an assessment of collagen and elastin concentrations in an area of concern along with the activity of sebaceous glands (as measured by number of glands, percent open/closed, level of clog/fill). The algorithm 150 may be able to overlay varying wavelengths and intensities and spectroscopic techniques, such as reflectance, excitation/emission, and the like. The algorithm 150 may be able to process and analyze 154 images collected by the device 108 or any other imaging device using unpolarized light, polarized light, or a combination thereof. The algorithm 150 may be able to process and analyze 154 many different types of images, such as thermoelectromagnetic (TEM) images or electromagnetic (EM) images, images collected with incident polarized light, traditional dermoscopy images, spectroscopically resolved images, conventional images, harmonized light images, and the like. The algorithm 150 may be able to calculate a variance measurement of skin state 158 over time. Determining a skin state 158 may also include, in addition to the processing and analysis of images of the skin for various measures and endpoints as described herein, a visual analysis of the images, user entered information, and third party information, such as lifestyle, smoking history, exercise habits, diet, allergies, and the like. For example, a user may enter anecdotal information, such as medication they may be taking, recent overexposure to sun, stage in a menstrual cycle, and the like.

Figure 35:
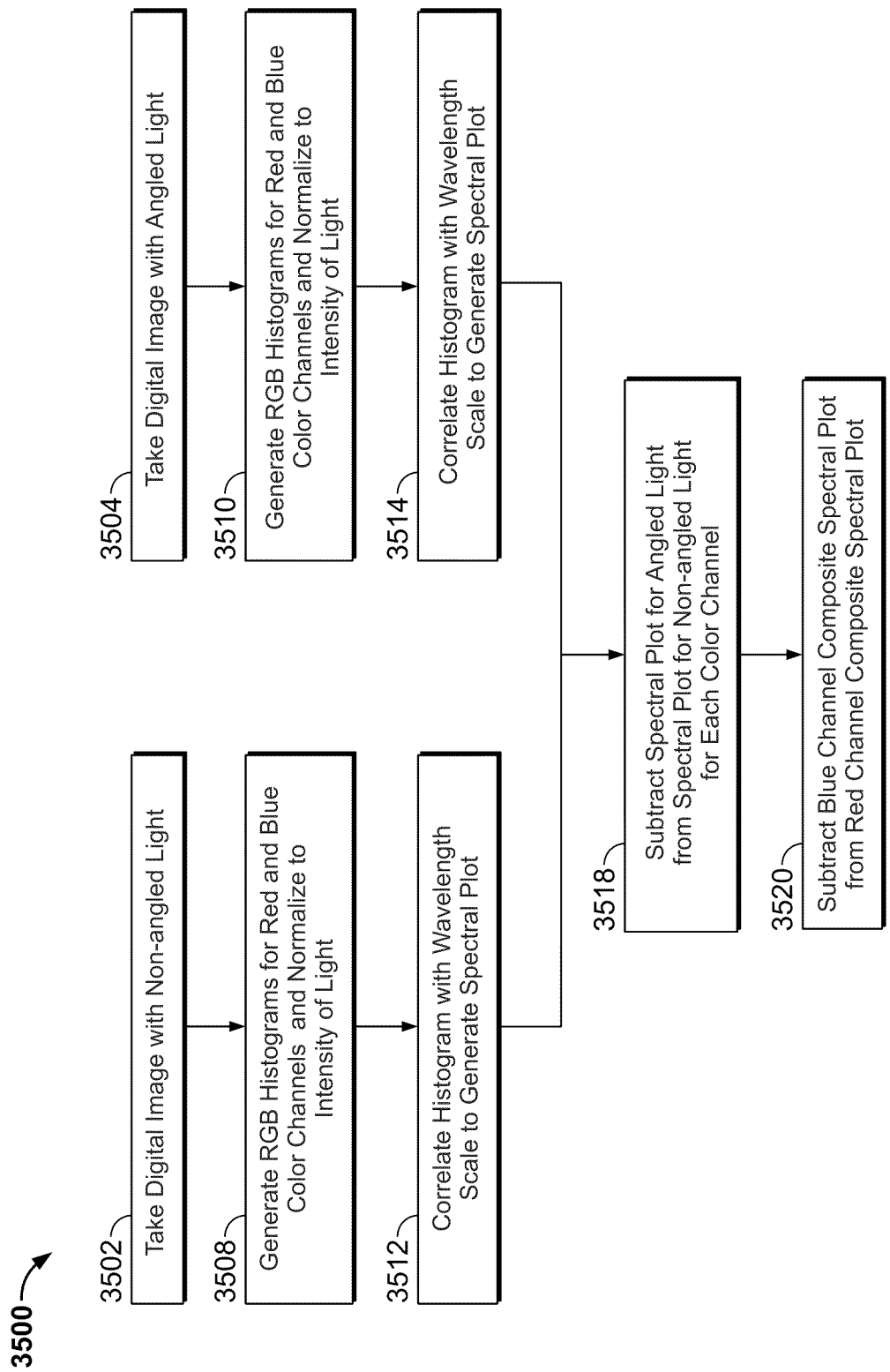
FIG. 35 depicts an algorithm and method for analyzing materials.

Referring to FIG. 35, in an embodiment, an algorithm 150 may comprise spectral convolution of digital images taken with: 1) "angled white light", or white light incident on an angle sufficient to produce a polarized reflection; and 2) "non-angled white light", or white light incident on an angle that produces substantially no polarized reflections. While the foregoing discussion will focus on skin as the primary specimen, it should be understood that any specimen, such as material characterized by covalence effects, ionic effects, and hydrogen bond effects, including skin, hair, biological materials, foodstuffs, liquid, wine, metallic materials, non-metallic materials, and the like may be specimens for the algorithm 150. Briefly, a digital image of a specimen is captured with non-angled light 3502 and angled light 3504, blue and red color channel histograms are generated for each image 3508, 3510 and are normalized to the relative intensity of the light, and the color channel histograms are correlated to a wavelength scale 3512, 2514. The spectral convolution proceeds in two steps. The first step involves subtracting, for each of the red and blue color channels, the color channel histogram for angled light from the color channel histogram for non-angled light 3518. Two composite histograms are generated, the blue color channel composite histogram and the red color channel composite histogram. The second step of the spectral convolution involves subtracting the blue channel composite histogram from the red channel composite histogram 3520. Continuing to refer to FIG. 35 throughout the discussion of FIGS. 36 through 43, the various steps of the algorithm will now be described in greater detail.

Figure 36:
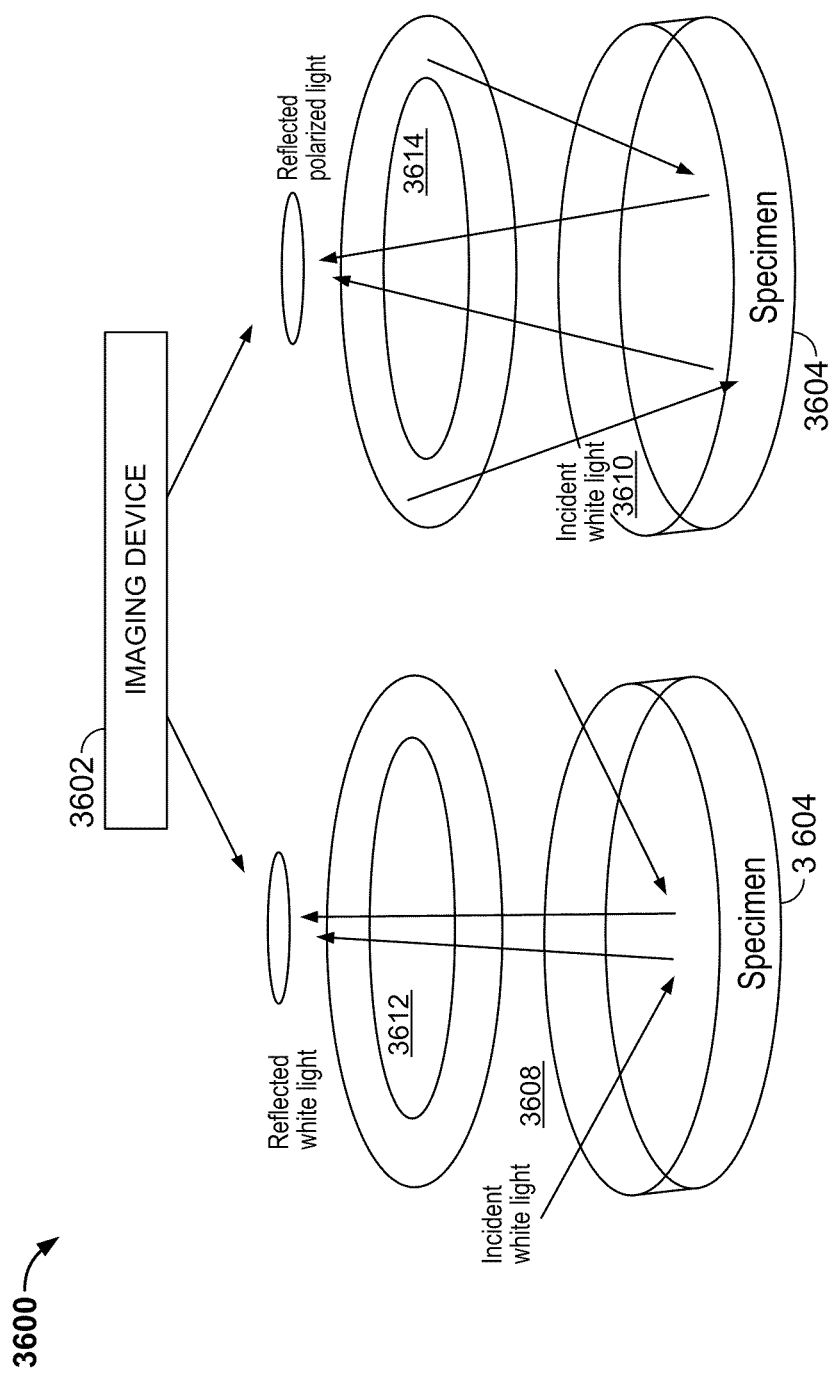
FIG. 36 depicts the reflection and capture of white light and reflected polarized light from a specimen based on varying angles.

Referring now to FIG. 36, a specimen 3604, which may be any suitable material for imaging as described previously, may be illuminated with non-angled white light 3608 and angled white light 3610. As described previously herein, varying the angle of incidence affects the depth of penetration of the light to various skin structures. For each skin structure which may correspond to a particular known depth within the skin, there may be an angle of incidence which produces a polarized reflection. By analyzing the reflected or re-emitted light, either polarized 3614 and/or diffusion 3612, captured by an imaging device 3602, information on the underlying skin structures responsible for the reflection may be obtained. The term "angled white light" 3610 refers to incident white light that is directed towards the specimen at an angle sufficient to produce a polarized reflection. The term "non-angled white light" refers to incident white light that is not directed at a specific angle towards the specimen and is diffuse. In this case, the non-angled white light may produce reflected white light, polarized light, or a combination thereof. In an embodiment, reflected polarized light generated by non-angled white light may be of a different characteristic than polarized light generated by angled white light.

Figure 37:
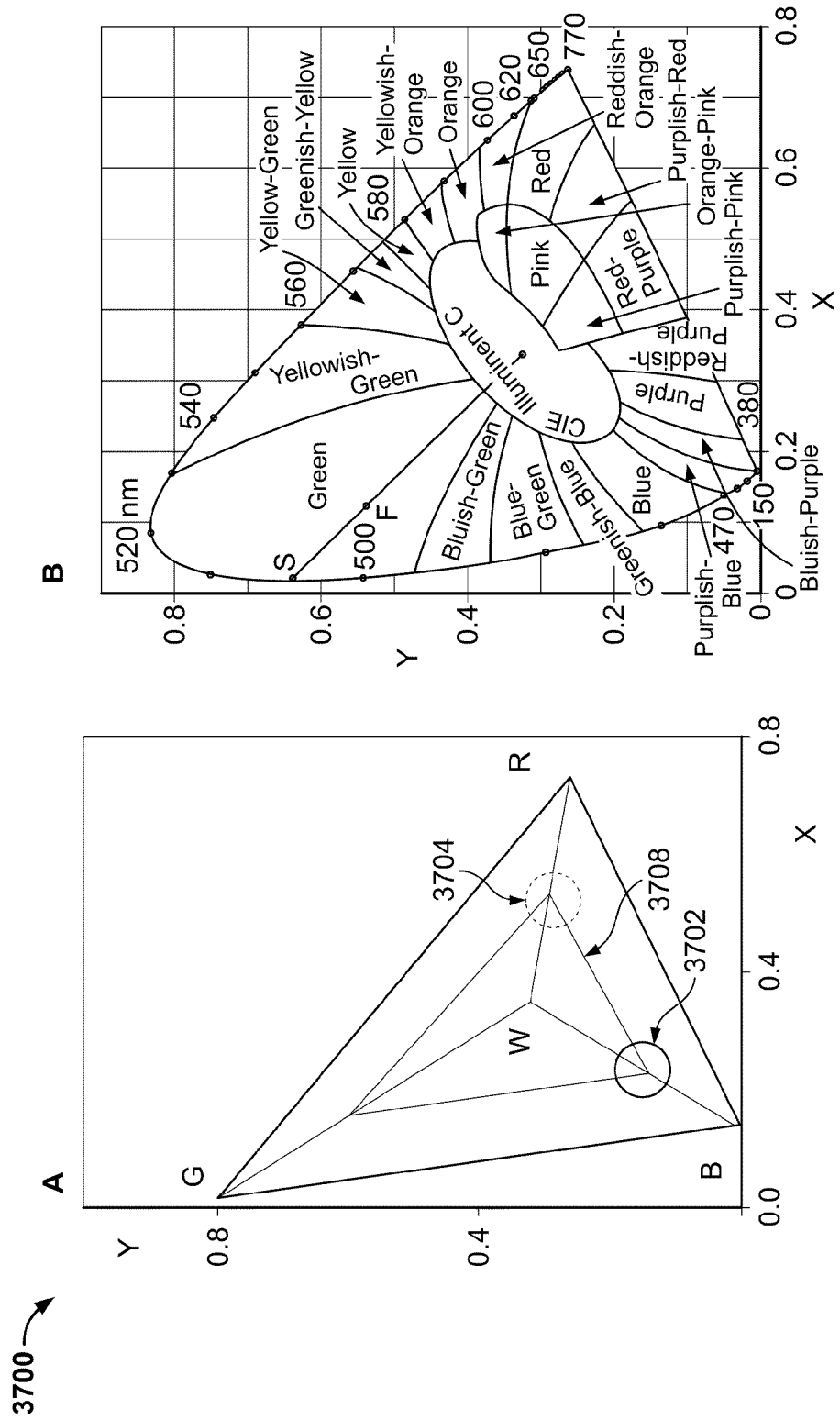
FIGS. 37A&B depict color coordinate systems that can be used in digital image processing.

Referring now to FIG. 37, Maxwell's color triangle, in FIG. 37B, may facilitate an understanding of the nature of white light. Maxwell's color triangle depicts the complete visible color spectrum, with reference to specific wavelengths. In order to establish a mathematical coordinate system for the RGB color space, a simplified version is used with straight lines, shown in FIG. 37A. Each of the vertices of the outer triangle corresponds to an ideal color, either ideal green, red, or blue going clockwise from the top. Along the sides of a Maxwell triangle mixing of two of the three color components occurs with every possible proportion. As one travels from the side towards the center, the third primary color becomes increasingly important. Near the center at the "equal energy" point, E, a true white is seen, with radial axes extending to each of the three vertices. Mixing of the full intensity of red, green, and blue gives this true white. Thus, every point on the triangle is a result of a mixture of at least one of red, green, and blue, including the point representing white light. For example, the solid circle 3702 represents a point in color that is between pure/dark blue and pure white. Similarly, the dashed circle 3704 represents a point in color that is between pure/dark red and pure white. Using digital photos of white paper, the coordinate system may be validated, as represented by the internal triangle 3708. The internal triangle 3708 validates the system when the sides are parallel to the limits of the color space lines of the original coordinate system. If they are not parallel, then the coordinate system is not valid.

Figure 38:
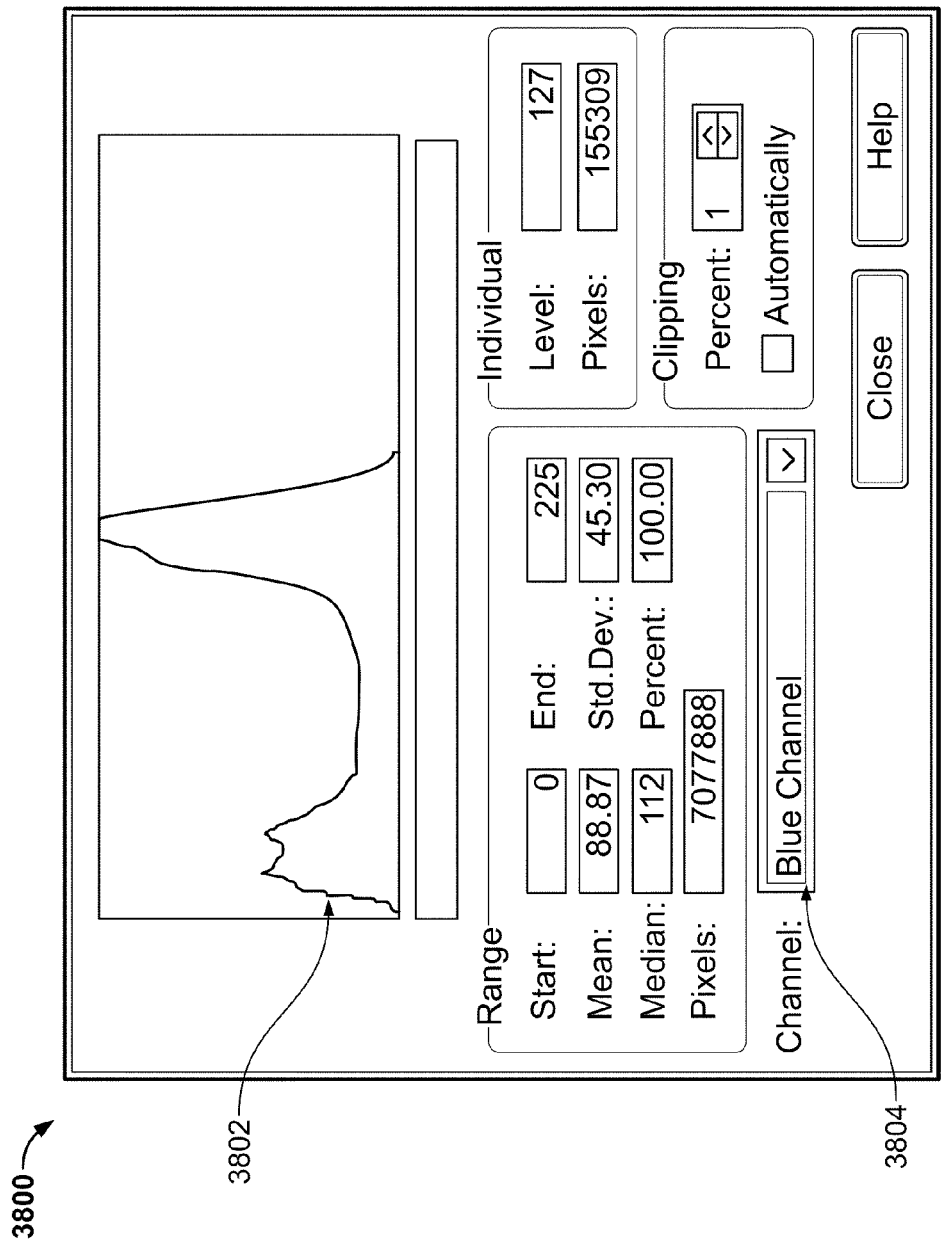
FIG. 38 depicts a histogram of color density.
Figure 39:
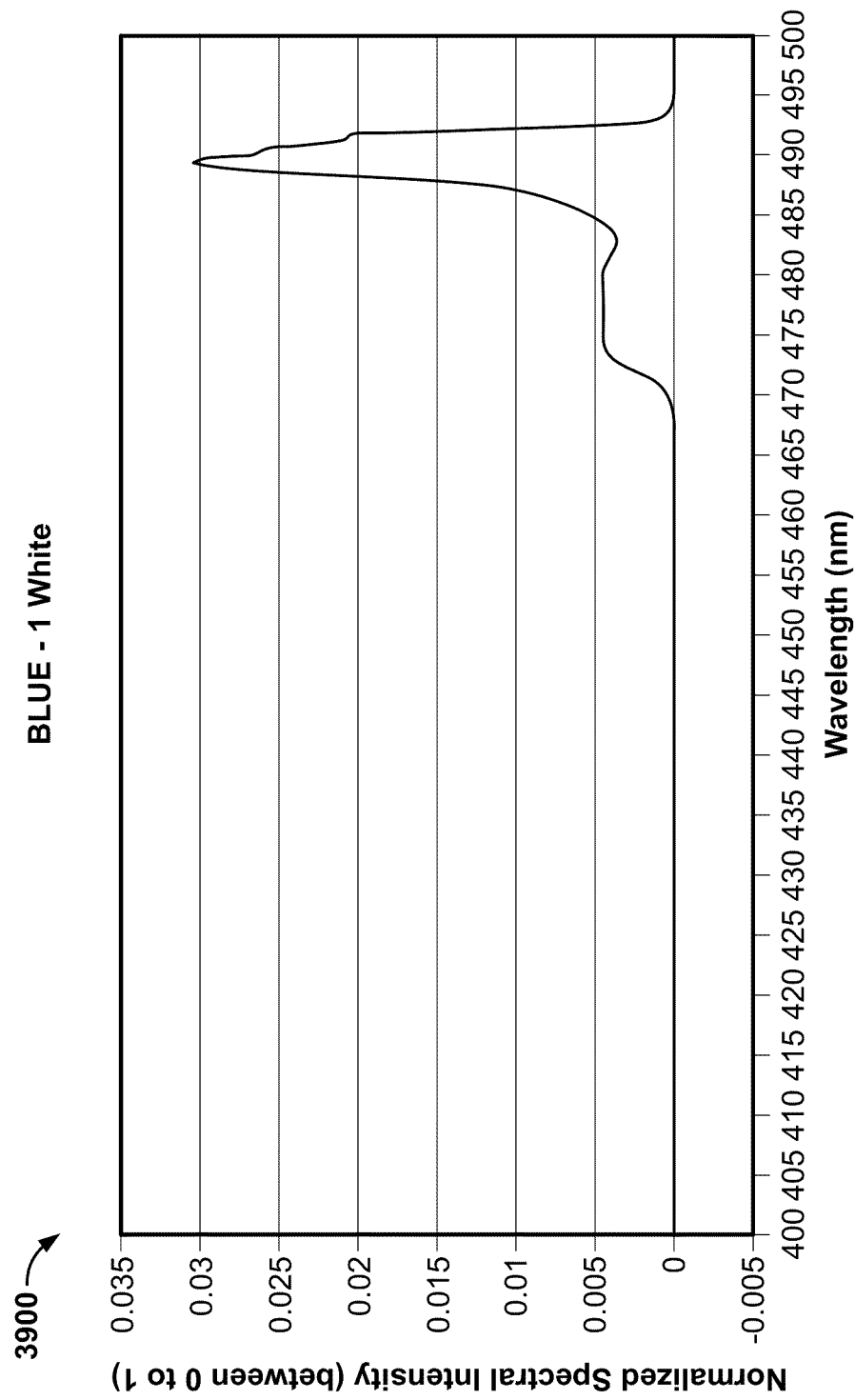
FIG. 39 depicts a normalized color channel histogram correlated to wavelength scale.

Referring now to FIG. 38, an RGB histogram for each color channel is generated for each of the images. An RGB digital image has three color channels: red, green, and blue. Each of these channels may be examined and analyzed separately. A blue color channel histogram is generated for the image taken with non-angled white light and another blue color channel histogram is generated for the image taken with angled white light. Similarly, a red color channel histogram is generated for the image taken with non-angled white light and another red color channel histogram is generated for the image taken with angled white light. For example, an automated system may be used to generate the histograms for each color channel, as shown in FIG. 38. By simply specifying which channel 3804 a user may wish to examine, a histogram 3802 may be generated for that channel. The histogram may be normalized to the relative intensity of the light. Normalizing the histograms to the intensity of incident light is important to be able to process the histograms generated from different images. Referring now to FIG. 39, the RGB color channel histograms are then correlated to a specific wavelength scale to generate RGB color channel spectral plots.

Figure 40A:
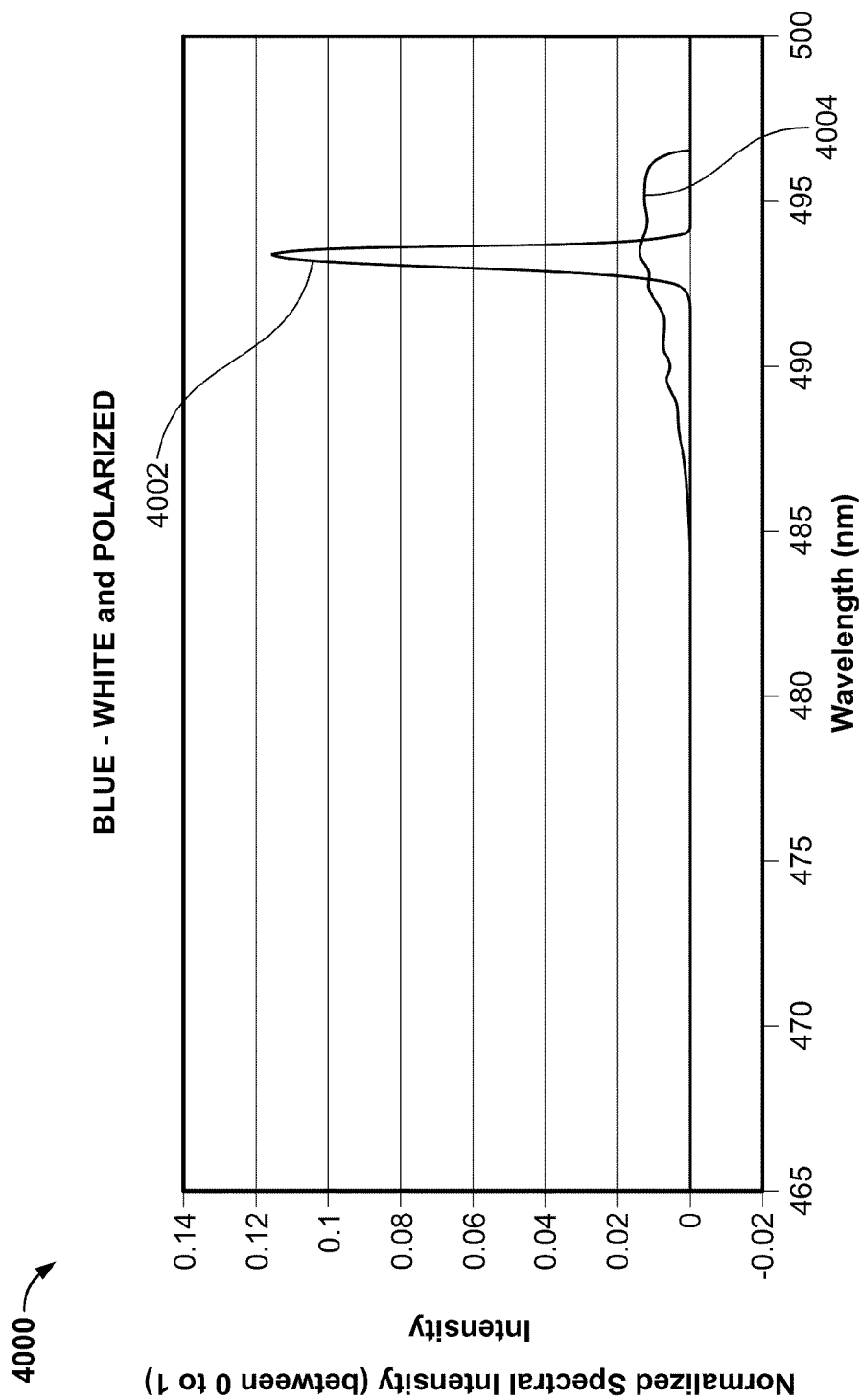
FIG. 40 depicts overlaid, normalized color channel histograms.
Figure 40B:
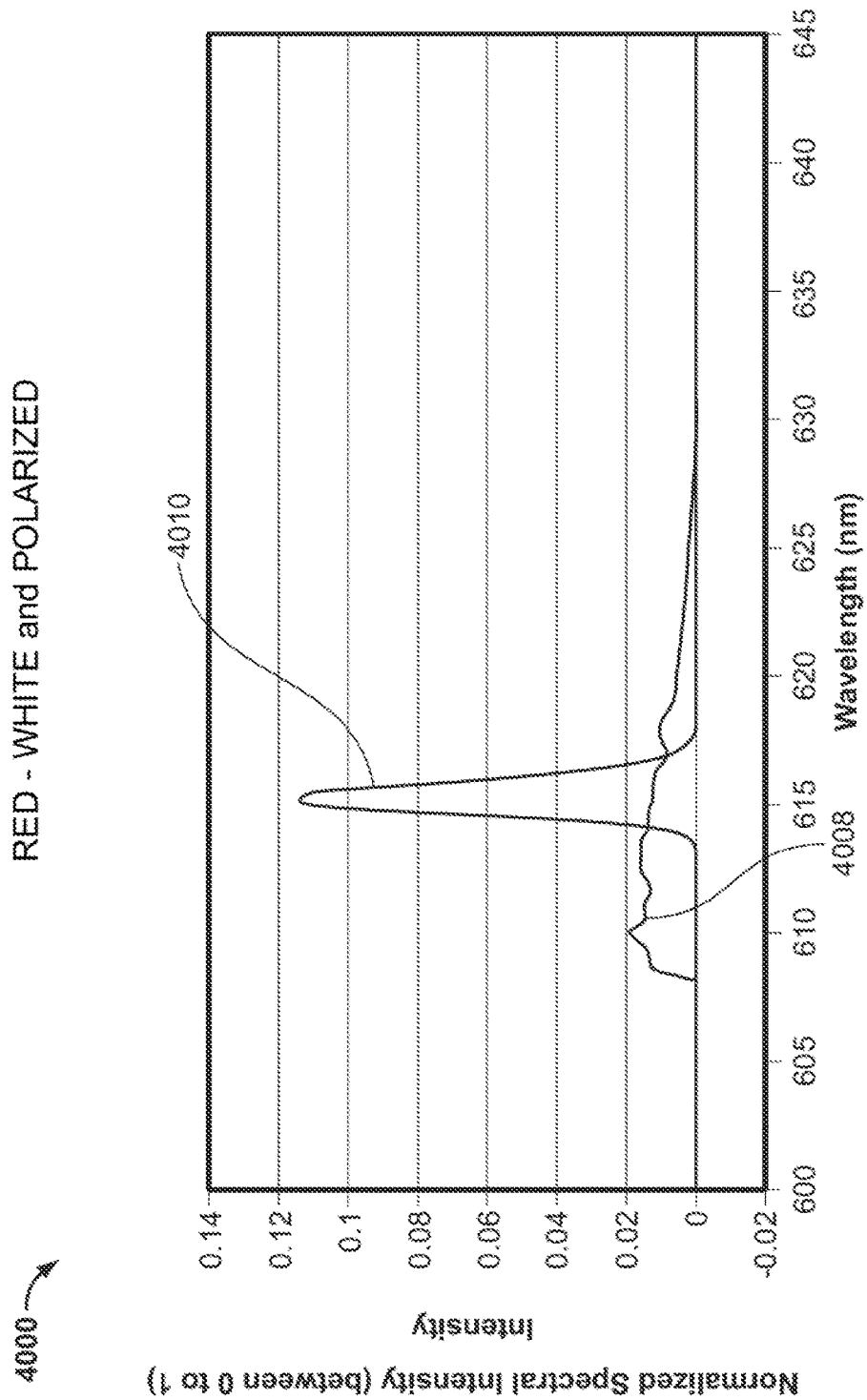
Figure 41A:
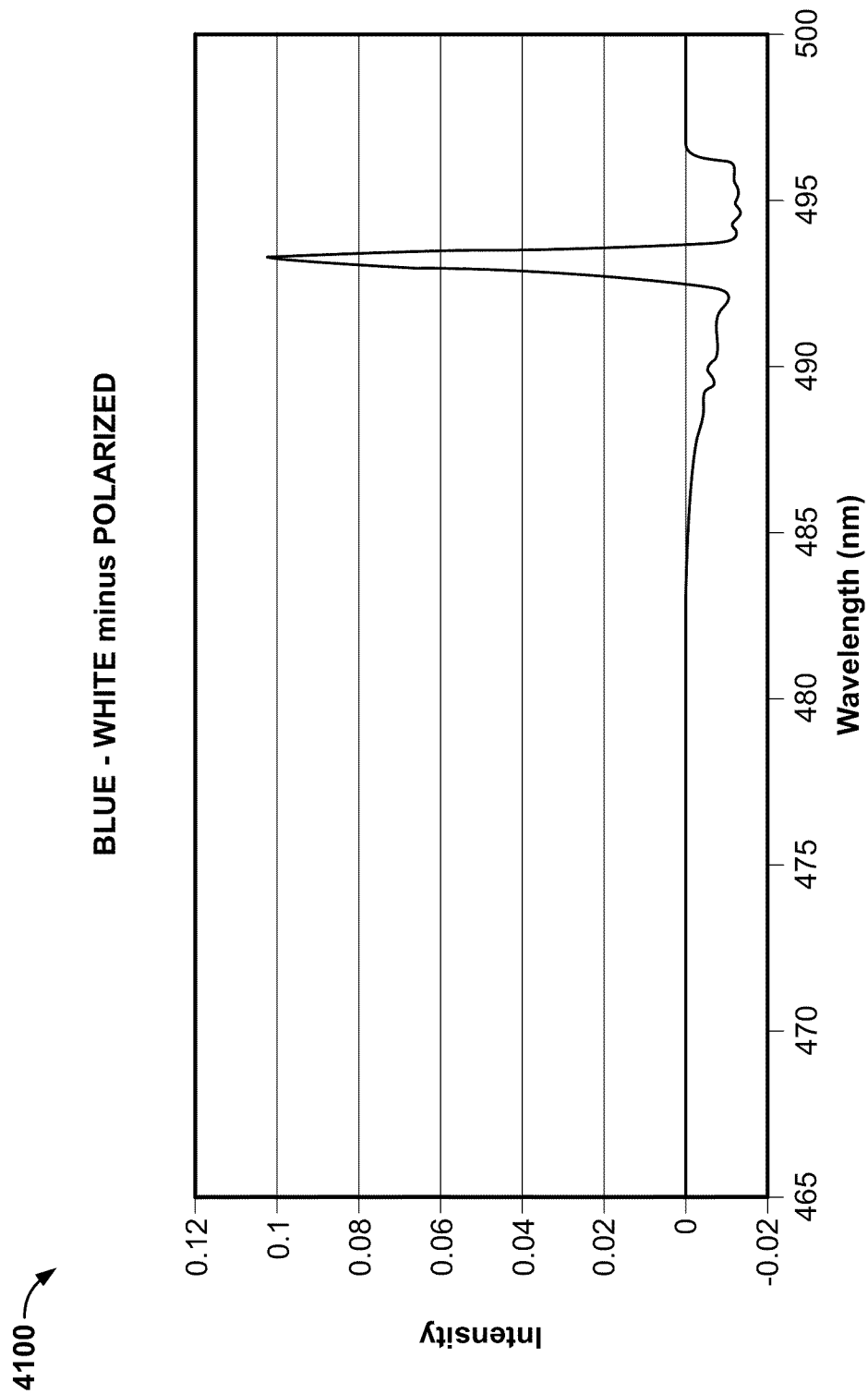
FIG. 41 depicts a convolution of individual color channel histograms.
Figure 41B:
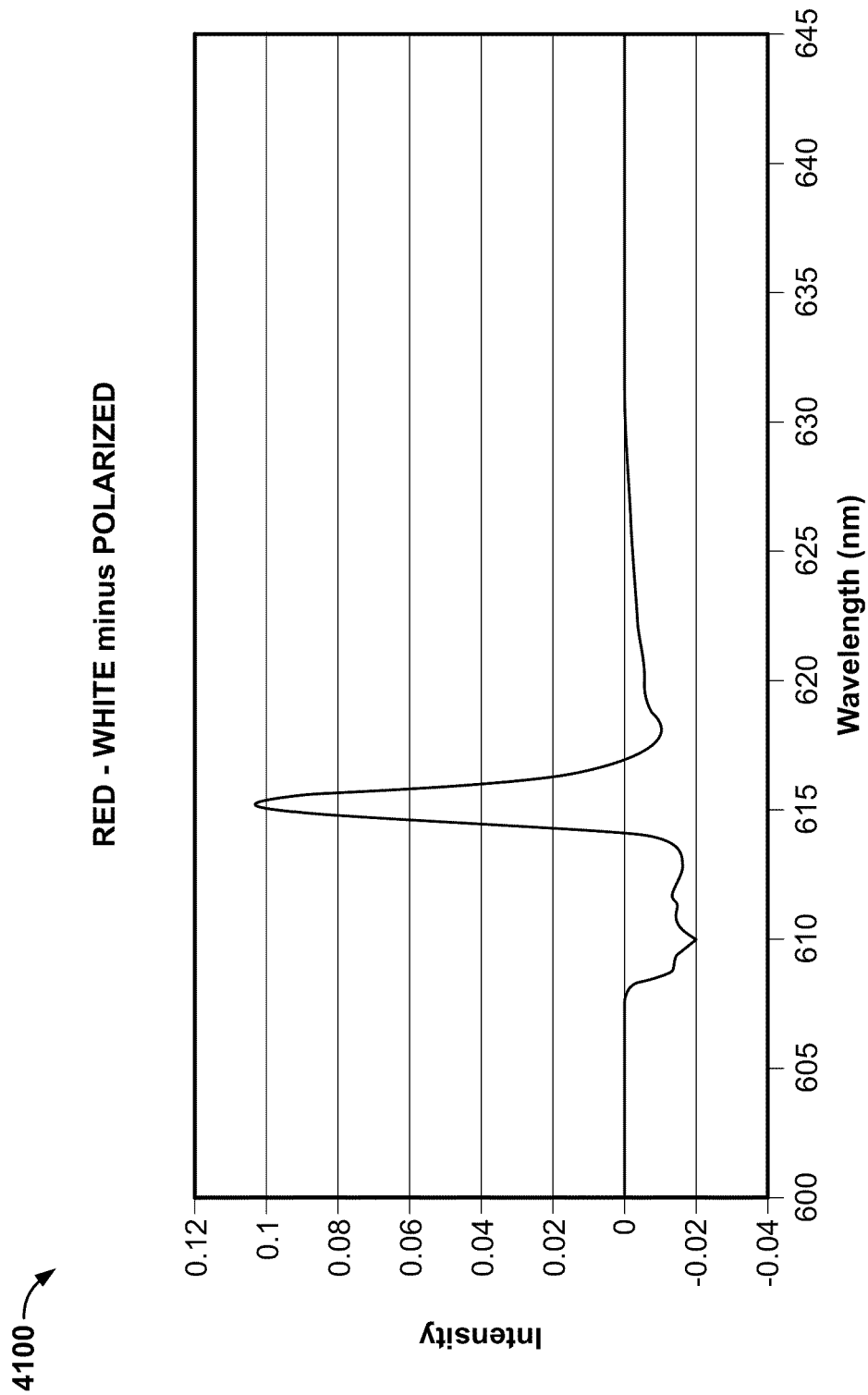

Referring now to FIG. 40, the data from the pair of images are then combined mathematically in two steps. In the first step, the blue color channel spectral plot generated from the image taken with angled white light 4004 is subtracted from the blue color channel spectral plot generated from the image taken with non-angled white light 4002 to generate a blue color channel composite spectral plot. The two spectral plots 4002, 4004 are shown first overlaid in FIG. 40A and then subtracted in FIG. 41A. Similarly, the red color channel spectral plot generated from the image taken with angled white light 4008 is subtracted from the red color channel spectral plot generated from the image taken with non-angled white light 4010 to generate a red color channel composite spectral plot. The two spectral plots 4008, 4010 are shown first overlaid in FIG. 40B and then subtracted in FIG. 41B. Subtraction may be facilitated by aligning the spectral plots by wavelength and mathematically subtracted the normalized intensities at each wavelength. For example, if the intensity is 0.005 at 470 nm for the blue channel spectral plot from angled white light and the intensity at the same wavelength of the blue channel spectral plot from non-angled white light is 0.003, the resultant spectral plot would comprise an intensity of −0.002 at 470 nm. The specific intensities and wavelengths in the spectral plots reflect the specific properties of the underlying material and the angle at which the material was exposed to light.

Figure 42:
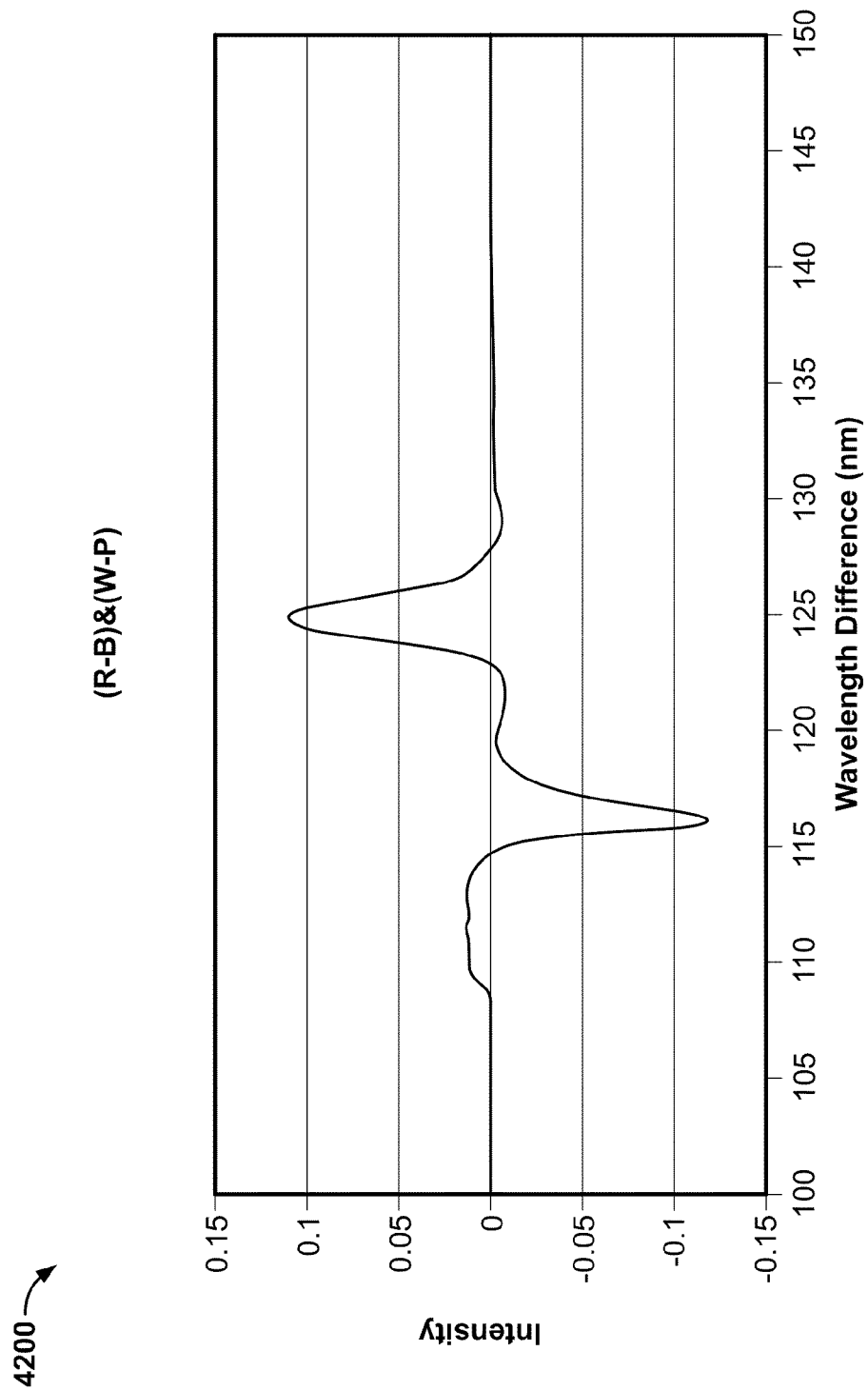
FIG. 42 depicts the combination of the two convolutions of the two color channel histograms.
Figure 43:
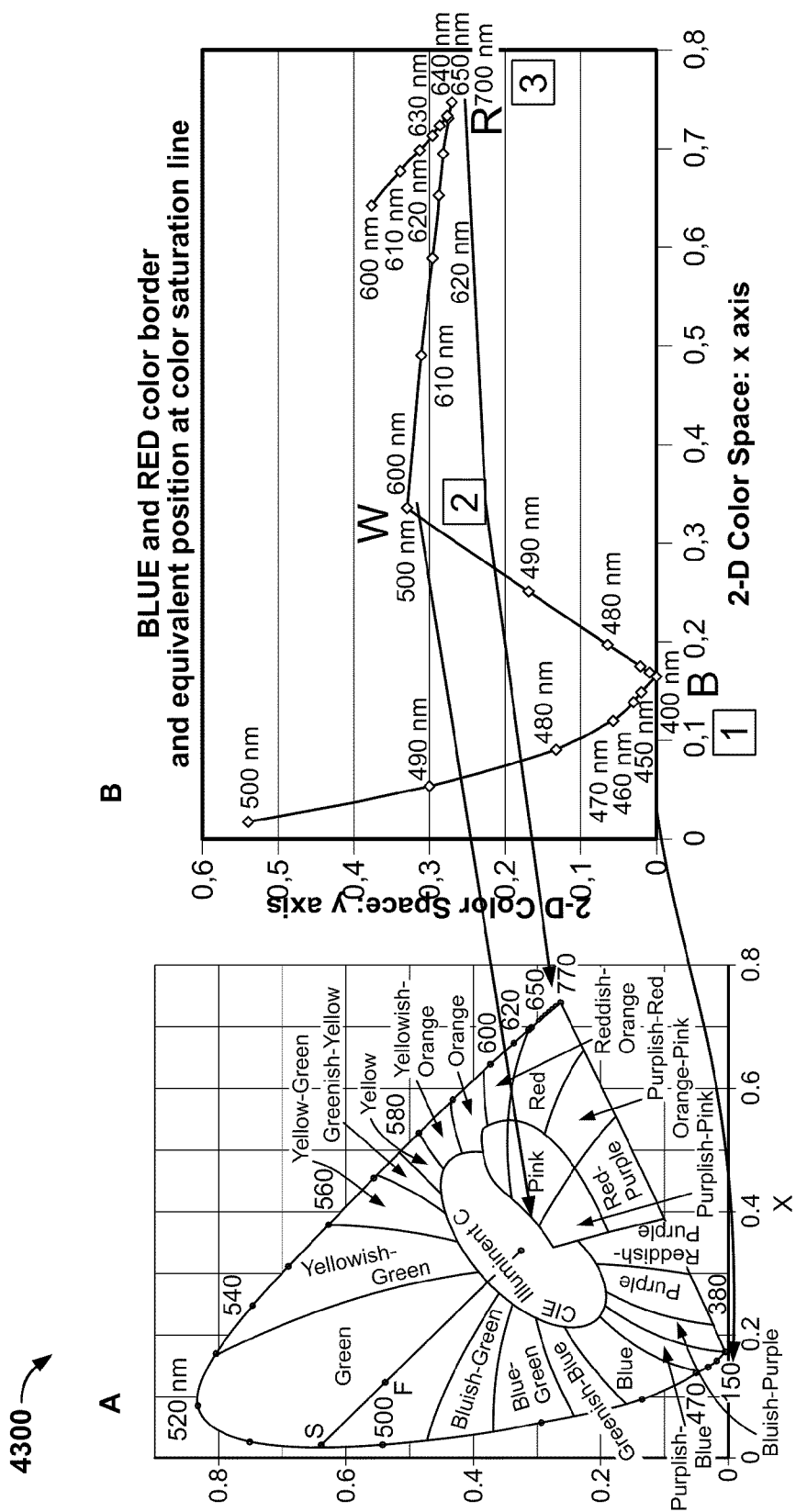
FIG. 43 depicts a mathematical modeling of a portion of Maxwell's color triangle.

Referring now to FIG. 42, the two color channel composite, normalized spectral plots are then combined to create a unique spectral signature of the specimen. The normalized, composite blue channel spectral plot is subtracted from the normalized, composite red channel spectral plot. The scale is determined as a difference in wavelengths between the red and blue color images, starting from the darkest point in both colors. This scale is based on the mathematical coordinate system for Maxwell's color triangle. For example, and referring to FIG. 43, the lower part of Maxwell's color triangle is shown plotted out in FIG. 43B, with arrows indicating the correspondence in the plot with the position on the color triangle shown in FIG. 43A. Position 1 in the plot corresponds to ideal blue in Maxwell's color triangle, position 2 corresponds to true white, and position 3 corresponds to ideal red. Points 1 and 3 are aligned when convoluting the composite spectral plots to obtain the spectral signature, hence the unit scale on the convoluted histogram is a difference of wavelength (e.g. 500-400 nm to 700-400 nm).

Figure 44A:
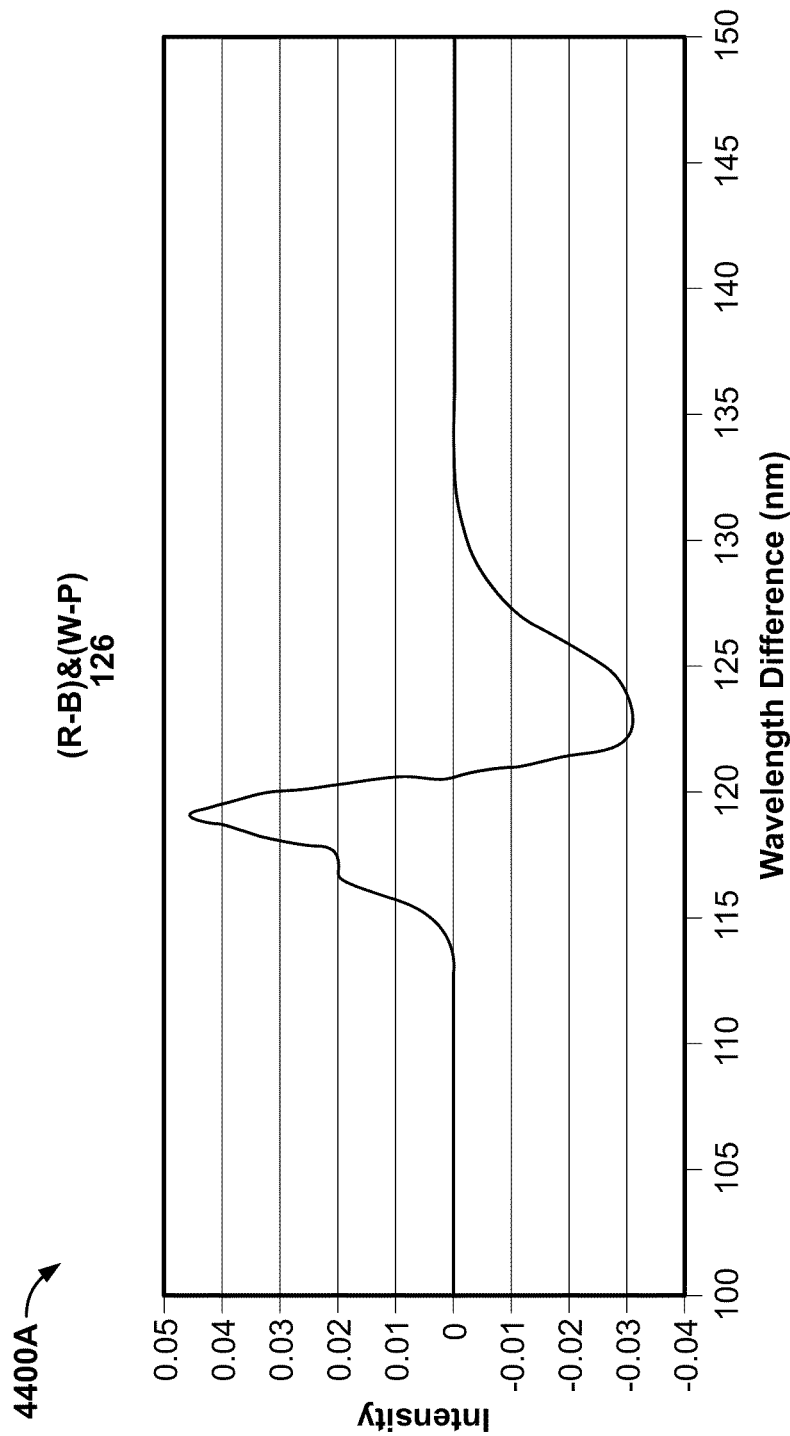
FIGS. 44A & B depict the resulting spectral signature for light and dark skin.
Figure 44B:
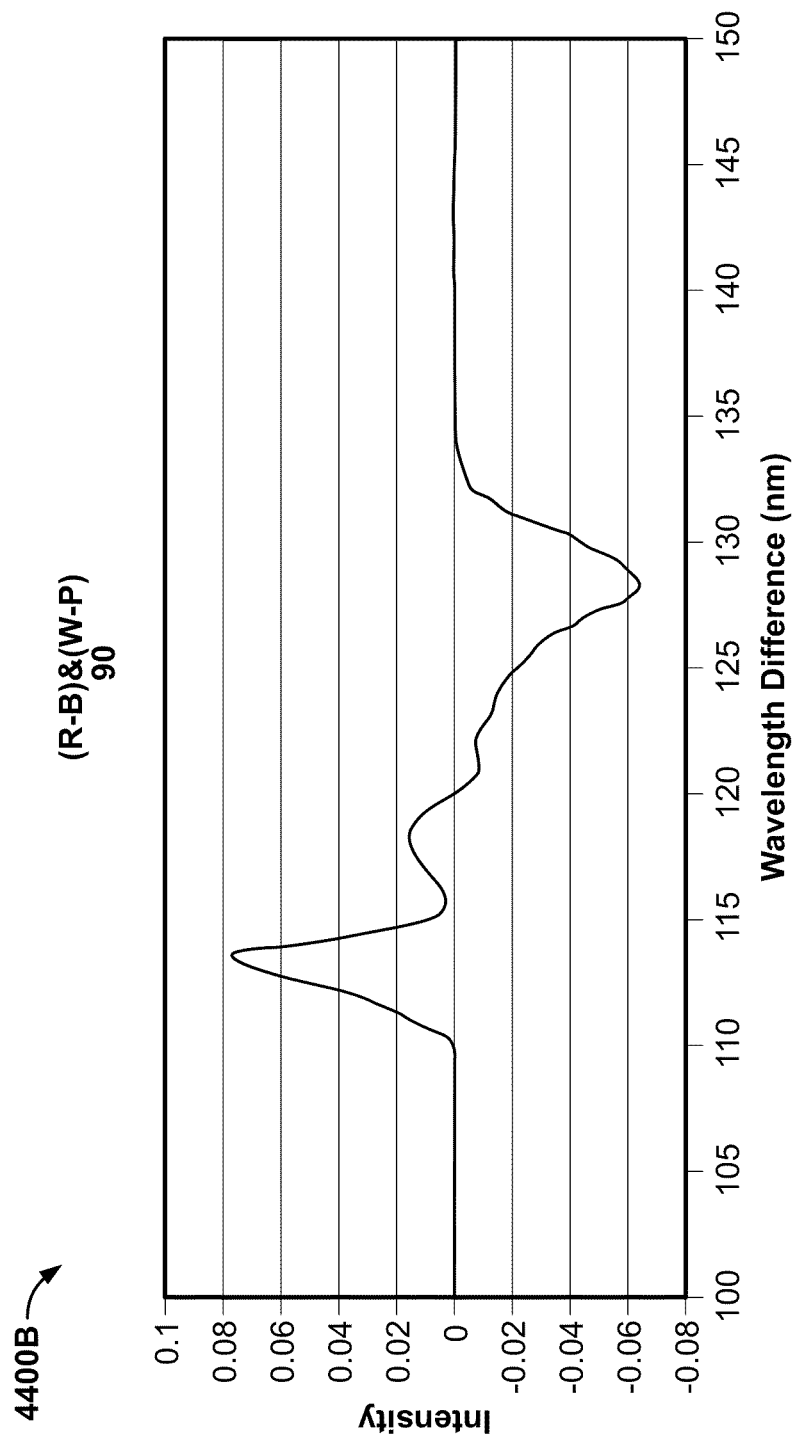

The spectral signature obtained may be analyzed for a number of characteristics, such as number of peaks and troughs, amplitude and shape of peaks and intermediate structures and patterns, and the like. Various mathematical, visual, and algorithm processing techniques may be used to process and analyze the spectral signatures. The spectral signatures obtained for various specimens may be unique, for example, the spectral signature in FIG. 44A is for light skin while the spectral signature in FIG. 44B is for dark skin.

Figure 45A:
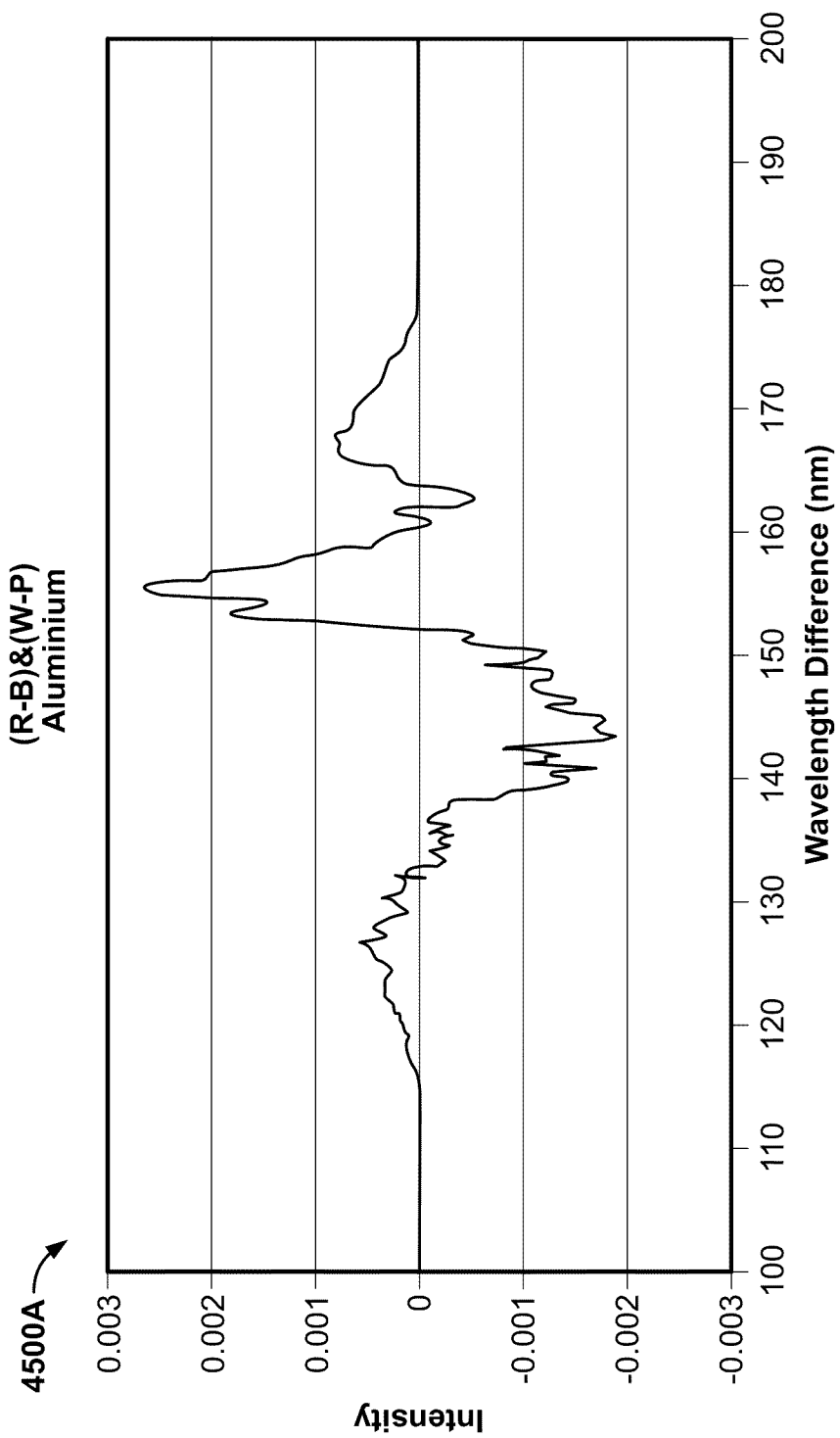
FIGS. 45A-C depict the resulting spectral signatures for pure and alloy metals.
Figure 45B:
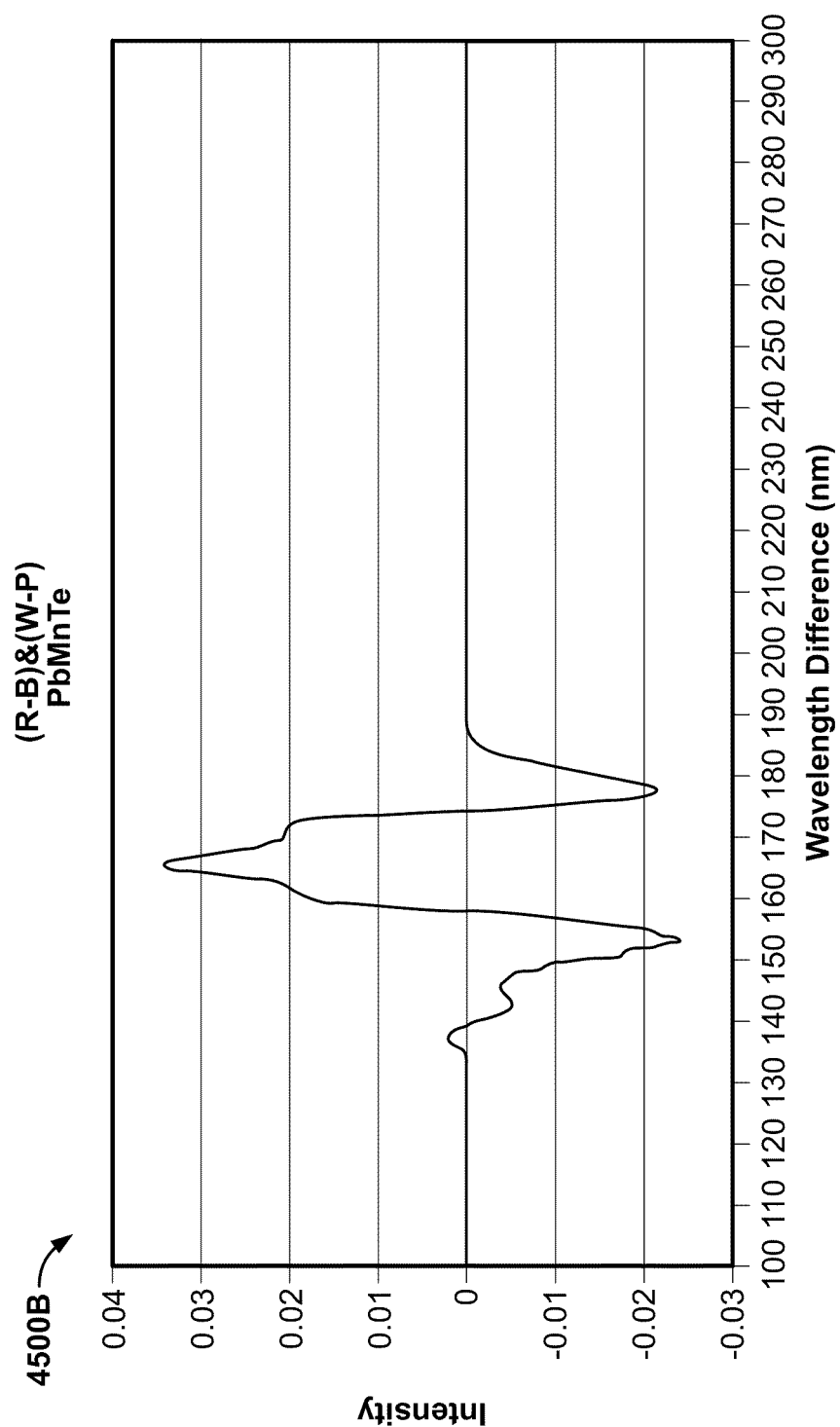
Figure 45C:
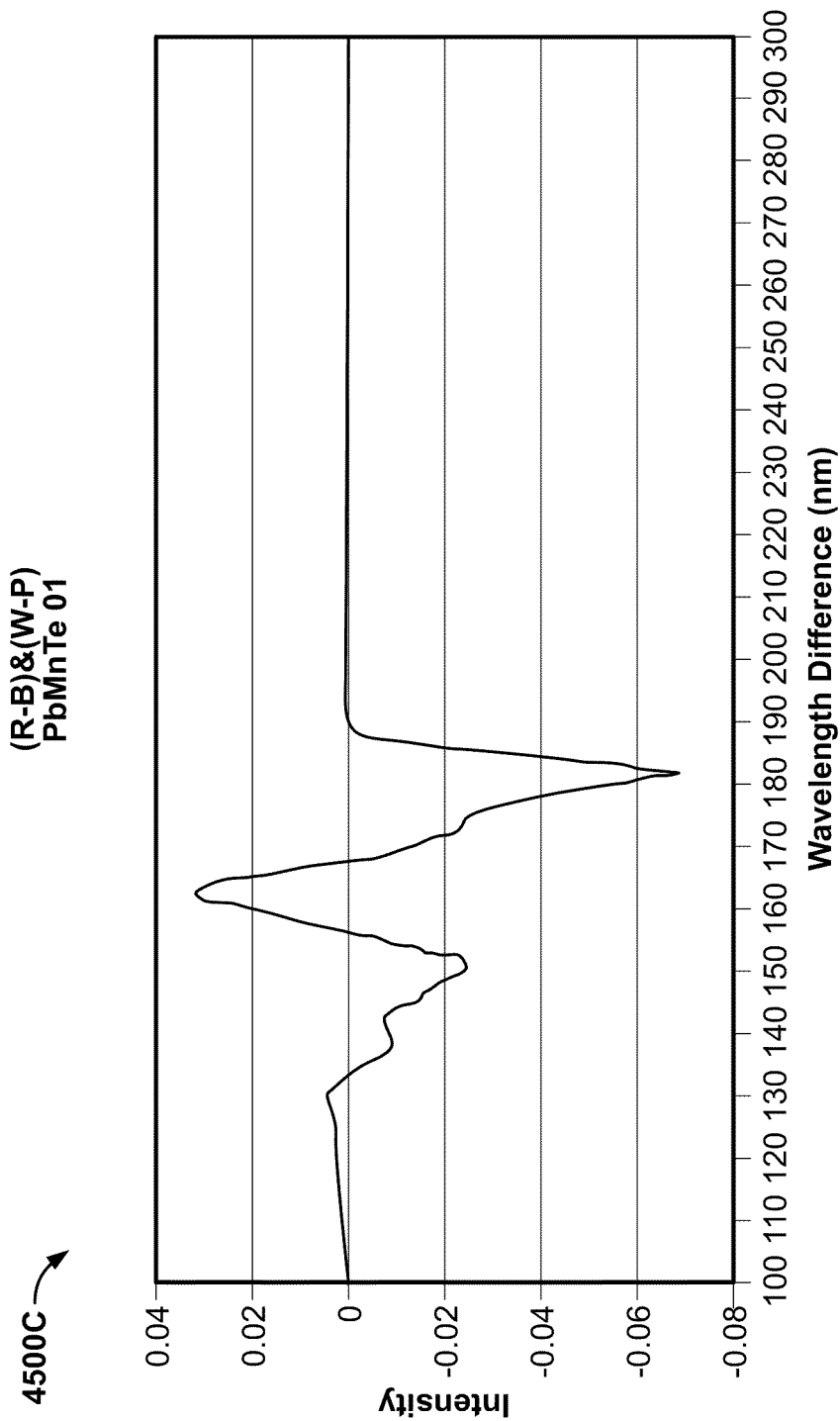

In an embodiment, the algorithm may be used for identifying metal composition, purity, strength, and the like. For example, the spectral signature may be used to distinguish between metals. The spectral signature in FIG. 45A is for a pure metal, aluminum, while the spectral signature in FIG. 45B is for an alloy of metals, PbMnTe. The spectral signature may also be used to distinguish between similar substances with different compositions. For example, the spectral signatures in FIG. 45B and FIG. 45C are both for the PbMnTe alloy but the alloy of FIG. 45B is of a different composition as compared to the one in FIG. 45A.

Figure 46A:
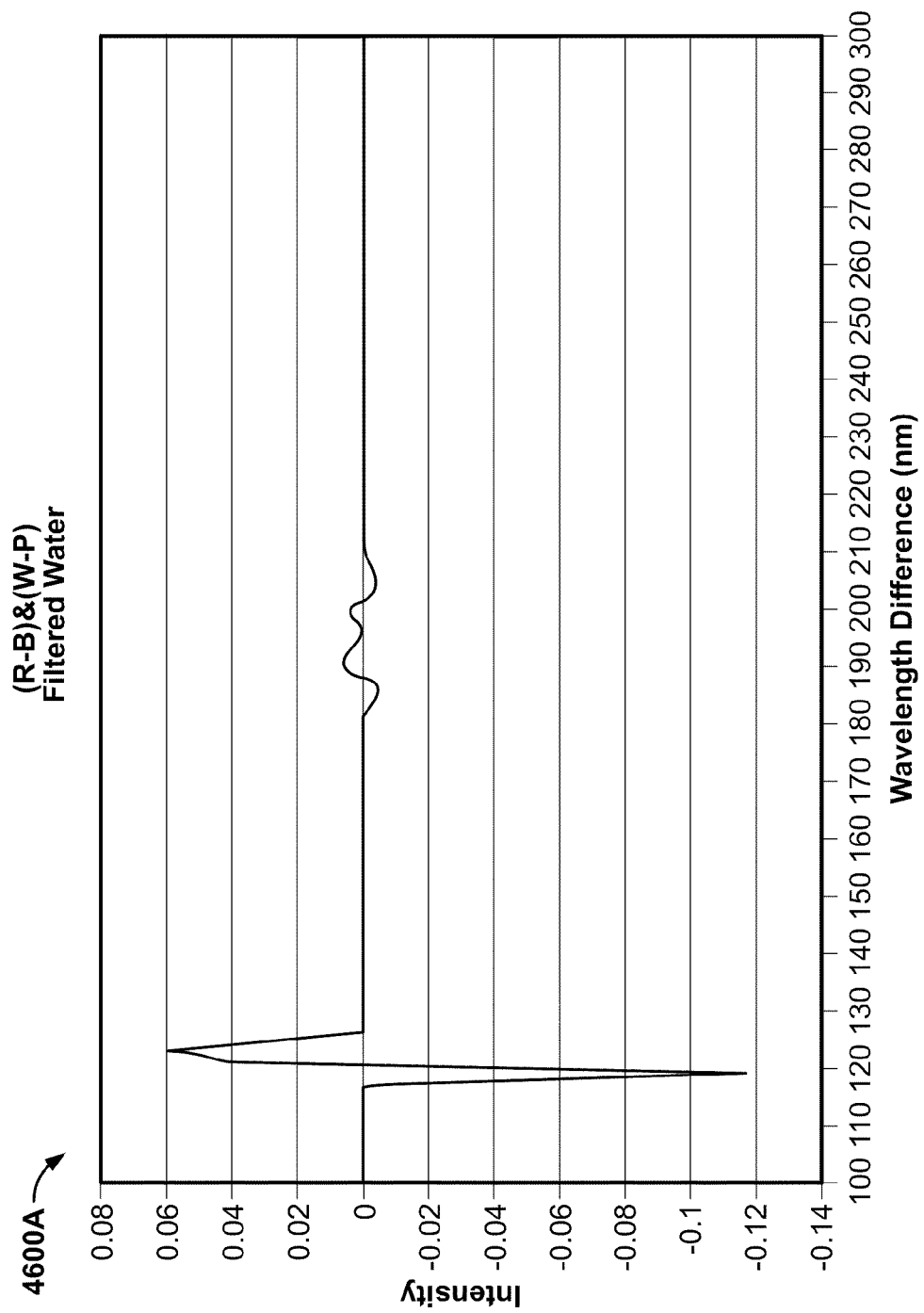
FIGS. 46A & B depict the resulting spectral signatures for different types of water.
Figure 46B:
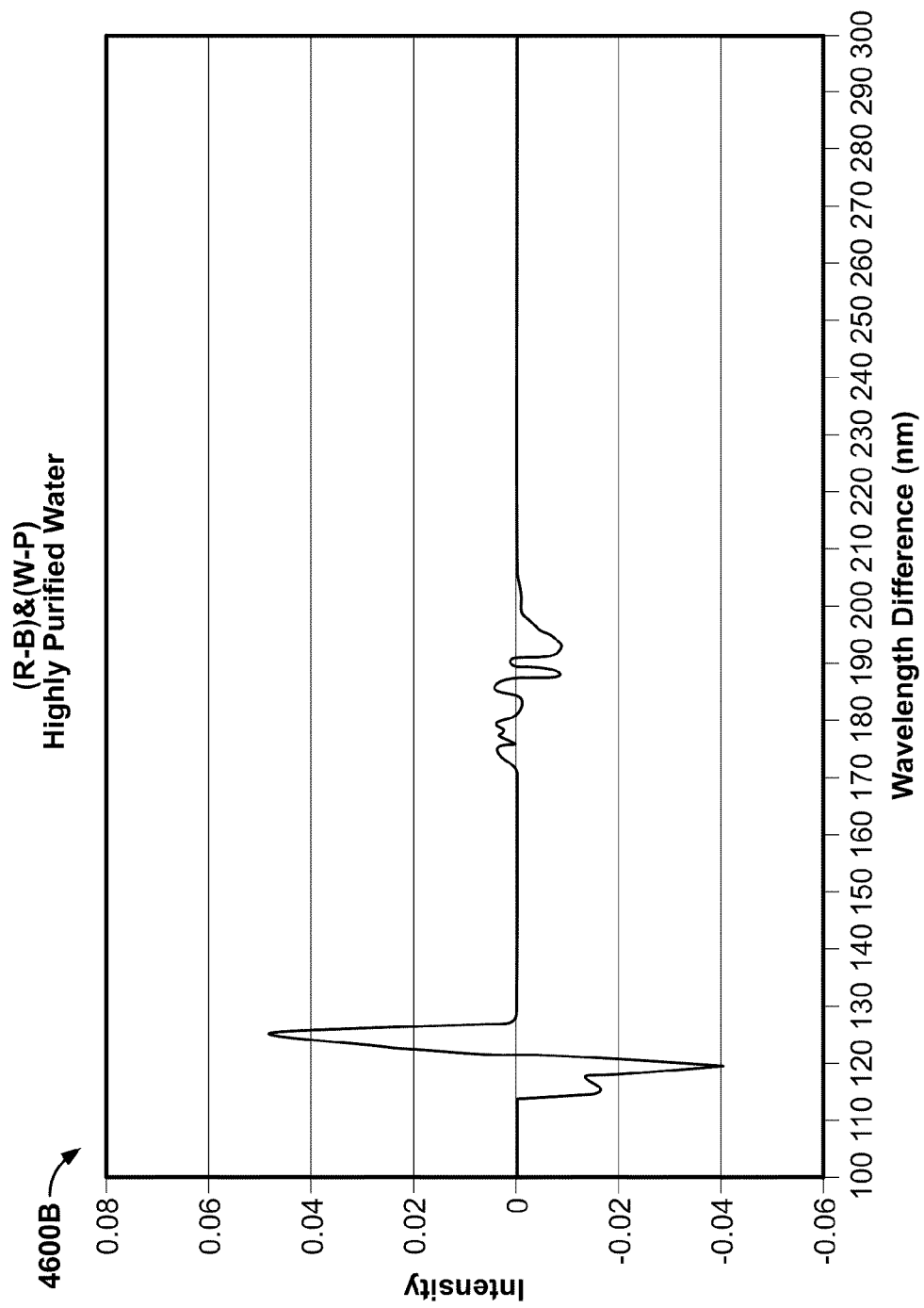

In an embodiment, the algorithm 150 may be used to analyze water quality, composition, purity, and the like. For example, the spectral signature for filtered water is shown in FIG. 46A in comparison with the spectral signature for highly purified water, shown in FIG. 46B.

The spectral signature may further be enhanced by subtracting the spectral contribution attributable to the source light from the reflected light spectrum in order to normalize the spectral signature to specific skin conditions. For example the spectral signatures in FIGS. 51 through 54 may be normalized by subtracting the source spectral signature from the reflected light spectral signature. By subtracting the source spectral signature, the resulting spectral waveform is normalized to only the changes in the skin from the interaction with incident light. In this way, specific type of incident light may be used which may be more amenable to detecting certain structures, compositions, or conditions. In some embodiments, a spectral signature for the subtraction of RGB histograms for angled light from non-angled light may be calculated and used to subtract from the final spectral signature for the material.

Other convolutions may be possible, such as for a yellow color channel or some other color channel. Additionally, pre-determined convolutions may also be possible.

Figure 51:
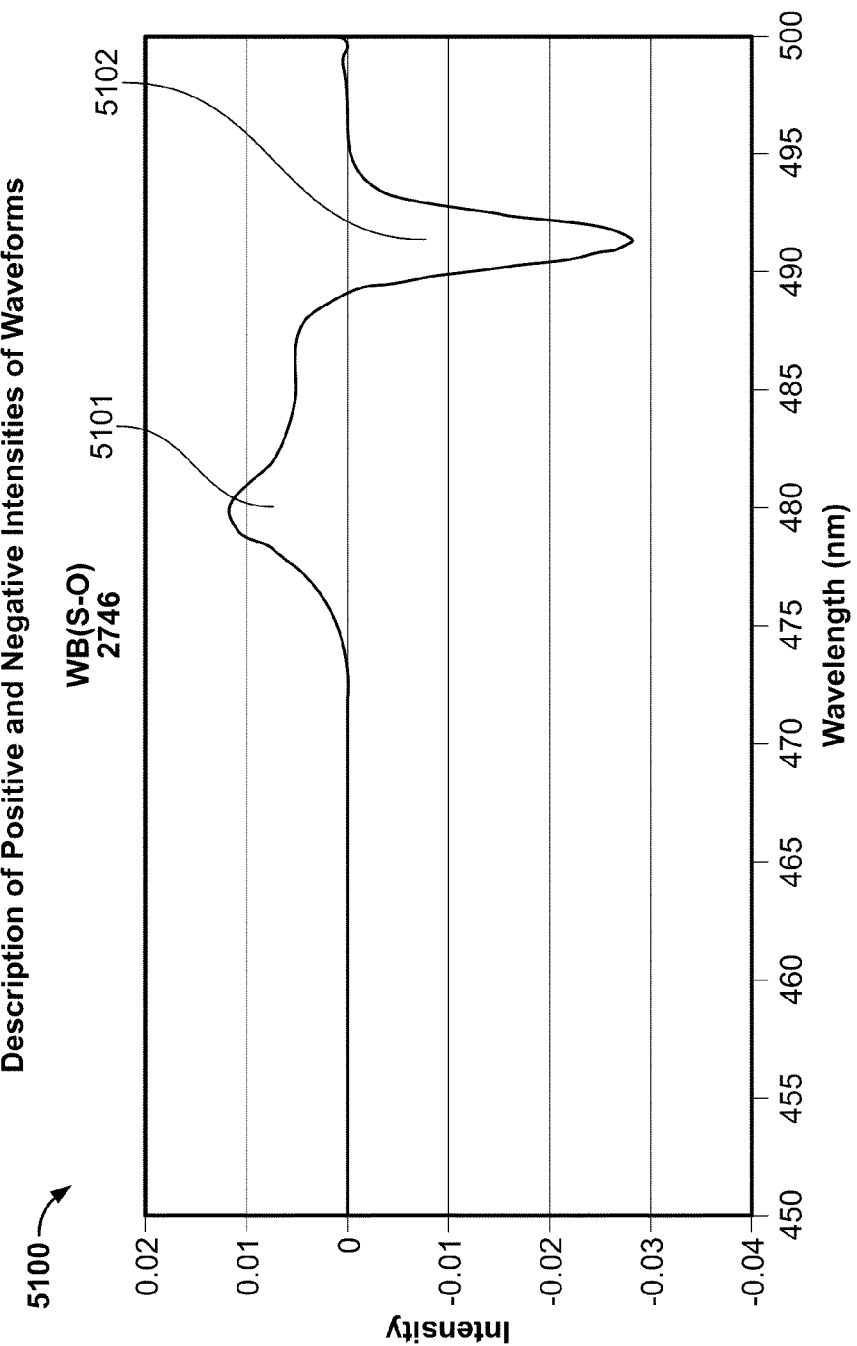
FIG. 51 depicts positive and negative intensities on a waveform as a function of emission and absorption of specific wavelengths within skin tissue.

Referring now to FIG. 51, positive intensities 5101 represent a net reflection or emission at specific wavelengths based on material characteristics while negative intensities 5102 represent a net absorption from the source light's spectral signature. Negative intensity 5102 indicates no absorption of source light at specific wavelengths based on material characteristics. The source may be selected for use in examining specific biophysical or material criteria in order to produce a specific waveform for analysis.

Figure 52A:
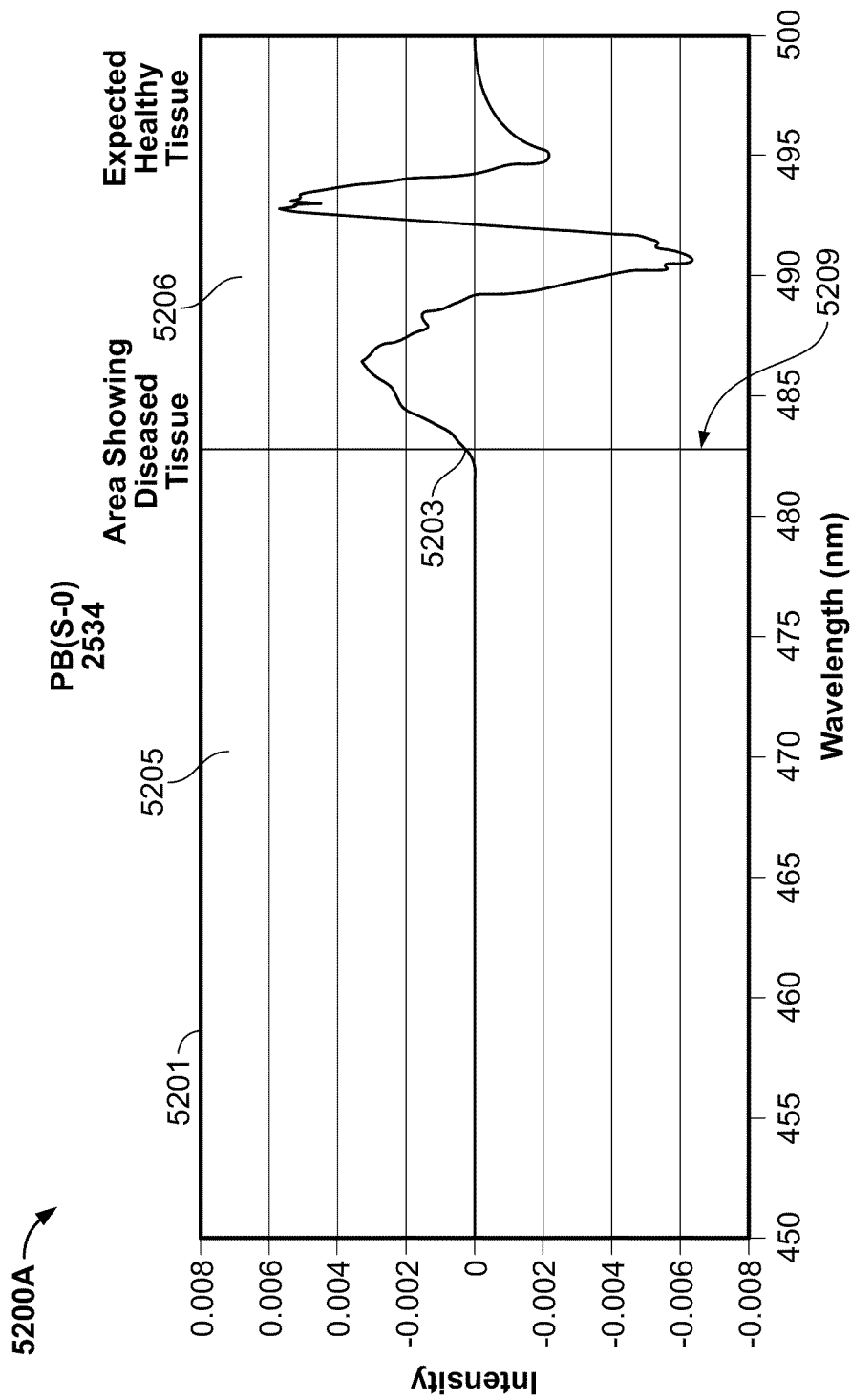
FIG. 52 depicts the comparison between spectral signatures of healthy skin and malignant skin around a reference wavelength.
Figure 52B:
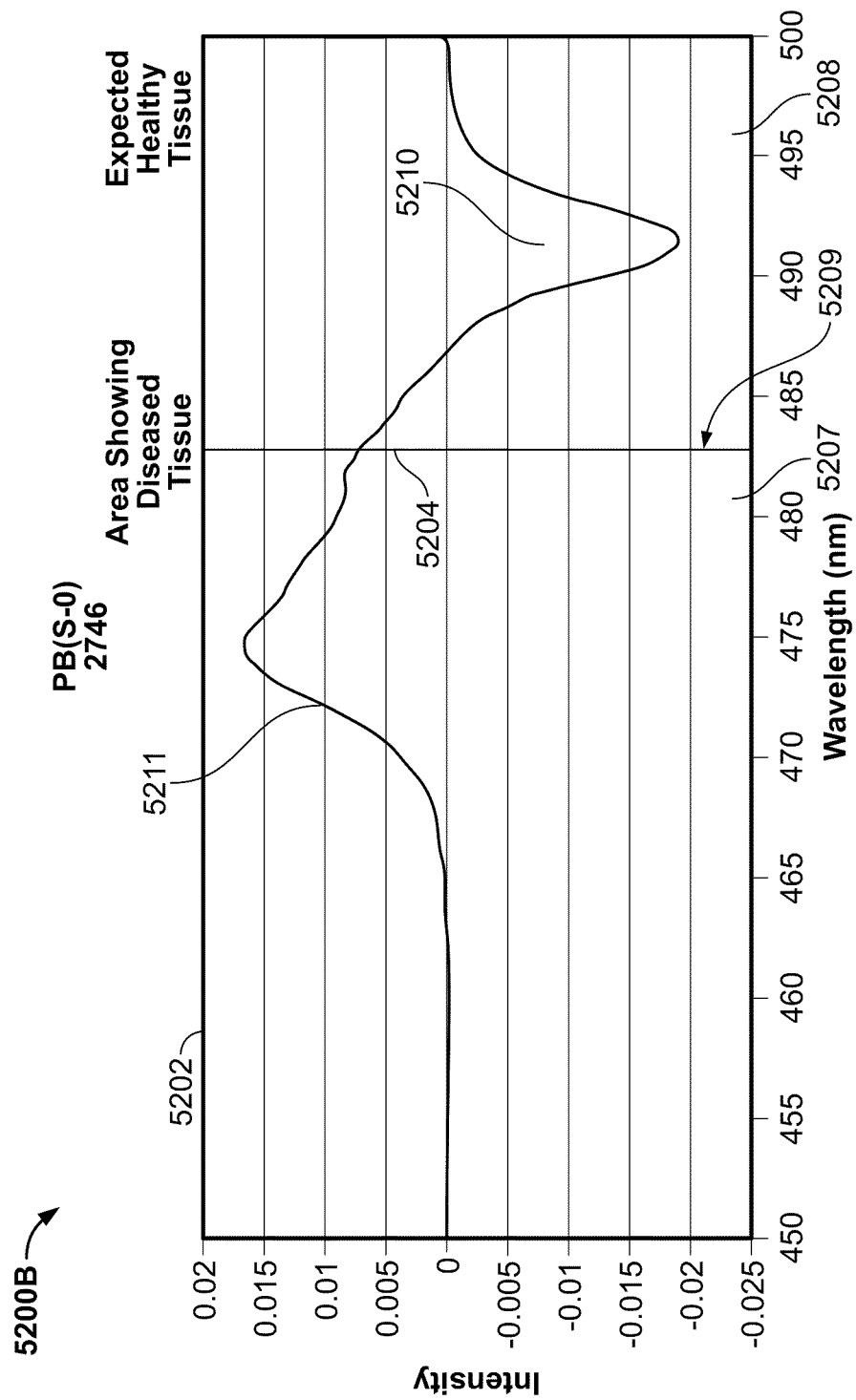

Referring now to FIG. 52, it is possible to determine changes in skin state 158 using spectral characteristics of specifically selected light sources based on specific biophysical criteria. FIG. 52 shows a comparison of PB(S—O) signatures showing an example for differences between benign/healthy expected tissues and diseased tissue. Changes, such as in the 462 nm-485 nm range in FIG. 52, such as absorption or emission within the spectral diagram may correspond to additional changes in tissue processes, tissue activity, or presence of other molecules that indicate a changed state of skin. By measuring these changes, it is possible to determine healthy and diseased or disturbed states of the skin. The characterization of healthy tissue based on emission and or absorption may be determined at a specific reference wavelength 5209 that is based on the source light selection. For example, the spectral signature of healthy skin 5201 using a specific source light shows little or no absorption or emission in the spectral range 5205. The spectral diagram shows normal spectral characteristics 5206 right of the reference wavelength at line 5203. Additionally, characteristics in the area 5207 to the left of the reference wavelength at the line 5204 indicate diseased characteristics due to re-emission or emission 5211, while the area 5208 to the right of the line 5204 indicates absorption 5210. The area 5207 corresponding to wavelengths 462 nm-485 nm shows additional activity due to additional changes in tissue processes, activity, or presence of other molecules that indicated a changed state of skin. The size and shape of peaks, troughs, curves, frequency, spacing, specific sections of wavelength differences, and the like may also correspond to concentrations of molecules, stages of disease progression, skin characteristics, and the like.

Figure 53A:
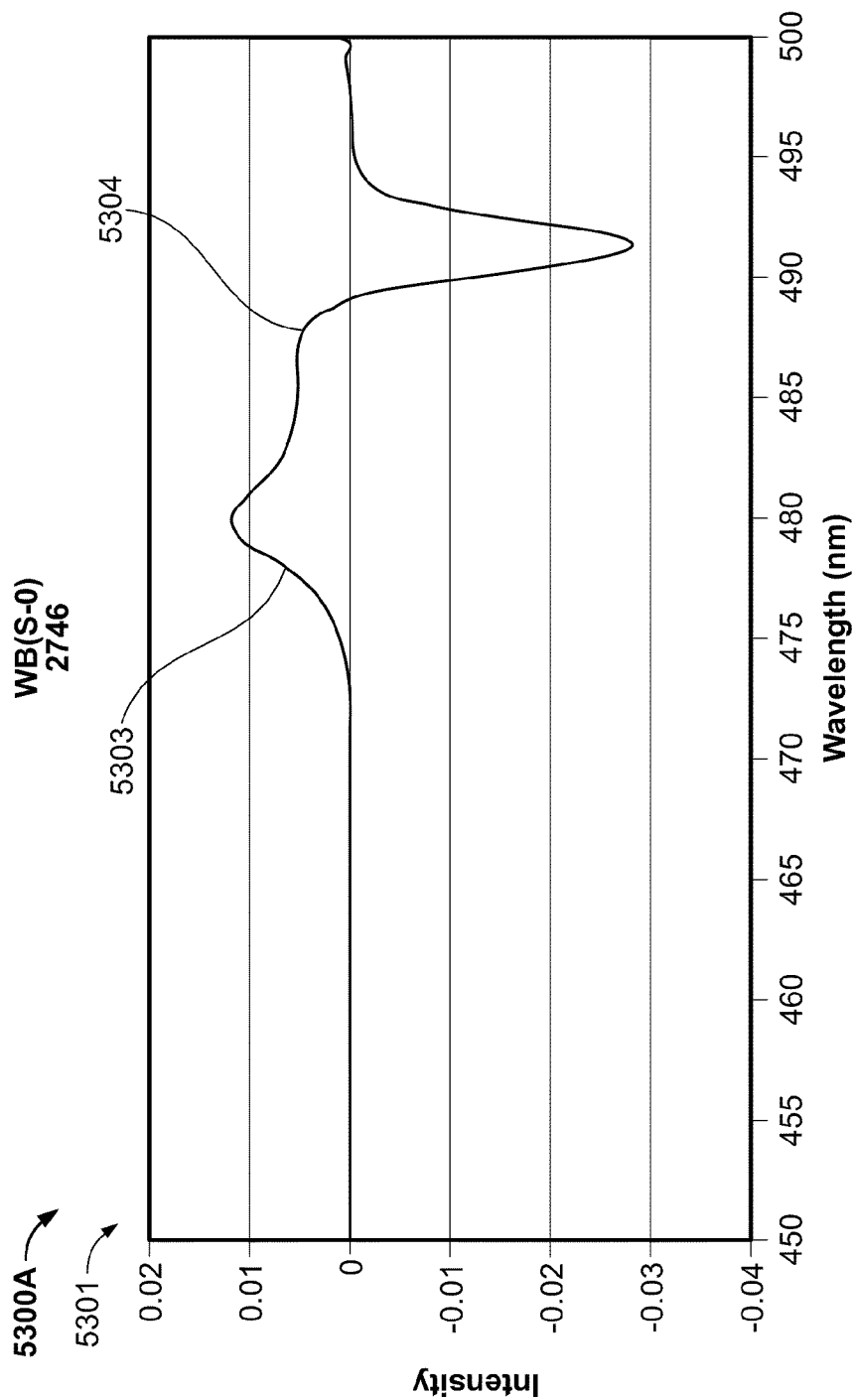
FIG. 53 depicts malignant pigmented skin in white and physiologically polarized white light.
Figure 53B:
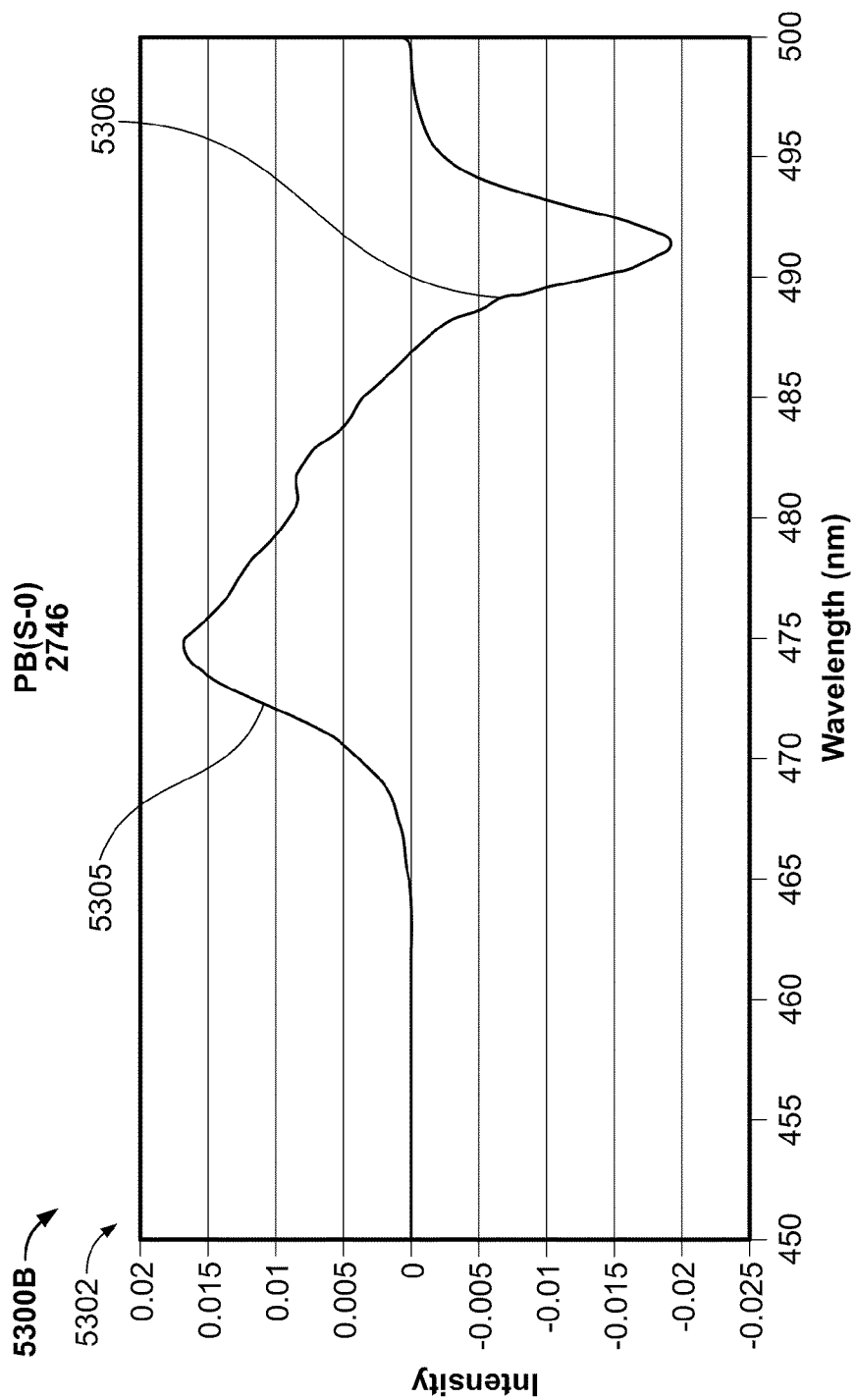
Figure 54A:
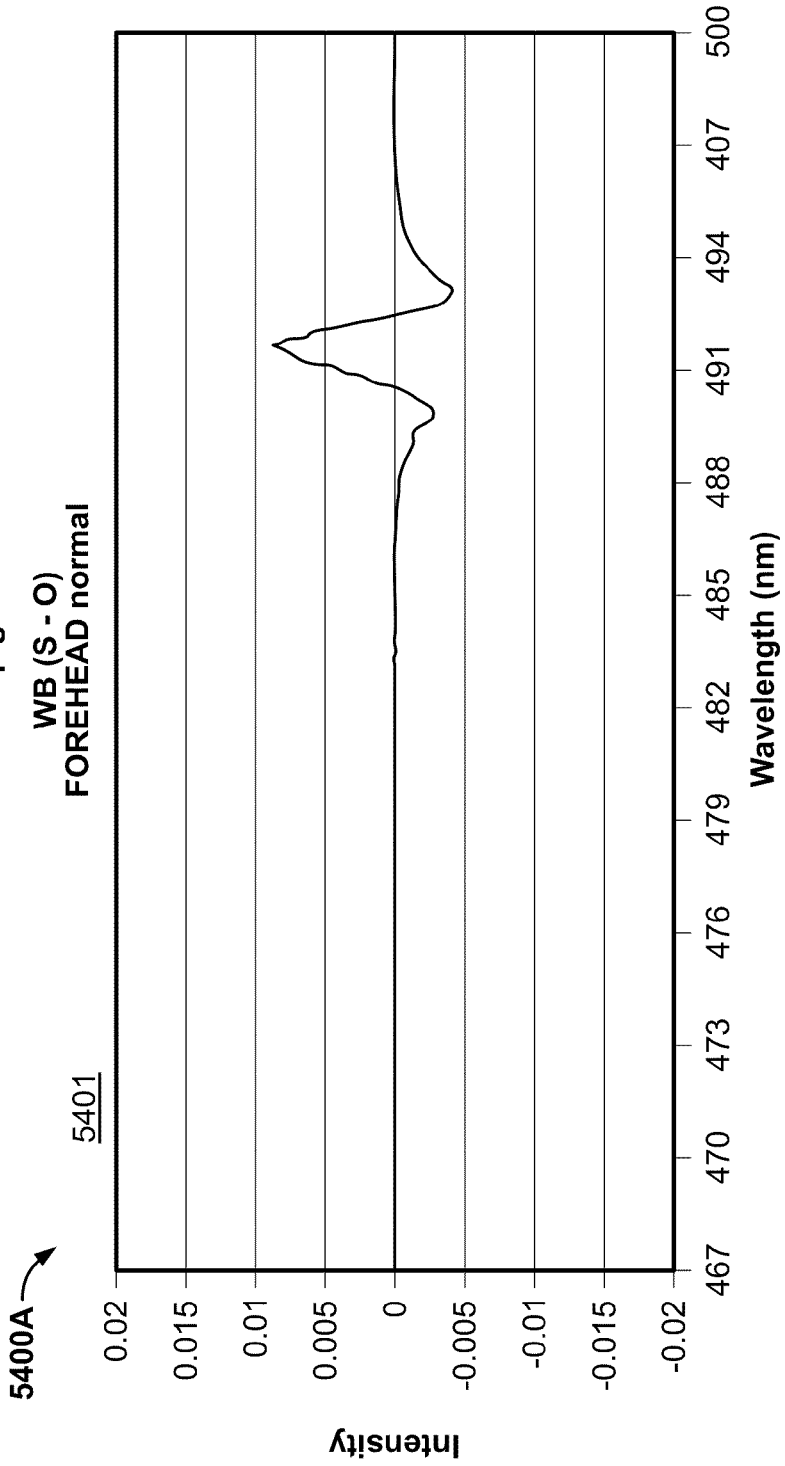
FIG. 54 depicts the comparison of convolutions between healthy, benign and malignant skin lesions.
Figure 54B:
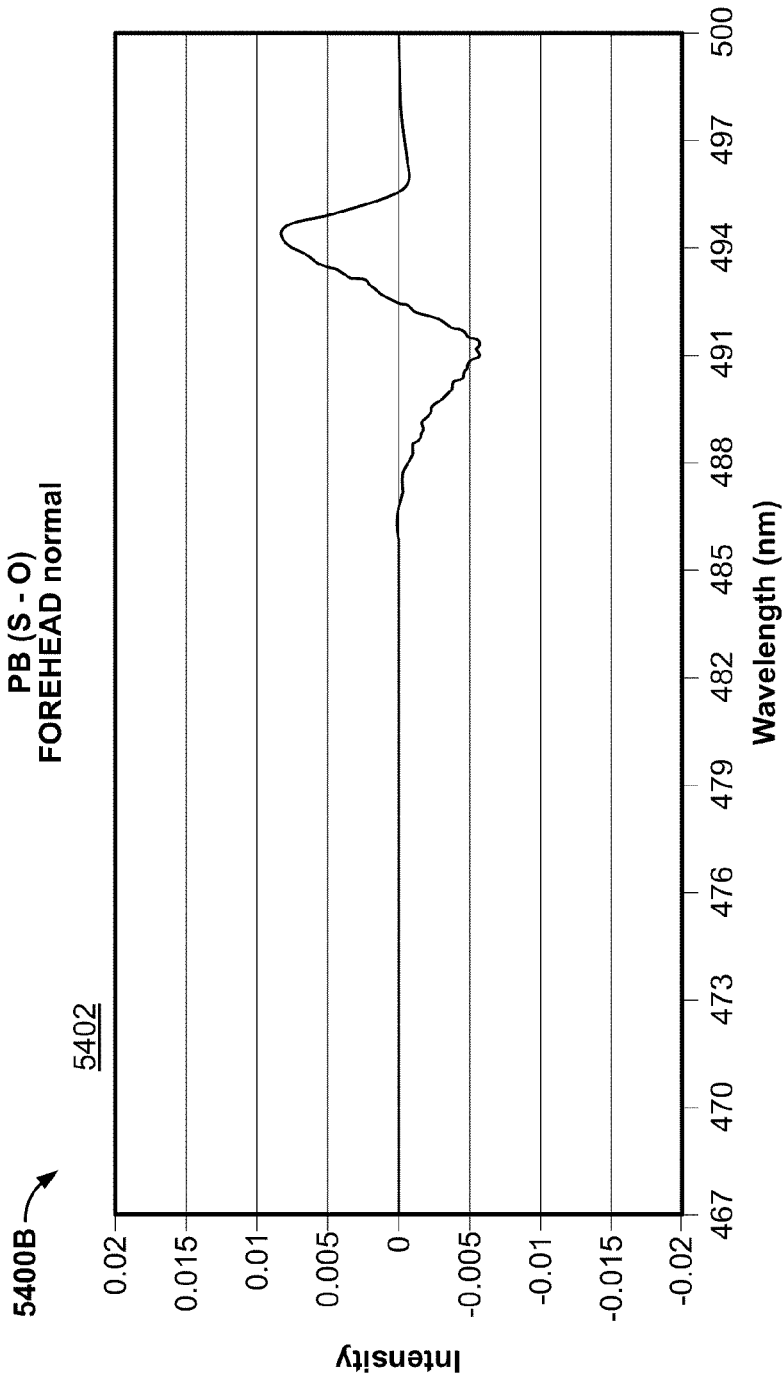
Figure 54C:
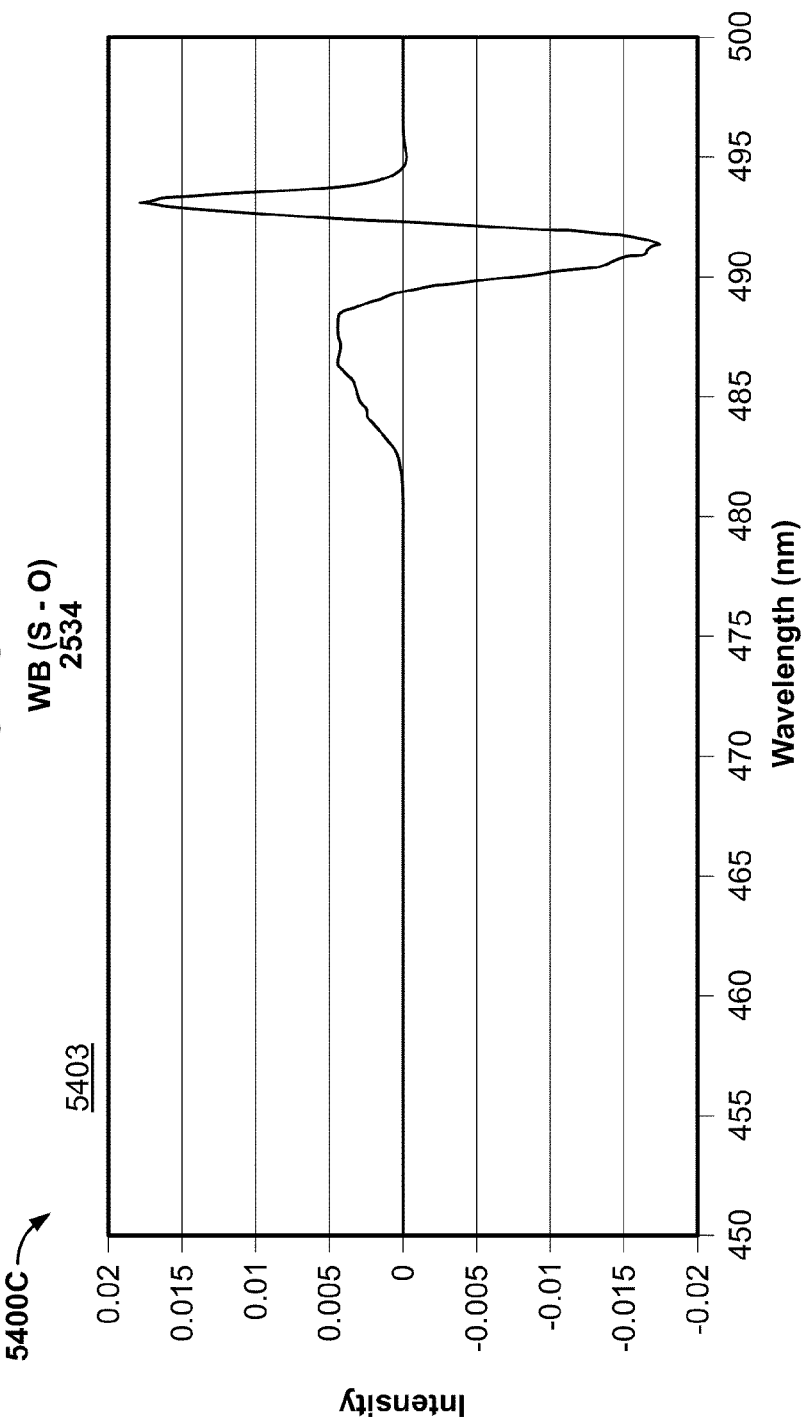
Figure 54D:
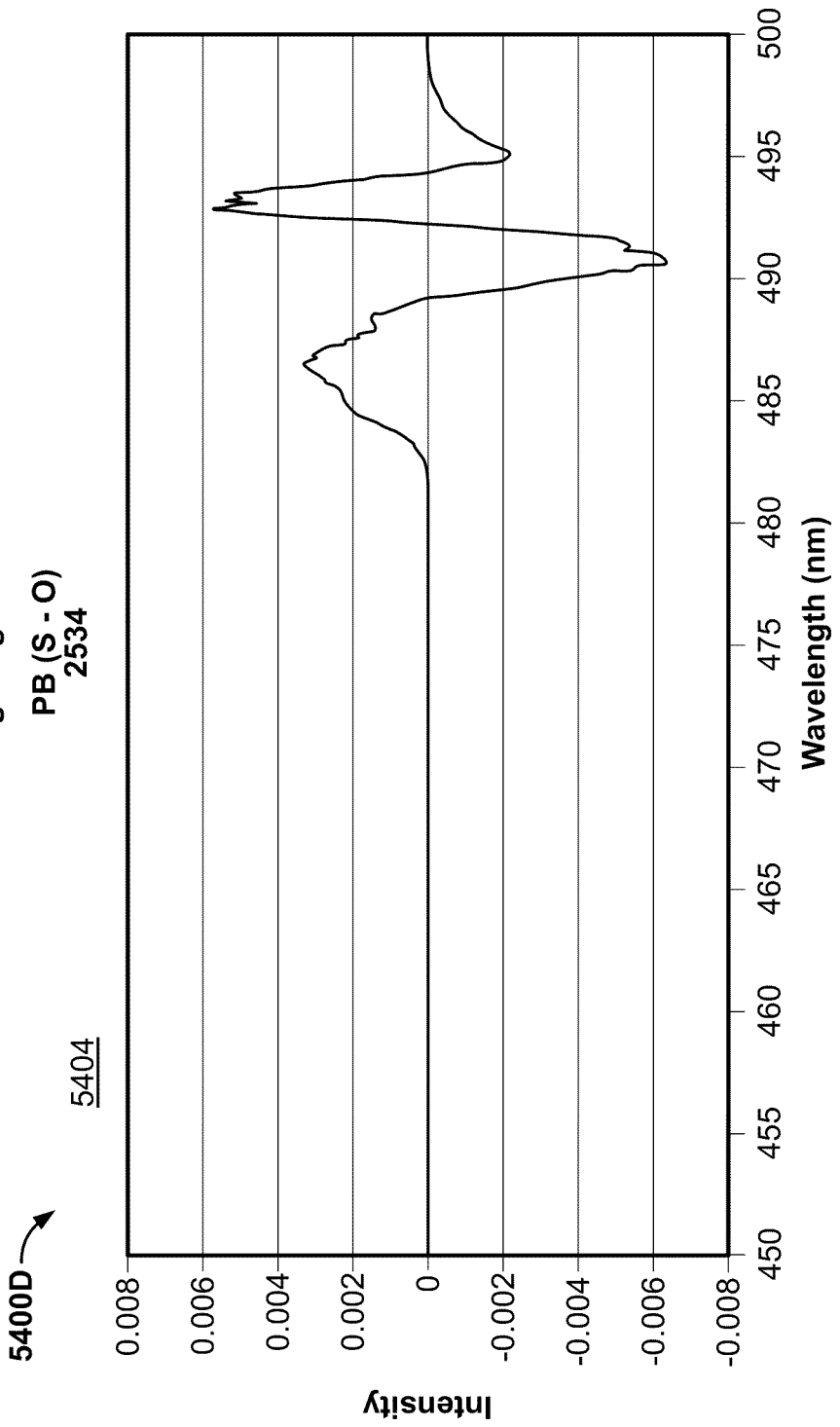
Figure 54E:
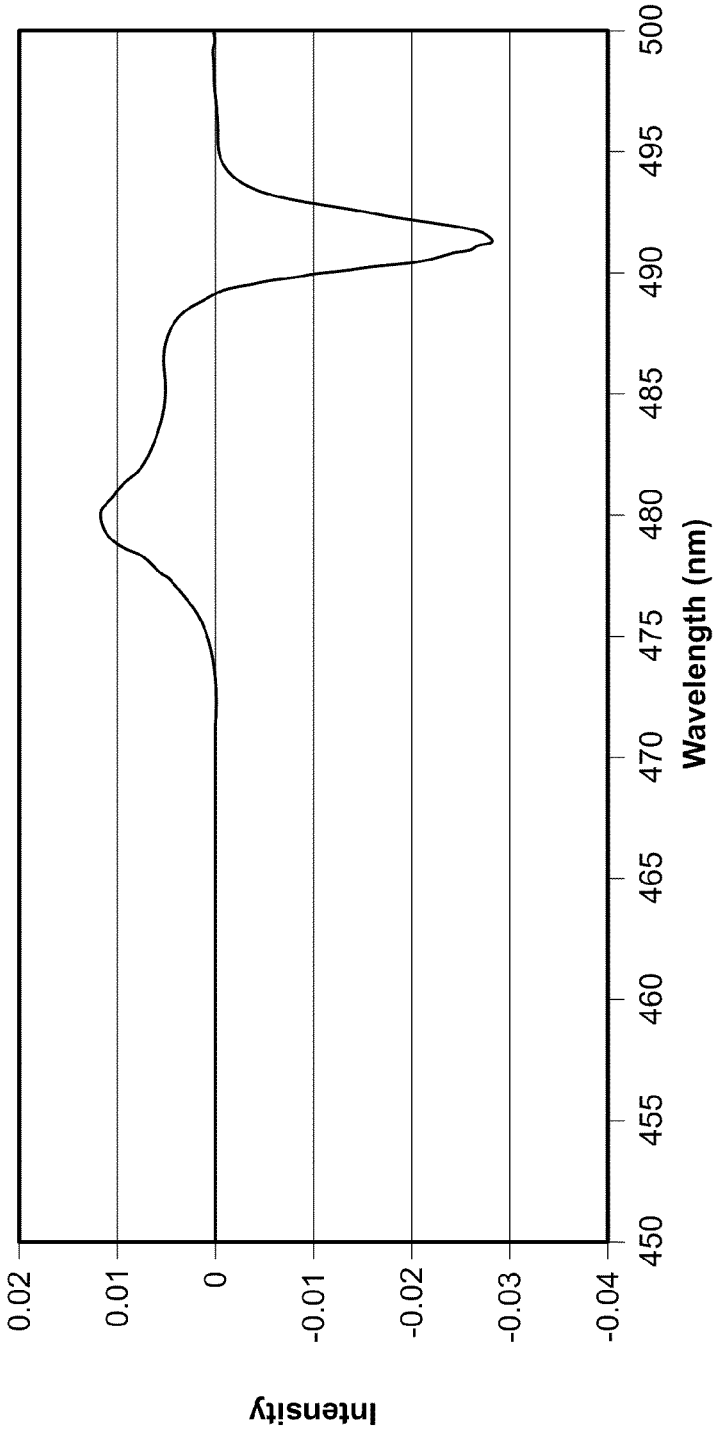
Figure 54F:
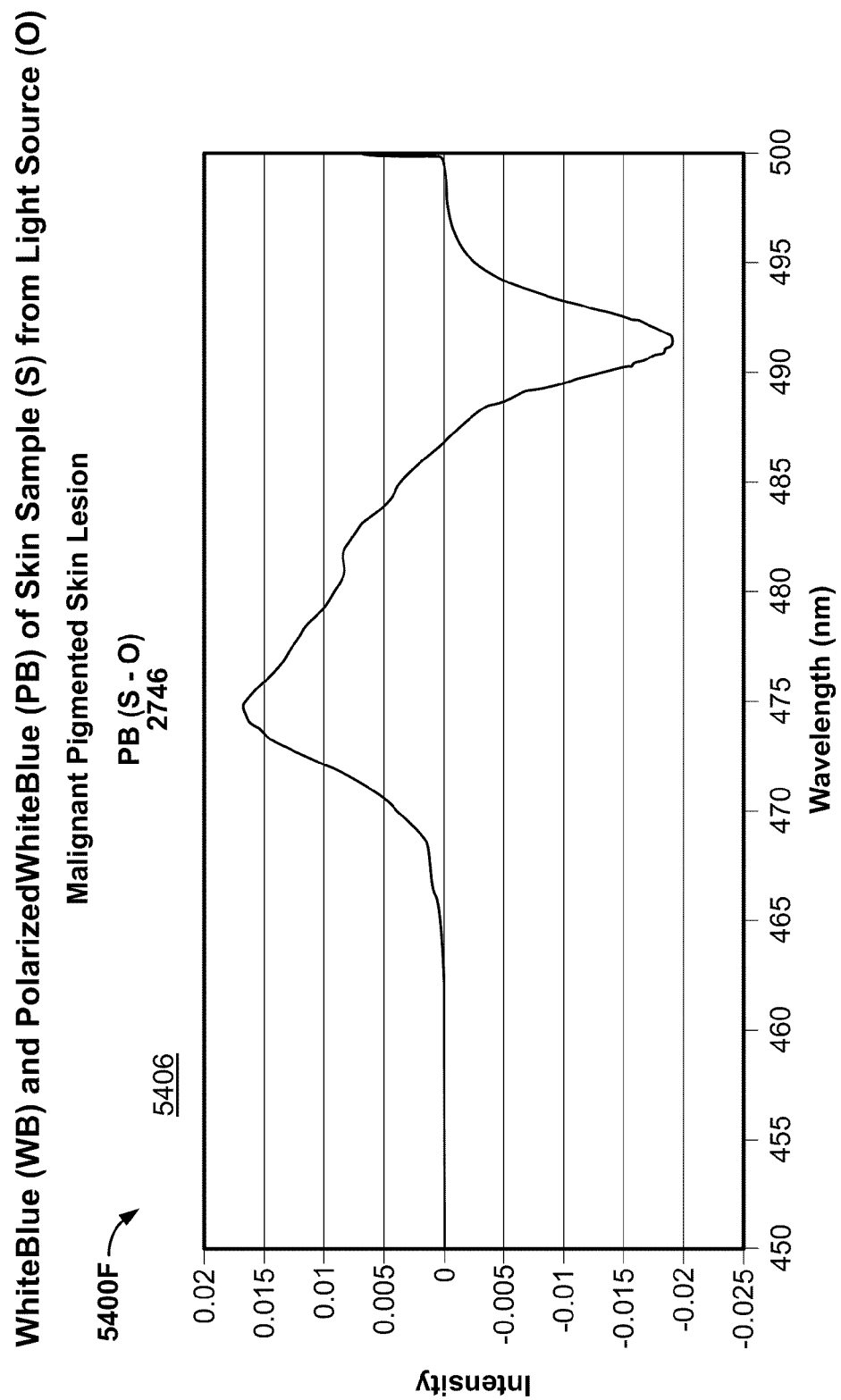

In an embodiment, the algorithm 150 may only use reflected polarized light due to increased selectivity for specific biophysical or material characteristics. For example and referring to FIG. 53, the reflected polarized and/or emitted polarized light spectral signature 5302 may be much more sensitive to certain biophysical characteristics than simple white light convolution 5301. FIG. 53 depicts the spectral signatures for malignant melanocytic lesions. The spectral diagram showing emission 5305 in the polarized 5302 spectral signature is much taller than the spectral diagram showing emission 5303 in the nonpolarized 5301 spectral signature. Similarly, the spectral diagram showing absorption 5306 in the polarized 5302 spectral signature is much deeper than the spectral diagram showing emission 5304 in the nonpolarized 5301 spectral signature.

In an embodiment, the algorithm 150 may be used to analyze healthy and non-healthy or malignant skin. For example, the spectral signatures for healthy, non-pigmented skin 5401 and 5402, healthy pigmented skin 5403 and 5404, and malignant pigmented skin 5405 and 5406 are shown in FIG. 54. Both polarized (bottom) and white light (top) spectral signature convolutions are shown for purposes of comparison. The spectral signature of normal, healthy skin 5401 and 5402 shows very little absorption or emission relative to the source light spectrum around referent wavelength 485 nm. Similarly, the healthy, benign pigmented skin lesion 5403 and 5404 shows very little absorption or emission to the left or right of the reference wavelength 485 nm. The malignant tissue, however, clearly shows absorption and emission effects around the referent wavelengths with higher amplitudes and shifting of the spectral diagram peaks and valleys.

In embodiments, these spectroscopic techniques may be useful for a variety of analytical tests where the test substrate comprises a light-sensitive component.

In an embodiment, elements of the waveform may be tagged and tracked over time in order to track changes in the characteristics of the material or specimen, such as peaks, troughs, curves, frequency, spacing, specific sections of wavelength differences, and the like.

In an embodiment, the algorithm 150 may be incorporated for automated measurement as part of an integrated device that conducts surface analysis, such as a skin imaging device or metal testing device. In an embodiment, the algorithm 150 may be part of a remote analysis system whereby a surface imaging device may capture images and send them to a processing center where the algorithmic computations may be made.

In an embodiment, the algorithm 150 may be used for the analysis of hair in order to determine the health of hair follicles, composition, and the like.

In an embodiment, the algorithm 150 may be used for the counterfeit analysis of money. For example, a unique signature may be created for each series of appointment and/or issue.

In an embodiment, the algorithm 150 may be useful for the analysis of anti-perspirant effectiveness. In certain cases, axillary odor may be an indication of sickness or some other medical condition, such as lymphoma, apocrine gland sweating, hyperhidrosis, hydradenitis suppurativa, or other sweat related medical problems. The algorithm 150 may be useful in determining a scale of deodorant effectiveness based on an individual's specific sweat gland activity and type. The algorithm 150 may enable measuring the activity of sweat glands located in the axilla, feet, palms, and the like. The algorithmic analysis may enable the classification of sweat glands and may enable the suggestion of appropriate products/ingredients for treatment. The algorithm 150 may be able to determine the effectiveness of an anti-perspirant based on the impact on sweat gland activity.

In an embodiment, the algorithm 150 may be useful for determining a veterinary condition, such as Mad Cow disease. For example, imaging the tongue of a cow or any mucosal or dermal area where the disease may manifest may allow for the detection of a disease state using the algorithm 150. White light imaging, as described herein, in combination with UV imaging may facilitate detection of a Mad Cow disease state.

In an embodiment, the algorithm 150 may be useful for monitoring post-operative cosmetic concerns, such as stretch mark progression and diminishment, and the like.

In an embodiment, the algorithm 150 may be useful for predicting and monitoring secretion from the mammary glands of lactating women. If milk production is predicted to be low based on the algorithmic analysis, suggestions may be made to increase milk production.

In an embodiment, an algorithm 150 for determining a skin state 158 may facilitate measuring, tracking, and monitoring a skin state 158 as well as the effectiveness of a regimen 118, topical and/or systemic therapies, avoidance routines, diet, and the like. For example, the skin state 158 may be measured at intervals and current measurements may be compared to previous measurements to determine skin health changes. As will be further described herein, the results from the algorithm 150 may feed into a recommendation engine to provide feedback and modifications to aspects of the regimen 118.

In an embodiment, an algorithm 150 for determining a skin state 158 may enable a diagnosis. The diagnosis may be an early diagnosis by distinguishing between critical and non-critical indications. For example, the algorithm 150 may be able to distinguish between a minor sunburn and a third degree sunburn requiring medical attention. Use of the device 108 to capture images enables a user to readily transmit the images to any practitioner for remote assessment, to track progression of a skin condition, rapidly compare images to previous images, other user images or third party images, such as images in a dermascopic database 115, and the like, and to make an immediate assessment with no need for historical knowledge, and the like. Historical data and the results of modeling tools 132 may be compared to the images to assist in analysis, either by an algorithm 150, a practitioner, or a practitioner employing an algorithm. Also, in addition to images, user input in the form of audio, video, or text anecdotes describing the issue, such as a level of pain, a sensation of heat, an itchiness, and the like, may be useful in analyzing the images to determine a diagnosis. The algorithm 150 may enable non-linear regression, such as principal component analysis (PCA), which may be a biomedical analysis used in conjunction with spectrometric analysis for analyzing medical and health conditions. The algorithm 150 may enable a simple pattern analysis for diagnosis. The algorithm 150 may be able to determine the thermo- and electroconductivity conditions of skin lesions. In an embodiment, the algorithm 150 may be able to diagnose a melanocytic lesion by examining the images for the relationship of changes in collagen and porphyrin, as a change in collagen but not porphyrin may indicate a change from a normal lesion to a dysplastic lesion. The skin state 158 may be compared with a table of indicators for various types of lesions. In an embodiment, the algorithm 150 may be able to diagnose UV damage. UV damage may be difficult to assess from a conventional superficial view as UV damage may be present even in wrinkle-free skin. However, UV damage may be assessed by examining skin structures for an increase in melanin production; global distribution, damage and count of superficial blood vessels; change in hemoglobin count: changes in the thickness of the epidermis; changes in the quantity and global distribution of collagen, and the like. In an embodiment, diagnosis may not require processing the border of the lesion, as it may not be a key factor in final analysis of the skin lesion. In an embodiment, the algorithm 150 may be able to diagnose oral cancer.

In an embodiment, an algorithm 150 for determining a skin state 158 may enable cosmetics manufacturing validation or cutaneous clinical trials. For example, a skin state 158 may be determined prior to medical, non-medical, skin care product or cosmetics application and a time lapse series of images may be acquired to track the medical, non-medical, skin care product, and cosmetics effectiveness.

In an embodiment, there may be methods for storing, handling, integrating, and analyzing a skin state 158. The skin state 158 may be stored in the device 108 itself, on a PC, in a central server, a salon record, an e-medicine record, a medical repository, a cosmetic clinical studies database 115, a mobile device, and the like. The device 108 may communicate with a user interface 102, an online platform 120, a mobile platform 124, and the like to upload, deliver, share, and/or port images, analysis 154, skin states 158, data, track history, user profiles, and the like, as will be further described herein. For example, a user may use a device 108 embodied in a mobile device to capture an image of the skin and upload it to a mobile platform 124 for analysis 154 to determine a skin state 158. In response, the user may receive a personalized regimen 118 for sun protection given the user's skin state 158. Other factors that may be used to determine the regimen 118 may be the current UV Index, time of day, location, kind of sun protection product the user prefers, and the like. In the same example, the user may have already obtained a skin state 158 determination and they need not upload a new image but simply request a regimen 118 recommendation from the mobile platform 124 given the already determined and stored skin state 158. Once a skin state 158 is determined, it may be accessible by and/or integrated with any element of the user interface 102, online platform 120, mobile platform 124 and the like. A user may choose to share the skin state 158 as part of a practitioner record 180.

In an embodiment, an algorithm 150 for determining a skin state 158 may enable an analysis of differences and similarities among peers. The algorithm 150 may determine peers of a user who may be most like them in terms of skin state 158 or other criteria such as gender, age, ethnicity, behaviors such as smoking, working outdoors, and the like, diet, regimen 118, and any other identifying factors. The algorithm 150 may be able to interface with an online platform 120, third party database 115, or third party service provider 111 to access skin states 158 and demographic information for comparison. For example, a user may wish to know what other women in their mid-30's of the same skin color are using for foundation. By employing the algorithm 150, a user may be able to determine their own skin color, identify peers according to the search criteria, and view details on their peers' regimen 118 or the results of the specific search query 103. The algorithm 150 may enable grading of the skin relative to a peer group. Using the algorithm 150, a user's skin state 158 may be compared to a previously defined skin state 158 in order to monitor the skin state 158 over time. A user's skin state 158 may also be compared to the skin state 158 of other individuals or groups of individuals to identify peers whose skin state 158 is closest to the user. Once a peer, such as a similar individual or group, is identified, the system may display the skin care products and/or skin care regimen that is effective for the peer. Similarly, any comparison among users may be made by the system, such as a comparison of at least one of age, gender, location, climate, skin color, ethnicity, and the like, to identify a peer. In an embodiment, as the device 108 captures data from users and determines skin states 158, the information may be fed back into the algorithm 150 to further enhance the peer identification and product recommendation process.

Figure 6:
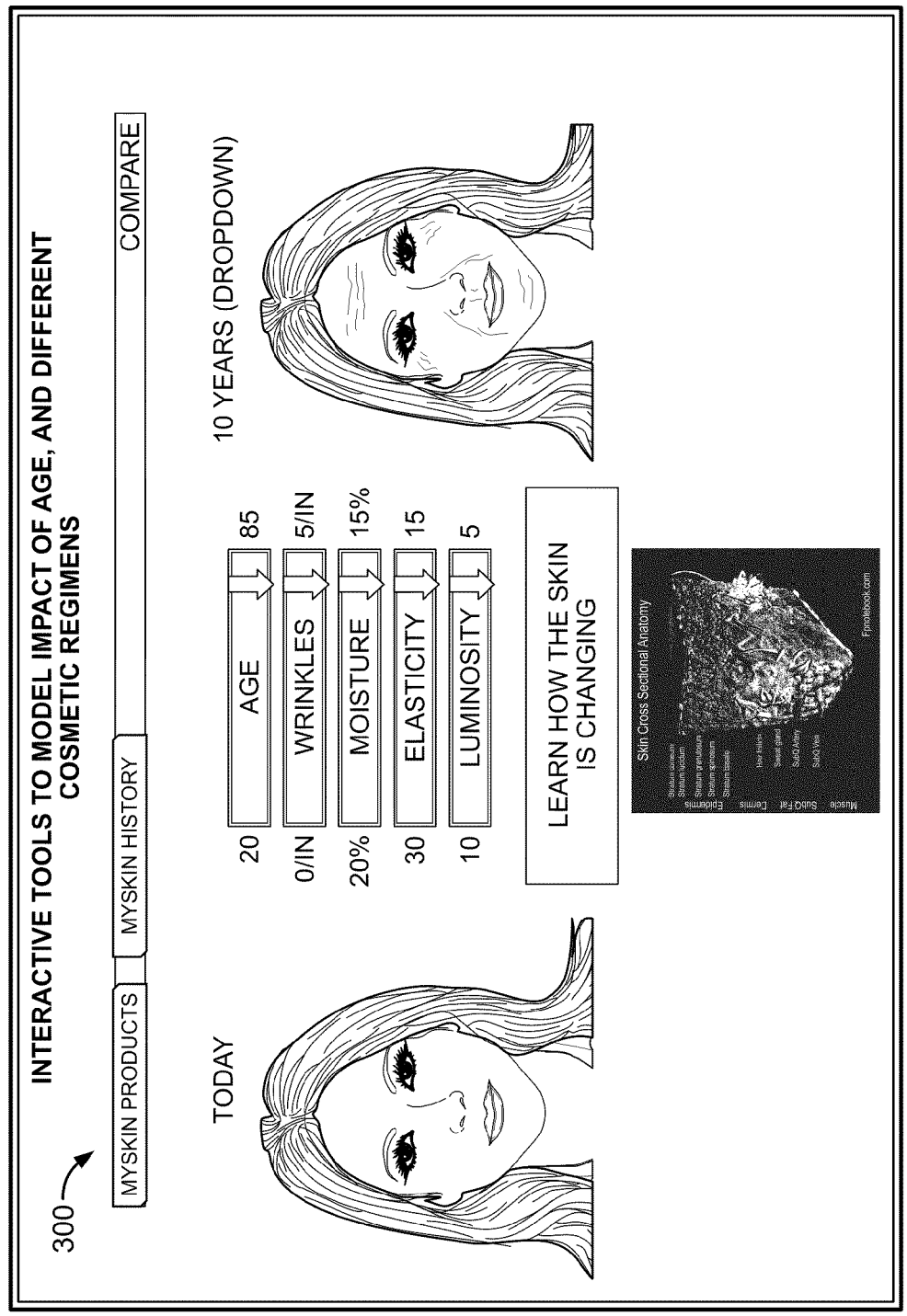
FIG. 6 depicts an interactive modeling tool of a skin care system.

In an embodiment, an algorithm 150 for determining a skin state 158 may enable prediction/simulation tools 132. Having determined a skin state 158, an algorithm 150 may be able to simulate progression of aging, simulate skin care treatment effects and skin care and cosmetic regimens 118, simulate progression of a skin condition, and the like. Referring to FIG. 6, a user may use a user interface 102 to access the simulation tools 132. In the example, the image of an entire face may be used but it should be understood that simulation tools 132 may be used to generate simulations for any size area of concern. After selecting or capturing a starting image, a user may indicate the kind of simulation they would like to perform. For example, the user may like to perform a simulation of aging only, or a simulation of aging and treatment effects. The simulation tool 132 may return data on overall appearance, wrinkle count, elasticity, luminosity, moisture, product usage simulation, and the like. For example, the output may also include a split image with the original face on one half and a new simulated output on the other half.

In an embodiment, an algorithm 150 for determining a skin state 158 may enable skin cycle monitoring 140. By monitoring skin at determined intervals, skin conditions with a cyclical nature may be monitored, predicted, preempted and the like. For example, skin conditions associated with a season, weather, pollen count, hormone level, environmental condition and the like may be identified and monitored by a skin cycle monitor 140.

In an embodiment, an algorithm 150 may be used to generate searchable and/or indexable tags to associate with images and may take advantage of image tagging. Images may be tagged with information relating to the content of the image, such as information relating to a skin state, a skin condition, a gender, an ethnicity, an age, a regimen, a treatment, and the like. The information may be gathered by algorithmic analysis, user input, visual inspection of the image, and the like. An algorithm 150 may be used to perform a search 103 using the information associated with the image as a search term. In embodiments, the information may be stored separately from the image, such as an entry in a user profile, or may be stored in association with an image. In an embodiment, a search 103 may be performed against information or images from other users' or a third party database 115 to identify similarities or differences in images or information. For example, a user may use information to search for peers with a similar skin condition in order to determine what to expect as the condition progresses. In another embodiment, the search 103 or query for advice or recommendation from experts may be performed against product information 190, wellness information 192, skin care regimens 118, third party experts 105, and the like. For example, a user may use information to search for product information 190 indicating an effectiveness of a product for the user's skin condition. In an embodiment, the search 103 may be performed to determine an availability of a product, an inventory of a product, a price of a product, and the like. For example, a user may use the information to search a store catalog for a specific product that may be effective for the user. In the example, the user may be pale skinned and be interested in identifying an inventory of a self-tanning product formulated specifically for pale skin. In an embodiment, the image itself may be used as a search query 103. For example, the image itself may be used to search a database 115 of skin images. In an embodiment, images and information entered into the system 104 may be leveraged to develop new algorithms 150 for enhanced diagnosis. For example, algorithms 150 may be developed for non-skin specific diseases with dermal manifestations, such as rheumatoid arthritis.

In an embodiment, an algorithm 150 may be useful for analyzing product characteristics. For example, an algorithm 150 may be able to take product ingredients and match the product up with a projected effectiveness on a particular skin state 158.

In an embodiment, an algorithm 150 may use RGB color analysis. The algorithm may employ standard RGB analysis and correlation with skin structures in determining skin phototype. The calculation of parameters for determining skin phototype is fast and the skin phototype can be found in a very short period of time using a simple skin and cosmetic parameters classification routine.

Exemplary embodiments of the present invention are directed to a method and system for determining skin characteristics and cosmetic features. The method and system provide a minimal error and speed efficient skin analysis. The present technique describes a method and a system for determining a skin phototype of acquired digital image in a Red Green Blue (RGB) color system.

In an exemplary embodiment of the present invention, a method for determining skin characteristics and cosmetic features using color analysis includes a step of analyzing the color of skin images in a pixel by pixel manner in a Red Green Blue (RGB) color system for an acquired digital image. The colors obtained in a device dependent RGB color system are then converted into device independent standard RGB color system (sRGB) which will be used in subsequent color analysis. The step of analyzing the color of skin images in a pixel by pixel manner in a sRGB color system for an acquired digital image comprises analyzing a picture of a part of a person's skin by generating a table of most frequent colors appearing in the picture.

In this embodiment of the invention, the sRGB color system has been used for image analysis. Determination of other skin characteristics (e.g. elasticity, melanin, oil concentration etc.), melanoma, skin related tumors and skin related disorders may require image analysis based on various color systems such as YIQ, YCbCr, L*a*b*, L*u*v* and HSL/HSV. The enhancement of the current algorithm 150 may include at least one of these color systems and its/their correlation with presented sRGB analysis. This will most likely lead to in-depth refinement and overall accuracy of the current results as well as further embodiments of the present invention. Apart from the human skin related issues, this method of image analysis is also applicable to any content whether it be animals, products, plants or any other material whose surface needs to be analyzed by a digital image.

A method for determining skin characteristics and cosmetic features using color analysis includes a step of generating a sample of most frequent sRGB colors responsive to analyzing the color of skin images in a pixel by pixel manner in the RGB color system for the acquired digital image after converting colors obtained in a device-dependent RGB color system into a device-independent standard RGB color system (sRGB). The step of generating a sample of most frequent sRGB colors responsive to analyzing the color of skin images in the sRGB color system for the acquired digital image comprises preserving a plurality of sRGB color values.

A method for determining skin characteristics and cosmetic features using color analysis includes a step of modeling the standard R, G and B component color distribution with Gaussian probabilistic distribution with estimated parameters (expected value and standard deviation) of the generated sRGB color sample for the acquired digital image further including approximating colors of the generated sRGB color samples by a Gaussian normal distribution. In accordance with an exemplary embodiment of the present invention the step of approximating colors of the generated sRGB color samples by a Gaussian normal distribution comprises approximating colors of the generated sRGB color samples by a superposition of a plurality of Gaussian normal distributions.

A method for determining skin characteristics and cosmetic features using color analysis includes a step of generating a phototype of the skin through a decision tree unit responsive to the estimated distribution model parameters colors. The phototype of the skin is generated according to a corrected Fitzpatrick classification, or any other applicable color classifier. In accordance with an exemplary embodiment of the present invention, the step of generating a phototype of the skin according to corrected Fitzpatrick classification includes generating a phototype of the skin according to a skin type scale which ranges from very fair skin to very dark skin.

According to an exemplary embodiment of the present invention, the system for skin phototype determination using photograph analysis includes a subsystem for determination of cosmetic features for a human element and a veterinary element. The cosmetic features further include features pertaining to hair, nail and skin.

According to an exemplary embodiment of the present invention, the image of the skin sample of a person's body can be captured by any digital camera. The acquired digital image sample of the person's skin may be analyzed in a pixel by pixel manner in the RGB color system. After the conversion of colors from a device-dependent RGB color system into a device-independent standard RGB color system (sRGB), a table of most frequent sRGB colors which appear in the image may be generated. According to an example, the generated table may consist of 256 most frequent colors which appear in the image of the person's skin. The color samples obtained from the image may be approximated by a Gaussian normal distribution (or a (scaled) superposition of few Gaussian normal distributions). Therefore the estimates of expected value (using weighted mean) and standard deviation (using unbiased (n−1) method as the precise expected value is unknown/estimated) for each of the acquired digital images may be evaluated. The phototype of the skin may be determined through a decision tree with the estimated expected value and standard deviation. Fitzpatrick classification may be used for categorizing a skin phototype in accordance with a skin type scale which ranges from very fair skin to very dark skin.

Referring to FIG. 58, a flowchart 5800 illustrating a process for determining a skin phototype of an acquired digital image of a part of a person's skin is shown. The process starts at block 5810 wherein an image of a part of a person's skin is captured. The image capturing device may be a digital camera or the like. Processing flow continues to logical block 5820 wherein analysis of the acquired digital image is done in a pixel by pixel manner in a RGB color system. After converting all colors from the device-dependent RGB color system into a device-independent standard RGB color system (sRGB), a table of most frequent colors which appear in the acquired digital image may be generated using a quantization technique at block 5830. In accordance with an example of the invention, at block 5840 a plurality of sRGB color values/samples generated between a range of values 0 and 255 may be preserved for further analysis. This range of values has been proven to be more convenient for skin type determination than the one between 0 and 1. The transformation from one to another can be done simply by dividing the values with 255 and vice versa. In the next stage 5850 and 5860 approximations of colors on the samples are done by Gaussian normal distribution, at block 5860 the estimates expected value and standard deviation are evaluated. Finally at block 5870, the phototype of skin of the acquired digital image is determined according to the corrected Fitzpatrick classification using a decision tree.

According to an exemplary embodiment of the present invention, the decision tree may be an algorithm wherein the estimated expected value and standard deviation are equated to the values of Fitzpatrick classification/notation values in determining the phototype of the skin. The effectiveness of this approach may be seen in research regarding parametric skin distribution modeling for skin segmentation/detection.

Figure 59:
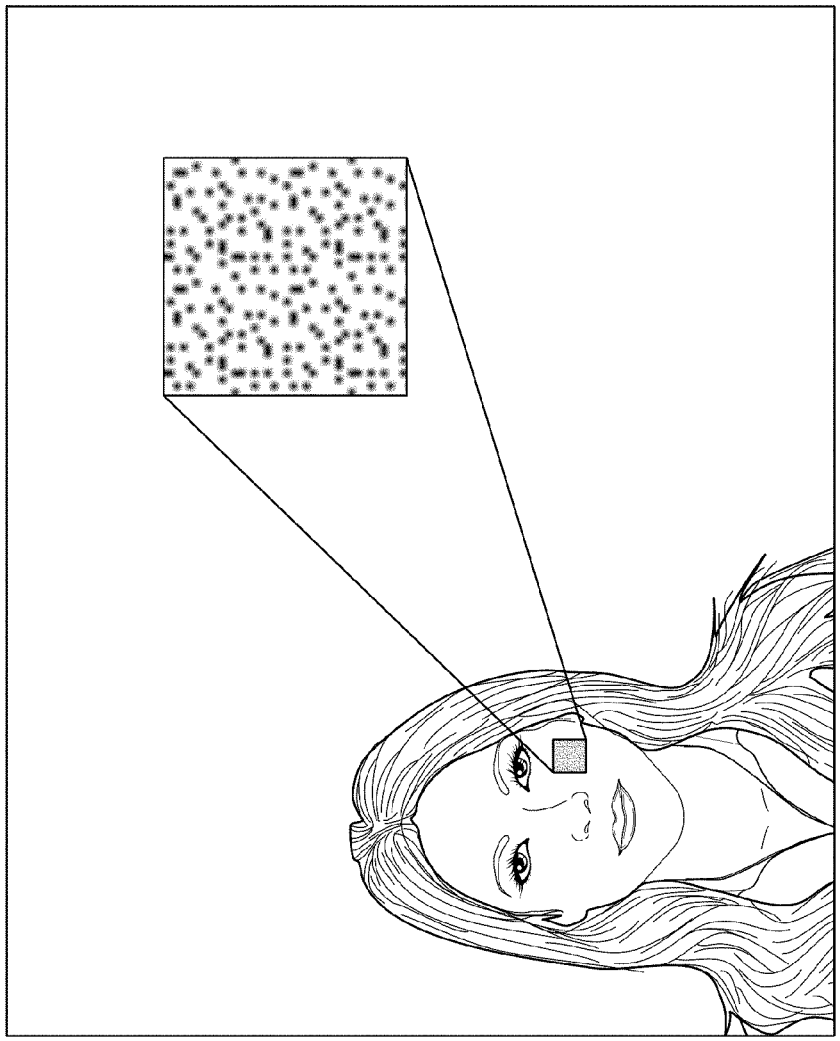
FIG. 59 is a diagram depicting a pixel view of an acquired digital image of a sample of person's skin.

Referring to FIG. 59, a diagram depicting a pixel view of an acquired digital image of a sample of person's skin is shown. The image of a sample of a person's skin is captured under white emitting light. The image may be captured by any digital camera and the like under white emitting light. An analyzer coupled to the image capturing device may analyze the acquired digital image in a pixel by pixel manner in the RGB color system. The analysis of the acquired digital image in a pixel by pixel manner in the sRGB (after RGB to sRGB color system conversion) is not only limited for determining skin phototype but also may be useful for other purposes like classification of other skin characteristics (e.g. elasticity, melanin, oil concentration etc.), melanomas and other skin tumors/disorders and the like.

Digital images captured from a sample of person's skin are usually given in the RGB color system. The present technique employing an algorithm 150 for determining skin phototype in one aspect is dependent on this color system, although device independent due to conversion to the sRGB color system. The calibration of the image capturing device, such as a digital camera or the like, should be taken into consideration carefully, so that the eventual color offset could be corrected. The color offset correction in the present technique can be implemented from any known techniques in the previous art and color offset correction can also be implemented in software used in the present technique in determining skin phototype.

Figure 60:
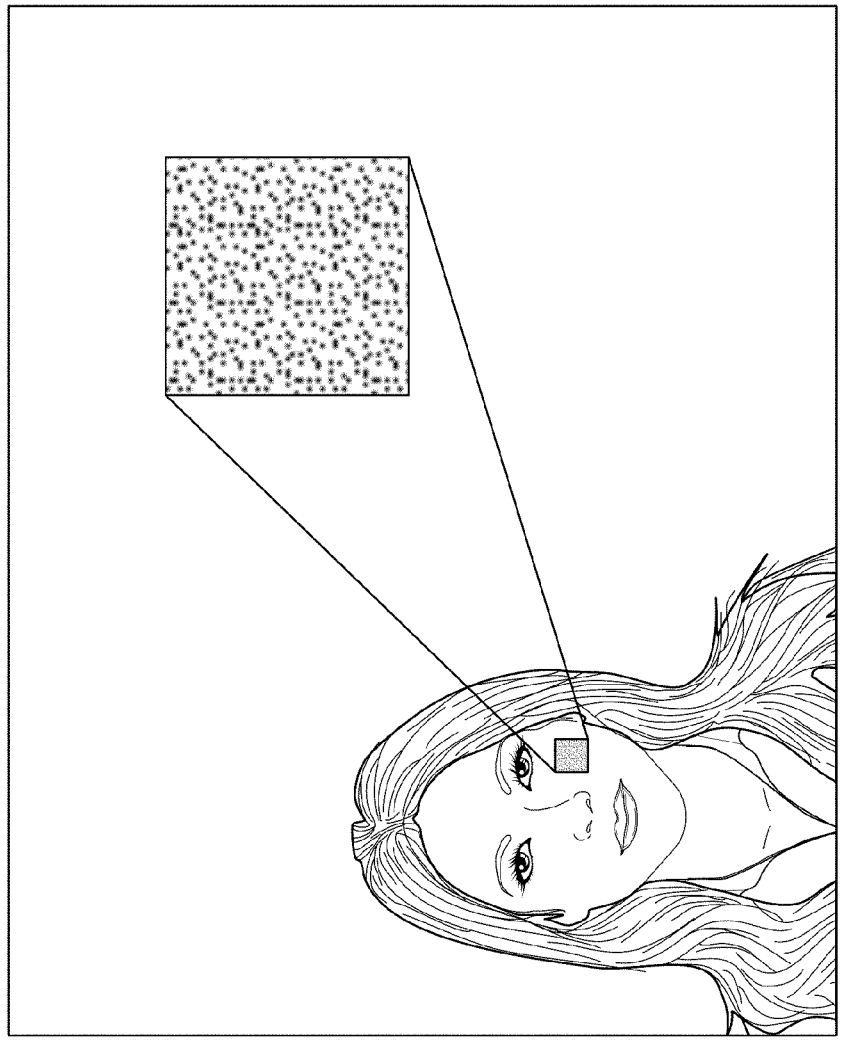
FIG. 60 is a diagram depicting a pixel view of the acquired digital image of a sample of person's skin after quantization.

Referring to FIG. 60, a diagram depicting a pixel view of the acquired digital image of a part of person's skin after quantization is shown. The image of the sample of the person's skin is captured under the white emitting light. The image may be captured by any digital camera and the like under white emitting light. The analyzer coupled to the image capturing device analyzes the acquired digital image in a pixel by pixel manner in the RGB color system. The analysis of acquired digital image in a pixel by pixel manner in the sRGB (after RGB to sRGB color system conversion) is not only limited for determining skin phototype but also may be useful for other purposes like classification of other skin characteristics (e.g. elasticity, melanin, oil concentration etc.), melanomas and other skin tumors/disorders and the like. Color quantization or color image quantization is a process that reduces the number of distinct colors used in an image, usually with the intention that the new image should be as visually similar as possible to the original image. Color quantization is critical for displaying images with many colors on devices that can only display a limited number of colors, usually due to memory limitations, and enables efficient compression of certain types of images.

An image quantization technique may be applied to the captured image. A table of 256 most frequent colors which appear on the acquired digital image of the part of person's skin may be generated using a sampling device coupled to the analyzer. The acquired color samples from a digital image may be preserved in the sRGB color system. In accordance with an example of the present invention, the generated color samples may be preserved in their range of values between 0 and 255 in the sRGB color system. This range of values has been proven to be more convenient for skin type determination than the interval ranging between 0 and 1.

Accordingly colors of the samples may be approximated by a Gaussian normal distribution (or a (scaled) superposition of few Gaussian normal distributions) through an approximating device coupled to the sampling device. Further the estimates of expected value (using weighted mean) and standard deviation (using unbiased (n−1) method as the precise expected value is unknown/estimated) for each of the acquired digital image may be calculated with the approximating device coupled to the sampling device.

Figure 61:
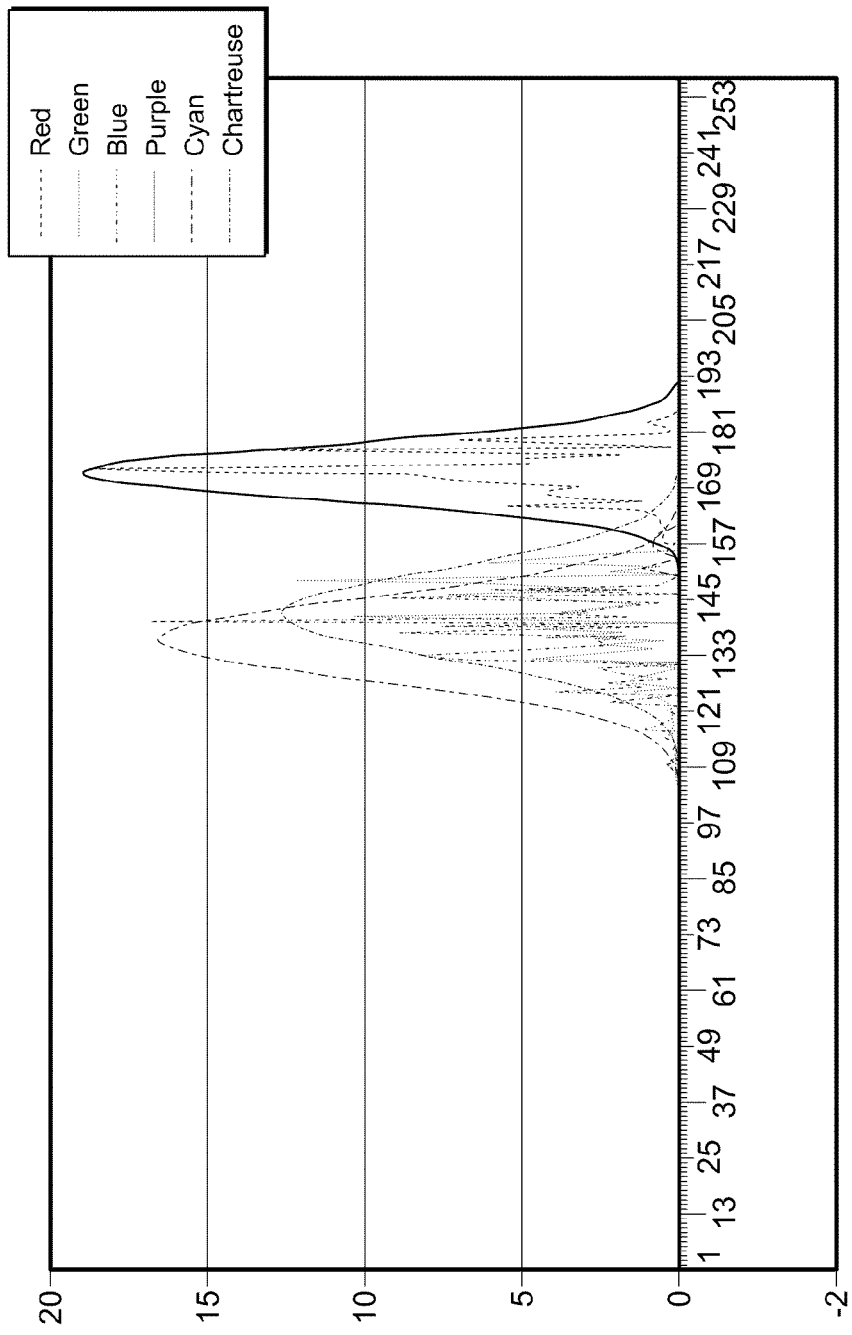
FIG. 61 is a diagram depicting a Histogram/Distribution of standard R, G and B colors on one of the taken photographs of a patient whose skin phototype is classified as type III by Fitzpatrick, and their Gaussian normal approximation/hull.
Figure 62:
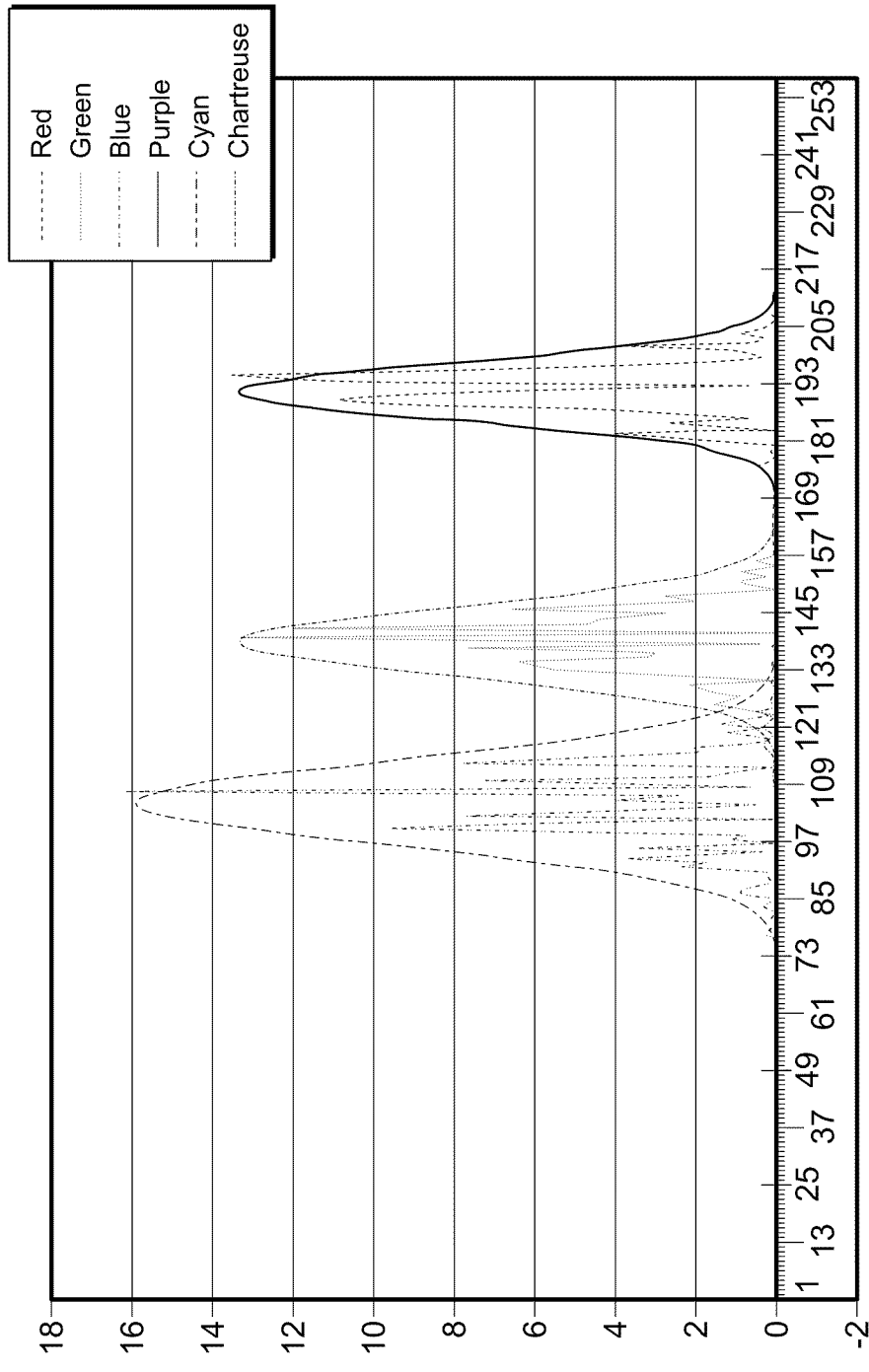
FIG. 62 is a diagram depicting a Histogram/Distribution of standard R, G and B colors on one of the patient's photographs whose skin phototype is classified as type VI by Fitzpatrick, and their Gaussian normal approximation/hull.
Figure 63:
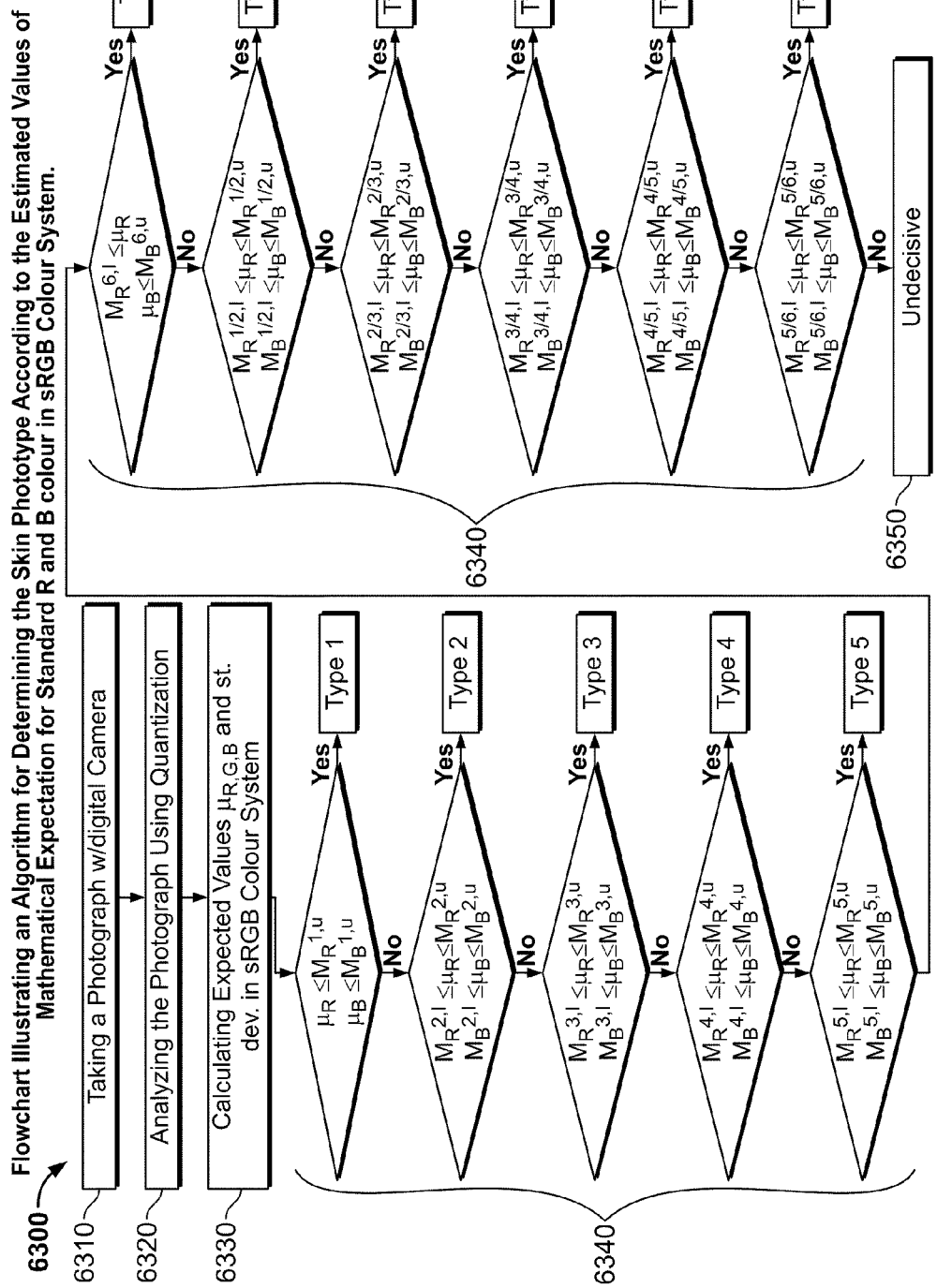
FIG. 63 is a flowchart illustrating an algorithm for determining the skin phototype according to the estimated values of mathematical expectation for R and B colors in a standard RGB color system.

Usage of an algorithm 150 of the present technique is depicted in FIG. 61 and FIG. 62 and the algorithm 150 for RGB color analysis is depicted in FIG. 63.

Referring to FIG. 61, a diagram depicting a Histogram/Distribution of standard R, G and B colors of one of the taken photographs of a patient whose skin phototype is classified as type III by Fitzpatrick, and their Gaussian normal approximation/hull is shown. The relevant estimates are μR (expected value of red)=171.1304 and μB (expected value of blue)=135.3047, for example. The estimates are compared with the decision tree described below for determining skin phototype. The phototype of skin is determined according to corrected Fitzpatrick classification. The Fitzpatrick Skin Typing Test questionnaire (skin type scale) which ranges from very fair (skin type I) to very dark (skin type VI) is often used to determine skin phototype.

Dermatologists use the Fitzpatrick Classification Scale to classify a person's complexion and tolerance to sunlight. In accordance with an exemplary embodiment of the present invention, the Fitzpatrick scale classifies skin types from 1 to VI.

Type I—Very white or freckled skin, always burns with sun exposure (very fair; often in people with red or blond hair and blue eyes)

Type II—White skin, usually burns with sun exposure (fair; often in people with red or blond hair and blue, green, or hazel eyes)

Type III—White or olive skin tone, sometime burns with sun exposure (fair; seen in people with any hair or eye color)

Type IV—Brown skin, rarely burns with sun exposure (common in people of Mediterranean descent)

Type V—Dark brown skin, very rarely burns with sun exposure (common in people of Middle-Eastern descent)

Type VI—Black skin, never burns with sun exposure

The images of skin are captured under white emitting light with an image capturing device, such as a digital camera, video camera or the like. An analyzer analyzes the captured image pixel by pixel of a part/sample of a person's skin. A sampling device coupled to the analyzer generates a table of 256 most frequently occurring colors in the captured image. The acquired color samples from the digital image are preserved in the sRGB color system. The generated color samples are preserved in their range of values between 0 and 255 in the sRGB color system. An approximating device coupled to the sampling device may calculate the estimates of expected value (using weighted mean) and standard deviation (using unbiased (n−1) method as the precise expected value is unknown/estimated) for each of the acquired digital images. A decision tree coupled to the approximating device determines the skin phototype. From this imaging, it turns out that expected values of R and B may be sufficient for determining skin phototype according to the following decision tree. An exemplary embodiment of the present invention is illustrated below.

Phototype =

$$\begin{cases} 1, & (\mu_R \leq M_R^{1,u}) \wedge (\mu_B \leq M_B^{1,u}) \\ 2, & (M_R^{2,l} \leq \mu_R \leq M_R^{2,u}) \wedge (M_B^{2,l} \leq \mu_B \leq M_B^{2,u}) \\ 3, & (M_R^{3,l} \leq \mu_R \leq M_R^{3,u}) \wedge (M_B^{3,l} \leq \mu_B \leq M_B^{3,u}) \\ 4, & (M_R^{4,l} \leq \mu_R \leq M_R^{4,u}) \wedge (M_B^{4,l} \leq \mu_B \leq M_B^{4,u}) \\ 5, & (M_R^{5,l} \leq \mu_R \leq M_R^{5,u}) \wedge (M_B^{5,l} \leq \mu_B \leq M_B^{5,u}) \\ 6, & (M_R^{6,l} \leq \mu_R) \wedge (\mu_B \leq M_B^{6,u}) \\ 1/2, & (M_R^{1/2,l} \leq \mu_R \leq M_R^{1/2,u}) \wedge (M_B^{1/2,l} \leq \mu_B \leq M_B^{1/2,u}) \\ 2/3, & (M_R^{2/3,l} \leq \mu_R \leq M_R^{2/3,u}) \wedge (M_B^{2/3,l} \leq \mu_B \leq M_B^{2/3,u}) \\ 3/4, & (M_R^{3/4,l} \leq \mu_R \leq M_R^{3/4,u}) \wedge (M_B^{3/4,l} \leq \mu_B \leq M_B^{3/4,u}) \\ 4/5, & (M_R^{4/5,l} \leq \mu_R \leq M_R^{4/5,u}) \wedge (M_B^{4/5,l} \leq \mu_B \leq M_B^{4/5,u}) \\ 5/6, & (M_R^{5/6,l} \leq \mu_R \leq M_R^{5/6,u}) \wedge (M_B^{5/6,l} \leq \mu_B \leq M_B^{5/6,u}) \\ \text{Further examination} & \text{all other cases} \end{cases}$$

The values $M_{R,B}^{n,u\ or\ l}$, n=1, 2, 3, 4, 5, 6, ½, ⅔, ¾, ⅘, ⅚ have been determined from the images analyzed by using the programmed neural network.

FIG. 62 is a diagram depicting a Histogram/Distribution of R, G and B colors of one of the patient's photographs whose skin phototype is classified as type VI by Fitzpatrick, and their Gaussian normal approximation/hull. Here the relevant estimates are μR (expected value of red)=189.7173 and μB (expected value of blue)=103.537, in accordance with an example of the present invention. The estimates are compared with the decision tree mentioned above for determining the phototype of the skin.

Referring to FIG. 63, a flowchart 6300 illustrating an algorithm 150 for determining the skin phototype according to the estimated values of mathematical expectation for standard R and B color in sRGB color system is shown. The flow chart describes the algorithm 150 developed in accordance with the present technique wherein the photograph of a part of person's skin is captured with a digital camera or the like under white emitting light at logical block 6310. At logical block 6320 the captured digital image is analyzed in a pixel by pixel manner in the RGB color system. A quantization technique is employed for analyzing the captured image in a pixel by pixel manner in the sRGB color system at logical block 6330. The color samples obtained from the image can be approximated by a Gaussian normal distribution (or a (scaled) superposition of few Gaussian normal distributions). Therefore the estimates of expected value (using weighted mean) and standard deviation unbiased (n−1) method (as the precise expected value is unknown/estimated) for each of the acquired digital images may be evaluated. Now at logical block 6330 the phototype of the skin is determined according to the decision tree.

As will be appreciated by a person skilled in the art, the various implementations of the present technique provide a variety of advantages. Firstly, the present technique determines skin phototype using regular low-cost digital photography equipment under standard environmental conditions. Secondly, the analysis performed on the captured digital image may be useful in recommendation of cosmetic product and medical or surgical purposes. Thirdly, the picture quantization algorithm and calculation of estimates expected value and standard deviation are fast, this makes it easier to determine skin phototype in a short span of time using a simple routine. Fourthly, the analysis performed may be useful for classification of other skin characteristics (e.g. elasticity, melanin, oil concentration etc.), melanomas, skin tumors or disorders and the like.

In an embodiment, new algorithm 150 development by practitioners, users, service providers 111, and the like may be enabled by a software development kit that anyone could use to develop new algorithms 150 and APIs 154 for the device 108.

Figure 3:
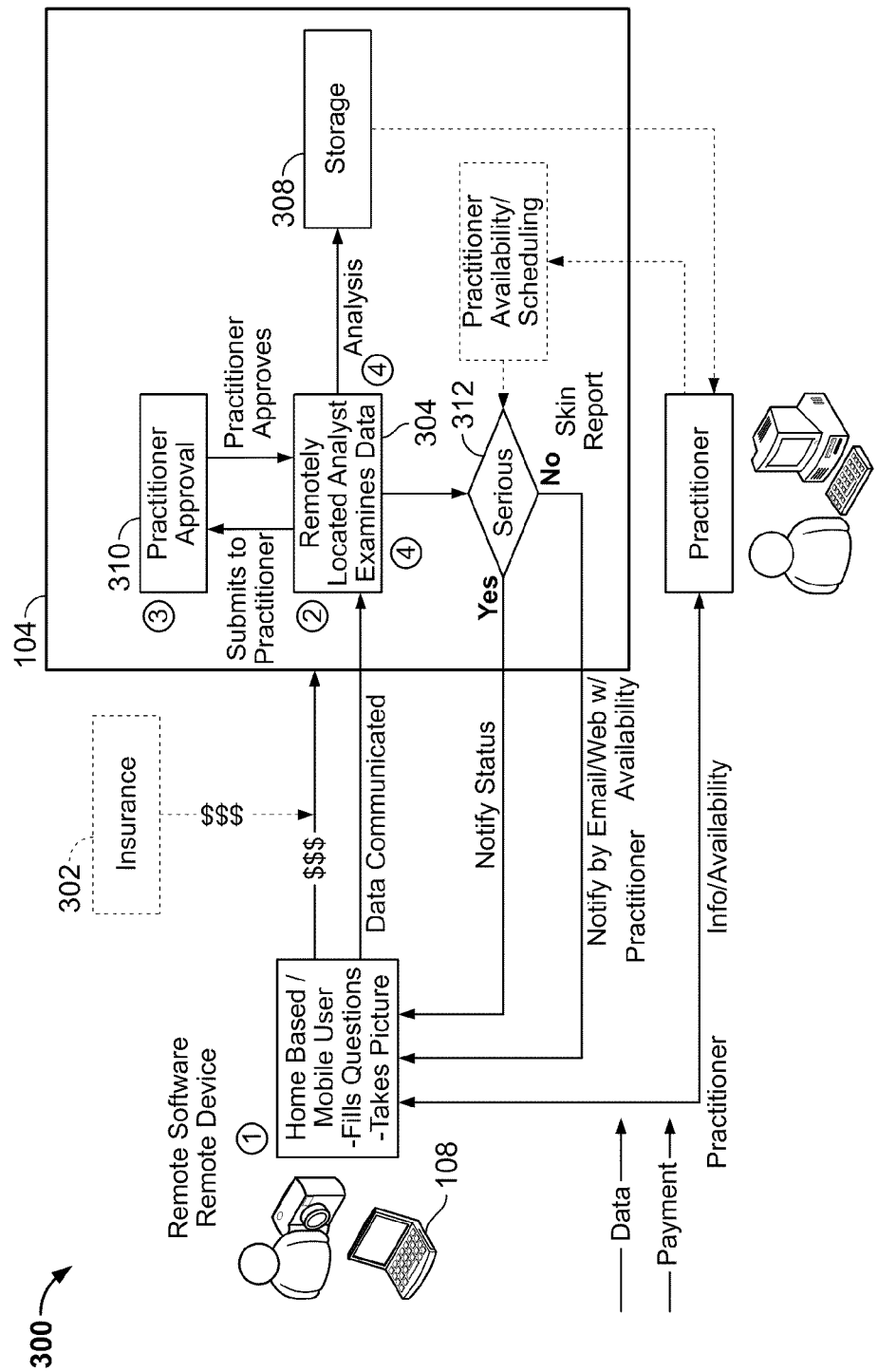
FIG. 3 depicts a process for skin care examination.

Referring now to FIG. 3, in an embodiment, a process for collecting images, performing skin analysis, communicating findings and scheduling follow up, if required may commence with image capture by a user using a device 108. The user may also answer questions or provide additional details regarding a user-entered imaging, cosmetic regimen, area of concern, or the like. Using the user interface 102, the data may be communicated to an analyst 304 or a computer for analysis 154 by any communication method, such as over a network, the Internet, wirelessly, and the like. In certain embodiments, as the data are collected or communicated, a payment system 302 may be accessed by the user. In the example shown, an insurance company may access the data, however, payment may be effected or requested by any interested entity such as a one-time payment by the user, a subscription by the user, a third party service provider 111, a platform 120,124, a practitioner, and the like. The entered data may be analyzed by the analyst, by software in real-time, by analysts assisted by software assistance, and the like. An initial analysis may be to determine data integrity. In instances where the data do not pass the integrity test, it may be communicated back to the user. The analyst's assessment may be assisted by software that uses an algorithm to determine type of condition and/or recommended care/treatment. Historical analysis and data, and modeling tools may be used to assist the analyst's assessment. Relevant parties (company personnel, payment providers, physicians, medical personnel, users, amongst others) may receive the analysis and/or user specific details for follow up or other actions that may be required. The analysis 154 may be stored 308 by the system and/or submitted to a practitioner for approval 310. In embodiments, storage 308 may require practitioner approval 310. A test of the severity 312 may determine the selection of an appropriate method of communication with the user. If the result of the test 312 is positive, the user may be notified immediately by a preferred communication method, such as telephone, instant message, and the like. If the result of the test 312 is negative, the user may similarly be notified, however, the notification may take a less urgent route, such as by email or postal mail. In any event, the software tool may recommend an appropriate communication method and media, based on the assessment and may populate preset templates with the information/message to be communicated. In addition, notification by any means may also include a notification of practitioner availability. The analysis 154 may trigger a practitioner availability/scheduling tool. For example, prior to transmitting the results on severity 312 to the user, a practitioner availability may be assessed and transmitted simultaneously. The user may access availability and scheduling tools in order to obtain and confirm an appointment time.

In an embodiment, a user interface 102 for a skin analysis system 104 may be used to interface with the device 108, store images, deploy algorithms 150, track a skin state 158 by keeping track of images from any number of areas of concern, the interval between image capture, a projected next image capture date, communicate findings to a practitioner, interact with simulation tools 132, skin type determination tools 130, a skin cycle monitor 140, practitioner availability/scheduling tools, and the like.

In embodiments, the user interface 102 may be operable as an application running on a device 108, a computer, server, kiosk, or the like, on an online platform 120, on a mobile platform 124, and the like. Any and all aspects of the user interface 102 described herein may be applicable to the user interface 102 running in any environment.

In an embodiment, the user interface 102 for the device, as will be further described herein, may be integral with the device 108, such as embodied in the keypad of a communications device or a series of buttons, switches, keys and the like disposed on the device 108, or may be external to the device 108, such as software running on a computer, on the Internet, on an intranet, on a mobile communications device, on an online platform 102, on a mobile platform 124, and the like. The user interface 102 may be used to modify a setting of the device 108, such as the magnification, light source, light intensity, wavelength of light, angle of light, electrical and magnetic properties of the light, positioning of sensor, duration of image capture, image size, data storage, data transmittal, and the like.

Figure 5:
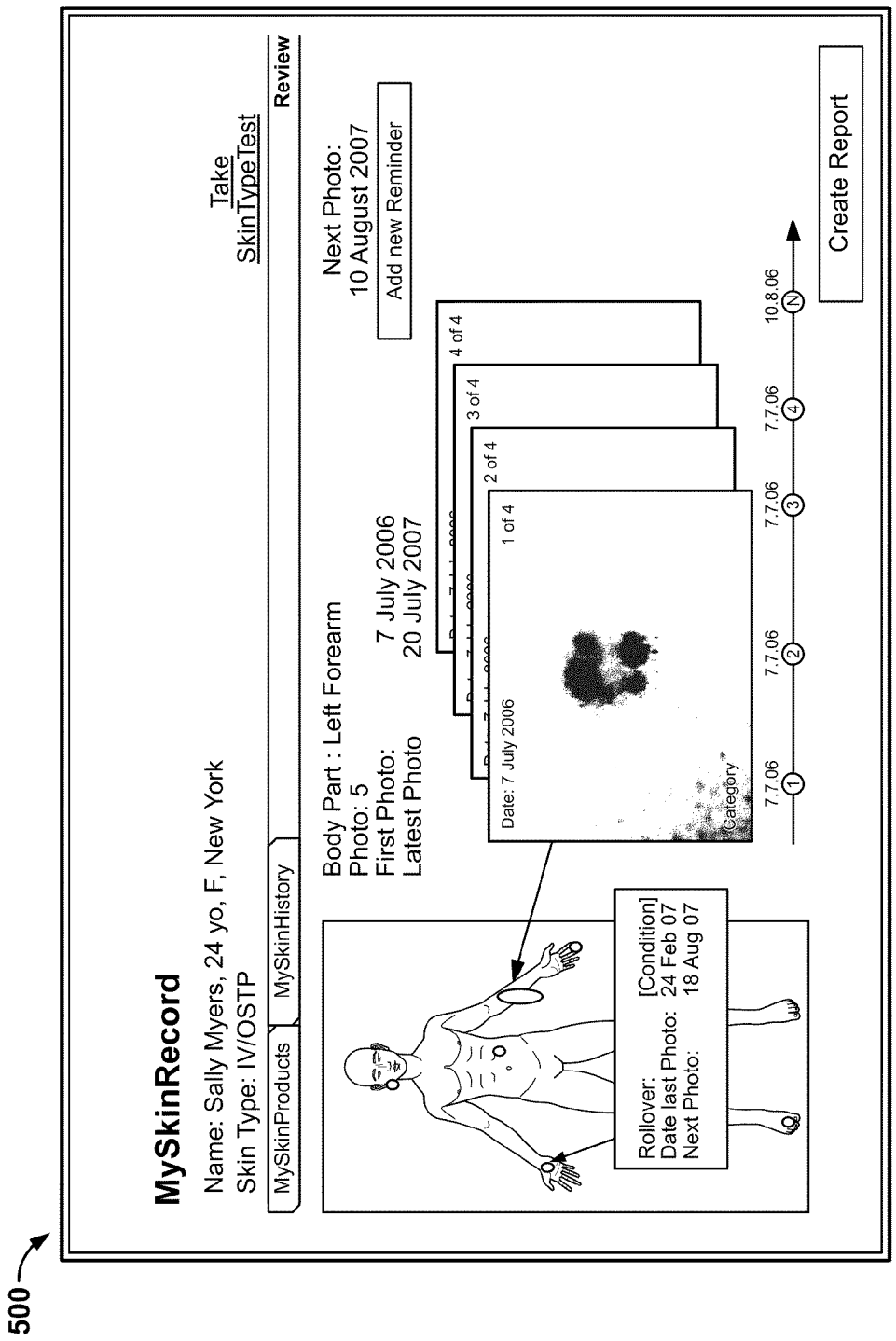
FIG. 5 depicts a skin health monitoring page of a skin care system.

Referring now to FIG. 5, the user interface 102 may organize and index images captured by date, area of concern, skin state, and the like. For example and without limitation, as seen in the FIG. 5, four images captured from the same area of concern are indexed by their number within the series. In an embodiment, the user interface 102 may show in real time the field of view on the skin being imaged as well as populate the user interface 102 with the images once taken or once submitted by the user. The user interface 102 may keep track of the first image, latest image, next image, and the like. The user interface 102 may allow users to shuffle through image s and use the images as a basis for simulation 132, as described herein. The user interface 102 may be used to set a reminder for next image capture. The user interface 102 may be used to create a report of the images and skin state 158. The user interface 102 may be used to transmit the report to a practitioner. In an embodiment, the user interface 102 may be used to launch a skin type test. In an embodiment, the user interface 102 may depict a form of a body. As a user interacts with the depiction of the body, such as with an indicating device, the portions of the body that have been imaged may be linked with the images such that the images may pop-up or be otherwise accessed. The user interface 102 may be adapted to collect data from the user in response to prompts. The user interface 102 may employ an algorithm 150 to check the integrity of the captured images. The user interface 102 may guide the user in capturing images and providing user input in association with the images.

In an embodiment, the user interface 102 may interface with host hardware 108 or third party hardware 109. Hardware 108, 109 may comprise an imaging device that may connect with a computer, online platform 120, mobile platform 124, and the like via the user interface 102 and enable users to capture an image that enables measure various skin health, condition and type parameters. The hardware device 108,109 may be a standalone device or connect via or be embodied in a computing device of either medical or non-medical use. The user interface 102 may guide the connection process for the hardware device 108, 109. The device 108, 109 may store images, reports and recommendations generated and maintain a repository of the image, all as part of a skin health record 121. It may enable a systematic storing of the skin health record 121. Third party hardware 109 may comprise devices such as moisture sensors, cosmetic analysis machines, dermascopes, cameras, x-ray machines, MRIs, medical record providers and software, web cameras, communication devices, and the like. Third party hardware 109 may connect to the system 104 seamlessly to enable the user to gain a better analysis, and share such sets of data with other experts or users.

In an embodiment, the user interface 102 may enable type determination 130. Characteristics may be captured to determine the skin characteristics and the skin state 158 of the users' skin. Broad genetic parameters, such as ethnicity, skin color, location factors, environmental factors (such as pollen count, weather, etc.), and lifestyle factors may be collected in addition to image and skin health data to determine the users' skin state 158. This skin state 158 may be correlated with product experience ranking and ratings 138 to enable providing a recommendation for most effective products.

The user interface 102 may display a regimen 118. The regimen 118 may be a feature that enables users to learn what products and product usage pattern would work best for their skin based on a hardware- or community-led personalized skin care assessment 160 and/or type determination 130 and product experience sharing via ranking and rating 138 and/or comments regarding product effectiveness and experience (such as smell, taste, feel, texture, color, and the like). The regimen 118 may be a dynamic recommendation based on users' collective inputs as well as experts' inputs on products that would best suit the user's individual needs.

In an embodiment, the user interface 102 may enable simulation tools 132. Users may be able to upload an image and model various skin parameters (such as moisture level in skin, collagen level, age, and the like.) and observe changes in the image. Additionally, users may be able to model the impact of various products and regimens 118 (skin care, cosmetic, medical, nail care, hair care, and the like) on the image. Simulation tools 132 may enable users to view changes on the entire image or split half of the image to show a comparison of modeled change with current image. The user's images could also be automatically or manually optimized for the best look and the products or regimen 118 to obtain that look may be provided. Simulation tools 132 may also enable consumers to model the skin characteristics or state 158 of other selected users or non-users, such as celebrities, luminaries, average users, and the like.

In an embodiment, the user interface 102 may enable a daily report 134. The daily report 134 may be a report that provides the user information largely customized and most relevant to the user based on their skin state 158. The daily report 134 may list skin care regimen 118 to be followed based on the environmental and lifestyle factors relevant to the user, may indicate new product information 190, show the current skin care shelf 114 and rankings 138 or change in rankings 138, feedback from users or experts 105 on products most relevant to the user, and the like. The daily report 134 may include information about clinical trials and upcoming results, new product releases and status, events, various factors affecting the skin such as the day's weather forecast, UV index, temperature, pollen count, and the like, and other data to provide value to the user. The daily report 134 may report on whether a product is nearing its shelf life or may require replenishment based on a recommended usage protocol. The daily report 134 may be provided to the user by the user interface 102, paper, email, SMS, RSS, video or any other communication media.

In an embodiment, the user interface 102 may enable a wishlist 134. The wishlist 134 may be a function that a user could select and add products to a part of the skin care shelf 114 using drag and drop functionality or other selection mechanism as they surf the web or otherwise access product information 190. They could share this function with other users, friends and/or family so that other people could see the wish list 134. Other users could then select the products off the wish list 134 and purchase and send the product to the user.

In an embodiment, the user interface 102 may enable ranking and rating 138. Ranking and rating 138 may be performed for various product characteristics as well as on the various raters and rankers. Product experience may be collected from users in simple ranking and rating 138 format as well as textual comment data to be stored in a database. This ranking and rating 138 may be real time, and may be synthesized to show what is most relevant to the user based on like users or peers, such as users with any of the following characteristics: same age, same sex, same skin type, same ethnicity, geography, moisture levels, and the like. These ranking and ratings 138 may be dynamic ranking and ratings 138. The users may be shown either the total number of rankers/raters and/or the weighted percent score ranking or rating 138. The ranking and rating 138 may comprise any of the following characteristics: perceived effectiveness, smell, touch, feel, texture, ability to absorb product, stains left by product, ease of use, and the like. Users may also be able to upload their images and obtain effectiveness/look ranking and rating 138 for different product recommendations from other users or experts 105. For example and without limitation, a user may upload data and/or images and request rating and feedback on better products from an herbal expert in India, aging expert in Japan, and the like. Users providing ranking and rating 138 for various products may themselves be rated by other users. This may enable selection of the most effective and unbiased users and help identify potential experts 105. A small select group of highly ranked users may be offered exclusive writing/publishing and ranking/rating privileges.

In an embodiment, the user interface 102 may enable a skin cycle monitor 140. The skin cycle monitor 140 may indicate when the last image was collected and countdown to the next scan based on a time interval, such as the time required to replenish the skin or any other interval. Currently, it is believed that the skin replenishes itself every 28 days. The skin cycle monitor 140 may take into consideration age, environmental changes, and other factors to indicate the upcoming scan schedule.

In an embodiment, the user interface 102 may enable wellness/health 142. The user interface 102 may collect lifestyle data and also provide lifestyle (such as sleep, rest, exercise, and the like) and health (such as vitamins, food, products usage, and the like) recommendations based on the users particular skin state 158 and characteristics. The wellness and health module 142 may enable the user to obtain a personalized best fit health and wellness schedule and regimen 118.

In an embodiment, the user interface 102 may enable games 148. Users may be able to play games 148 that may enable users to model various products, try different hairstyles, model different hairstyles and clothes, and the like. Users may interact with other users or the computer to make the product selection a fun process. This process could also be used to collect information on user preferences and looks.

In an embodiment, the user interface 102 may enable a gift guide 144. Based on the user's skin state 158, personalized gift advice may be provided to others in the user's network.

In an embodiment, the user interface 102 may be embodied in touch screen user navigation. A touch screen system may be employed to enable the user to obtain a visual look and navigate to various parts of the user interface 102, such as navigate to the simulation tools 132, change picture orientation, drag and drop, and the like. Touch screen navigation may be particularly helpful as the hardware device 108 is connected to a computing platform. The user interface 102 may also enable collecting and coordinating information from other devices 109 and/or assessments, such as a dermascope, blood report, biopsy report, and the like to provide additional information for the skin record 121.

In an embodiment, the user interface 102 may enable a purchase/sample portal. The user interface 102 may include a purchase/sample portal that may enable the user to select products and complete a purchase or request a sample to be delivered to a pre-entered address. The portal may be available in various social networking platforms 188 as well as over various computing platforms, such as an online platform 120, mobile platform 124, computer, laptop, mobile phones, and other mobile devices, medical-use devices, and the like.

In an embodiment, the user interface 102 may enable scheduling and data sharing functionality. A user may be able to schedule online a meeting with a particular expert or practitioner and, if willing, then share a skin state 158 or specific parts of the skin record 121 and history in part or its entirety with the expert or practitioner. Ranked experts and practitioners, availability, and other criteria to aid the selection and scheduling process may be indicated to the user. Experts may also be able to share particular sets of data amongst themselves, such as among practitioners, physician to another physician, physician to spa, spa to spa, and the like.

Other inputs 112, such as devices, features and data, may be used to augment the data submitted by the user or as the primary data to obtain a personalized assessment regarding the users' beauty, cosmetic, or medical concerns related to skin, hair, nails, and the like. For example, certain devices may be available commercially off the shelf, purchased, proprietary, and the like.

In an embodiment, a wearable monitor 182 may be an input 112 to the system 104 and user interface 102. Wearable skin health monitors 182 may enable real time tracking of changes in the environment and the skins health. These devices could be worn directly on the body, or integrated into clothing, apparel and/or accessories carried by the user. An example would be a user having a device that monitors the UV level, and provides a warning if the sun protection level accorded by a product used by the user falls below a set target level. These wearable monitors 182 may have independent user interfaces 102 or can be programmed for personalized parameters using other input devices. Wearable monitors 182 may also capture various physical parameters like heart rate, blood pressure, exercise rate, water consumption, fat counter, calorie meter, and the like. The monitors 182 may be able to assess hydration levels.

In an embodiment, a social network 188 may be an input 112 to the system 104 and user interface 102. The beauty social network 188 may be a collection of users interested in knowing and sharing information on beauty or medical concerns in a personal, private, and social interactive setting. The intent may be to create a beauty social network 188 where users invite and link to other users to discuss such concerns; obtain information 190, 192; perform ranking, rating, and review of products, regimens, experts, practitioners, other rankers/raters, and the like; complete purchases; access a wishlist 119; access a gift guide 144; play a game 148; review their daily report 134; and the like, all the while sharing experiences with other users in their network.

In an embodiment, product information 190 may be an input 112 to the system 104 and user interface 102. A database of product information 190 may comprise product, name, claims, manufacturer information, ranking and ratings 138, packaging information, images, usage parameters, product development history or forecast, special handling, upcoming changes, safety information, effectiveness information, smell, taste, color, texture, price, geography of manufacturing, brand information, consumer feedback and experiences, and other such parameters that may be obtained and/or maintained to assist in the selection of the best product suited to the users' individual preferences or conditions to obtain the best beauty or medical outcome for their skin, hair, nails, and the like. Additionally, similar information on service oriented products such as massages, facials, hair toning, and the like may also be captured as well as information on procedures such as liposuction, Botox treatments, laser hair removal and other beauty, cosmetic and/or medical procedures related to helping the user look good, improve or maintain a skin state 158, and the like. Manufacturers may register product information 190, contribute information on procedures, products in the pipeline, products in clinical trials, and the like. Users may rank and rate 138 products. A database update utility may update the database with new product information 190, store inventory, and the like.

In an embodiment, wellness information 192 may be an input 112 to the system 104 and user interface 102. Health and wellness information 192 may be captured, such as the impact of various products, primarily but not limited to non-prescription medications, supplements and other consumables that assist and maintain health and wellness (such as vitamins, protein shakes, supplements, and the like). Additionally, information on lifestyle recommendations (such as sleep, rest, diet and exercise recommendations for particular age groups/ethnicities, etc.) may be collected and correlated with user preferences and characteristics to enable and provide a holistic health, wellness, and beauty/cosmetic optimal personalized solution and service.

In an embodiment, a plug-in web capture 194 may be an input 112 to the system 104 and user interface 102. A software component-plug in for internet web browsers and basket or repository may recognize graphic objects on any browsed web page and allow the user to select, and drag-and-drop the graphic object onto a basket or repository onto a page of the web browser, such as a page comprising the skin care shelf 114. The graphic objects would be recognized through a standard reference table that would be accessed remotely or reside on the user's PC as part of the plug-in module 194, or as part of a resident software program on the computing platform. Graphic objects may include images for commercial products, such as skin care products or creams, or other objects that are part of any web e-commerce site. Once recognized, the plug-in 194 may highlight the picture, notifying the user that is it recognized, or provide additional information or reference. The plug-in 194 may also recognize brand names, trade names, generic pharmaceutical names, trademarks, and the like.

In an embodiment, barcode scan 198 may be an input 112 to the system 104 and user interface 102. Bar code information on various products may be captured to assist tracking, identification, price determination and correlation with other product information 190 for identifying similar substitute products, or other allied product information, usage recommendation, other user experience, pricing and delivery information, amongst other relevant sets of data. The bar code scanner 198 could be part of the hand held user device 108, a standalone system, a manual entry mechanism, and the like.

In an embodiment, conventional information/questionnaires 101 may be an input 112 to the system 104 and user interface 102. Information 101 on the users and products may be captured via dynamic and static questions. Information such as age, sex, location, personal lifestyle traits, smoking habits, sleep patterns, skin dryness/oiliness and moisture levels, product likes and dislikes, experiences with other products along parameters such as smell, taste, absorption, staining propensity, and the like may be captured in a fun manner using questions and answers, games and other interactive tools interspersed at various points of the users' interaction with the service product, system 104, or user interface 102. Information 101 may be captured directly form the user or via an intermediary, and augmented automatically via computer data population, as an output of an algorithm 150 or by experts based on their assessment. Information 101 may be obtained by quizzes, badge- and widget-based forms, on-the-fly, through adaptive, investigative questioning, and the like. Information 101 may be obtained through questionnaires, such as How often do you go shopping?, When do you shop for cosmetics?, Where do you typically go? Why that spot?, Who do you shop with? Why?, What do you ask your friends when asking for advice?, Where do you go for new products/information about cosmetics?, When do you have to go to a dept store, vs buying online?, When would you want to know something immediately from your friends?, What do you ask from your friends?, How do you choose a mobile phone?, What do you care about menus on a cell phone?, When do you get a new cell phone?, and the like.

In an embodiment, third party experts 105 may be an input 112 to the system 104 and user interface 102. The system 104 may connect various experts such as practitioners, physicians, medical experts, aestheticians, schedulers, product ingredient experts, cosmetologists, herbal, ayurvedic and homeopathic experts, health and wellness experts, media experts, photograph enhancement experts, and the like with users and one another. Users may be able to direct questions to such experts 105 who may be located at different places geographically over the system to obtain personalized advice. The experts 105 may be provided with users' data and characteristics collected and a record of the experts assessment may be retained in the record 121. The recommendation provided by the expert may be offered to the user for purchase/sample request, and the like. Experts may also be able to flag certain cases or sets of data for discussion or referrals within the expert community or with users.

In an embodiment, third party hardware 109 may be an input 112 to the system 104 and user interface 102. The system may connect with various third party hardware 109, such as existing imaging solutions, camera devices, computers, lighting systems, sports devices such as pedometers, and the like.

In an embodiment, third party service providers 111 may be an input 112 to the system 104 and user interface 102. Third party service providers 111 may be integrated into the system 104 to enable users to make the best personalized product or service selection for their hair, skin, nails, and the like for medical or cosmetic/beauty needs, and the like. Third party service providers 111 may include hospitals, physicians, spas, salons, aestheticians, beauticians, cosmetic counters, drug stores, cosmetics sales representatives and websites, ranking and rating services, product information databases, testing laboratories, magazines and information providers, insurance companies, social networking sites, health and wellness services, photograph enhancement services, and the like. For example, based on a skin concern, the scheduling system for a physician may be integrated and scheduling options offered online to users, while also connecting with insurance providers to confirm coverage with the user. In addition, pre-assessments on the condition, availability of historical medical and/or cosmetic products prescribed either over the counter or by medical prescription, and/or recommended services may be captured to make the selection process for the user convenient and easy.

Figure 7:
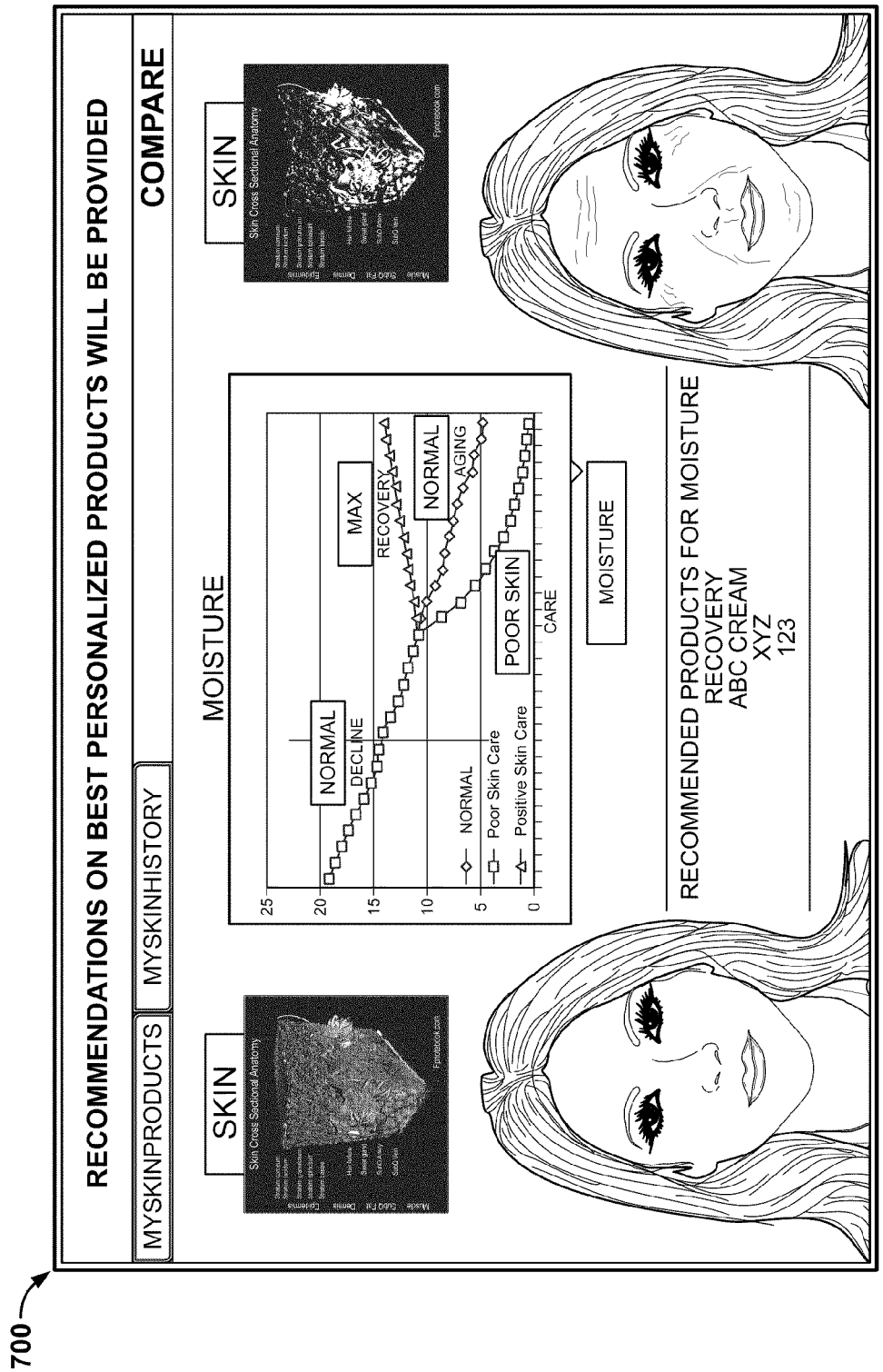
FIG. 7 depicts a recommendations page of a skin care system.
Figure 8:
FIG. 8 depicts a user interface of a skin care system.

Referring to FIG. 7, a system for providing recommendations for skin care based on a skin state 158, a skin care goal, and environmental factors affecting the skin may comprise obtaining a skin state 158 of an individual, categorizing the individual by skin state 158, and recommending products and regimens that may be effective in achieving a skin care goal. The system may be computer-based, Internet based, network based, and the like. The system may be a community-led provision of skin services. In an embodiment, the recommendation may be made on the basis of identifying other users with similar skin states and identifying a product or regimen that is effective for them. In an embodiment, the recommendation may be made on the basis of product information 190, wellness information 192, a third party database 115, an expert 105, a service provider 111, and the like. As seen in FIG. 7, a user may acquire an initial image and perform an analysis for a specific endpoint, such as moisture in this case. The system may automatically recommend certain products based on the moisture level that may be effective given the moisture level, a skin state 158, and the like. Additionally, the system may perform a projection of skin state 158 based on various skin care regimens 118, such as maximum care, normal care, or poor care. In an embodiment, the images may be captured using the device 108 or third party hardware 109. Images may be captured using any image capture device or technique, employing any kind of incident light, such as unpolarized light, polarized light, monochromatic light, diffuse light, white light, multiple single wavelength light, and the like. Any captured image may be used to obtain a skin state 158.

An embodiment of a skin care recommendation page of a skin care system may include a report of products the user is currently using, user input to obtain a skin state 158, a recommendation request, and the like. The report on the products the user is currently using may include ranking or ratings 138. For example, when a user accesses the user interface 102, they may access an adaptive questionnaire to determine their experience with their current regimen 118, current products or therapies used, or any products or regimens 118 used in the past. For example, the user may be asked to respond to questions such as How effective is it?, How is its fragrance?, How does it absorb?, Does it cause breakouts?, How does it feel?, Do you think this product is of good value?, and the like. Of course, rankings and ratings need not be prompted by questions but may simply be anecdotal, deployed in a non-question format, deployed in a drop down menu, and the like. To obtain a skin state 158, the user may enter data relating to aspects such as gender, age, ethnicity, location, skin color, environmental factors, and the like. In embodiments, analysis 154 of images obtained from the device 108 or third party hardware 109 may also be used to determine a skin state 158. Based on the skin state 158, either derived from user input, analysis of images, or a combination thereof, users may be able to determine products and regimens 118 that may work best for their skin state 158 by connecting to a database containing wellness 192, regimen 118, expert 105, service provider 111, and product information 190, wherein the information may comprise product ingredients, product claims, product indications, product pairing, product usage protocol, product ratings and rankings 138, and the like. By including rankings and ratings 138, community-led recommendations may be made for skin related products adjusted for age, skin color, location, ethnicity, environmental factors, and the like. In an embodiment, the user may perform a recommendation request which may involve selecting a skin goal, such as moisturize, protect, cleanse, tone, beautify, anti-aging, wrinkle protection, skin tightening, deep cleanse, pore diminishing, treat rosacea, exfoliate, lighten skin, tan, sun protect, self-tan, treat acne, avoid pimples, improve luminosity, skin rejuvenation, treat spots, treat Crow's feet, hair removal, scar treatment, and the like. In embodiments, a skin goal may be automatically selected by the system 104. Automatic selection may be based on an aspect of the skin state 158. For example, if analysis 154 reveals that the skin is severely dry, the system may recommend moisturizing products for severely dry skin, or the system may recommend ingredients to look for in a product. The user may be able to purchase products directly from the recommendations page, such as by placing the product in an electronic shopping cart 113, or may be directed to another site for purchase. In an embodiment, the user may add the product to a wishlist 119 for future purchasing. In an embodiment, the user may add the product to a skin care shelf 114, which may be an interface to or depiction of a regimen 118 that enables users to organize their products and regimen 118 in a logical fashion based on the user's specific skin characteristics 130, by usage scenario (e.g. Morning, afternoon, night, etc.), intent (e.g. work, fun, etc.), and the like. The beauty shelf 114 may have multiple screens for recommendations by various bodies (e.g. Physicians, dermatologists, aestheticians, spa specialists, overall users, experts, people most like you, etc.). The beauty shelf 114 may be a personalized arrangement of products. Users may drag and drop products (or select to add) as they are surfing the web and discover new products as well as having auto-populated recommendations. The functionality may include a program that will highlight products of interest while surfing the web. The beauty shelf 114 may be an application that can also sit independently on social networking sites and other personal pages and or toolbars. The beauty shelf 114 may also indicate purchase date and purchase history, product expiration alerts and other usage updates. A purchase made off the website may automatically add to the user's beauty shelf 114, while manual entries for offline purchases may also be possible.

In an embodiment, the user may be able to obtain samples of recommended or non-recommended products directly from the recommendations page. The shopping cart 113 may be a functionality that integrates with the skin care shelf 114. Users may be able to use the personalized recommendations and select products either for purchase, or for sample delivery. The user may be prompted for personal information such as address, shipping method, credit card number and the like, and that information may be retained by the shopping cart 113. The shopping cart 113 may be an independent program, in similar fashion to the skin care shelf 114, that may reside in a toolbar, as part of a user interface 102 or as a program on a webpage, so that products could be highlighted and dragged into the shopping cart 113 for later purchase. Dragging the product into the cart 113 may also initiate queries across the database and across various websites for best price, location and availability of product, consumer experience, rankings and ratings and the like.

Figure 9:
FIG. 9 depicts a welcome page of a skin care system.

Referring to FIG. 9, a product rating page of a skin care system is depicted. To obtain recommendations, users may be asked to respond to their medical, non-medical, cosmetic and skin care product experiences, thereby scaling data collection inexpensively. For example, a user may identify a product and provide an effectiveness assessment, rankings and ratings 138 for the product, anecdotal information, usage information, and the like. This information may be stored in a wellness 192, regimen 118, and product information 190 database in order to refine future recommendations. In an embodiment, user responses to product experiences may be shared with friends and/or other users automatically or upon request.

Referring to FIG. 10, a user interface 102 home page 1000 of a skin care system 104 is depicted. The user may be prompted to input demographic information such as name, gender, age, occupation, ID, address, telephone number, email address, payment information, new related users, and the like, which may be stored in a user profile or as part of a skin record 121. The home page may show a skin record 121, or a listing of areas imaged, date imaged, and status of analysis. Once a task is complete in the skin history/record 121, an icon may be displayed near the Status. The user may be able to launch a new Skin Health Test from the home page 1000 or submit a new skin concern. The user may be able to forward the analysis 154 to an interested party; Ask an Expert a question regarding an aspect of the skin, skin history/record 121, image analysis, and the like; view payment information and history; and the like.

Figure 11:
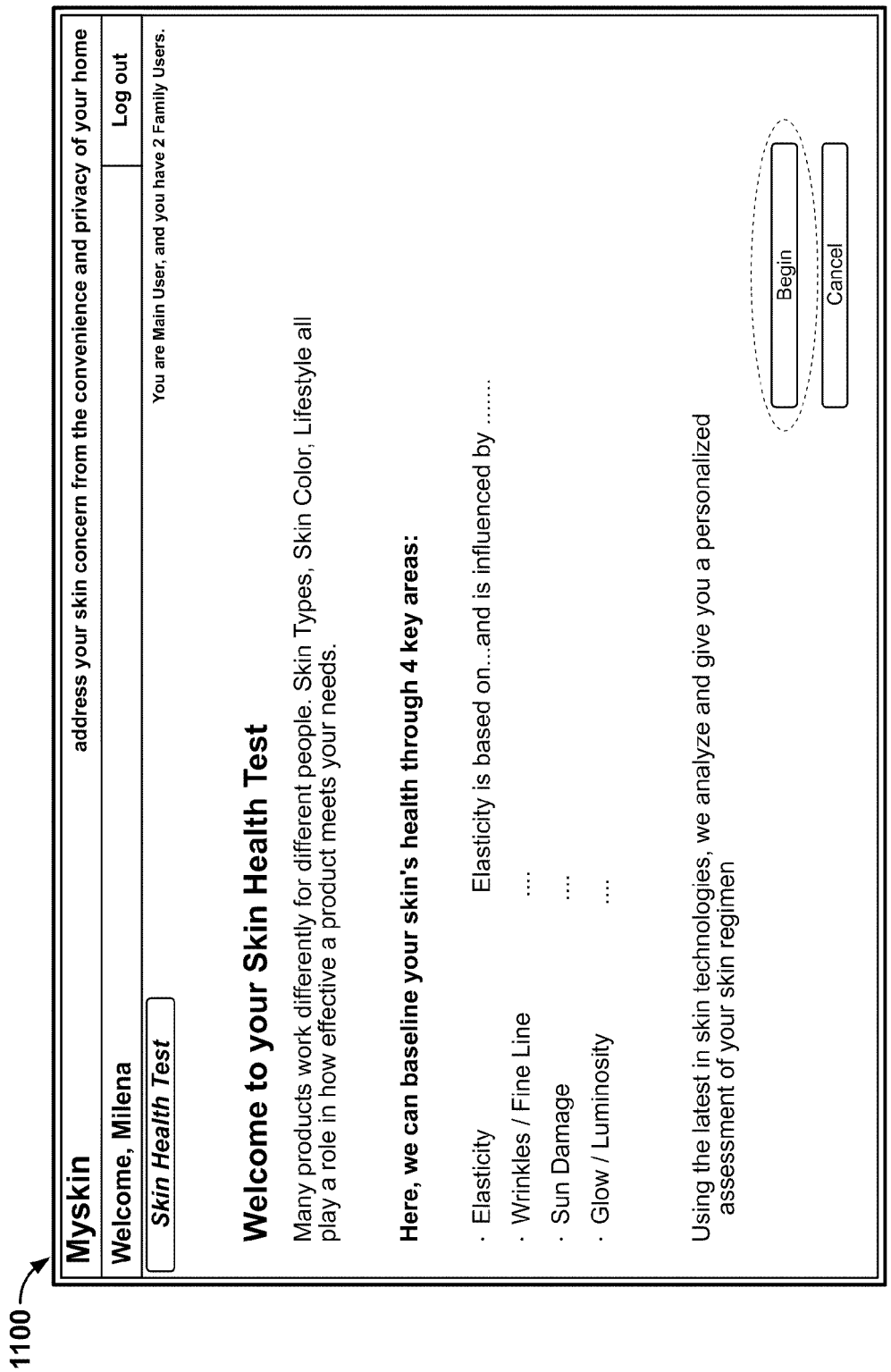
FIG. 11 depicts a skin image capture page of a skin care system.

Referring to FIG. 11, a welcome page 1100 of a skin health test is depicted. The welcome page may provide information on the skin health test, what endpoints will be tested for, such as elasticity, wrinkles/fine lines, sun damage, glow/luminosity, and the like. Using the analysis of the skin health test, the system may provide a personalized assessment of the user's skin regimen 118. The user may initiate the skin health test from the welcome page 1100.

Referring to FIG. 12, a questionnaire page 1200 of a skin care system is depicted. The questionnaire may capture relevant skin history that may be useful for subsequent image analysis. The questions may be asked in multiple choice fashion or as open-ended questions. For example, a question may be 'Where do you use your product?' with responses including face, hands, neck, legs, torso, and the like. Another question may be 'Why are you using your product?' with responses including to protect, repair, moisturize, and any other skin care goal. Another question may be, 'Why are/will you be using your product?' with responses including reduce wrinkles/fine lines, increase shine/luminosity, increase softness/elasticity, and any other skin care goal. Other questions may include, 'How long have you been using your product?', 'How often do you apply your product?', 'When do you apply your product?', and the like, with responses including stated intervals of time. Other information gathered may be how the user prefers notification, where products were purchased, if the user employs a seasonal usage of products, and the like. From the questionnaire page 1200, the user may launch the skin health test.

Figure 13:
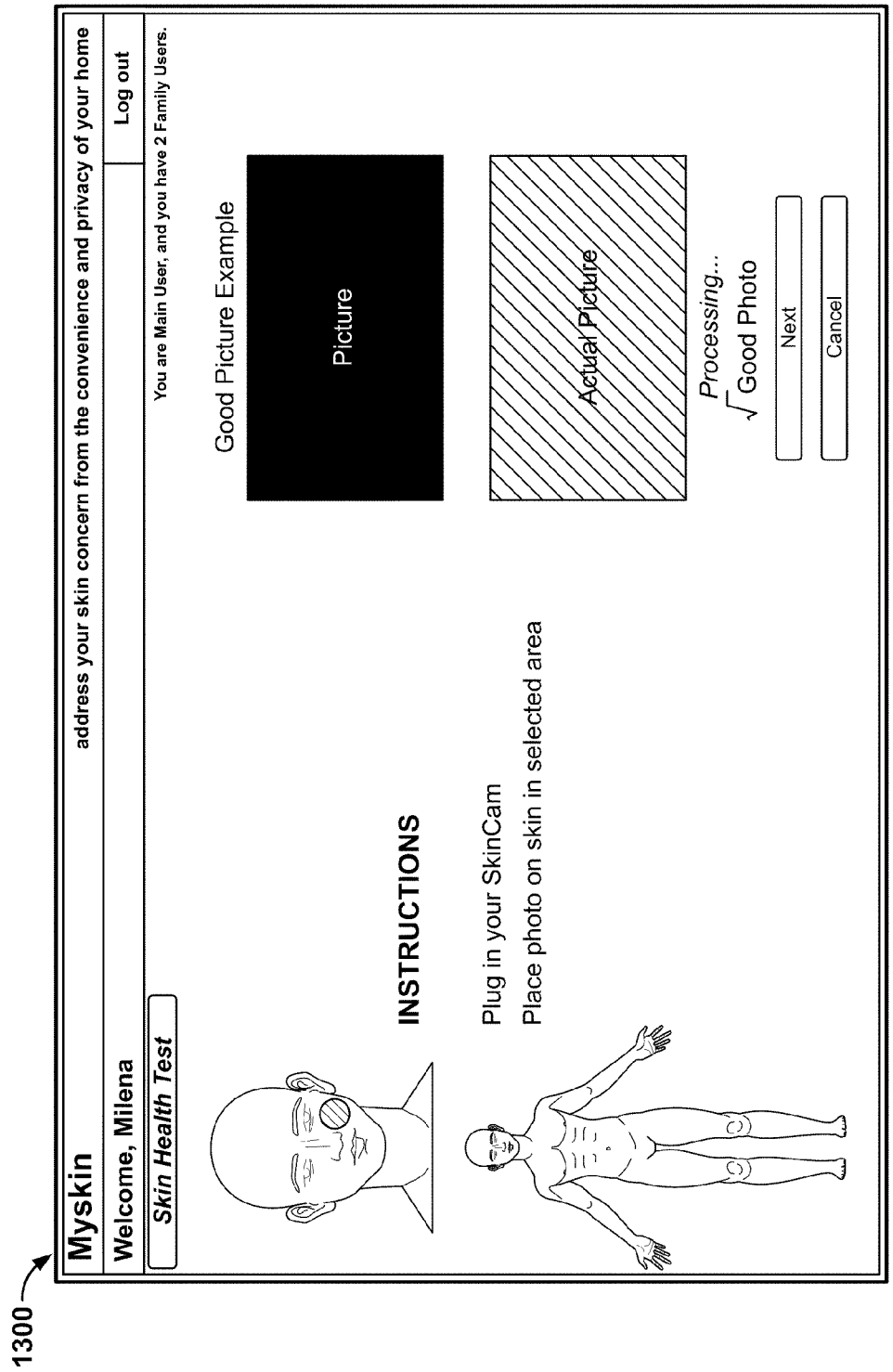
FIG. 13 depicts a results page with line graphs of a skin care system.

Referring to FIG. 13, a skin image capture page 1300 of a skin care system is depicted. In the example, the user interface 102 may access a device 108 in order to capture images, however, it should be understood that other devices 109 may be conveniently used in the system. The page 1300 may show a real time view of the area being imaged. The user may be able to employ positioning tools to be able to take an exact image of an area previously imaged. Once an image has been captured and submitted, an algorithm 150 may verify the integrity of the image. Once an image suitable for analysis has been captured, the user may proceed to an analysis page 1400.

Referring to FIG. 14, a results page of a skin care system with bar graphs is depicted. Algorithms 150 may be used to analyze the image and provide measurements of wrinkles, elasticity, luminosity, firmness, tightness, and the like, as described previously herein. In an embodiment, the measurements may be quantitative measurements. The first analysis may be considered a baseline for purposes of tracking. For each measure, the user may be compared against the baseline for their age, skin state, gender, ethnicity, or any other category. For example, the graph depicts the reading for the user in the first bar on each graph and the average baseline for people of the same age in the second bar. It is apparent from visual inspection that the user is better than average, in this case. These results may be color-coded for ease of interpretation. The results page 1400 may include a description of each measure. The user may be able to request More Information for each of the measures, such as why a certain condition is caused and hints and tips on how to improve a skin condition. The user may be given instructions on when to re-scan the area, which products to use, which regimen 118 to employ, and the like. Desired improvements may be correlated to ingredients and most effective products for the user's skin may be recommended. The user may access and/or edit a skin record 121, which may contain information about the user, images, a chronology of images, information derived from the images, recommendations, products, regimen 118, and the like. The user may access a report facility to obtain a report.

Figure 15:
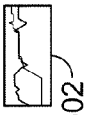
FIG. 15 depicts an elasticity summary screen of a skin care system.

Referring to FIG. 15, a results page of a skin care system with trend analysis is depicted. A method for tracking the effectiveness of a skin care product or regimen may comprise obtaining a baseline skin health assessment; recommending a monitoring interval based on at least one of the skin care goal, product, and regimen; obtaining a second skin health assessment; comparing the second assessment to the baseline assessment to determine progress towards a skin care goal; and, optionally, optimizing the regimen 118 or product in order to improve a skin health assessment. When a subsequent image is acquired and submitted to the system 104, a trend analysis may be performed. Subsequent images may be used to track effectiveness of products and/or regimens 118 and, ultimately, advise the user on and optimize their skin regimen 118, product and/or condition. The trend analysis 1502 may be useful for determining an intermediate skin state 158 during a regimen 118. The trend analysis 1502 may show a baseline reading, an average reading for healthy skin for someone of the user's age, and individual measurements for each type of skin condition. Progress may be shown over time. A time series of images, such as over a twenty-eight day skin cycle, over a treatment timeframe, seasonally, periodically over a year and the like may be captured in order to track progress of a skin state 158. The data may be presented in a pictorial view with data on the picture, graphical view, trend view, numerical view, text view, and the like. Progress may be sorted by the concerns/skin care goals that the user may have indicated at the beginning of the test. The user may be told when to take the next image, how much longer to continue with a regimen 118, how to modify the regimen 118, be reassured about the effectiveness of a product or regimen 118, receive useful tips, and the like. The user may view and/or edit a skin record 121. The user may be able to view past images and perform a simulation 132 of future progress. The user may access a report facility to obtain a report.

Figure 16:
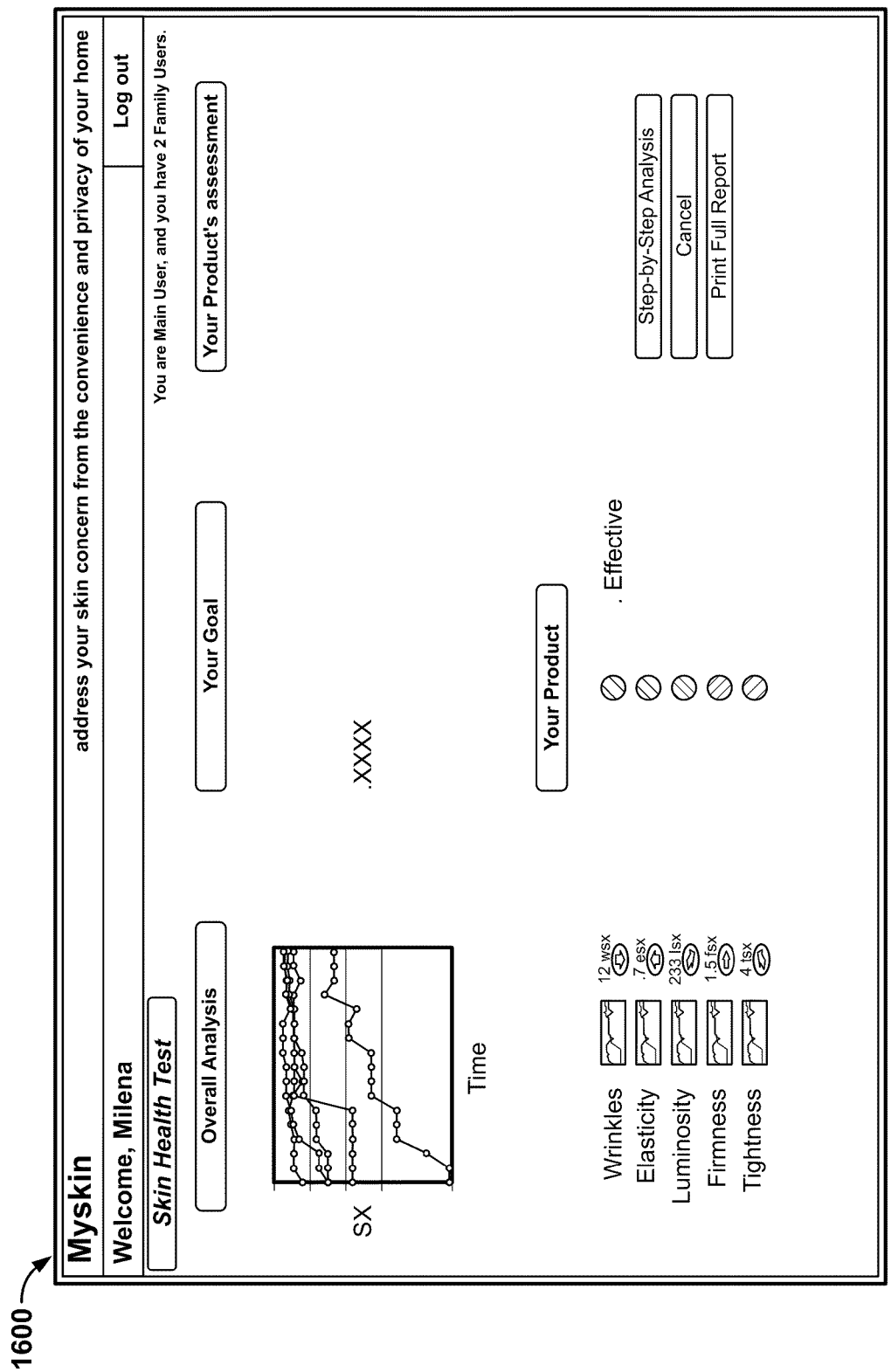
FIG. 16 depicts a summary screen of a skin care system.

Referring to FIG. 16, a summary screen of a skin care system is depicted. An overall analysis for a time interval may be shown, current measurements, progress towards reaching a skin care goal, a product assessment, a regimen 118 assessment, advice on continuing, modifying, or terminating a regimen 118 or product usage, and the like. The user may view a step-by-step analysis or obtain a full report. At an interval, such as at the end of a suggested regimen 118, a report may include information on how the user's skin state 158 changed over time, if the user's skin is healthier than when they started the regimen 118, if the product or regimen 118 met their initial goals, feedback on regimen 118/product effectiveness, and the like. Given the current skin state 158, a new product or regimen 118 may be recommended. For example, the system may recommend specific ingredients to look for in order to increase a user's luminosity given a current skin state 158. Reports may be on-screen, printed, custom, and the like. Reports may be shared with a practitioner for ongoing treatment and consultation.

Referring to FIG. 17, an elasticity summary page 1700 of a skin care system is depicted. A step-by-step analysis of each indicator may be performed. For example, a step-by-step analysis of the elasticity measurement is shown in FIG. 17. The summary page 1700 may depict all of the data captured over an interval, such as in a bar graph, for each indicator on separate summary pages 1700. It should be understood that while FIG. 17 depicts an elasticity summary page, the summary page may summarize data related to any and all concerns. Progress towards meeting a skin care goal may be indicated by the data and its analysis or from user input. An assessment of a user's product or regimen 118 in meeting the skin care goal may be made. Products or regimens 118 that may enable meeting future needs may be indicated. The system may also indicate products used or regimens 118 employed by other users in meeting the stated skin care goal.

Figure 68:
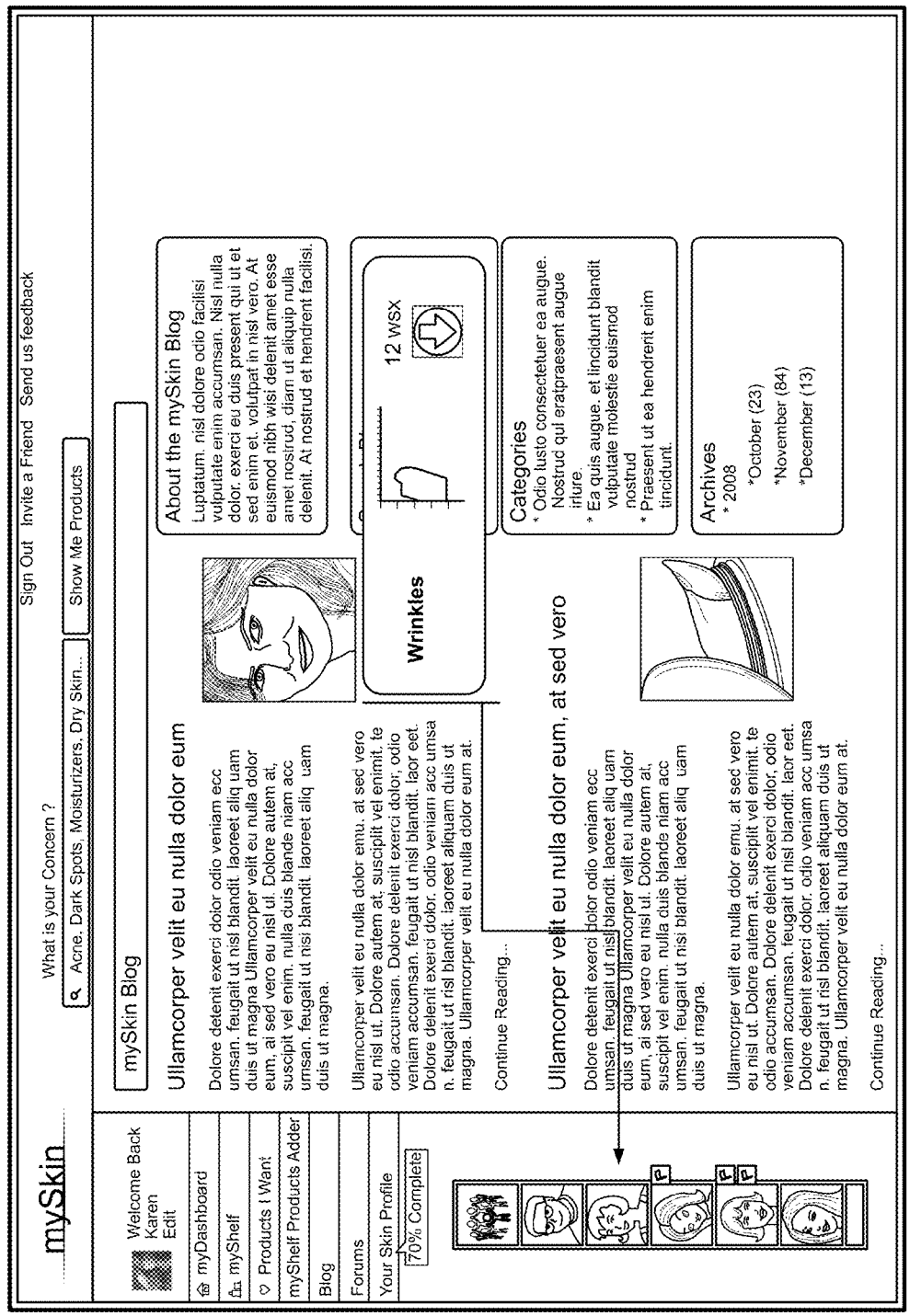
FIG. 68 depicts sharing skin data as a data object with friends.
Figure 69:
FIG. 69 depicts posting skin care data as a data object on a blog or forum where users may discuss the data.
Figure 70:
FIG. 70 depicts sharing skin data as a data object where the data object becomes part of the content that a user may wish to discuss.

In an embodiment, the data acquired at a single timepoint or over a time interval may be shared with other users of the skin care system, practitioners, and the like. In an embodiment, the data may be shared as a data object with users of an online platform 120 or mobile platform 124 of the skin care system, posted to blogs, e-mailed to third parties, and the like. In some embodiments, the data may be a drag-and-droppable data object. For example, the wrinkle trend analysis 1502 shown in FIG. 15 may be shared with friends as in FIG. 68, posted on a blog or forum where users may discuss the data as in FIG. 69, become part of the content that a user may wish to discuss as in FIG. 70, and the like.

In embodiments, a system for providing recommendations for skin care based on a skin state 158, a skin care goal, and environmental factors affecting the skin may comprise interaction with tools and algorithms 150 on an online platform 120, a mobile platform 124, a social networking interface, and the like to receive product and regimen recommendations and track product and regimen 118 effectiveness. The system may be a communication platform, online 120 or mobile 124, that connects geographically separate consumers, manufacturers, product information, experts, service providers and others related to or allied to the beauty and medical field to provide personalized assessment regarding the consumers skin, hair, or nails queries and concerns. The user interface 102 may reside on an online platform 120, mobile platform 124, or social networking interface. In some embodiments, a skin care assessment may be provided by algorithms 150 operating on an online platform 120 without the use of images or data from a device 108, that is, a user need not have data from a device 108 to participate in the online platform 120. The online platform 120 may be a standalone skin health assessment and skin care recommendation tool. However, in embodiments, image data may also be used by the online platform 120 to provide skin health assessments and skin care recommendations. A user interface 102 may interface with the online platform 120. For example, a user may access an online platform 120 of the system for skin health analysis, monitoring, and recommendation to: monitor skin health, download, process, analyze, track, and store data from an imaging device 108 or other device 109 or monitor 182, receive product and/or regimen recommendations from an analysis/API 154 or from peers, compare skin state 158 and regimen 118 with peers, receive product information 190, purchase products; add recommendations to a skin care shelf 114; organize a skin care shelf 114 by regimen 118, rankings, expiration date, cost, skin care goal, time of day, frequency, friends, and the like; view community ratings, rankings and comments on products/regimen in a skin care shelf 114; rank/rate products; leave comments on products, regimens, peers products and/or regimens; and the like, receive new product alerts or product recalls, receive a daily report 134, interact with a social network 188, and the like. The user interface 102 may enable users to conveniently take and submit images, enter data, track history, obtain recommendations and analysis and perform a purchase regarding their skin, hair, and/or nail's beauty/cosmetic or medical concern. The user interface 102 may reside on an online platform 120 and guide the user while also serving as a data repository to maintain a skin record 121 and history tracking tool, and may help the user organize information relevant to their condition in a logical fashion.

In an embodiment, the user interface may comprise a skin care shelf 114. The skin care shelf 114 may be a structure that enables users to organize their products and regimen 118 in a logical fashion based on users' specific skin characteristics 130/skin state 158 by usage scenario (such as morning, afternoon, night, and the like), intent (such as work, fun, etc.), skin care goal (such as moisture, glow, protect, and the like), and the like. The skin care shelf 114 may have multiple "pages" for recommendations by various entities (such as practitioner, physicians, dermatologists, aestheticians, spa specialists, overall users, experts, people most like you, and the like). The skin care shelf 114 may be a personalized arrangement of products, regimen 118, and/or information 190, 192. Users may drag and drop products (or select to add) as they are surfing the web and discover new products as well as having auto populated recommendations. The functionality may include a facility that may highlight products of interest while surfing the web. For example, a plug-in 194 may be used to allow a user to capture information from any location on the Internet. For example, a user may access a web page for a makeover article in a beauty magazine and wish to include the products from the makeover in their skin care shelf 114 and/or shopping cart 113. The user may click on the product name and drag it over to at least one of the skin care shelf 114 and shopping cart 113 to obtain additional product information 190, include in their regimen 118, purchase, request samples, and the like. The skin care shelf 114 may an application that may also sit independently on social networking sites 188 and other personal pages and or toolbars. The skin care shelf 114 may also indicate purchase date and purchase history, product expiration alerts and other usage updates. In an embodiment, a purchase made off a website may automatically add to the users' shelf 114, while manual entries for offline purchases may also be possible.

In an embodiment, the user interface 102 may interface with a mobile platform 124. The user interface 102 may support plug and play with various mobile devices 184 such as mobile phones, laptops, digital cameras, medical-use devices, and the like. For example, the mobile phone may have an attachment or an integrated feature that may enable a user to take an image of the skin and input/capture data and have it connect via the web, wirelessly or via cable, to the user interface 102 and enable seamless connectivity and data transfer. The mobile device could be used to take images and data at various locations for obtaining various information from the community (such as at the beach to measure effectiveness of sun screen, an image of a specific location, a product image or a bar code image to get product feedback, best price, nearest physical selling location, coupons, and the like). Users may also be able to share data/ask questions regarding products instantaneously to other users. The mobile device could have an internal lens system that may be internally charges or an independently attached lens system that would enable using the battery power and light source of the device to take an image and use the in-built communication method for submitting the image.

Referring to FIG. 18, the user interface for the online platform 120 may be depicted as a map. The home page may have a different theme or feel depending on the user profile, the user preference, or any other criteria. For example, it may be fun, serious, clinical, and the like. From the user interface, a user may review products, contribute anecdotes, report, review reports, review blogs by product, skin type, and the like, visit their beauty shelf 114, and the like. Information may be accessed freely, with registration, or only partially freely and partly with registration. All products and pages may link through the beauty shelf 114.

For example, FIG. 19 depicts a review page of the user interface of a skin care system. The menu across the top of the user interface may enable a user to access Reviews, Experience, Recommendation, Info For Me, Checkout, and the like. The user interface may depict a portion of the user profile, such as the age, gender, location, skin type, skin color, skin goal, picture, and the like for the user. The user interface may also depict what products or regimen 118 the user may be using and any associated review, rating, or comments of the product. Other users accessing a user profile may make comments on the regimen 118 or products in use, give the products or regimen 118 a rating, recommend a different product or regimen 118, and the like. The user interface may present tools to aid a user in selecting a product or regimen 118. For example, the tools may be in the form a questionnaire or wizard guising the user to describe their skin. The user may provide age, gender, skin type (oiliness, sensitivity), skin color, goal, current brand or product, current regimen 118 and the like. In some embodiments, the skin type and/or color may be detected automatically if the user interface is interfaced with an imaging device 108. The user may also access their beauty shelf 114 from the user interface.

Referring to FIG. 20, a review page of a user interface of a skin care system is depicted. The review page is shown in a different layout than the compact view depicted in FIG. 19.

Referring to FIG. 21, an experience page of a user interface of a skin care system is depicted. The experience page allows users to provide a detailed report of experience with a product or regimen 118. For example, the user may note the effectiveness of a product or regimen 118, such as by answering questions. For example, the questions may be "How effective is it?", "How does it feel?", "How is its fragrance?", "How does it absorb?", "Does it cause breakouts?", and the like. The experience page may also allow a user to update a user profile with age, gender, nickname, location, a photo, skin type, skin color, goal, and the like. The user may be able to query other users for their experience or make a general inquiry by submitting a request to an email, MMS, SMS, phone number, mobile device, social network, and the like.

Figure 22:
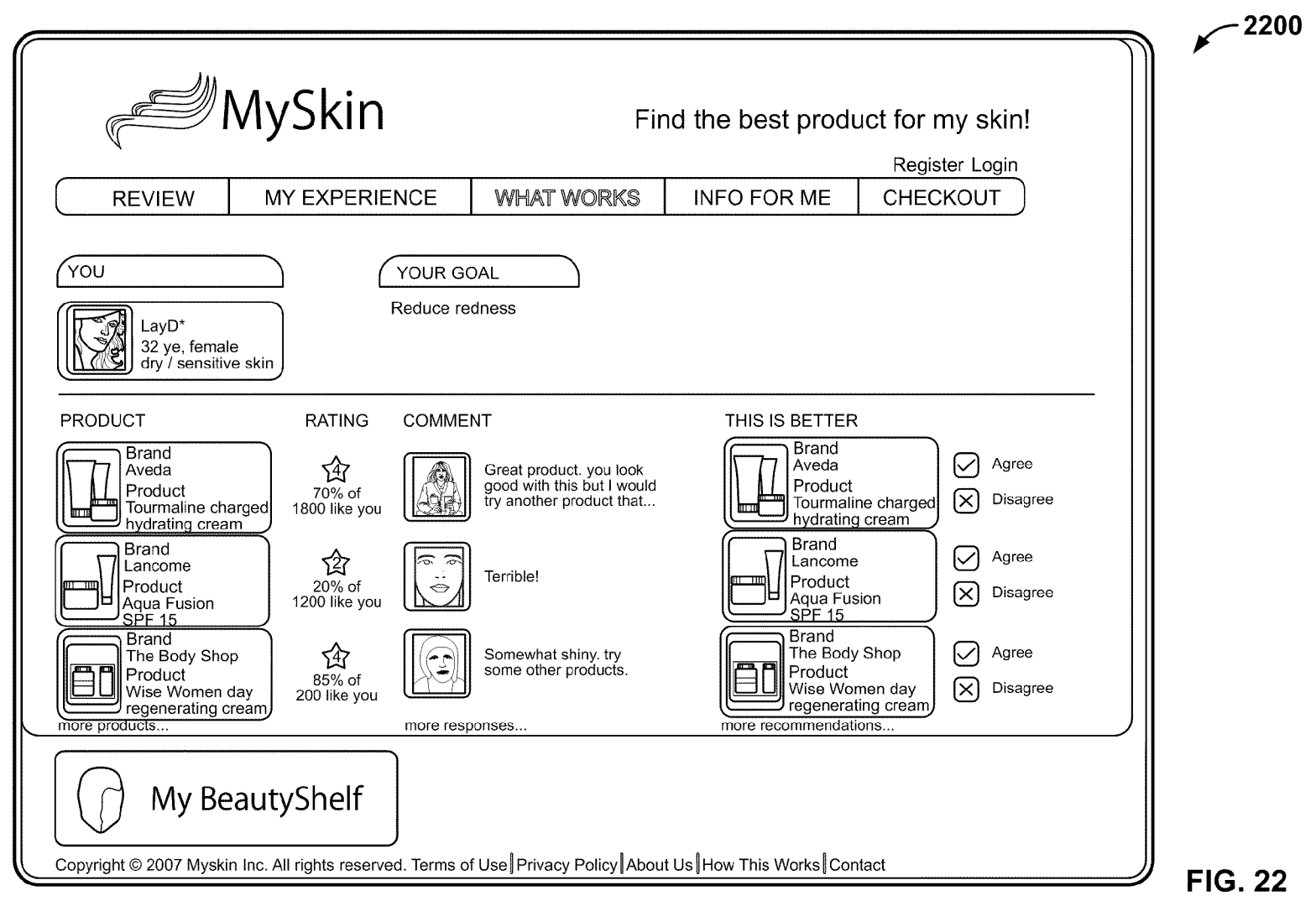

Referring to FIG. 22, a recommendation page of a user interface of a skin care system is depicted. Given the goal, various products or regimens 118 that may be effective in meeting the goal may be shown on the recommendation page. The brand and product or regimen 118 may be shown along with a rating from the community of users, comments from users, the ability to indicate of the user believes the product may better than the current product or regimen 118 in use, and the like. If the user believes the product or regimen 118 may be better than what they are currently using, the product or regimen 118 may be stored for future consideration on the beauty shelf 114.

Figure 23:
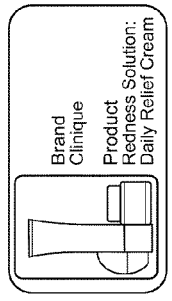
FIG. 23 depicts an Info For Me page of a skin care system.

Referring to FIG. 23, an Info For Me page of a user interface of a skin care system is shown. A People Like Me algorithm 150 may be used to sort the community of users of the skin care system. Given the aspects of the user profile, the algorithm 150 may determine which other users are most similar along all criteria, along custom-selected criteria, along a combination of skin color and skin type, and the like. Once the algorithm 150 has determined a subset of the community of users who are most like the user, the user can view data for the community. For example, the user can find out which products work best for the subset generally, for a specific issue, for a specific time of day, for a specific season, and the like. The Info for Me page may also depict the weather for the location given in the user profile and a UV rating and any specific tips given the location/weather/environment. The Info for Me page may also alert the users of new products being launched. The user may sort the products according to effectiveness.

Figure 24:
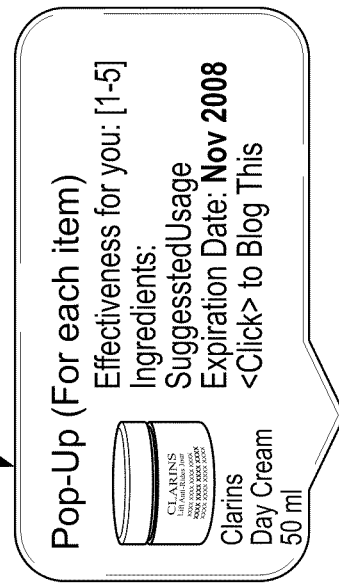
FIG. 24 depicts an example of a skin care shelf portion of a user interface of a skin care system.
Figure 25:
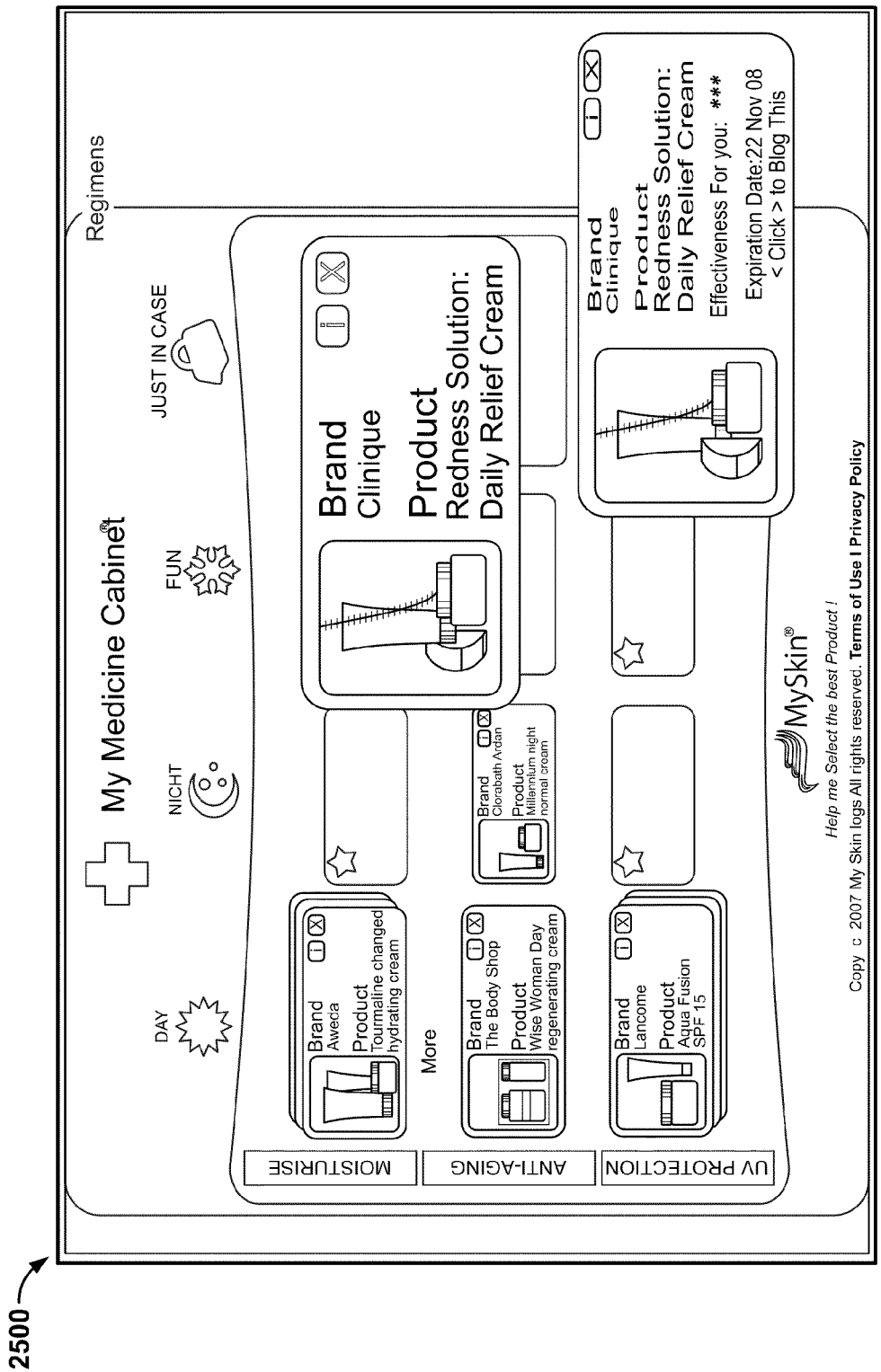
FIG. 25 depicts an example of a skin care shelf portion of a user interface of a skin care system.
Figure 26:
FIG. 26 depicts a user interface of a skin care system.

Referring to FIG. 24, an example of a beauty shelf 114 portion of a user interface of a skin care system is shown. Products or regimens 118 used by the user may be categorized by time of day use, specific effectiveness, cost, expiration, and the like. Each item may be clicked on to pop-up additional details about the product or regimen 118, such as effectiveness, ingredients, suggested use, expiration date, a link to purchase more, a link to blog about the product or regimen 118, a link to write a review or read reviews, a link to the manufacturer's site, a link to an in-store coupon, and the like. FIG. 25 depicts another example of a beauty shelf 114 portion of a user interface of a skin care system. FIG. 26 depicts an alternate view of the beauty shelf 114 of the user interface of a skin care system. In this example, friends have the ability to comment on the products or regimen 118 and suggest an alternative product or regimen 118. The user also has the option to receive price alerts, new product launch alerts, new user comment alerts, and the like.

Referring to FIG. 27, a registration page of a user interface of a skin care system is depicted. Information may be entered by the user, goals may be indicated, a security code may be entered, skin concerns, color, and/or type may be entered, samples may be registered for, and the like. Additionally, the user may indicate that the want to add a feed from the skin care system to their RSS feed, and application from the skin care system to a social networking site, and the like. The user may have the option to opt-in to alerts, to be notified of samples and products, and the like.

Referring to FIG. 28, another embodiment of a recommendation page of a user interface of a skin care system is shown. This page may show people in the user's category, such as number of people of the same gender, same age group, with similar skin type, with similar concerns, and the like. For each stated goal, a product may be recommended that is most popular, has the most buzz, has been reviewed, has been rated, has been blogged about, and the like.

Figure 65:
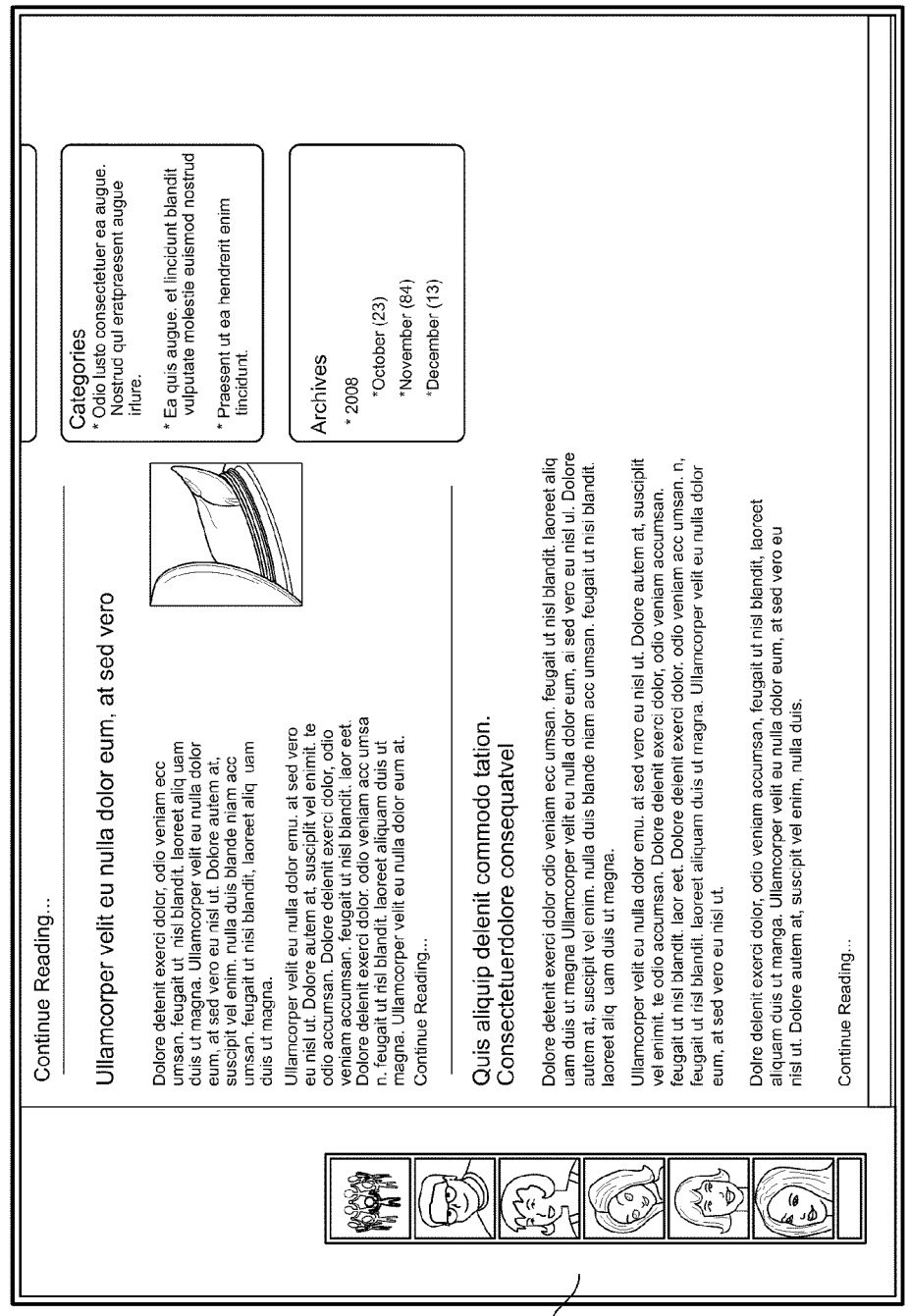
FIG. 65 depicts the auto-scroll feature of the friend toolbar.
Figure 66:
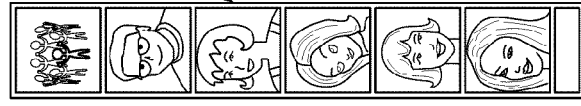
FIG. 66 depicts the drag-and-drop share functionality of the friend toolbar.
Figure 67:
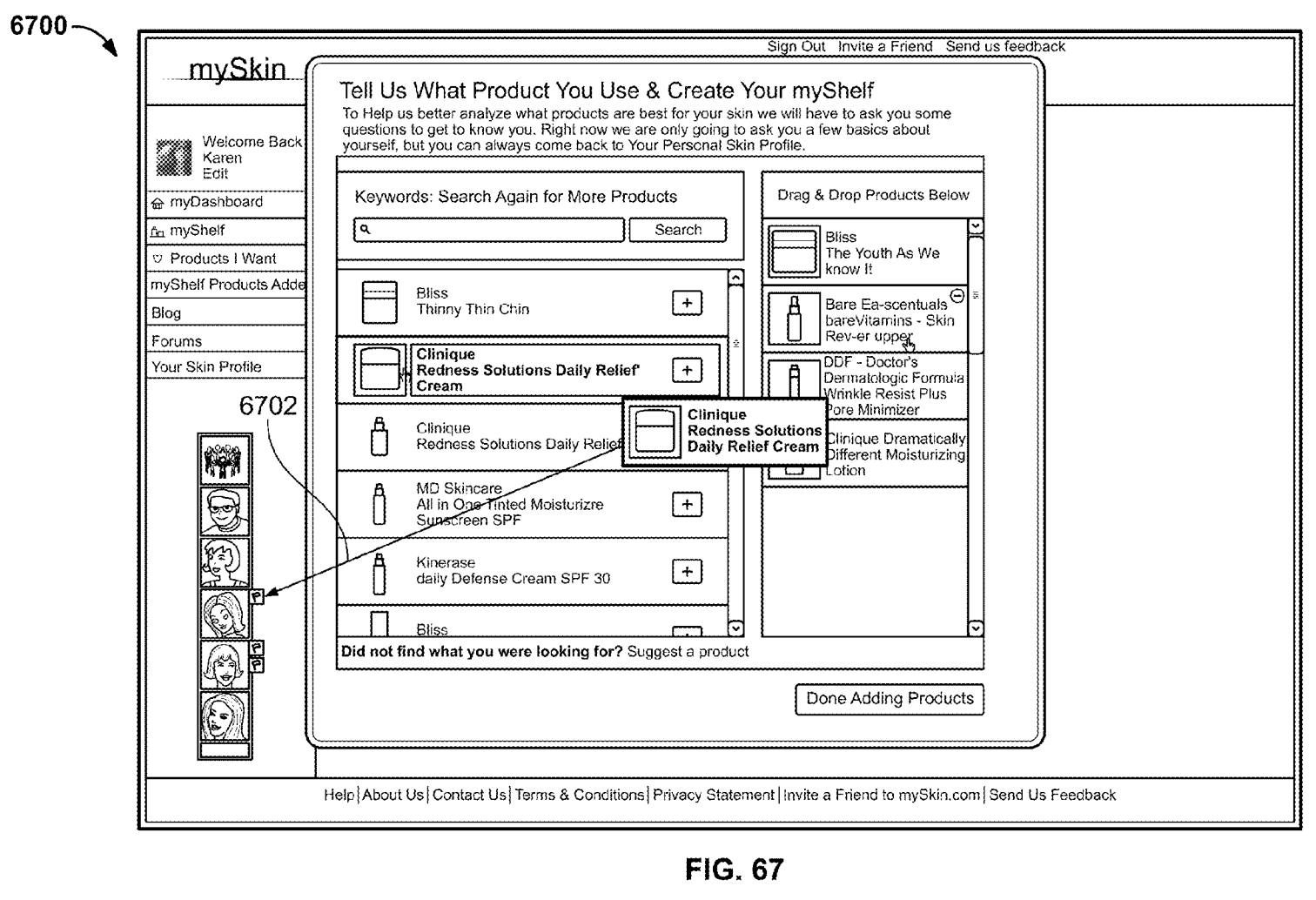

Referring to FIG. 64, the user interface may include a friend toolbar. The friend toolbar may float over a current website, or any website, such as by using a plug-in. Friends may upload images and the images 6408 may be displayed on the friend toolbar 6402. A home key 6404 may be part of the toolbar 6402, where the whole toolbar can be reduced to just the home key 6404. When an alert is associated with a friend, such as a new product being added to their beauty shelf 114 or a new review being written, a flag alert 6410 may pop-up next to their image on the toolbar 6402. A bottom bar 6412 may be used for shuffling friends or accessing other options related to the toolbar 6402. Referring to FIG. 65, the toolbar 6402 may auto-scroll 6502 as the user scrolls the webpage they are viewing. Referring to FIG. 66, objects may be shared with friends in the friends' toolbar 6402 using a drag-and-drop functionality 6602. For example, a blog posting may be shared as in FIG. 66 by dragging and dropping the blog title onto a friend's image. Similarly, products may be recommended to a friend by dragging and dropping 6702 the product into the friends' image, as in FIG. 67. Rolling over a friends' image may result in a pop-up, dialog box or other manifestation of additional information about the friend, such as a view of their user profile, beauty shelf 114, reviews, blogs, and the like.

Figure 29:
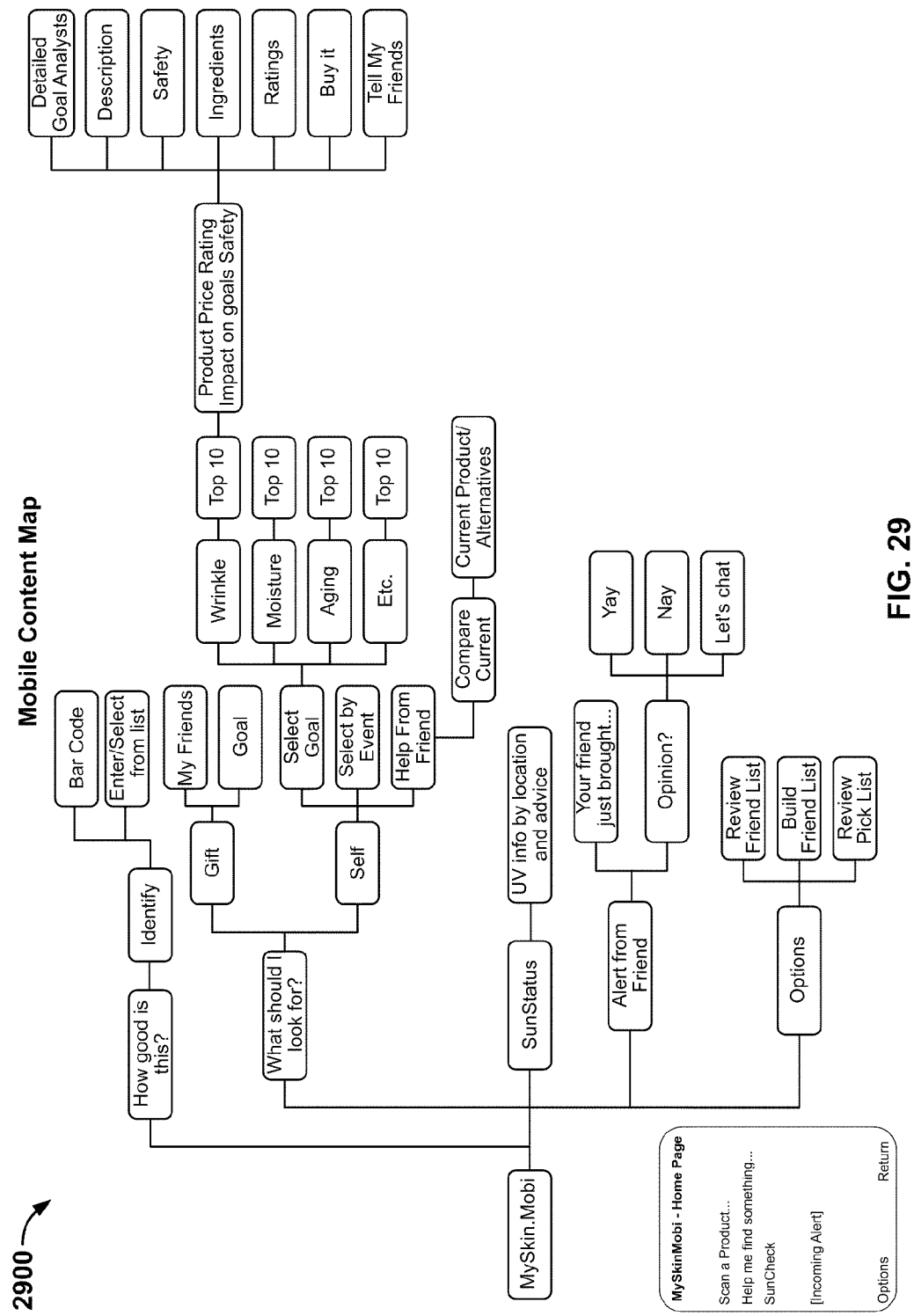
FIG. 29 depicts a mobile content map for a mobile user interface of a skin care system.

Referring to FIG. 29, a mobile content map for a mobile user interface of a skin care system on a mobile platform 124 is depicted. The content map depicted shows an example of content that can be accessed from a mobile platform 124 home page. For example, starting from the home page, a product may be scanned or identified from a list and searched for using the internet on the mobile device. For example, a bar code may be scanned for a product and prices, reviews, ratings and the like for the product may be returned. The user may be helped to find something, such as an item for themselves, a gift for a friend, and the like. The product may be searched for based on a goal, an issue, a skin type, a skin color, and the like. The mobile skin care system may return a list of products, such as the top 10 products, and information about the products such as rating, impact on goals, safety, reviews, and the like. The user may access a Suncheck application to be given UV information by location and advice, as well as based on an image captured by an imaging device 108 embodied in a mobile device, as described previously herein.

Figure 30:
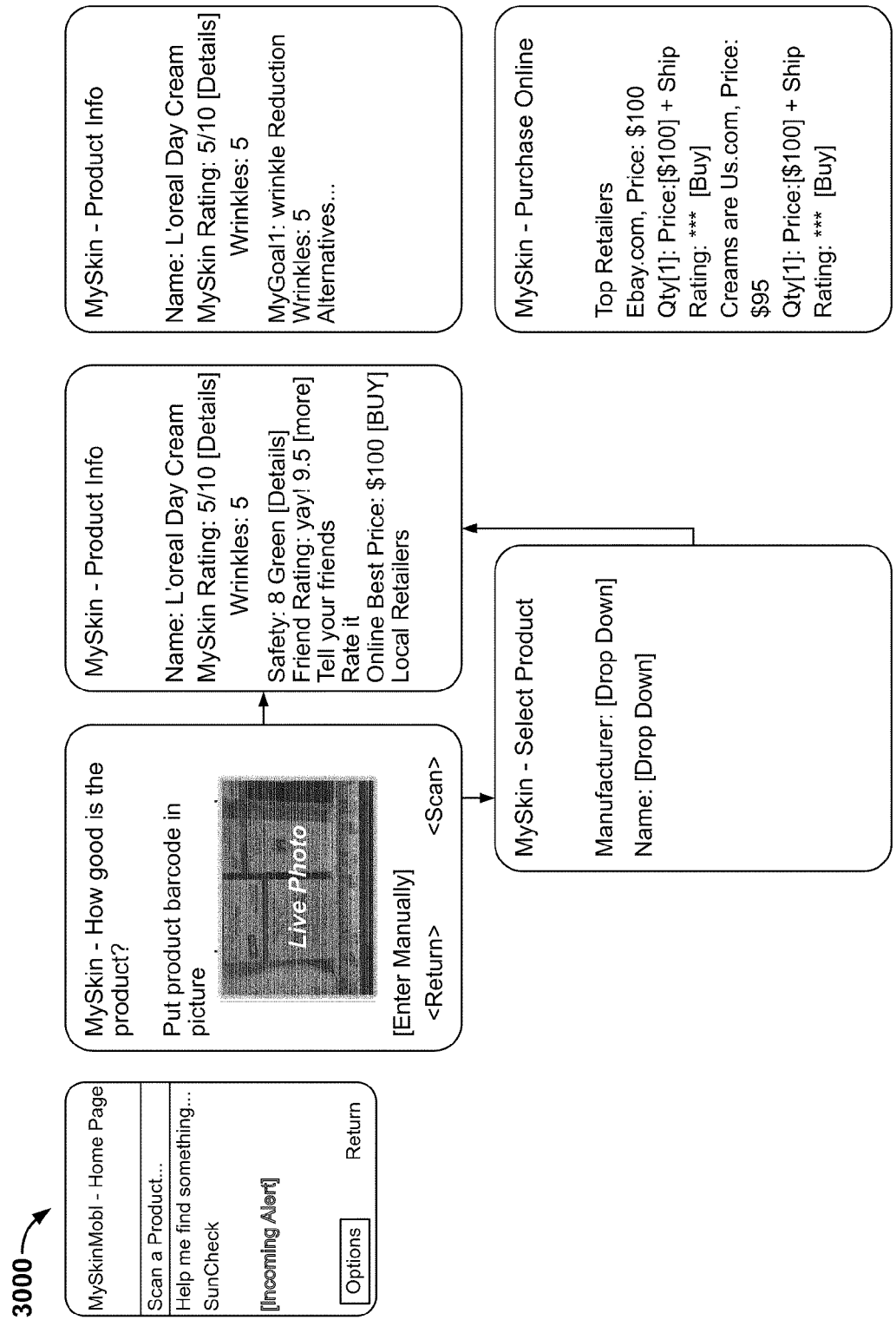
FIG. 30 depicts a How Good Is This Product message flow.

Referring to FIG. 30, a How Good Is This Product message flow is depicted. In the example, a bar code may be scanned to obtain product info, the bar code numbers may be manually entered, or the product may be chosen from a list. The system may return product information such as the product name, rating, ingredients, a general rating, a rating for a specific concern, a friend's rating, a price, where the product can be found, and the like. If the mobile device is enabled, a purchase may be initiated on the mobile platform 124.

Figure 31:
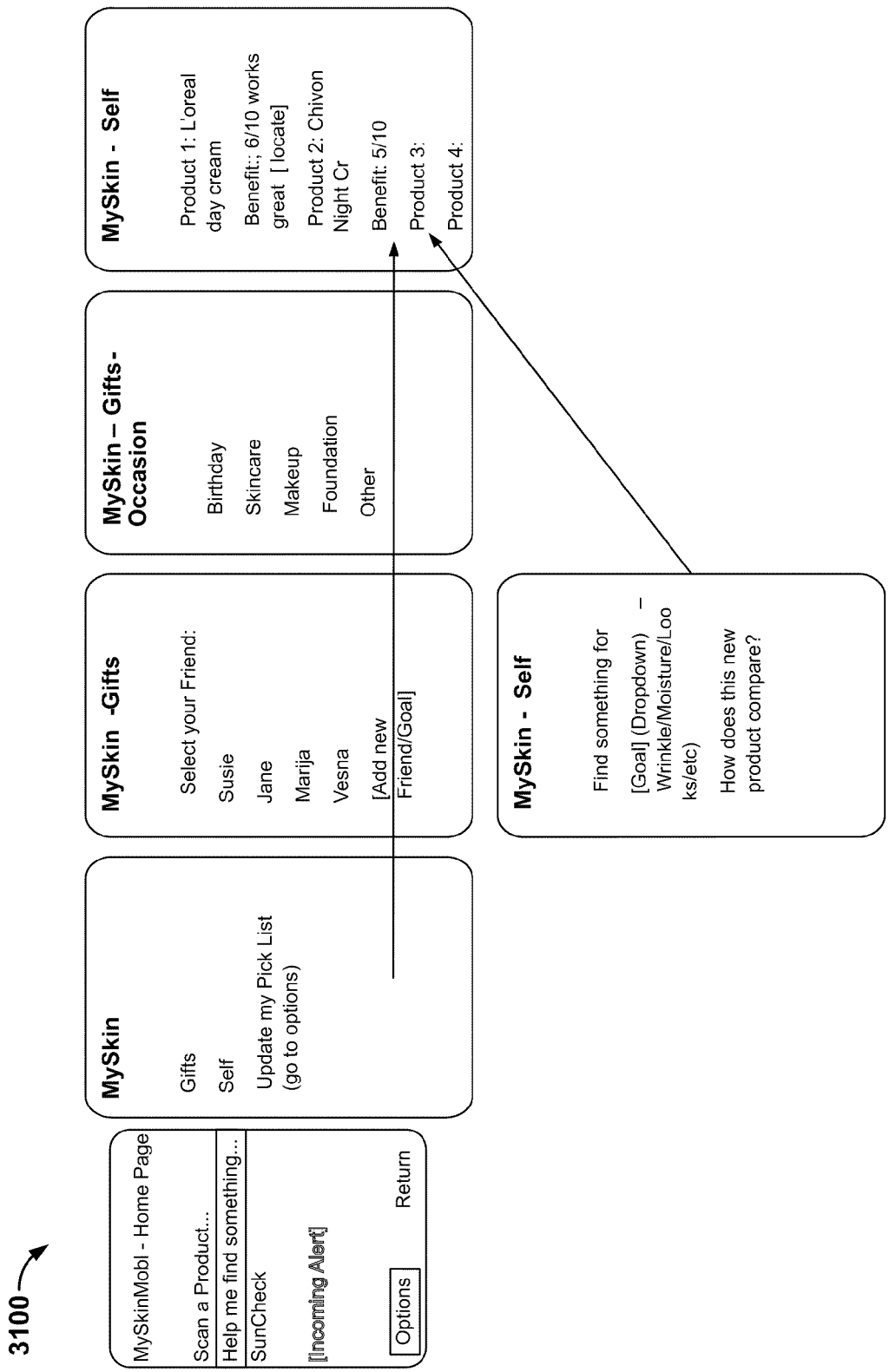
FIG. 31 depicts a What Should I Look For? message flow

Referring to FIG. 31, a What Should I Look For? message flow is depicted. The message flow may begin by giving the user the option to indicate if the item searched for is a gift, for the user, to update a pick list, and the like. For gifts, a recipient may be selected from a pre-populated list or a new recipient may be indicated. An occasion may be indicated. Based on the recipient and occasion and any other criteria entered, products may be recommended along with any information associated with the product, a price, a location, and an option to purchase on the mobile platform 124. In looking for something for the user, the user may indicate a goal, such as from a drop down menu, and receive a list of recommended products. Once a product is selected, the user may request to locate the product at a store or initiate a purchase on the mobile platform 124, or the like.

Referring to FIG. 32, a Suncheck message flow is depicted. The initial message may contain information about the user's location, the weather, a UV index, a sun impact rating, an indication of the maximum exposure time, and a timer for measuring the current time in the sun. Advice may be generated based on the information, such as what level of sun protection factor to apply, a maximum recommended time of exposure, and the like.

Referring to FIG. 33, an Alert message flow is depicted. The user may be linked to other users on the mobile platform 124 so that when another user requests a review or rating of a product, an alert may be sent to the user. The user may respond with a review, a rating, a chat message, an SMS, an MMS, a phone call, a voicemail, and the like.

Figure 34:
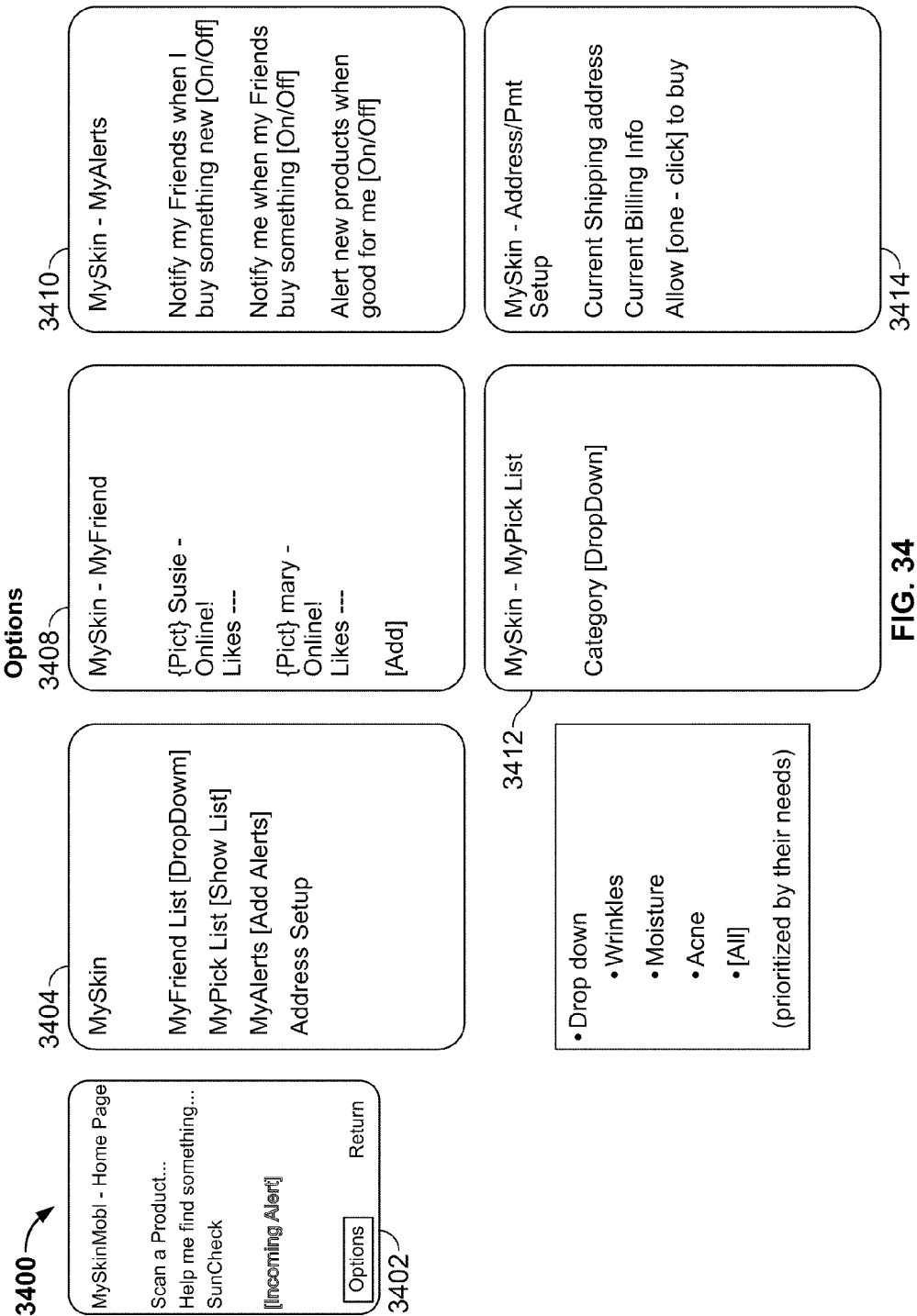
FIG. 34 depicts an Options message flow.

Referring to FIG. 34, an Options message flow is depicted. From the mobile platform 124 home page 3402, Options may be selected. Options 3404 may be a friend list, a pick list, alerts, address/location, and the like. For example, a friend list 3408 may be accessed to pick and choose friends to follow, receive alerts from and the like. The friends list may indicate if the friend is online. Alerts 3410 may also be set on the mobile platform 124, for example to notify the user when their friends buy something new, notify the user when a new product that is good for them is available, and the like. Address/location/payment setup may allow the user to initiate purchases from the mobile platform 124.

In certain aspects of the invention, systems and methods for analysis of skin diseases (or disorders) by image processing detection (or image processing-based detection) of dermoscopic structures (or skin lesions) are disclosed. More particularly, there is disclosed the design and implementation of a system for automated diagnosis of seborrheic keratosis by image processing detection of multiple milia-like cysts or comedo-like openings and methods thereof. Still more specifically, there is a disclosed an improved system with enhanced qualitative and quantitative parameters, such as non-invasive, automatic, reliable, accurate and easily operable, for automated diagnosis of seborrheic keratosis by image processing detection of multiple milia-like cysts or comedo-like openings and methods thereof and a method for the design and implementation of such a system.

Figure 71:
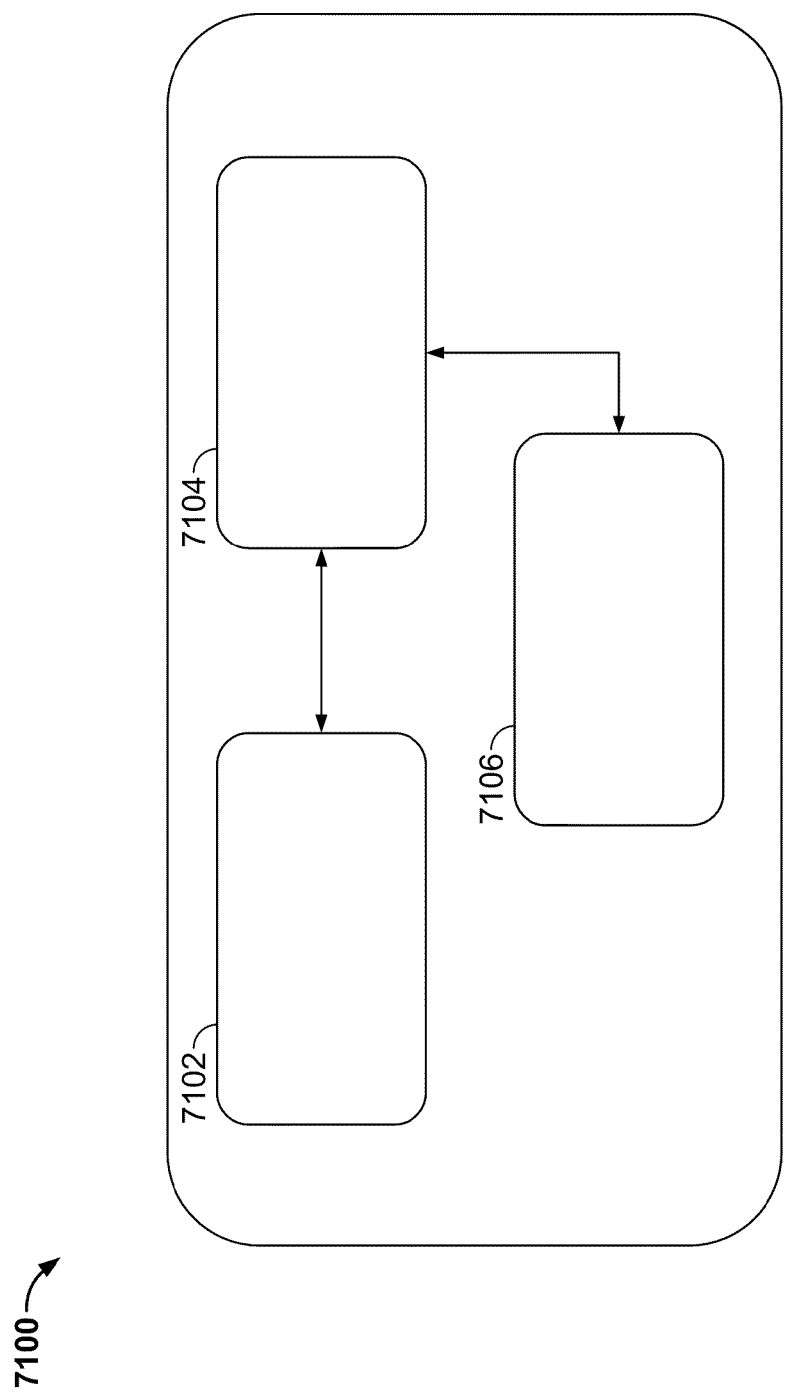
FIG. 71 is a schematic view of a system for automated diagnosis of skin disorders by image processing detection of skin lesions or dermascopic structures, designed and implemented in accordance with at least some embodiments of the invention.

FIG. 71 is a schematic view of a system for automated diagnosis of skin disorders by image processing detection of skin lesions or dermoscopic structures, designed and implemented in accordance with at least some embodiments of the invention.

The system 7100 is in essence an Automatic Seborrheic Keratosis Diagnosis System (or ASKDS).

The ASKDS 100 consists of an illumination subsystem 7102, a sensor subsystem 7104 and a host computing subsystem 7106.

The ASKDS 100, by virtue of its design and implementation, facilitates automatic diagnosis of seborrheic keratosis based on detection of multiple milia-like cysts or comedo-like openings through image processing.

In certain embodiments, the ASKDS 7100 for automated diagnosis of skin disorders and processes thereof has been disclosed. Specifically, in such embodiments, the ASKDS 7100 comprises one or more illumination sources. The illumination sources comprise incident light sources to direct light upon skin. In consequence, the incident light sources may be unpolarized or polarized light sources. For example, and by no way of limitation, the unpolarized light may be white light, multiple selected wavelengths, or a single wavelength. Further, the illumination source may be positioned to direct light at a selected angle alpha. By way of example, and in no way limiting the scope of the invention, the ASKDS 7100 implements the processes for non-invasive processing including, but not limited to, imaging, analysis, and the like, as disclosed in United States Provisional Patent Applications "METHOD AND ALGORITHM FOR ANALYSIS OF LIGHT-MATTER INTERACTION BASED ON SPECTRAL CONVOLUTION" and "IMAGING DEVICE UTILIZING WHITE LIGHT FOR COMPOSITION ANALYSIS" and United States Non-Provisional Patent Applications, "SYSTEM, DEVICE, AND METHOD FOR DERMAL IMAGING" to MYSKIN, INC., the disclosure of which is incorporated herein by reference in its entirety. Thus, all remaining ins-and-outs in connection with the process of non-invasive processing of materials, both organic and inorganic, will not be further detailed herein.

As shown in the FIG. 71, in certain embodiments, the illumination subsystem 7102 may be coupled to the sensor subsystem 7104.

As shown in the FIG. 71, the sensor subsystem 7104 may in essence be a device that converts optical images (or optical signals) to electric signals. In certain embodiments, the sensor subsystem 7104 captures continuous digital images of skin. Specifically, in such embodiments, the sensor subsystem 7104 captures continuous digital images of the metallic surface illuminated with white light both, non-angled and angled. By way of, and by no way of limitation, the sensor subsystem 7104 may be anyone selected from a group consisting of a Complementary Metal-Oxide-Semiconductor (CMOS) image sensor, Charged Coupled Device (CCD) image sensor, and the like.

Again, as shown in FIG. 71, the sensor subsystem 7104 may be coupled to the host computing subsystem 7106 and the illumination subsystem 7102, respectively.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

For example, and in no way limiting the scope of the invention, in certain embodiments the sensor subsystem 7104 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

In certain embodiments, the host computing subsystem 7106 may comprise a skin disorder management module designed and implemented, in accordance with the principles of the invention.

Figure 72:
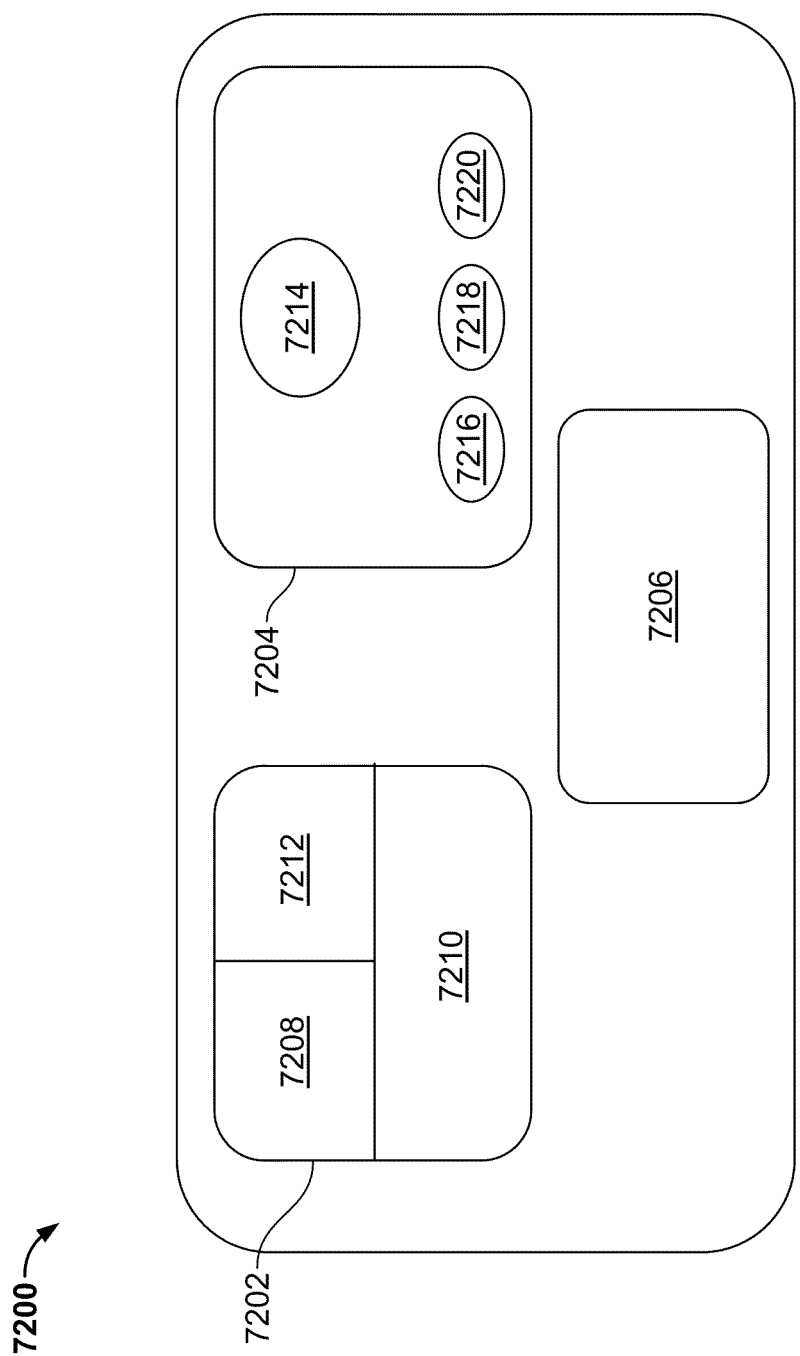
FIG. 72 is an exploded diagrammatic representation of the host computing subsystem, of FIG. 1, comprising the skin disorder management module designed and implemented in accordance with at least some embodiments of the invention.

FIG. 72 is an exploded diagrammatic representation of the host computing subsystem, of the FIG. 71, comprising the skin disorder management module designed and implemented in accordance with at least some embodiments.

The host computing subsystem 7200 may comprise a processing unit 7202, a memory unit 7204 and an Input/Output (or I/O) unit 7206 respectively.

The host computing subsystem 7200, by virtue of its design and implementation, performs overall management of one or more disorders of skin.

The processing unit 7202 may comprise an Arithmetic Logic Unit (or ALU) 7208, a Control Unit (or CU) 7210 and a Register Unit (or RU) 7212.

The memory unit 7204 comprises a skin disorder management module 7214.

In certain embodiments, the skin disorder management module for real- or point-time analysis of the continuously captured digital skin information and methods thereof is disclosed, in accordance with the principles of the invention. Specifically, in such embodiments, the skin disorder management module captures the skin information using at least one of Diffused Reflectance Spectroscopy, Red (R)-Green (G)-Blue (B) analysis of re-emitted white light and any combination thereof.

The terms "Diffused (or Diffuse) Reflectance Spectroscopy (or DRS)" and "Diffuse Reflectance Infrared Fourier Transform Spectroscopy (DRIFTS)" refer to a technique that collects and analyzes scattered Infrared (or IR) energy. It is used for measurement of fine particles, powders as well as rough surface. Specifically, it assesses the interaction of a surfactant with the inner particle or the adsorption of molecules on the particle surface. In DRS or DRIFTS, sampling is fast and easy because little or no sample preparation is required.

In certain other embodiments, the skin disorder management module may comprise one or more processes for determination of an assortment of qualitative and quantitative parameters thereby facilitating overall management of disorders of skin. In such embodiments, at least a first process of the one or more processes determines moisture levels of skin. Specifically, this process may comprise one or more phases comprising emission of incident electromagnetic signals to skin, detection of degree of polarization of the electromagnetic signals reflected or re-emitted from skin and determination of the moisture levels based on the amount of polarized and reflected or re-emitted electromagnetic signals. Yet, in such embodiments, the first process may comprise one or more phases comprising combination of the determined moisture levels with skin color measurements thereby resulting in determination of skin luminosity.

Still, in certain such embodiments, at least a second process of the processes determines elasticity of skin. Specifically, this process may comprise one or more phases comprising the emission of the incident electromagnetic signals to skin, detection of a first aspect of polarization of the electromagnetic signals reflected by skin, correlation of the aspect of polarization with a concentration of elastin and determination of elasticity level based on the concentration of elastin.

Still further, in certain such embodiments, at least a third process of the processes determines firmness of skin. Specifically, this process may comprise or more phases comprising the of the incident electromagnetic signals to skin, the detection of a second aspect of polarization of the electromagnetic signals reflected by skin, the correlation of the aspect of polarization with the concentration of at least one of the elastin, a collagen, an activity of a sebaceous gland and any combination thereof and determination of the firmness based on the concentration of at least one of the elastin, collagen and sebaceous gland activity. In such embodiments, the sebaceous gland activity may be indicated by at least one of a number of glands, percent of glands open/closed and level of clog/fill.

Yet, in certain such embodiments, at least a fourth process of the processes obtains biophysical properties and may comprise performing a spectral analysis of image data acquired from the degree of polarization of reflections and absorption and re-emission of incident light from skin. Specifically, the biophysical properties is at least one of a structure, form, concentration, number, size, state, and stage of at least one of a: melanocyte, melanin, hemoglobin, porphyrin, keratin, carotene, collagen, elastin, sebum, sebaceous gland activity, pore (sweat and sebaceous), moisture level, elasticity, luminosity, firmness, fine line, wrinkle count and stage, pore size, percent of open pores, skin elasticity, skin tension line, spot, skin color, psoriasis, allergy, red area, general skin disorder or infection, tumor, sunburn, rash, scratch, pimple, acne, insect bite, itch, bleeding, injury, inflammation, photodamage, pigmentation, tone, tattoo, percent burn/burn classification, mole (naevi, nevus), aspect of a skin lesion (structure, color, dimensions/asymmetry), melanoma, dermally observed disorder, cutaneous lesion, cellulite, boil, blistering disease, congenital dermal syndrome, (sub)-cutaneous mycoses, melasma, vascular condition, rosacea, spider vein, texture, skin ulcer, wound healing, post-operative tracking, melanocytic lesion, non-melanocytic lesion, basal cell carcinoma, seborrhoic keratosis, sebum (oiliness), nail- and/or hair-related concern, and the like.

Alternatively, in certain embodiments, there is disclosed a system for obtaining dermal biophysical properties, designed and implemented in accordance with the principles of the invention. In certain such embodiments, the skin disorder management module facilitates acquisition of dermal biophysical properties.

As shown in the FIG. 72, the skin disorder management module 7214 comprises a Fourier transform sub-module 7216, a spectral analyzer sub-module 7218 and a diagnostics sub-module 7220.

In certain embodiments, the Fourier transform sub-module 7216 is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

The DTFT 7216 converts time-domain digital signals into corresponding frequency-domain digital signals.

The DTFT 7216 is coupled to the spectrum analyzer sub-module 7218.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In operation, the illumination subsystem 7102 illuminates the skin. It may be noted here that all ins-and-outs in connection with the illumination subsystem 7102 has been disclosed earlier and thus will not be detailed herein. The sensor subsystem 104 captures the electromagnetic signals reflected, absorbed and re-emitted from the skin. As mentioned earlier, the ADC integrated in the sensor subsystem 7104 converts the analog electromagnetic signals into corresponding digital signals. The skin disorder management module 7214 of the host computing subsystem 7106 facilitates automated diagnosis of seborrheic keratosis based on detection of multiple milia-like cysts or comedo-like openings through image processing. Specifically, the DTFT 7216, of the skin disorder management module 7214, converts time-domain digital signals into corresponding frequency-domain digital signals. The spectrum analyzer sub-module 7218, of the skin disorder management module 7214, performs a spectral analysis of the corresponding frequency-domain digital signals. The diagnostics sub-module 7220, of the skin disorder management module 7214, detects the presence of one or more skin lesions or dermascopic structures, such as milia-like cysts or comedo-like openings through implementation of suitable image processing algorithms.

In certain other embodiments, the host computing subsystem configuration, discussed in conjunction with FIG. 72, implements one or more processes facilitating acquisition of biophysical properties of organ systems, analysis of characteristics of the organ systems and determination of a state of the organ systems. Specifically, the processes comprise one or more sequences of process stages comprising acquisition of dermal biophysical properties of skin, analysis of the skin characteristics and determination of a skin state and potential permutations and combinations thereof.

Specifically, in certain such embodiments, a customized image processing algorithm (not depicted herein), designed and implemented in accordance with the principles of the invention, may be useful for the analysis of skin characteristics, obtaining the biophysical properties of the skin and determining a skin state. The skin state may capture a combination of underlying skin structure with time-based variance. Some variation may be predictable but some may be based on a transient condition like infection, sunburn, hormonal imbalance, and the like. The algorithm may be able to measure aspects such as the structure, form, concentration, number, size, state, stage, and the like of melanocytes/melanin, hemoglobin, porphyrin, keratin, carotene, collagen, elastin, sebum, sebaceous gland activity, pores (sweat and sebaceous), wrinkles, moisture, elasticity, luminosity, all forms of the aforementioned, such as derivatives, salts, complexes, and the like. The algorithm may be used to make a quantitative assessment of clinical, medical, non-medical, and cosmetic indications, such as moisture level, firmness, fine lines, wrinkle count and stage, pore size, percent of open pores, skin elasticity, skin tension lines, spots, skin color, psoriasis, allergies, red areas, general skin disorders and infections, or other skin related concerns for the user such as tumors, sunburns, rashes, scratches, pimples, acne, insect bites, itches, bleeding, injury, inflammation, photodamage, pigmentation, tone, tattoos, percent burn/burn classification, moles (naevi, nevus), aspects of skin lesions (structure, color, dimensions/asymmetry), melanoma, dermally observed disorders and cutaneous lesions, cellulite, boils, blistering diseases, management of congenital dermal syndromes, (sub)-cutaneous mycoses, melasma, vascular conditions, rosacea, spider veins, texture, skin ulcers, wound healing, post-operative tracking, melanocytic lesions, non-melanocytic lesions, basal cell carcinoma, seborrhoic keratosis, sebum (oiliness), nail- and/or hair-related concerns, and the like. The algorithm may also be useful for the analysis of and obtaining the physical properties and composition of hair, nails, biological substances, gaseous substances, food, wine, water, liquid, metal, non-metals, plastics, polymers, and the like. Either manually or as determined by an algorithm, a targeted wavelength or wavelengths may be employed for specific endpoint measurements.

Figure 73:
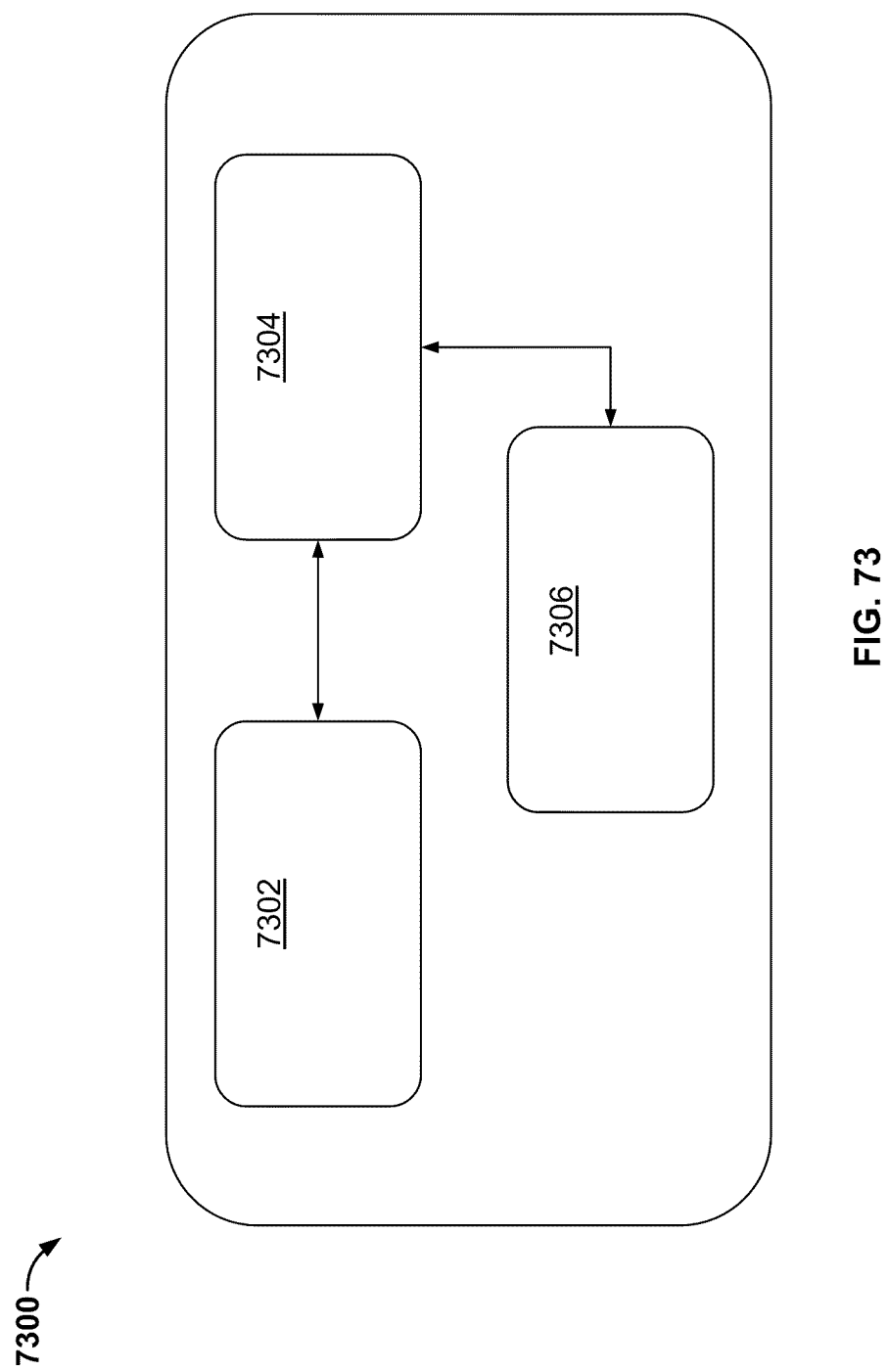
FIG. 73 is a block diagrammatic view of a system facilitating implementation of an Opto-Magnetic process based on light-matter interaction using digital imaging for detection of EPV and CMV viruses in blood plasma samples, designed and implemented in accordance with certain embodiments of the invention.
Figure 74:
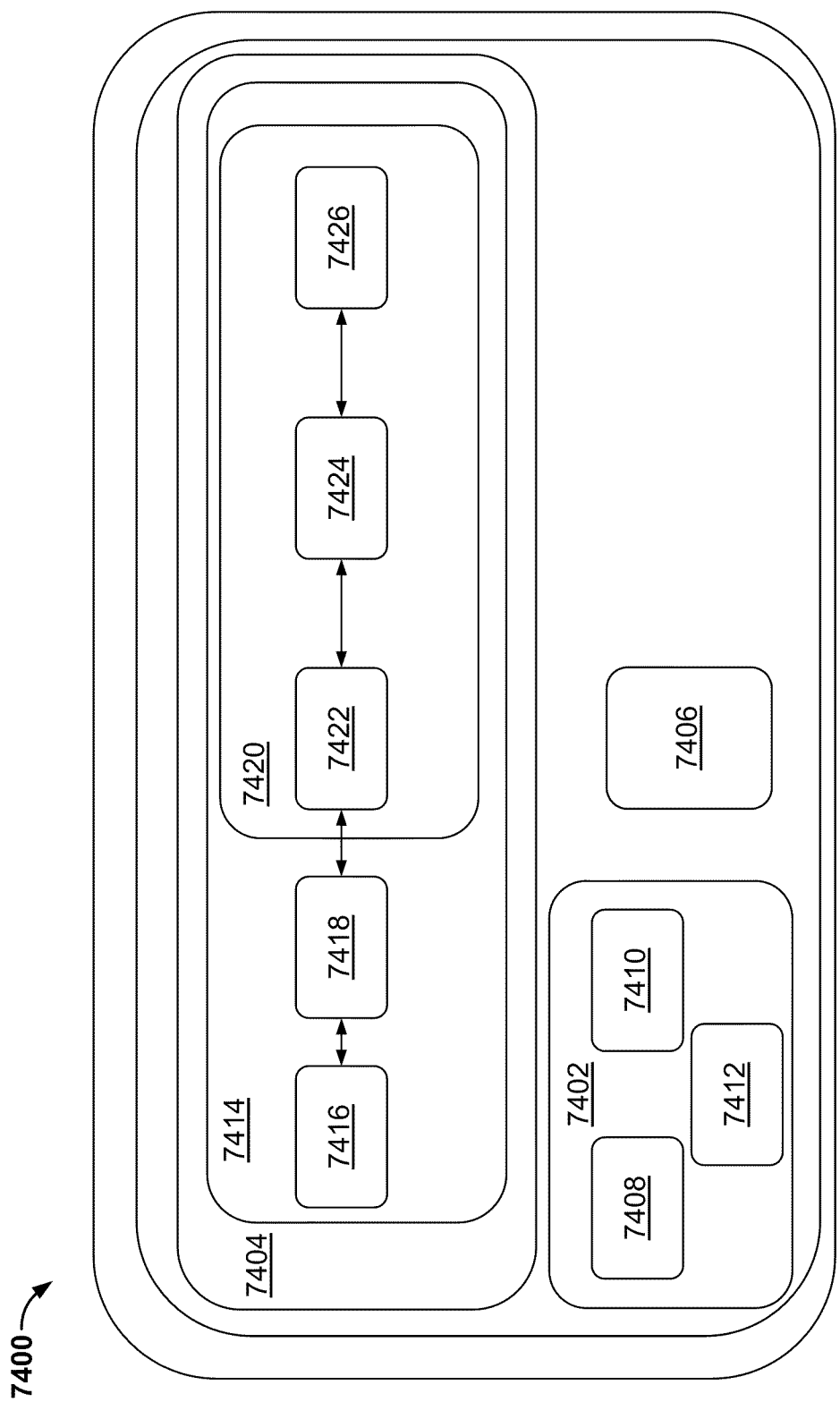
FIG. 74 is an exploded diagrammatic representation of the host computing subsystem, of the FIG. 1, comprising the Opto-Magnetic Fingerprint (or OMF) Generator module designed and implemented in accordance with at least some embodiments of the invention.
Figure 75:
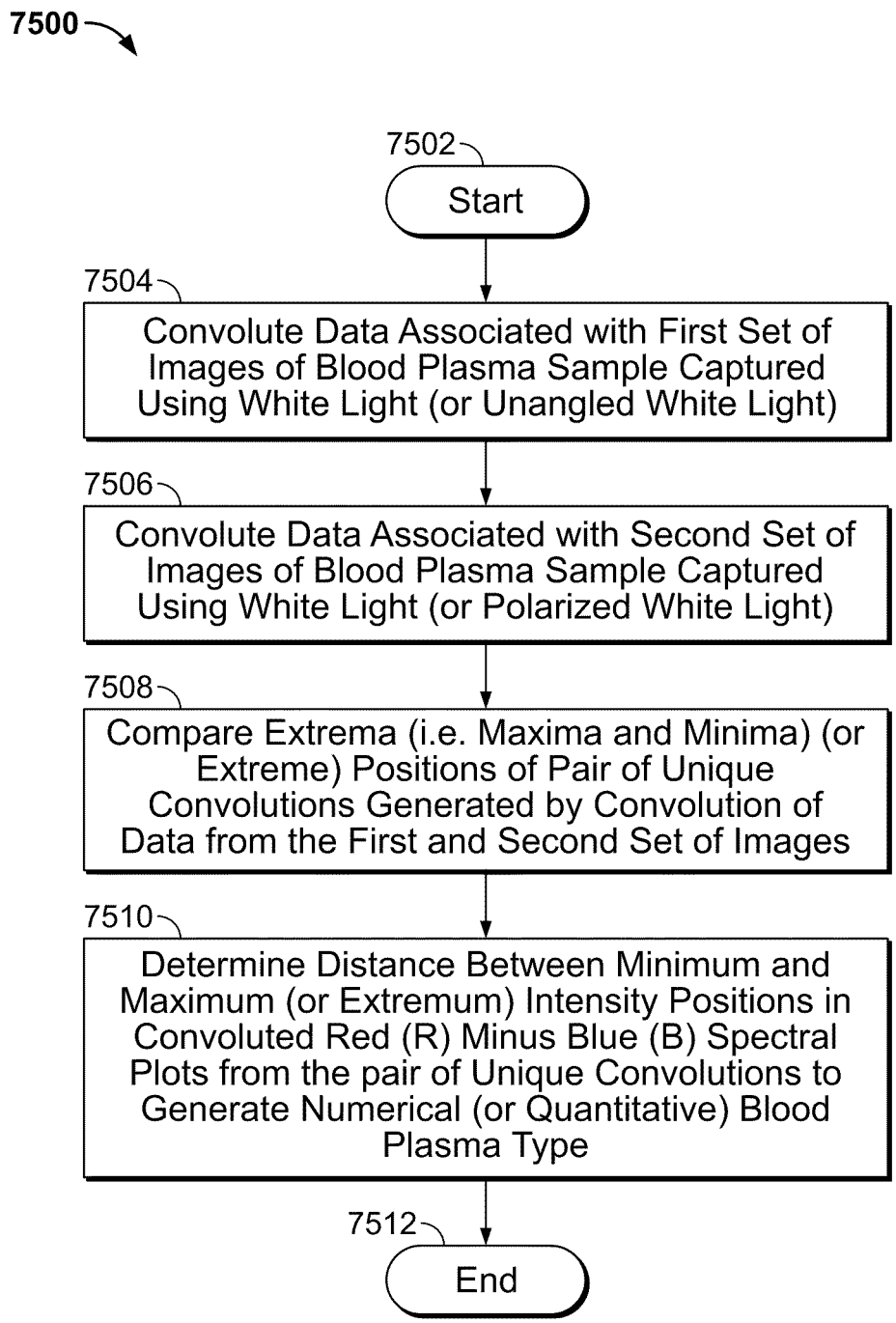
FIG. 75 depicts a flow diagram delineating at least one process implemented by the system configuration of FIGS. 1 and 2 thereby facilitating estimation of blood plasma type and properties (or characteristics) thereof and creation of a unique spectral signature.
Figure 77A:
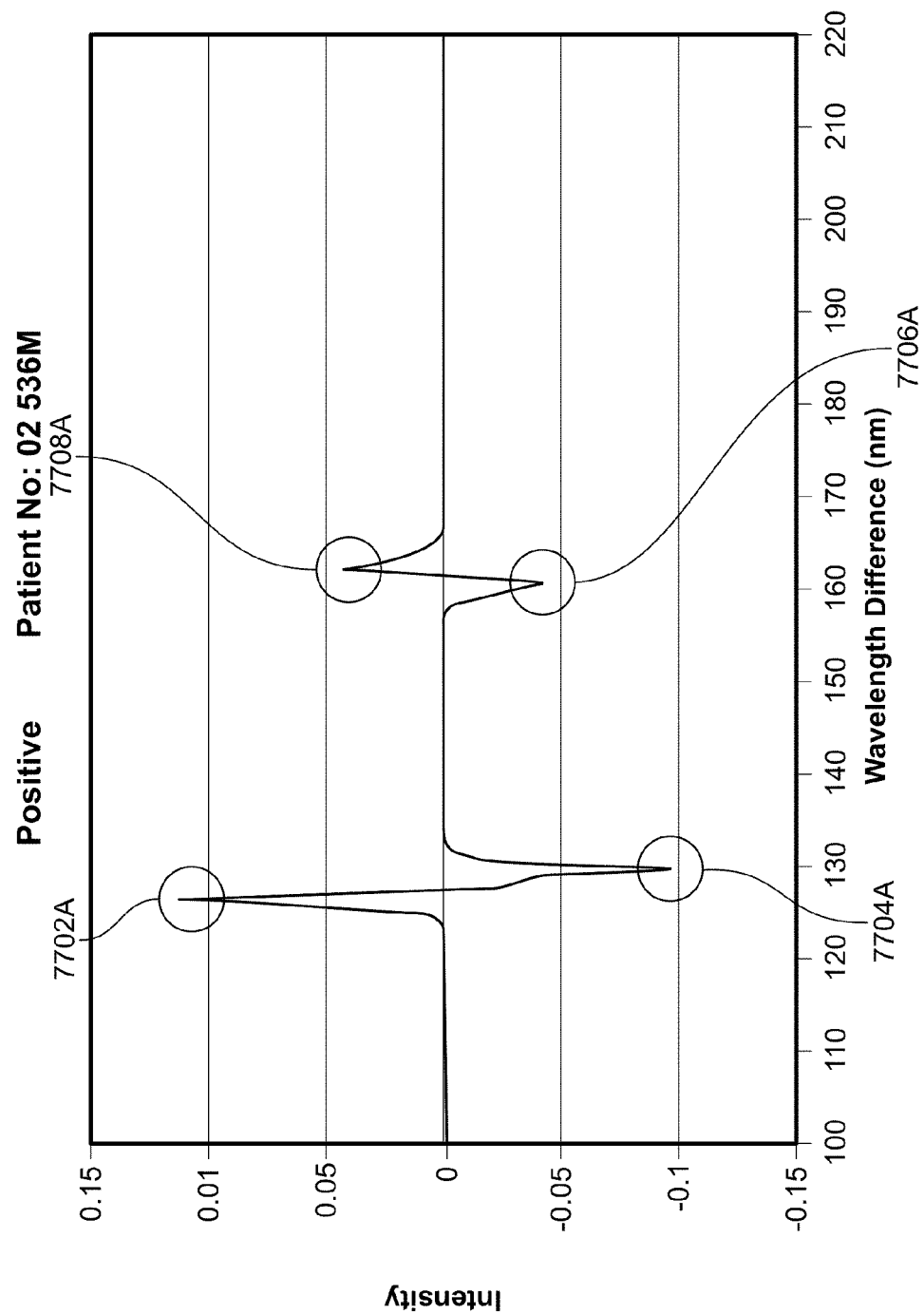
FIGS. 77A and 77B depict a first pair of plots of typical spectral data obtained on implementation of the OMF method for processing digital images of unique samples from a first set of two patients subjected to a first test case for confirmation of EBV, namely "Case I: EBV-IgM", designed and implemented in accordance with certain embodiments of the invention.
Figure 77B:
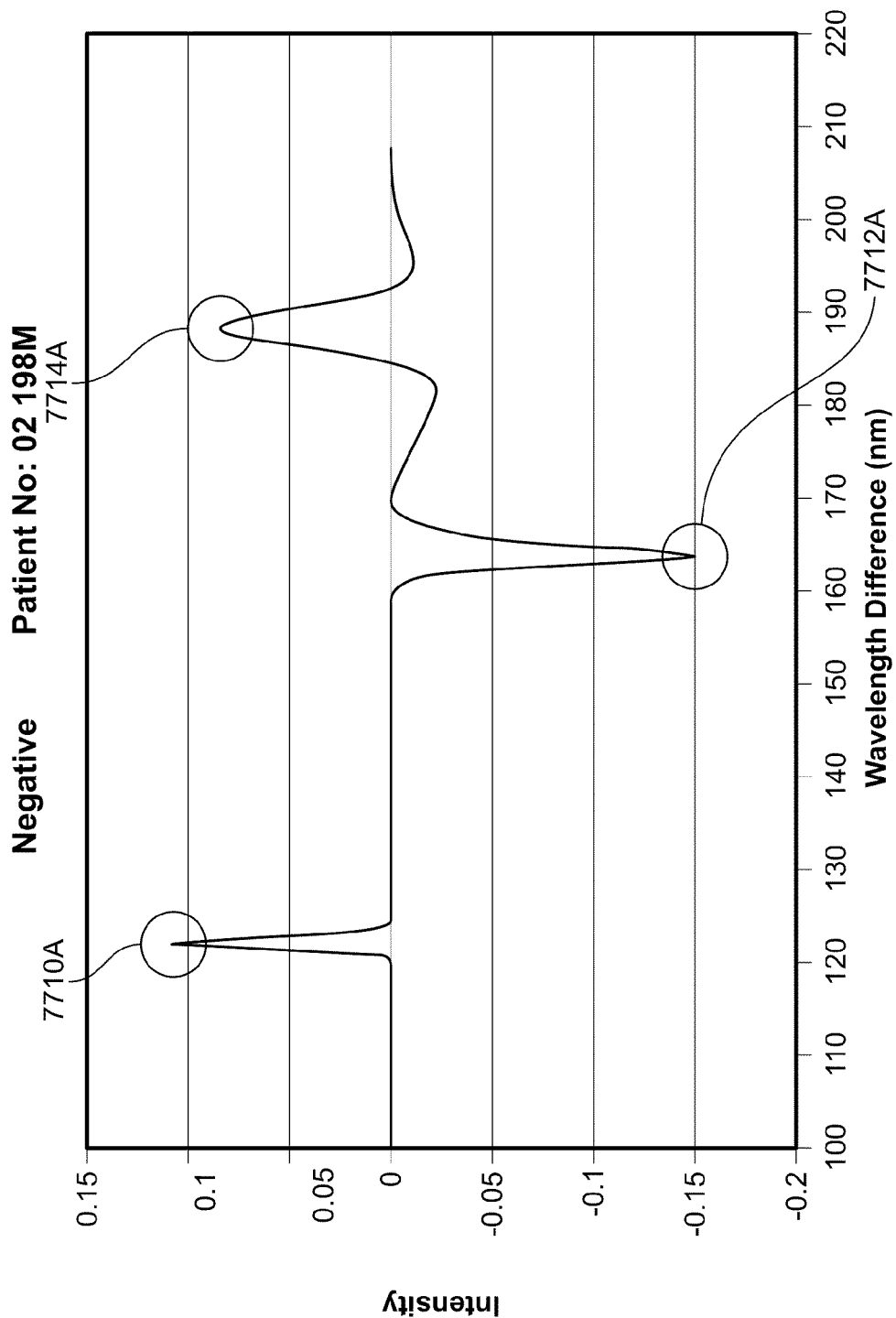
Figure 78A:
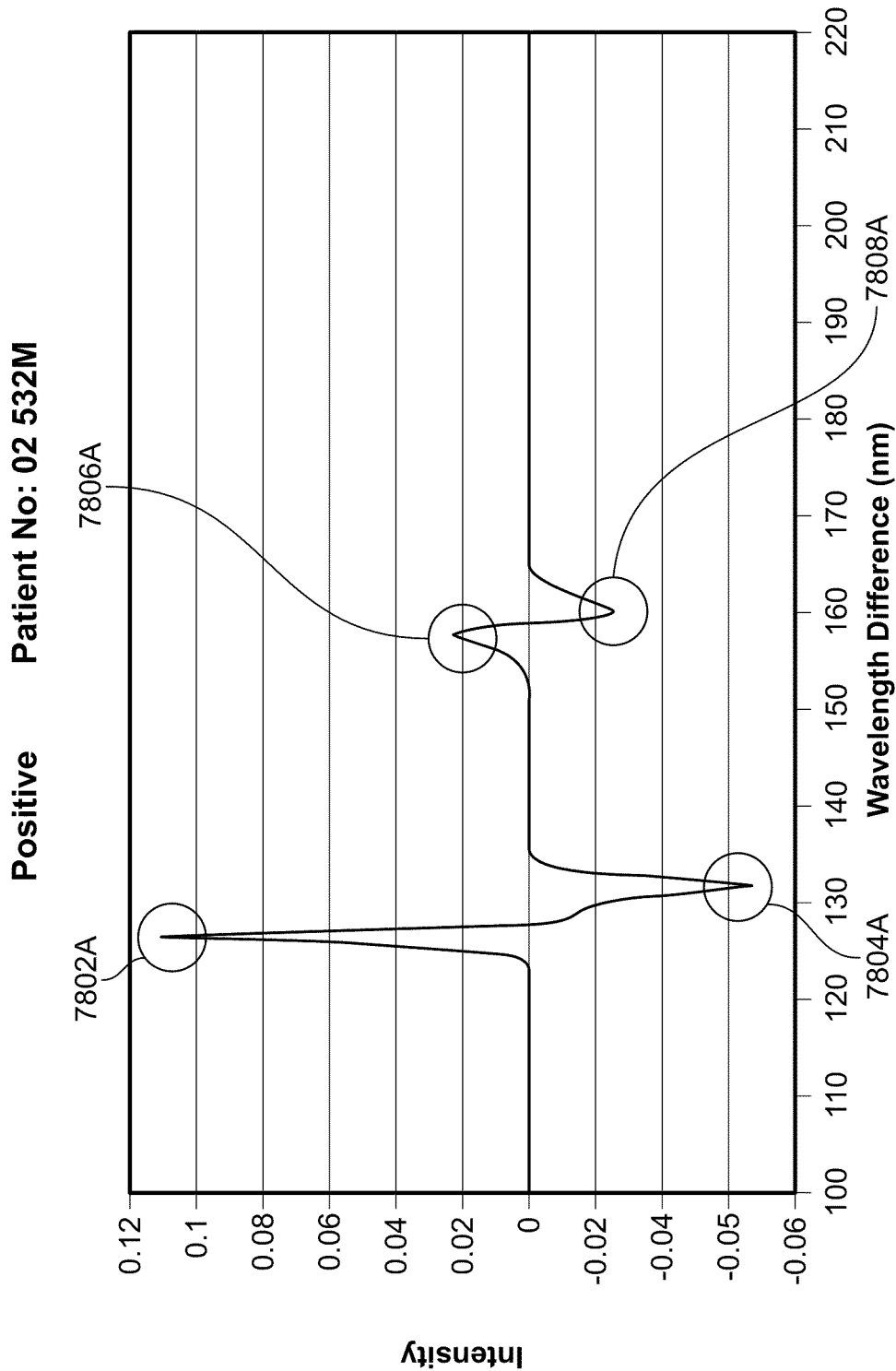
FIGS. 78A and 78B depict a second pair of plots of typical spectral data obtained on implementation of the OMF method for processing digital images of unique samples from a second set of two different patients subjected to a second test case for confirmation of EBV, namely "Case II: EBV-IgM", designed and implemented in accordance with certain embodiments of the invention.
Figure 78B:
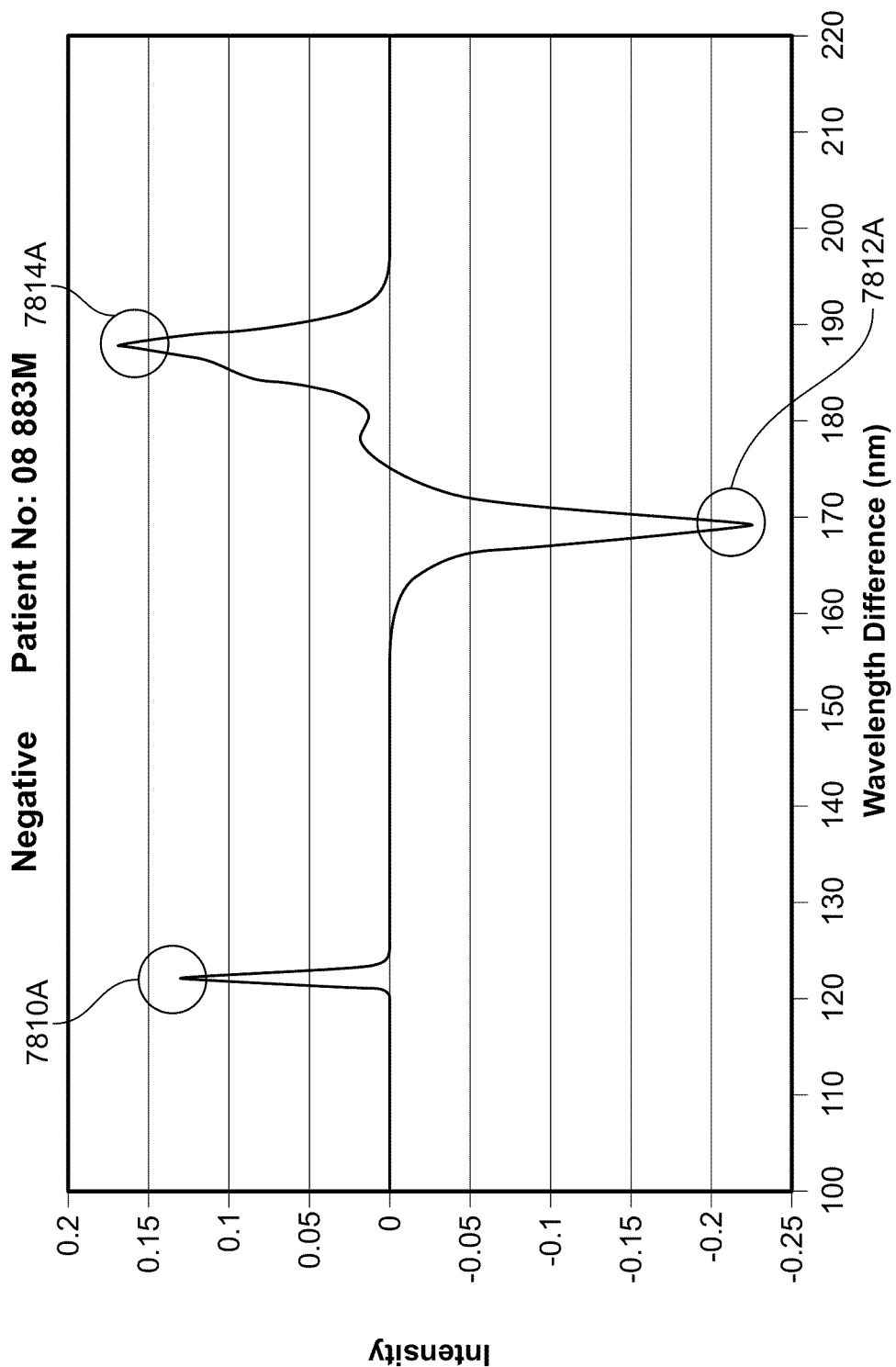
Figure 79B:
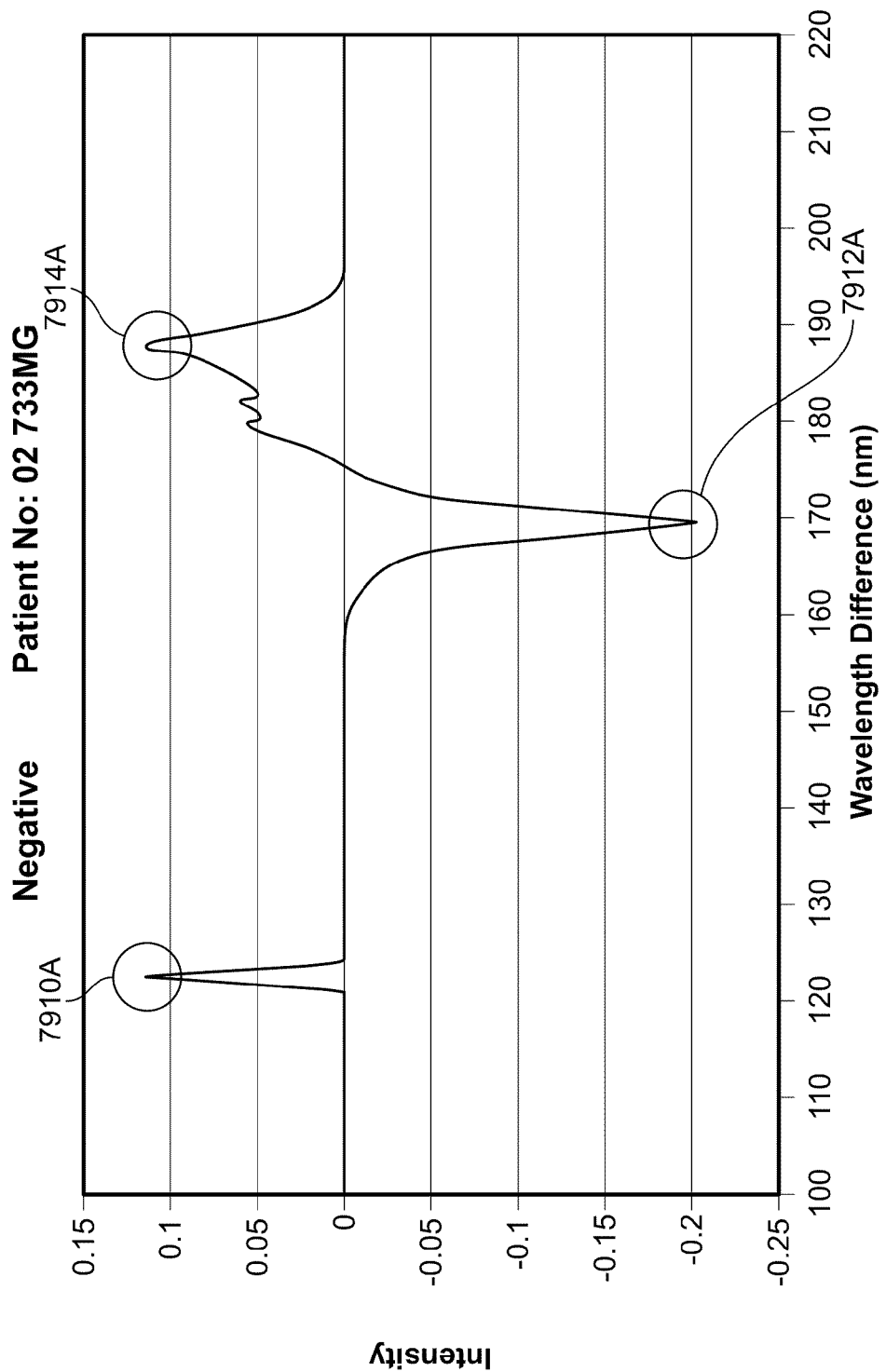
Figure 80A:
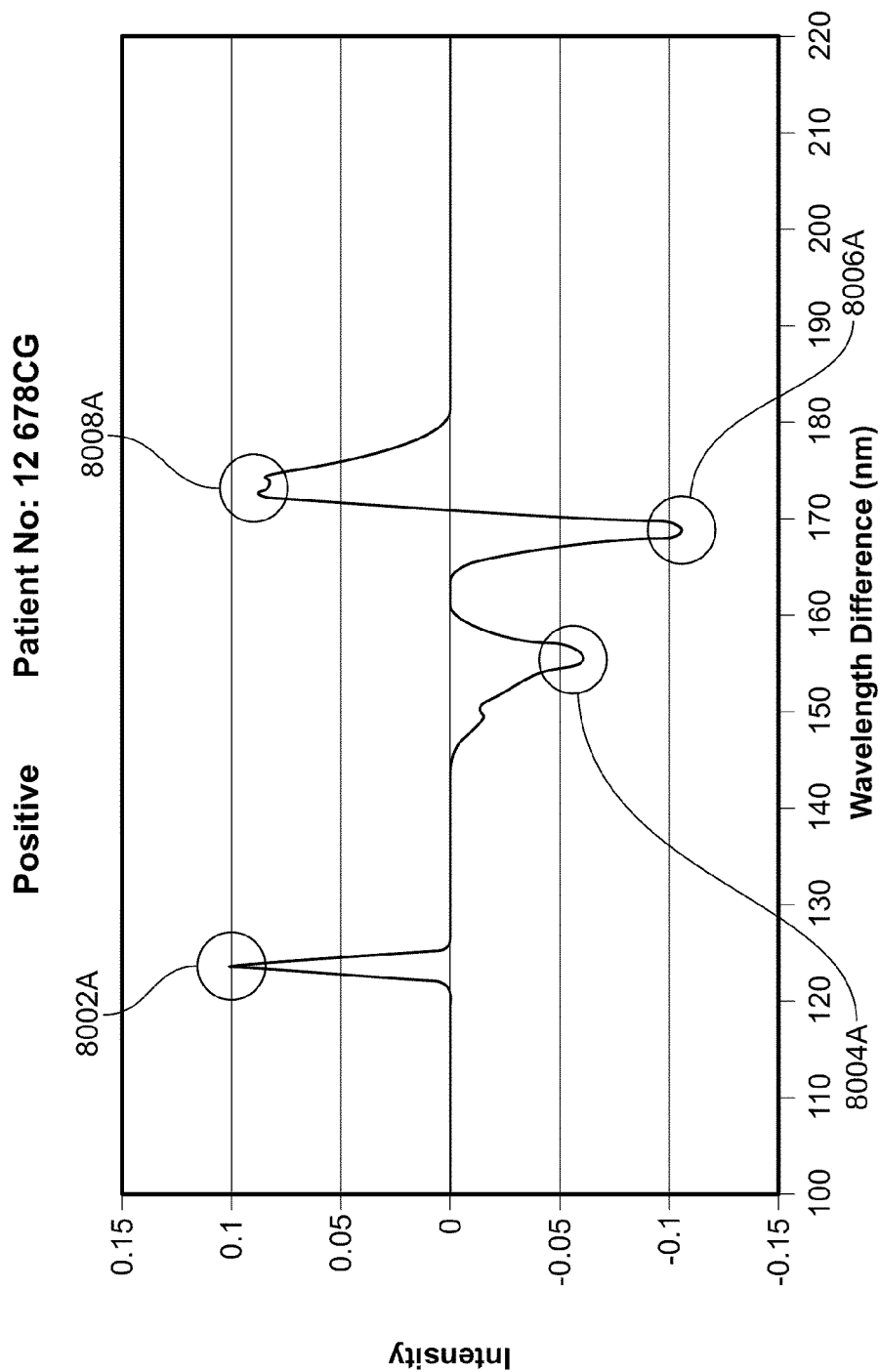
FIGS. 80A and 80B depict a fourth pair of plots of typical spectral data obtained on implementation of the OMF method for processing digital images of unique samples from a fourth set of two different patients subjected to a fourth test case for confirmation of EBV, namely "Case IV: EBV-IgG", designed and implemented in accordance with certain embodiments of the invention.
Figure 80B:
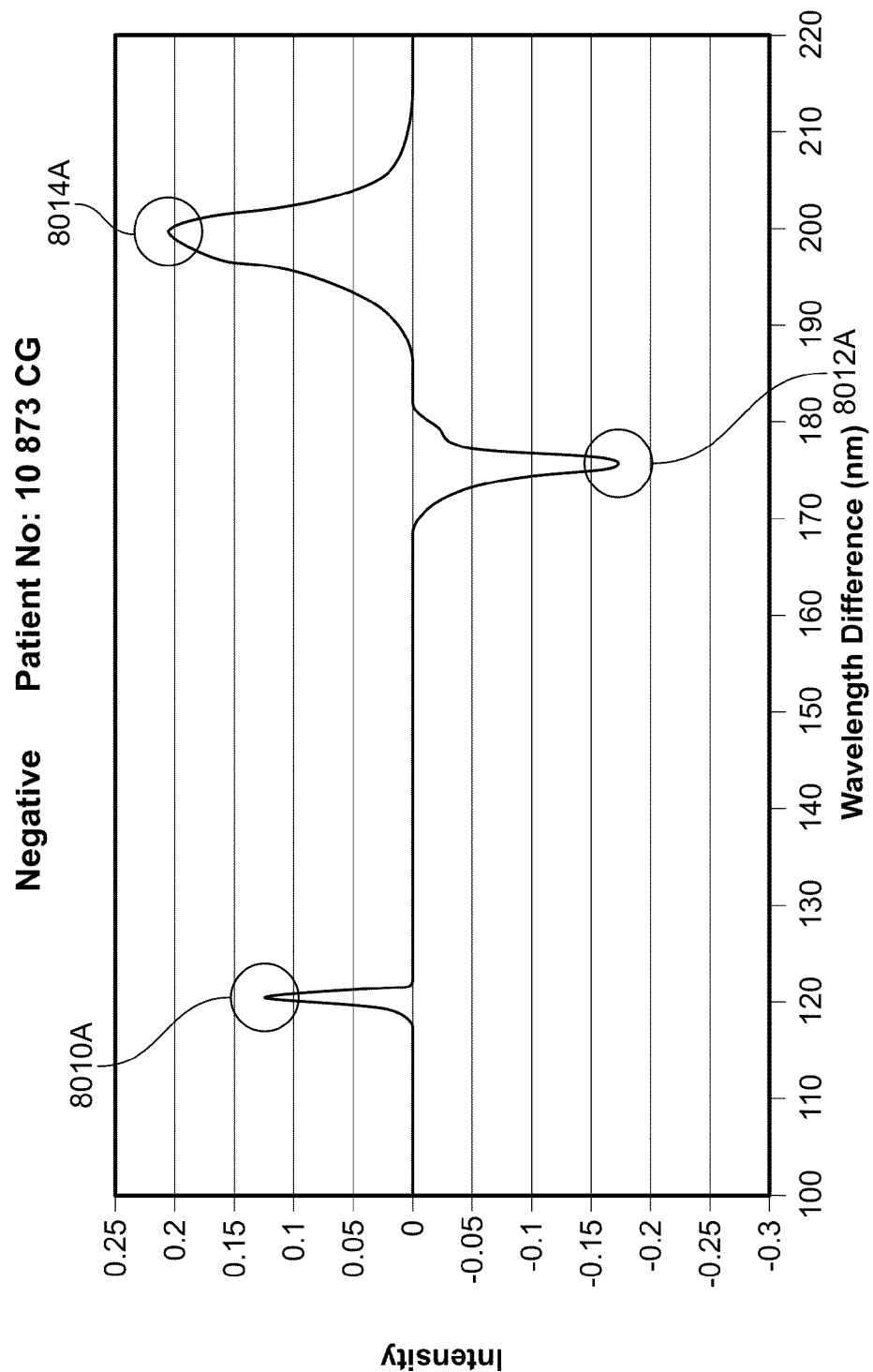

FIG. 73 is a block diagrammatic view of a system facilitating implementation of an Opto-Magnetic process based on light-matter interaction using digital imaging for detection of EPV and CMV viruses in blood plasma samples, designed and implemented in accordance with certain embodiments of the invention;

FIG. 74 is an exploded diagrammatic representation of the host computing subsystem, of the FIG. 1, comprising the Opto-Magnetic Fingerprint (or OMF) Generator module designed and implemented in accordance with at least some embodiments;

FIG. 75 depicts a flow diagram delineating at least one process implemented by the system configuration of FIGS. 1 and 2 thereby facilitating estimation of blood plasma type and properties (or characteristics) thereof and creation of a unique spectral signature;

FIGS. 76A and 76B depict a dual pair of typical digital images of samples, tested positive and negative for EBV and CMV, captured with diffuse white light (W) and reflected polarized light (P), in that order;

FIGS. 77A and 77B depict a first pair of plots of typical spectral data obtained on implementation of the OMF method for processing digital images of unique samples from a first set of two patients subjected to a first test case for confirmation of EBV, namely "Case I: EBV-IgM", designed and implemented in accordance with certain embodiments of the invention;

FIGS. 78A and 78B depict a second pair of plots of typical spectral data obtained on implementation of the OMF method for processing digital images of unique samples from a second set of two different patients subjected to a second test case for confirmation of EBV, namely "Case II: EBV-IgM", designed and implemented in accordance with certain embodiments of the invention;

FIGS. 79A and 79B depict a third pair of plots of typical spectral data obtained on implementation of the OMF method for processing digital images of unique samples from a third set of two different patients subjected to a third test case for confirmation of EBV, namely "Case III: EBV-IgG", designed and implemented in accordance with certain embodiments of the invention; and FIGS. 80A and 80B depict a fourth pair of plots of typical spectral data obtained on implementation of the OMF method for processing digital images of unique samples from a fourth set of two different patients subjected to a fourth test case for confirmation of EBV, namely "Case IV:

EBV-IgG", designed and implemented in accordance with certain embodiments of the invention.

In certain embodiments, methods for detection of DNA viruses based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for detection of Herpesviridae in blood plasma samples based on Opto-Magnetic properties of light-matter interaction. Still more specifically, the systems and apparatuses facilitate implementation of an Opto-Magnetic method with enhanced qualitative and quantitative parameters, such as novel, easily operable, rapid, economical, precise, timely and minute variation sensitive, for detection of EPV and CMV in blood plasma samples based on Opto-Magnetic properties of light-matter interaction.

In certain other situations, the sample set is subjected to diagnosis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul. 17 "SYSTEM, DEVICE AND METHOD FOR DERMAL IMAGING" to J. Bandic, Dj. Koruga, R. Mehendale and S. Marinkovich of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for detection of EPV and CMV in blood plasma samples has been disclosed. Specifically, the OMF process is based on electron properties of matter and its interaction with light. By way of example, and in no way limiting the scope of the invention, the concept of light-matter interaction and Opto-magnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

Typically, valence electrons build a major link network of matter. The orbital velocity of the valence electrons in atoms is on the order of $10^6$ m/s. This gives the ratio between magnetic force ($F_M$) and electrical force ($F_E$) of matter of approximately $10^{-4}$ (or $F_M/F_E \approx 10^{-4}$.) Since, force (F) is directly related to quantum action (or Planck action) through the following equation: $h=F \times d \times t=6.626 \times 10^{-34}$ Js, where F is force, d is displacement and t is time of action. This means that the action of magnetic forces is four orders of magnitude closer to quantum action than the electrical ones. Further, since the quantum state of matter is primarily responsible for conformational changes on the molecular level, this means that detecting differences between tissue states is by far more likely to give greater sensitivity on the level of magnetic forces than it would be on the level of measurement of electrical forces.

The term "conformational change" refers to a transition in shape of a macromolecule. Typically, a macromolecule is flexible or dynamic. Thus, it can change its shape in response to changes in its environment or other factors. Each possible shape is called a conformation. A macromolecular conformational change may be induced by many factors, such as a change in temperature, pH, voltage, ion concentration, or the binding of a ligand.

In certain other embodiments, a comparative analysis of pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

In here, the fact that the angle of reflected polarized light of blood plasma is about 52±0.8 degree is disclosed. Since, reflected polarized light contains electrical component of light-matter interaction. Thus, taking the difference between white light (i.e. electromagnetic) and reflected polarized light (i.e. electrical) yields magnetic properties of matter based on light-matter interaction.

FIG. 73 is a block diagrammatic view of a system facilitating implementation of an Opto-Magnetic process based on light-matter interaction using digital imaging for detection of EPV and CMV viruses in blood plasma samples, designed and implemented in accordance with certain embodiments of the invention.

System 7300 is in essence a Virus Detection System (or VDS). The VDS 100 includes an illumination subsystem 7302, an imaging (or sensor) subsystem 7304 and a host computing subsystem 7306.

VDS 7300, by virtue of its design and implementation, facilitates execution of an Opto-Magnetic method based on interaction between electromagnetic radiation and matter, for instance light-matter interaction, using digital imaging for detection of EPV and CMV viruses in blood plasma samples. Specifically, the Opto-Magnetic process employs apparatuses for generation of unique spectral signatures from digitally captured images of blood plasma samples thereby facilitating detection of EPV and CMV viruses in blood plasma samples based on Opto-Magnetic properties of light-blood plasma interaction.

Illumination subsystem 7302 may be one or more electromagnetic radiation sources. In certain specific embodiments, the Illumination subsystem 7302 may be a set of Light Emitting Diodes (LEDs).

Illumination subsystem 7302 may be adapted to emit polarized and unpolarized electromagnetic signals. The polarized electromagnetic signal is angled white light and unpolarized electromagnetic signal is non-angled white light.

As shown in the FIG. 73, in certain embodiments, the illumination subsystem 7302 may be coupled to the sensor subsystem 7304.

As shown in the FIG. 73, the sensor subsystem 7304 may in essence be a device that converts optical images (or optical signals) to electric signals. In certain embodiments, the sensor subsystem 7304 captures continuous digital images of blood plasma samples. Specifically, in such embodiments, the sensor subsystem 7304 captures continuous digital images of the blood plasma samples illuminated with white light both, non-angled and angled. By way of, and by no way of limitation, the sensor subsystem 7304 may be anyone selected from a group consisting of a Complementary Metal-Oxide-Semiconductor (CMOS) image sensor, Charged Coupled Device (CCD) image sensor, and the like.

Again, as shown in FIG. 73, the sensor subsystem 7304 may be coupled to the host computing subsystem 7306.

FIG. 74 is an exploded diagrammatic representation of the host computing subsystem, of the FIG. 73, comprising the Opto-Magnetic Fingerprint (or OMF) Generator module designed and implemented in accordance with at least some embodiments.

The host computing subsystem 7400 may comprise a processing unit 7402, a memory unit 204 and an Input/Output (or I/O) unit 206 respectively.

The host computing subsystem 7400, by virtue of its design and implementation, performs overall management of blood plasma samples.

The processing unit 7402 may comprise an Arithmetic Logic Unit (or ALU) 7408, a Control Unit (or CU) 7410 and a Register Unit (or RU) 7412.

As shown in FIG. 74, the memory unit 7404 comprises a blood plasma virus detection module 7414.

In certain embodiments, the blood plasma virus detection module for detection of EPV and CMV via generation of unique spectral signatures from the digitally captured images of blood plasma samples and methods thereof are disclosed, in accordance with the principles of the invention. Specifically, in such embodiments, the blood plasma virus detection module utilizes the continuously captured digital images of the blood plasma samples illuminated with white light both, non-angled and angled. More specifically, the blood plasma virus detection module takes into consideration the digital images in Red (R), Green (G) and Blue (B) (or RGB) system for purposes of analysis.

Further, as shown in FIG. 74, the blood plasma virus detection module 7414 includes a Fourier transform sub-module 7416, a spectral analyzer sub-module 7418 and an Opto-Magnetic Fingerprint Generator (or OMFG) sub-module 7420, respectively.

In certain embodiments, the Fourier transform sub-module 7416 is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 7416 converts time-domain digital signals into corresponding frequency-domain digital signals.

DTFT 7416 is coupled to the spectrum analyzer sub-module 7418.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of blood plasma samples thereby facilitating detection of EBV and CMV is disclosed. Specifically, the spectrum (or spectral) analyzer sub-module in order to analyze the blood plasma samples takes into consideration digital images of blood plasma in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on a chromaticity diagram called "Maxwell's triangle" and spectral convolution operation, in accordance with a ratio of (R−B) & (W−P). Noticeably, the abbreviated designation implies that Red (R) minus Blue (B) wavelength of White light (W) and reflected Polarized light (P) are used in a spectral convolution algorithm to calculate data for an Opto-Magnetic Fingerprint (OMF) of matter both, organic and inorganic. Consequently, the method and algorithm for creating unique spectral fingerprints are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layers of matter, such as a blood plasma sample surface, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 74, the spectrum analyzer sub-module 7418 may be coupled to the OMFG sub-module 7420.

OMFG sub-module 7420 includes a color histogram generator unit 7422, a spectral plot generator unit 7424 and a convolution unit 7426.

OMFG sub-module 7414, by virtue of its design and implementation, facilitates generation of unique spectral signatures from digitally captured images of blood plasma samples. Specifically, the generated spectral signatures of blood plasma samples facilitate detection of EPV and CMV based on Opto-Magnetic properties of light-blood plasma interaction.

Color histogram generator unit 7422, by virtue of its design, generates a normalized Red (R) and Blue (B) color channel histogram for each of the one or more images of the blood plasma samples.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that is similar to Table 2:

Table 2 exhibits a tabular representation in connection with a 2D Red-Blue chromaticity histogram generated by first normalizing color pixel values by dividing RGB values by R+G+B, then quantizing the normalized R and B coordinates into N bins each, where N=4.

|   |         | R    |        |         |         |
|---|---------|------|--------|---------|---------|
|   |         | 0-63 | 64-127 | 128-191 | 192-255 |
| B | 0-63    | 43   | 78     | 18      | 0       |
|   | 64-127  | 45   | 67     | 33      | 2       |
|   | 128-191 | 127  | 58     | 25      | 8       |
|   | 192-255 | 140  | 47     | 47      | 13      |

As shown in FIG. 74, the color histogram generator unit 7422 may be coupled to the spectral plot generator unit 7424.

Spectral plot generator unit 7424 generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 7426 convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the blood plasma samples.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

In certain other embodiments, the system configuration, discussed in conjunction with FIGS. 73 and 74, implement one or more processes facilitating estimation of blood plasma type and properties (or characteristics) thereof to create a unique spectral signature.

FIG. 75 depicts a flow diagram delineating at least one process implemented by the system configuration of FIGS. 73 and 74 thereby facilitating estimation of blood plasma type and properties (or characteristics) thereof and creation of a unique spectral signature.

The process 7500 starts at stage 7502 and proceeds to stage 7504, wherein the process 7500 comprises the phase of convolution of data associated with a first set of images of a blood plasma sample captured by illuminating the sample with a white light (or unangled white light.) Noticeable here is the fact that the data associated with the first set of images of the blood plasma sample illuminated with the white light (or unangled white light) may comprise one or more combinations of reflected and re-emitted angled and unangled white light.

At stage 7506, the process 7500 comprises the phase of convolution of data associated with a second set of images of the blood plasma sample captured by illuminating the sample with an angled white light. It must be noted here that the data associated with the second set of images of the blood plasma sample illuminated with the angled white light may comprise one or more combinations of reflected and re-emitted angled white light.

At stage 7508, the process 7500 comprises the phase of comparison of extrema (i.e. maxima and minima) (or extreme) positions of at least a pair of unique convolutions generated by convolution of data from the first set of images and second set of images.

At stage 7510, the process 7500 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) blood plasma type. The process 7500 ends at stage 7512.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R–B) (W–P)) versus a second component Red (R) minus Blue (B) of unangled white light (or W) (i.e. (R–B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R–B) (W–P) for the reflected and/or re-emitted polarized light, and a component (R–B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

In certain circumstances, the investigation of viral infection performed over a sample set taken from 40 pregnant women is disclosed. In such circumstances, the sample set is classified by blood test in two groups, namely EBV group (32 cases, M, GM) and CMV group (8 cases M, GM). Further, each group is separated into two categories, namely positive (virus present, 16 EBV and 4 CMV) and negative (virus absent, 16 EBV and 4 CMV) respectively.

Still further, in certain situations the sample set is subjected to diagnosis using standard Enzyme Immunoassay Method (or ELISA).

FIGS. 76A and 76B depict a dual pair of typical digital images of samples, tested positive and negative for EBV and CMV, captured with diffuse white light (W) and reflected polarized light (P), in that order.

As shown in FIG. 76A, a first pair of the dual pair of digital photography images of blood plasma samples of pregnant women captured with diffuse white light and reflected polarized tested positive for presence of EBV. For purposes of expediency and clarity, both the positively tested blood plasma samples have been referred to as "POSITIVE 00 30MG".

In contrast, a second pair of the dual pair of digital photography images of blood plasma samples of pregnant women captured with diffuse white light and reflected polarized tested negative for presence of EBV are shown in FIG. 76B. For purposes of expediency and clarity, both the negatively tested blood plasma samples have been referred to as "NEGATIVE 02 733MG".

Observation of images in FIGS. 76A and 76B by naked eye would probably testify that there are no differences between them. However, using Computer Assisted Analysis (CAA) based on pixel by pixel count and Spectral Convolution Algorithm (SCA), significant differences are found, the final result of which is illustrated in conjunction with FIGS. 77A-B, 78A-B, 79A-B and 80A-B, respectively.

In certain embodiments, a limited number of typical cases of EBV are selected and presented for purposes of illustration. Specifically, four typical cases of EBV, namely two IgM and two IgG, to illustrate the difference between positive and negative of same cases (i.e. IgM or IgG) and similarity of spectral data.

The term "IgG or Immunoglobulin G" refers to a monomeric immunoglobulin built of two heavy chains γ and two light chains. Each IgG has two antigen binding sites. It is the most abundant immunoglobulin and is approximately equally distributed in blood and in tissue liquids, constituting 75% of serum immunoglobulins in humans. IgG molecules are synthesized and secreted by plasma B cells.

The term "Immunoglobulin M or IgM" refers to a basic antibody that is present on B cells. It is the primary antibody against A and B antigens on red blood cells. IgM is by far the physically largest antibody in the human circulatory system. It is the first antibody to appear in response to initial exposure to antigen.

In certain specific embodiments, CAA based on pixel by pixel count and SCA is implemented taking into consideration only four typical cases of EBV, namely two IgM and two IgG, thereby facilitating illustration of difference between positive and negative of same cases (i.e. IgM or IgG) and similarity of spectral data. In such specific embodiments, for purposes of illustration of the spectral data obtained on implementation of the CAA and SCA, a two (or 2 D)-dimensional coordinate system including a horizontal X-axis and a vertical Y-axis is selected. Specifically, the horizontal X-axis represents the wavelength difference in nanometers whereas the vertical Y-axis represents the intensity in suitable units. More specifically, the 2D coordinate system exhibits the comparative analysis of wavelength difference versus intensity for given samples collected from given patients and subjected to tests for presence or absence of EBV, wherein the wavelength difference is the independent variable and the intensity is the dependent variable.

FIGS. 77A and 77B depict a first pair of plots of typical spectral data obtained on implementation of the OMF method for processing digital images of unique samples from a first set of two patients subjected to a first test case for confirmation of EBV, namely "Case I: EBV-IgM", designed and implemented in accordance with certain embodiments of the invention.

As shown in FIGS. 77A-B, the 2D coordinate system is in essence a Difference Versus Intensity plot (or DI plot) obtained on plotting a plurality of DI ordered pairs. Each of the plurality of ordered pairs includes a Wavelength Difference value and a corresponding Intensity value. It must be noted here that the plurality of ordered pairs are obtained on processing the digital images of blood plasma samples, captured using diffuse white light and reflected polarized light, using the OMF method. Specifically, the OMF method implements the SCA and CAA to analyze the processed digital images of the blood plasma samples. Further, the blood plasma samples are collected from two different patients subjected to test for presence or absence of EBV-IgM.

As depicted in FIG. 77A, a first DI plot of the first pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.15 to a maximum of equal to +0.15; test is analysis for confirmation of presence or absence of EBV in blood plasma sample; patient information is a first patient of the first set is a pregnant woman bearing optional or exemplary patient number is patient no. 02 536M; test input sample is blood plasma of the patient; test case is EBV-IgM; test output is positive; operation is OMF method; number of intensity peaks (or extrema or maxima and minima) is 4; identifiers for the 4 intensity peaks are first 7702A, second 7704A, third 7706A and fourth 7708A respectively; values for Wavelength Difference/Intensity associated with the first 7702A, second 7704A, third 7706A and fourth 7708A intensity peaks are 126.6 nm/0.113, 129.7 nm/–0.095, 160.8 nm/–0.041, 162.1 nm/0.041 in that order.

As depicted in FIG. 77B, a second DI plot of the first pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to –0.2 to a maximum of equal to +0.15; test is analysis for confirmation of presence or absence of EBV in blood plasma sample; patient information is a second patient of the first set is a pregnant woman bearing optional or exemplary patient number is patient no. 09 198M; test input sample is blood plasma of the patient; test case is EBV-IgM; test output is negative; number of intensity peaks (or extrema or maxima and minima) is 3; identifiers for the 3 intensity peaks are fifth 7710A, sixth 7712A and seventh 7714A respectively; values for Wavelength Difference/Intensity associated with the fifth, sixth and seventh intensity peaks are 122.0 nm/0.107, 163.4 nm/–0.151, 187.8 nm/0.084 in that order.

FIGS. 78A and 78B depict a second pair of plots of typical spectral data obtained on implementation of the OMF method for processing digital images of unique samples from a second set of two different patients subjected to a second test case for confirmation of EBV, namely "Case II: EBV-IgM", designed and implemented in accordance with certain embodiments of the invention.

As depicted in FIG. 78A, a third DI plot of the second pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to –0.06 to a maximum of equal to +0.12; test is analysis for confirmation of presence or absence of EBV in blood plasma sample; patient information is a first patient of the second set is a pregnant woman bearing optional or exemplary patient number is patient no. 02 532M; test input sample is blood plasma of the patient; test case is EBV-IgM; test output is positive; operation is OMF method; number of intensity peaks (or extrema or maxima and minima) is 4; identifiers for the 4 intensity peaks are first 7802A, second 7804A, third 7806A and fourth 7808A respectively; values for Wavelength Difference/Intensity associated with the first 7802A, second 7804A, third 7806A and fourth 7808A intensity peaks are 126.6 nm/0.110, 132.3 nm/–0.060, 157.8 nm/0.023, 160.2 nm/–0.026 in that order.

As depicted in FIG. 78B, a fourth DI plot of the second pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to –0.25 to a maximum of equal to +0.2; test is analysis for confirmation of presence or absence of EBV in blood plasma sample; patient information is a second patient of the second set is a pregnant woman bearing optional or exemplary patient number is patient no. 08 883M; test input sample is blood plasma of the patient; test case is EBV-IgM; test output is negative; number of intensity peaks (or extrema or maxima and minima) is 3; identifiers for the 3 intensity peaks are fifth 7810A, sixth 7812A and seventh 7814A respectively; values for Wavelength Difference/Intensity associated with the fifth 7810A, sixth 7812A and seventh 7814A intensity peaks are 122.2 nm/0.132, 169.3 nm/–0.225, 187.8 nm/0.169 in that order.

FIGS. 79A and 79B depict a third pair of plots of typical spectral data obtained on implementation of the OMF method for processing digital images of unique samples from a third set of two different patients subjected to a third test case for confirmation of EBV, namely "Case III: EBV-IgG", designed and implemented in accordance with certain embodiments of the invention.

As depicted in FIG. 79A, a fifth DI plot of the third pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to –0.15 to a maximum of equal to +0.15; test is analysis for confirmation of presence or absence of EBV in blood plasma sample; patient information is a first patient of the third set is a pregnant woman bearing optional or exemplary patient number is patient no. 00 30MG; test input sample is blood plasma of the patient; test case is EBV-IgG; test output is positive; operation is OMF method; number of intensity peaks (or extrema or maxima and minima) is 4; identifiers for the 4 intensity peaks are first 7902A, second 7904A, third 7906A and fourth 7908A respectively; values for Wavelength Difference/Intensity associated with the first 7902A, second 7904A, third 7906A and fourth 7908A intensity peaks are 121.7 nm/0.120, 151.3 nm/–0.059, 166.3 nm/–0.117, 168.4 nm/0.121 in that order.

As depicted in FIG. 79B, a sixth DI plot of the third pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to –0.25 to a maximum of equal to +0.15; test is analysis for confirmation of presence or absence of EBV in blood plasma sample; patient information is a second patient of the third set is a pregnant woman bearing optional or exemplary patient number is patient no. 02 733MG; test input sample is blood plasma of the patient; test case is EBV-IgG; test output is negative; number of intensity peaks (or extrema or maxima and minima) is 3; identifiers for the 3 intensity peaks are fifth 7910A, sixth 7912A and seventh 7914A respectively; values for Wavelength Difference/Intensity associated with the fifth 7910A, sixth 7912A and seventh 7914A intensity peaks are 122.0 nm/0.115, 169.3 nm/−0.203, 187.8 nm/0.114 in that order.

FIGS. 80A and 80B depict a fourth pair of plots of typical spectral data obtained on implementation of the OMF method for processing digital images of unique samples from a fourth set of two different patients subjected to a fourth test case for confirmation of EBV, namely "Case IV: EBV-IgG", designed and implemented in accordance with certain embodiments of the invention.

As depicted in FIG. 80A, a seventh DI plot of the fourth pair of DI plots possess the following specifications and associated test information thereof: ordered (or DI) pair is (Wavelength Difference Value, Intensity. Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.15 to a maximum of equal to +0.15; test is analysis for confirmation of presence or absence of EBV in blood plasma sample; patient information is a first patient of the fourth set is a pregnant woman bearing optional or exemplary patient number is patient no. 12 678 CG; test input sample is blood plasma of the patient; test case is EBV-IgG; test output is positive; operation is OMF method; number of intensity peaks (or extrema or maxima and minima) is 4; identifiers for the 4 intensity peaks are first 8002A, second 8004A, third 8006A and fourth 8008A respectively; values for Wavelength Difference/Intensity associated with the first 8002A, second 8004A, third 8006A and fourth 8008A intensity peaks are 123.6 nm/0.098, 155.7 nm/−0.061, 168.4 nm/−0.106, 172.2 nm/0.087 in that order.

As depicted in FIG. 80B, a eighth DI plot of the fourth pair of DI plots possess the following specifications and associated test information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.3 to a maximum of equal to +0.25; test is analysis for confirmation of presence or absence of EBV in blood plasma sample; patient information is a second patient of the fourth set is a pregnant woman bearing optional or exemplary patient number is patient no. 10 873 CG; test input sample is blood plasma of the patient; test case is EBV-IgG; test output is negative; number of intensity peaks (or extrema or maxima and minima) is 3; identifiers for the 3 intensity peaks are fifth, sixth and seventh respectively; values for Wavelength Difference/Intensity associated with the fifth, sixth and seventh intensity peaks are 120.5 nm/0.123, 176.1 nm/−0.175, 200.3 nm/0.203 in that order.

Noticeable here is the fact that the 40 samples examined for presence of EBV or CMV the following distinctive features are observed in the FIGS. 77A-B, 78A-B, 79A-B and 80A-B: number of peaks, position of peaks, distribution of peaks (up and down), and individual peak intensity. Regarding all the aforementioned features it is seen that it is possible to group the FIGS. 77A-B, 78A-B, 79A-B and 80A-B based on the antibody type (i.e. IgG/IgM) and the test results (i.e. positive/negative). The intensities as well as wavelength differences for IgM antibodies differ from those for IgG antibodies. All positive samples are approximated by four peaks while negative ones are approximated by only three. As a consequence, this is a promising evidence for using this OMF process as a fast, accurate and economically affordable screening tool. Another feature, visible in the group of negative samples (i.e. around 180 nm), does not exhibit an easily observable shape or peak position therefore is excluded from this analysis.

In addition, spectral data of all 40 cases presented in the FIGS. 77A-B, 78A-B, 79A-B and 80A-B display information regarding the difference between normal (i.e. negative) and virus infected (i.e. positive) blood plasma samples. Owing to the fact that the OMF spectral plots (or DI-OMF) for EBV-GM and CMV-GM appear similar, this algorithm still needs to be refined in order to more clearly distinguish which type of virus infection is present. However, OMF method could be used as an adjunct method in virus detection since it yields good results in quick identification of virus infection presence. It can save time and money when used in parallel with expensive biochemical analysis.

Figure 81:
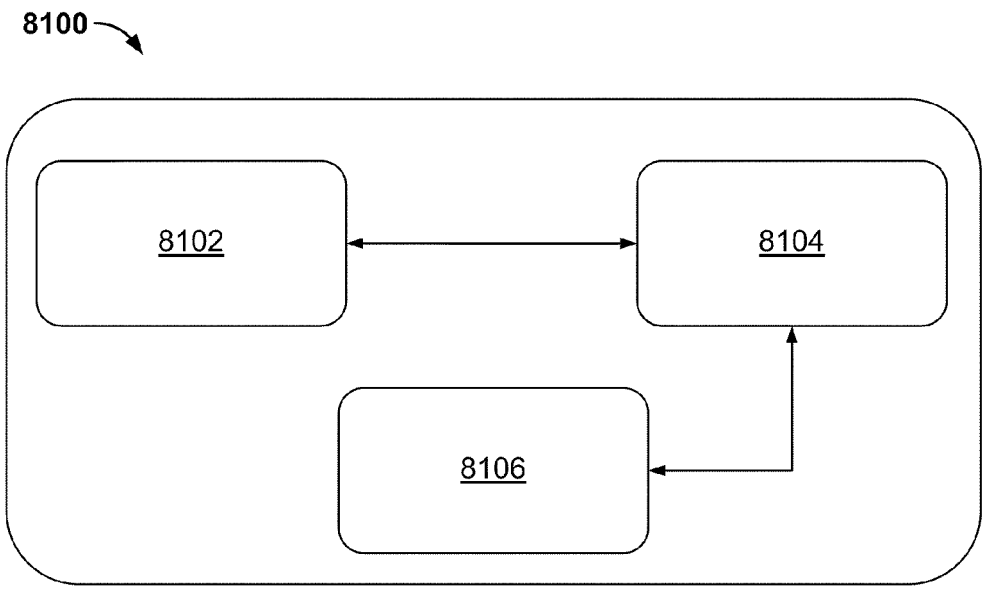
FIG. 81 is a block diagrammatic view of a system facilitating implementation of an Opto-Magnetic process based on light-matter interaction using digital imaging for Papanicolau Test Analysis of samples, designed and implemented in accordance with certain embodiments of the invention.
Figure 81A:
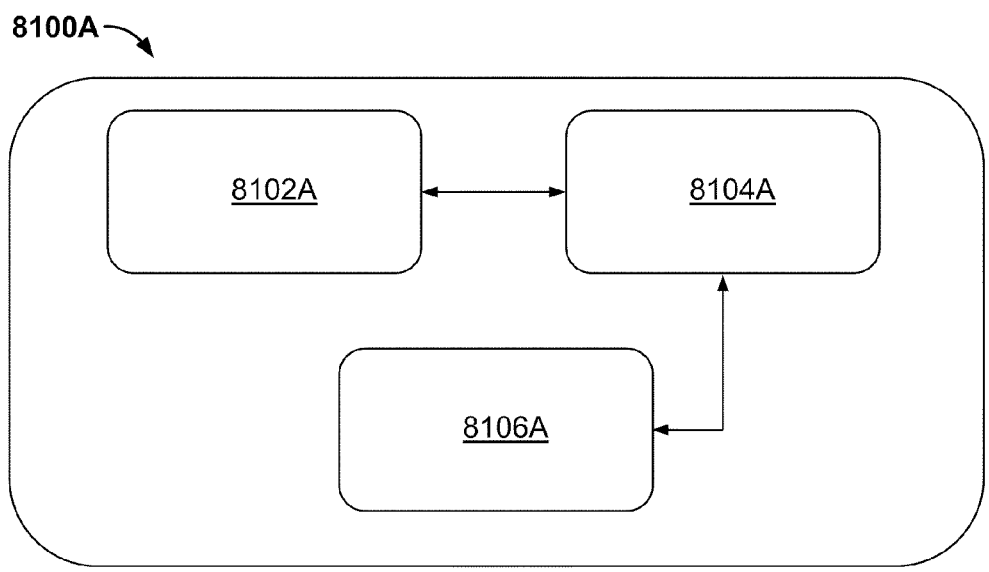

FIG. 81 is a block diagrammatic view of a system facilitating implementation of an Opto-Magnetic process based on light-matter interaction using digital imaging for Papanicolau Test Analysis of samples, designed and implemented in accordance with certain embodiments of the invention.

System 8100 is in essence a Papanicolau Test Analyzer (or PTA). The PTA 8100 includes an illumination subsystem 8102, an imaging (or sensor) subsystem 8104 and a host computing subsystem 8106.

PTA 8100, by virtue of its design and implementation, facilitates execution of an Opto-Magnetic method based on interaction between electromagnetic radiation and matter, for instance light-matter interaction, using digital imaging for analysis of samples subjected to Papanicolau Test. Specifically, the Opto-Magnetic process employs apparatuses for generation of unique spectral signatures from digitally captured images of samples thereby facilitating analysis of the samples subjected to Papanicolau Test based on Opto-Magnetic properties of light-blood plasma interaction.

Illumination subsystem 8102 may be one or more electromagnetic radiation sources. In certain specific embodiments, the Illumination subsystem 8102 may be a set of Light Emitting Diodes (LEDs).

Illumination subsystem 8102 may be adapted to emit polarized and unpolarized electromagnetic signals. The polarized electromagnetic signal is angled white light and unpolarized electromagnetic signal is non-angled white light.

As shown in the FIG. 81, in certain embodiments, the illumination subsystem 8102 may be coupled to the sensor subsystem 8104.

As shown in the FIG. 81, the sensor subsystem 804 may in essence be a device that converts optical images (or optical signals) to electric signals. In certain embodiments, the sensor subsystem 8104 captures continuous digital images of blood plasma samples. Specifically, in such embodiments, the sensor subsystem 8104 captures continuous digital images of the blood plasma samples illuminated with white light both, non-angled and angled. By way of, and by no way of limitation, the sensor subsystem 8104 may be anyone selected from a group consisting of a Complementary Metal-Oxide-Semiconductor (CMOS) image sensor, Charged Coupled Device (CCD) image sensor, and the like.

Again, as shown in FIG. 81, the sensor subsystem 8104 may be coupled to the host computing subsystem 8106.

For example, and in no way limiting the scope of the invention, in certain embodiments the sensor subsystem 8104 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

Figure 82:
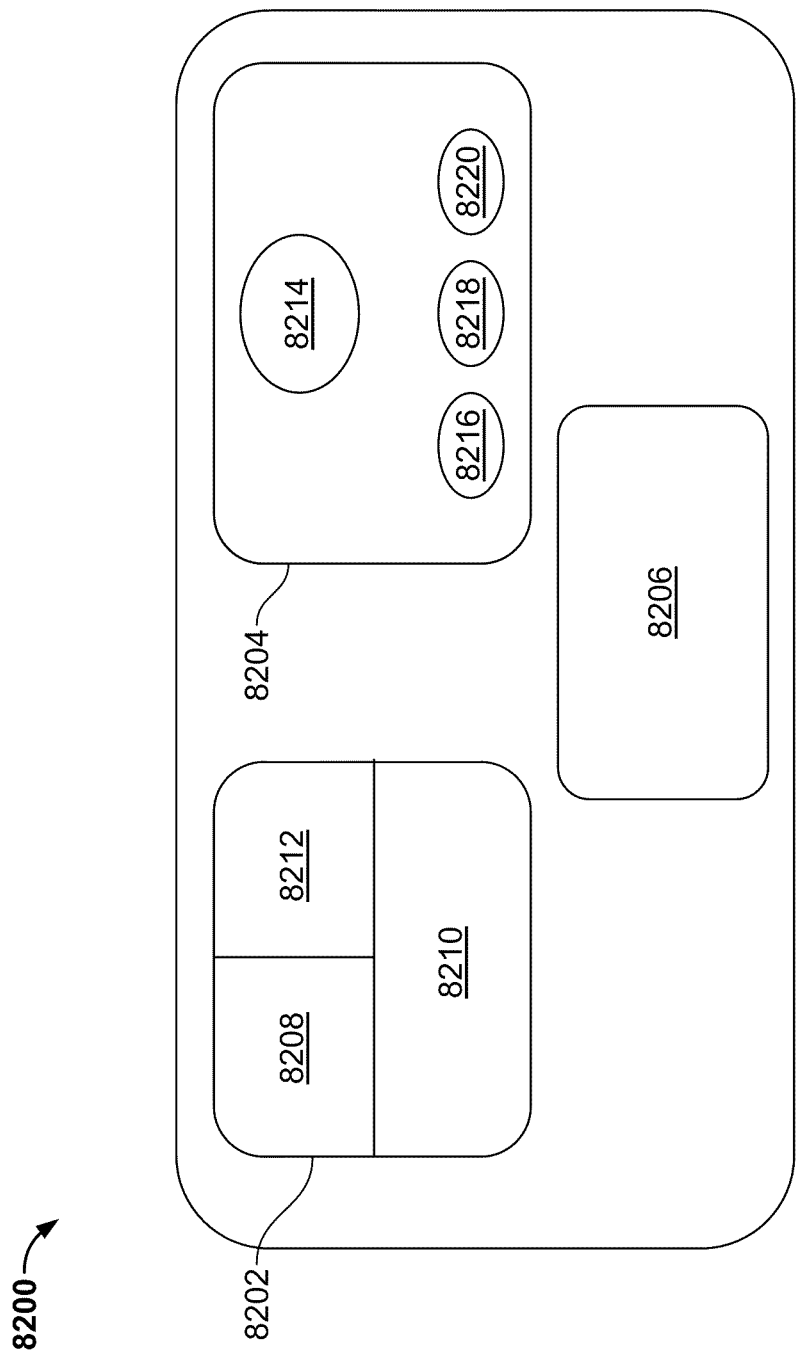
FIG. 82 is an exploded diagrammatic representation of the host computing subsystem, of FIG. 81, comprising the Opto-Magnetic Fingerprint (or OMF) Generator module designed and implemented in accordance with at least some embodiments.

FIG. 82 is an exploded diagrammatic representation of the host computing subsystem, of the FIG. 81, comprising the Opto-Magnetic Fingerprint (or OMF) Generator module designed and implemented in accordance with at least some embodiments.

The host computing subsystem 8200 may comprise a processing unit 8202, a memory unit 8204 and an Input/Output (or I/O) unit 206 respectively.

The host computing subsystem 8200, by virtue of its design and implementation, performs overall management of blood plasma samples.

The processing unit 8202 may comprise an Arithmetic Logic Unit (or ALU) 8208, a Control Unit (or CU) 8210 and a Register Unit (or RU) 8212.

As shown in FIG. 82, the memory unit 8204 comprises a test analysis module 8214.

In certain embodiments, the test analysis module for analysis of samples subjected to Papanicolau Test via generation of unique spectral signatures from the digitally captured images of the samples and methods thereof are disclosed, in accordance with the principles of the invention. Specifically, in such embodiments, the test analysis module utilizes the continuously captured digital images of the samples illuminated with white light both, non-angled and angled. More specifically, the blood plasma virus detection module takes into consideration the digital images in Red (R), Green (G) and Blue (B) (or RGB) system for purposes of analysis.

Further, as shown in FIG. 82, the test analysis module 8214 includes a Fourier transform sub-module 8216, a spectral analyzer sub-module 8218 and an Opto-Magnetic Fingerprint Generator (or OMFG) sub-module 8220, respectively.

In certain embodiments, the Fourier transform sub-module 8216 is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 8216 converts time-domain digital signals into corresponding frequency-domain digital signals.

DTFT 8216 is coupled to the spectrum analyzer sub-module 8218.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of samples thereby facilitating analysis of the samples subjected to Papanicolau Test is disclosed. Specifically, the spectrum (or spectral) analyzer sub-module in order to analyze the samples takes into consideration digital images of the samples in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R−B) & (W−P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as blood plasma sample surface, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 82, the spectrum analyzer sub-module 8218 may be coupled to the OMFG sub-module 8220.

OMFG sub-module 8220 includes a color histogram generator unit 8222, a spectral plot generator unit 8224 and a convolution unit 8226.

OMFG sub-module 8214, by virtue of its design and implementation, facilitates generation of unique spectral signatures from digitally captured images of Pap test samples. Specifically, the generated spectral signatures of Pap test samples facilitate detection of cancer based on Opto-Magnetic properties of light-blood plasma interaction.

Color histogram generator unit 8222, by virtue of its design, generates a normalized Red (R) and Blue (B) color channel histogram for each of the one or more images of the blood plasma samples.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 3 exhibits a tabular representation in connection with a 2D Red-Blue chromaticity histogram generated by first normalizing color pixel values by dividing RGB values by R+G+B, then quantizing the normalized R and B coordinates into N bins each, where N=4.

|   |         | R    |        |         |         |
|---|---------|------|--------|---------|---------|
|   |         | 0-63 | 64-127 | 128-191 | 192-255 |
| B | 0-63    | 43   | 78     | 18      | 0       |
|   | 64-127  | 45   | 67     | 33      | 2       |
|   | 128-191 | 127  | 58     | 25      | 8       |
|   | 192-255 | 140  | 47     | 47      | 13      |

As shown in FIG. 82, the color histogram generator unit 8222 may be coupled to the spectral plot generator unit 8224.

Spectral plot generator unit 224 generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 8226 convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the Pap test samples.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

In certain other embodiments, the system configuration, discussed in conjunction with FIGS. 81 and 82, implement one or more processes facilitating estimation of blood plasma type and properties (or characteristics) thereof to create a unique spectral signature.

Figure 83:
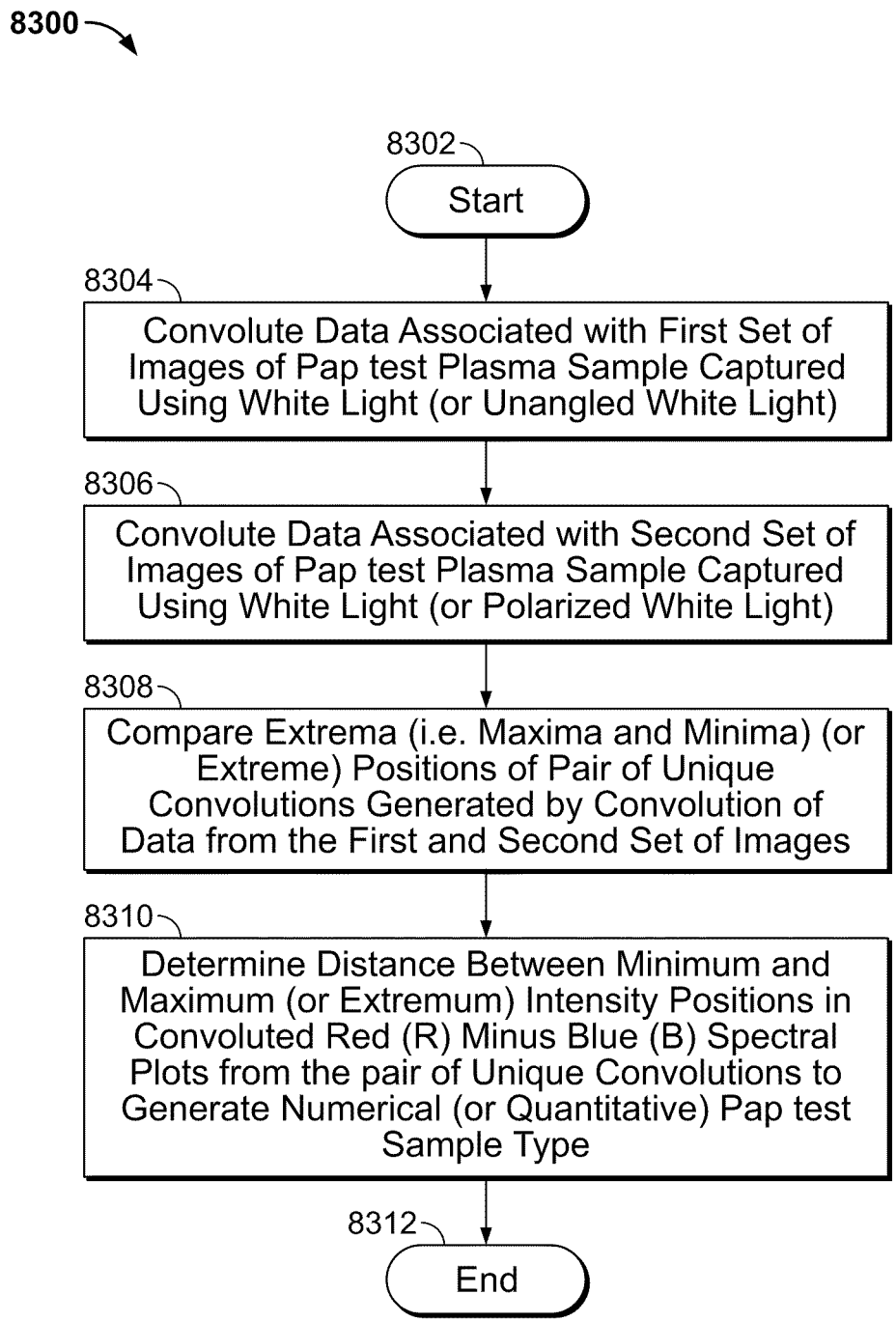
FIG. 83 depicts a flow diagram delineating at least one process implemented by the system configuration of FIGS. 81 and 82 thereby facilitating estimation of Pap test sample type and properties (or characteristics) thereof and creation of a unique spectral signature.

FIG. 83 depicts a flow diagram delineating at least one process implemented by the system configuration of FIGS. 81 and 82 thereby facilitating estimation of Pap test sample type and properties (or characteristics) thereof and creation of a unique spectral signature.

The process 8300 starts at stage 8302 and proceeds to stage 8304, wherein the process 8300 comprises the phase of convolution of data associated with a first set of images of a Pap test sample captured by illuminating the sample with a white light (or unangled white light.) Noticeable here is the fact that the data associated with the first set of images of the Pap test sample illuminated with the white light (or unangled white light) may comprise one or more combinations of reflected and re-emitted angled and unangled white light.

At stage 8306, the process 8300 comprises the phase of convolution of data associated with a second set of images of the Pap test sample captured by illuminating the sample with an angled white light. It must be noted here that the data associated with the second set of images of the Pap test sample illuminated with the angled white light may comprise one or more combinations of reflected and re-emitted angled white light.

At stage 8308, the process 8300 comprises the phase of comparison of extrema (i.e. maxima and minima) (or extreme) positions of at least a pair of unique convolutions generated by convolution of data from the first set of images and second set of images.

At stage 8310, the process 8300 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) Pap test sample type. The process 8300 ends at stage 8312.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W)

minus angled white light (or polarized white light or P) (i.e. (R−B) (W−P)) versus a second component Red (R) minus Blue (B) of unangled white light (or W) (i.e. (R−B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain embodiments, the exploded diagrammatic representation in FIG. 74 of the host computing subsystem, of the FIG. 71, may comprise the Opto-Magnetic Fingerprint (or OMF) Generator sub-module designed and implemented in accordance with at least some embodiments. Thus, all ins-and-outs in connection with the OMFG sub-module 8220 have not been detailed herein.

In certain alternative embodiments, the step of comparing extreme positions of at least two unique convolutions includes comparing a component (R−B) (W−P) for the reflected and/or re-emitted polarized light, and a component (R−B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

In certain circumstances, the investigation of Pap test performed, as adjunct to yearly screening, over a sample set taken from 40 women is disclosed. In such circumstances, the 40 samples are prepared for standard Pap test and examined as double-blind experiment using digital imaging software that analyzes the difference between reflected diffuse white light and reflected polarized light (Opto-Magnetic Fingerprint-OMF) in order to detect normal, dysplastic and cancerous cells. Specifically, the samples were prepared according to standard fixation and staining procedures used for Pap smear tests during regular colposcopic examination. More specifically, the Opto-magnetic images of samples are analyzed using a digital camera customized for capturing OMF pictures (or DI-OMF) and light-mater interaction analysis software (DI-OMF), which guides the diagnostic decision to more refined distinction between normal smear and the one containing either dysplastic or cancerous cells.

The term "double-blind experiment or double-blind trials" refers to an especially stringent way of conducting an experiment, usually on human subjects, in an attempt to eliminate subjective bias on the part of both experimental subjects and the experimenters. In most cases, double-blind experiments are held to achieve a higher standard of scientific rigor. In a double-blind experiment, neither the individuals nor the researchers know who belongs to the control group and the experimental group. Only after all the data have been recorded (and in some cases, analyzed) do the researchers learn which individuals are which. Performing an experiment in double-blind fashion is a way to lessen the influence of the prejudices and unintentional physical cues on the results (the placebo effect, observer bias, and experimenter's bias). Random assignment of the subject to the experimental or control group is a critical part of double-blind research design. The key that identifies the subjects and which group they belonged to is kept by a third party and not given to the researchers until the study is over.

Still, in certain situations, the DI-OMF diagrams are separated into five groups. Subsequent to completion of DI-OMF analysis, randomized samples codes were removed and a comparative analysis of results of DI-OMF vis-à-vis Pap test is performed. Analysis of the results of comparison show that 40 slides were categorized by standard Pap test examination into five groups, namely Group I (or normal tissue state) 7 cases, Group II (or non-typical inflammation) 8 cases, Group III (or dysplasia) 17 cases, Group IV (or carcinoma in situ) 5 cases and Group V (or suspicion to carcinoma) 3 cases.

Table 4 exhibits a tabular representation in connection with the comparative analysis of results of Pap test vis-à-vis DI-OMF and matching results thereof.

|  | CASE | | | | |
| --- | --- | --- | --- | --- | --- |
|  | TOTAL CASES | TRUE POSITIVE | FALSE POSITIVE | TRUE NEGATIVE | FALSE NEGATIVE |
| GROUP I - NORMAL | 7 | 0 | 1 | 6 | 0 |
| GROUP II - NON-TYPICAL INFLAMMATION | 8 | 7 | 0 | 0 | 1 |
| GROUP III - DYSPLASIA | 17 | 16 | 0 | 0 | 1 |
| GROUP IV - CARCINOMA IN SITU | 5 | 5 | 0 | 0 | 0 |
| GROUP V - SUSPICION TO CARCINOMA | 3 | 3 | 0 | 0 | 0 |
| TOTAL | 40 | 31 | 1 | 7 | 2 |

According to data from Table 3, for all 40 cases, sensitivity of DI-OMF method compared to Pap test is 93.9% and specificity is 87.5%.

In certain cases, one or more typical digital images of Pap smear slide samples, categorized as Group I, captured using diffuse white light and reflected polarized light are selected for purposes of observation and analysis.

FIGS. 84A-B, 85A-B and 86A-B depict a triple pair of typical digital images of samples (or Pap smear slides), categorized as Group I (or normal tissue state), captured with diffuse white light (W) and reflected polarized light (P), in that order.

Figure 84A:
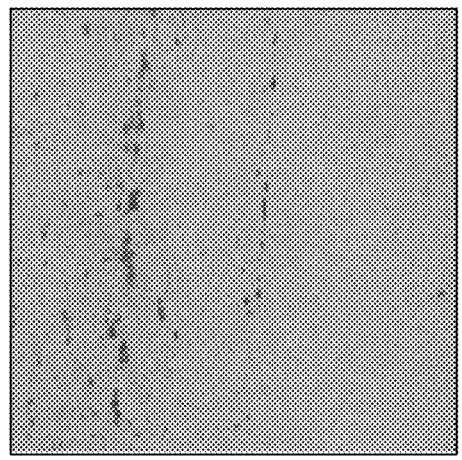
FIGS. 84A-B, 85A-B and 86A-B depict a triple pair of typical digital images of samples (or Pap smear slides), categorized as Group I (or normal tissue state), captured with diffuse white light (W) and reflected polarized light (P), in that order.
Figure 84B:
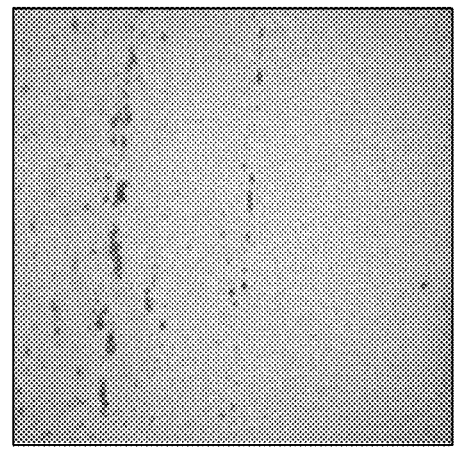

As shown in FIGS. 84A-B, a first pair of the triple pair of digital photography images of a given, selected first sample (or Pap smear slide) categorized as Group I (or normal tissue state), is captured with diffuse white light and reflected polarized light. For purposes of expediency and clarity, the sample categorized as Group I (or normal tissue state) is collected from a first patient herein referred to as Group I Patient 1. For purposes of further convenience, the digital photography images of the sample captured using the diffuse white light and reflected polarized light have been labeled as "LEFT" and "RIGHT", in that order.

Figure 85A:
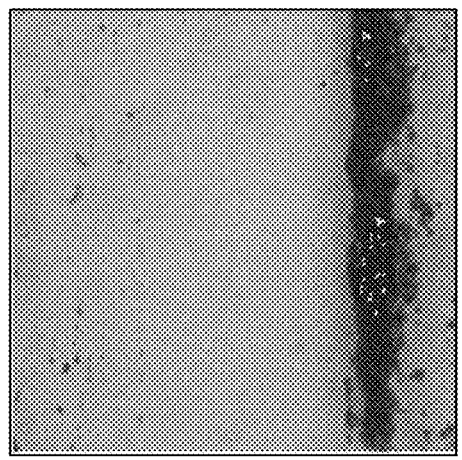
Figure 85B:
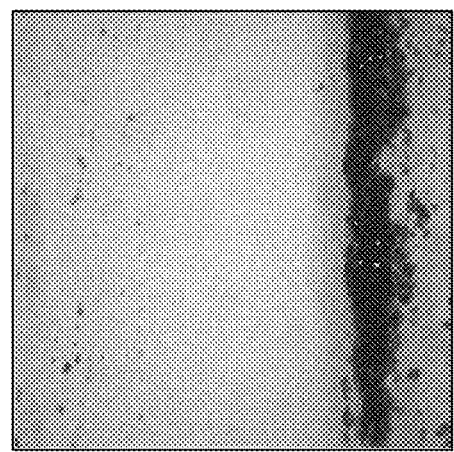

Likewise, as shown in FIGS. 85A-B, a second pair of the triple pair of digital photography images of a given, selected second sample (or Pap smear slide) categorized as group I (or normal tissue state), is captured with diffuse white light and reflected polarized light. For purposes of expediency and clarity, the sample categorized as Group I (or normal tissue state) is collected from a second patient herein referred to as Group I Patient 2. For purposes of further convenience, the digital photography images of the sample captured using the diffuse white light and reflected polarized light have been labeled as "LEFT" and "RIGHT", in that order.

Figure 86A:
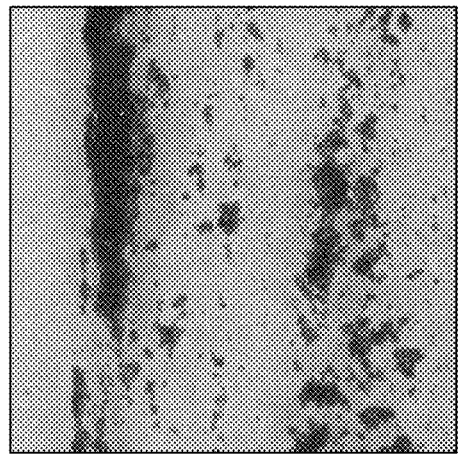
Figure 86B:
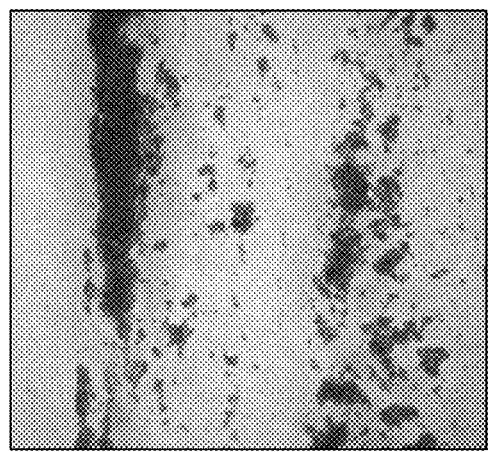

Likewise, as shown in FIGS. 86A-B, a third pair of the triple pair of digital photography images of a given, selected third sample (or Pap smear slide) categorized as group I (or normal tissue state), is captured with diffuse white light and reflected polarized light. For purposes of expediency and clarity, the sample categorized as Group I (or normal tissue state) is collected from a third patient herein referred to as Group I Patient 3. For purposes of further convenience, the digital photography images of the sample captured using the diffuse white light and reflected polarized light have been labeled as "LEFT" and "RIGHT", in that order.

Observation of the triple pair of digital photography images in FIGS. 84A-B, 85A-B and 86A-B by naked eye would probably testify that there are no quantifiable differences between them. However, using Computer Assisted Analysis (CAA) based on pixel by pixel count and Spectral Convolution Algorithm (SCA) significant differences are found the final result of whose is illustrated in conjunction with FIGS. 84C, 85C and 86C respectively.

In certain embodiments, a limited number of typical cases comprising samples (or Pap smear slides) categorized into one or more groups based on states of samples, such as "Group I (or normal tissue state)," "Group II (or non-typical inflammation)," "Group III (or dysplasia)," "Group IV (or carcinoma in situ)," and "Group V (or suspicion to carcinoma)", are selected and presented for purposes of illustration. Specifically, three typical cases of Group I, namely one "Group I Patient 1," one "Group I Patient 2," and one "Group I Patient 3", and one case from each of the Groups II, III, IV and V, namely "Group II Patient 17," "Group III Patient 16," "Group IV Patient 4," and "Group V Patient 7", are selected and presented for purposes of illustration.

In certain specific embodiments, CAA based on pixel by pixel count and SCA is implemented taking into consideration only three typical cases of Group I, namely one "Group I Patient 1," one "Group I Patient 2," and one "Group I Patient 3", and one case from each of the Groups II, III, IV and V, namely "Group II Patient 17," "Group III Patient 16," "Group IV Patient 4," and "Group V Patient 7", thereby facilitating illustration of characteristics of spectral data thereof. In such specific embodiments, for purposes of illustration of the spectral data obtained on implementation of the CAA and SCA, a two (or 2 D)-dimensional coordinate system including a horizontal X-axis and a vertical Y-axis is selected. Specifically, the horizontal X-axis represents the wavelength difference in nanometers whereas the vertical Y-axis represents the intensity in suitable units. More specifically, the 2D coordinate system exhibits the comparative analysis of wavelength difference versus intensity for given samples collected from given patients and subjected to tests for presence or absence of normal, dysplastic and cancerous cells, wherein the wavelength difference is the independent variable and the intensity is the dependent variable.

Figure 84C:
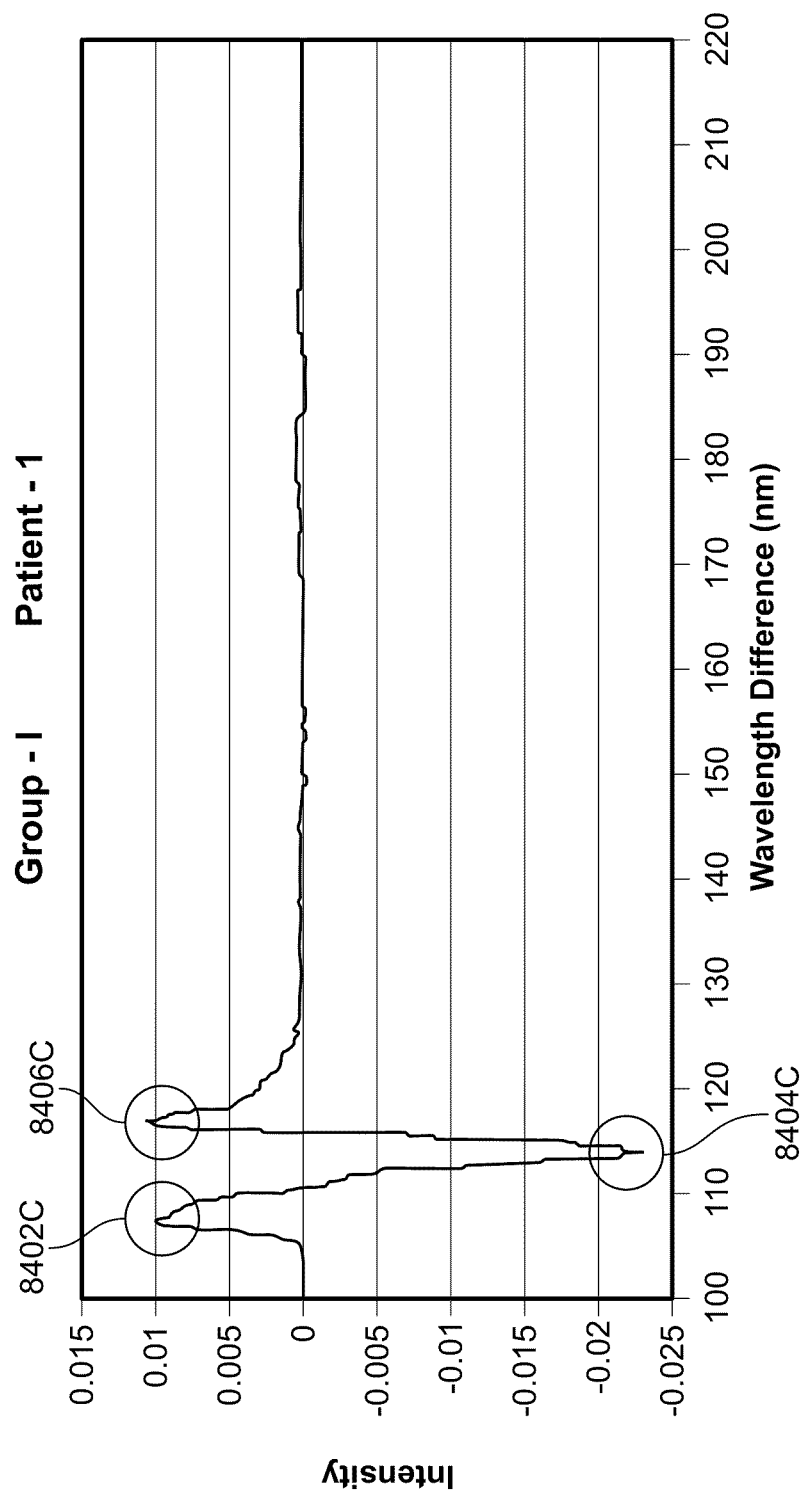
FIG. 84C depicts a plot of typical spectral data (or OMF diagram) obtained on implementation of the OMF method on digital images of FIGS. 84A-B of the given, selected first sample (or Pap smear slide) categorized as Group I (or normal tissue state), in accordance with certain embodiments of the invention.

FIG. 84C depicts a plot of a typical spectral data (or OMF diagram) obtained on implementation of the OMF method on digital images of FIGS. 84A-B of the given, selected first sample (or Pap smear slide) categorized as Group I (or normal tissue state), in accordance with certain embodiments of the invention.

As shown in FIG. 84C, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the first sample, captured using diffuse white light and reflected polarized light, using the OMF method. Specifically, the OMF method implements the SCA and CAA to analyze the processed digital image of the sample. Further, the sample is the given, selected first sample (or Pap smear slide) categorized as Group I (or normal tissue state) of the given, selected first patient subjected to Pap test.

Figure 4B:
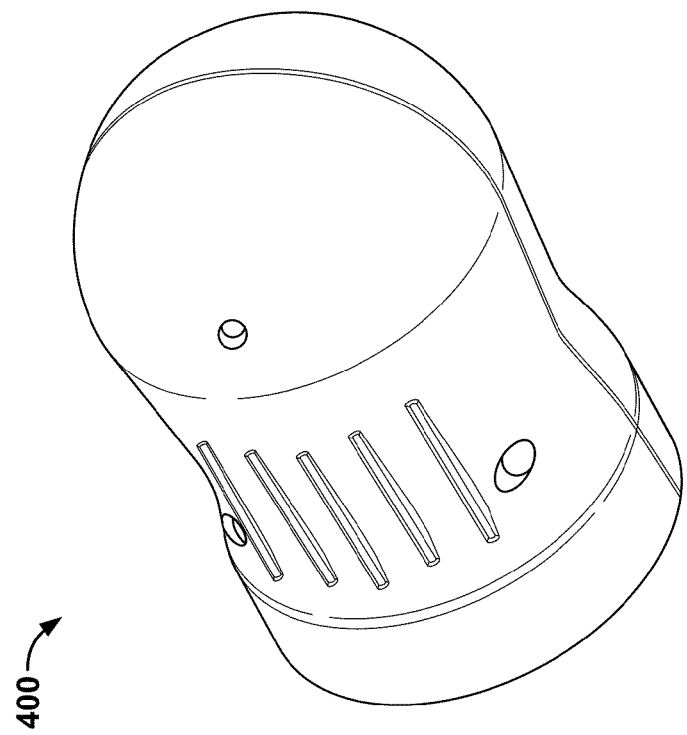
FIGS. 4A & B depict a front and back view of a dermal imaging device.
Figure 4A:
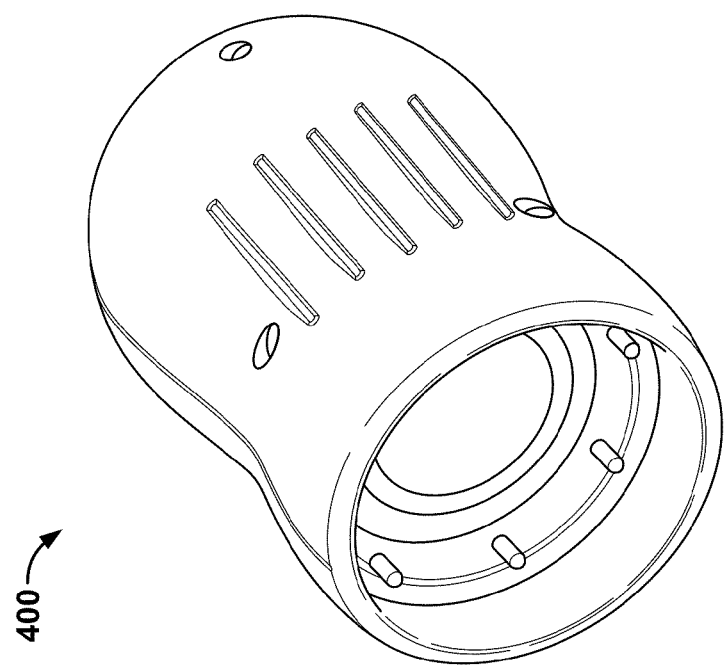

As depicted in FIG. 84C, a first DI plot possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.025 to a maximum of equal to +0.015; analytical information is analysis of the first DI plot (or OMF Diagram) of the sample; patient information is a given, selected first patient of the Group I (or normal tissue state) or Group I Patient 1; test input sample is the Pap smear slide categorized as the Group I (or normal tissue state) of the patient referred to as Group I Patient 1; operation is implementation of OMF method on digital images of FIGS. 4A-B of the given, selected first sample (or Pap smear slide) categorized as Group I (or normal tissue state); number of intensity peaks (or extrema or maxima and minima) is 3; number of peaks with positive intensity values is 2; number of peaks with negative intensity value is 1; identifiers for the 3 intensity peaks are first 8402A, second 8404A and third 8408A respectively; values for Wavelength Difference/Intensity associated with the first 8402A, second 8404A and third 8406A intensity peaks are 105.5 nm/0.095 Intensity (arb units), 113.7 nm/−0.022 arb and 119.2 nm/0.012 arb in that order.

Figure 85C:
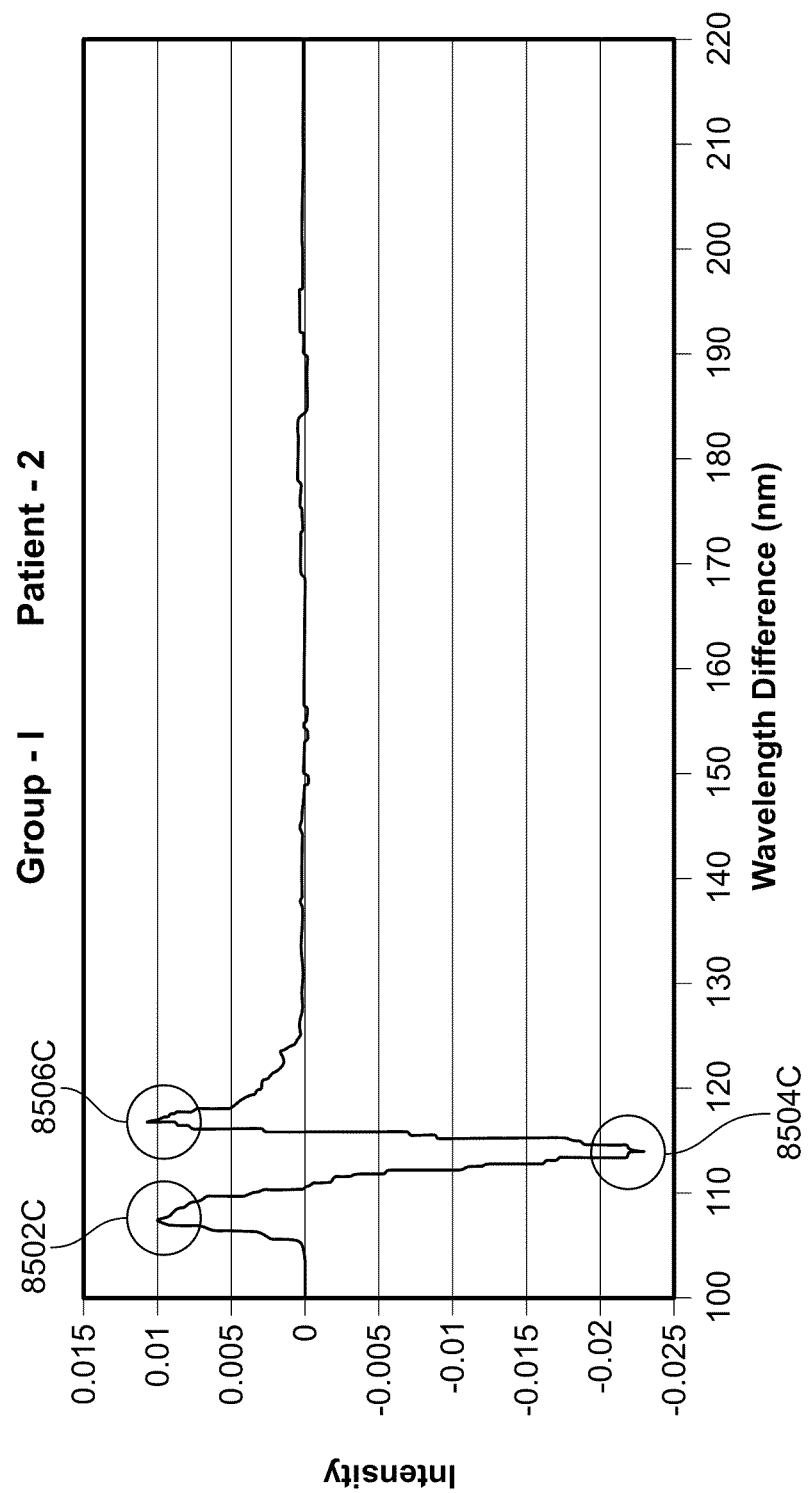
FIG. 85C depicts a plot of typical spectral data (or OMF diagram) obtained on implementation of the OMF method on digital images of FIGS. 85A-B of the given, selected second sample (or Pap smear slide) categorized as Group I (or normal tissue state), in accordance with certain embodiments of the invention.

FIG. 85C depicts a plot of a typical spectral data (or OMF diagram) obtained on implementation of the OMF method on digital images of FIGS. 85A-B of the given, selected second sample (or Pap smear slide) categorized as Group I (or normal tissue state), in accordance with certain embodiments of the invention.

As depicted in FIG. 85C, a second DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.025 to a maximum of equal to +0.015; analytical information is analysis of the second DI plot (or OMF Diagram) of the digital photography image of the sample; patient information is the given, selected second patient of the Group I (or normal tissue state) or Group I Patient 2; test input sample is the Pap smear slide categorized as the Group I (or normal tissue state) of the patient referred to as Group I Patient 2; operation is implementation of OMF method on digital images of FIGS. 85A-B of the given, selected second sample (or Pap smear slide) categorized as Group I (or normal tissue state); number of intensity peaks (or extrema or maxima and minima) is 3; number of intensity peaks (or extrema or maxima and minima) is 3; number of peaks with positive intensity values is 2; number of peaks with negative intensity value is 1; identifiers for the 3 intensity peaks are first 8502A, second 8504A and third 8506A respectively; values for Wavelength Difference/Intensity associated with the first, second and third intensity peaks are 107.5 nm/0.010 arb, 114.2 nm/−0.023 arb and 118.9 nm/0.011 arb in that order.

Figure 86C:
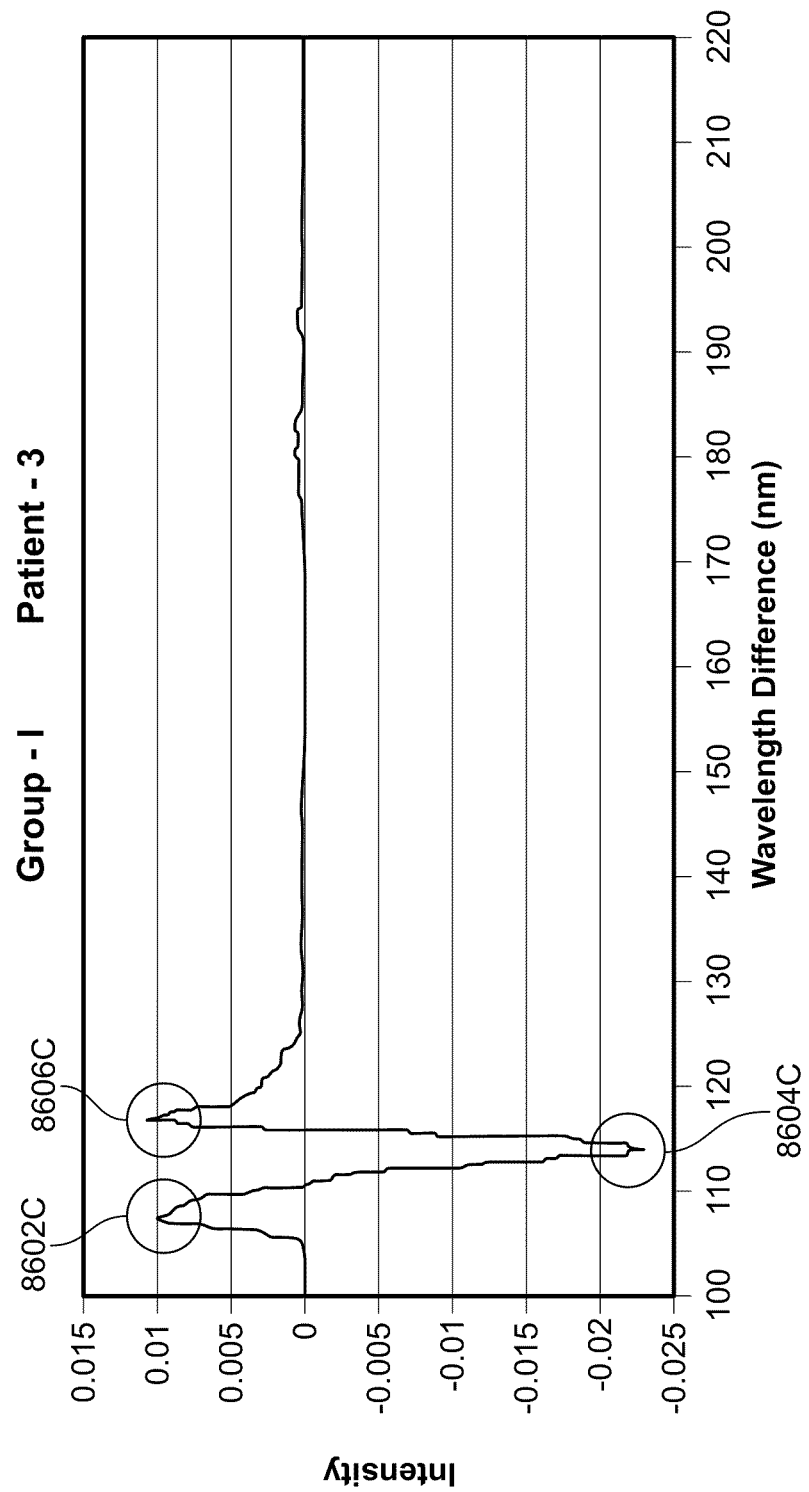
FIG. 86C depicts a plot of typical spectral data (or OMF diagram) obtained on implementation of the OMF method on digital images of FIGS. 86A-B of the given, selected third sample (or Pap smear slide) categorized as Group I (or normal tissue state), in accordance with certain embodiments of the invention.

FIG. 86C depicts a plot of a typical spectral data (or OMF diagram) obtained on implementation of the OMF method on digital images of FIGS. 86A-B of the given, selected third sample (or Pap smear slide) categorized as Group I (or normal tissue state), in accordance with certain embodiments of the invention.

As depicted in FIG. 86C, a third DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.025 to a maximum of equal to +0.015; analytical information is analysis of the third DI plot (or OMF Diagram) of the digital photography image of the sample; patient information is the given, selected third patient of the Group I (or normal tissue state) or Group I Patient 3; test input sample is the Pap smear slide categorized as the Group I (or normal tissue state) of the patient referred to as Group I Patient 3; operation is implementation of OMF method on digital images of FIGS. 86A-B of the given, selected third sample (or Pap smear slide) categorized as Group I (or normal tissue state); number of intensity peaks (or extrema or maxima and minima) is 3; number of intensity peaks (or extrema or maxima and minima) is 3; number of peaks with positive intensity values is 2; number of peaks with negative intensity value is 1; identifiers for the 3 intensity peaks are first 8602A, second 8604A and third 8606A respectively; values for Wavelength Difference/Intensity associated with the first, second and third intensity peaks are 109.0 nm/0.0098 arb, 114.0 nm/−0.024 arb and 117.9 nm/0.0102 arb in that order.

Despite the fact that the digital images in FIGS. 84A-B, 85A-B and 86A-B are different, their OMF diagrams appear almost identical. Apparently, in the FIGS. 84C, 85C and 86C three peaks are seen, wherein a pair of the peaks possesses very similar positive intensity values (i.e. 108 nm and 118 nm) and one with a larger negative intensity value (i.e. 113 nm). These values are valid for spectral convolution field. They are symmetrical and indicate normal tissue state. Reason for this is same Pap group, which is in this case normal.

However, the similarity of OMF diagrams for samples categorized as Group II (non-typical inflammation) is not nearly ubiquitous as for Group I (normal), while for Group III (dysplasia) there are significant differences between samples. Reason for this is because there is different intensity of dysplasia (week, middle, strong). All samples belong to the same group but with diversity from case to case, and peaks varying in intensity and in difference of their position.

In certain other embodiments, one or more typical cases comprising samples (or Pap smear slides) categorized as group II (or non-typical inflammation) are selected and presented for purposes of illustration. Specifically, one typical case including a sample categorized as group II (or non-typical inflammation) is taken into consideration and presented for purposes of illustration.

Figure 87:
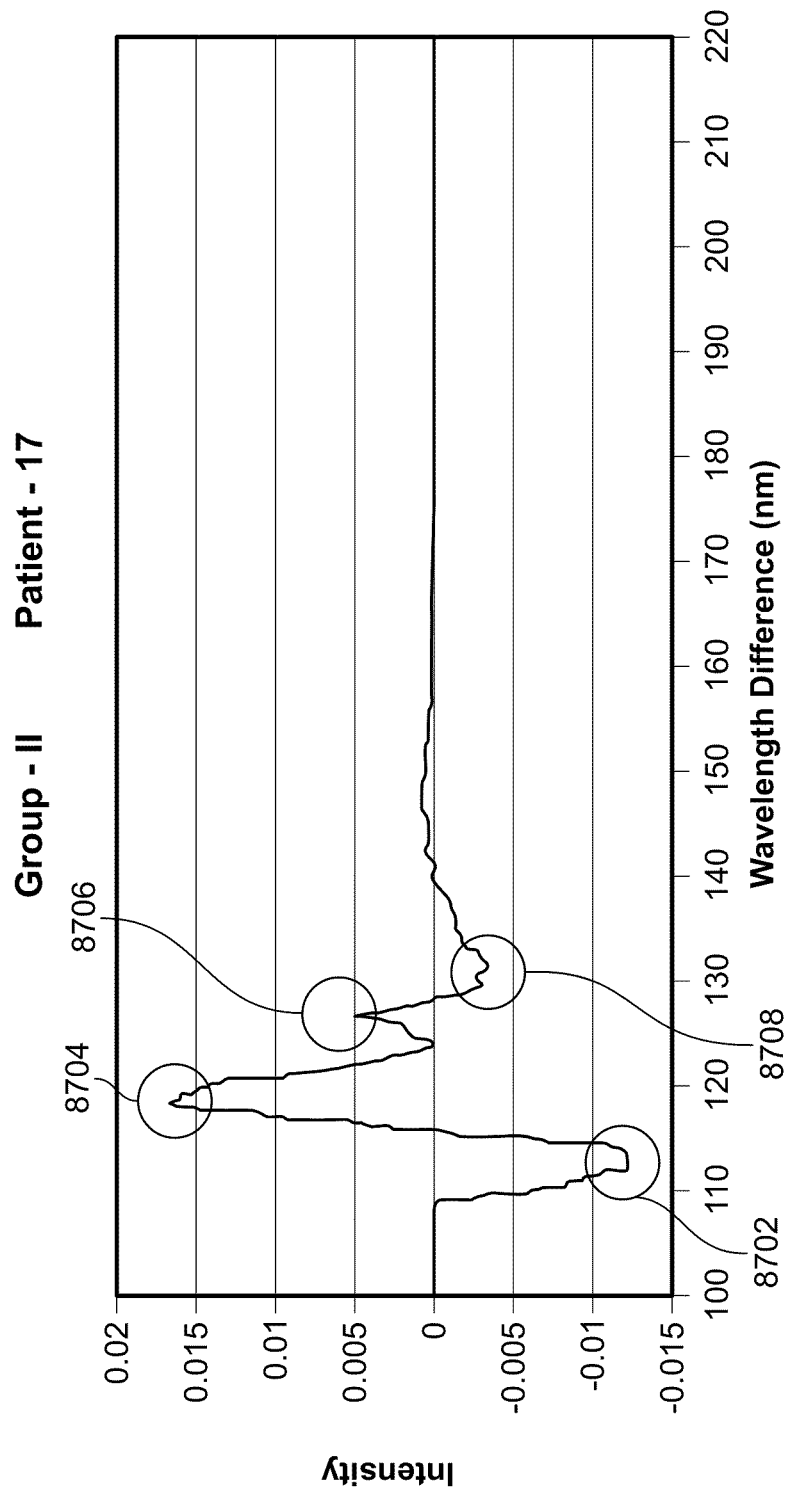
FIG. 87 depicts a plot of typical spectral data (or OMF diagram) obtained on implementation of the OMF method on digital images of a given, selected sample (or Pap smear slide) categorized as Group II (or non-typical inflammation), in accordance with certain embodiments of the invention.

FIG. 87 depicts a plot of a typical spectral data (or OMF diagram) obtained on implementation of the OMF method on digital images of a given, selected sample (or Pap smear slide) categorized as Group II (or non-typical inflammation), in accordance with certain embodiments of the invention.

As depicted in FIG. 87, a fourth DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.015 to a maximum of equal to +0.02; analytical information is analysis of the fourth DI plot (or OMF Diagram) of the digital photography image of the sample; patient information is the given, selected seventeenth patient of the Group II (or non-typical inflammation) or Group II Patient 17; test input sample is the Pap smear slide categorized as the Group II (or non-typical inflammation) of the patient referred to as Group II Patient 17; operation is implementation of OMF method on digital images of the given, selected seventeenth sample (or Pap smear slide) categorized as the Group II (or non-typical inflammation); number of intensity peaks (or extrema or maxima and minima) is 4; number of peaks with positive intensity values is 2; number of peaks with negative intensity value is 2; identifiers for the 4 intensity peaks are first 8702, second 8704, third 8706 and fourth 8708 respectively; values for Wavelength Difference/Intensity associated with the first, second, third and fourth intensity peaks are 112.5 nm/−0.013 arb, 118.9 nm/0.016 arb, 126.8 nm/0.005 arb, 131.4 nm/−0.003 arb in that order.

Investigation of FIG. 87 suggests that the OMF diagram presented therein has a different diagram pattern vis-à-vis the diagrams discussed in conjunction with the FIGS. 84C, 85C and 86C. Noteworthy is the fact that all higher order Pap groups can be described with distinctive diagrams depicting the characteristic intensity to wavelength relationship thereof. Particularly, noteworthy is the fact that these patterns differ in an easily detectable manner. For example, the diagram for Group II shown in FIG. 87 has one peak more than the sample from Group I. More particularly, four peaks belonging to following wavelengths: 112 nm, 120 nm, 128 nm and 132 nm, have intensities and wavelengths whose distribution differs from that of the group I.

The same kind of analysis can be conducted in a straightforward manner for the sample diagram in Group III, shown in FIG. 86. The four peaks for Group III differ from FIG. 85 in intensities and also possess a slight shift in corresponding wavelengths.

Figure 88:
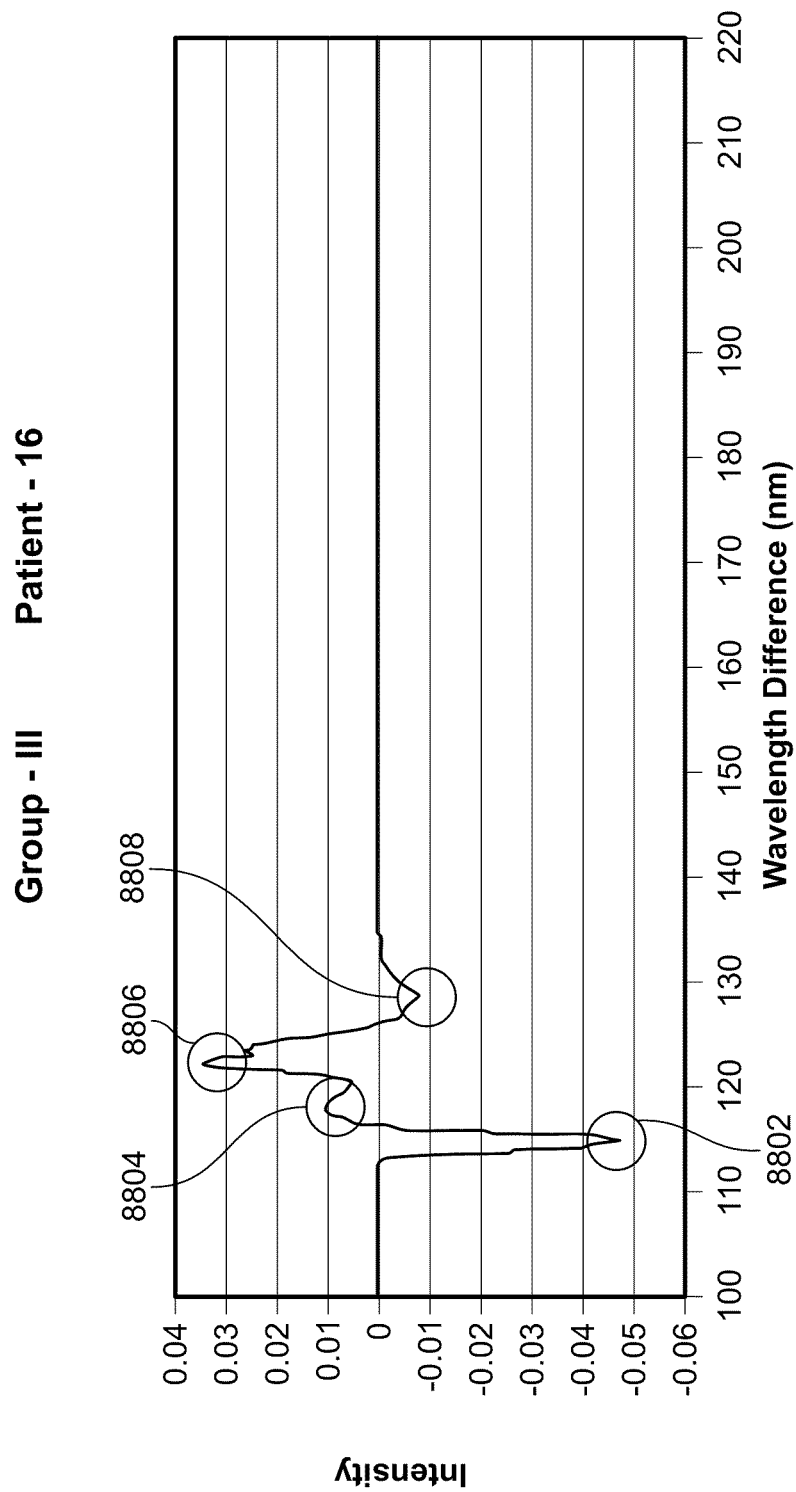
FIG. 88 depicts a plot of typical spectral data (or OMF diagram) obtained on implementation of the OMF method on digital images of a given, selected sample (or Pap smear slide) categorized as Group III (dysplasia), in accordance with certain embodiments of the invention.

FIG. 88 depicts a plot of a typical spectral data (or OMF diagram) obtained on implementation of the OMF method on digital images of a given, selected sample (or Pap smear slide) categorized as Group III (dysplasia), in accordance with certain embodiments of the invention.

As depicted in FIG. 88, a fifth DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.06 to a maximum of equal to +0.04; analytical information is analysis of the fifth DI plot (or OMF Diagram) of the sample; patient information is a given, selected seventeenth patient of the Group III (or non-typical inflammation); test input sample is the Pap smear slide categorized as Group III of a patient referred to as Group III Patient 16; operation is implementation of OMF method on digital images of the given, selected seventeenth sample (or Pap smear slide) categorized as the group II (or non-typical inflammation); number of intensity peaks (or extrema or maxima and minima) is 4; number of peaks with positive intensity values is 2; number of peaks with negative intensity value is 2; identifiers for the 4 intensity peaks are first 8802, second 8804, third 8806 and fourth 8808 respectively; values for Wavelength Difference/Intensity associated with the first, second, third and fourth intensity peaks are 112.5 nm/−0.013 arb, 118.9 nm/0.016 arb, 126.8 nm/0.005 arb, 131.4 nm/−0.003 arb in that order.

Figure 89:
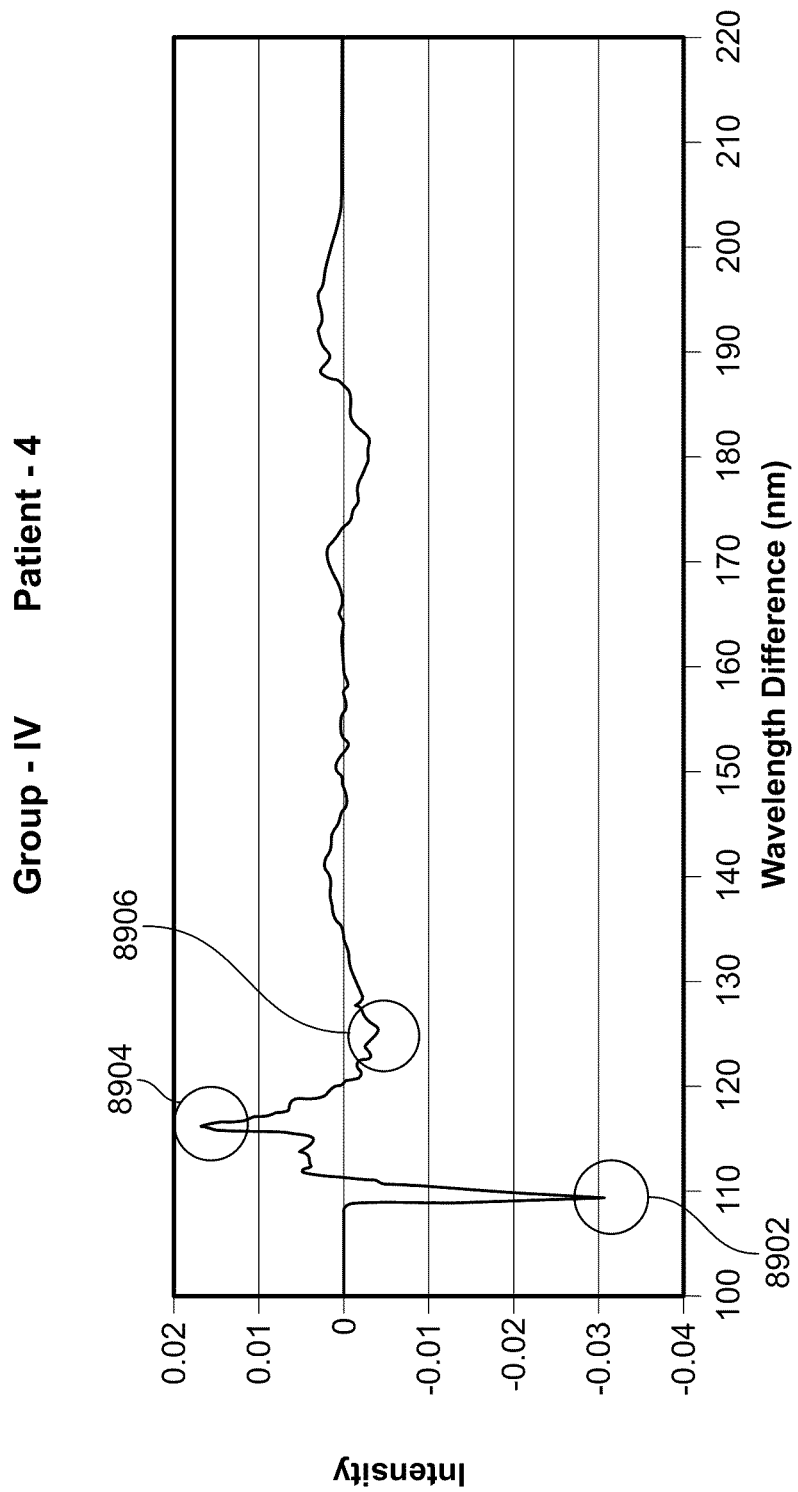
FIG. 89 depicts a plot of typical spectral data (or OMF diagram) obtained on implementation of the OMF method on digital images of a given, selected sample (or Pap smear slide) categorized as Group IV (carcinoma in situ), in accordance with certain embodiments of the invention.

FIG. 89 depicts a plot of a typical spectral data (or OMF diagram) obtained on implementation of the OMF method on digital images of a given, selected sample (or Pap smear slide) categorized as Group IV (carcinoma in situ), in accordance with certain embodiments of the invention.

As depicted in FIG. 89, a sixth DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.04 to a maximum of equal to +0.02; analytical information is analysis of the sixth DI plot (or OMF Diagram) of the sample; patient information is a given, selected fourth patient of the Group IV (or carcinoma in situ) or Group IV Patient 4; test input sample is the Pap smear slide categorized as the Group IV (or carcinoma in situ) of the patient referred to as Group IV Patient 4; operation is implementation of OMF method on digital images of the sample; number of intensity peaks (or extrema or maxima and minima) is 3; number of peaks with positive intensity values is 1; number of peaks with negative intensity value is 2; identifiers for the 3 intensity peaks are first 8902, second 8904 and third 8906 respectively; values for Wavelength Difference/Intensity associated with the first, second and third intensity peaks are 109.4 nm/−0.031 arb, 115.9 nm/0.016 arb and 125.0 nm/−0.004 arb in that order.

Table 5 exhibits a tabular representation in connection with parameter values of OMF study for 5 cases (carcinoma in situ) as True Positive.

| | VALUE OF GROUP IV | |
|---|---|---|
| PEAK | WAVELENGTH DIFFERENCE | INTENSITY (ARB) |
| FIRST | 110 ± 3.0 NM | −0.03 ± 0.008 |
| SECOND | 116 ± 3.0 NM | 0.01 ± 0.008 |
| THIRD | 126 ± 5.0 NM | −0.005 ± 0.003 |
| A FEW | 140-220 NM | WEEK CORRUGATION |

Figure 90:
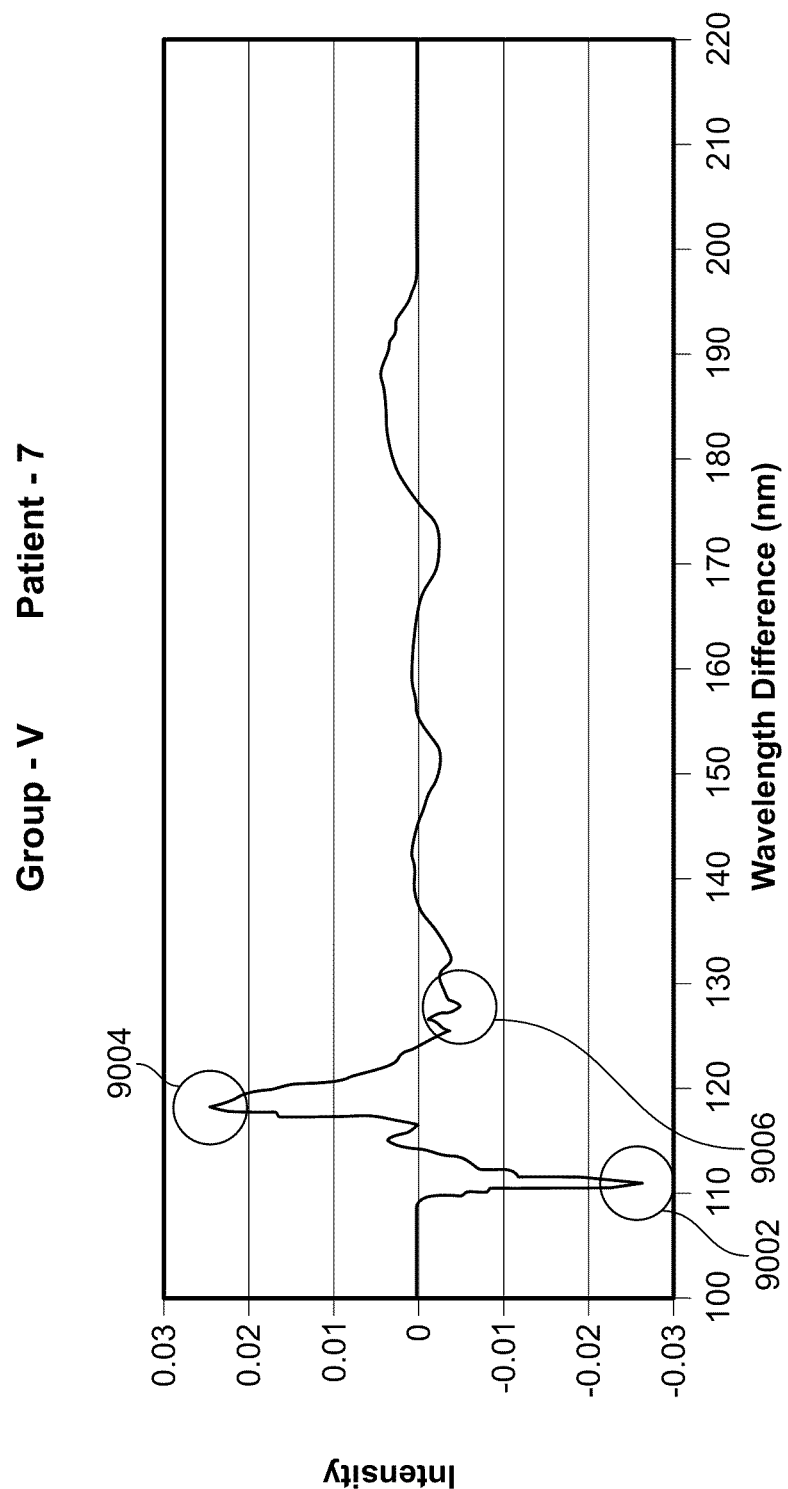
FIG. 90 depicts a plot of typical spectral data (or OMF diagram) obtained on implementation of the OMF method on digital images of a given, selected sample (or Pap smear slide) categorized as Group V (suspicion to carcinoma), in accordance with certain embodiments of the invention.

FIG. 90 depicts a plot of a typical spectral data (or OMF diagram) obtained on implementation of the OMF method on digital images of a given, selected sample (or Pap smear slide) categorized as Group V (suspicion to carcinoma), in accordance with certain embodiments of the invention.

As depicted in FIG. 90, a seventh DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.03 to a maximum of equal to +0.03; analytical information is analysis of the seventh DI plot (or OMF Diagram) of the sample; patient information is a given, selected seventh patient of the Group V (suspicion to carcinoma) or Group V Patient 7; test input sample is the Pap smear slide categorized as the Group V (suspicion to carcinoma) of the patient referred to as Group V Patient 7; operation is implementation of OMF method on digital images of the sample; number of intensity peaks (or extrema or maxima and minima) is 3; number of peaks with positive intensity values is 1; number of peaks with negative intensity value is 2; identifiers for the 3 intensity peaks are first 9002A, second 9004A and third 9006A respectively; values for Wavelength Difference/Intensity associated with the first, second and third intensity peaks are 110.9 nm/−0.027 arb, 118.2 nm/0.025 arb and 128.1 nm/−0.005 arb in that order.

OMF diagrams for samples categorized as Group IV (carcinoma in situ) and Group V (suspicion to carcinoma) share some qualitative similarity but differ markedly from Groups I, II, and III. The difference is obvious not only in distribution of peaks within lower wavelength difference range (<140 nm) but also throughout the higher spectral range of wavelength differences that is captured by this method (100-220 nm). The patterns in higher wavelength differences are unseen in lower grade groups and are likely to be produced by malignant cells.

In certain embodiments, systems for generating enhanced heterogeneous signals for use in non-invasive processing of materials using an Opto-Magnetic Antenna (or OMA), and methods thereof are disclosed.

In the description, the terms "system" and "Opto-Magnetic Amplifier (or OMA)" are used interchangeably, unless otherwise prescribed. For example, in some embodiments, the terms "system" and "Opto-Magnetic Amplifier (or OMA)" are used interchangeably to refer to a system which has been designed and implemented herein for generating enhanced heterogeneous (or mixed) signals for use in non-invasive processing of materials. Whereas, in some other embodiments, the terms "first signal processing subsystem" and "Opto-Magnetic Signal Processor (or OMSP)" are used interchangeably to refer to a subsystem which has been designed and implemented herein for generating spectral signatures for materials. In yet other some embodiments, the terms "second signal processing subsystem" and "Direct EM Signal Processor (or DEMSP)" are used interchangeably to refer to a subsystem which has been designed and implemented to process EM signals.

In certain embodiments, systems and/or methods for non-invasive surface and/or bulk processing of materials have been disclosed. Specifically, such systems and/or methods for non-invasive detection, analysis, characterization, indication, identification, and determination of materials are based on valence electrons. Such systems and/or methods measure the magnetic change in the valence orbitals. This implies that such methods measure Electro-Magnetic (EM) changes in underlying structures, such as skin, collagen, elastin or a metal. Thus, such systems and/or methods can provide information about the composition of the materials. For example, theoretically such systems and/or methods can be used down to a level approximately 1 millimeter by 1 millimeter to measure material properties.

In addition, the aforementioned systems and/or methods may be implemented as an antenna amplifier. These systems and/or methods can measure the variance in the magnetic receptance of the antenna and get highly enhanced antenna reception. In certain situations involving antennae supplied with an input signal, such systems and/or methods can give a result based on the antennae properties of the input signal. In such situations, the output signal can be enhanced based on the antenna properties.

As used in the current context, the term "magnetic reception" refers to sensitivity to magnetic stimuli. For example, the very weak magnetic stimuli occurring naturally in the environment.

In certain dermatological applications, on illuminating the skin with polarized light only the electrical properties of skin will be apparent. But, on illuminating the skin with unpolarized incident light may reveal both the electrical and magnetic properties of skin. Further, usage of the polarized light may generate improved induction of optical activity. However, the data sets generated on illumination of skin with polarized light may be of less value as compared to the data sets captured using incident unpolarized light. For example, by measuring the effects between $10^{-34}$ and $10^{-30}$ Js measurements can be made at the border area of quantum and classical physics effects on skin and as a difference of action of electrical and magnetic forces of valence electrons of skin's biomolecules.

In general, unpolarized light includes any permutations and/or combinations of diffused light, white light, monochromatic light, light of multiple single wavelengths and the like. Specifically, the white light is a light consisting of photons of all wavelengths. Thus, when a material is illuminated by the white light, photons can make the valence electrons of an atom transition to a higher electronic energy level.

Figure 91:
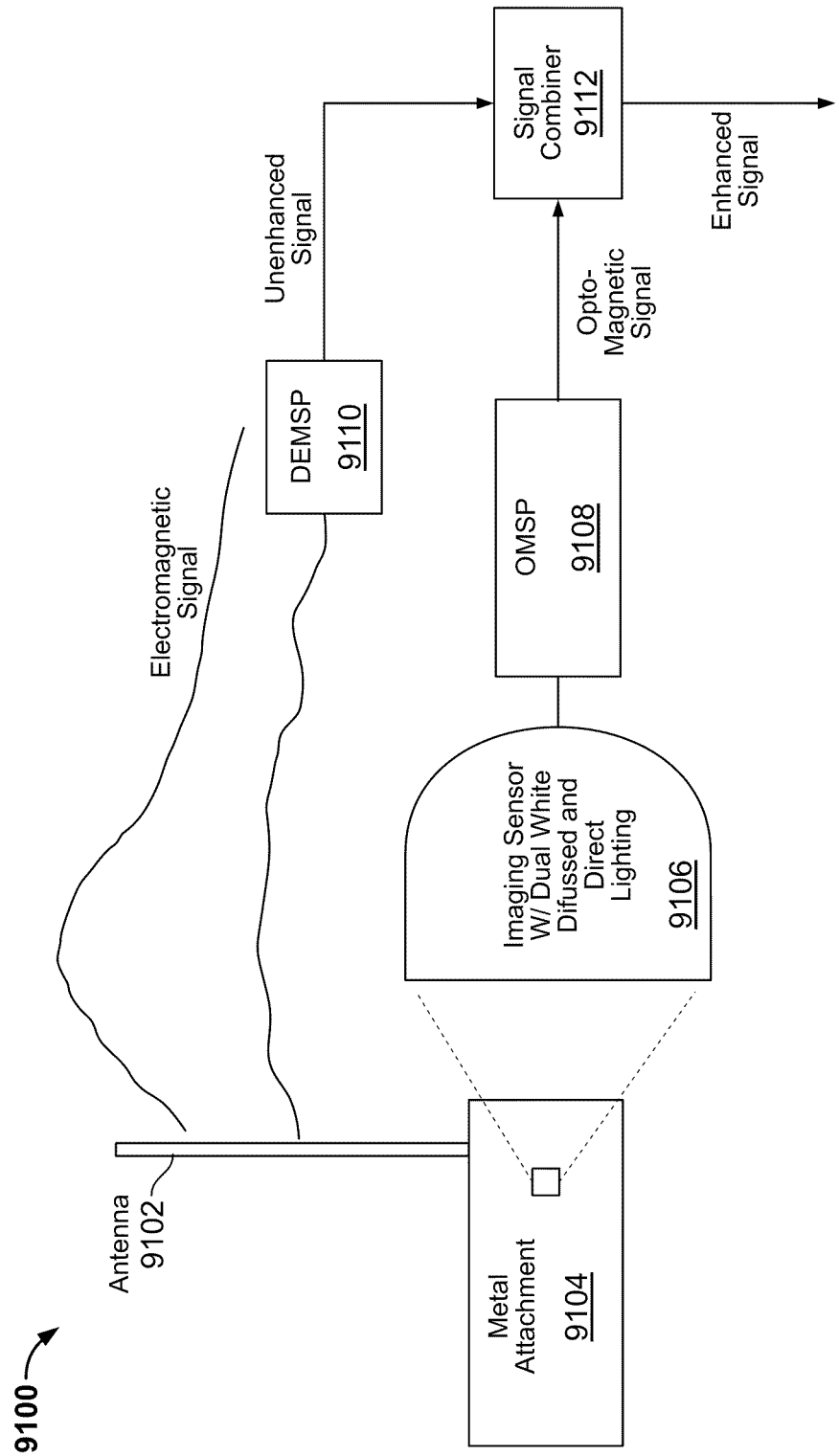
FIG. 91 depicts a system for generating enhanced heterogeneous signals for use in non-invasive processing of materials utilizing an Opto-Magnetic Antenna (or OMA), designed and implemented in accordance with certain embodiments of the invention.

FIG. 91 depicts a system for generating enhanced heterogeneous signals for use in non-invasive processing of materials utilizing an Opto-Magnetic Antenna (or OMA), designed and implemented in accordance with certain embodiments of the invention.

The system 9100 is in essence an Opto-Magnetic Amplifier (or OMAMP.)

The OMAMP 9100 consists of the OMA 9102, a metal attachment 9104, an imaging sensor 9106, an Opto-Magnetic Signal Processor (or OMSP) 9108, a Direct Electro-Magnetic Signal Processor (or DEMSP) 9110 and a signal combiner (or mixer) 9112.

The OMAMP 9100, by virtue of its design and implementation, processes Electro-Magnetic (or EM) and photo-magnetic (or photo-magnetic Optomagnetic or Opto-Magnetic) signals thereby facilitating detection, analysis, characterization, indication, identification, assessment and determination of the materials.

The OMAMP 9100 can be coupled to a metallic surface (not shown), for example as a regular antenna.

In certain embodiments, the OMA 9102 may be a transmitting antenna.

The OMA 9102 transmits EM signals. The OMA 9102 receives the EM signals and generates a response based on the received EM signals. It must be noted here that the output signal of the OMA 9102 can be boosted based on the response of the OMA 102.

The OMA 9102 is coupled to the metal attachment 9104 and the DEMSP 9110. This is shown in FIG. 91. Specifically, the OMA 9102 feeds the EM signals to an input of the DEMSP 9110.

The term "transmitting antenna or transmitter" refers to an electronic device which, usually with the aid of an antenna, propagates an EM signal, such as in radio, television, or other telecommunications applications. In other applications signals can also be transmitted using an analog 0/4-20 mA current loop signal.

The metal attachment 9104 is in essence a receiving antenna. The metal attachment 9104 receives EM signals.

The term "metal attachment or attachment", as used in the current context refers to a special hardware specific to an antenna model for attachment to an antenna mounting pipe or concealment structure. The antenna attachment is located at the base end of the antenna element. The antenna attachment has a capacitive reactance. In addition, the antenna attachment can cancel the inductive reactance of the antenna thereby causing the impedance of the antenna to approach a prescribed value.

As depicted in FIG. 91, the metal attachment 9104 is coupled to the OMA 9102.

The imaging sensor 9106 is in essence a device that converts an optical image to an electric signal. In certain embodiments, the imaging sensor 9106 captures continuous digital images of the metallic surface. Noticeable here is the fact that the OMAMP 9100 is attached to the metallic surface. Specifically, in such embodiments, the imaging sensor 9106 captures continuous digital images of the metallic surface illuminated with white light both, non-angled and angled. By way of, and by no way of limitation, the imaging sensor 106 may be anyone selected from a group consisting of a Complementary Metal-Oxide-Semiconductor (CMOS) image sensor, Charged Coupled Device (CCD) image sensor, and the like.

The imaging sensor 9106 is coupled to the metal attachment 9104, as depicted in FIG. 91. In addition, the imaging sensor 9106 is coupled to the OMSP 9108. Specifically, an output of the imaging sensor 9106 is coupled to an input of the OMSP 9108.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

For example, and in no way limiting the scope of the invention, in certain embodiments the imaging sensor 9106 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

The OMSP 9108 may be a customized digital signal processor.

As seen in FIG. 91, the OMSP 9108 has a single input and a single output.

The OMSP 9108 processes the continuously captured non-angled and angled white light digital images of the metallic surface.

In certain embodiments, the process of generating a spectral signature for materials and the system thereof (for implementing or facilitating implementation of) the process is disclosed, in accordance with the principles of the invention. In certain specific embodiments, the OMSP 9108 implements the process of generating the spectral signature for materials.

Specifically, the process comprises the stages of capturing an image of a material illuminated with incident non-angled and angled white light, generating a normalized red and blue color channel histogram for each image, correlating the normalized red and blue color channel histograms to a wavelength scale to obtain red and blue color channel spectral plots, and convoluting the spectral plots by subtracting the spectral plot for angled light from the spectral plot for non-angled light for each color channel to generate red and blue normalized, composite color channel spectral plots, and subtracting the normalized, composite blue channel spectral plot from the normalized, composite red channel spectral plot to generate a spectral signature for the material. By way of example, and in no way limiting the scope of the invention, the OMSP 108 implements a process for generating the spectral signature for materials as disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

As seen in FIG. 91, the input of the OMSP 9108 is coupled to the output of the imaging sensor 9106. Thus, the input of the OMSP 9108 is fed with the continuously captured non-angled and angled white light digital images of the material.

Further, the output of the OMSP 9108 generates Opto-Magnetic signals.

The output of the OMSP 9108 is coupled to the signal combiner 9112.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

The term "spectral signatures" as used herein refers to specific combination of reflected and absorbed electromagnetic radiation at varying wavelengths that can uniquely identify an object. The spectral signature of an object is a function of incidental Electro-Magnetic (EM) wavelength and material interaction with that section of the electromagnetic spectrum. The measurements can be made with various instruments, including but not limited to, a task specific spectrometer. For instance, the most common method is separation of the Red (R), Green (G), Blue (B) and Near Infrared (NIR) portion of the EM spectrum as acquired by digital cameras. In certain airborne or satellite imagery applications, calibrations of spectral signatures under specific illumination are collected in order to apply an empirical correction to airborne or satellite imagery digital images.

In general, all of the antenna parameters are expressed in terms of a transmission antenna, but are identically applicable to a receiving antenna, due to reciprocity. However, impedance is not applied in an obvious way. The impedance at the load, where the power is consumed, is most critical. For a transmitting antenna, this is the antenna. On the other hand, for a receiving antenna this is at the radio receiver rather than at the antenna. Tuning is done by adjusting the length of an electrically long linear antenna to alter the electrical resonance of the antenna.

Antenna tuning is done by adjusting an inductance or capacitance combined with the active antenna (but distinct and separate from the active antenna). The inductance or capacitance provides the reactance which combines with the inherent reactance of the active antenna to establish a resonance in a circuit including the active antenna. The established resonance being at a frequency other than the natural electrical resonant frequency of the active antenna. Adjustment of the inductance or capacitance changes this resonance.

Antennas used for transmission have a maximum power rating, beyond which heating, arcing or sparking may occur in the components, which may cause them to be damaged or destroyed. Raising this maximum power rating usually requires larger and heavier components, which may require larger and heavier supporting structures. This is a concern only for transmitting antennas, as the power received by an antenna rarely exceeds the microwatt range.

Antennas designed specifically for reception might be optimized for noise rejection capabilities. An antenna shield is a conductive or low reluctance structure (such as a wire, plate or grid) which is adapted to be placed in the vicinity of an antenna to reduce, as by dissipation through a resistance or by conduction to ground, undesired electromagnetic radiation, or electric or magnetic fields, which are directed toward the active antenna from an external source or which emanate from the active antenna. Other methods to optimize for noise rejection can be done by selecting a narrow bandwidth so that noise from other frequencies is rejected, or selecting a specific radiation pattern to reject noise from a specific direction, or by selecting a polarization different from the noise polarization, or by selecting an antenna that favors either the electric or magnetic field.

For instance, an antenna to be used for reception of low frequencies (below about ten megahertz) will be subject to both man-made noise from motors and other machinery, and from natural sources such as lightning. Successfully rejecting these forms of noise is an important antenna feature. A small coil of wire with many turns is more able to reject such noise than a vertical antenna. However, the vertical will radiate much more effectively on transmit, where extraneous signals are not a concern.

The term "tuning" refers to adjusting a device to a desired frequency.

In general, there are two basic types of mixer, namely additive mixers and multiplying mixers. Additive mixers add two or more input (or source) signals thereby outputting a composite signal that contains the frequency components of each of the input signals. For example, the simplest additive mixers are simple resistor networks, and thus purely passive, whereas more complex mixers employ active components such as, buffer amplifiers for impedance matching and better isolation.

On the other hand, the multiplying mixers (or product) multiply two or more input (or source) signals together thereby producing an output containing both the input signals and new signals that comprise the sum and difference of the frequency of the input signals. For example, ideal product mixers act as signal multipliers thereby producing an output signal equal to the product of the input signals. In certain communications-based applications, the product mixers are often used in conjugation with an oscillator to modulate signal frequencies. For instance, the product mixers can either up-convert or down-convert an input signal frequency, but it is more common to down-convert to a lower frequency to allow for easier filter design. In many typical circuits, the single output signal actually contains multiple waveforms, namely those at the sum and difference of the two input frequencies and harmonic waveforms. The ideal signal may be obtained by removing the other signal components with a filter.

As shown in FIG. 91, the DEMSP 9110 has a single input and a single output. For example, and by no way of limitation, in certain embodiments the DEMSP 9110 may be a customized Analog Signal Processor (ASP). Thus, in such embodiments, the DEMSP 9110 may employ analog signal processing to process the EM signals.

The term "analog signal processing" refers to any signal processing conducted on analog signals by analog means. For example, analog signal processing include crossover filters in loudspeakers, "bass", "treble" and "volume" controls on stereos, and "tint" controls on TVs. Common analog processing elements include capacitors, resistors, inductors and transistors.

The input of the DEMSP 9110 is fed with the EM signals. The input of the DEMSP 9110 is coupled to the OMA 9102.

The output of the DEMSP 9110 outputs unenhanced signals. The output of the DEMSP 9110 is coupled to the signal combiner 9112.

In general, the signal combiner 9112 combines (or mixes) two or more signals into one composite output signal.

As shown in FIG. 91, the signal combiner 9112 consists of a pair of inputs and a single output.

The first input of the pair of inputs of the signal combiner 9112 is coupled to the DEMSP 9110. The first input of the pair of inputs of the signal combiner 9112 is fed with the unenhanced signal.

The second input of the pair of inputs of the signal combiner 9112 is coupled to the OMSP 9108. The second input of the pair of inputs of the signal combiner 9112 is fed with the Opto-magnetic signal.

In operation, the signal combiner 9112 combines (or mixes) the unenhanced signal from the DEMSP 9110 and the Opto-magnetic signal from the OMSP 9108 thereby producing the enhanced signal.

In operation, the OMAMP 9100 is coupled to a test material surface. The imaging sensors 9106 capture continuous digital images of the material illuminated with non-angled and angled white light. The output of the imaging sensors 9106 is fed as input to the OMSP 9108. The OMSP 9108 processes the continuously captured digital images of the material to generate a spectral signature of the material, in accordance with the principles of the invention disclosed earlier. The antenna 9102 transmits EM signals to the DEMSP 9110. The DEMSP 9110 processes the EM signals and outputs an unenhanced EM signal. The output of the OMSP 9108 (i.e. the Opto-Magnetic signal) and the output of DEMSP 9110 (i.e. the unenhanced EM signal) are fed as inputs to the signal combiner 9112. The signal combiner 9112 combines (or mixes) the Opto-Magnetic signal and unenhanced signal to generate an enhanced mixed signal.

In certain embodiments, the wavelengths and algorithm varies by the frequency of the target antenna. Multiple detectors may be placed on the same metal surface in order to take images in parallel in order to increase processing speed based on wavelength, etc. Tuning to different frequencies is done by analyzing the resulting spectrum as well as adjusting the speed of the images taken.

In certain embodiments, design and implementation of one or more workable configurations for the system of FIG. 91 for facilitating high frequency imaging and processes thereof have been disclosed. Specifically, such configurations can use multiple sensors that allow rapid lighting sequences for rapid imaging thereby resulting in high frequency imaging of materials.

Figure 92:
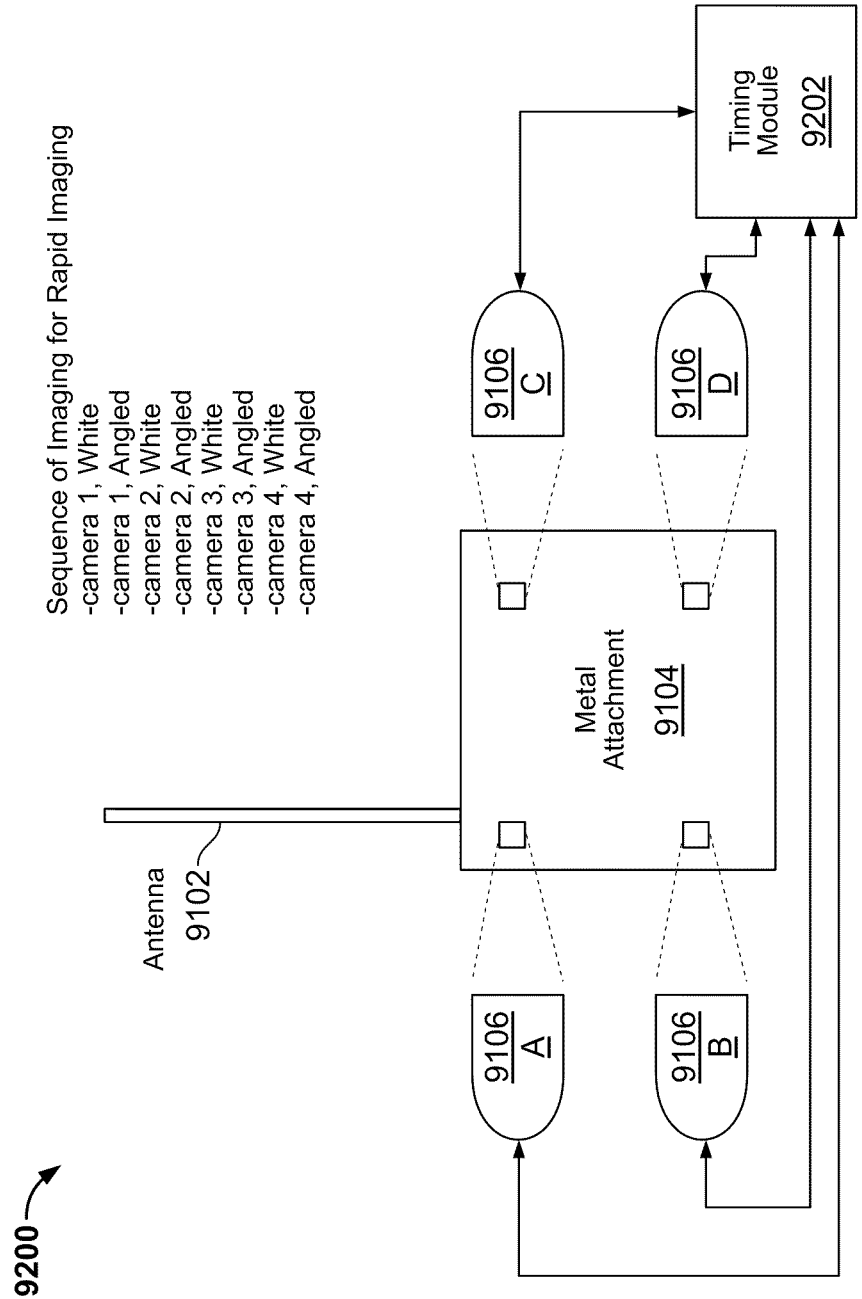
FIG. 92 is block diagrammatic view of at least one workable configuration for use in tandem with the system of FIG. 91.

FIG. 92 is block diagrammatic view of at least one workable configuration for use in tandem with the system of FIG. 91.

The configuration 9200 comprises the OMA 9102, metal attachment 9104, at least two pairs of the imaging sensors 9106 and a timing module 9202.

The configuration 9200 may be coupled to surface of materials. For example, and by no way of limitation, materials may be anyone selected from a group of both inorganic and organic materials consisting of skin, collagen, elastin, metal and the like.

The two pairs of imaging sensors 9106 consists of a first imaging sensor 9106A, second imaging sensor 9106B, third imaging sensor 9106C and fourth imaging sensor 9106D.

Reiterating again, each individual sensor 9106 of the two pairs of imaging sensors 9106 captures continuous digital images of materials illuminated with the unangled and angled white light.

Timing module (or Timer) 9202 is a specialized type of clock. The timer 9202 can be used to control the sequence of an event or process.

In operation, the configuration 9200 implements a process facilitating high frequency imaging of materials by employment of multiple sensors. Specifically, the process implements a sequence of process stages of imaging for rapid imaging using the multiple sensors. It must be noted here that the use of the multiple sensors allow rapid lighting sequences thereby resulting in high frequency imaging of materials. This sequence has been explained in conjunction with the process of FIG. 93 and TABLE 1.

As seen in FIG. 91, the timing module 9202 is separately coupled to each individual sensor 9106 of the two pairs of the imaging sensors 9106.

In certain other embodiments, the system configuration, discussed in conjunction with FIG. 92, implement one or more processes facilitating high frequency imaging by employment of multiple sensors. Specifically, the processes comprise one or more sequences of process stages of imaging for rapid imaging using the multiple sensors. It must be noted here that the use of the multiple sensors allow rapid lighting sequences thereby resulting in high frequency imaging of materials.

Figure 93:
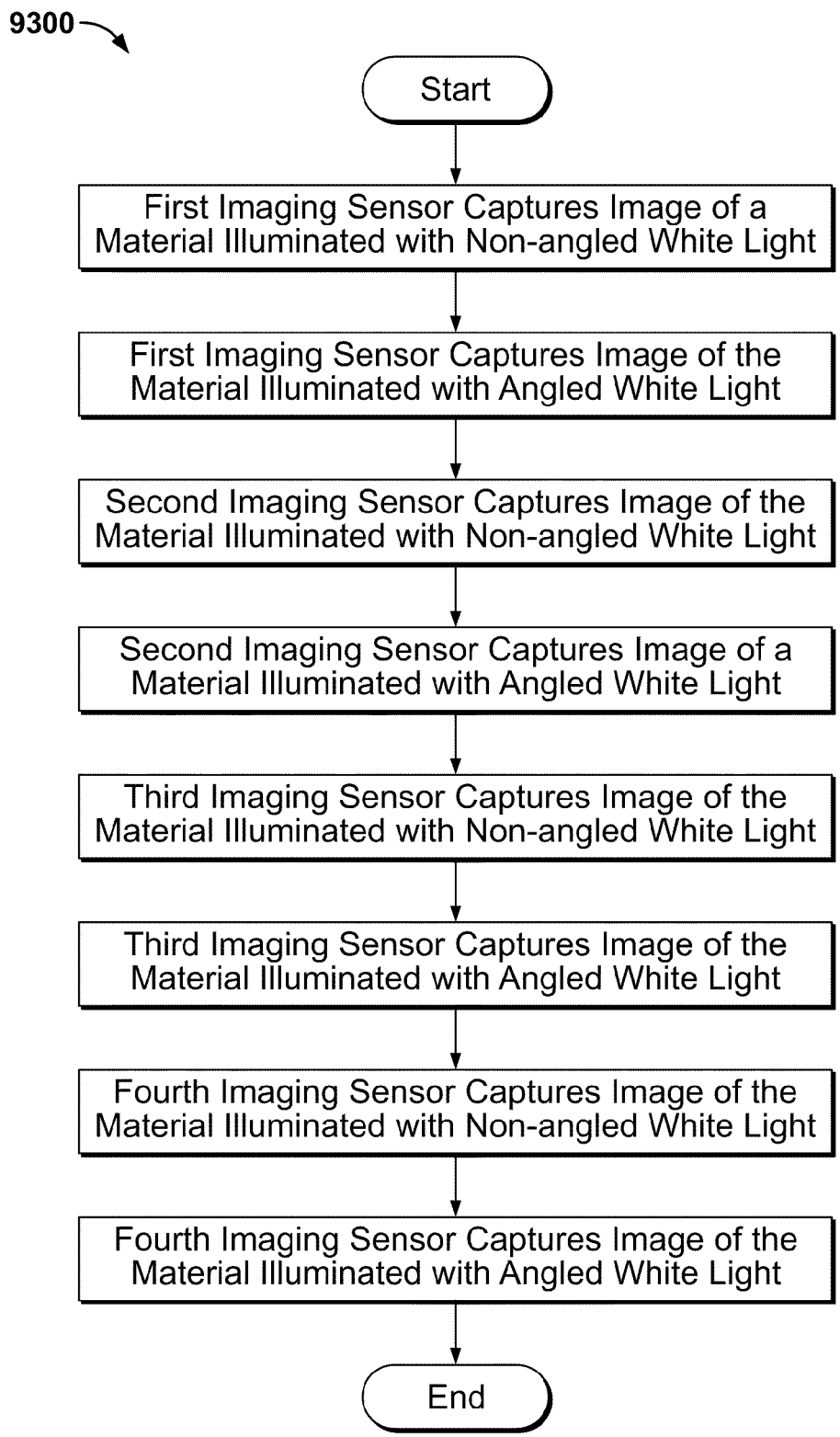
FIG. 93 depicts a flow diagram delineating at least one process implemented by the system configuration of FIG. 92 thereby facilitating multi sensor high frequency imaging.

FIG. 93 depicts a flow diagram delineating at least one process implemented by the system configuration of FIG. 92 thereby facilitating multi sensor high frequency imaging.

The process 9300 starts at stage 9301 and proceeds to stage 9302, where the process 9300 comprises the phase of capturing images of a material illuminated with a white light (or unangled white light.) Noticeable here is the fact that the process 9300 initiates the first imaging sensor for capturing images of the material illuminated with the white light.

At stage 9304, the process 9300 comprises the phase of capturing images of the material illuminated with an angled white light. In here, it is worth notable that the process 9300 initiates the first imaging sensor for capturing images of the material illuminated with the angled white light.

At stage 9306, the process 9300 comprises the phase of capturing images of the material illuminated with the white light. It must be noted here that the process 9300 initiates the second imaging sensor for capturing images of the material illuminated with the white light.

At stage 9308, the process 9300 comprises the phase of capturing images of the material illuminated with the angled white light using the second imaging sensor.

At stage 9310, the process 9300 comprises the phase of capturing images of the material illuminated with the white light using the third imaging sensor.

At stage 9312, the process 9300 comprises the phase of capturing images of the material illuminated with the angled white light using the third imaging sensor.

At stage 9314, the process 9300 comprises the phase of capturing images of the material illuminated with the white light using the fourth imaging sensor.

At stage 9316, the process 9300 comprises the phase of capturing images of the material illuminated with the angled white light using the fourth imaging sensor.

The process 9300 ends at the stage 9318. It is worth notable that the timer 9202 can be used to control the sequence of the process 9300.

Table 6 below provides at least one sequence of imaging for rapid imaging.

| SEQUENCE EVENT # | IMAGING SENSOR OR CAMERA # | TYPE OF WHITE LIGHT (POLARIZED/ NON-POLARIZED) |
| --- | --- | --- |
| 1. | FIRST IMAGING SENSOR (OR CAMERA 1) 9106 A | WHITE (NON-ANGLED WHITE) |
| 2. | FIRST IMAGING SENSOR (CAMERA 1) 9106A | ANGLED (OR ANGLED WHITE) |
| 3. | SECOND IMAGING SENSOR (OR CAMERA 2) 9106B | WHITE (NON-ANGLED WHITE) |
| 4. | SECOND IMAGING SENSOR (OR CAMERA 2) 9106B | ANGLED (OR ANGLED WHITE) |
| 5. | THIRD IMAGING SENSOR (OR CAMERA 3) 9106C | WHITE (NON-ANGLED WHITE) |
| 6. | THIRD IMAGING SENSOR (OR CAMERA 3) 9106C | ANGLED (OR ANGLED WHITE) |
| 7. | FOURTH IMAGING SENSOR (OR CAMERA 4) 9106D | WHITE (NON-ANGLED WHITE) |
| 8. | FOURTH IMAGING SENSOR (OR CAMERA 4) 9106D | ANGLED (OR ANGLED WHITE) |

Advantageously, in certain embodiments, the invention may find application in highly accurate Digital Video Disc (or DVD) readings. Still advantageously, the invention may find application in material optical characterization. For example, the invention may be used in material identification, lot-based assessment of materials, and the like.

In certain embodiments, a system for managing physiological state, based on one or more physiological parameters, with improved qualitative and quantitative parameters and methods thereof are disclosed.

In the description of this invention, the terms "system," "device" and "Wearable Hydration Monitor (or WHM)" are used interchangeably, unless otherwise prescribed. For example, in some embodiments, the terms "system," "device" and "Wearable Hydration Monitor (or WHM)" are used interchangeably to refer to a wearable computing system, which has been designed and implemented herein for managing (i.e. monitoring) hydration level of skin. Whereas, in some other embodiments, the terms "sensor subsystem" and "sensor" are used interchangeably to refer to a device for capturing the polarized and unpolarized electromagnetic signals reflected from the physiological organs. In yet other some embodiments, the terms "physiological parameter management module," "skin hydration management module" and "hydration management module" are used interchangeably to refer to a software module which has been designed and implemented for overall management of hydration level of skin.

Typically, there are many factors that can impact on the hydration status of sports people, such as social activities, diet, climate and activity level. It is very important for sports people to be well hydrated. As far as health is concerned, dehydrated athletes competing in a hot climate are at greater risk of heat injury. In addition, as far as performance is concerned, research has shown that a dehydration percentage of 2% of body weight or greater can have a significant effect on performance.

Conventionally, there are many methods for determining hydration status including, but not limited to, monitoring body mass changes, measuring sweat, various blood markers and analysis of urine. For example, USG measurement using refractometers, urine color, sweat analysis, sweat rate, and the like.

In certain embodiments, the skin care devices and systems may be adapted for managing physiological state based on one or more physiological parameters. Specifically, such skin care devices and systems can be worn by a user in one or more forms, such as necklace, ear-rings, bracelets, a patch, or as a sensor attached to a strap, and the like. For example, and by no way of limitation, such wearable devices and systems can be persistent, personalized skin care monitors.

In certain specific embodiments, the wearable skin care devices and systems may be a Wearable Hydration Monitor (or WHM). Similar to the skin care device, the WHM may comprise an electromagnetic radiation source, a radiation detector, and a skin condition analysis module. In such embodiments of the wearable skincare device and systems, the electromagnetic radiation source may be one or more LEDs. Each of the LEDs may have unique predetermined frequencies. In other such embodiments, the one or more LEDs may be arranged in a line to form a light strip.

Figure 94:
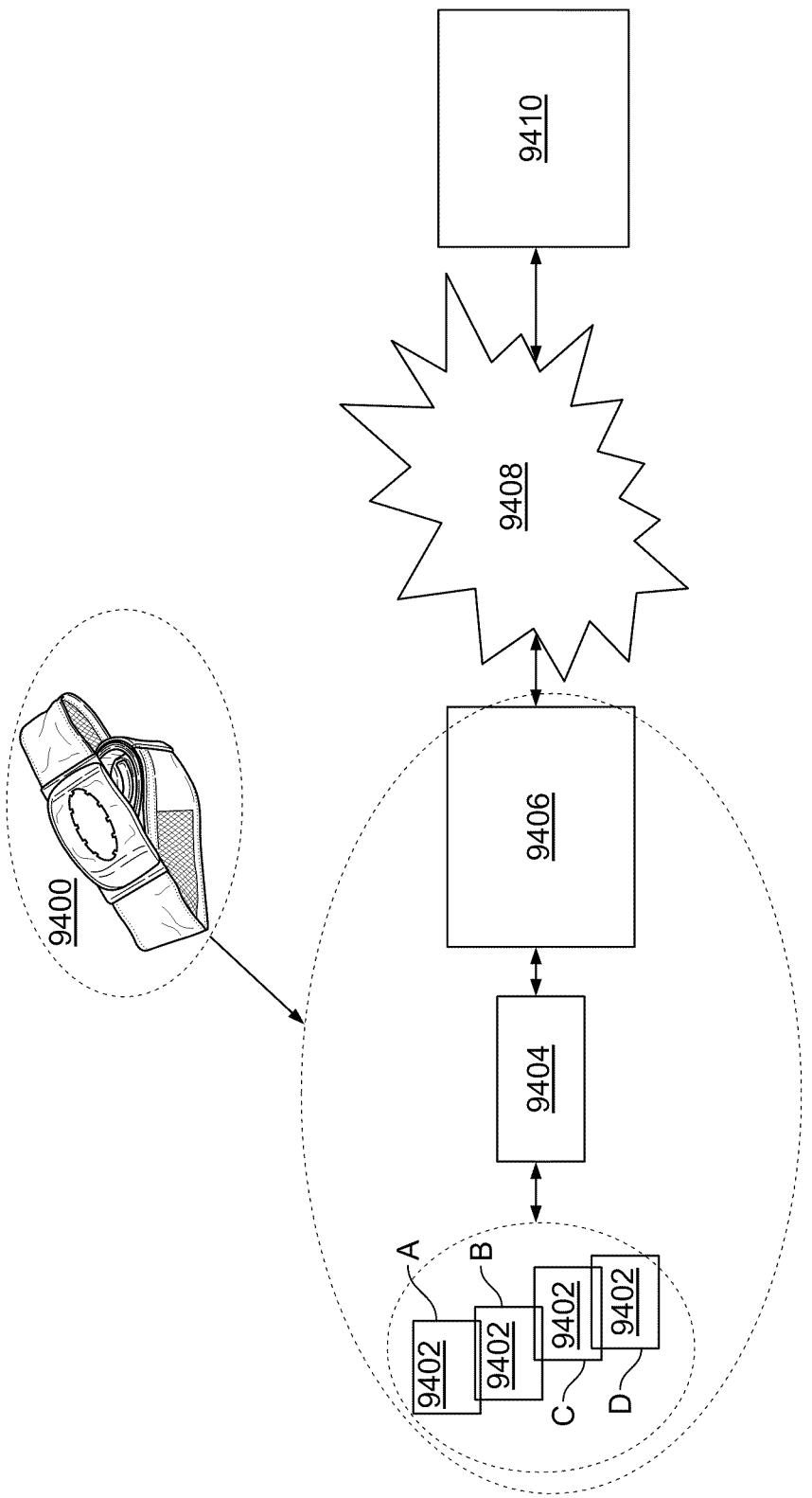
FIG. 94 is a schematic view of a wearable computing system for monitoring of one or more physiological parameters designed and implemented in accordance with at least some embodiments of the invention.

FIG. 94 is a schematic view of a wearable computing system for monitoring of one or more physiological parameters designed and implemented in accordance with at least some embodiments of the invention.

The system 9400 may in essence be a Wearable Hydration Monitor (or WHM.) The WHM 9400 may consist of one or more Light Emitting Diodes (LEDs) 9402, a sensor subsystem 9404, a host computing subsystem 9406, an optional network 9408 and a remote computing subsystem 9410. By way of example and by no way of limitation the WHM 9400 may be a polar arm or chest band. This is shown in FIG. 94.

As depicted in a partially disassembled view of FIG. 94, in certain specific embodiments, the one or more Light Emitting Diodes (LEDs) 9402 consists of a first LED 9402A, a second LED 9402B, a third LED 9402C, a fourth LED 9402D respectively.

In some embodiments, the WHM 9400 may be powered via a USB coupled to an external power source or through built-in batteries, motion power, solar power, or other similar power source. All these have not been shown explicitly in FIG. 94.

In certain embodiments, the WHM 9400 for managing one or more physiological parameters and processes thereof has been disclosed, in accordance with the principles of the invention. Specifically, in such embodiments, the WHM 9400 comprises one or more illumination sources. The illumination sources comprise incident light sources to direct light upon skin. In consequence, the incident light sources may be unpolarized or polarized light sources. For example, and by no way of limitation, the unpolarized light may be white light, multiple selected wavelengths, or a single wavelength. Further, the illumination source may be positioned to direct light at a selected angle alpha. By way of example, and in no way limiting the scope of the invention, the WHM 9400 implements the processes for non-invasive processing including, but not limited to, imaging, analysis, of materials, as disclosed in United States Provisional Patent Applications "METHOD AND ALGORITHM FOR ANALYSIS OF LIGHT-MATTER INTERACTION BASED ON SPECTRAL CONVOLUTION" and "IMAGING DEVICE UTILIZING WHITE LIGHT FOR COMPOSITION ANALYSIS" and United States Non-Provisional Patent Applications "SYSTEM, DEVICE, AND METHOD FOR DERMAL IMAGING" to MYSKIN, INC., the disclosure of which is incorporated herein by reference in its entirety. Thus, all remaining ins-and-outs in connection with the process of non-invasive processing of materials will not be further detailed herein.

Embodiments of the WHM 9400 may also have one or more sensors for measuring various body and environmental parameters. Examples of body parameters that could be measured by the wearable skincare device are hydration level, skin turgor, body temperature, hemoglobin antioxidant level, etc. Examples of environmental parameters that could be measured by the WHM 9400 are air cleanliness, humidity, temperature, UV index, external air quality, smoke index, etc.

As shown in FIG. 94, the sensor subsystem 9404 may in essence be a device that converts optical images (or optical signals) to electric signals. In certain embodiments, the sensor subsystem 9404 captures continuous digital images of skin. Specifically, in such embodiments, the sensor subsystem 9404 captures continuous digital images of the metallic surface illuminated with white light both, non-angled and angled. By way of, and by no way of limitation, the sensor subsystem 9404 may be anyone selected from a group consisting of a Complementary Metal-Oxide-Semiconductor (CMOS) image sensor, Charged Coupled Device (CCD) image sensor, and the like.

Again, as shown in FIG. 94, the sensor subsystem 9404 may be coupled to the host computing subsystem 9406 and the first, second, third and fourth LEDs 9402A, 9402B, 9402C and 9402D, respectively.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

For example, and in no way limiting the scope of the invention, in certain embodiments the sensor subsystem 9404 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

In certain embodiments, the host computing subsystem 9406 may comprise a skin hydration management module designed and implemented, in accordance with the principles of the invention.

Figure 95:
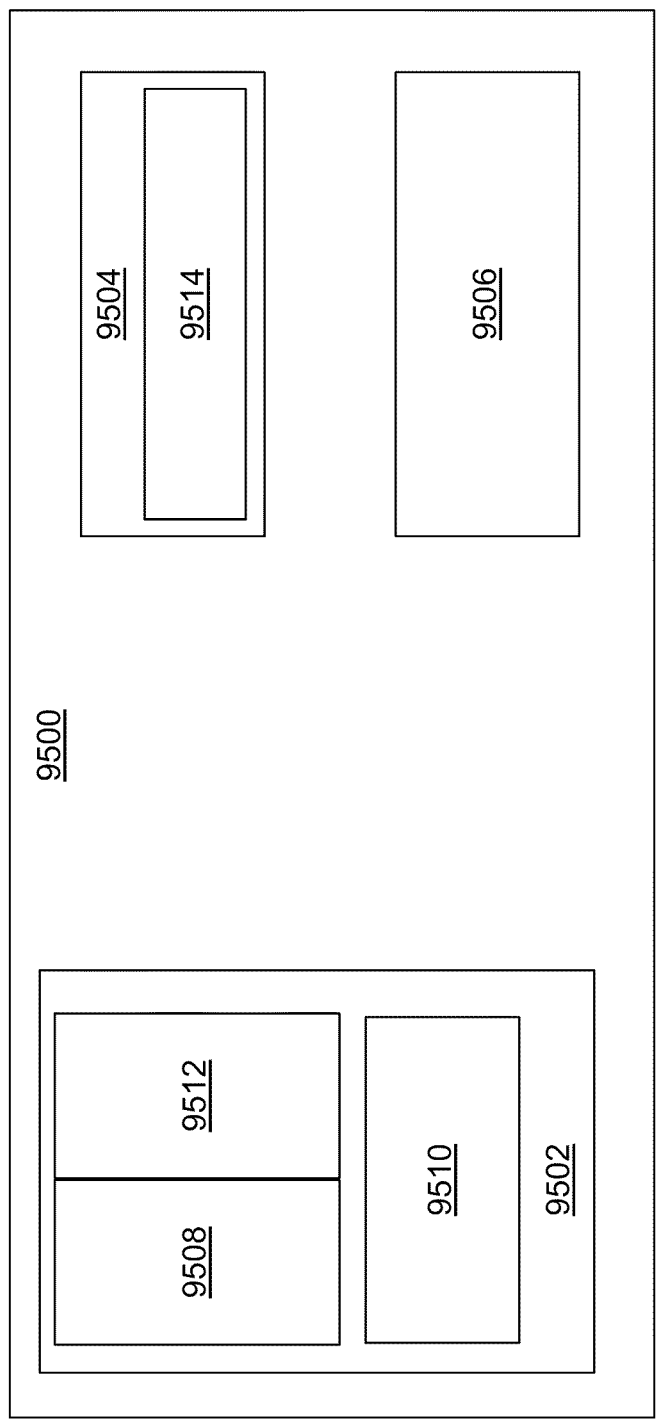
FIG. 95 is an exploded diagrammatic representation of the host computing subsystem, of FIG. 94, comprising the skin hydration management module designed and implemented in accordance with at least some embodiments of the invention.

FIG. 95 is an exploded diagrammatic representation of the host computing subsystem, of FIG. 1, comprising the skin hydration management module designed and implemented in accordance with at least some embodiments.

The host computing subsystem 9500 may comprise a processing unit 9502, a memory unit 9504 and an Input/Output (or I/O) unit 9506 respectively.

The host computing subsystem 9500, by virtue of its design and implementation, performs overall management of the hydration level of skin.

The processing unit 9502 may comprise an Arithmetic Logic Unit (or ALU) 9508, a Control Unit (or CU) 9510 and a Register Unit (or RU) 9512.

The memory unit 9504 comprises a skin hydration management module 9514.

In certain embodiments, the skin hydration management module for real- or point-time analysis of the continuously captured digital skin information and methods thereof is disclosed, in accordance with the principles of the invention. Specifically, in such embodiments, the skin hydration management module captures the skin information using at least one of Diffused Reflectance Spectroscopy, Red (R)-Green (G)-Blue (B) analysis of re-emitted white light and any combination thereof.

The terms "Diffused (or Diffuse) Reflectance Spectroscopy (or DRS)" and "Diffuse Reflectance Infrared Fourier Transform Spectroscopy (DRIFTS)" refer to a technique that collects and analyzes scattered Infrared (or IR) energy. It is used for measurement of fine particles, powders as well as rough surface. Specifically, it assesses the interaction of a surfactant with the inner particle or the adsorption of molecules on the particle surface. In DRS or DRIFTS, sampling is fast and easy because little or no sample preparation is required.

In certain other embodiments, the skin hydration management module may comprise one or more processes for determination of an assortment of qualitative and quantitative parameters thereby facilitating overall management of hydration level of skin. In such embodiments, at least a first process of the one or more processes determines moisture levels of skin. Specifically, this process may comprise one or more phases comprising emission of incident electromagnetic signals to skin, detection of degree of polarization of the electromagnetic signals reflected or re-emitted from skin and determination of the moisture levels based on the amount of polarized and reflected or re-emitted electromagnetic signals. Yet, in such embodiments, the first process may comprise one or more phases comprising combination of the determined moisture levels with skin color measurements thereby resulting in determination of skin luminosity.

Still, in certain such embodiments, at least a second process of the processes determines elasticity of skin. Specifically, this process may comprise one or more phases comprising the emission of the incident electromagnetic signals to skin, detection of a first aspect of polarization of the electromagnetic signals reflected by skin, correlation of the aspect of polarization with a concentration of elastin and determination of elasticity level based on the concentration of elastin.

Still further, in certain such embodiments, at least a third process of the processes determines firmness of skin. Specifically, this process may comprise or more phases comprising the of the incident electromagnetic signals to skin, the detection of a second aspect of polarization of the electromagnetic signals reflected by skin, the correlation of the aspect of polarization with the concentration of at least one of the elastin, a collagen, an activity of a sebaceous gland and any combination thereof and determination of the firmness based on the concentration of at least one of the elastin, collagen and sebaceous gland activity. In such embodiments, the sebaceous gland activity may be indicated by at least one of a number of glands, percent of glands open/closed and level of clog/fill.

Yet, in certain such embodiments, at least a fourth process of the processes obtains biophysical properties may comprise performing a spectral analysis of image data acquired from the degree of polarization of reflections and absorption and re-emission of incident light from skin. Specifically, the biophysical properties is at least one of a structure, form, concentration, number, size, state, and stage of at least one of a: melanocyte, melanin, hemoglobin, porphyrin, keratin, carotene, collagen, elastin, sebum, sebaceous gland activity, pore (sweat and sebaceous), moisture level, elasticity, luminosity, firmness, fine line, wrinkle count and stage, pore size, percent of open pores, skin elasticity, skin tension line, spot, skin color, psoriasis, allergy, red area, general skin disorder or infection, tumor, sunburn, rash, scratch, pimple, acne, insect bite, itch, bleeding, injury, inflammation, photodamage, pigmentation, tone, tattoo, percent burn/burn classification, mole (naevi, nevus), aspect of a skin lesion (structure, color, dimensions/asymmetry), melanoma, dermally observed disorder, cutaneous lesion, cellulite, boil, blistering disease, congenital dermal syndrome, (sub)-cutaneous mycoses, melasma, vascular condition, rosacea, spider vein, texture, skin ulcer, wound healing, post-operative tracking, melanocytic lesion, non-melanocytic lesion, basal cell carcinoma, seborrhoic keratosis, sebum (oiliness), nail- and/or hair-related concern, and the like.

In certain embodiments, the WHM 9400 may include the one or more LEDs 9402 capable of directing incident electromagnetic radiation to a location on the skin of a user, the sensor subsystem 9404 for measuring various parameters of radiation re-emitted from the location, and the skin hydration management module 9514, as disclosed in FIG. 95, capable of managing skin hydration level in real- or point-time, based partly on at least one of RGB analysis and diffused reflectance analysis of the radiation parameters. It must be noted here that the aforementioned embodiments have been explained in conjunction with FIGS. 94 and 95.

Typically, imaging spectroscopy (or spectral imaging or chemical imaging) is similar to color photography. But, unlike color photography, in imaging spectroscopy each pixel acquires many bands of light intensity data from the spectrum, instead of just the three bands of the RGB color model. More precisely, it is the simultaneous acquisition of spatially coregistered images in many spectrally contiguous bands.

Further, hyperspectral data is often used to determine materials present in images. For example, materials of interest could include roadways, vegetation, and specific targets (i.e. pollutants, hazardous materials, etc.) Trivially, each pixel of a hyperspectral image could be compared to a material database to determine the type of material making up the pixel. However, many hyperspectral imaging platforms have low resolution (i.e. >5 m per pixel) thereby causing each pixel to be a mixture of several materials. The process of unmixing one of these 'mixed' pixels is called hyperspectral image unmixing or simply hyperspectral unmixing.

In general, there are many algorithms to unmix hyperspectral data each with their own strengths and weaknesses. Many such algorithms assume that pure pixels (i.e. pixels that contain only one material) are present in images. For example, some algorithms to perform unmixing are Pixel Purity Index (or PPI), N-Finder Algorithm (or NFINDR), Gift Wrapping Algorithm, Independent Component Analysis Endmember Extraction Algorithm (or ICA-EEA), Vertex Component Analysis (or VCA), Principal component analysis (or PCA), Multi Endmembers Spatial Mixture Analysis (or MESMA), Support Vector Machines (or SVM) or Analytical Neural Network (or ANN), and the like.

In certain embodiments, the WHM 9400 employs white light (or other specific wavelengths) for measuring the concentration of specific ions in the blood stream and the skin layers. By way of example, and in no way limiting the scope of the invention, the specific ions may be at least one of sodium ([Na+]), potassium ([K+]), and chloride ([Cl—]). It must be noted here that the presence of these salts/ions and levels thereof tracked in due course indicates normal level of user vis-à-vis specific metabolism and body of the user.

The term "skin turgor" as used herein refers to an abnormality in the skin's ability to change shape and return to normal (i.e. elasticity.) Skin turgor is a sign commonly used by health care workers to assess the degree of fluid loss or dehydration. Fluid loss can occur from common conditions, such as diarrhea or vomiting. In certain situations, infants and young children with vomiting, diarrhea and decreased or no fluid intake can rapidly lose a significant amount of fluid. Fever speeds up this process. To determine skin turgor, the health care provider grasps the skin on the back of the hand, lower arm, or abdomen between two fingers so that it is tented up. The skin is held for a few seconds then released. Skin with normal turgor snaps rapidly back to its normal position. Skin with decreased turgor remains elevated and returns slowly to its normal position.

In certain such embodiments, the WHM 9400 measures skin turgor as a secondary measurement tool to create a combined hydration impact score. By way of example, and in no way limiting the scope of the invention, the WHM 100 may implement methods and systems for management of skin hydration as disclosed in an article "SENSITIVITY AND SPECIFICITY OF CLINICAL SIGNS FOR ASSESSMENT OF DEHYDRATION IN ENDURANCE ATHLETES" to James McGarvey et al. and published online in Br J Sports Med. on 3 Nov. 2008, the disclosure of which is incorporated herein by reference in its entirety. Thus, all other ins-and-outs in connection with the aforementioned embodiment have not been further disclosed herein.

In certain embodiments, the WHM 9400 of FIG. 94 may be capable of transmitting to and/or receiving from the remote computing subsystem 9410 pluralities of information including the skin hydration assessment information through the network 9408. Specifically, the skin hydration management module, residing in the memory of the host computing subsystem, generates the skin hydration assessment information that is transmitted to the remote computing subsystem 9410 through the network 9408.

In certain specific embodiments, the remote computing subsystem 9410 may in essence be similar to the host computing subsystem 9406. Specifically, the remote computing subsystem 9410 may comprise a processing unit, a memory unit and an Input/Output (or I/O) unit (all not shown explicitly) respectively. By way of example, and in no way limiting the scope of the invention, the remote computing subsystem 9410 may be a wristwatch or a Bluetooth™-enabled or -capable device.

The remote computing subsystem 9410 may be coupled to the WHM 9400. Specifically, the remote computing subsystem 9410 may be coupled to the I/O unit of the host computing subsystem of the WHM 9400, through the network 9408.

The remote computing subsystem 9410, by virtue of its design and implementation, may perform at least one of the following operations: processing the received (or unprocessed) skin hydration assessment information, displaying the processed and/or received skin hydration assessment information and performing any combination thereof.

The processing unit may comprise an Arithmetic Logic Unit (or ALU), a Control Unit (or CU) and a Register Unit (or RU).

Figure 96:
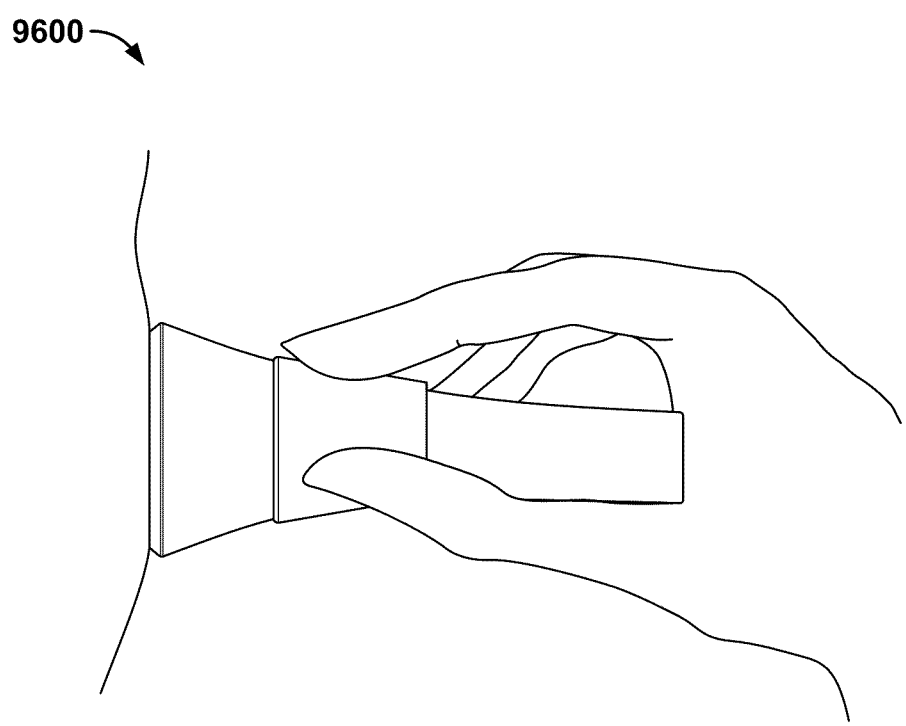
FIG. 96 is a perspective view of the WHM of FIG. 94 designed and implemented as a handheld monitor for measurement of hydration status, in accordance with some other embodiments of the invention.

FIG. 96 is a perspective view of the WHM of FIG. 94 designed and implemented as a handheld hydration monitor, in accordance with some other embodiments of the invention As shown in FIG. 96, the WHM 9400 may be a simple handheld device that checks for hydration status. In such specific embodiments, the WHM 9400 could be used in places, such as saunas, spas, desert environments, and the like.

Electrical Impedance Tomography (or EIT) is a medical imaging technique in which an image of the conductivity or permittivity of part of the body is inferred from surface electrical measurements. Typically, conducting electrodes are attached to the skin of the subject and small alternating currents are applied to some or all of the electrodes. The resulting electrical potentials are measured, and the process may be repeated for numerous different configurations of applied current.

In general, the electrical conductivity and permittivity in biological tissues varies between tissue types and depending on temperature and physiological factors. For example, lungs become less conductive as the alveoli become filled with air. In EIT, adhesive electrodes are applied to the skin and an electric current, typically a few milli-Amperes (or mA) of Alternating Current (or AC) at a frequency of 10–100 kHz, is applied across two or more electrodes. Other electrodes are used to measure the resulting voltage. This is repeated for numerous "stimulation patterns", such as successive pairs of adjacent electrodes.

Operationally, the currents used are relatively small and certainly below the threshold at which they would cause stimulation of nerves. The frequency of the AC is sufficiently high not to give rise electrolytic effects in the body. In addition, the Ohmic power dissipated is sufficiently small and diffused over the body to be easily handled by the body's thermoregulatory system. Specifically, the current is applied using current sources, either a single current source switched between electrodes using a multiplexor or a system of Voltage-to-Current converters, one for each electrode, each controlled by a Digital-to-Analog Converter (or DAC). The measurements again may be taken either by a single voltage measurement circuit multiplexed over the electrodes or a separate circuit for each electrode. Earlier systems typically used an analog demodulation circuit to convert the alternating voltage to a direct current level then an analog to digital converter. Many recent systems convert the alternating signal directly, the demodulation then being performed digitally. Many EIT systems are capable of working at several frequencies and can measure both the magnitude and phase of the voltage.

The voltages measured are then passed to a computer to perform the reconstruction and display of the image. If images are required in real time a typical approach is the application of some form of regularized inverse of a linearization of the forward problem. In most practical systems used in a medical setting a 'difference image' is formed. That is, the differences in voltage between two time points are left-multiplied by the regularized inverse to produce an approximate difference between the permittivity and conductivity images. Another approach is to construct a finite element model of the body and adjust the conductivities (for example using a variant of Levenburg-Marquart method) to fit the measured data. This is more challenging as it requires an accurate body shape and the exact position of the electrodes.

In certain specific embodiments, the WHM 9400 may employ electrical impedance techniques for imaging skin, in accordance with the principles of the invention.

In certain embodiments, the WHM 9400 may operate in one or more distinct modes thereby performing at least one of State-Independent and State-Dependent Hydration Management of organ systems.

In certain such embodiments, the WHM 9400 may be implemented as an Organ System State-Independent WHM. By way of example and in now way limiting the scope of the invention, in a first mode of operation the WHM 9400 may be applied to the epidermal layer. In such embodiments, the WHM 9400 may measure the amount of intracellular water/hydration level in the skin.

In yet certain other embodiments, the WHM 9400 may be implemented as an Organ System State-Dependent WHM. By way of example and in now way limiting the scope of the invention, in a second mode of operation, the WHM 9400 may be implemented as a dynamic hydration level indicator. In the second mode of operation, the WHM 9400 may measure the sweat from sweat pores and ions thereof, such as Potassium (or K), Sodium (or Na), and the like, to measure the current activity level and hydration, where user is in a state of motion (or inertia of motion).

Likewise, in a third mode of operation, the WHM 9400 may be implemented as a static hydration level indicator. In the third mode of operation, the WHM 9400 may measure the hydration level in the epidermal and dermal layers and the blood stream when user is in a state of rest (or inertia of rest).

In general, hydrogen bonds have dual properties, namely classical, i.e. electrostatic interaction based on Coulomb's law, and quantum, i.e. wave function based on Schrödinger equation. In certain embodiments, there are disclosed methods, apparatuses and systems for analysis of water using OMF. In certain such embodiments, owing to the fact that Planck's constant is one of the main criteria for decisions in connection with processes and quantum properties thereof use is made of electrical and magnetic forces of valence electrons as a point of departure to develop the method for Opto-Magnetic Fingerprinting of matter. It must be noted here that during the study of different types of matter, observation of a phenomena is obtained from spectral convolution data of digital images. These digital images characterize matter from both covalent and non-covalent bonding. By way of example, and in no way limiting the scope of the invention, water is matter that is most abundant with hydrogen bonds. In certain such situations, the results of 18.2 MΩ water investigations at different temperatures and under the influence of constant and variable magnetic fields by OMM are disclosed.

In certain specific embodiments, based on the data obtained neutron diffraction experiments it is observable that the product of distance between center of hydrogen and oxygen atoms in a covalent bond, i.e. d (O—H), of different structures is between 95 pm and 120 pm, while distance of center of hydrogen and oxygen atoms in non-covalent bond d (O.H) is between 120 pm and 200 pm. However, for each type of matter product value d (O—H)×d (O.H) is about 162 pm. Still further, systematic investigation and quantitative analysis of bond lengths of O—H.O showed that bond-valence parameters of hydrogen bonds follow Golden ratio rule, whose value is around 1.62.

As a general rule, taking into consideration the fact that water is matter that is most abundant with hydrogen bonds, which may be organized in molecular networks thereby providing an indication that water via hydrogen bonds (i.e. with classical and quantum properties), may play a role in molecular and biomolecular recognition. From this viewpoint, there two primary goals in modern day pharmacy are: (1) understanding mechanism of molecular recognition in water solution and (2) water structure for drug design. Further, some pharmacologists are aware of importance of water structure for drug design owing to the fact that modeling ligand-receptor interaction has to include specific geometry, which relates to water structure. Still further, it is well known that hydrogen bonds are a link between two nucleotide chains in DNA and support existence of secondary, ternary and quaternary structure of proteins. Since, hydrogen bonds play important role in water, biomolecular structures, hydrated crystals and nanostructures research to characterize water and its hydrogen bonds by Opto-Magnetic Method. By this method, based on light-water interaction, it is possible to collect data of both classical and quantum actions of water molecules and interactions between them.

Operationally, this method is based on light-matter interaction and ratio of electrical and magnetic forces of covalent bonds and intermolecular bonds of matter. DNA research indicates that both classical and quantum mechanical approach give same phenomenological results for structures thereof. This is owing to one simple reason that is for stationary quantum state Hamiltonian is a sum of kinetic (T) and potential (V) energy, while Lagrangian is a difference between them when system is in equilibrium with external forces. Two similar pictures, one classical and another quantum, of same object with very close similar results from energy point of view exist. The goal is to find out how hydrogen bonds participate in water to be more or less classical or quantum entity. Therefore, use is made of Planck's constant (h) as the first criteria to estimate whether an object is classical or quantum. Since Planck's constant by nature is action than product of force (F), distance (d) and time (t) of action have to has value h ($6.626 \times 10^{-34}$ Js), or close to if system is quantum one. However, what will be value for coupling quantum-classical system, and when classical one becomes dominant, it is unknown.

Reiterating again, Planck's constant is link between energy (E) and electromagnetic wave oscillation (v), as E=hv. In certain situations, an analysis of the electrical vis-à-vis magnetic interaction between two electron charges in neighboring atoms in relative motion in matter may provide a solution. Further, it is known that is exigent to calculate the magnetic interaction between two charged particles in motion relative to an observer O in a form similar to the electric interaction given by Coulomb's law. In operation, a comparative study of the order of magnitude of the magnetic interaction with the electrical interaction. For example, and in no way of limiting the inventions, on taking into consideration two charges q and q' of neighboring atoms moving with velocities v and v' relative to observer may simplify the formulas, because only order of magnitude is important. Thus, the electrical force produced by q' on q as measured by O is qE.

Further, the magnetic field produced by q', on using equation B=1/c2 (v×E), is of order of magnitude of v'E/c2 and the magnetic force on q is of the order of qvB=(vv'/c2) qE. Since, qE is the electrical force on q than magnetic force/electrical force (FM/FE)≈vv'/c2. Still further, if the velocities of the charges are small compared with the velocity of light c, the magnetic force is negligible compared to the electrical force and in many cases can be ignored. The orbital velocity of valence electrons in atoms is about 106 m/s, FM/FE≈10−4. This implies that existence of semi-classical/quantum could be 6,626×10−34<h*<6,626×10−30. In this action area, from energy point of view, simultaneously exists both classical and quantum phenomena. Because, this value of action coupling classical and quantum phenomena, means that this action area is perfect one for hydrogen bond investigation. Therefore, if action is h*>6, 626×10−30 Js than phenomena are classical, while if it is 6,626×10−34 Js, it is quantum. Electrical force is closer to classical interaction (Coulomb's law), while magnetic force is closer for order four to quantum interaction than electrical one.

Specifically, in order to calculate action we should know values of force, distance and time of hydrogen bonds activity. In certain specific embodiments, the hydrogen bonds may posses the following specifications: Average values for force 2.5×10−10 N, distance 1.6×10−10 m and time 50×10−15 s. Based on the quantitative parameters and the values thereof the values give action of h*=F×d×t=(2.5×10−10)× (1.6×10−10)×(50×10−15)=0.5×10−33 Js, what is semi-quantum action. Hydrogen bond in water is for three orders closer to quantum (6,626×10−34 Js) than to classical (6,626×10−30 Js) action. According to ratio FM/FE≈10−4 it means that magnetic and electrical fingerprint of hydrogen bond of water will be different, because action of magnetic force is separated it two pats (quantum and classical), while electrical force is only classical, because domain of its action is 10−29 Js (0.5×10−33×104≈10−29 Js).

In certain other embodiments, experimental measurements of quantum and classical contribution of hydrogen bonds action in water are disclosed. Specifically, there is disclosed experimental measurements of quantum and classical contribution of hydrogen bonds action in water using OMF device. Further, there is also disclosed separate electrical and magnetic action in light-water interaction. In operation, pictures of surfaces that are captured by classical optical microscope is based on electromagnetic property of light, while OMF is based on difference between diffuse white light and reflected polarized light. In here, reflected polarized light is produced when source of diffuse light irradiates the surface of matter under certain angle (Brewster's angle). Each type of matter has special different angle value of light polarization.

Further, it is found that angle of reflected polarized light of water is about 53 degree. Since reflected polarized light contains electrical component of light-matter interaction, taking the difference between white light (electromagnetic) and reflected polarized light (electrical) fields gives magnetic properties of matter (Opto-Magnetic Fingerprint).

Still further, digital images in RGB (R-red, G-green, B-blue) system are used in analysis, therefore basic pixel data in red and blue channels for white diffuse light (W) and reflected polarized white light (P). Algorithm for data analysis is based on chromaticity diagram called "Maxwell's triangle" and spectral convolution operation according to ratio of (R−B)&(W−P). The abbreviated designation means that Red minus Blue wavelength of White light and reflected Polarized light are used in spectral convolution algorithm to calculate data for Opto-Magnetic Fingerprint of matter. Therefore, method and algorithm for creating unique spectral fingerprint are based on the convolution of RGB color channel spectral plots generated from digital images that capture single and multi-wavelength light-matter interaction.

Figure 97:
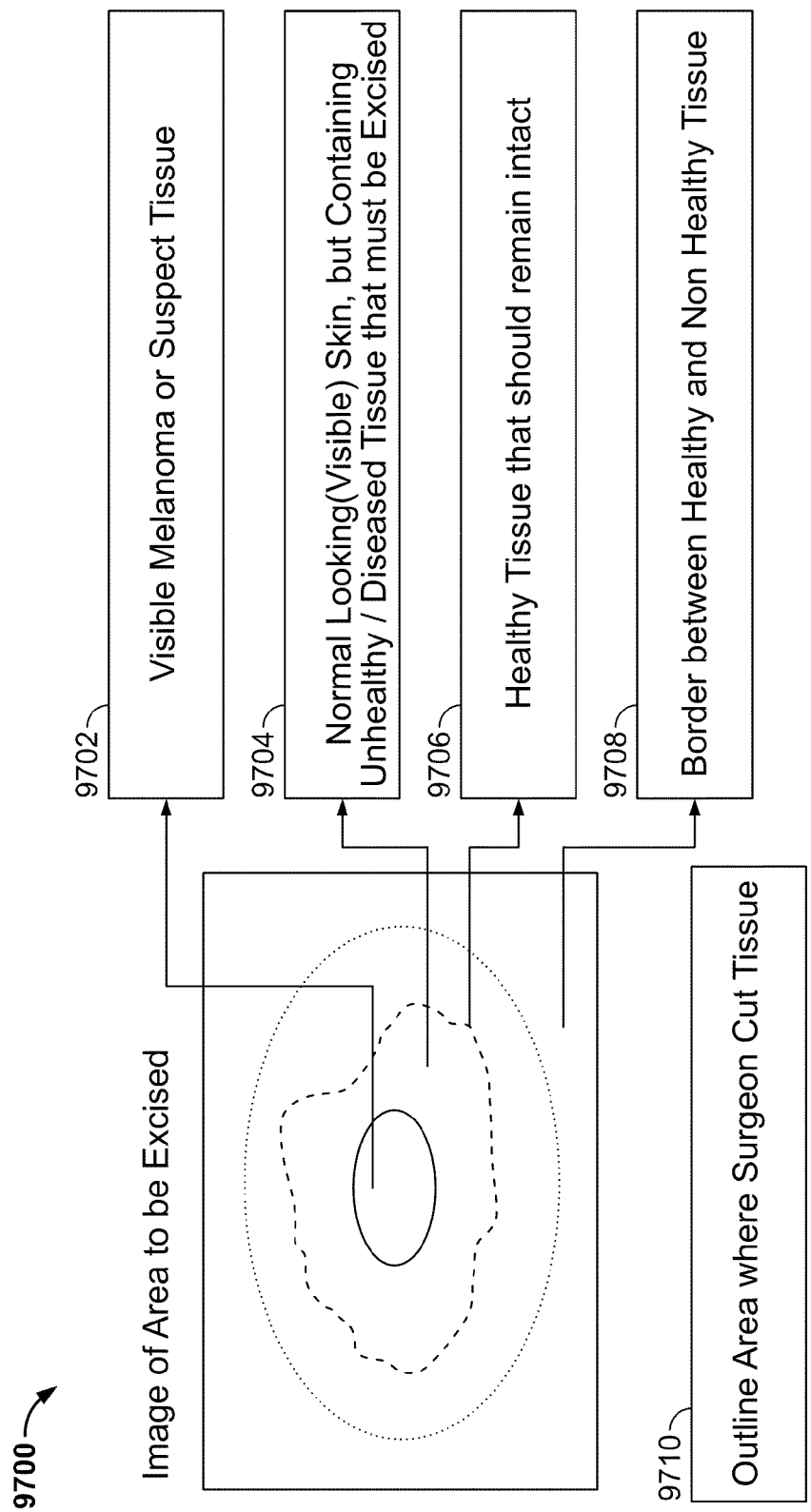
FIG. 97 is a diagram depicting an image of area to be excised.

Accordingly, the foregoing description of the present technique should be considered as merely illustrative of the principles of the present technique and not in limitation thereof. Referring to FIG. 97 is a diagram 9700 depicting an image of area to be exercised. The image of the skin is captured for distinguishing between a healthy biological skin tissue and an unhealthy biological skin tissue for enabling an excision proximate to the healthy biological skin tissue. The biological skin tissue may be of the human skin tissue, the veterinary skin tissue, the agricultural product skin tissue including a finite and natural life cycle, and the like. In accordance with an example of the present invention, 9702 depicts the visible melanoma or suspect tissue in the captured, 9704 depicts the normal looking (visible) skin (this comprises unhealthy/diseased tissue that must be excised), 9706 depicts the healthy skin tissue that should remain intact, 9708 depicts the border between healthy and non healthy tissue and 9710 depicts the outlined area for where the surgeon should cut the tissue. The image capturing device captures the image of the skin site for identifying the healthy biological skin tissue, the diseased biological skin tissue and tracking growth of the unhealthy biological skin tissue. The biological skin tissue comprises a finite and natural life cycle. The captured image of the particular site of skin is analyzed in pixel by pixel manner by analyzer of skin images for generating a sample of most frequent of a standard R G B (sRGB) color component.

According to an exemplary embodiment of the present invention, an algorithmic method based on optical analysis of skin biophysical characteristics of captured image under white light and standard RGB analysis of image in pixel by pixel manner may be employed for precisely determining the presence of a healthy tissue and suspect tissue. This helps the surgeon for leaving a larger amount of healthy tissue around a site, decrease recurrance and micrometastasis in surrounding skin while allowing minimal surgical morbidity. The method may be used to image a particular site, and determine border area, suspect tissue, either before surgery, in pre-surgery, or during surgery. The method would also show post surgical analysis of affected skin tissue.

Figure 98:
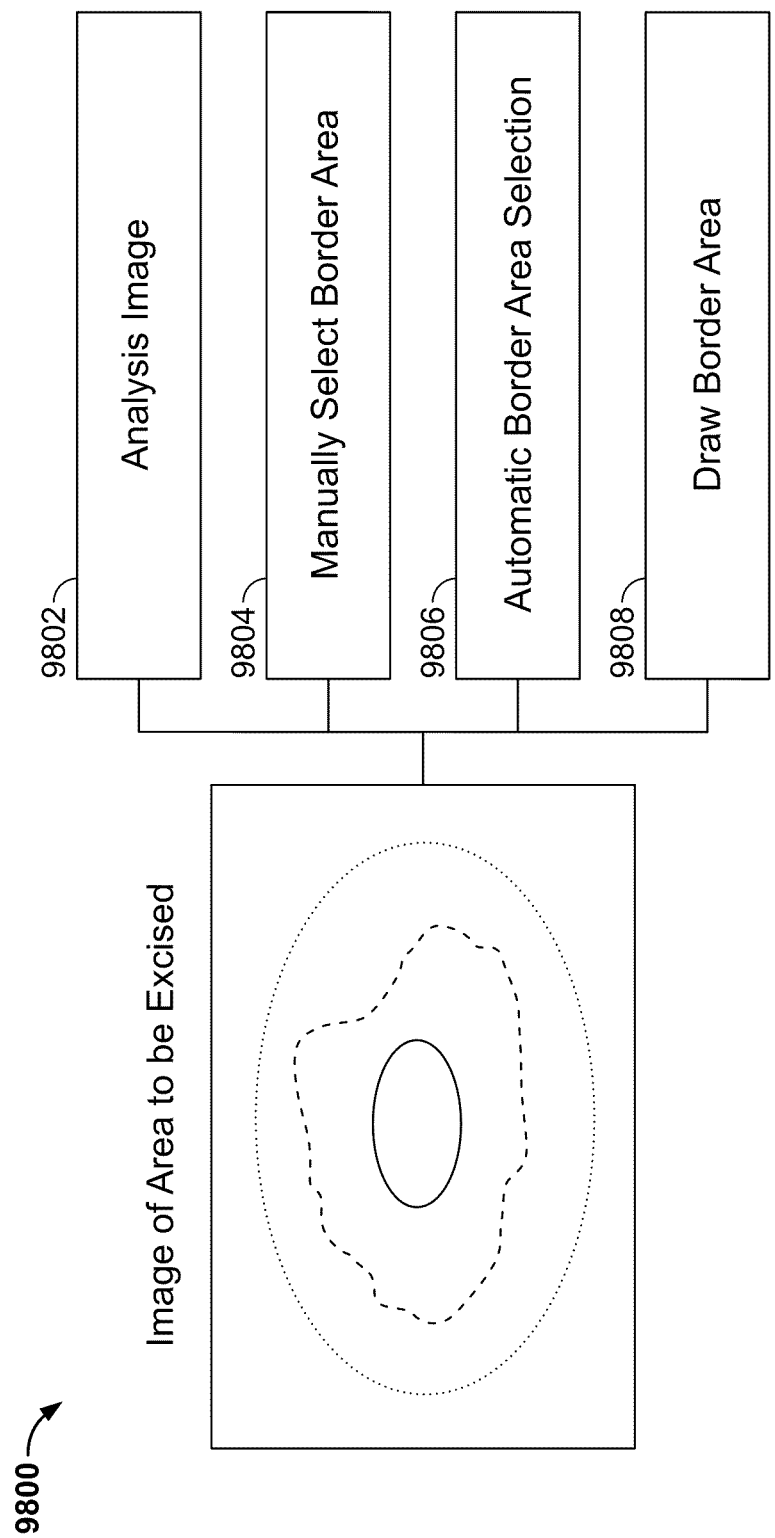
FIG. 98 is a diagram depicting the process employed for automatically determining the area to be excised.

Referring to FIG. 98 is a diagram 9800 depicting the process employed for automatically determining the area to be exercised. According to an example, analysis of image 9802 is done using an optical analysis device coupled to the image capturing device and the surgical intervention unit. The analysis would include controls for type of diseased tissue. The border area is selected manually 9804 for distinguishing between healthy biological skin tissue and suspect skin tissue. Border area is selected manually based on the implied healthy non healthy tissue. In accordance with an example of the present invention, automatically the border area is selected 9806 by the system so that the surgeon could leave a larger amount of healthy tissue around a site, decrease recurrance and micrometastasis in surrounding skin while allowing minimal surgical morbidity. The algorithmic method to best determine the border area based on user-definable parameters such as minimally width, desired shape (circular, square, for example). Finally a border area is drawn 9808 for determining the exact area to be excised for treatment. A hypo-allergenic ink or other marking substance may be used to draw on the surface of the skin automatically using an attached device.

Figure 99:
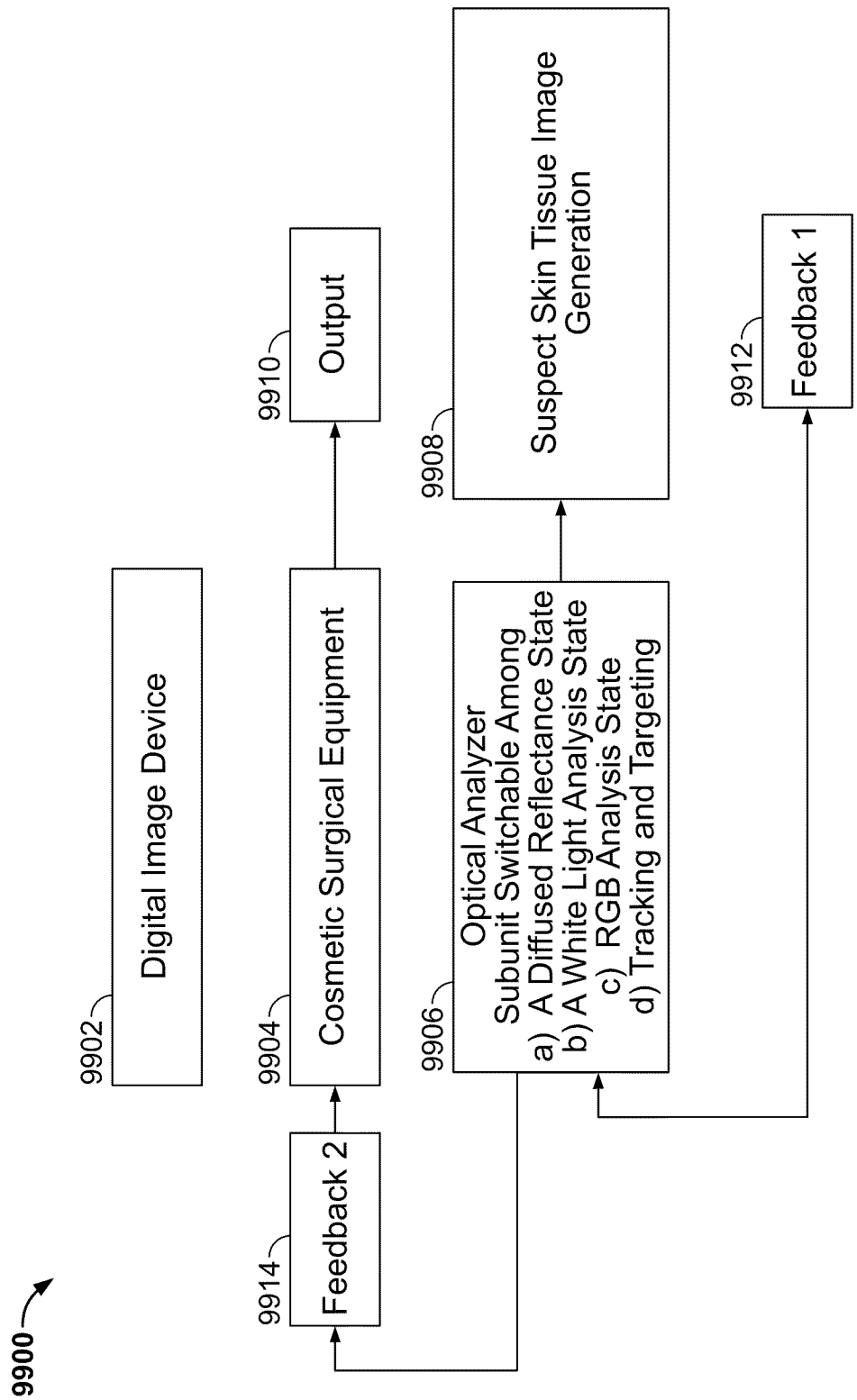
FIG. 99 is a diagram depicting a system for distinguishing between a healthy skin biological tissue and an unhealthy biological skin tissue for enabling an excision proximate to the healthy biological tissue.

Referring to FIG. 99 is a diagram 9900 depicting a system for distinguishing between the healthy skin biological skin tissue and an unhealthy biological skin tissue for enabling an excision proximate to the healthy biological tissue. The image of skin site may be captured by the digital imaging device 9902. The digital imaging device may be used for identifying a healthy biological skin tissue; a diseased biological skin tissue; and tracking growth of the unhealthy biological skin tissue. The digital imaging device may comprise a real time digital camera device. The captured image may be submitted to cosmetic surgical equipment 9904 for further analysis of the image for distinguishing between the healthy biological skin tissue and the suspect biological skin tissue. The optical analyzer 9906 is coupled to the feedback unit 9912 and cosmetic surgical unit. The optical analyzer further comprises sub unit switchable among a diffused reflectance state, a white light analysis state, RGB analysis state and tracking and targeting state. The optical analysis device coupled to the image capturing device comprises the Red Green Blue (RGB) unit further comprising, the sampler coupled to a pixel by pixel by analyzer of skin images for generating a sample of most frequent of a standard R G B (sRGB) color component, the Gaussian probabilistic distributer for modeling the sRGB component color distribution with estimated parameters on the generated sRGB color sample for the captured image and the photo type generator coupled to the Gaussian probabilistic distributer for generating the phototype of the biological skin tissue through a decision tree unit.

According to an exemplary embodiment of the present invention, the white light unit further comprises the comparison unit for comparing extreme positions of at least two unique convolutions in white light and in polarized light responsive to convoluting data of the first skin image and a second skin image and an output unit for determining a distance between minimum and maximum intensity positions in convoluted red minus blue wavelength scale in the at least two unique convolutions for generating a numerical skin type output. According to an example, the optical analyzer further comprises the skin biophysical analysis unit further including at least one of the following parameters: a skin fairness parameter, a skin darkness parameter, systemic hydration, skin hydration, skin firmness, skin wrinkles, pore size on skin, spots on skin, glow on skin, melanocyte, melanin, hemoglobin, porphyrin, keratin, carotene, collagen, elastin, sebum, sebaceous gland activity, sweat pore, sebaceous pore, moisture level, elasticity, luminosity, firmness, fine line, wrinkle count, pore size, percent of open pores, skin elasticity, skin tension line, spots, viscosity, epidermal, dermal sebum levels, skin color, psoriasis, allergy, red area, general skin disorder, infection, tumor, sunburn, rash, scratch, pimple, acne, insect bite, itch, bleeding, injury, inflammation, photodamage, pigmentation, tone, tattoo, percent burn, burn classification, mole, aspect of a skin lesion, melanoma, dermally observed disorder, cutaneous lesion, cellulite, boil, blistering disease, congenital dermal syndrome, cutaneous mycoses, melasma, vascular condition, rosacea, spider vein, texture, skin ulcer, wound healing, post-operative tracking, melanocytic lesion, nonmelanocytic lesion, basal cell carcinoma and seborrhoic keratosis.

According to an example, the optical analysis device further comprising a diffused reflectance unit for generating the predetermined set of wavelengths for reflection intensity measurement of the spectral data, utilizing the plurality of reflection intensity values and the plurality of reflection intensity ratio values of the spectral data for classification of the skin type responsive to generating a predetermined set of wavelengths, normalizing the reflection intensity values of spectral data with respect to spectral source and spectral classification of the skin type and generating a skin photo type output by applying nonparametric regression analysis on measured spectral data responsive to normalizing the reflection intensity values of spectral data.

In accordance with an example of the present invention, the output of optical analyzer is fed to the suspect skin tissue image generation unit 9908. The suspect skin tissue image generator coupled to the optical analysis device for imaging a site on the biological skin area, determining the border area on the site and determining the suspect skin tissue. The suspect tissue image generator comprises the image of an area to be excised which includes the visible suspect skin tissue, the normal visible skin tissue surrounding the visible suspect tissue for excision, the border between the visible suspect tissue and the normal visible skin tissue, the healthy skin tissue surrounding both the visible suspect skin tissue and the normal visible skin tissue, outlined area for the surgeon to cut a predetermined skin tissue portion including the visible suspect skin tissue, the normal visible skin tissue, the border and the healthy skin tissue.

The output of suspect skin tissue image generation unit 9908 is fed to the feed back unit 9912. The feed back obtained is fed to the optical analyzer 9906 wherein the analysis is further done based on the obtained feedback. The analysis data is further fed to the cosmetic surgical equipment 9904 through another additional feed back unit 9914 coupled between the optical analyzer 9906 and cosmetic surgical equipment 9904. Finally an accurate area to be excised is given as output 9910.

As will be appreciated by a person skilled in the art, the various implementations of the present technique provide a variety of advantages. Firstly, the process employed for distinguishing between a healthy biological skin tissue and an unhealthy biological skin tissue for enabling an excision proximate to the healthy biological skin tissue Allows more precise determination of the border area instead of relying on subjective experience or fixed tables. Secondly, the algorithmic method may be used to image a particular site, and automatically determine border area, suspect tissue, either before surgery, in pre-surgery, or during surgery. The algorithmic method would also show post surgical analysis of affected skin tissue. Thirdly, the advantage of this system is better isolated suspect tissue and retaining a greater degree of healthier tissue. Fourthly, the system allows a surgeon or other specialist to precisely determine the border area around a surgical intervention for primary cutaneous melanoma, skin cancers, and other skin diseases that require excision around the skin.

Figure 100:
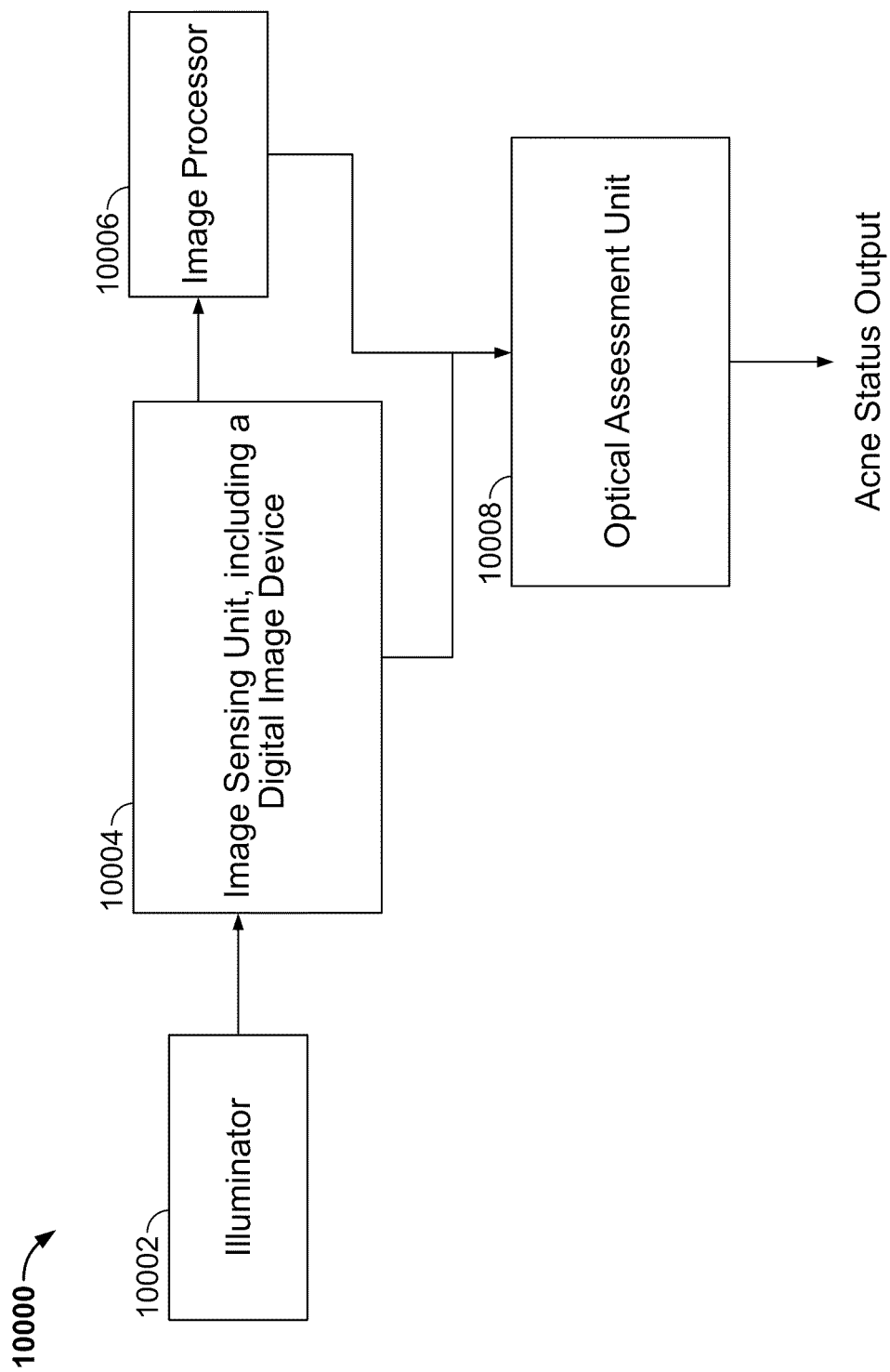
FIG. 100 is a schematic diagram depicting a system for determining a predisposition of sebaceous pores and skin structures.

Referring to FIG. 100 is a schematic diagram 10000 depicting a system for determining a predisposition of sebaceous pores and skin structures. The system may include an illuminator 10002, an image sensing unit including a digital imaging device 10004 coupled to the illuminator and image processor 10006 for imaging the portion of the surface on the skin and an optical assessment unit 10008 is coupled to the image sensing unit including the digital imaging device 10004 and the image processor 10006. According to an example of the present invention, the optical assessment unit 10008 may include a spectroscopic analysis unit, which may further include a diffused reflectance color analysis unit.

In accordance with an exemplary embodiment of the present invention, the illuminator 10002 for illuminating a portion of a surface on the skin may include the white light source, the blue light source, and an ultraviolet light source and the like. The images of skin are captured with the imaging sensing unit including the digital imaging device 10004 coupled to the illuminator 10002. The images may be captured under white light or blue light or ultra violet light source and the like. According to an example, the propensity to get acne and acne status output can be ascertained based on anatomical-physiological factors. The characteristics of the skin may be measured on at least one of discrete scale and a continuous scale. The continuous scale comprises a plurality of acne improvement and worsening conditions further including a predetermined number of acne status outcomes. The continuous scale and discrete scale may include at least one of the following acne conditions of an acne condition unit closed, partially open and open for sebaceous pore opening; full, partially full and empty for sebaceous pore contents; blocked, partially blocked and clear for gland and hair connection; full, partially full and empty for sebaceous gland contents; active, partially active and inactive for sebaceous gland activity; and high, medium, low and none for inflammation. The acne condition unit may comprise a questionnaire unit for generating an acne status questionnaire.

According to an exemplary embodiment of the present invention, the image processor may include a plurality of characteristic acne elements elimination unit for isolating sebaceous pore openings, sebaceous pore channel, sebaceous pore intersection, sebaceous gland intersection, blockage of sebaceous pore openings, contents of the sebaceous pore, unhealthiness arising out of age of the sebaceous gland, inflammation around the gland, inflammation around the sebaceous pores, inflammation around the sebaceous gland, inflammation around hair follicles and level of p-acne bacteria. The plurality of characteristic acne elements elimination unit may also include determining age of sebum, whether the sebaceous gland is actively producing sebum and a level of p-acne bacteria.

In accordance with an exemplary embodiment of the present invention, the output of the image processor 10006 is fed to the optical assessment unit 10008. The optical assessment unit 10008 may include Red Green Blue (RGB) analysis device further including a standard RGB (sRGB) color unit for analysis of the captured digital image. The white light polarization device coupled to the RGB analysis device compares extreme positions of at least two unique convolutions in white light and in polarized light in response to the convoluting data of the first captured image and the second captured image. According to an example, the white light polarization device may further include an output generator for determining the distance between minimum and maximum intensity positions in the convoluted red minus blue wavelength scale in the at least two unique convolutions to generate a numerical skin type output. The correlation level may include at least one of a fuzzy logic, a non-linear regression, a genetic algorithm and a neural network The digital color analysis device coupled to both the white light polarization device and the RGB analysis device for generating a combination of color systems for determining the health status of the imaged portion of the surface on the skin. The combination of color systems may include at least one of the YIQ, YCbCr, L*a*b* (CIELAB color space); L*u*v* (CIELUV color space); HSL (Hue, Saturation, Lightness) and HSV (Hue, Saturation, Value) color systems for image analysis in accordance with an example of the present invention, which is not limited to the listed color systems. According to an example of the present invention the system may further include a marking unit for outlining and marking areas on the surface on the skin to thereby enable surgical excision of the skin structure. Finally the optical assessment unit 10008 outputs the acne status.

Figure 101:
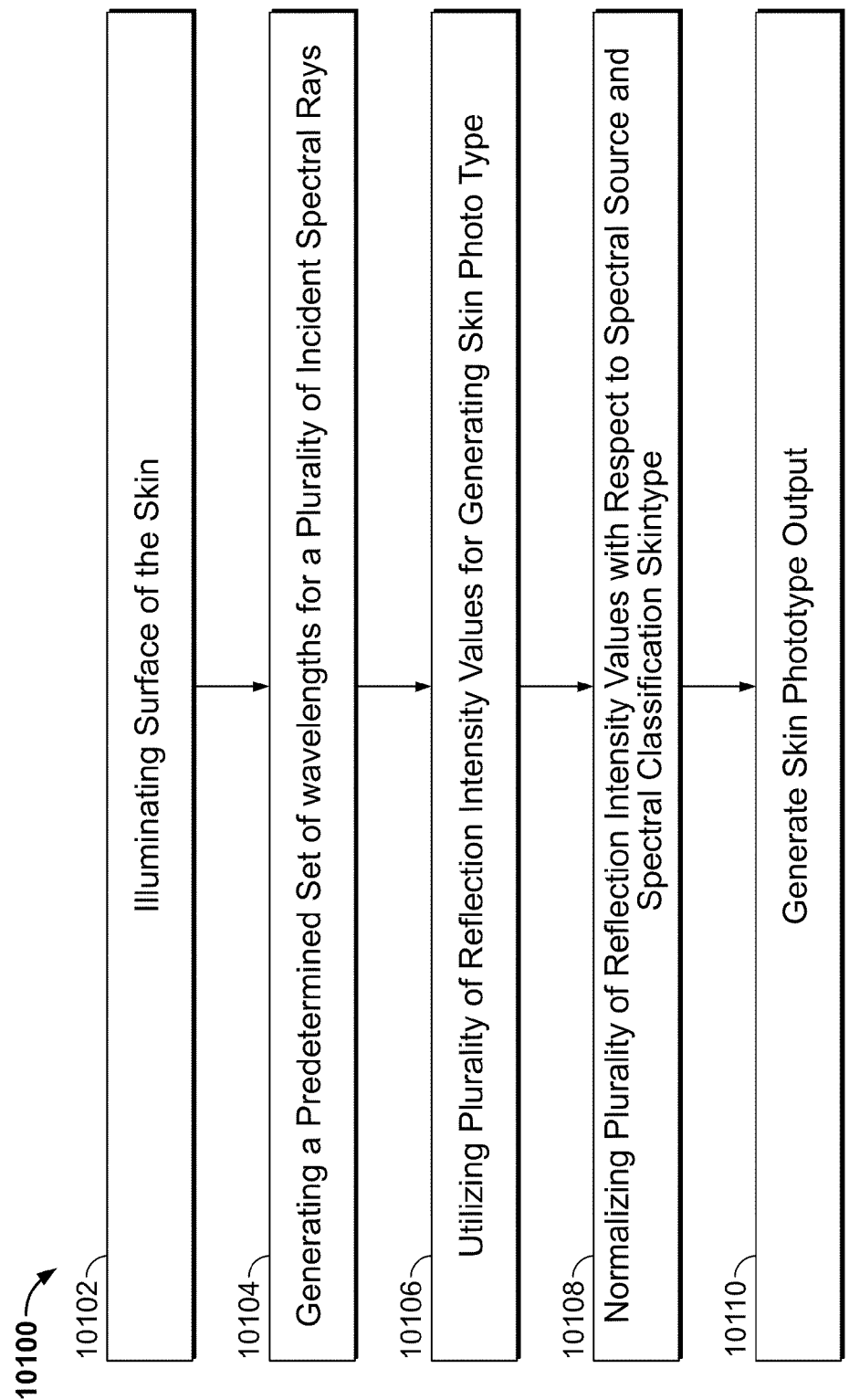
FIG. 101 is a flowchart illustrating a process for generating a skin phototype, in accordance with an aspect of the present technique.

Referring to FIG. 101 is a flowchart 10100 illustrating a process for, in accordance with an aspect of the present technique. The process starts at block 10100 wherein the surface of the skin is illuminated by a light source. Spectral rays are reflected back once the light is illuminated on the surface of the skin. Now at block 10102, a predetermined set of wave lengths may be generated for reflection intensity measurements of the spectral data. The set of wave lengths may be generated for a plurality of incident spectral rays. In accordance with an example of the invention, at block 10103 a plurality of reflection intensity values and plurality of reflection intensity ratio values of diffusely reflected spectral data may be utilized for classification of skin type in response to generating the predetermined set of wavelengths. The process continues to block 10104, wherein normalization of reflection intensity values of spectral data may be done with respect to spectral source and spectral classification of skin type. The step of normalizing the reflection intensity values of diffusely reflected spectral data with respect to light source and detector spectral characteristics comprises a sub step of making diffusely reflected spectral data independent of measurement instrument. Finally at block 10105 skin photo type output may be generated by applying nonparametric regression analysis on diffusely reflected spectral data in response to normalizing the reflection intensity values of spectral data. The step of generating a skin photo type output by applying nonparametric regression analysis on measured spectral data comprises a sub step of using a plurality of intensity of reflection values, a plurality of differential reflection intensity (for example difference in reflection intensities: I(400 nm)–I(424 nm), I(474 nm)–I(424 nm), I(512 nm)–I(540 nm), I(512 nm)–I(578 nm), and ratios of reflection intensities: I(400 nm)/I(424 nm), I(474 nm)/I(424 nm), I(512 nm)/I(540 nm), I(512 nm)/I(578 nm)) values and a plurality of ratios of reflection intensity values for deriving a skin photo type from regression tree previously generated by applying nonparametric regression analysis on measured spectral data.

Figure 102:
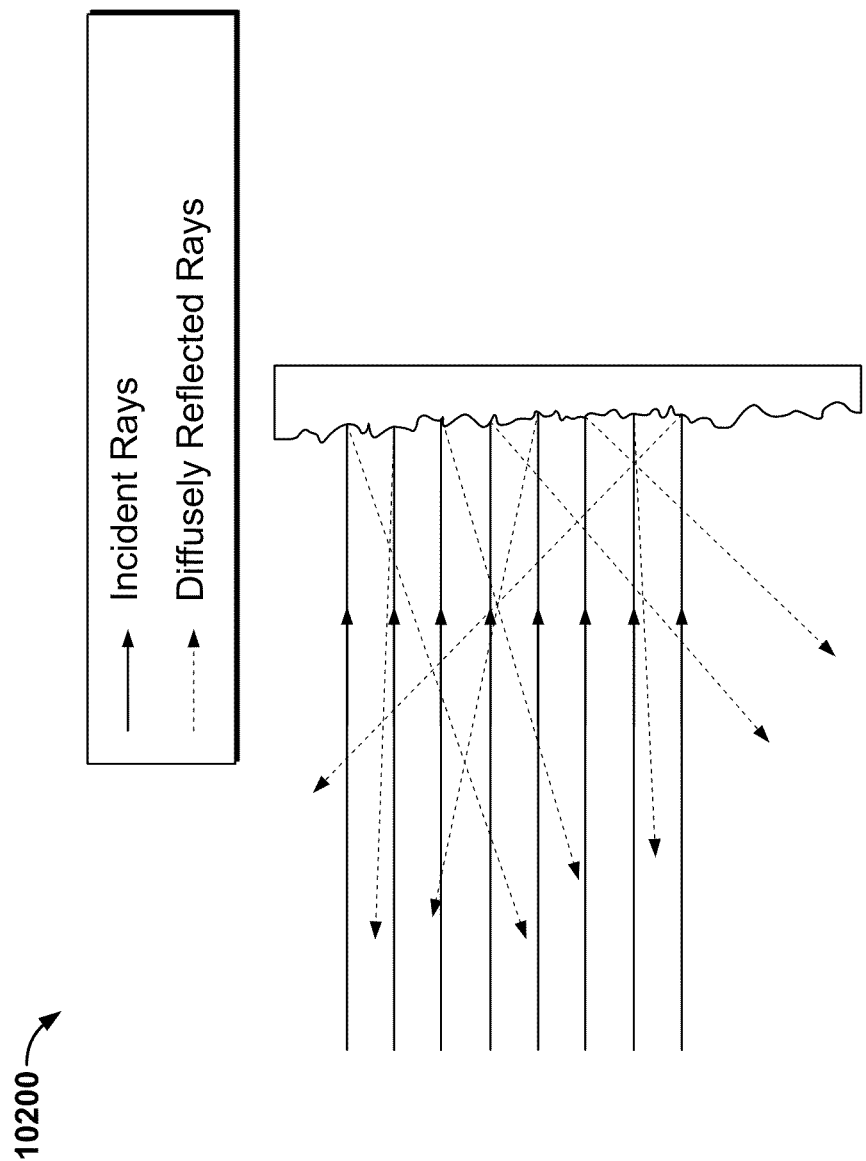
FIG. 102 is a diagram depicting reflectance of spectral rays (diffusely reflected spectral rays) in all directions from the surface of the skin.

Referring to FIG. 102 a diagram depicting reflectance of spectral rays (diffusely reflected spectral rays) in all directions from the surface of the skin is depicted. In accordance with an example, when light is illuminated on the surface of the skin, spectral rays are reflected.

According to an exemplary embodiment of the present invention, the diffusely reflected spectral rays are analyzed for generation of skin photo type. Analysis of diffusely reflected spectral rays for determining skin photo type may be done by nonparametric classification of diffuse reflectance spectral data. The skin photo type may be of a human skin or a veterinary skin or the like. The diffuse reflectance measurements for determination of skin photo type may be performed in the Ultra-Violet spectral range (for example from 380 to 600 nm or at the specific wavelengths (for example 400, 424, 474, 512, 540 and 578 nm). The nonparametric classification of diffuse reflectance spectral data is free from potential errors due to human interpretation. Further, the method for skin photo type determination by nonparametric classification of diffuse reflectance spectral data is machine autonomous and may be applicable to any diffused reflectance measurement system operating in the Ultraviolet-Visible Spectroscopy spectral range.

In accordance with an example of the present invention, skin photo type is determined by non-parametric classification of diffuse reflectance spectral data. The following steps are involved for generation of skin photo type. A predetermined set of wave lengths are generated for reflection intensity measurement of the spectral data. Generating a predetermined set of wavelengths for reflection intensity measurement of the spectral data comprises a sub step of generating a predetermined set of wavelengths for a plurality of incident spectral rays. The method for skin photo type determination by nonparametric classification of diffuse reflectance spectral data is machine autonomous and may be applicable to any diffused reflectance measurement system operating in the Ultraviolet-Visible Spectroscopy spectral range. According to an example, the nonparametric classification of diffuse reflectance spectral data is free from potential errors due to human interpretation.

According to an exemplary embodiment of the present invention, a plurality of reflection intensity values and a plurality of reflection intensity ratio values of the spectral data may be utilized for classification of a skin type response to generating the predetermined set of wavelengths. The step of utilizing a plurality of reflection intensity values and a plurality of reflection intensity ratio values of the spectral data for classification of a human skin type responsive to generating an original set of chosen wavelengths comprising a sub step of utilizing a plurality of differential reflection intensity values (for example difference in reflection intensities: I(400 nm)–I(424 nm), I(474 nm)–I(424 nm), I(512 nm)–I(540 nm), I(512 nm)–I(578 nm), and ratios of reflection intensities: I(400 nm)/I(424 nm), I(474 nm)/I(424 nm), I(512 nm)/I(540 nm), I(512 nm)/I(578 nm)).

In accordance with an example of the present, normalization of the reflection intensity values of spectral data may be done with respect to spectral source and spectral classification of the skin type. The step of normalizing the reflection intensity values of spectral data with respect to light source and detector spectral characteristics comprises a sub step of making spectral data independent of measurement instrument. Non parametric regression analysis may be applied on measured spectral data for generating the skin photo type in response to normalizing the reflection intensity values of spectral data. The step of generating a skin photo type output by applying nonparametric regression analysis on measured spectral data comprising a sub step of using a plurality of intensity of reflection values, a plurality of differential reflection intensity values and a plurality of ratios of reflection intensity values for deriving a skin photo type from regression tree previously generated by applying nonparametric regression analysis on measured spectral data.

In certain embodiments, methods, apparatuses and systems for management of overall health status of teeth has been disclosed. In certain such embodiments, design and implementation of methods for management of overall health status of teeth and systems and apparatuses thereof has been disclosed. Specifically, there is disclosed the design and implementation of methods for management of overall health status of teeth, such as determination of tooth enamel and other dermal structures thereof, determination of depth of enamel and predisposition of dental cavities and other dental problems, and systems and apparatuses thereof.

Figure 103A:
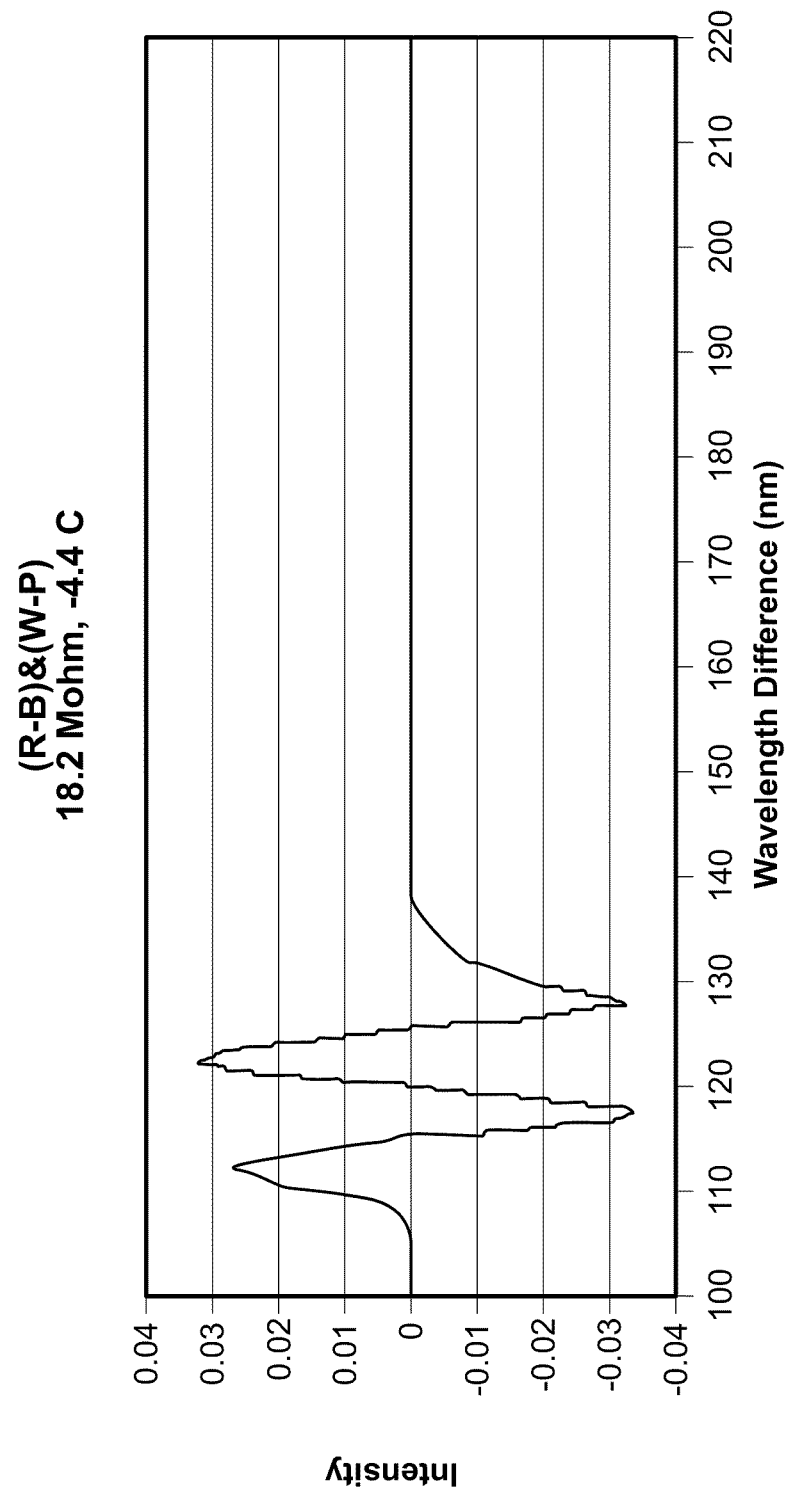
FIG. 103 depicts Opto-magnetic diagrams for 18.2 MΩ water at −4.4° C.
Figure 103B:
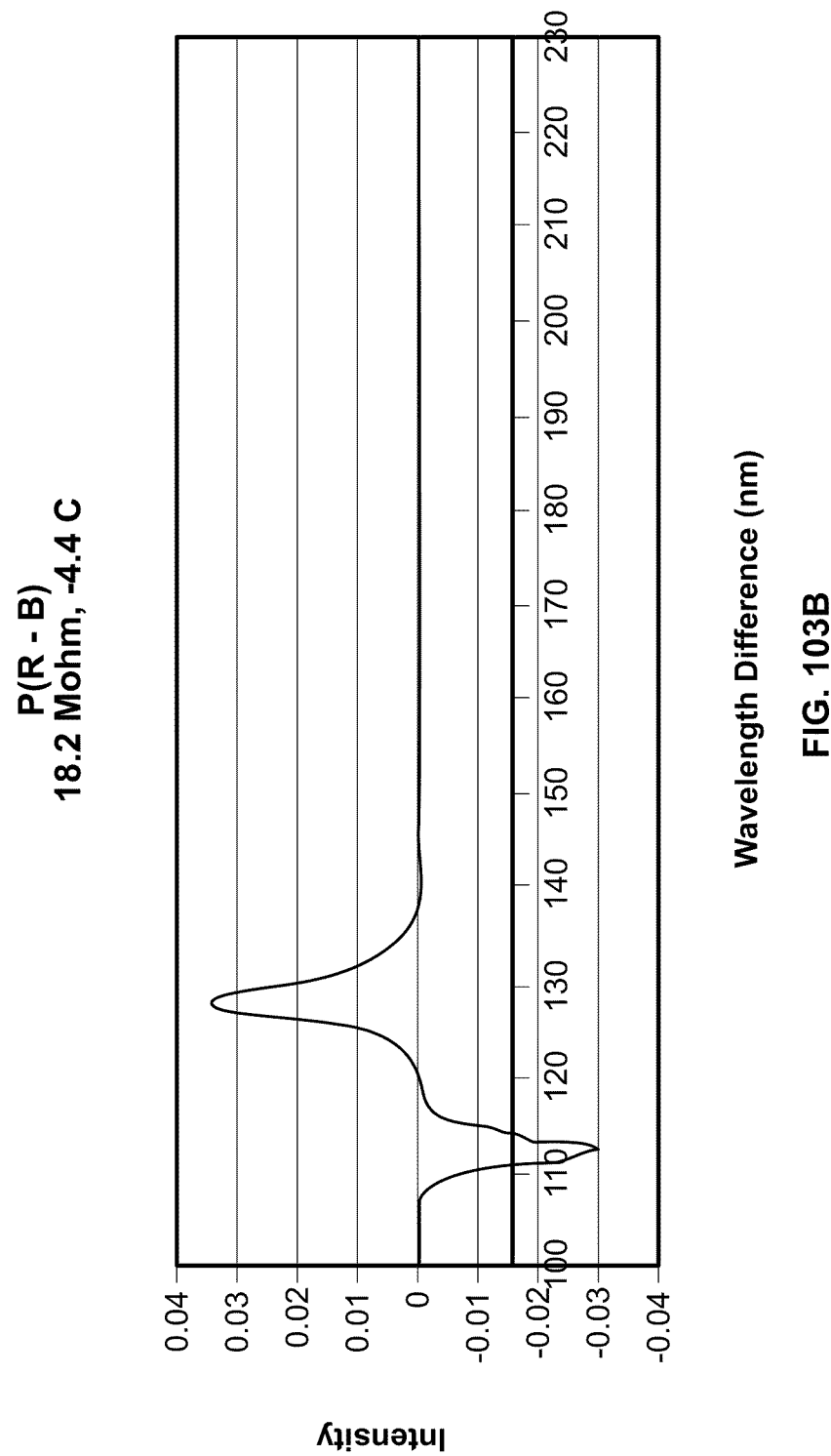
Figure 104A:
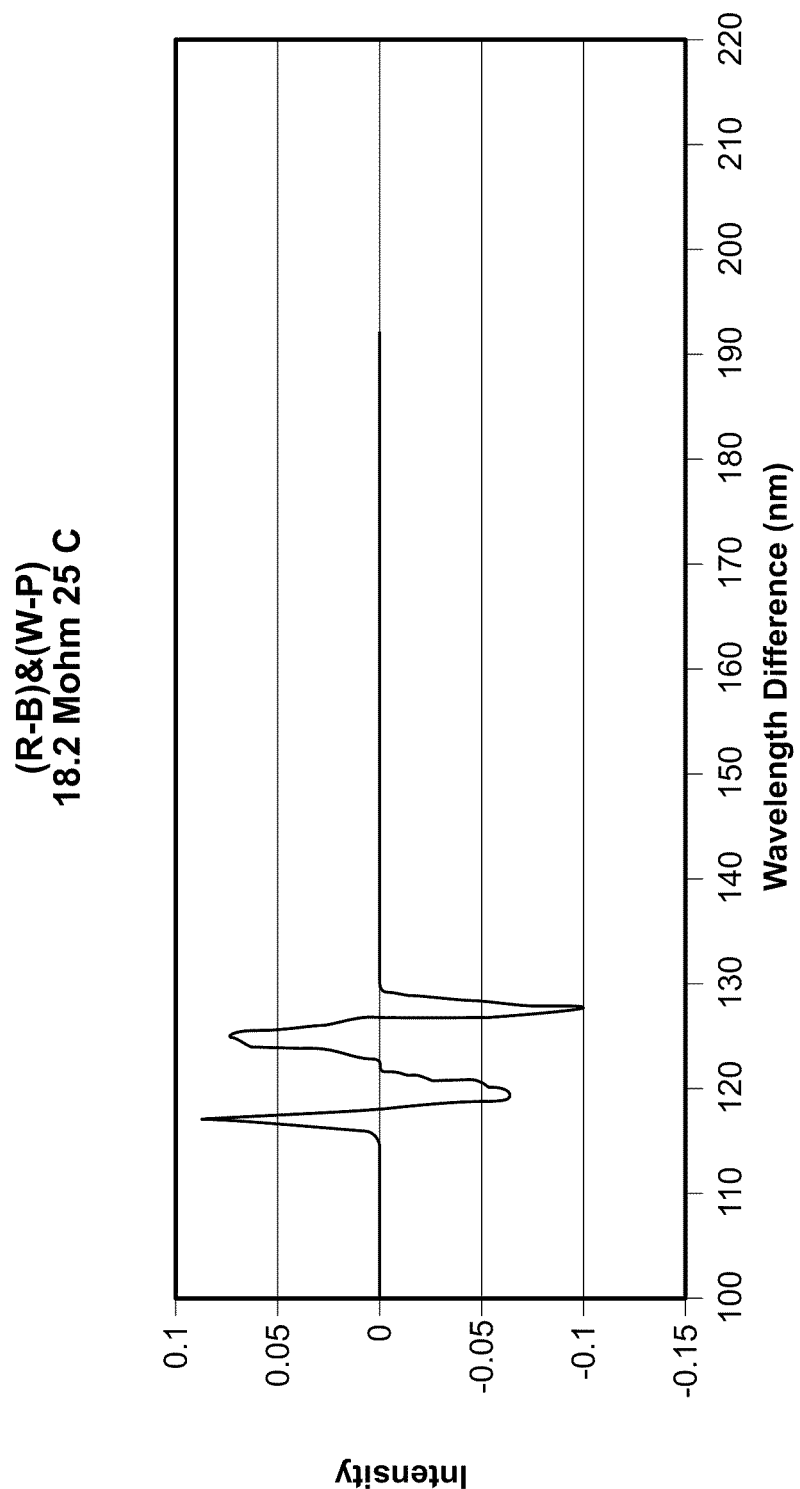
FIG. 104 depicts Opto-magnetic diagrams for 18.2 MΩ water at 25° C.
Figure 104B:
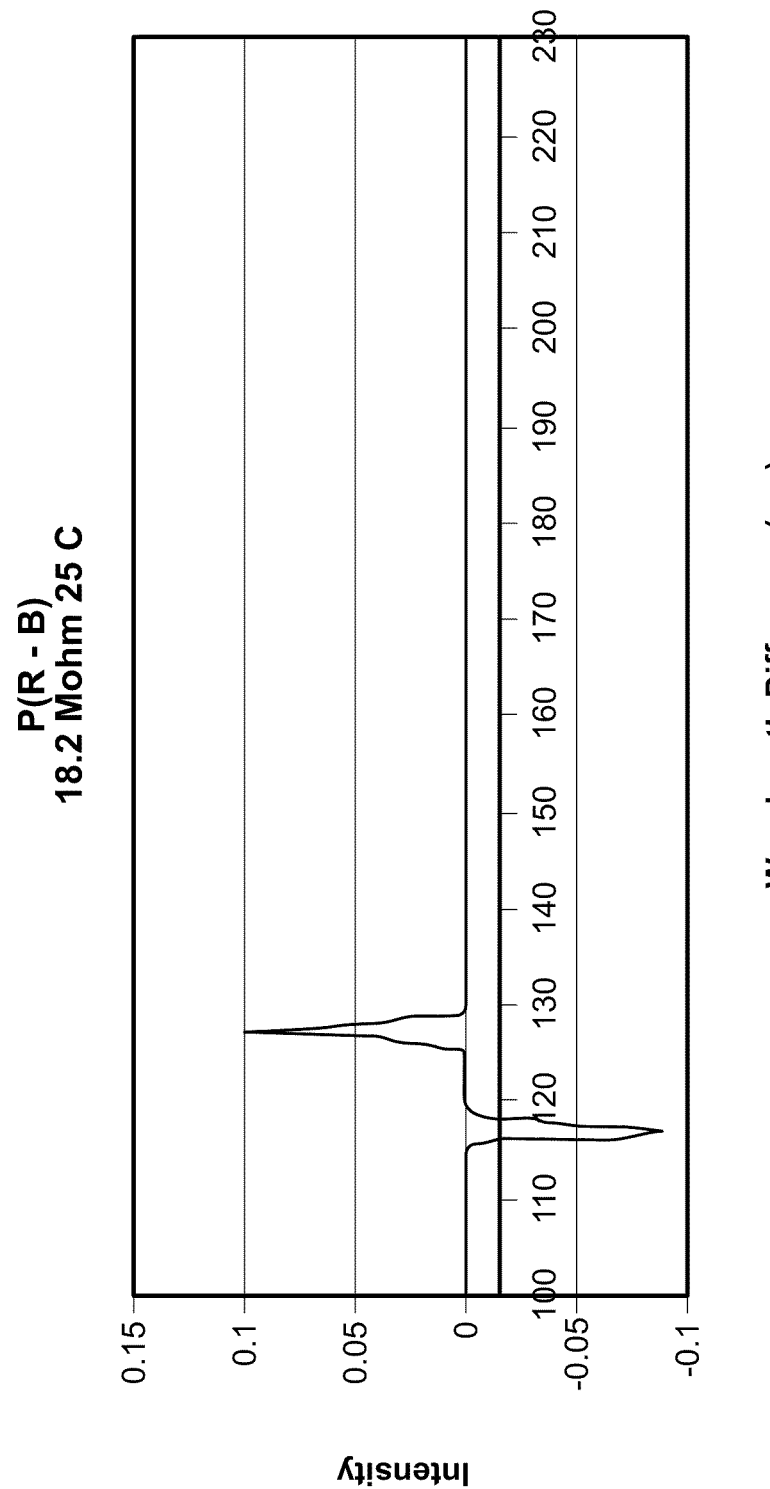

FIG. 103 depicts Opto-magnetic diagrams for 18.2 MΩ water at −4.4° C. a) characteristics points for magnetic domain [(R–B)&(W–P)]: (105.16 nm, 0), (111.69 nm, +0.0256), (114.95 nm, 0), (117.07 nm, −0.0323), (120.24 nm, 0), (121.99 nm, 0.0307), (125.49 nm, 0), (127.6 nm, −0.03063), (140.37, 0); b) Characteristics points for electrical domain [P(R–B)]: (104.01 nm, 0), (111.31 nm, −0.0237), (118.45 nm, 0), (127.88 nm, 0.0333), (137.61 nm, 0), in accordance with certain embodiments of the invention; and FIG. 104 depicts Opto-magnetic diagrams for 18.2 MΩ water at 25° C. a) Characteristics points for magnetic domain [(R–B)&(W–P)]: (113.81 nm, 0), (116.69 nm, +0.0781), (117.95 nm, 0), (118.92 nm, −0.0627), (121.7 nm, 0), (124.79 nm, 0.0722), (126.19 nm, 0), (127.3 nm, −0.0978), (130.73, 0) b) Characteristics points for electrical domain [P(R–B)]: (113.29 nm, 0), (116.67 nm, −0.0782), (118.71 nm, 0), (124.16 nm, 0), (127.33 nm, 0.1003), (129.07 nm, 0), in accordance with certain embodiments of the invention.

In certain embodiments, methods for overall management of dental or oral health based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for overall management of dental or oral health based on Opto-Magnetic properties of light-matter interaction. Still more specifically, the systems and apparatuses facilitate implementation of an Opto-Magnetic method with enhanced qualitative and quantitative parameters, novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for overall analysis of teeth based on Opto-Magnetic properties of light-matter interaction.

In certain other situations, the teeth are subjected to analysis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul. 17 "SYSTEM, DEVICE AND METHOD FOR DERMAL IMAGING" to J. Bandic, Dj. Koruga, R. Mehendale and S. Marinkovich of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for overall management of dental or oral health based on the interaction between matter and electromagnetic radiation and systems and apparatuses facilitating implementation of such methods has been disclosed. Specifically, there is disclosed the design and implementation of an Opto-Magnetic method with enhanced qualitative and quantitative parameters for overall management of dental or oral health based on Opto-Magnetic properties of light-matter interaction and systems and apparatuses thereof. Still more specifically, there is disclosed design and implementation of an Opto-Magnetic method with enhanced qualitative and quantitative parameters, such as novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for overall management of dental or oral health based on Opto-Magnetic properties of light-matter interaction and systems and apparatuses thereof.

Further, the Opto-Magnetic method is in essence an Opto-Magnetic Fingerprint (OMF) method based on electron properties of matter and its interaction with light. By way of example, and in no way limiting the scope of the invention, the concept of light-matter interaction and Opto-magnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

Typically, valence electrons build major link network of matter. The orbital velocity of the valence electrons in atoms is of the order of $10^6$ m/s. This gives the ratio between magnetic force ($F_M$) and electrical force ($F_E$) of matter of approximately $10^{-4}$ (or $F_M/F_E \approx 10^{-4}$.) Since, force (F) is directly related to quantum action (or Planck action) through the following equation: $h = F \times d \times t = 6.626 \times 10^{-34}$ Js, where F is force, d is displacement and t is time of action. This means that the action of magnetic forces is four orders of magnitude closer to quantum action than the electrical ones. Further, since quantum state of matter is primarily responsible for conformational changes on the molecular level, this means that detecting differences between tissue states is by far more likely to give greater sensitivity on the level of magnetic forces than it would be on the level of measurement of electrical forces.

The term "conformational change" refers to a transition in shape of a macromolecule. Typically, a macromolecule is flexible or dynamic. Thus, it can change its shape in response to changes in its environment or other factors. Each possible shape is called a conformation. A macromolecular conformational change may be induced by many factors, such as a change in temperature, pH, voltage, ion concentration, or the binding of a ligand.

In certain other embodiments, a comparative analysis of pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

Since, reflected polarized light contains electrical component of light-matter interaction. Thus, taking the difference between white light (i.e. electromagnetic) and reflected polarized light (i.e. electrical) yields magnetic properties of matter based on light-matter interaction.

Further since, reflected polarized light is composed of longitudinal wave (i.e. electrical component) and transverse wave (i.e. magnetic component). This implies that only electrical component as a longitudinal wave contains data (i.e. image) of light-matter interaction, which activates either CMOS or CCD image sensor.

In certain embodiments, the methods and systems for overall management of dental or oral health performs one or more functions. By way of example, and in no way limiting the scope of the invention, the methods and systems for overall management of dental or oral health exhibition of degree of mineralization of enamel and ratio of minerals to water and other organic material thereof, color of enamel, comparison of enamel over time, validation of a person's hygienic routine by determining progress of enamel cleaning, thickness of enamel, health of cementoenamel junction (or CEJ), measurement of strength on a relative scale or in comparison with peers, on custom scales or on Mohs hardness scale, for example, presence of proteins called amelogenins and enamelins, determination of type of Dentin, such as primary, secondary and tertiary, porosity, verification of the health and status of a teeth enamel and other dermal structures thereof, determination of depth of enamel towards application, determination of predisposition of dental cavities and other dental problems, identification and presence of rod sheath, Striae of Retzius, neonatal line, Perikymata, Gnarled Enamel, Keratin levels, Nasmyth's membrane or enamel cuticle, acquired pellicle, food debris, presence microcracks within the tooth, degree of microcracking within the tooth, amount of Plaque, tooth decay or attrition, sensitivity of teeth, gum diseases, such as gingivitis, Peridontis, color of gums (e.g. bright-red, or purple gums) that gives indication of gum health, degree of swelling of gums, presence of mouth sores, tracking of progress of mouth sores over time, shinyness of gums, presence of pus in gums, presence of new teeth coming, status of fillings, presence of plaque/level of plaque, determination of the extent of a cavity, determination of the propensity/predisposition of developing carries or cavities, Chronic Bilirubin Encephalopathy, Enamel Hypoplasia, Erythropoietic Porphyria, Fluorosis, Celiac Disease, presence of Tetracycline, presence and status of composites and sealants, determination of health and structural integrity of crowns and veneers, amalgams and the like, track the progress of conditions like Bruxism (i.e. grinding of the teeth) and indication of attrition over time, determination of presence of amelogenins, ameloblastins, enamelins, and tuftelins.

Figure 105A:
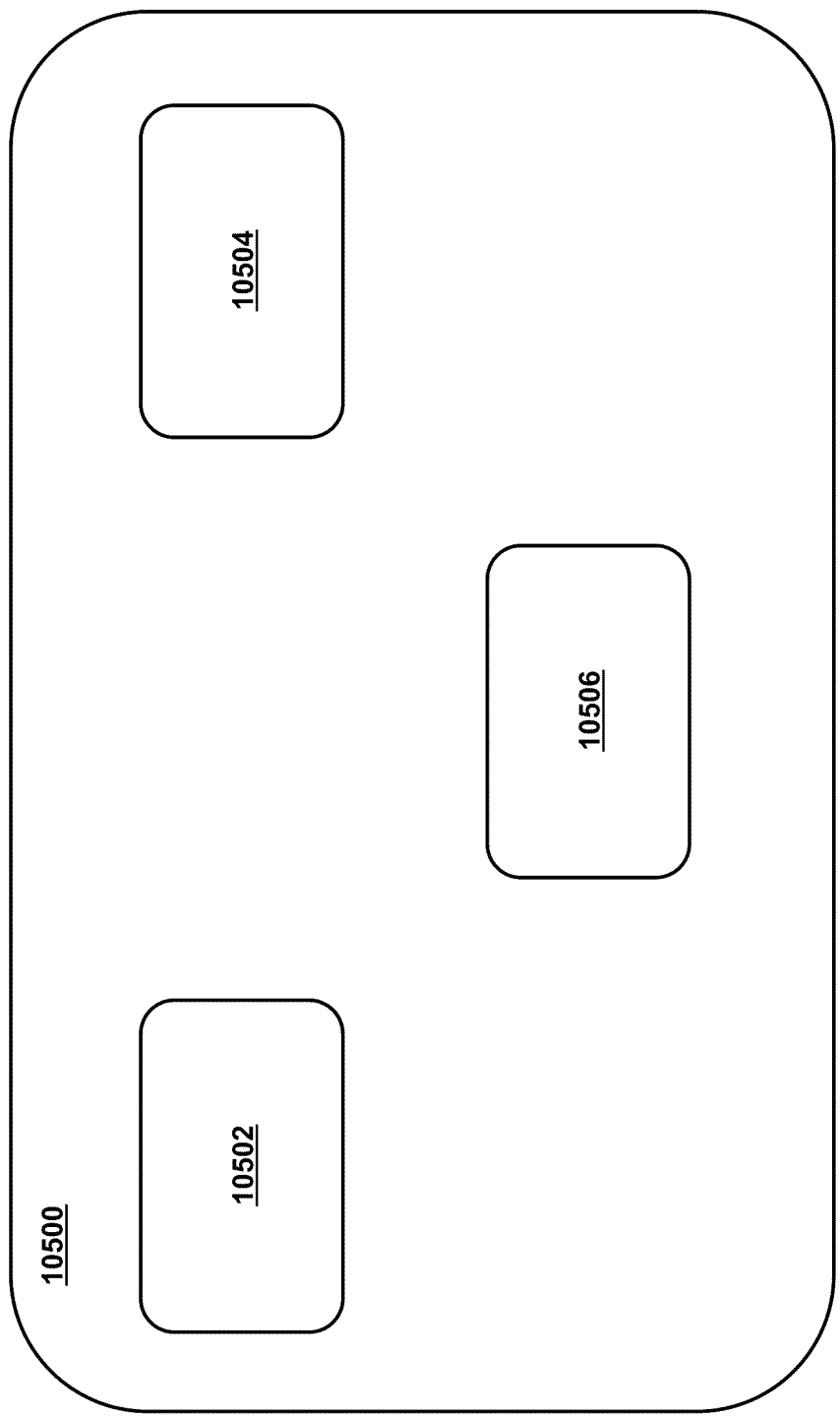
FIG. 105 is a block diagrammatic view of a system facilitating overall management of dental or oral health through implementation of an Opto-Magnetic process based on light-matter interaction using digital imaging for diagnosis of teeth, designed and implemented in accordance with certain embodiments of the invention.

FIG. 105 is a block diagrammatic view of a system facilitating overall management of dental or oral health through implementation of an Opto-Magnetic process based on light-matter interaction using digital imaging for diagnosis of teeth, designed and implemented in accordance with certain embodiments of the invention.

System 10500 is in essence a Dental Health Management System (or DHMS) or Oral Health Management System. The DHMS 10500 includes an illumination subsystem 10502, an imaging (or sensor) subsystem 10504 and a host computing subsystem 10506.

DHMS 10500, by virtue of its design and implementation, facilitates execution of an Opto-Magnetic method based on interaction between electromagnetic radiation and matter, for instance light-matter interaction, using digital imaging for diagnosis of teeth. Specifically, the Opto-Magnetic process employs apparatuses for generation of unique spectral signatures from digitally captured images of samples thereby facilitating analysis of teeth based on Opto-Magnetic properties of light-test sample matter interaction.

Illumination subsystem 10502 may be one or more electromagnetic radiation sources. In certain specific embodiments, the Illumination subsystem 10502 may be a set of Light Emitting Diodes (LEDs). By way of example, and in no way limiting the scope of the invention, the illumination subsystem 10502 is a set of six LEDs. For illustrative purposes, and for clarity and expediency of expediency, the set of six LEDs have been referred to as 10508, 10510, 10512, 10514, 10516, and 10518 respectively, all not shown here explicitly.

Illumination subsystem 10502 may be adapted to emit polarized and unpolarized electromagnetic signals. The polarized electromagnetic signal is angled white light and unpolarized electromagnetic signal is non-angled white light.

As used in the current context, the term "Light-Emitting Diode or LED" refers to a semiconductor light source. LEDs are PN junction devices that give off light radiation when biased in the forward direction. LEDs are solid-state devices requiring little power and generating little heat. Because their heat generation is low and because they do not rely on a deteriorating material to generate light, LEDs have long operating lifetimes. LEDs can be divided into three types based on LED construction, namely edge emitting, surface emitting, and super luminescent. Firstly, an edge emitting LED is a LED with output that emanates from between the heterogeneous layers. Secondly, a surface emitting LED is a LED that emits light perpendicular to the active region. Eventually, super luminescent LEDs are based on stimulated emission with amplification but insufficient feedback for oscillation to build up.

In general, some important performance specifications parameters considered in identification and selection of LED include LED type, peak wavelength, viewing angle, optical power output, luminous intensity, forward current and forward voltage. For example, based on color LED types include infrared, red, orange, yellow, green, blue, white, and ultraviolet. Peak wavelength is the desired output wavelength of LED. Dependent upon diffusion from the lens, usually the larger the viewing angle, the less bright the LED. Diffused types generally have larger viewing angles and non-diffused types have smaller viewing angles. The optical power output of the LED is expressed in mW. The luminous intensity of the LED is expressed in mcd. The candela (cd) is the luminous intensity of a light source producing light at a wavelength of 555.17 nm with a power of $1/683$ watt per steradian, or 18.3988 milliwatts over a complete sphere centered at the light source.

Common features of LEDs include lens type choices, bipolar construction, dual LEDs, and arrays. For example, lens type choices include flat lenses and domed lenses. Specifically, bipolar LEDs work even if voltage is reversed. Dual LEDs are two LED lamps in the same housing. In an LED array the LEDs are packaged as multiples. LED arrays will contain a certain number of elements (LEDs).

In certain such embodiments, the illumination subsystem 10502 possess the following specifications: electromagnetic radiation source LED, number of LEDs 6; LED color type white; color temperature 5000° K and the like.

As shown in the FIG. 105, in certain embodiments, the illumination subsystem 10502 may be coupled to the sensor subsystem 10504.

As shown in the FIG. 105, the sensor subsystem 10504 may in essence be a device that converts optical images (or optical signals) to electric signals. In certain embodiments, the sensor subsystem 10504 captures continuous digital images of teeth. Specifically, in such embodiments, the sensor subsystem 10504 captures continuous digital images of the teeth illuminated with white light both, non-angled and angled. By way of, and by no way of limitation, the sensor subsystem 10504 may be anyone selected from a group consisting of a Complementary Metal-Oxide-Semiconductor (CMOS) image sensor, Charged Coupled Device (CCD) image sensor, and the like.

As used herein, the term "Charge-Coupled Device or CCD" refers to a device for the movement of electrical charge, usually from within the device to an area where the charge can be manipulated, for example conversion into a digital value. This is achieved by "shifting" the signals between stages within the device one at a time. Technically, CCDs are implemented as shift registers that move charge between capacitive bins in the device, with the shift allowing for the transfer of charge between bins. Often the device is integrated with a sensor, such as a photoelectric device to produce the charge that is being read, thus making the CCD a major technology for digital imaging. Although CCDs are not the only technology to allow for light detection, CCDs are widely used in professional, medical, and scientific applications where high-quality image data is required.

In certain specific applications, digital color cameras generally use a Bayer mask over the CCD. Each square of four pixels has one filtered red, one blue, and two green (the human eye is more sensitive to green than either red or blue). The result of this is that luminance information is collected at every pixel, but the color resolution is lower than the luminance resolution.

In certain other specific applications, better color separation can be reached by three-CCD devices (or 3CCD) and a dichroic beam splitter prism that splits the image into red, green and blue components. Specifically, each of the three CCDs is arranged to respond to a particular color. For example, some semi-professional digital video camcorders and most professional camcorders use this technique. Another advantage of 3CCD over a Bayer mask device is higher quantum efficiency and therefore higher light sensitivity for a given aperture size. This is because in a 3CCD device most of the light entering the aperture is captured by a sensor, while a Bayer mask absorbs a high proportion (i.e. approximately ⅔) of the light falling on each CCD pixel.

For example, and in no way limiting the scope of the invention, in certain embodiments the sensor subsystem 10504 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

In certain such embodiments, the sensor subsystem 10504 may possess the following specifications: pick up element is CCD image sensor or camera; CCD image sensor or camera type is color; array type is linear array, frame transfer area array, full frame area array or interline transfer area array; optical format is ¼" (or inch); horizontal resolution; format/output is National Television System Committee (NTSC) or Phase Alternate Line (PAL); total number of pixels for NTSC is 270K whereas for PAL is 320K; resolution is 350TV line; shutter control is electronic shutter; shutter speed for 1/60~1/100,000 seconds whereas 1/50~1/100,000 seconds; gain control is automatic; Video Out is 1.0Vp-p composite/75 Ohm; power supply is 5V DC; dimensions (i.e. Length L, Width W and Height H or L*W*H) are 185*25*20 mm$^3$; TV system NTSC or PAL; Video In is 1.0Vp-p, 75 Ohm ($\Omega$); digital resolution is 8-bit 256 grad, 512*1024 pixels; digital I/O is 16 bits; signal is 52 dB; power source is DC 9V; freeze mode is frame; dimensions (i.e. Length L, Width W and Height H or L*W*H) are 110*82*37 mm$^3$ and the like.

The term "electronic shutter control" refers to the light gathering period. This may be programmed or altered with a digital electronic interface.

The term "gain control" refers to Automatic Gain Control (or AGC) that uses electronic circuitry to increase video signals in low-light conditions. This can introduce noise and, subsequently, graininess in the picture. Typically, AGC is disabled and specifications are presented with this feature turned off.

The term "shutter speed" refers to the time of exposure or light collection. Typically, it may be set across a wide range.

The term "horizontal resolution" refers to the maximum number of individual picture elements that can be distinguished in a single scanning line. This measurement is used to characterize the horizontal video resolution corrected for the image aspect ratio, or to specify the resolution in the largest circle than can fit in a rectangular image. A 640×480 image would, for example, be specified as 480 horizontal lines.

The term "optical format" refers to a digital imaging optical format that is a measure of the size of the imaging area. Optical format is used to determine size of lens necessary for use with the imager. Optical format refers to the length of the diagonal of the imaging area.

Again, as shown in FIG. 105, the sensor subsystem 10504 may be coupled to the host computing subsystem 10506.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional signal and applying standard signal-processing techniques to it.

Image processing usually refers to digital image processing, but optical and analog image processing is also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

Figure 106:
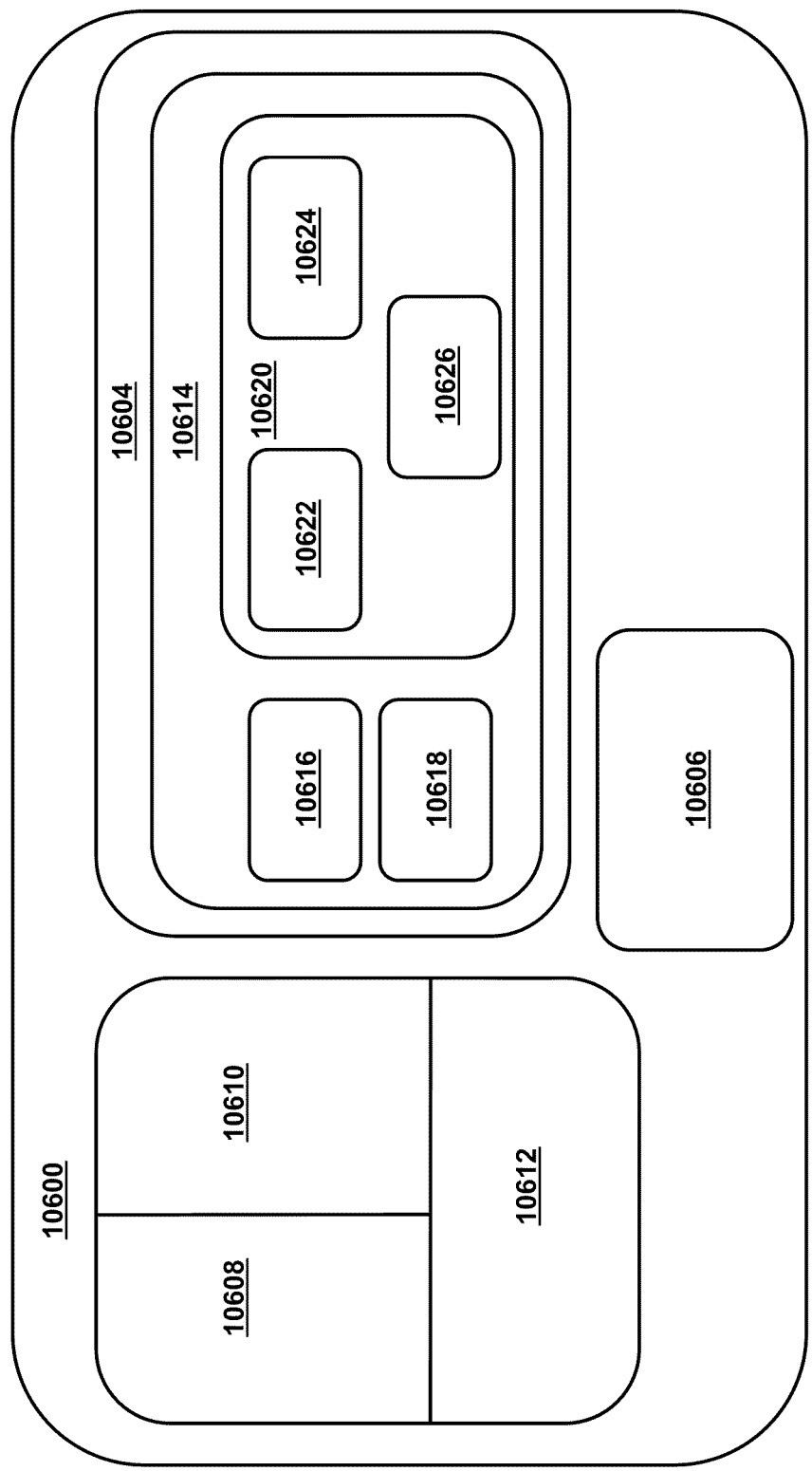
FIG. 106 is an exploded diagrammatic representation of the host computing subsystem, of the FIG. 105, comprising an Opto-Magnetic Fingerprint (or OMF) Generator submodule designed and implemented in accordance with at least some embodiments.

FIG. 106 is an exploded diagrammatic representation of the host computing subsystem, of the FIG. 105, comprising an Opto-Magnetic Fingerprint (or OMF) Generator sub-module designed and implemented in accordance with at least some embodiments.

The host computing subsystem 10600 may comprise a processing unit 10602, a memory unit 10604 and an Input/Output (or I/O) unit 10606 respectively.

The host computing subsystem 10600, by virtue of its design and implementation, performs overall management of dental or oral health.

The processing unit 10602 may comprise an Arithmetic Logic Unit (or ALU) 10608, a Control Unit (or CU) 10610 and a Register Unit (or RU) 10612.

In certain specific embodiments, the processing unit 10602 may be a Video Processing Unit (or VPU). Specifically, in certain such embodiments, the VPU 10602 may possess the following specifications: the sensor subsystem 104 in conjunction with the VPU 10602 may possess the following specifications: pick up element is CCD image sensor or camera; CCD image sensor or camera type is color; array type is linear array, frame transfer area array, full frame area array or interline transfer area array; optical format is ¼" (or inch); horizontal resolution; format/output is National Television System Committee (NTSC) or Phase Alternate Line (PAL); total number of pixels for NTSC is 270K whereas for PAL is 320K; resolution is 350TV line; shutter control is electronic shutter; shutter speed for ⅙₀~¹⁄₁₀₀,₀₀₀ seconds whereas ⅕₀~¹⁄₁₀₀,₀₀₀ seconds; gain control is automatic; Video Out is 1.0Vp-p composite/75 Ohm; power supply is 5V DC; dimensions (i.e. Length L, Width W and Height H or L*W*H) are 185*25*20 mm³; TV system NTSC or PAL; Video In is 1.0Vp-p, 75 Ohm (Ω); digital resolution is 8-bit 256 grad, 512*1024 pixels; digital I/O is 16 bits; signal is 52 dB; power source is DC 9V; freeze mode is frame; dimensions (i.e. Length L, Width W and Height H or L*W*H) are 110*82*37 mm³ and the like.

As used herein, the term "Video Processing Unit or VPU" refers to a Graphics Processing Unit or GPU (also occasionally called Visual Processing Unit) is a specialized processor that offloads 3D graphics rendering from the microprocessor.

In certain specific embodiments, the I/O unit 10606 may comprise of at least a Video In port and Video Out port, and any potential permutations or combinations of Video In port and a Video Out port.

The term "Video In Video Out or VIVO" refers to a graphics port which enables some video cards to have bidirectional (input and output) analog video transfer through a mini-DIN connector, usually of the 9-pin variety, and a specialized splitter cable, which can sometimes also transfer analog audio.

As shown in FIG. 106, the memory unit 10604 comprises an oral or dental analysis module 10614.

In certain embodiments, the oral or dental analysis module for examination of teeth via generation of unique spectral signatures from the digitally captured images of the teeth and methods thereof are disclosed, in accordance with the principles of the invention. Specifically, in such embodiments, the oral or dental analysis module utilizes the continuously captured digital images of teeth illuminated with white light both, non-angled and angled. More specifically, the oral or dental analysis module takes into consideration the digital images in Red (R), Green (G) and Blue (B) (or RGB) system for purposes of analysis.

Further, as shown in FIG. 106, the oral or dental analysis module 10614 includes a Fourier transform sub-module 10616, a spectral analyzer sub-module 10618 and an Opto-Magnetic Fingerprint Generator (or OMFG) sub-module 10620, respectively.

In certain embodiments, the Fourier transform sub-module 10616 is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 10616 converts time-domain digital signals into corresponding frequency-domain digital signals.

DTFT 10616 is coupled to the spectrum analyzer sub-module 10618.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of teeth is disclosed. Specifically, the spectrum (or spectral) analyzer sub-module in order to analyze the samples takes into consideration digital images of the samples in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R−B) & (W−P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as teeth surface, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 106, the spectrum analyzer sub-module 10618 may be coupled to the OMFG sub-module 10620.

OMFG sub-module 10620 includes a color histogram generator unit 10622, a spectral plot generator unit 10624 and a convolution unit 10626.

OMFG sub-module 10620, by virtue of its design and implementation, facilitates generation of unique spectral signatures from digitally captured images of teeth. Specifically, the generated spectral signatures of teeth facilitate detection of pluralities of problems in connection with teeth based on Opto-Magnetic properties of light-test sample interaction.

Color histogram generator unit 10622, by virtue of its design, generates a normalized Red (R) and Blue (B) color channel histogram for each of the one or more images of the teeth.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 1 exhibits a tabular representation in connection with a 2D Red-Blue chromaticity histogram generated by first normalizing color pixel values by dividing RGB values by R+G+B, then quantizing the normalized R and B coordinates into N bins each, where N=4.

|   |         | R    |         |         |         |
|---|---------|------|---------|---------|---------|
|   |         | 0-63 | 64-127  | 128-191 | 192-255 |
| B | 0-63    | 43   | 78      | 18      | 0       |
|   | 64-127  | 45   | 67      | 33      | 2       |
|   | 128-191 | 127  | 58      | 25      | 8       |
|   | 192-255 | 140  | 47      | 47      | 13      |

As shown in FIG. 106, the color histogram generator unit 10622 may be coupled to the spectral plot generator unit 10624.

Spectral plot generator unit 10624 generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 10626 convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the teeth.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

In certain other embodiments, the system configuration, discussed in conjunction with FIGS. 105 and 106, implement one or more processes facilitating estimation of sample type and properties (or characteristics) thereof to create a unique spectral signature.

Figure 107:
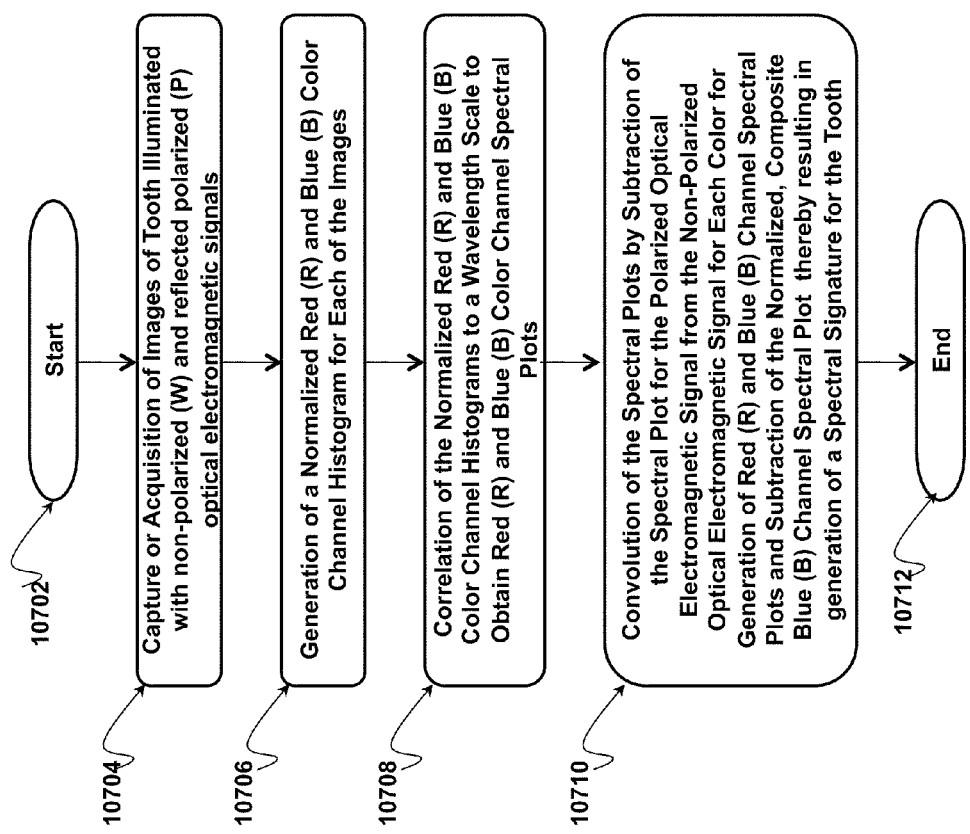
FIG. 107 depicts a flow diagram delineating at least one process implemented by the system configuration of FIGS. 105 and 106 thereby facilitating determination of teeth type and properties (or characteristics) thereof and creation of a unique spectral signature.

FIG. 107 depicts a flow diagram delineating at least one process implemented by the system configuration of FIGS. 105 and 106 thereby facilitating determination of teeth type and properties (or characteristics) thereof and creation of a unique spectral signature.

The process 10700 starts at stage 10702 and proceeds to stage 10704, wherein the process 10700 comprises the phase of convolution of data associated with a first set of images of a teeth captured by illuminating the sample with a white light (or unangled white light.) Noticeable here is the fact that the data associated with the first set of images of the teeth illuminated with the white light (or unangled white light) may comprise one or more combinations of reflected and re-emitted angled and unangled white light.

At stage 10706, the process 10700 comprises the phase of convolution of data associated with a second set of images of the teeth captured by illuminating the sample with an angled white light. It must be noted here that the data associated with the second set of images of the teeth illuminated with the angled white light may comprise one or more combinations of reflected and re-emitted angled white light.

At stage 10708, the process 10700 comprises the phase of comparison of extrema (i.e. maxima and minima) (or extreme) positions of at least a pair of unique convolutions generated by convolution of data from the first set of images and second set of images.

At stage 10710, the process 10700 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) teeth type. The process 10700 ends at stage 10712.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R–B) (W–P)) versus a second component Red (R) minus Blue (B) of unangled white light (or W) (i.e. (R–B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R–B) (W–P) for the reflected and/or re-emitted polarized light, and a component (R–B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

Figure 108:
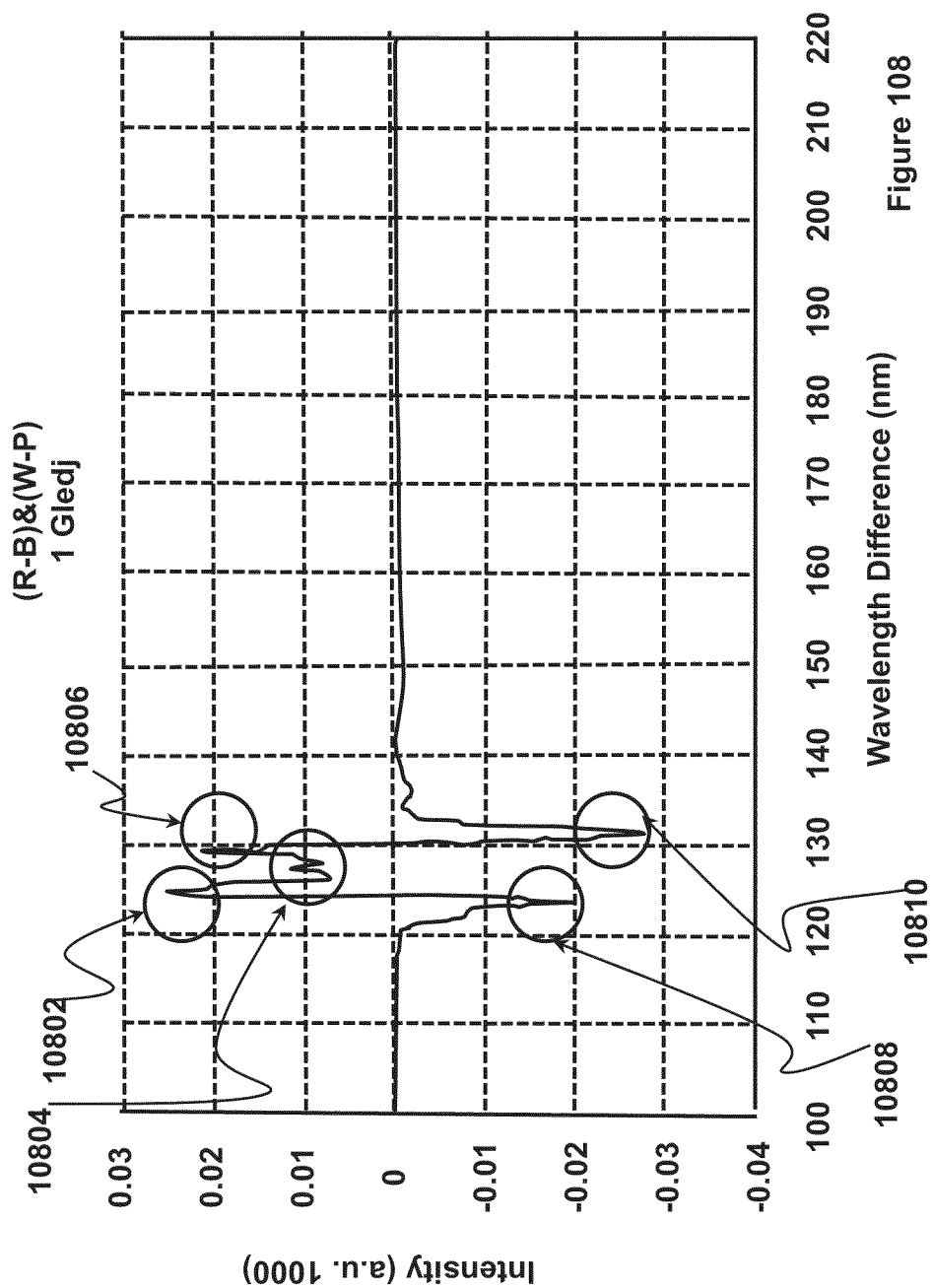
FIG. 108 depicts a first plot of a typical spectral data (or OMF diagram) for enamel obtained on implementation of the OMF method on digital images of the teeth, in accordance with certain embodiments of the invention.

FIG. 108 depicts a first plot of a typical spectral data (or OMF diagram) for enamel obtained on implementation of the OMF method on digital images of the teeth, in accordance with certain embodiments of the invention.

As shown in FIG. 108, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the teeth, captured using diffuse white light and reflected polarized light, using the OMF method. Specifically, the OMF method implements the SCA and CAA to analyze the processed digital image of the sample.

As depicted in FIG. 108, the first DI plot may possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.04 a.u. to a maximum of equal to +0.03 a.u. (or [−0.04, +0.03]); analytical information is analysis of the first DI plot (or OMF Diagram) of the enamel of the teeth; input sample is the teeth; operation is implementation of OMF method on digital images of the teeth; number of intensity peaks (or extrema or maxima and minima) is approximately 5; number of peaks with positive intensity values is approximately 3; number of peaks with negative intensity value is approximately 2; identifiers for the 5 intensity peaks are first 10802A, second 10804A, third 10806A, fourth 10818A and fifth 10810A respectively in that order.

Figure 109:
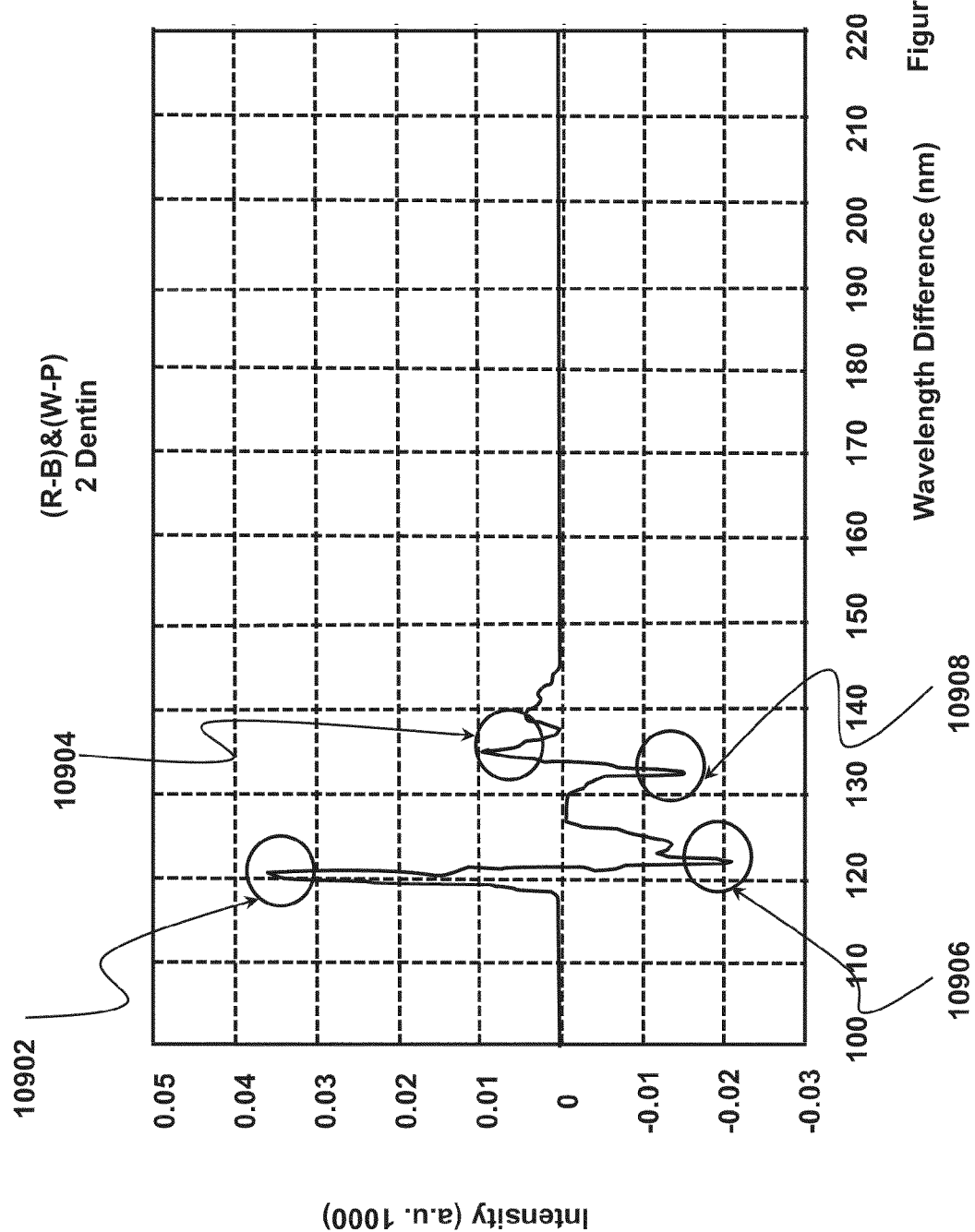
FIG. 109 depicts a second plot of a typical spectral data (or OMF diagram) for dentin obtained on implementation of the OMF method on digital images of the teeth, in accordance with certain embodiments of the invention.

FIG. 109 depicts a second plot of a typical spectral data (or OMF diagram) for dentin obtained on implementation of the OMF method on digital images of the teeth, in accordance with certain embodiments of the invention.

As depicted in FIG. 109, the second DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.03 a.u. to a maximum of equal to +0.05 a.u.; analytical information is analysis of the second DI plot (or OMF Diagram) of the digital photography image of the dentin of the teeth; input sample is the teeth; operation is implementation of OMF method on digital images of the teeth; number of intensity peaks (or extrema or maxima and minima) is approximately 4; number of peaks with positive intensity values is approximately 2; number of peaks with negative intensity value is approximately 2; identifiers for the 4 intensity peaks are first 10902A, second 10904A, third 10906A and fourth 10908A in that order.

Figure 110:
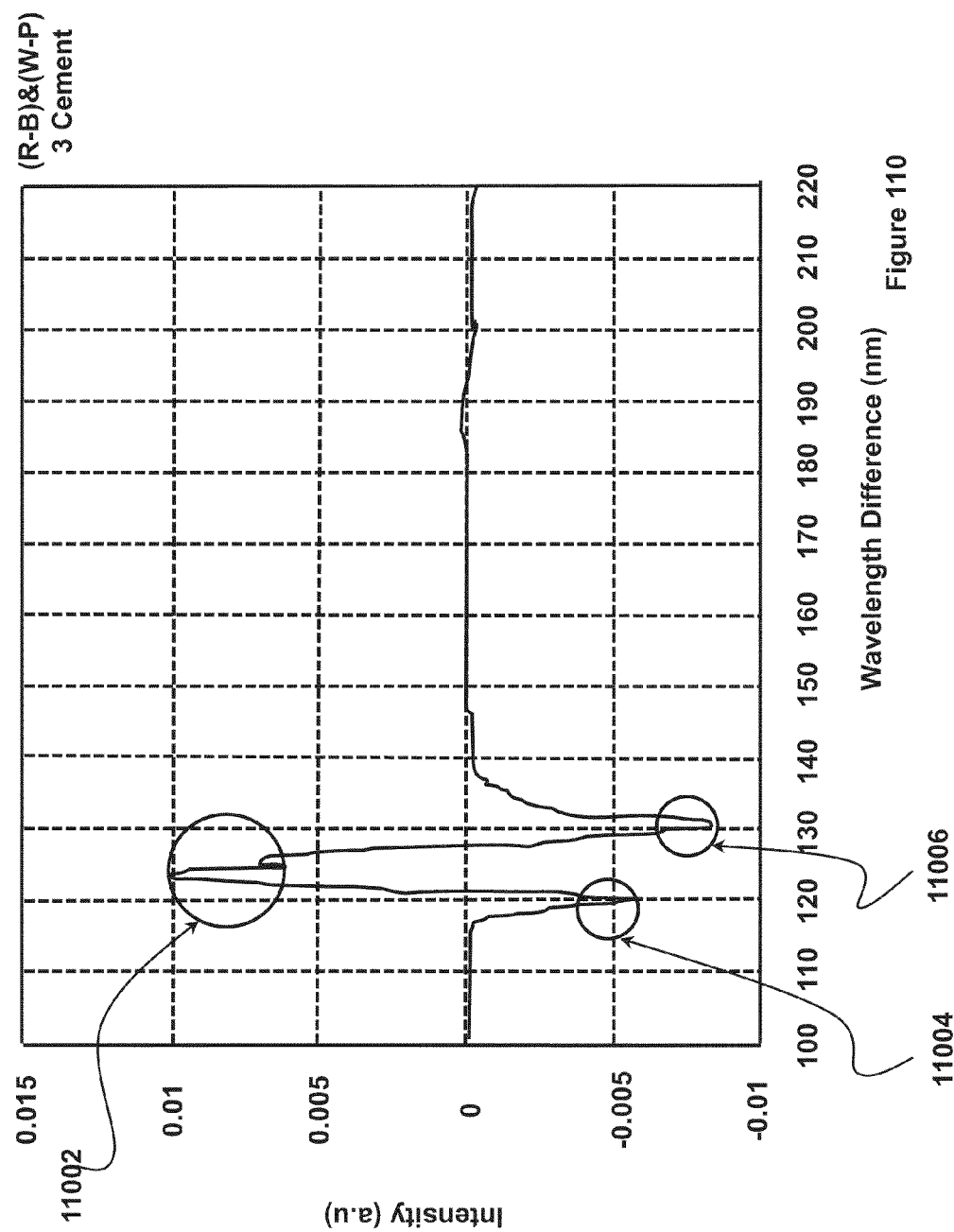
FIG. 110 depicts a third plot of a typical spectral data (or OMF diagram) of cement obtained on implementation of the OMF method on digital images of the teeth, in accordance with certain embodiments of the invention.

FIG. 110 depicts a third plot of a typical spectral data (or OMF diagram) of cement obtained on implementation of the OMF method on digital images of the teeth, in accordance with certain embodiments of the invention.

As depicted in FIG. 110, the third DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.01 a.u. to a maximum of equal to +0.015 a.u.; analytical information is analysis of the third DI plot (or OMF Diagram) of the digital photography image of the cement of the teeth; operation is implementation of OMF method on digital images of the teeth; number of intensity peaks (or extrema or maxima and minima) is approximately 3; number of peaks with positive intensity values is approximately 1; number of peaks with negative intensity value is approximately 2; identifiers for the 3 intensity peaks are first 11002A, second 11004A and third 11006A in that order.

In certain embodiments, methods for overall management of dental or oral health based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for overall management of dental or oral health based on Opto-Magnetic properties of light-matter interaction. Still more specifically, the systems and apparatuses facilitate implementation of an Opto-Magnetic method with enhanced qualitative and quantitative parameters, novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for overall analysis of teeth based on Opto-Magnetic properties of light-matter interaction.

In certain other situations, the teeth are subjected to analysis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul. 17 "SYSTEM, DEVICE AND METHOD FOR DERMAL IMAGING" to J. Bandic, Dj. Koruga, R. Mehendale and S. Marinkovich of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for overall management of dental or oral health based on the interaction between matter and electromagnetic radiation and systems and apparatuses facilitating implementation of such methods has been disclosed. Specifically, there is disclosed the design and implementation of an Opto-Magnetic method with enhanced qualitative and quantitative parameters for overall management of dental or oral health based on Opto-Magnetic properties of light-matter interaction and systems and apparatuses thereof. Still more specifically, there is disclosed design and implementation of an Opto-Magnetic method with enhanced qualitative and quantitative parameters, such as novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for overall management of dental or oral health based on Opto-Magnetic properties of light-matter interaction and systems and apparatuses thereof.

Further, the Opto-Magnetic method is in essence an Opto-Magnetic Fingerprint (OMF) method based on electron properties of matter and its interaction with light. By way of example, and in no way limiting the scope of the invention, the concept of light-matter interaction and Opto-magnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

Typically, valence electrons build major link network of matter. The orbital velocity of the valence electrons in atoms is of the order of $10^6$ m/s. This gives the ratio between magnetic force ($F_M$) and electrical force ($F_E$) of matter of approximately $10^{-4}$ (or $F_M/F_E \approx 10^{-4}$.) Since, force (F) is directly related to quantum action (or Planck action) through the following equation: $h = F \times d \times t = 6.626 \times 10^{-34}$ Js, where F is force, d is displacement and t is time of action. This means that the action of magnetic forces is four orders of magnitude closer to quantum action than the electrical ones. Further, since quantum state of matter is primarily responsible for conformational changes on the molecular level, this means that detecting differences between tissue states is by far more likely to give greater sensitivity on the level of magnetic forces than it would be on the level of measurement of electrical forces.

The term "conformational change" refers to a transition in shape of a macromolecule. Typically, a macromolecule is flexible or dynamic. Thus, it can change its shape in response to changes in its environment or other factors. Each possible shape is called a conformation. A macromolecular conformational change may be induced by many factors, such as a change in temperature, pH, voltage, ion concentration, or the binding of a ligand.

In certain other embodiments, a comparative analysis of, pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

Since, reflected polarized light contains electrical component of light-matter interaction. Thus, taking the difference between white light (i.e. electromagnetic) and reflected polarized light (i.e. electrical) yields magnetic properties of matter based on light-matter interaction.

Further since, reflected polarized light is composed of longitudinal wave (i.e. electrical component) and transverse wave (i.e. magnetic component). This implies that only electrical component as a longitudinal wave contains data (i.e. image) of light-matter interaction, which activates either CMOS or CCD image sensor.

In certain embodiments, the methods and systems for overall management of dental or oral health performs one or more functions. By way of example, and in no way limiting the scope of the invention, the methods and systems for overall management of dental or oral health exhibition of degree of mineralization of enamel and ratio of minerals to water and other organic material thereof, color of enamel, comparison of enamel over time, validation of a person's hygienic routine by determining progress of enamel cleaning, thickness of enamel, health of cementoenamel junction (or CEJ), measurement of strength on a relative scale or in comparison with peers, on custom scales or on Mohs hardness scale, for example, presence of proteins called amelogenins and enamelins, determination of type of Dentin, such as primary, secondary and tertiary, porosity, verification of the health and status of a teeth enamel and other dermal structures thereof, determination of depth of enamel towards application, determination of predisposition of dental cavities and other dental problems, identification and presence of rod sheath, Striae of Retzius, neonatal line, Perikymata, Gnarled Enamel, Keratin levels, Nasmyth's membrane or enamel cuticle, acquired pellicle, food debris, presence microcracks within the tooth, degree of microcracking within the tooth, amount of Plaque, tooth decay or attrition, sensitivity of teeth, gum diseases, such as gingivitis, Peridontis, color of gums (e.g. bright-red, or purple gums) that gives indication of gum health, degree of swelling of gums, presence of mouth sores, tracking of progress of mouth sores over time, shinyness of gums, presence of pus in gums, presence of new teeth coming, status of fillings, presence of plaque/level of plaque, determination of the extent of a cavity, determination of the propensity/predisposition of developing carries or cavities, Chronic Bilirubin Encephalopathy, Enamel Hypoplasia, Erythropoietic Porphyria, Fluorosis, Celiac Disease, presence of Tetracycline, presence and status of composites and sealants, determination of health and structural integrity of crowns and veneers, amalgams and the like, track the progress of conditions like Bruxism (i.e. grinding of the teeth) and indication of attrition over time, determination of presence of amelogenins, ameloblastins, enamelins, and tuftelins.

Figure 111:
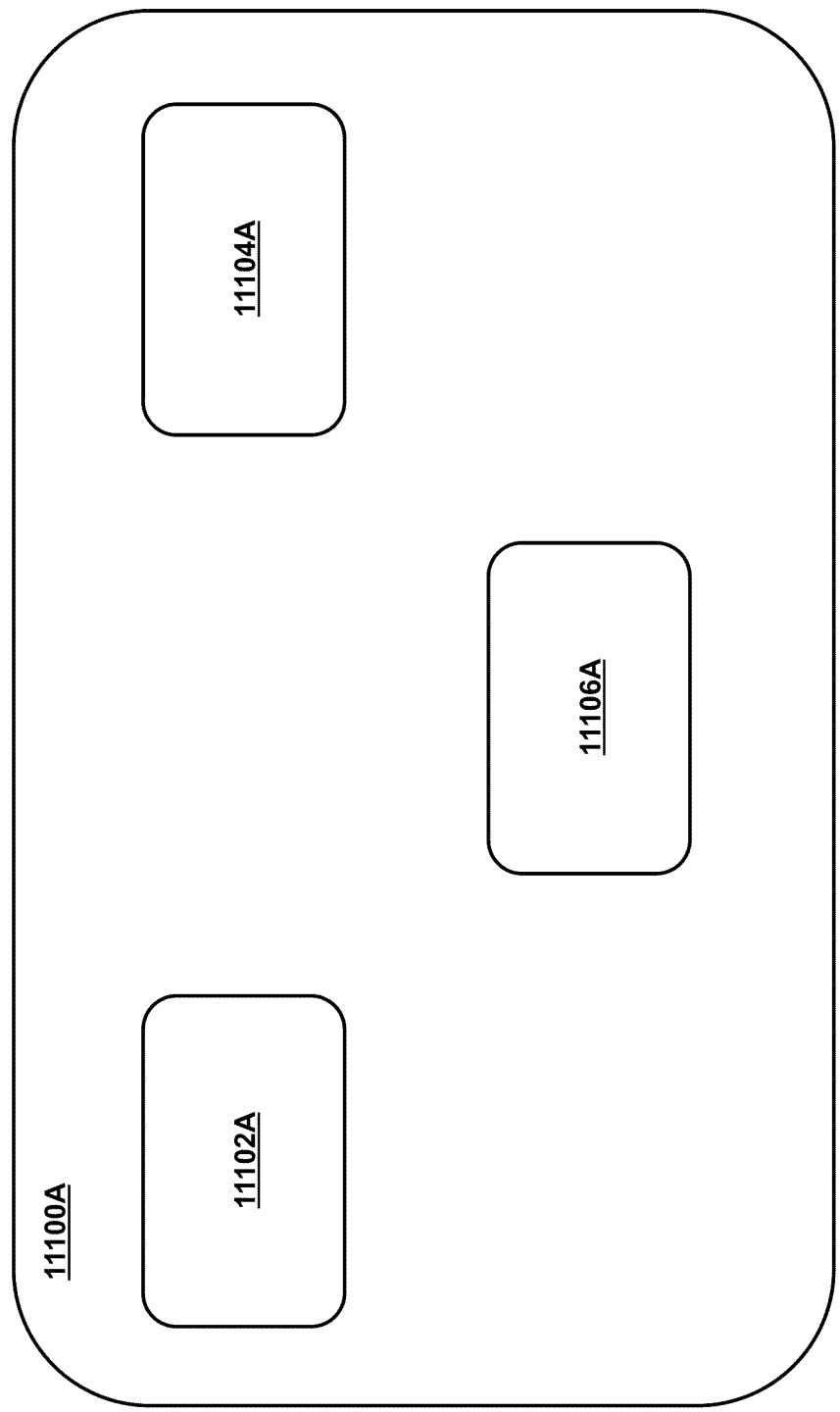
FIG. 111A is a block diagrammatic view of a system facilitating overall management of dental or oral health through implementation of an Opto-Magnetic process based on light-matter interaction using digital imaging for diagnosis of teeth, designed and implemented in accordance with certain embodiments of the invention.

FIG. 111A is a block diagrammatic view of a system facilitating overall management of dental or oral health through implementation of an Opto-Magnetic process based on light-matter interaction using digital imaging for diagnosis of teeth, designed and implemented in accordance with certain embodiments of the invention.

System 11100A is in essence a Dental Health Management System (or DHMS) or Oral Health Management System. The DHMS 11100A includes an illumination subsystem 11102A, an imaging (or sensor) subsystem 11104A and a host computing subsystem 11106A.

DHMS 11100A, by virtue of its design and implementation, facilitates execution of an Opto-Magnetic method based on interaction between electromagnetic radiation and matter, for instance light-matter interaction, using digital imaging for diagnosis of teeth. Specifically, the Opto-Magnetic process employs apparatuses for generation of unique spectral signatures from digitally captured images of samples thereby facilitating analysis of teeth based on Opto-Magnetic properties of light-test sample matter interaction.

Illumination subsystem 11102A may be one or more electromagnetic radiation sources. In certain specific embodiments, the Illumination subsystem 11102A may be a set of Light Emitting Diodes (LEDs). By way of example, and in no way limiting the scope of the invention, the illumination subsystem 11102A is a set of six LEDs.

Illumination subsystem 11102A may be adapted to emit polarized and unpolarized electromagnetic signals. The polarized electromagnetic signal is angled white light and unpolarized electromagnetic signal is non-angled white light.

As used in the current context, the term "Light-Emitting Diode or LED" refers to a semiconductor light source. LEDs are PN junction devices that give off light radiation when biased in the forward direction. LEDs are solid-state devices requiring little power and generating little heat. Because their heat generation is low and because they do not rely on a deteriorating material to generate light, LEDs have long operating lifetimes. LEDs can be divided into three types based on LED construction, namely edge emitting, surface emitting, and super luminescent. Firstly, an edge emitting LED is a LED with output that emanates from between the heterogeneous layers. Secondly, a surface emitting LED is a LED that emits light perpendicular to the active region. Eventually, super luminescent LEDs are based on stimulated emission with amplification but insufficient feedback for oscillation to build up.

In general, some important performance specifications parameters considered in identification and selection of LED include LED type, peak wavelength, viewing angle, optical power output, luminous intensity, forward current and forward voltage. For example, based on color LED types include infrared, red, orange, yellow, green, blue, white, and ultraviolet. Peak wavelength is the desired output wavelength of LED. Dependent upon diffusion from the lens, usually the larger the viewing angle, the less bright the LED. Diffused types generally have larger viewing angles and non-diffused types have smaller viewing angles. The optical power output of the LED is expressed in mW. The luminous intensity of the LED is expressed in mcd. The candela (cd) is the luminous intensity of a light source producing light at a wavelength of 555.17 nm with a power of $1/683$ watt per steradian, or 18.3988 milliwatts over a complete sphere centered at the light source.

Common features of LEDs include lens type choices, bipolar construction, dual LEDs, and arrays. For example, lens type choices include flat lenses and domed lenses. Specifically, bipolar LEDs work even if voltage is reversed. Dual LEDs are two LED lamps in the same housing. In an LED array the LEDs are packaged as multiples. LED arrays will contain a certain number of elements (LEDs).

In certain such embodiments, the illumination subsystem 102 possess the following specifications: electromagnetic radiation source LED, number of LEDs 6; LED color type white; color temperature 5000° K and the like.

As shown in the FIG. 111A, in certain embodiments, the illumination subsystem 11102A may be coupled to the sensor subsystem 11104A.

As shown in the FIG. 111A, the sensor subsystem 11104A may in essence be a device that converts optical images (or optical signals) to electric signals. In certain embodiments, the sensor subsystem 11104A captures continuous digital images of teeth. Specifically, in such embodiments, the sensor subsystem 11104A captures continuous digital images of the teeth illuminated with white light both, non-angled and angled. By way of, and by no way of limitation, the sensor subsystem 11104A may be anyone selected from a group consisting of a Complementary Metal-Oxide-Semiconductor (CMOS) image sensor, Charged Coupled Device (CCD) image sensor, and the like.

As used herein, the term "Charge-Coupled Device or CCD" refers to a device for the movement of electrical charge, usually from within the device to an area where the charge can be manipulated, for example conversion into a digital value. This is achieved by "shifting" the signals between stages within the device one at a time. Technically, CCDs are implemented as shift registers that move charge between capacitive bins in the device, with the shift allowing for the transfer of charge between bins. Often the device is integrated with a sensor, such as a photoelectric device to produce the charge that is being read, thus making the CCD a major technology for digital imaging. Although CCDs are not the only technology to allow for light detection, CCDs are widely used in professional, medical, and scientific applications where high-quality image data is required.

In certain specific applications, digital color cameras generally use a Bayer mask over the CCD. Each square of four pixels has one filtered red, one blue, and two green (the human eye is more sensitive to green than either red or blue). The result of this is that luminance information is collected at every pixel, but the color resolution is lower than the luminance resolution.

In certain other specific applications, better color separation can be reached by three-CCD devices (or 3CCD) and a dichroic beam splitter prism that splits the image into red, green and blue components. Specifically, each of the three CCDs is arranged to respond to a particular color. For example, some semi-professional digital video camcorders and most professional camcorders use this technique. Another advantage of 3CCD over a Bayer mask device is higher quantum efficiency and therefore higher light sensitivity for a given aperture size. This is because in a 3CCD device most of the light entering the aperture is captured by a sensor, while a Bayer mask absorbs a high proportion (i.e. approximately $2/3$) of the light falling on each CCD pixel.

For example, and in no way limiting the scope of the invention, in certain embodiments the sensor subsystem 11104A may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

In certain such embodiments, the sensor subsystem 11104A may possess the following specifications: pick up element is CCD image sensor or camera; CCD image sensor or camera type is color; array type is linear array, frame transfer area array, full frame area array or interline transfer area array; optical format is ¼" (or inch); horizontal resolution; format/output is National Television System Committee (NTSC) or Phase Alternate Line (PAL); total number of pixels for NTSC is 270K whereas for PAL is 320K; resolution is 350TV line; shutter control is electronic shutter; shutter speed for $1/60$~$1/100,000$ seconds whereas $1/50$~$1/100,000$ seconds; gain control is automatic; Video Out is 1.0Vp-p composite/75 Ohm; power supply is 5V DC; dimensions (i.e. Length L, Width W and Height H or L*W*H) are 185*25*20 mm$^3$; TV system NTSC or PAL; Video In is 1.0Vp-p, 75 Ohm ($\Omega$); digital resolution is 8-bit 256 grad, 512*1024 pixels; digital I/O is 16 bits; signal is 52 dB; power source is DC 9V; freeze mode is frame; dimensions (i.e. Length L, Width W and Height H or L*W*H) are 110*82*37 mm$^3$ and the like.

The term "electronic shutter control" refers to the light gathering period. This may be programmed or altered with a digital electronic interface.

The term "gain control" refers to Automatic Gain Control (or AGC) that uses electronic circuitry to increase video signals in low-light conditions. This can introduce noise and, subsequently, graininess in the picture. Typically, AGC is disabled and specifications are presented with this feature turned off.

The term "shutter speed" refers to the time of exposure or light collection. Typically, it may be set across a wide range.

The term "horizontal resolution" refers to the maximum number of individual picture elements that can be distinguished in a single scanning line. This measurement is used to characterize the horizontal video resolution corrected for the image aspect ratio, or to specify the resolution in the largest circle than can fit in a rectangular image. A 640×480 image would, for example, be specified as 480 horizontal lines.

The term "optical format" refers to a digital imaging optical format that is a measure of the size of the imaging area. Optical format is used to determine size of lens necessary for use with the imager. Optical format refers to the length of the diagonal of the imaging area.

Again, as shown in FIG. 111A, the sensor subsystem 11104A may be coupled to the host computing subsystem 11106A.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional signal and applying standard signal-processing techniques to it.

Image processing usually refers to digital image processing, but optical and analog image processing are also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

Figure 112:
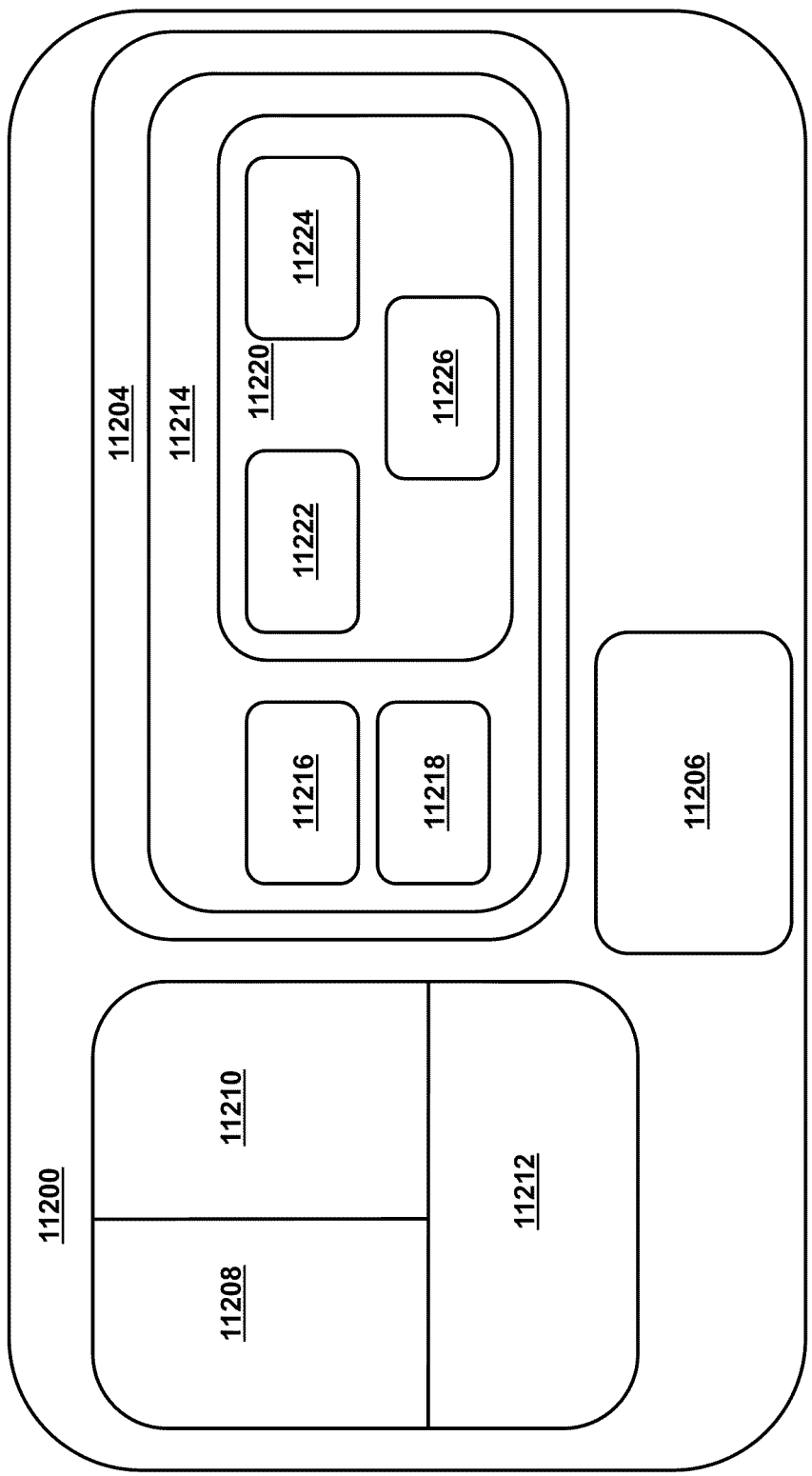
FIG. 112 is an exploded diagrammatic representation of the host computing subsystem, of the FIG. 111A, comprising an Opto-Magnetic Fingerprint (or OMF) Generator submodule designed and implemented in accordance with at least some embodiments.

FIG. 112 is an exploded diagrammatic representation of the host computing subsystem, of the FIG. 111A, comprising an Opto-Magnetic Fingerprint (or OMF) Generator sub-module designed and implemented in accordance with at least some embodiments.

The host computing subsystem 11200 may comprise a processing unit 11202, a memory unit 11204 and an Input/Output (or I/O) unit 11206 respectively.

The host computing subsystem 11200, by virtue of its design and implementation, performs overall management of dental or oral health.

The processing unit 11202 may comprise an Arithmetic Logic Unit (or ALU) 11208, a Control Unit (or CU) 11210 and a Register Unit (or RU) 11212.

In certain specific embodiments, the processing unit 11202 may be a Video Processing Unit (or VPU). Specifically, in certain such embodiments, the VPU 11202 may possess the following specifications: the sensor subsystem 10504 in conjunction with the VPU 11202 may possess the following specifications: pick up element is CCD image sensor or camera; CCD image sensor or camera type is color; array type is linear array, frame transfer area array, full frame area array or interline transfer area array; optical format is ¼" (or inch); horizontal resolution; format/output is National Television System Committee (NTSC) or Phase Alternate Line (PAL); total number of pixels for NTSC is 270K whereas for PAL is 320K; resolution is 350TV line; shutter control is electronic shutter; shutter speed for $\frac{1}{60}$~$\frac{1}{100,000}$ seconds whereas $\frac{1}{50}$~$\frac{1}{100,000}$ seconds; gain control is automatic; Video Out is 1.0Vp-p composite/75 Ohm; power supply is 5V DC; dimensions (i.e. Length L, Width W and Height H or L*W*H) are 185*25*20 mm$^3$; TV system NTSC or PAL; Video In is 1.0Vp-p, 75 Ohm ($\Omega$); digital resolution is 8-bit 256 grad, 512*1024 pixels; digital I/O is 16 bits; signal is 52 dB; power source is DC 9V; freeze mode is frame; dimensions (i.e. Length L, Width W and Height H or L*W*H) are 110*82*37 mm$^3$ and the like.

As used herein, the term "Video Processing Unit or VPU" refers to a Graphics Processing Unit or GPU (also occasionally called Visual Processing Unit) is a specialized processor that offloads 3D graphics rendering from the microprocessor.

In certain specific embodiments, the I/O unit 806 may comprise of at least a Video In port and Video Out port, and any potential permutations or combinations of Video In port and a Video Out port.

The term "Video In Video Out or VIVO" refers to a graphics port which enables some video cards to have bidirectional (input and output) analog video transfer through a mini-DIN connector, usually of the 9-pin variety, and a specialized splitter cable, which can sometimes also transfer analog audio.

As shown in FIG. 112, the memory unit 11204 comprises an oral or dental analysis module 11214.

In certain embodiments, the oral or dental analysis module for examination of teeth via generation of unique spectral signatures from the digitally captured images of the teeth and methods thereof are disclosed, in accordance with the principles of the invention. Specifically, in such embodiments, the oral or dental analysis module utilizes the continuously captured digital images of teeth illuminated with white light both, non-angled and angled. More specifically, the oral or dental analysis module takes into consideration the digital images in Red (R), Green (G) and Blue (B) (or RGB) system for purposes of analysis.

Further, as shown in FIG. 112, the oral or dental analysis module 11214 includes a Fourier transform sub-module 11216, a spectral analyzer sub-module 11218 and an Opto-Magnetic Fingerprint Generator (or OMFG) sub-module 11220, respectively.

In certain embodiments, the Fourier transform sub-module 11216 is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 11216 converts time-domain digital signals into corresponding frequency-domain digital signals.

DTFT 11216 is coupled to the spectrum analyzer sub-module 11218.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of teeth is disclosed. Specifically, the spectrum (or spectral) analyzer sub-module in order to analyze the samples takes into consideration digital images of the samples in Red (R), Green (G) and Blue (B) (or RGB) system. In certain such embodiments, basic pixel data in Red (R) and Blue (B)

channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R−B) & (W−P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as teeth surface, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 112, the spectrum analyzer sub-module 11218 may be coupled to the OMFG sub-module 11220.

OMFG sub-module 11220 includes a color histogram generator unit 11222, a spectral plot generator unit 11224 and a convolution unit 11226.

OMFG sub-module 11220, by virtue of its design and implementation, facilitates generation of unique spectral signatures from digitally captured images of teeth. Specifically, the generated spectral signatures of teeth facilitate detection of pluralities of problems in connection with teeth based on Opto-Magnetic properties of light-test sample interaction.

Color histogram generator unit 11222, by virtue of its design, generates a normalized Red (R) and Blue (B) color channel histogram for each of the one or more images of the teeth.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram, which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 1 exhibits a tabular representation in connection with a 2D Red-Blue chromaticity histogram generated by first normalizing color pixel values by dividing RGB values by R+G+B, then quantizing the normalized R and B coordinates into N bins each, where N=4.

|   |         | R    |         |         |         |
|---|---------|------|---------|---------|---------|
|   |         | 0-63 | 64-127  | 128-191 | 192-255 |
| B | 0-63    | 43   | 78      | 18      | 0       |
|   | 64-127  | 45   | 67      | 33      | 2       |
|   | 128-191 | 127  | 58      | 25      | 8       |
|   | 192-255 | 140  | 47      | 47      | 13      |

As shown in FIG. 112, the color histogram generator unit 11222 may be coupled to the spectral plot generator unit 11224.

Spectral plot generator unit 11224 generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 11226 convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the teeth.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

In certain other embodiments, the system configuration, discussed in conjunction with FIGS. 111A and 112, implement one or more processes facilitating estimation of sample type and properties (or characteristics) thereof to create a unique spectral signature.

Figure 113:
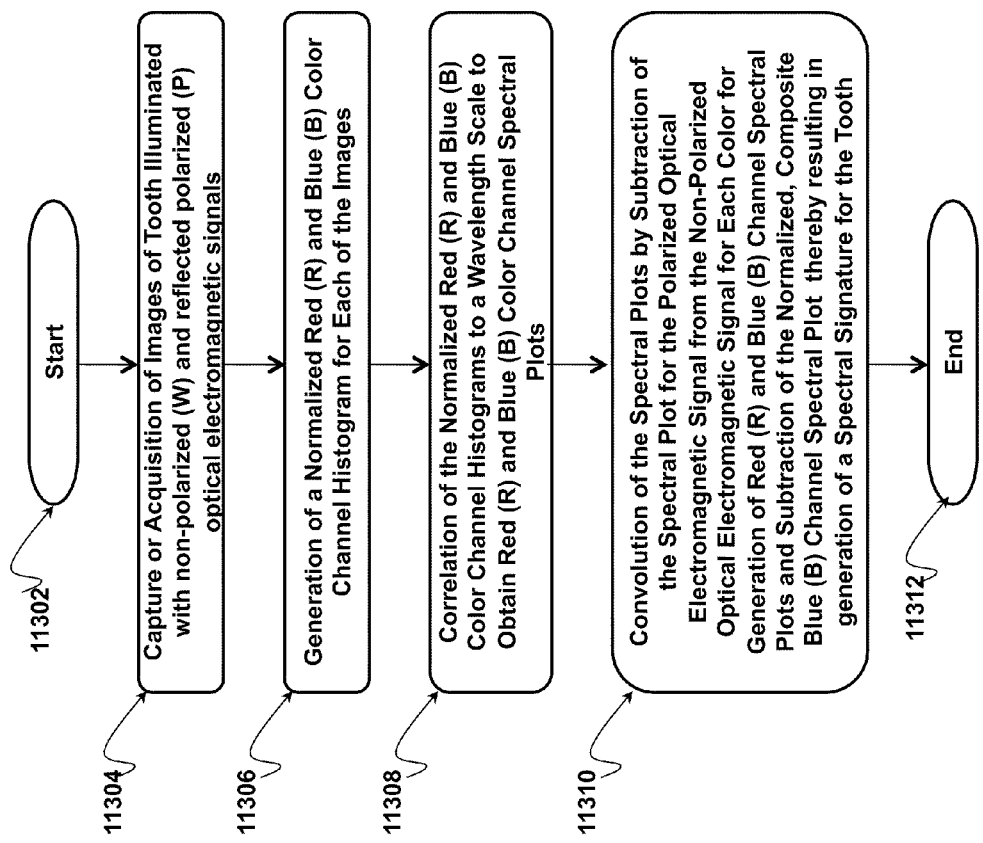
FIG. 113 depicts a flow diagram delineating at least one process implemented by the system configuration of FIGS. 111A and 112 thereby facilitating determination of teeth type and properties (or characteristics) thereof and creation of a unique spectral signature.

FIG. 113 depicts a flow diagram delineating at least one process implemented by the system configuration of FIGS. 111A and 112 thereby facilitating determination of teeth type and properties (or characteristics) thereof and creation of a unique spectral signature.

The process 11300 starts at stage 11302 and proceeds to stage 11304, wherein the process 11300 comprises the phase of convolution of data associated with a first set of images of a teeth captured by illuminating the sample with a white light (or unangled white light.) Noticeable here is the fact that the data associated with the first set of images of the teeth illuminated with the white light (or unangled white light) may comprise one or more combinations of reflected and re-emitted angled and unangled white light.

At stage 11306, the process 11300 comprises the phase of convolution of data associated with a second set of images of the teeth captured by illuminating the sample with an angled white light. It must be noted here that the data associated with the second set of images of the teeth illuminated with the angled white light may comprise one or more combinations of reflected and re-emitted angled white light.

At stage 11308, the process 11300 comprises the phase of comparison of extrema (i.e. maxima and minima) (or extreme) positions of at least a pair of unique convolutions generated by convolution of data from the first set of images and second set of images.

At stage 11310, the process 11300 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) teeth type. The process 11300 ends at stage 11312.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R-B) (W-P)) versus a second component Red (R) minus Blue (B) of unangled white light (or W) (i.e. (R-B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R-B) (W-P) for the reflected and/or re-emitted polarized light, and a component (R-B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

Figure 114:
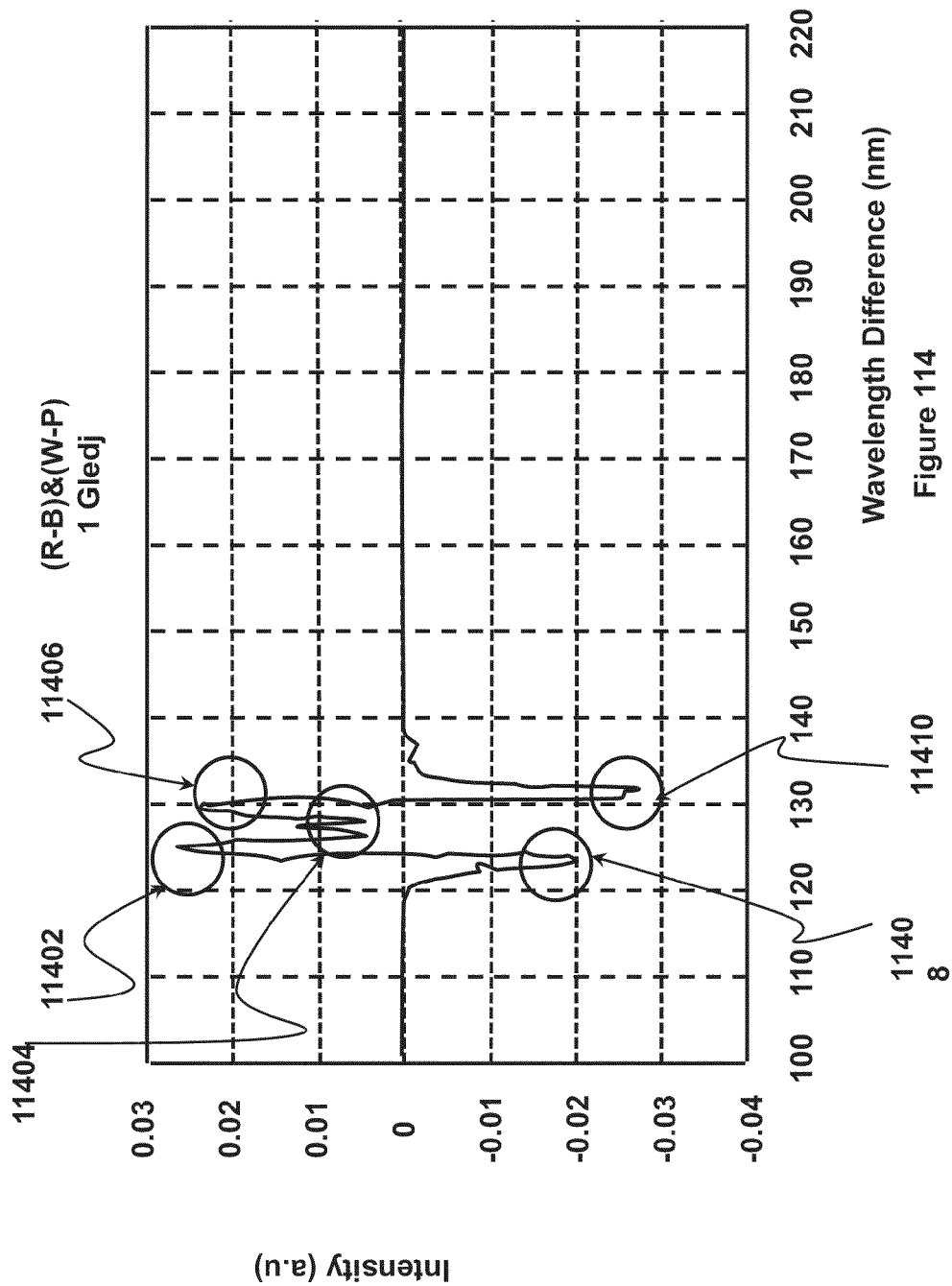
FIG. 114 depicts a first plot of a typical spectral data (or OMF diagram) for enamel obtained on implementation of the OMF method on digital images of the teeth, in accordance with certain embodiments of the invention.

FIG. 114 depicts a first plot of a typical spectral data (or OMF diagram) for enamel obtained on implementation of the OMF method on digital images of the teeth, in accordance with certain embodiments of the invention.

As shown in FIG. 114, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the teeth, captured using diffuse white light and reflected polarized light, using the OMF method. Specifically, the OMF method implements the SCA and CAA to analyze the processed digital image of the sample.

As depicted in FIG. 114, the first DI plot may possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.04 a.u. to a maximum of equal to +0.03 a.u. (or [−0.04, +0.03]); analytical information is analysis of the first DI plot (or OMF Diagram) of the enamel of the teeth; input sample is the teeth; operation is implementation of OMF method on digital images of the teeth; number of intensity peaks (or extrema or maxima and minima) is approximately 5; number of peaks with positive intensity values is approximately 3; number of peaks with negative intensity value is approximately 2; identifiers for the 5 intensity peaks are first 11402A, second 11404A, third 11406A, fourth 11418A and fifth 11410A respectively in that order.

Figure 115:
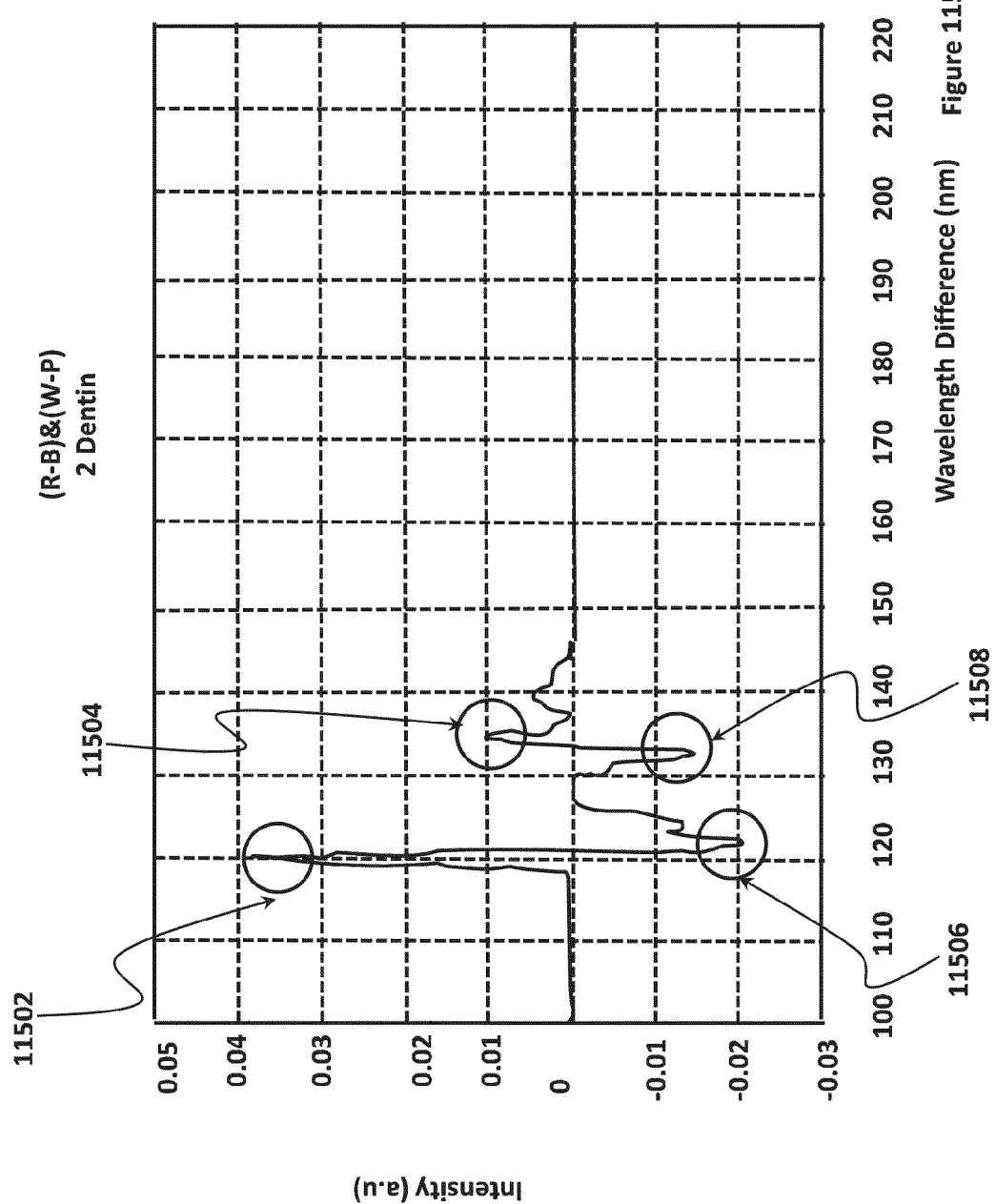
FIG. 115 depicts a second plot of a typical spectral data (or OMF diagram) for dentin obtained on implementation of the OMF method on digital images of the teeth, in accordance with certain embodiments of the invention.

FIG. 115 depicts a second plot of a typical spectral data (or OMF diagram) for dentin obtained on implementation of the OMF method on digital images of the teeth, in accordance with certain embodiments of the invention.

As depicted in FIG. 115, the second DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.03 a.u. to a maximum of equal to +0.05 a.u.; analytical information is analysis of the second DI plot (or OMF Diagram) of the digital photography image of the dentin of the teeth; input sample is the teeth; operation is implementation of OMF method on digital images of the teeth; number of intensity peaks (or extrema or maxima and minima) is approximately 4; number of peaks with positive intensity values is approximately 2; number of peaks with negative intensity value is approximately 2; identifiers for the 4 intensity peaks are first 11502A, second 11504A, third 11506A and fourth 11508A in that order.

Figure 116:
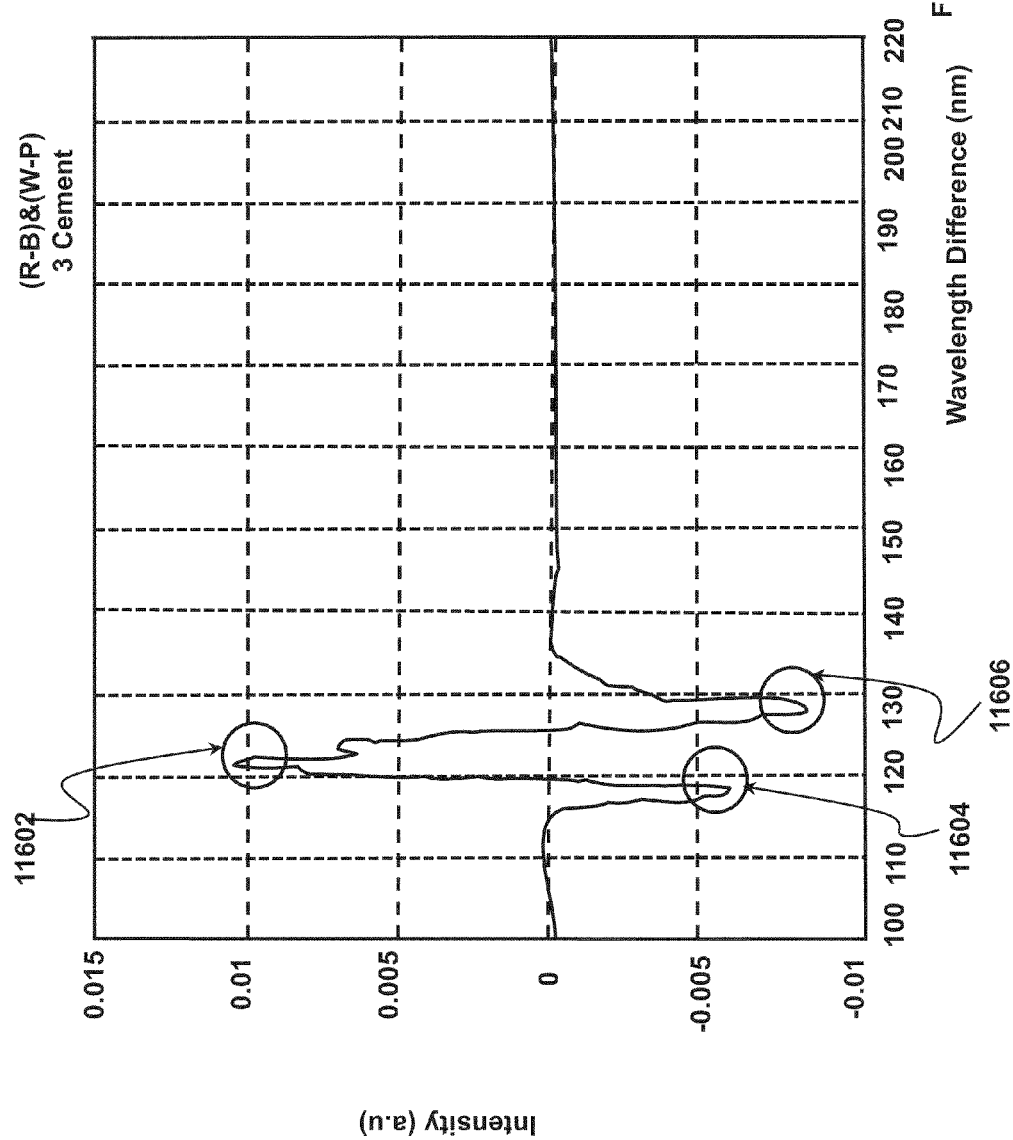
FIG. 116 depicts a third plot of a typical spectral data (or OMF diagram) of cement obtained on implementation of the OMF method on digital images of the teeth, in accordance with certain embodiments of the invention.

FIG. 116 depicts a third plot of a typical spectral data (or OMF diagram) of cement obtained on implementation of the OMF method on digital images of the teeth, in accordance with certain embodiments of the invention.

As depicted in FIG. 116, the third DI plot possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical X-axis includes a closed interval of Intensity Values ranging from a minimum of equal to −0.01 a.u. to a maximum of equal to +0.015 a.u.; analytical information is analysis of the third DI plot (or OMF Diagram) of the digital photography image of the cement of the teeth; operation is implementation of OMF method on digital images of the teeth; number of intensity peaks (or extrema or maxima and minima) is approximately 3; number of peaks with positive intensity values is approximately 1; number of peaks with negative intensity value is approximately 2; identifiers for the 3 intensity peaks are first 602A, second 11604A and third 11606A in that order.

Dentin and other samples are prepared from sound human permanent cutters and molars. A total of 11 teeth (i.e. 3 canines, 6 premolars and 2 molars) are embedded in epoxy-resin molds, for fixation purposes. The molds are cut using microtome. As a result, a total number of 45 cross-sections are obtained. On examination, 41 cross-sections are used and remaining 4 are rejected, owing to the fact that these remaining 4 did not posses adequate distribution of tissues thereof. The slice thickness of the cross-sections is around 1 mm on an average, with the aim to avoid translucency, since OMF is a technique based on reflected and diffusely reflected light.

Figure 117:
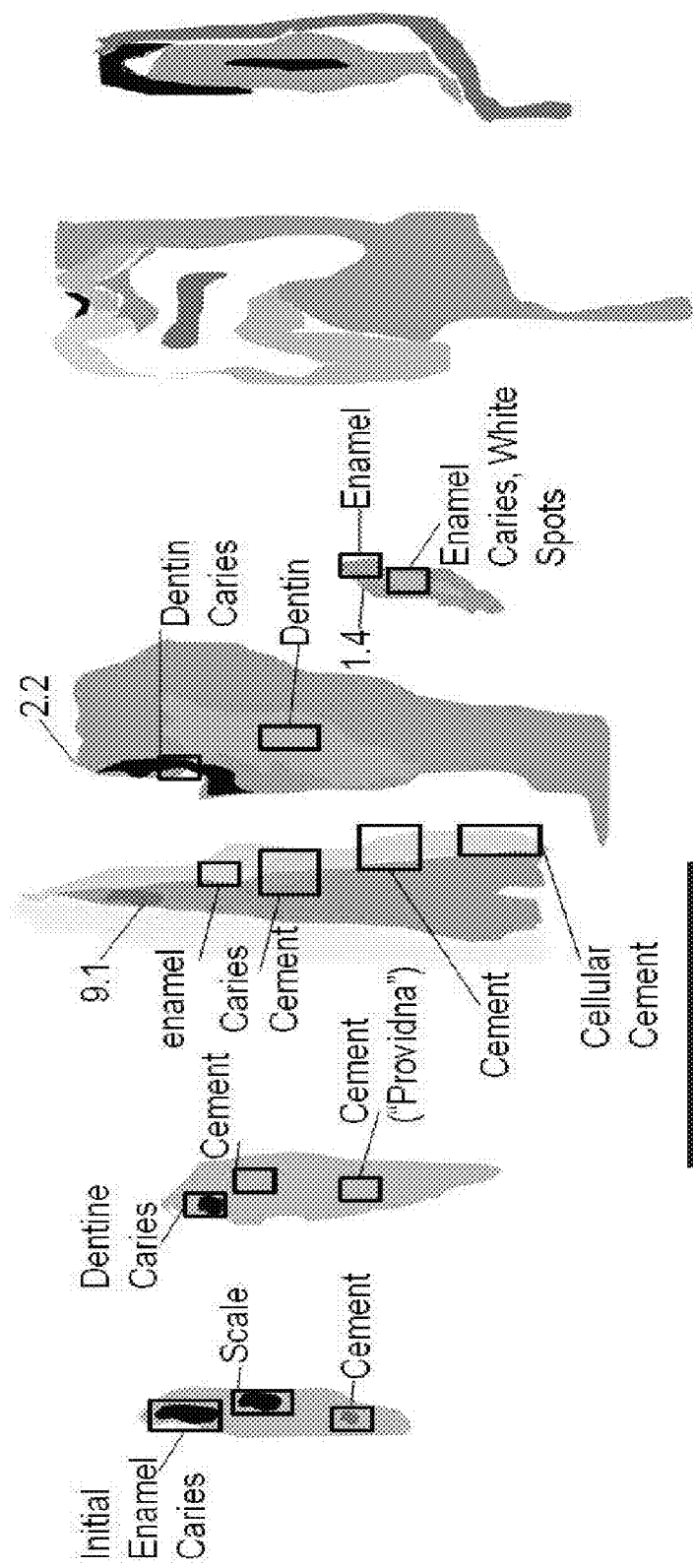
FIG. 117 depicts a pair of snapshots of a pair of canine teeth prior and subsequent to cross-sectional cutting in juxtaposition with a third snapshot depicting main dental tissues thereof for clarification purposes.

FIG. 117 depicts a pair of snapshots of a pair of canine teeth prior and subsequent to cross-sectional cutting in juxtaposition with a third snapshot depicting main dental tissues thereof for clarification purposes.

FIG. 118 depicts the results of the implementation of the OMF method on 44 cross-sections on multiple locations and the high sensitivity of the OMF method in terms of wavelength and reflected light intensities.

FIG. 119A depicts images for the comparative analysis of the teeth with healthy enamel obtained using AFM/MFM and OMF methods, in accordance with the principles of the invention.

FIG. 119B depicts images for the comparative analysis of the teeth with enamel affected with caries obtained using AFM/MFM and OMF methods, in accordance with the principles of the invention.

FIG. 119C depicts images for the comparative analysis of the teeth with healthy dentin obtained using AFM/MFM and OMF methods, in accordance with the principles of the invention.

FIG. 119D depicts images for the comparative analysis of the teeth with dentin affected with caries obtained using AFM/MFM and OMF methods, in accordance with the principles of the invention.

FIG. 119E depicts images for the comparative analysis of the teeth with healthy cement obtained using AFM/MFM and OMF methods, in accordance with the principles of the invention.

FIG. 119F depicts images for the comparative analysis of the teeth with cement affected with caries obtained using AFM/MFM and OMF methods, in accordance with the principles of the invention.

In certain embodiments, methods for analyzing water based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for analysis of water samples based on Opto-Magnetic properties of light-matter interaction. Still more specifically, the systems and apparatuses facilitate implementation of an Opto-Magnetic method with enhanced qualitative and quantitative parameters, novel, enhanced and easy interpretability, enhanced and easy detectability, enhanced sensitivity, enhanced specificity, enhanced efficiency, greater accuracy, easily operable, rapid, economical, precise, timely and minute variation sensitive, for analysis of water samples based on Opto-Magnetic properties of light-matter interaction, i.e. light-water interaction.

Typically, water is matter that is most abundant with hydrogen bonds, which may be organized in molecular networks, indicates that water via hydrogen bonds (with classical and quantum properties), may play a role in molecular and biomolecular recognition.

In certain specific embodiments, water via hydrogen bonds may play a significant role in molecular and biomolecular recognition thereby facilitating selection of water as test input sample, has been discussed from a kwon point of view. In such embodiments, based on the aforesaid point of view, two primary goals in connection with modern pharmacy are taken into consideration, namely (1) understanding mechanism for molecular recognition in water solution, and (2) water structure for drug design. In here, note is taken of the fact that water structure for drug design is important. This is because modeling ligand-receptor interaction has to include specific geometry, which relates to water structure. In addition, it is well known that hydrogen bonds are a link between two nucleotide chains in DNA and support existence of secondary, ternary and quaternary structure of proteins.

In certain specific embodiments, the method of the present invention is based on light-matter interaction and ratio of electrical and magnetic forces of covalent bonds and intermolecular bonds of matter. Deoxyribonucleic acid (or DNA) research indicates that both classical and quantum mechanical approach give same phenomenological results for those structures. The reason for similar result is simple. For stationary quantum state Hamiltonian H is a sum of kinetic T and potential V energy, while Lagrangian is a difference between them when system is in equilibrium with external forces. From the energy viewpoint, a pair of similar pictures, one classical and another quantum, of same object with similar results exist. Thus, the goal is to detect how hydrogen bonds participate in water to be more or less at least one of classical and quantum entity.

In such specific embodiments, the Planck's constant h is used as the first criterion to estimate whether an object is classical or quantum. Since Planck's constant by nature is action than product of force F, distance d and time t of action and has value $h=6.626\times10^{-34}$ Js or close to if system is quantum. However, answers to one or more tactical queries, such as "what is the value for coupling quantum-classical system?," "when classical system becomes dominant?," and the like, is unknown, and needs answer.

In accordance with specific embodiments, in light of the Planck's constant as a link between energy E and electromagnetic wave oscillation v and is represented by the following Equation 1:

$$E=h^*v.$$

Thus, a comparative analysis of the electrical and magnetic interaction between two electron charges in neighboring atoms in relative motion in matter may render a solution. The calculation of the magnetic interaction between two charged particles in motion relative to an observer O in a form similar to the electric interaction given by Coulomb's law is a simple task. However, it is important to compare the order of magnitude of the magnetic interaction with the electrical interaction. In response, taking into consideration, two charges q and q' of neighboring atoms moving with velocities v and v' relative to a given observer O simplifies the formulas, because only order of magnitude is required. Accordingly, the electrical force produced by q' on q as measured by the observer O is given by the following Equation 2:

$q*E$, where $E$ is the electrical force.

Further, in light of the following Equation 3:

$B=(1/c^2)(v\times E)$, where B is the magnetic force, c is the velocity of light, v is the velocity of a given charge q, the magnetic field produced by q' is of order of magnitude of $(v'*E/c^2)$ whereas the magnetic force on q is of the order of $\{q*v*B=(v*v'/c^2)*q*E\}$. Since, $q*E$ is the electrical force on q than the ratio of the magnetic force is to electrical force (i.e. magnetic force/electrical force or $F_M/F_E)\approx(v*v'/c^2)$. In certain circumstances involving specific embodiments, if the velocities of the charges are small compared with the velocity of light c, the magnetic force is negligible compared to the electrical force and in such circumstances thus ignored. Further, the orbital velocity of valence electrons in atoms is about $10^6$ m/s, which gives $F_M/F_E\approx10^{-4}$. This implies that existence of semi-classical/quantum may be $6.626\times10^{-34}<h*<6.626\times10^{-30}$. From energy point of view, in this action area, both classical and quantum phenomena exist simultaneously. Based on the aforementioned value of action coupling classical and quantum phenomena, means that the aforementioned action area is perfect one for hydrogen bond analysis. Consequently, if action is $h*>6.626\times10^{-30}$ Js than phenomena are classical, whereas if it is $6,626\times10^{-34}$ Js, it is quantum. Electrical force is closer to classical interaction (i.e. Coulomb's law), whereas magnetic force is closer for order four to quantum interaction than electrical one.

In certain specific embodiments, calculation of action requires or is based on known values of force, distance and time of hydrogen bonds activity. In such specific embodiments, average values for force, distance and time are: force $2.5\times10^{-13}$ N, distance $1.6\times10^{-10}$ m and time $50\times10^{-15}$ s. Thus, based on the average values of the force, distance and time the action of $h*=F*d*t=(2.5\times10^{-10})\times(1.6\times10^{-10})\times(50\times10^{-15})=0.5\times10^{-33}$ Js, which is semi-quantum action. Further, Hydrogen bond in water is for three orders closer to quantum (i.e. $6.626\times10^{-34}$ Js) than to classical (i.e. $6.626\times10^{-30}$ Js) action. According to the ratio $F_M/F_E\approx10^{-4}$, magnetic and electrical fingerprint of hydrogen bond of water will be different, because action of magnetic force will be separate it two parts (quantum and classical), while electrical force will be only classical, because domain of its action is $10^{-29}$ Js ($0.5\times10^{-33}\times10^4\approx10^{-29}$ Js).

In certain embodiments, on analysis of different types of matter it is observed that spectral convolution data of digital images characterize matter from both covalent and non-covalent bonding. Since water is matter that is most abundant with hydrogen bonds, results are presented for investigation of 18.2 MΩ (or megohm) water sample at different temperatures and under influence of constant and variable magnetic fields by Opto-Magnetic method.

In certain experimental embodiments, the system and apparatus facilitating implementation of an Opto-Magnetic method for analysis of water samples based on Opto-Magnetic properties of light-matter interaction is put into operation to measure quantum and classical contribution of hydrogen bonds action in water. Additionally, in such embodiments, a method to separate electrical and magnetic action in light-water interaction is implemented. In here, note must be taken of the fact that picture (or image) of surface captured by classical optical microscope is based on electromagnetic property of light, while OMF is based on difference between diffuse white light (i.e. like that of daily light) and reflected polarized light. Specifically, reflected polarized light is produced when source of diffuse light irradiates the surface of matter under certain angle (Brewster's angle). More specifically, each type of matter has a special different angular value of light polarization. In certain scenarios involving such experimental embodiments, it is found that angle of reflected polarized light of water is about 53° (or degrees). Further, since reflected polarized light contains electrical component of light-matter interaction, taking the difference between white light (electromagnetic) and reflected polarized light (electrical) fields gives magnetic properties of matter (i.e. Opto-Magnetic Fingerprint or OMF).

In certain specific embodiments, digital images in RGB (R-red, G-green, B-blue) system are utilized in analysis, therefore basic pixel data in red and blue channels for white diffuse light (W) and reflected polarized white light (P) are chosen. In such embodiments, algorithm for data analysis is based on chromaticity diagram called "Maxwell's triangle" and spectral convolution operation according to ratio of (R−B)&(W−P). The abbreviated designation means that Red minus Blue wavelength of White light and reflected Polarized light are used in spectral convolution algorithm to calculate data for Opto-Magnetic Fingerprint (or OMF) of matter. Therefore, method and algorithm for creating unique spectral fingerprint are based on the convolution of RGB color channel spectral plots generated from digital images that capture single and multi-wavelength light-matter interaction.

In certain embodiments, the analysis of water through investigation performed over one or more water samples subjected to one or more trials is disclosed. By way of example, and in no way limiting the scope of the invention, 8 water samples are subjected to 3 trials, i.e. 24 experiments. In such circumstances, 24 (8 samples*3 trials) similar experiments are conducted to test value differences of one or more parameters. In response, it is found that from an average the value difference of wavelength difference is ±0.14 nm, whereas for intensity is ±0.0032.

In certain specific embodiments, the sample is pure water with impurities thereby facilitating high percentage of pure hydrogen bonds interaction between water molecules. By way of example, and in no way limiting the scope of the invention, the sample is 18.2 MΩ water (pure water) with impurities in parts-per-billion (or ppb).

In certain other situations, the sample set is subjected to analysis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul.

17 "SYSTEM, DEVICE AND METHOD FOR DERMAL IMAGING" to J. Bandic, Dj. Koruga, R. Mehendale and S. Marinkovich of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for analysis of water based on the interaction between matter and electromagnetic radiation and systems and apparatuses facilitating implementation of such methods has been disclosed. Specifically, there is disclosed the design and implementation of an Opto-Magnetic method with enhanced qualitative and quantitative parameters for water samples based on Opto-Magnetic properties of light-matter interaction and systems and apparatuses thereof. Still more specifically, there is disclosed design and implementation of an Opto-Magnetic method with enhanced qualitative and quantitative parameters, such as novel, enhanced and easy interpretability, enhanced and easy detectability, enhanced sensitivity, enhanced specificity, enhanced efficiency, greater accuracy, easily operable, rapid, economical, precise, timely and minute variation sensitive, for analysis of water samples based on Opto-Magnetic properties of light-matter interaction and systems and apparatuses thereof.

Further, the Opto-Magnetic method is in essence an Opto-Magnetic Fingerprint (OMF) method based on electron properties of matter and its interaction with light. By way of example, and in no way limiting the scope of the invention, the concept of light-matter interaction and Optomagnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

Reiterating again, in certain other embodiments, a comparative analysis of pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

Since, reflected polarized light contains electrical component of light-matter interaction. Thus, taking the difference between white light (i.e. electromagnetic) and reflected polarized light (i.e. electrical) yields magnetic properties of matter based on light-matter interaction.

Since, reflected polarized light is composed of longitudinal wave (i.e. electrical component) and transverse wave (i.e. magnetic component). This implies that only electrical component as a longitudinal wave contains data (i.e. image) of light-matter interaction, which activates either CMOS or CCD image sensor.

Figure 120:
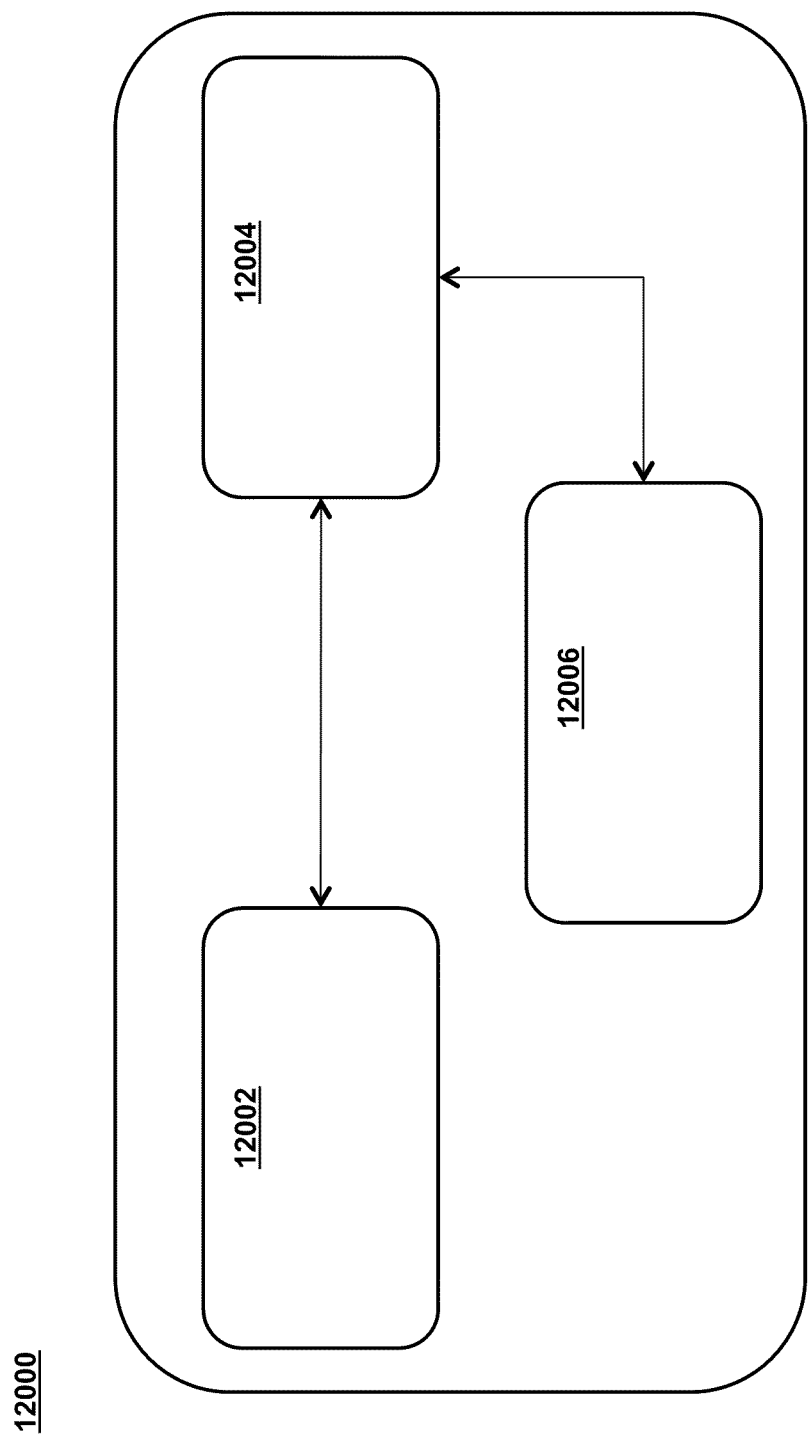

FIG. 120 is a block diagrammatic view of a system facilitating implementation of an Opto-Magnetic process based on light-water interaction using digital imaging for analysis of water samples, designed and implemented in accordance with certain embodiments of the invention.

System 12000 is in essence a Water Analyzer (or WA). The WA 12000 includes an illumination subsystem 12002, an imaging (or sensor) subsystem 12004 and a host computing subsystem 12006.

WA 12000, by virtue of its design and implementation, facilitates execution of an Opto-Magnetic process based on interaction between electromagnetic radiation and matter, for instance light-water interaction, using digital imaging for analysis of water samples. Specifically, the Opto-Magnetic process employs apparatuses for generation of unique spectral signatures from digitally captured images of water samples thereby facilitating analysis of the water samples based on Opto-Magnetic properties of light-water interaction.

Illumination subsystem 12002 may be one or more electromagnetic radiation sources. In certain specific embodiments, the Illumination subsystem 12002 may be a set of Light Emitting Diodes (LEDs).

Illumination subsystem 12002 may be adapted to emit polarized and unpolarized electromagnetic signals. The polarized electromagnetic signal is angled white light and unpolarized electromagnetic signal is non-angled white light.

As shown in the FIG. 120, in certain embodiments, the illumination subsystem 12002 may be coupled to the sensor subsystem 12004.

As shown in the FIG. 120, the sensor subsystem 12004 may in essence be a device that converts optical images (or optical signals) to electric signals. In certain embodiments, the sensor subsystem 12004 captures continuous digital images of water samples. Specifically, in such embodiments, the sensor subsystem 12004 captures continuous digital images of the water samples illuminated with white light both, non-angled and angled. By way of, and by no way of limitation, the sensor subsystem 12004 may be anyone selected from a group consisting of a Complementary Metal-Oxide-Semiconductor (CMOS) image sensor, Charged Coupled Device (CCD) image sensor, and the like.

Again, as shown in FIG. 120, the sensor subsystem 12004 may be coupled to the host computing subsystem 12006.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

For example, and in no way limiting the scope of the invention, in certain embodiments the sensor subsystem 12004 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional signal and applying standard signal-processing techniques to it.

Image processing usually refers to digital image processing, but optical and analog image processing are also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

As used in quantum mechanics, the term "Hamiltonian (or H or $\mathcal{H}$)" refers to the operator corresponding to the total energy of the system. Its spectrum is the set of possible outcomes when one measures the total energy of a system. It is of fundamental importance in most formulations of quantum theory because of its close relation to the time-evolution of a system. By analogy with classical mechanics, the Hamiltonian is commonly expressed as the sum of operators corresponding to the kinetic and potential energies of a system in the following form through Equation 4:

$\mathcal{H}$ =T+V. Note must be taken of the fact that although the Equation 16 is not the technical definition of the Hamiltonian in classical mechanics, it is the form it most commonly takes.

Further, the value of the Hamiltonian is the total energy of the system described. For a closed system, it is the sum of the kinetic and potential energy in the system. There is a set of differential equations known as the Hamilton equations which give the time evolution of the system. Hamiltonians can be used to describe simple systems, such as a bouncing ball, a pendulum or an oscillating spring, in which energy changes from kinetic to potential and back again over time. Hamiltonians can also be employed to model the energy of other more complex dynamic systems such as planetary orbits in celestial mechanics and also in quantum mechanics.

Still further, the Hamilton equations are generally represented through the following pair of Equations 5 and 6:

$$\dot{p} = -\frac{\partial \mathcal{H}}{\partial q}$$

$$\dot{q} = \frac{\partial \mathcal{H}}{\partial p}.$$

In the above pair of Equations 5 and 6, the dot denotes the ordinary derivative with respect to time of the functions p=p (t) (called generalized momenta) and q=q (t) (called generalized coordinates), taking values in some vector space, and H=H (p, q, t) is the so-called Hamiltonian, or (scalar valued) Hamiltonian function. Thus, more explicitly, the above pair of Equations 5 and 6 is equivalently represented by the following pair of Equations 7 and 8, wherein the domain of values in which the parameter t ("time") varies is specified:

$$\frac{d}{dt}p(t) = -\frac{\partial}{\partial q}\mathcal{H}(p(t), q(t), t)$$

$$\frac{d}{dt}q(t) = \frac{\partial}{\partial p}\mathcal{H}(p(t), q(t), t)$$

From the standpoint of interpretation of the Hamilton Equations, applying the pair of Equations 4 and 5 to a one-dimensional system consisting of one particle of mass m under time independent boundary conditions and exhibiting conservation of energy the Hamiltonian H represents the energy of the system. Reiterating again, H is the sum of kinetic and potential energy, T and V, respectively. Here q is the x-coordinate and p is the momentum, m*v.

In here, the potential operator V typically takes the form of a function V(r, t) of position and time, which simply acts on states as a multiplicative factor. The operator T corresponding to kinetic energy is constructed by analogy with the classical formula given by the following Equation 9:

$T=p^2/2*m$

Figure 121:
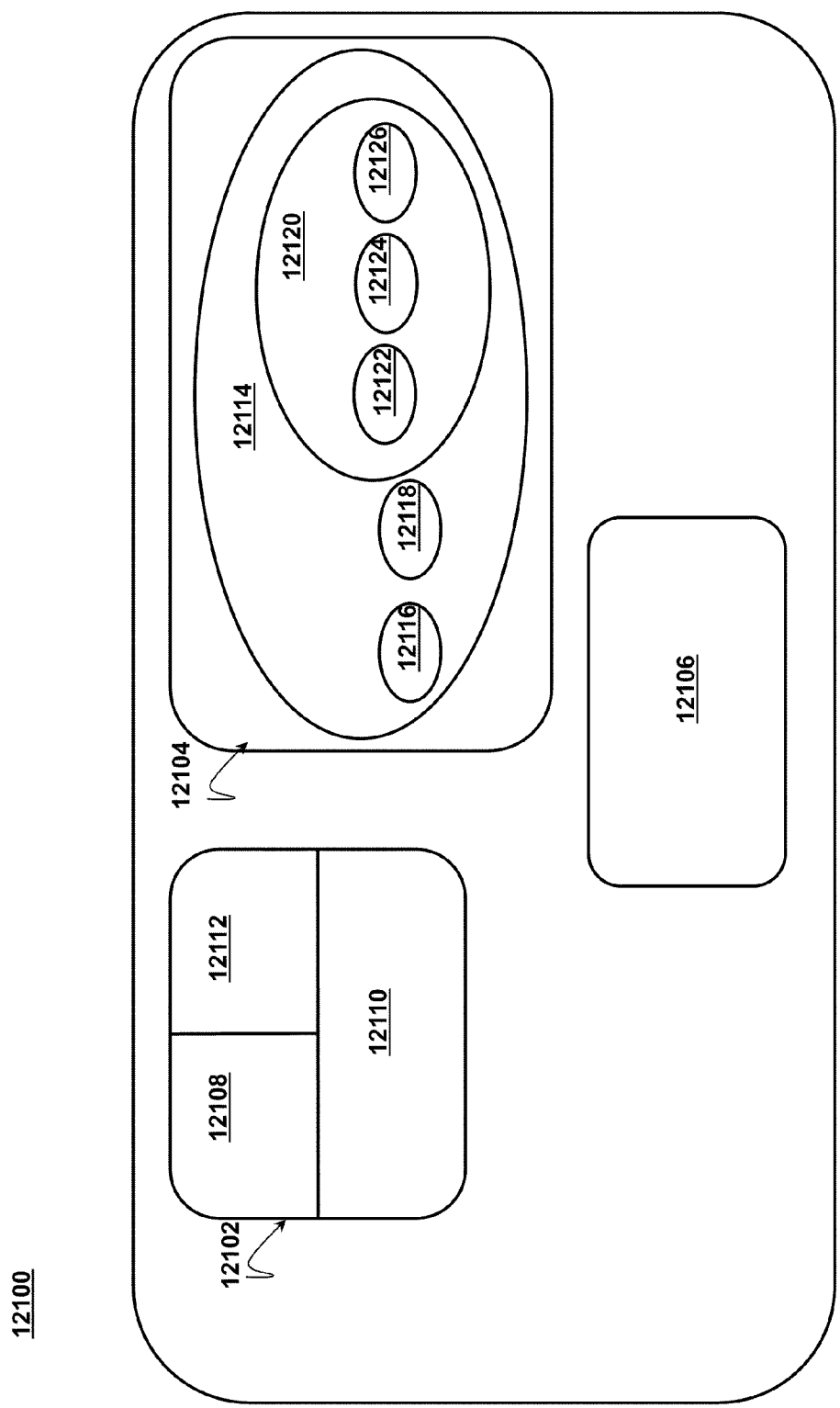

FIG. 121 is an exploded diagrammatic representation of the host computing subsystem, of the FIG. 120, comprising an Opto-Magnetic Fingerprint (or OMF) Generator sub-module designed and implemented in accordance with at least some embodiments.

The host computing subsystem 12100 may comprise a processing unit 12102, a memory unit 12104 and an Input/Output (or I/O) unit 12106 respectively.

The host computing subsystem 12100, by virtue of its design and implementation, performs overall management of samples.

The processing unit 12102 may comprise an Arithmetic Logic Unit (or ALU) 12108, a Control Unit (or CU) 12110 and a Register Unit (or RU) 12112.

As shown in FIG. 121, the memory unit 12104 comprises a test analysis module 12114.

In certain embodiments, the test analysis module for analysis of water samples subjected to test via generation of unique spectral signatures from the digitally captured images of the water samples and methods thereof are disclosed, in accordance with the principles of the invention. Specifically, in such embodiments, the test analysis module utilizes the continuously captured digital images of the water samples illuminated with white light both, non-angled and angled. More specifically, the test analysis detection module takes into consideration the digital images in Red (R), Green (G) and Blue (B) (or RGB) system for purposes of analysis.

Further, as shown in FIG. 121, the test analysis module 12114 includes a Fourier transform sub-module 12116, a spectral analyzer sub-module 12118 and an Opto-Magnetic Fingerprint Generator (or OMFG) sub-module 12120, respectively.

In certain embodiments, the Fourier transform sub-module 12116 is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 12116 converts time-domain digital signals into corresponding frequency-domain digital signals.

DTFT 12116 is coupled to the spectrum analyzer sub-module 12118.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of water samples thereby facilitating analysis of the water is disclosed. Specifically, the spectrum (or spectral) analyzer sub-module in order to analyze the samples takes into consideration digital images of the water samples in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R–B) & (W–P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as water sample, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 121, the spectrum analyzer sub-module 12118 may be coupled to the OMFG sub-module 121170.

OMFG sub-module 121170 includes a color histogram generator unit 12122, a spectral plot generator unit 12124 and a convolution unit 12126.

OMFG sub-module 12120, by virtue of its design and implementation, facilitates generation of unique spectral signatures from digitally captured images of water samples. Specifically, the generated spectral signatures of water samples facilitate analysis of water based on Opto-Magnetic properties of light-water sample interaction.

Color histogram generator unit 12122, by virtue of its design, generates a normalized Red (R) and Blue (B) color channel histogram for each of the one or more images of the water samples.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 1 exhibits a tabular representation in connection with a 2D Red-Blue chromaticity histogram generated by first normalizing color pixel values by dividing RGB values by R+G+B, then quantizing the normalized R and B coordinates into N bins each, where N=4.

| | | R | | | |
|---|---|---|---|---|---|
| | | 0-63 | 64-127 | 128-191 | 192-255 |
| B | 0-63 | 43 | 78 | 18 | 0 |
| | 64-127 | 45 | 67 | 33 | 2 |
| | 128-191 | 127 | 58 | 25 | 8 |
| | 192-255 | 140 | 47 | 47 | 13 |

As shown in FIG. 121, the color histogram generator unit 12122 may be coupled to the spectral plot generator unit 12124.

Spectral plot generator unit 12124 generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 12126 convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the water samples.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

In certain other embodiments, the system configuration, discussed in conjunction with FIGS. 120 and 121, implement one or more processes facilitating estimation of sample type and properties (or characteristics) thereof to create a unique spectral signature.

Figure 122:
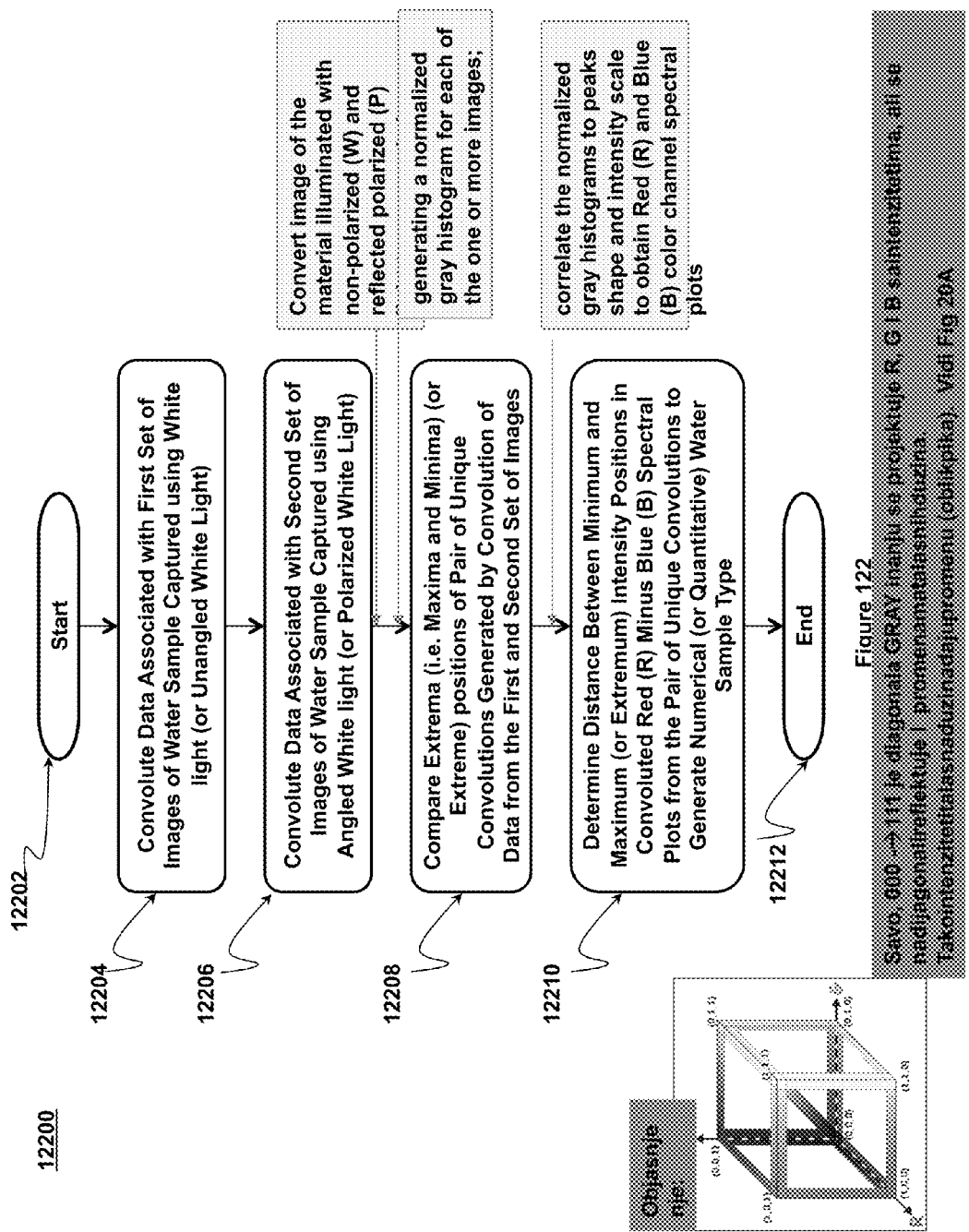

FIG. 122 depicts a flow diagram delineating at least one process implemented by the system configuration of FIGS. 120 and 121 thereby facilitating estimation of water sample type and properties (or characteristics) thereof and creation of a unique spectral signature.

The process 12200 starts at stage 12202 and proceeds to stage 12204, wherein the process 12200 comprises the phase of convolution of data associated with a first set of images of a water sample captured by illuminating the sample with a white light (or unangled white light.) Noticeable here is the fact that the data associated with the first set of images of the water sample illuminated with the white light (or unangled white light) may comprise one or more combinations of reflected and re-emitted angled and unangled white light.

At stage 12206, the process 12200 comprises the phase of convolution of data associated with a second set of images of the water sample captured by illuminating the sample with an angled white light. It must be noted here that the data associated with the second set of images of the water sample illuminated with the angled white light may comprise one or more combinations of reflected and re-emitted angled white light.

At stage 12208, the process 12200 comprises the phase of comparison of extrema (i.e. maxima and minima) (or extreme) positions of at least a pair of unique convolutions generated by convolution of data from the first set of images and second set of images.

At stage 12210, the process 12200 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) water sample type. The process 12200 ends at stage 12212.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R–B) (W–P)) versus a second component Red (R) minus Blue (B) of unangled white light (or W) (i.e. (R–B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R–B) (W–P) for the reflected and/or re-emitted polarized light, and a component (R–B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

As used in general, the term "calibration" refers to the validation of specific measurement techniques and equipment. At the simplest level, calibration is a comparison between measurements-one of known magnitude or correctness made or set with one device and another measurement made in as similar a way as possible with a second device. The device with the known or assigned correctness is called the standard. The second device is the unit under test (UUT), test instrument (TI), or any of several other names for the device being calibrated.

The term "reproducibility" refers to one of the main principles of the scientific method, and refers to the ability of a test or experiment to be accurately reproduced, or replicated, by someone else working independently. Reproducibility is different from repeatability, which measures the success rate in successive experiments, possibly conducted by the same experimenters. Reproducibility relates to the agreement of test results with different operators, test apparatus, and laboratory locations. It is often reported as a standard deviation.

In certain circumstances, the analysis of water through investigation performed over one or more water samples subjected to one or more trials is disclosed. By way of example, and in no way limiting the scope of the invention, 8 water samples are subjected to 3 trials, i.e. 24 experiments. In such circumstances, 24 (8 samples*3 trials) similar experiments are conducted to test value differences of one or more parameters. In response, it was found that from an average the value difference of wavelength difference is ±0.14 nm, whereas for intensity is ±0.0032.

In certain specific implementation scenarios, characterization of water samples maintained at one or more distinct temperatures by employment of the device facilitating implementation of the OMF method on digital images is disclosed, in accordance with the principles of the invention. By way of example, and in no way limiting the scope of the invention, the water samples are 18.2 MΩ maintained at one or more distinct temperatures, such as −4.4° C., 25.0° C., 50° C. and 91.2° C. respectively. The discussion below in conjunction with FIGS. 108A-B, 109A-B, 110A-B and 111A-B delineates the ins-and-outs in connection with the characterization of water samples maintained at one or more distinct temperatures, such as −4.4° C., 25.0° C., 50° C. and 91.2° C.

FIGS. 123A-B depict a first pair of plots for typical spectral data (or OMF diagrams) obtained by the device facilitating implementation of the OMF method on digital images of the given, selected first pair of samples at a given, selected first temperature for characterization of the same in magnetic and electric domains, in accordance with certain embodiments of the invention.

As shown in FIGS. 123A-B, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the first sample, captured using diffuse white light and reflected polarized light, using the OMF method. Specifically, the OMF method implements the SCA and CAA to analyze the processed digital image of the sample. Further, the sample is the given, selected first sample (i.e. 18.2 MΩ water at −4.4° C. temperature).

As depicted in FIG. 123A, a first DI plot of the first pair of DI plots possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical Y-axis includes a closed interval of Intensity Values ranging from a minimum of equal to −0.04 to a maximum of equal to +0.04 (or [−0.04, +0.04]); analytical information is analysis of the first DI plot (or OMF Diagram) of the sample; test input sample information is a given, selected first sample at the given, selected first temperature; operation is usage of the device facilitating implementation of OMF method on digital image of the 18.2 MΩ water at −4.4° C.; number of characteristic points for magnetic domain [(R−B)&(W−P)] is 9; number of characteristic points with positive intensity values is 2; number of characteristic points with negative intensity value is 2; number of characteristic points with zero intensity value is 5; reference numerals (or identifiers) for the 9 characteristic points are first 12302A, second 12304A, third 12308A, fourth 12310A, fifth 12312A, sixth 12314A, seventh 12316A, eighth 12318A and ninth 12320A respectively; values for (Wavelength Difference, Intensity) ordered pairs associated with the first 12302A, second 12304A, third 12308A, fourth 12310A, fifth 12312A, sixth 12314A, seventh 12316A, eighth 12318A and ninth 12320A characteristic points are (105.16 nm, 0), (111.69 nm, +0.0256), (114.95 nm, 0), (117.07 nm, −0.0323), (120.24 nm, 0), (121.99 nm, 0.0307), (125.49 nm, 0), (127.6 nm, −0.03063) and (140.37, 0) in that order.

As depicted in FIG. 123B, a second DI plot of the first pair of DI plots possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 230 nanometers (nm) (or [100, 230]); vertical Y-axis includes a closed interval of Intensity Values ranging from a minimum of equal to −0.04 to a maximum of equal to +0.04 (or [−0.04, +0.04]); analytical information is analysis of the second DI plot (or OMF Diagram) of the digital photography image of the sample; test input sample is the given, selected first sample at the given, selected first temperature; operation is usage of the device facilitating implementation of OMF method on digital image of the 18.2 MΩ water at −4.4° C.; number of characteristic points for electrical domain [P(R−B)] is 5; number of characteristic points with positive intensity values is 1; number of characteristic points with negative intensity value is 1; number of characteristic points with zero intensity value is 3; reference numerals (or identifiers) for the 5 characteristic points are first 12302B, second 12304B, third 12308B, fourth 12310B and fifth 12312B respectively; values for (Wavelength Difference, Intensity) ordered pairs associated with the first 12302B, second 12304B, third 12308B, fourth 12310B and fifth 12312B characteristic points are (104.01 nm, 0), (111.31 nm, −0.0237), (118.45 nm, 0), (127.88 nm, 0.0333) and (137.61 nm, 0) in that order.

FIGS. 124A-B depict a second pair of plots for typical spectral data (or OMF diagrams) obtained by the device facilitating implementation of the OMF method on digital images of the given, selected second pair samples at a given, selected second temperature for characterization of the same in magnetic and electric domains, in accordance with certain embodiments of the invention.

As depicted in FIG. 124A, a third DI plot of the second pair of DI plots possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical Y-axis includes a closed interval of Intensity Values ranging from a minimum of equal to −0.15 to a maximum of equal to +0.1 (or [−0.15, +0.1]); analytical information is analysis of the third DI plot (or OMF Diagram) of the sample; test input sample information is a given, selected third sample at the given, selected second temperature; operation is usage of the device facilitating implementation of OMF method on digital image of the 18.2 MΩ water at 25° C.; number of characteristic points for magnetic domain [(R−B)&(W−P)] is 9; number of characteristic points with positive intensity values is 2; number of characteristic points with negative intensity value is 2; number of characteristic points with zero intensity value is 5; reference numerals (or identifiers) for the 9 characteristic points are first 12402A, second 12404A, third 12408A, fourth 12410A, fifth 12412A, sixth 12414A, seventh 12416A, eighth 12418A and ninth 12420A respectively; values for (Wavelength Difference, Intensity) ordered pairs associated with the first 12402A, second 12404A, third 12408A, fourth 12410A, fifth 12412A, sixth 12414A, seventh 12416A, eighth 12418A and ninth 12420A characteristic points are (113.81 nm, 0), (116.69 nm, +0.0781), (117.95 nm, 0), (118.92 nm, −0.0627), (121.7 nm, 0), (124.79 nm, 0.0722), (126.19 nm, 0), (127.3 nm, −0.0978) and (130.73, 0) in that order.

As depicted in FIG. 124B, a fourth DI plot of the second pair of DI plots possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 230 nanometers (nm) (or [100, 230]); vertical Y-axis includes a closed interval of Intensity Values ranging from a minimum of equal to −0.1 to a maximum of equal to +0.15 (or [−0.1, +0.15]); analytical information is analysis of the fourth DI plot (or OMF Diagram) of the digital photography image of the sample; test input sample is the given, selected fourth sample at the given, selected second temperature; operation is usage of the device facilitating implementation of OMF method on digital image of the 18.2 MΩ water at 25° C.; number of characteristic points for electrical domain [P(R−B)] is 6; number of characteristic points with positive intensity values is 1; number of characteristic points with negative intensity value is 1; number of characteristic points with zero intensity value is 4; reference numerals (or identifiers) for the 5 characteristic points are first 12402B, second 12404B, third 124086, fourth 12410B, fifth 12412B and sixth 12414B respectively; values for (Wavelength Difference, Intensity) ordered pairs associated with the first 12402B, second 12404B, third 12408B, fourth 12410B, fifth 12412B and sixth 12414B characteristic points are (113.29 nm, 0), (116.67 nm, −0.0782), (118.71 nm, 0), (124.16 nm, 0), (127.33 nm, 0.1003) and (129.07 nm, 0) in that order.

As depicted in FIGS. 123A-B and 124A-B, for temperatures −4.4° C. and 25° C. there are two pair of peaks for magnetic domain, whereas for electrical domain there is only one pair (up and down). This implies that hydrogen bonds posses both classical and quantum properties (i.e. sigma bond). The existence of both classical and quantum properties was already observed for ice (i.e. solid state), but it is found that quantum states of hydrogen bond also exists on 25° C. In accordance with known references, quantum state of hydrogen bond may have more values of lengths: 0.172 nm, 0.285 nm and 0.412 nm, 0.510 nm and 5.80 nm, which are different intensities. Thus, it is obvious that intensities of first and second are close enough, third is 15% of them while fourth and fifth are 5% and 3%, respectively.

As seen from FIGS. 123B and 124B, the shape and intensity of electrical interaction are different at −4.4° C. and 25° C.

FIGS. 125A-B depict a third pair of plots for typical spectral data (or OMF diagrams) obtained by the device facilitating implementation of the OMF method on digital images of the given, selected third pair of samples at a given, selected third temperature for characterization of the same in magnetic and electric domains, in accordance with certain embodiments of the invention.

As depicted in FIG. 125A, a fifth DI plot of the third pair of plots possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical Y-axis includes a closed interval of Intensity Values ranging from a minimum of equal to −0.03 to a maximum of equal to +0.03 (or [−0.03, +0.03]); analytical information is analysis of the fifth DI plot (or OMF Diagram) of the sample; test input sample information is a given, selected fifth sample at the given, selected third temperature; operation is usage of the device facilitating implementation of OMF method on digital image of the 18.2 MΩ water at 50° C.; number of characteristic points for magnetic domain [(R−B)&(W−P)] is 5; number of characteristic points with positive intensity values is 1; number of characteristic points with negative intensity value is 1; number of characteristic points with zero intensity value is 3; reference numerals (or identifiers) for the 5 characteristic points are first 12502A, second 12504A, third 12508A, fourth 12510A and fifth 12512A respectively; values for (Wavelength Difference, Intensity) ordered pairs associated with the first 12502A, second 12504A, third 12508A, fourth 12510A and fifth 12512A characteristic points are (112.84 nm, 0), (120.49 nm, −0.0241), (125.49 nm, 0), (130.76 nm, 0.0249) and (140.76 nm, 0) in that order.

As depicted in FIG. 125B, a sixth DI plot of the third pair of DI plots possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 230 nanometers (nm) (or [100, 230]); vertical Y-axis includes a closed interval of Intensity Values ranging from a minimum of equal to −0.0015 to a maximum of equal to +0.002 (or [−0.0015, +0.002]); analytical information is analysis of the sixth DI plot (or OMF Diagram) of the digital photography image of the sample; test input sample is the given, selected sixth sample at the given, selected third temperature; operation is usage of the device facilitating implementation of OMF method on digital image of the 18.2 MΩ water at 50° C.; number of characteristic points for electrical domain [P(R−B)] is 5; number of characteristic points with positive intensity values is 1; number of characteristic points with negative intensity value is 1; number of characteristic points with zero intensity value is 3; reference numerals (or identifiers) for the 5 characteristic points are first 12502B, second 12504B, third 12508B, fourth 12510B and fifth 12512B respectively; values for (Wavelength Difference, Intensity) ordered pairs associated with the first 12502B, second 12504B, third 12508B, fourth 12510B and fifth 12512B characteristic points are (100.00 nm, 0), (113.42 nm, −0.0011), (116.63 nm, 0), (120.49 nm, 0.0014) and (137.61 nm, 0) in that order.

FIGS. 126A-B depict a fourth pair of plots for typical spectral data (or OMF diagrams) obtained by the device facilitating implementation of the OMF method on digital images of the given, selected fourth pair of samples at a given, selected fourth temperature for characterization of the same in magnetic and electric domains, in accordance with certain embodiments of the invention.

As depicted in FIG. 126A, a seventh DI plot of the fourth pair of plots possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical Y-axis includes a closed interval of Intensity Values ranging from a minimum of equal to −0.0025 to a maximum of equal to +0.015 (or [−0.0025, +0.015]); analytical information is analysis of the seventh DI plot (or OMF Diagram) of the sample; test input sample information is a given, selected seventh sample at the given, selected fourth temperature; operation is usage of the device facilitating implementation of OMF method on digital image of the 18.2 MΩ water at 91.2° C.; number of characteristic points for magnetic domain [(R−B)&(W−P)] is 5; number of characteristic points with positive intensity values is 1; number of characteristic points with negative intensity value is 1; number of characteristic points with zero intensity value is 3; reference numerals (or identifiers) for the 5 characteristic points are first 12602A, second 12604A, third 12608A, fourth 12610A and fifth 12612A respectively; values for (Wavelength Difference, Intensity) ordered pairs associated with the first 12602A, second 12604A, third 12608A, fourth 12610A and fifth 12612A characteristic points are (114.38 nm, 0), (125.26 nm, 0.0131), (127.32 nm, 0), (133.28 nm, −0.0192) and (141.51 nm, 0) in that order.

As depicted in FIG. 126B, a eighth DI plot of the fourth pair of DI plots possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 230 nanometers (nm) (or [100, 230]); vertical Y-axis includes a closed interval of Intensity Values ranging from a minimum of equal to −0.03 to a maximum of equal to +0.04 (or [−0.03, +0.04]); analytical information is analysis of the eighth DI plot (or OMF Diagram) of the digital photography image of the sample; test input sample is the given, selected eighth sample at the given, selected fourth temperature; operation is usage of the device facilitating implementation of OMF method on digital image of the 18.2 MΩ water at 91.2° C.; number of characteristic points for electrical domain [P(R−B)] is 5; number of characteristic points with positive intensity values is 1; number of characteristic points with negative intensity value is 1; number of characteristic points with zero intensity value is 3; reference numerals (or identifiers) for the 5 characteristic points are first 12602B, second 12604B, third 12608B, fourth 12610B and fifth 12612B respectively; values for (Wavelength Difference, Intensity) ordered pairs associated with the first 12602B, second 12604B, third 12608B, fourth 12610B and fifth 12612B characteristic points are (112.46 nm, 0), (124.16 nm, −0.0149), (126.77 nm, 0), (132.55 nm, 0.0278) and (137.61 nm, 0) in that order.

As shown in FIGS. 125A-B and 126A-B, for temperature 50° C. sigma bond of hydrogen bonds disappear (i.e. only one pair of peak), because length of hydrogen bonds increase and become more than 0.412 nm. For hydrogen bond length higher than 0.412 nm only classical interaction exist for both magnetic and electrical interaction.

In yet another specific implementation scenarios, characterization of water samples maintained at a given, selected temperature and under the influence of a given, selected constant magnetic field for a given, selected time duration by employment of the device facilitating implementation of the OMF method on digital images is disclosed, in accordance with the principles of the invention. By way of example, and in no way limiting the scope of the invention, the water samples are 18.2 MΩ maintained at a given, selected temperature of 25° C. and under the influence of a given, selected constant magnetic field of 50 mT for a given, selected time duration of 9 minutes respectively. The discussion below in conjunction with FIGS. 127A and 127B delineates the ins-and-outs in connection with the characterization of water samples maintained at a given, selected temperature of 25° C. and under the influence of a given, selected constant magnetic field of 50 mT for a given, selected time duration of 9 minutes.

FIGS. 127A-B depict a fifth pair of plots for typical spectral data (or OMF diagrams) obtained by the device facilitating implementation of the OMF method on digital images of the given, selected fifth pair of samples at the given, selected second temperature and under the influence a given, selected magnetic flux density for a given, selected time duration for characterization of the samples in magnetic and electric domains, in accordance with certain embodiments of the invention.

As depicted in FIG. 127A, a ninth DI plot of the fifth pair of plots possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical Y-axis includes a closed interval of Intensity Values ranging from a minimum of equal to −0.15 to a maximum of equal to +0.15 (or [−0.15, +0.15]); analytical information is analysis of the ninth DI plot (or OMF Diagram) of the sample; test input sample information is a given, selected ninth sample at the given, selected second temperature and under the influence a given, selected magnetic flux density for a given, selected time duration; operation is usage of the device facilitating implementation of OMF method on digital image of the 18.2 MΩ water at 25° C. and under the influence a magnetic field of 50 mT (or millitesla) for a duration of 9 minutes; number of characteristic points for magnetic domain [(R−B)&(W−P)] is 10; number of characteristic points with positive intensity values is 2; number of characteristic points with negative intensity value is 2; number of characteristic points with zero intensity value is 6; reference numerals (or identifiers) for the 10 characteristic points are first 12702A, second 12704A, third 12706A, fourth 12710A and fifth 12712A, sixth 12714A, seventh 12716A, eighth 12718A, ninth 12720A and tenth 12722A respectively; values for (Wavelength Difference, Intensity) ordered pairs associated with the first 12702A, second 12704A, third 12706A, fourth 12710A, fifth 12712A, sixth 12714A, seventh 12716A, eighth 12718A, ninth 12720A and tenth 12722A characteristic points are (113.80 nm, 0), (116.63 nm, 0.0888), (117.99 nm, 0), (118.96 nm, −0.0690), (121.22 nm, 0), (123.24 nm, 0), (124.98 nm, 0.0715), (127.10 nm, 0), (128.37 nm, −0.0937) and (130.46 nm, 0) in that order.

As depicted in FIG. 127B, a tenth DI plot of the fifth pair of DI plots possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 230 nanometers (nm) (or [100, 230]); vertical Y-axis includes a closed interval of Intensity Values ranging from a minimum of equal to −0.15 to a maximum of equal to +0.15 (or [−0.15, +0.15]); analytical information is analysis of the tenth DI plot (or OMF Diagram) of the digital photography image of the sample; test input sample is the given, selected tenth sample at the given, selected second temperature and under the influence the given, selected magnetic flux density for the given, selected time duration; operation is usage of the device facilitating implementation of OMF method on digital image of the 18.2 MΩ water at 25° C. and under the influence the given magnetic field of 50 mT (or millitesla) for the given duration of 9 minutes; number of characteristic points for electrical domain [P(R−B)] is 6; number of characteristic points with positive intensity values is 1; number of characteristic points with negative intensity value is 1; number of characteristic points with zero intensity value is 4; reference numerals (or identifiers) for the 5 characteristic points are first 12702B, second 12704B, third 12708B, fourth 12710B, fifth 12712B and sixth 12714B respectively; values for (Wavelength Difference, Intensity) ordered pairs associated with the first 12702B, second 12704B, third 12708B, fourth 12710B, fifth 12712B and sixth 12714B characteristic points are (113.80 nm, 0), (116.63 nm, −0.0889), (118.45 nm, 0), (126.32 nm, 0) (128.37 nm, 0.0939) and (130.46 nm, 0) in that order.

In aforementioned implementation scenarios, water is sensitive when exposed to influence of constant magnetic field of 50 mT. As depicted in FIGS. 112A-B, shape (or geometry) of OMF diagram for magnetic interaction is a little different and peaks value increase by about 15%. However, when magnetic field change discretely from 40 to 64 mT, (and vice versa) for four times in 9 minutes diagram of both electrical and magnetic domains become more similar to diagrams when water was without influence of dominant external magnetic field (50 mT is dominant external magnetic field because Earth magnetic field is about 50 µT).

In certain other specific implementation scenarios, characterization of water samples maintained at a given, selected temperature and under the influence of a given, selected exchangeable (or variable) magnetic field changing at a given, selected frequency involving two distinct magnetic fields is disclosed, in accordance with the principles of the invention. By way of example, and in no way limiting the scope of the invention, the water samples are 18.2 MΩ maintained at a given, selected temperature of 25° C. and under the influence of a given, selected exchangeable (or variable) magnetic field changing at a given, selected frequency of ¹⁄₁₃₅ cycles per second (i.e. four times per 9 minutes) involving only two distinct magnetic fields with given, selected intensities of 40 mT and 64 mT. The discussion below in conjunction with FIGS. 113A and 113B delineates the ins-and-outs in connection with the characterization of water samples maintained at a given, selected temperature of 25° C. and under the influence of a given, selected exchangeable (or variable) magnetic field changing at a given, selected frequency of ¹⁄₁₃₅ cycles per second (i.e. four times per 9 minutes) involving only two distinct magnetic fields with given, selected intensities of 40 mT and 64 mT.

FIGS. 127A-B depict a sixth pair of plots for typical spectral data (or OMF diagrams) obtained by the device facilitating implementation of the OMF method on digital images of the given, selected sixth pair of samples at the given, selected second temperature and under the influence a changeable (or exchangeable) magnetic flux density (or magnetic field intensity) for characterization of the samples in magnetic and electric domains, in accordance with certain embodiments of the invention.

As depicted in FIG. 127A, an eleventh DI plot of the sixth pair of plots possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 220 nanometers (nm) (or [100, 220]); vertical Y-axis includes a closed interval of Intensity Values ranging from a minimum of equal to −0.15 to a maximum of equal to +0.15 (or [−0.15, +0.15]); analytical information is analysis of the eleventh DI plot (or OMF Diagram) of the sample; test input sample information is a given, selected eleventh sample at the given, selected second temperature and under the influence changeable (or exchangeable) magnetic flux density (or magnetic field intensity); operation is usage of the device facilitating implementation of OMF method on digital image of the 18.2 MΩ water at 25° C. and under the influence of exchangeable magnetic field changing at a frequency of ¹⁄₁₃₅ cycles per second (i.e. four times per 9 minutes) involving two distinct magnetic fields with intensities 40 mT and 64 mT; number of characteristic points for magnetic domain [(R−B)&(W−P)] is 9; number of characteristic points with positive intensity values is 2; number of characteristic points with negative intensity value is 2; number of characteristic points with zero intensity value is 5; reference numerals (or identifiers) for the 9 characteristic points are first 12702A, second 12704A, third 12708A, fourth 12710A, fifth 12712A, sixth 12714A, seventh 12716A, eighth 12718A and ninth 12720A respectively; values for (Wavelength Difference, Intensity) ordered pairs associated with the first 12702A, second 12704A, third 12708A, fourth 12710A, fifth 12712A, sixth 12714A, seventh 12716A, eighth 12718A and ninth 12720A characteristic points are (114.38 nm, 0), (116.87 nm, 0.0850), (118.45 nm, 0), (119.48 nm, −0.0702), (121.99 nm, 0), (124.43 nm, 0.0769), (126.32 nm, 0), (127.60 nm, −0.0982) and (130.46 nm, 0) in that order.

As depicted in FIG. 127B, a twelfth DI plot of the sixth pair of DI plots possess the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 230 nanometers (nm) (or [100, 230]); vertical Y-axis includes a closed interval of Intensity Values ranging from a minimum of equal to −0.1 to a maximum of equal to +0.15 (or [−0.1, +0.15]); analytical information is analysis of the twelfth DI plot (or OMF Diagram) of the digital photography image of the sample; test input sample information is a given, selected twelfth sample at the given, selected second temperature and under the influence changeable (or exchangeable) magnetic flux density (or magnetic field intensity); operation is usage of the device facilitating implementation of OMF method on digital image of the 18.2 MΩ water at 25° C. and under the influence of exchangeable magnetic field changing at a frequency of ¹⁄₁₃₅ cycles per second (i.e. four times per 9 minutes) between only two distinct magnetic fields with intensities 40 mT and 64 mT; number of characteristic points for electrical domain [P(R−B)] is 6; number of characteristic points with positive intensity values is 1; number of characteristic points with negative intensity value is 1; number of characteristic points with zero intensity value is 4; reference numerals (or identifiers) for the 5 characteristic points are first 12702B, second 12704B, third 12708B, fourth 12710B, fifth 12712B and sixth 12714B respectively; values for (Wavelength Difference, Intensity) ordered pairs associated with the first 12702B, second 12704B, third 12708B, fourth 12710B, fifth 12712B and sixth 12714B characteristic points are (113.60 nm, 0), (116.87 nm, −0.0850), (118.71 nm, 0), (125.26 nm, 0) (127.60 nm, 0.0987) and (130.36 nm, 0) in that order.

In all of the aforementioned implementation scenarios, water is sensitive when exposed to influence of constant magnetic field of 50 mT. As depicted in FIGS. 127A-B, shape (or geometry) of OMF diagram for magnetic interaction is a little different and peaks value increase by about 15%. However, when magnetic field change discretely from 40 to 64 mT, (and vice versa) for four times in 9 minutes the OMF diagrams of both electrical and magnetic domains, as shown in FIGS. 127A-B, become more analogous to the OMF diagrams when water was without influence of dominant external magnetic field. Note must be taken of the fact that 50 mT is dominant external magnetic field because Earth magnetic field is about 50 µT.

In some of the aforementioned implementation scenarios, it is observed that hydrogen bonds of water molecules possess both quantum and classical properties up to a temperature of 50° C., whereas for higher temperatures the hydrogen bonds of water molecules possess only classical electromagnetic properties. Further, in some other aforementioned implementation scenarios, under the influence of 50 mT (and higher) at 25° C. hydrogen bonds of water molecules respond. This implies that water may be treated by magnetic field for its ordering (clustering). Particularly, water may be clustering and ordering by Golden mean law.

As used in mathematics, the terms "golden ratio," "golden section" or "golden mean" refer to a ratio of two quantities such that the ratio of the sum of the two quantities to the larger quantity is equal to the ratio of the larger quantity to the smaller one. The golden ratio is an irrational mathematical constant, approximately 1.6180339887. Other names frequently used for the golden ratio are the golden section and golden mean. Other terms encountered include extreme and mean ratio, medial section, divine proportion, divine section, golden proportion, golden cut, golden number, and mean of Phidias. The golden ratio is often denoted by the Greek letter phi, usually lower case ($\varphi$).

In general, hydrogen bonds possess Golden mean properties, which imply that investigation of DNA double helix that is composed of hydrogen bonds network. This is the goal for future investigation. Advantageously, this will serve as very important field of study for one or more domains, such as medicine (i.e. from embryology to stem cell therapy), pharmacy (i.e. from understanding how existing drugs work to designing new drugs) and nanotechnology (i.e. from materials science to nanomedicine).

Still advantageously, water structure is important for pharmacy because it has a direct implication for drug design. Knowledge of magnetic properties of hydrogen bond, both classical and quantum may play crucial role for design of new types of drugs. For final conclusion more research from hydrogen bonding, molecular recognition, and magnetic and electrical properties of existing drags is still needed.

In certain embodiments, methods for imaging and analyzing skin based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for imaging and analysis of skin based on Opto-Magnetic properties of light-matter interaction. Still more specifically, the systems and apparatuses facilitate implementation of an Opto-Magnetic method with enhanced qualitative and quantitative parameters, novel, enhanced and easy interpretability, enhanced and easy detectability, enhanced sensitivity, enhanced specificity, enhanced efficiency, greater accuracy, easily operable, rapid, economical, precise, timely and minute variation sensitive, single handed operability and adaptive dynamic configuration, for imaging and analysis of images of skin captured based on Opto-Magnetic properties of light-matter interaction, i.e. light-skin interaction.

In certain specific embodiments, digital images in RGB (R-red, G-green, B-blue) system are utilized in analysis, therefore basic pixel data in red and blue channels for white diffuse light (W) and reflected polarized white light (P) are chosen. In such embodiments, algorithm for data analysis is based on chromaticity diagram called "Maxwell's triangle" and spectral convolution operation according to ratio of (R−B)&(W−P). The abbreviated designation means that Red minus Blue wavelength of White light and reflected Polarized light are used in spectral convolution algorithm to calculate data for Opto-Magnetic Fingerprint (or OMF) of matter. Therefore, method and algorithm for creating unique spectral fingerprint are based on the convolution of RGB color channel spectral plots generated from digital images that capture single and multi-wavelength light-matter interaction.

In certain other situations, the sample set is subjected to imaging and analysis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul. 17 "SYSTEM, DEVICE AND METHOD FOR DERMAL IMAGING" to J. Bandic, Dj. Koruga, R. Mehendale and S. Marinkovich of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for imaging and analysis of skin based on the interaction between matter and electromagnetic radiation and systems and apparatuses facilitating implementation of such methods has been disclosed. Specifically, there is disclosed the design and implementation of an Opto-Magnetic method with enhanced qualitative and quantitative parameters for analysis of skin based on Opto-Magnetic properties of light-matter interaction and systems and apparatuses thereof. Still more specifically, there is disclosed design and implementation of an Opto-Magnetic method with enhanced qualitative and quantitative parameters, such as novel, enhanced and easy interpretability, enhanced and easy detectability, enhanced sensitivity, enhanced specificity, enhanced efficiency, greater accuracy, easily operable, rapid, economical, precise, timely and minute variation sensitive, for analysis of skin based on Opto-Magnetic properties of light-matter interaction and systems and apparatuses thereof.

Further, the Opto-Magnetic method is in essence an Opto-Magnetic Fingerprint (OMF) method based on electron properties of matter and its interaction with light. By way of example, and in no way limiting the scope of the invention, the concept of light-matter interaction and Opto-magnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

Reiterating again, in certain other embodiments, a comparative analysis of pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

Since, reflected polarized light contains electrical component of light-matter interaction. Thus, taking the difference between white light (i.e. electromagnetic) and reflected polarized light (i.e. electrical) yields magnetic properties of matter based on light-matter interaction.

Since, reflected polarized light is composed of longitudinal wave (i.e. electrical component) and transverse wave (i.e. magnetic component). This implies that only electrical component as a longitudinal wave contains data (i.e. image) of light-matter interaction, which activates either CMOS or CCD image sensor.

FIG. 129A is a block diagrammatic view of a system facilitating implementation of an Opto-Magnetic process based on light-matter interaction using digital imaging for analysis of skin samples, designed and implemented in accordance with certain embodiments of the invention.

System 12900A is in essence an Imaging System (or IS). The IS 12900A includes an illumination subsystem 12902A, an imaging (or sensor) subsystem 12904A and a host computing subsystem 12906A.

IS 12900A, by virtue of its design and implementation, facilitates execution of an Opto-Magnetic process based on interaction between electromagnetic radiation and matter, for instance light-skin interaction, using digital imaging for analysis of skin samples. Specifically, the Opto-Magnetic process employs apparatuses for generation of unique spectral signatures from digitally captured images of skin samples thereby facilitating analysis of the skin samples based on Opto-Magnetic properties of light-skin interaction.

Illumination subsystem 12902A may be one or more electromagnetic radiation sources. In certain specific embodiments, the Illumination subsystem 12902A may be a set of Light Emitting Diodes (LEDs).

Illumination subsystem 12902A may be adapted to emit polarized and unpolarized electromagnetic signals. The polarized electromagnetic signal is angled white light and unpolarized electromagnetic signal is non-angled white light.

As shown in the FIG. 129A, in certain embodiments, the illumination subsystem 12902 may be coupled to the sensor subsystem 12904A.

As shown in the FIG. 129A, the sensor subsystem 12904A may in essence be a device that converts optical images (or optical signals) to electric signals. In certain embodiments, the sensor subsystem 12904A captures continuous digital images of skin samples. Specifically, in such embodiments, the sensor subsystem 12904A captures continuous digital images of the skin samples illuminated with white light both, non-angled and angled. By way of, and by no way of limitation, the sensor subsystem 12904A may be anyone selected from a group consisting of a Complementary Metal-Oxide-Semiconductor (CMOS) image sensor, Charged Coupled Device (CCD) image sensor, and the like.

Again, as shown in FIG. 129A, the sensor subsystem 12904A may be coupled to the host computing subsystem 12906A.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

For example, and in no way limiting the scope of the invention, in certain embodiments the sensor subsystem 12904A may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional, signal and applying standard signal-processing techniques to it.

Image processing usually refers to digital image processing, but optical and analog image processing are also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

FIG. 129B is an exploded diagrammatic representation of the IS 12900 designed and implemented in accordance with at least some embodiments.

In certain embodiments, the IS 12900A may comprise a focusing subsystem 12902B, a rangefinder subsystem 12904B, a moving focus subsystem 12906B, an adaptive image sequencing subsystem 12908B and an exchangeable adapter subsystem 12910B respectively.

The term "focus stacking" refers to a digital image processing technique which combines multiple images taken at different focus distances to give a resulting image with a greater Depth of Field (or DOF) than any of the individual source images. Focus stacking can be used in any situation where individual images have a very shallow DOF, such as in macro photography and optical microscopy.

Specifically, in photography, getting sufficient DOF can be particularly challenging in macro photography, because depth of field is smaller (shallower) for objects nearer the camera, so if a small object fills the frame, it is often so close that its entire depth cannot be in focus at once. DOF is normally increased by stopping down aperture (using a larger f number), but beyond a certain point, stopping down causes blurring due to diffraction, which counteracts the benefit of being in focus. Focus stacking allows the depth of field of images taken at the sharpest aperture to be effectively increased. The images at right illustrate the increase in DOF that can be achieved by combining multiple exposures.

Focusing subsystem 12902B, by virtue of its design and implementation, is capable of combining of multiple images at various focal points at various spectral images in a handheld device.

As shown in FIG. 129B, the focusing subsystem 12902B may be coupled to the rangefinder subsystem 12904B.

The term "Digital Rangefinder or Rangefinder" refers to a user-operated optical mechanism to measure subject distance once widely used on film cameras. Most digital cameras measure subject distance automatically using electro-optical techniques, but it is not customary to say that they have a rangefinder.

Specifically, a rangefinder camera is a camera fitted with a rangefinder, which is a range-finding focusing mechanism allowing the photographer to measure the subject distance and take photographs that are in sharp focus. Most varieties of rangefinder show two images of the same subject, one of which moves when a calibrated wheel is turned. Further, when the two images coincide and fuse into one, the distance can be read off the wheel. Older, non-coupled rangefinder cameras display the focusing distance and require the photographer to transfer the value to the lens focus ring; cameras without built-in rangefinders could have an external rangefinder fitted into the accessory shoe. Earlier cameras of this type had separate viewfinder and rangefinder windows; later the rangefinder was incorporated into the viewfinder. More modern designs have rangefinders coupled to the focusing mechanism, so that the lens is focused correctly when the rangefinder images fuse; compare with the focusing screen in non-autofocus SLRs.

Rangefinder subsystem 12904B, by virtue of its design and implementation, employs a range-finding focusing method thereby allowing the photographer to measure the subject distance and take photographs that are in sharp focus.

As shown in FIG. 129B, the rangefinder subsystem 12904B may be coupled to the moving focus subsystem 12906B.

The term "AutoFocus or AF" refers to optical system that uses a sensor, a control system and a motor to focus fully automatic or on a manually selected point or area. An electronic rangefinder has a display instead of the motor, wherein the adjustment of the optical system has to be done manually until indication.

By way of example, and in no way limiting the scope of the invention, the moving focus subsystem 12904B may be at least one of an Active AF and a Passive AF.

As depicted in FIG. 129B, the moving focus subsystem 12906B may be coupled to the adaptive image sequencing subsystem 12908B.

Adaptive image sequencing subsystem 12908B, by virtue of its design and implementation, facilitates overall management, such as generation and manipulation, of adjustable sequence of images.

As shown in FIG. 129B, the adaptive image sequencing subsystem 12908B may be coupled to the exchangeable adapter subsystem 12910B respectively.

FIG. 130A is an exploded diagrammatic representation of the host computing subsystem, of the FIG. 129A, comprising an Opto-Magnetic Fingerprint (or OMF) Generator sub-module designed and implemented in accordance with at least some embodiments.

The host computing subsystem 13000A may comprise a processing unit 13002A, a memory unit 13004A and an Input/Output (or I/O) unit 13006A respectively.

The host computing subsystem 13000A, by virtue of its design and implementation, performs overall management of samples.

The processing unit 13002A may comprise an Arithmetic Logic Unit (or ALU) 13008A, a Control Unit (or CU) 13010A and a Register Unit (or RU) 13012A.

As shown in FIG. 130A, the memory unit 13004A comprises a test analysis module 13014A.

In certain embodiments, the test analysis module for analysis of skin samples subjected to test via generation of unique spectral signatures from the digitally captured images of the skin samples and methods thereof are disclosed, in accordance with the principles of the invention. Specifically, in such embodiments, the test analysis module utilizes the continuously captured digital images of the skin samples illuminated with white light both, non-angled and angled. More specifically, the test analysis detection module takes into consideration the digital images in Red (R), Green (G) and Blue (B) (or RGB) system for purposes of analysis.

Further, as shown in FIG. 130A, the test analysis module 13014A includes a Fourier transform sub-module 13016A, a spectral analyzer sub-module 13018A and an Opto-Magnetic Fingerprint Generator (or OMFG) sub-module 13020A, respectively.

In certain embodiments, the Fourier transform sub-module 13016A is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 13016A converts time-domain digital signals into corresponding frequency-domain digital signals.

DTFT 13016A is coupled to the spectrum analyzer sub-module 13018A.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a super-heterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of skin samples thereby facilitating analysis of the skin is disclosed. Specifically, the spectrum (or spectral) analyzer sub-module in order to analyze the samples takes into consideration digital images of the skin samples in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R−B) & (W−P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as skin sample, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 130A, the spectrum analyzer sub-module 13018A may be coupled to the OMFG sub-module 13020A.

OMFG sub-module 13020A includes a color histogram generator unit 13022A, a spectral plot generator unit 13024A and a convolution unit 13026A.

OMFG sub-module 13020A, by virtue of its design and implementation, facilitates generation of unique spectral signatures from digitally captured images of skin samples. Specifically, the generated spectral signatures of skin samples facilitate analysis of skin based on Opto-Magnetic properties of light-skin sample interaction.

Color histogram generator unit 13022A, by virtue of its design, generates a normalized Red (R) and Blue (B) color channel histogram for each of the one or more images of the skin samples.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 1 exhibits a tabular representation in connection with a 2D Red-Blue chromaticity histogram generated by first normalizing color pixel values by dividing RGB values by R+G+B, then quantizing the normalized R and B coordinates into N bins each, where N=4.

| | | R | | | |
|---|---|---|---|---|---|
| | | 0-63 | 64-127 | 128-191 | 192-255 |
| B | 0-63 | 43 | 78 | 18 | 0 |
| | 64-127 | 45 | 67 | 33 | 2 |
| | 128-191 | 127 | 58 | 25 | 8 |
| | 192-255 | 140 | 47 | 47 | 13 |

As shown in FIG. 130A, the color histogram generator unit 13022A may be coupled to the spectral plot generator unit 13024A.

Spectral plot generator unit 13024A generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 13026A convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the skin samples.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

FIG. 130B is a top view of the IS 12900 assembly illustrated in conjunction with FIG. 129A.

FIG. 130C depicts a cross-sectional view of the IS 12900 along a section line D-D thereof.

FIG. 130D is an exploded view of Optoelectronics sub-assembly, constituting the IS 12900 assembly, designed and implemented in accordance with certain embodiments of the invention.

FIG. 130E is an exploded view of handle and cradle sub-assembly, constituting the constituting the IS 12900 assembly, designed and implemented in accordance with certain embodiments of the invention.

FIG. 130F is an exploded view of the Optoelectronics sub-assembly incorporated in the handle and cradle sub-assembly, designed and implemented in accordance with certain embodiments of the invention.

In certain other embodiments, the system configuration, discussed in conjunction with FIGS. 129A-B and 130A-F, implement one or more processes facilitating estimation of sample type and properties (or characteristics) thereof to create a unique spectral signature.

FIG. 131 depicts a flow diagram delineating at least one process implemented by the system configuration of FIGS. 129A-B and 130A-F thereby facilitating estimation of skin sample type and properties (or characteristics) thereof and creation of a unique spectral signature.

The process 13100 starts at stage 13102 and proceeds to stage 13104, wherein the process 13100 comprises the phase of convolution of data associated with a first set of images of a skin sample captured by illuminating the sample with a white light (or unangled white light.) Noticeable here is the fact that the data associated with the first set of images of the skin sample illuminated with the white light (or unangled white light) may comprise one or more combinations of reflected and re-emitted angled and unangled white light.

At stage 13106, the process 13100 comprises the phase of convolution of data associated with a second set of images of the skin sample captured by illuminating the sample with an angled white light. It must be noted here that the data associated with the second set of images of the skin sample illuminated with the angled white light may comprise one or more combinations of reflected and re-emitted angled white light.

At stage 13108, the process 13100 comprises the phase of comparison of extrema (i.e. maxima and minima) (or extreme) positions of at least a pair of unique convolutions generated by convolution of data from the first set of images and second set of images.

At stage 13110, the process 13100 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) skin sample type. The process 13100 ends at stage 13112.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R−B) (W−P)) versus a second component Red (R) minus Blue (B) of unangled white light (or W) (i.e. (R−B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R−B) (W−P) for the reflected and/or re-emitted polarized light, and a component (R−B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 2700 nanometers.

In operation, in certain embodiments, consumer (or user) may use the IS 12900A, of FIG. 129A, anytime. By way of example, and by no way of limitation, the user may use the IS 12900A in at least one of given circumstances, i.e. prior to going out of the home, prior and subsequent to using an anti aging product on the skin. In operation, in such embodiments, the user activates the IS 12900A and moves slowly over their face. The IS 12900A facilitates analysis of the skin through utilization of proprietary imaging and light system with inbuilt software thereof. Noteworthy is the fact that the light sub-system (not shown here explicitly) of the proprietary imaging and light system (not shown here explicitly) may include one or more LEDs of predetermined frequencies arranged in a line. Further, in use, the reflected light and the image are analyzed. This analysis facilitates determination of the relative age of the skin as compared to a peer group. It could also be used to determine whether the optimal amount of product (e.g. anti aging) has been applied.

In operation, in such embodiments, the IS 12900A may be coupled to at least of a plurality of portable computing devices and non-computing objects and powered through a suitable source of power. By way of example, and in no way limiting the scope of the invention, the IS 12900A may be coupled to at least one of a standalone computing device, networked computing device, mobile computing device and mirror and can be powered via USB and inbuilt batteries. Specifically, the display portion of the computer or the mirror provides a Graphics User Interface (or GUI) for login, which facilitates generation of credentials, such as unique User Identifier (or User ID or UID) and password, for access to the IS 12900A through the computing device or mirror. The access to the IS 12900A through the computing device or mirror is controlled by identification of the user using credentials provided by the user. In such specific embodiments, a back-end database residing in the memory of the computing device facilitates overall management of information in connection with the given user. For example, and by no way of limitation, the back-end database facilitates maintenance of one or more records, document characteristics and historical data.

In certain embodiments, in operation, the IS 12900A may be able to overlay (or superimpose) the data collected as it is moved over a given part of the body on top of an image of the given part of the body, which is captured concurrently during the operation, or a cartoon of the body part. In such embodiments, as part of skin analysis, the consumer may be able to input age, sex and skin type aspects thereby facilitating development of benchmark against the skin health of like people and set the IS 12900A to measure against such a selected benchmark. Further, in such embodiments, the IS 12900A may require or may include a questionnaire that the consumer can answer to provide specific lifestyle, diet, medical history and other skin related aspects. In such specific embodiments, the questionnaire may be accessed via a different computing system or a simple screen or buttons on the IS 12900A. Yet, in certain embodiments, the IS 12900A and the consumer's history may also be accessed via mobile computing devices. In certain applications involving such embodiments, the IS 12900A may be coupled to service provider's network, such as physician's healthcare network or physicians office network, for them to gain access to the skin assessment and history.

In certain embodiments, in operation, the IS 12900A may provide an appropriate warning signal using one or more methods on detection of a point on skin where the skin health (or age) is most different from any other spot, in accordance with the principles of the invention. In such embodiments, the one or more methods may be at least one of a small electric signal (or tingle), a mark, an audio signal (or sound), an optical signal (or light), a thermal signal (or heat emitting signal) and the like, to highlight areas that are not clean or open. By way of example, and in no way limiting the scope of the invention, the warning signal is provided by at least one of shining a light and applying a warm glow on detection of a point on skin where the skin health (or age) is most different from any other spot.

In some real-time scenarios, the IS 12900A may be coupled to a back-end database of products, residing in the memory of a computing device, to identify the best product that based on the customers' skin type and relative age, in retail locations. In such scenarios, the IS 12900A may facilitate recommendations of skin care products, within the retail store or in the aisle, skin care procedures (or regimen) offered, or general care and prevention tips and suggestions. In certain specific embodiments, the IS 12900A may be coupled to one or more parts of the cosmetic shelves to at least light up (or illuminate) the recommendations, enable printing out the analysis and recommendations, enable purchasing from specific vendors by clicking on the recommendations and any permutations and combinations thereof.

Advantageously, in certain embodiments, the invention enables consumers either at home or in the aisle, in a retail location, to perform one or more tasks related to personal skin care, such as assessment of the health of their skin, determination of relative age and identification and selection of products that are best to apply to their skin. Additionally, consumers can measure the immediate impact of the product that they applied.

Advantageously, in certain other embodiments, the consumers may get recommendations based on at least of analysis of ingredients of products, efficacy or impact of products and ingredients thereof on wrinkles like theirs and all potential permutations and combinations thereof. In addition, the invention removes the subjectivity of determination of the relative age of the skin. Still in addition, the invention enables consumers to maintain a record of their skin health, relative age and track changes.

Still advantageously, the invention provides science led (or knowledge-based) systems, apparatuses and methods facilitating determination of the relative age of the skin and comparison with a peer group. Specifically, the invention provides scientific and unbiased systems, apparatuses and methods at the Point of Sale (or POS) facilitating measurement of the relative age of the skin and providing recommendations. By way of example, and in no way limiting the scope of the invention, these recommendations may be based on various factors that impact skin, such as recommendations on lifestyle including, but not limited to, exercise, location, smoking, stress and stress relief, and the like, diet including, but not limited to, composition, water intake, etc., products and procedures, and so forth. Thus, derived or secondary benefits may be product recommendations in view of the fact that today most products are selected based on the laborious process of talking to people, reading about the products, and then closing the sale based on smelling the product, seeing the packaging, looking at the color or feeling the product.

Still more advantageously, the invention provides an analysis and indication of the relative age of the skin, so that the consumer can determine whether to apply product further. Product effectiveness can be assessed and recommendations may be obtained by showing the product on a screen. Real people's experiences are factored into the recommendation process to learn what works on real people.

In certain embodiments, methods for imaging and analyzing skin based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for imaging and analysis of skin based on Opto-Magnetic properties of light-matter interaction. Still more specifically, the systems and apparatuses facilitate implementation of an Opto-Magnetic method with enhanced qualitative and quantitative parameters, novel, enhanced and easy interpretability, enhanced and easy detectability, enhanced sensitivity, enhanced specificity, enhanced efficiency, greater accuracy, easily operable, rapid, economical, precise, timely and minute variation sensitive, single handed operability and adaptive dynamic configuration, for imaging and analysis of images of skin captured based on Opto-Magnetic properties of light-matter interaction, i.e. light-skin interaction.

In certain specific embodiments, digital images in RGB (R-red, G-green, B-blue) system are utilized in analysis, therefore basic pixel data in red and blue channels for white diffuse light (W) and reflected polarized white light (P) are chosen. In such embodiments, algorithm for data analysis is based on chromaticity diagram called "Maxwell's triangle" and spectral convolution operation according to ratio of (R−B)&(W−P). The abbreviated designation means that Red minus Blue wavelength of White light and reflected Polarized light are used in spectral convolution algorithm to calculate data for Opto-Magnetic Fingerprint (or OMF) of matter. Therefore, method and algorithm for creating unique spectral fingerprint are based on the convolution of RGB color channel spectral plots generated from digital images that capture single and multi-wavelength light-matter interaction.

In certain other situations, the sample set is subjected to imaging and analysis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul. 17 "SYSTEM, DEVICE AND METHOD FOR DERMAL IMAGING" to J. Bandic, Dj. Koruga, R. Mehendale and S. Marinkovich of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for imaging and analysis of skin based on the interaction between matter and electromagnetic radiation and systems and apparatuses facilitating implementation of such methods has been disclosed. Specifically, there is disclosed the design and implementation of an Opto-Magnetic method with enhanced qualitative and quantitative parameters for analysis of skin based on Opto-Magnetic properties of light-matter interaction and systems and apparatuses thereof. Still more specifically, there is disclosed design and implementation of an Opto-Magnetic method with enhanced qualitative and quantitative parameters, such as novel, enhanced and easy interpretability, enhanced and easy detectability, enhanced sensitivity, enhanced specificity, enhanced efficiency, greater accuracy, easily operable, rapid, economical, precise, timely and minute variation sensitive, for analysis of skin based on Opto-Magnetic properties of light-matter interaction and systems and apparatuses thereof.

Further, the Opto-Magnetic method is in essence an Opto-Magnetic Fingerprint (OMF) method based on electron properties of matter and its interaction with light. By way of example, and in no way limiting the scope of the invention, the concept of light-matter interaction and Opto-magnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

Reiterating again, in certain other embodiments, a comparative analysis of pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

Since, reflected polarized light contains electrical component of light-matter interaction. Thus, taking the difference between white light (i.e. electromagnetic) and reflected polarized light (i.e. electrical) yields magnetic properties of matter based on light-matter interaction.

Since, reflected polarized light is composed of longitudinal wave (i.e. electrical component) and transverse wave (i.e. magnetic component). This implies that only electrical component as a longitudinal wave contains data (i.e. image) of light-matter interaction, which activates either CMOS or CCD image sensor.

FIG. 132A is a block diagrammatic view of a system facilitating implementation of an Opto-Magnetic process based on light-matter interaction using digital imaging for analysis of skin samples, designed and implemented in accordance with certain embodiments of the invention.

System 13200A is in essence an Imaging System (or IS). The IS 13200A includes an illumination subsystem 13202A, an imaging (or sensor) subsystem 13204A and a host computing subsystem 13206A.

IS 13200A, by virtue of its design and implementation, facilitates execution of an Opto-Magnetic process based on interaction between electromagnetic radiation and matter, for instance light-skin interaction, using digital imaging for analysis of skin samples. Specifically, the Opto-Magnetic process employs apparatuses for generation of unique spectral signatures from digitally captured images of skin samples thereby facilitating analysis of the skin samples based on Opto-Magnetic properties of light-skin interaction.

Illumination subsystem 13202A may be one or more electromagnetic radiation sources. In certain specific embodiments, the Illumination subsystem 13202A may be a set of Light Emitting Diodes (LEDs).

Illumination subsystem 13202A may be adapted to emit polarized and unpolarized electromagnetic signals. The polarized electromagnetic signal is angled white light and unpolarized electromagnetic signal is non-angled white light.

As shown in the FIG. 132A, in certain embodiments, the illumination subsystem 13202 may be coupled to the sensor subsystem 13204A.

As shown in the FIG. 132A, the sensor subsystem 13204A may in essence be a device that converts optical images (or optical signals) to electric signals. In certain embodiments, the sensor subsystem 13204A captures continuous digital images of skin samples. Specifically, in such embodiments, the sensor subsystem 13204A captures continuous digital images of the skin samples illuminated with white light both, non-angled and angled. By way of, and by no way of limitation, the sensor subsystem 13204A may be anyone selected from a group consisting of a Complementary Metal-Oxide-Semiconductor (CMOS) image sensor, Charged Coupled Device (CCD) image sensor, and the like.

Again, as shown in FIG. 132A, the sensor subsystem 13204A may be coupled to the host computing subsystem 13206A.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

For example, and in no way limiting the scope of the invention, in certain embodiments the sensor subsystem 13204A may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional signal and applying standard signal-processing techniques to it.

Image processing usually refers to digital image processing, but optical and analog image processing are also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

FIG. 132B is an exploded diagrammatic representation of the IS 13200 designed and implemented in accordance with at least some embodiments.

In certain embodiments, the IS 13200 may comprise a focusing subsystem 13202B, a rangefinder subsystem 13204B, a moving focus subsystem 13206B, an adaptive image sequencing subsystem 13208B and an exchangeable adapter subsystem 13210B respectively.

The term "focus stacking" refers to a digital image processing technique, which combines multiple images taken at different focus distances to give a resulting image with a greater Depth of Field (or DOF) than any of the individual source images. Focus stacking can be used in any situation where individual images have a very shallow DOF, such as in macro photography and optical microscopy.

Specifically, in photography, getting sufficient DOF can be particularly challenging in macro photography, because depth of field is smaller (shallower) for objects nearer the camera, so if a small object fills the frame, it is often so close that its entire depth cannot be in focus at once. DOF is normally increased by stopping down aperture (using a larger f number), but beyond a certain point, stopping down causes blurring due to diffraction, which counteracts the benefit of being in focus. Focus stacking allows the depth of field of images taken at the sharpest aperture to be effectively increased. The images at right illustrate the increase in DOF that can be achieved by combining multiple exposures.

Focusing subsystem 13202B, by virtue of its design and implementation, is capable of combining of multiple images at various focal points at various spectral images in a handheld device.

As shown in FIG. 132B, the focusing subsystem 13202B may be coupled to the rangefinder subsystem 13204B.

The term "Digital Rangefinder or Rangefinder" refers to a user-operated optical mechanism to measure subject distance once widely used on film cameras. Most digital cameras measure subject distance automatically using electro-optical techniques, but it is not customary to say that they have a rangefinder.

Specifically, a rangefinder camera is a camera fitted with a rangefinder, which is a range-finding focusing mechanism allowing the photographer to measure the subject distance and take photographs that are in sharp focus. Most varieties of rangefinder show two images of the same subject, one of which moves when a calibrated wheel is turned. Further, when the two images coincide and fuse into one, the distance can be read off the wheel. Older, non-coupled rangefinder cameras display the focusing distance and require the photographer to transfer the value to the lens focus ring; cameras without built-in rangefinders could have an external rangefinder fitted into the accessory shoe. Earlier cameras of this type had separate viewfinder and rangefinder windows; later the rangefinder was incorporated into the viewfinder. More modern designs have rangefinders coupled to the focusing mechanism, so that the lens is focused correctly when the rangefinder images fuse; compare with the focusing screen in non-autofocus SLRs.

Rangefinder subsystem 13204B, by virtue of its design and implementation, employs a range-finding focusing method thereby allowing the photographer to measure the subject distance and take photographs that are in sharp focus.

As shown in FIG. 132B, the rangefinder subsystem 13204B may be coupled to the moving focus subsystem 13206B.

The term "AutoFocus or AF" refers to optical system that uses a sensor, a control system and a motor to focus fully automatic or on a manually selected point or area. An electronic rangefinder has a display instead of the motor, wherein the adjustment of the optical system has to be done manually until indication.

By way of example, and in no way limiting the scope of the invention, the moving focus subsystem 13204B may be at least one of an Active AF and a Passive AF.

As depicted in FIG. 132B, the moving focus subsystem 13206B may be coupled to the adaptive image sequencing subsystem 13208B.

Adaptive image sequencing subsystem 13208B, by virtue of its design and implementation, facilitates overall management, such as generation and manipulation, of adjustable sequence of images.

As shown in FIG. 132B, the adaptive image sequencing subsystem 13208B may be coupled to the exchangeable adapter subsystem 13210B respectively.

FIG. 133A is an exploded diagrammatic representation of the host computing subsystem, of the FIGS. 132A-B, comprising an Opto-Magnetic Fingerprint (or OMF) Generator sub-module designed and implemented in accordance with at least some embodiments.

The host computing subsystem 13300A may comprise a processing unit 13302A, a memory unit 13304A and an Input/Output (or I/O) unit 13306A respectively.

The host computing subsystem 13300A, by virtue of its design and implementation, performs overall management of samples.

The processing unit 13302A may comprise an Arithmetic Logic Unit (or ALU) 13308A, a Control Unit (or CU) 13310A and a Register Unit (or RU) 13312A.

As shown in FIG. 133A, the memory unit 13304A comprises a test analysis module 13314A.

In certain embodiments, the test analysis module for analysis of skin samples subjected to test via generation of unique spectral signature from the digitally captured images of the skin samples and methods thereof are disclosed, in accordance with the principles of the invention. Specifically, in such embodiments, the test analysis module utilizes the continuously captured digital images of the skin samples illuminated with white light both, non-angled and angled. More specifically, the test analysis detection module takes into consideration the digital images in Red (R), Green (G) and Blue (B) (or RGB) system for purposes of analysis.

Further, as shown in FIG. 133A, the test analysis module 13314A includes a Fourier transform sub-module 13316A, a spectral analyzer sub-module 13318A and an Opto-Magnetic Fingerprint Generator (or OMFG) sub-module 13320A, respectively.

In certain embodiments, the Fourier transform sub-module 13316A is in essence a Discrete-Time Fourier Transform (or DTFT).

The term "DTFT", as used herein, refers to one of the specific forms of Fourier analysis. As such, it transforms one function into another, which is called the frequency domain representation, or simply the "DTFT", of the original function, which is often a function in the time-domain. But, the DTFT requires an input function that is discrete. Such inputs are often created by sampling a continuous function, like a person's voice. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 13316A converts time-domain digital signals into corresponding frequency-domain digital signals.

DTFT 13316A is coupled to the spectrum analyzer sub-module 13318A.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a superheterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of skin samples thereby facilitating analysis of the skin is disclosed. Specifically, the spectrum (or spectral) analyzer sub-module in order to analyze the samples takes into consideration digital images of the skin samples in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R−B) & (W−P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as skin sample, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 133A, the spectrum analyzer sub-module 13318A may be coupled to the OMFG sub-module 13320A.

OMFG sub-module 13320A includes a color histogram generator unit 13322A, a spectral plot generator unit 13324A and a convolution unit 13326A.

OMFG sub-module 13320A, by virtue of its design and implementation, facilitates generation of unique spectral signatures from digitally captured images of skin samples. Specifically, the generated spectral signatures of skin samples facilitate analysis of skin based on Opto-Magnetic properties of light-skin sample interaction.

Color histogram generator unit 13322A, by virtue of its design, generates a normalized Red (R) and Blue (B) color channel histogram for each of the one or more images of the skin samples.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram, which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 1 exhibits a tabular representation in connection with a 2D Red-Blue chromaticity histogram generated by first normalizing color pixel values by dividing RGB values by R+G+B, then quantizing the normalized R and B coordinates into N bins each, where N=4.

|   |         | R    |        |         |         |
|---|---------|------|--------|---------|---------|
|   |         | 0-63 | 64-127 | 128-191 | 192-255 |
| B | 0-63    | 43   | 78     | 18      | 0       |
|   | 64-127  | 45   | 67     | 33      | 2       |
|   | 128-191 | 127  | 58     | 25      | 8       |
|   | 192-255 | 140  | 47     | 47      | 13      |

As shown in FIG. 133A, the color histogram generator unit 13322A may be coupled to the spectral plot generator unit 13324A.

Spectral plot generator unit 13324A generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance; an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 13326A convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the skin samples.

In certain embodiments, the spectral signature is analyzed for at least one of number of crests and troughs, amplitude, shape of peaks, intermediate structures and patterns. In certain such embodiments, the spectral signature is analyzed for material composition, identification, purity and the like.

In certain other embodiments, the system configuration, discussed in conjunction with FIGS. 132A-B and 133A-B, implement one or more processes facilitating estimation of sample type and properties (or characteristics) thereof to create a unique spectral signature.

FIG. 134 depicts a flow diagram delineating at least one process implemented by the system configuration of FIGS. 132A-B and 133A-B thereby facilitating estimation of skin sample type and properties (or characteristics) thereof and creation of a unique spectral signature.

The process 13400 starts at stage 13402 and proceeds to stage 13404, wherein the process 13400 comprises the phase of convolution of data associated with a first set of images of a skin sample captured by illuminating the sample with a white light (or unangled white light.) Noticeable here is the fact that the data associated with the first set of images of the skin sample illuminated with the white light (or unangled white light) may comprise one or more combinations of reflected and re-emitted angled and unangled white light.

At stage 13406, the process 13400 comprises the phase of convolution of data associated with a second set of images of the skin sample captured by illuminating the sample with an angled white light. It must be noted here that the data associated with the second set of images of the skin sample illuminated with the angled white light may comprise one or more combinations of reflected and re-emitted angled white light.

At stage 13408, the process 13400 comprises the phase of comparison of extrema (i.e. maxima and minima) (or extreme) positions of at least a pair of unique convolutions generated by convolution of data from the first set of images and second set of images.

At stage 13410, the process 13400 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) skin sample type. The process 1340 ends at stage 13412.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R–B) (W–P)) versus a second component Red (R) minus Blue (B) of unangled white light (or W) (i.e. (R–B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R–B) (W–P) for the reflected and/or re-emitted polarized light, and a component (R–B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

In operation, in certain embodiments, consumer (or user) may use the IS 13200A, of FIG. 132A, anytime. By way of example, and by no way of limitation, the user may use the IS 13200A in at least one of given circumstances, i.e. prior to going out of the home, prior and subsequent to using an anti aging product on the skin. In operation, in such embodiments, the user activates the IS 13200A and moves slowly over their face. The IS 13200A facilitates analysis of the skin through utilization of proprietary imaging and light system with inbuilt software thereof. Noteworthy is the fact that the light sub-system (not shown here explicitly) of the proprietary imaging and light system (not shown here explicitly) may include one or more LEDs of predetermined frequencies arranged in a line. Further, in use, the reflected light and the image are analyzed. This analysis facilitates determination of the relative age of the skin as compared to a peer group. It could also be used to determine whether the optimal amount of product (e.g. anti aging) has been applied.

In operation, in such embodiments, the IS 13200A may be coupled to at least of a plurality of portable computing devices and non-computing objects and powered through a suitable source of power. By way of example, and in no way limiting the scope of the invention, the IS 13200A may be coupled to at least one of a standalone computing device, networked computing device, mobile computing device and mirror and can be powered via USB and inbuilt batteries. Specifically, the display portion of the computer or the mirror provides a Graphics User Interface (or GUI) for login, which facilitates generation of credentials, such as unique User Identifier (or User ID or UID) and password, for access to the IS 13200A through the computing device or mirror. The access to the IS 13200A through the computing device or mirror is controlled by identification of the user using credentials provided by the user. In such specific embodiments, a back-end database residing in the memory of the computing device facilitates overall management of information in connection with the given user. For example, and by no way of limitation, the back-end database facilitates maintenance of one or more records, document characteristics and historical data.

In certain embodiments, in operation, the IS 13200A may be able to overlay (or superimpose) the data collected as it is moved over a given part of the body on top of an image of the given part of the body, which is captured concurrently during the operation, or a cartoon of the body part. In such embodiments, as part of skin analysis, the consumer may be able to input age, sex and skin type aspects thereby facilitating development of benchmark against the skin health of like people and set the IS 13200A to measure against such a selected benchmark. Further, in such embodiments, the IS 13200A may require or may include a questionnaire that the consumer can answer to provide specific lifestyle, diet, medical history and other skin related aspects. In such specific embodiments, the questionnaire may be accessed via a different computing system or a simple screen or buttons on the IS 13200A. Yet, in certain embodiments, the IS 13200A and the consumer's history may also be accessed via mobile computing devices. In certain applications involving such embodiments, the IS 13200A may be coupled to service provider's network, such as physician's healthcare network or physicians office network, for them to gain access to the skin assessment and history.

In certain embodiments, in operation, the IS 13200A may provide an appropriate warning signal using one or more methods on detection of a point on skin where the skin health (or age) is most different from any other spot, in accordance with the principles of the invention. In such embodiments, the one or more methods may be at least one of a small electric signal (or tingle), a mark, an audio signal (or sound), an optical signal (or light), a thermal signal (or heat emitting signal) and the like, to highlight areas that are not clean or open. By way of example, and in no way limiting the scope of the invention, the warning signal is provided by at least one of shining a light and applying a warm glow on detection of a point on skin where the skin health (or age) is most different from any other spot.

In some real-time scenarios, the IS 13200A may be coupled to a back-end database of products, residing in the memory of a computing device, to identify the best product that based on the customers' skin type and relative age, in retail locations. In such scenarios, the IS 13200A may facilitate recommendations of skin care products, within the retail store or in the aisle, skin care procedures (or regimen) offered, or general care and prevention tips and suggestions. In certain specific embodiments, the IS 13200A may be coupled to one or more parts of the cosmetic shelves to at least light up (or illuminate) the recommendations, enable printing out the analysis and recommendations, enable purchasing from specific vendors by clicking on the recommendations and any permutations and combinations thereof.

Advantageously, in certain embodiments, the invention enables consumers either at home or in the aisle, in a retail location, to perform one or more tasks related to personal skin care, such as assessment of the health of their skin, determination of relative age and identification and selection of products that are best to apply to their skin. Additionally, consumers can measure the immediate impact of the product that they applied.

Advantageously, in certain other embodiments, the consumers may get recommendations based on at least of analysis of ingredients of products, efficacy or impact of products and ingredients thereof on wrinkles like theirs and all potential permutations and combinations thereof. In addition, the invention removes the subjectivity of determination of the relative age of the skin. Still in addition, the invention enables consumers to maintain a record of their skin health, relative age and track changes.

Still advantageously, the invention provides science led (or knowledge-based) systems, apparatuses and methods facilitating determination of the relative age of the skin and comparison with a peer group. Specifically, the invention provides scientific and unbiased systems, apparatuses and methods at the Point of Sale (or POS) facilitating measurement of the relative age of the skin and providing recommendations. By way of example, and in no way limiting the scope of the invention, these recommendations may be based on various factors that impact skin, such as recommendations on lifestyle including, but not limited to, exercise, location, smoking, stress and stress relief, and the like, diet including, but not limited to, composition, water intake, etc., products and procedures, and so forth. Thus, derived or secondary benefits may be product recommendations in view of the fact that today most products are selected based on the laborious process of talking to people, reading about the products, and then closing the sale based on smelling the product, seeing the packaging, looking at the color or feeling the product.

Still more advantageously, the invention provides an analysis and indication of the relative age of the skin, so that the consumer can determine whether to apply product further. Product effectiveness can be assessed and recommendations may be obtained by showing the product on a screen. Real people's experiences are factored into the recommendation process to learn what works on real people.

Typically, in signal processing applications, an artifact is any error in the perception or representation of any visual or aural information introduced by the involved equipment or technique(s). For example, in digital signal processing applications, digital artifacts are anomalies introduced into digital signals.

Specifically, in signal processing and related applications, artifact or aliasing refers to causes that affect different signals thereby making them indistinguishable (or aliases of one another), when sampled. Furthermore, it also refers to the distortions or artifacts that result when the signal reconstructed from samples is different from the original continuous signal. More specifically, aliasing can be caused by at least one of the sampling stage and the reconstruction stage. These may be distinguished by calling sampling aliasing as pre-aliasing and reconstruction aliasing as post-aliasing. For example, when viewing a digital image a reconstruction, also known as an interpolation, is performed by display or printing devices, eyes and brain. In such cases, if the resolution is too low the reconstructed image differs from the original image, thus an alias is seen. For instance, the Moiré pattern observed in a poorly pixelized image of a brick wall is owing to spatial aliasing.

Likewise, temporal aliasing is a major concern in the sampling of video and audio signals. In general circumstances, music may contain high-frequency components that are inaudible to humans. For example, if a piece of music is sampled at 32000 samples per second (sps), frequency components above 16000 Hz (the Nyquist frequency) cause aliasing, when the Digital-to-Analog Converter (or DAC) reproduces the original music.

In such circumstances, to prevent aliasing it is customary to remove components above the Nyquist frequency with an anti-aliasing filter, prior to sampling. However, any realistic filter or DAC will also affect (or attenuate) the components just below the Nyquist frequency. Therefore, it is also customary to choose a higher Nyquist frequency by sampling faster (typically 44100 sps (CD), 48000 (professional audio), or 96000).

Further, in applications involving a video camera, most sampling schemes are periodic that is they have a characteristic sampling frequency in time or in space. For example, digital cameras provide a certain number of samples (pixels) per degree or per radian, or samples per mm in the focal plane of the camera. Likewise, audio signals are sampled (digitized) with an analog-to-digital converter, which produces a constant number of samples per second. However, some of the most dramatic and subtle examples of aliasing occur when the signal being sampled also has periodic content.

In general, one or more distinct solutions to the problems owing to aliasing are called anti-aliasing. Specifically, anti-aliasing means removing signal components that have a higher frequency than those that can be properly resolved by the recording (or sampling) device. This removal is done before (re)sampling at a lower resolution. For example, if sampling is performed without removing this part of the signal, it causes undesirable artifacts, such as the black-and-white noise.

Anti-aliasing filters refer to filters used before signal samplers, to restrict the bandwidth of a signal to approximately satisfy the sampling theorem. Since the theorem states that unambiguous interpretation of the signal from its samples is possible when the power of frequencies above the Nyquist frequency is zero, a real anti-aliasing filter can generally not completely satisfy the theorem. Thus, a realizable anti-aliasing filter typically permits some aliasing to occur. The amount of aliasing that occurs depends on quality of the filter is and the frequency content of the input signal.

Further, anti-aliasing filters are commonly used at the input of digital signal processing systems, for example in sound digitization systems. Still further, similar filters are used as reconstruction filters at the output of such systems, for example in music players. In the later case, the filter is to prevent aliasing in the conversion of samples back to a continuous signal, where again perfect stop-band rejection would be required to guarantee zero aliasing.

In certain applications involving optical image sampling, as in image sensors in digital cameras, the anti-aliasing filter is also known as an optical low-pass filter (or blur filter or AA filter). The mathematics of sampling in two spatial dimensions is similar to the mathematics of time-domain sampling, but the filter implementation technologies are different. The typical implementation in digital cameras is two layers of birefringent material such as lithium niobate, which spreads each optical point into a cluster of four points.

Specifically, in digital signal processing applications, spatial anti-aliasing is the technique of minimizing the distortion artifacts known as aliasing when representing a high-resolution image at a lower resolution. Anti-aliasing is used in digital photography, computer graphics, digital audio, and many other applications. For example, in signal acquisition and audio applications, anti-aliasing is often done using an analog anti-aliasing filter to remove the out-of-band component of the input signal prior to sampling with an analog-to-digital converter. For example, in digital photography, optical anti-aliasing filters are made of birefringent materials that smooth the signal in the spatial optical domain. The anti-aliasing filter essentially blurs the image slightly in order to reduce resolution to below the limit of the digital sensor (the larger the pixel pitch, the lower the achievable resolution at the sensor level).

In particular, one or more distinct solutions to the problems owing to temporal aliasing are temporal anti-aliasing.

Temporal anti-aliasing seeks to reduce or remove the effects of temporal aliasing. Temporal aliasing is caused by the sampling rate (i.e. number of frames per second) of a scene being too low compared to the transformation speed of objects inside of the scene; this causes objects to appear to jump or appear at a location instead of giving the impression of smoothly moving towards them. To avoid aliasing artifacts altogether, the sampling rate of a scene must be at least twice as high as the fastest moving object. The shutter behavior of the sampling system (typically a camera) strongly influences aliasing, as the overall shape of the exposure over time determines the band-limiting of the system before sampling, an important factor in aliasing. A temporal anti-aliasing filter can be applied to a camera to achieve better band-limiting. A common example of temporal aliasing in film is the appearance of vehicle wheels traveling backwards, the so-called wagon-wheel effect.

Likewise, temporal aliasing is a major concern in the sampling of video and audio signals. In general circumstances, music may contain high-frequency components that are inaudible to humans. For example, if a piece of music is sampled at 32000 samples per second (sps), any frequency components above 16000 Hz (the Nyquist frequency) causes aliasing, when the Digital-to-Analog Converter (or DAC) reproduces the.

In such circumstances, to prevent aliasing it is customary to remove components above the Nyquist frequency with an anti-aliasing filter, prior to sampling. However, any realistic filter or DAC will also affect (or attenuate) the components just below the Nyquist frequency. Therefore, it is also customary to choose a higher Nyquist frequency by sampling faster (typically 44100 sps (CD), 48000 (professional audio), or 96000).

Still likewise, in video or cinematography applications, temporal aliasing results from the limited frame rate thereby causing the wagon-wheel effect, whereby a spoked wheel appears to rotate too slowly or even backwards. This is due to the fact that aliasing alters its apparent frequency of rotation. A reversal of direction can be described as a negative frequency. In such applications, temporal aliasing frequencies are determined by the frame rate of the camera, but the shutter timing (exposure time) and the use of a temporal aliasing reduction filter during filming facilitates determination of the relative intensity of the aliased frequencies.

In medical imaging applications, artifacts are misrepresentations of material, such as organic or inorganic, structures seen in medical images produced by one or more distinct modalities, including, but not limited to, Ultrasonography, X-ray Computed Tomography, Magnetic Resonance Imaging and the like. These artifacts may be caused by a variety of phenomena, such as the underlying physics of the energy-matter interaction (i.e. ultrasound-matter), data acquisition errors (i.e. patient motion), or a reconstruction algorithm's inability to represent the structure of matter.

One crude solution to this is manual recognition of these artifacts by Physicians to avoid mistaking them for actual pathology.

Likewise, in medical electrophysiological monitoring applications, artifacts are anomalous (or interfering signals) that originate from some source other than the electrophysiological structure, under analysis. These artifact signals may stem from an assortment of sources, including, but are not limited to light sources, monitoring equipment issues, utility frequencies (50 Hz and 60 Hz), or undesired electrophysiological signals, such as Electromyography (or EMG) presenting on an Electroencephalography (or EEG), Evoked Potential (or EP), Electrocardiography (or ECG or EKG), or Electrooculography (or EOG) signal. In such applications, a major problem is from offending artifacts that may obscure, distort, or completely misrepresent the true underlying electrophysiological signal sought.

Still likewise, in digital graphics and imagery applications, visual artifacts are anomalies during visual representation. For example, in digital graphics, digital artifacts are visual artifacts resulting from digital image processing. Specifically, digital artifacts are undesired alterations in data introduced in a digital process by an involved technique and/or technology.

In such applications, there are assortments of causes of digital artifacts, including, but not limited to, hardware and software malfunctions, compression and aliasing. For example, in computer graphics, visual artifacts may be generated whenever a hardware component (e.g. processor, memory chip, cabling) malfunctions, causing data corruption. Such malfunctions may be caused by physical damage, overheating (sometimes due to GPU over clocking), etc. Common types of hardware artifacts are texture corruption and T-vertices in 3D graphics, and pixelization in MPEG compressed video. Similar to hardware malfunction, artifacts may be caused by software issues, such as bugs in the algorithms, for instance decoding/encoding introduce artifacts into audio or video, or a poor pseudo-random number generator would introduce artifacts into statistical research models. Further, controlled amounts of unwanted information may be generated as a result of the use of lossy compression techniques. For example, one of such cases is the artifact seen in JPEG and MPEG compression algorithms. Still further, in computer graphics application, digital imprecision (or aliasing) is generated in the process of converting analog information into digital space due to the limited granularity of digital numbering space. This is seen as pixelation.

The term "blind signal separation or blind source separation" refers to the separation of a set of signals from a set of mixed signals, without the aid of information (or with very little information) about the source signals or the mixing process. Blind signal separation relies on the assumption that the source signals do not correlate with each other. For example, the signals may be mutually statistically independent or decorrelated. Blind signal separation thus separates a set of signals into a set of other signals, such that the regularity of each resulting signal is maximized, and the regularity between the signals is minimized (i.e. statistical independence is maximized).

Independent component analysis (ICA) is a computational method for separating a multivariate signal into additive subcomponents supposing the mutual statistical independence of the non-Gaussian source signals. It is a special case of blind source separation.

In certain embodiments, systems and methods for cancellation (i.e. minimization or zeroization) of artifacts from physiological signals, designed and implemented in accordance with the principles of the invention, are disclosed. In such embodiments, the systems may comprise a data acquisition unit, which in turn may comprise a sensor sub-unit, a signal-conditioning unit and an Analog-to-Digital Converter (or ADC) respectively. In certain specific embodiments, the systems and methods for cancellation of artifacts from physiological signals may be integrated into the systems and methods of imaging and analysis of biological and/or non-biological materials. Specifically, the systems and methods for cancellation of artifacts facilitate detection and correction of errors in physiological assessments.

In certain embodiments, a mobile device-based health assessment system and method, designed in accordance with the principles of the invention, are disclosed. In such embodiments, the mobile device-based health assessment system may include a photograph capturing device for capturing a skin image of a mobile device user, a transmission unit coupled with the photograph capturing device for uploading the captured skin image to a network location, a global positioning device coupled to the photograph capturing device for determining a location of the photograph capturing device, and a weather estimation device coupled to the photograph capturing device to determine a weather condition at a location of the mobile device user to thereby obtain a remote diagnosis report. In the system and method, the photograph capturing device further comprises at least one of a skin photograph assessment unit, a nail photograph assessment unit, and a hair photograph assessment unit. In the system and method, the global positioning device comprises a location tracker for answering user raised questions pertaining to geographical positioning of the user. In the system and method, the location tracker includes a database pertaining to weather intensive cosmetics. The system and method may further include a phone number tracker for enabling a mobile device user to contact health assessment and cosmetic outlets.

In certain embodiments, an improved imaging system with enhanced qualitative and quantitative parameters for capturing images of skin samples and methods thereof, designed and implemented in accordance with the principles of the invention are disclosed. In such embodiments, design and implementation of the improved imaging system with enhanced qualitative and quantitative parameters, such as lens-independent (or -free), reduced complexity or simplicity, economical, disease diagnosability, rapid drug screenability or high throughput screenability, easy integrability or couplability to portable communication devices and slim configuration, for capturing images of skin samples and methods thereof thereby facilitating diagnosis of diseases and high throughput screening of drugs.

FIG. 135 is a block diagrammatic view of an improved system facilitating implementation of an Opto-Magnetic process based on light-matter interaction using lens-free digital imaging for analysis of skin samples, designed and implemented in accordance with certain embodiments of the invention.

System 13500 is in essence a Lens-Less (or -free or -Independent) Surface Scanning System (or LSSS). The LSSS 13500 includes the illumination subsystem 13202A, imaging (or sensor) subsystem 13204A, host computing subsystem 13206A (not shown here explicitly), of FIG. 132A, a Printed Circuit Board (or PCB) 13502, a clear (or customized) optical material 13504 and a target surface 13506.

LSSS 13500, by virtue of its design and implementation, facilitates execution of an Opto-Magnetic process based on interaction between electromagnetic radiation and matter, for instance light-skin interaction, using lens-free digital imaging for analysis of skin samples. Specifically, the Opto-Magnetic process employs apparatuses for generation of unique spectral signatures from digitally captured images of skin samples thereby facilitating analysis of the skin samples based on Opto-Magnetic properties of light-skin interaction.

Customized optical material 13504 facilitates shaping of light from the target surface to the imaging (or sensor) subsystem 13204A.

As shown in FIGS. 132A-B and 133A-B, the memory unit 13304A of the host computing 13206A includes algorithms that facilitate management of Depth-of-Field and Depth-of-Focus (or DOF) issues.

In certain embodiments, methods for characterization of skin based on the interaction between matter and electromagnetic radiation and systems and apparatuses facilitating implementation of such methods are disclosed. Stated differently, in certain such embodiments, systems and apparatuses for practicing the principles of the invention are disclosed. More specifically, the systems and apparatuses facilitate implementation of an Opto-Magnetic method with enhanced qualitative and quantitative parameters for characterization of skin in samples based on Opto-Magnetic properties of light-matter interaction. Still more specifically, the systems and apparatuses facilitate implementation of an Opto-Magnetic method with enhanced qualitative and quantitative parameters, novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for characterization of skin in samples based on Opto-Magnetic properties of light-matter interaction.

In certain other situations, the sample set is subjected to analysis using OMF method. Specifically, the preparation of digital pictures for OMF is made by usage of non-invasive imaging device that has previously been successfully used in biophysical skin characterization, such as skin photo type, moisture, conductivity, etc. By way of example and in no way limiting the scope of the invention, systems, devices and methods for non-invasive dermal imaging has been disclosed in US Pat. App. No. PCT/US2008/050438, Publication No: WO/2008/086311, Publication Date: 2008 Jul. 17 "SYSTEM, DEVICE AND METHOD FOR DERMAL IMAGING" to J. BANDIC, D J. KORUGA, R. MEHENDALE AND S. MARINKOVICH of MYSKIN, INC., the disclosure of which is incorporated herein by reference in its entirety. Thus, all remaining ins-and-outs in connection with the process of generating the spectral signature will not be further detailed herein.

In certain specific embodiments, the design and implementation of an Opto-Magnetic Fingerprint (OMF) process for characterization of skin based on the interaction between matter and electromagnetic radiation and systems and apparatuses facilitating implementation of such methods has been disclosed. Specifically, there is disclosed the design and implementation of an Opto-Magnetic method with enhanced qualitative and quantitative parameters for characterization of skin samples based on Opto-Magnetic properties of light-matter interaction and systems and apparatuses thereof. Still more specifically, there is disclosed design and implementation of an Opto-Magnetic method with enhanced qualitative and quantitative parameters, such as novel, early or premature detectability, practitioner capability, subjectivity or knowledge independent diagnosability, enhanced sensitivity, enhanced specificity, enhanced efficiency, greater accuracy, easily operable, rapid, economical, precise, timely and minute variation sensitive, for detection of cervical and endometrial cancer in samples based on Opto-Magnetic properties of light-matter interaction and systems and apparatuses thereof.

Further, the Opto-Magnetic method is in essence an Opto-Magnetic Fingerprint (OMF) method based on electron properties of matter and its interaction with light. By way of example, and in no way limiting the scope of the invention, the concept of light-matter interaction and Optomagnetic thereof has been disclosed in United States Provisional Patent Application "METHOD AND ALGORITHM FOR ANALYSIS OF LIGHT-MATTER INTERACTION BASED ON SPECTRAL CONVOLUTION" to MYSKIN, INC., the disclosure of which is incorporated herein by reference in its entirety. Thus, all remaining ins-and-outs in connection with the process of generating the spectral signature will not be further detailed herein.

In certain other embodiments, a comparative analysis of pictures of materials captured by classical optical microscopy and OMF has been discussed. Specifically, pictures captured by classical optical microscopy are based on electromagnetic property of light. On the contrary, in OMF pictures captured are based on difference between diffuse white light and reflected polarized light. Noticeable, here is the fact that reflected polarized light is produced when source of diffuse light irradiates the surface of matter under certain angle, such as Brewster's angle. Each type of matter has special different angle value of light polarization.

Since, reflected polarized light contains electrical component of light-matter interaction. Thus, taking the difference between white light (i.e. electromagnetic) and reflected polarized light (i.e. electrical) yields magnetic properties of matter based on light-matter interaction.

Since, reflected polarized light is composed of longitudinal wave (i.e. electrical component) and transverse wave (i.e. magnetic component). This implies that only electrical component as a longitudinal wave contains data (i.e. image) of light-matter interaction, which activates either CMOS or CCD image sensor.

FIG. 136 is a block diagrammatic view of a system facilitating implementation of an Opto-Magnetic process based on light-matter interaction using digital imaging for characterization of samples of skin, designed and implemented in accordance with certain embodiments of the invention.

System 13600 is in essence a Skin Characterization System (or SCS). The SCS 13600 includes an illumination subsystem 13602, an imaging (or sensor) subsystem 13604 and a host computing subsystem 13606.

SCS 13600, by virtue of its design and implementation, facilitates execution of an Opto-Magnetic method based on interaction between electromagnetic radiation and matter, for instance light-matter interaction, using digital imaging for analysis of samples subjected to skin characterization. Specifically, the Opto-Magnetic process employs apparatuses for generation of unique spectral signatures from digitally captured images of samples thereby facilitating analysis of the samples subjected to skin characterization based on Opto-Magnetic properties of light-test sample matter interaction.

Illumination subsystem 13602 may be one or more electromagnetic radiation sources. In certain specific embodiments, the Illumination subsystem 13602 may be a set of Light Emitting Diodes (LEDs).

Illumination subsystem 13602 may be adapted to emit polarized and unpolarized electromagnetic signals. The polarized electromagnetic signal is angled white light and unpolarized electromagnetic signal is non-angled white light.

As shown in the FIG. 136, in certain embodiments, the illumination subsystem 13602 may be coupled to the sensor subsystem 13604.

As shown in the FIG. 136, the sensor subsystem 13604 may in essence be a device that converts optical images (or optical signals) to electric signals. In certain embodiments, the sensor subsystem 13604 captures continuous digital images of skin test samples. Specifically, in such embodiments, the sensor subsystem 13604 captures continuous digital images of the skin test samples illuminated with white light both, non-angled and angled. By way of, and by no way of limitation, the sensor subsystem 13604 may be anyone selected from a group consisting of a Complementary Metal-Oxide-Semiconductor (CMOS) image sensor, Charged Coupled Device (CCD) image sensor, and the like.

Again, as shown in FIG. 136, the sensor subsystem 13604 may be coupled to the host computing subsystem 13606.

The term "digital image" refers to a representation of a two-dimensional image using ones and zeros (or binary digits or bits). The digital image may be of vector or raster type depending on whether or not the image resolution is fixed. However, without qualifications the term "digital image" usually refers to raster images.

Likewise, the term "digital imaging or digital image acquisition" refers to creation of digital images, typically from a physical object. The term is often assumed to imply or include the processing, compression, storage, printing and display of such images.

Digital image processing is the use of computer algorithms to perform image processing on digital images. As a subfield of digital signal processing, digital image processing has many advantages over analog image processing; it allows a much wider range of algorithms to be applied to the input data, and can avoid problems such as the build-up of noise and signal distortion during processing.

For example, and in no way limiting the scope of the invention, in certain embodiments the sensor subsystem 13604 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

The term "image processing", as used herein, refers to any form of signal processing for which the input is an image, such as photographs or frames of video. The output of image processing can be either an image or a set of characteristics or parameters related to the image. Most image-processing techniques involve treating the image as a two-dimensional signal and applying standard signal-processing techniques to it.

Image processing usually refers to digital image processing, but optical and analog image processing is also possible. The acquisition of images, i.e. producing the input image in the first place, is referred to as imaging.

The term "digital image processing", as used herein, refers to the use of computer algorithms to perform image processing on digital images. As a subfield of digital signal processing, digital image processing has many advantages over analog image processing. For example, digital image processing allows a much wider range of algorithms to be applied to the input data and can avoid problems, such as the build-up of noise and signal distortion during processing.

Medical imaging refers to the techniques and processes used to create images of the human body (or parts thereof) for clinical purposes (medical procedures seeking to reveal, diagnose or examine disease) or medical science (including the study of normal anatomy and physiology).

As a discipline and in its widest sense, it is part of biological imaging and incorporates radiology (in the wider sense), radiological sciences, endoscopy, (medical) thermography, medical photography and microscopy (e.g. for human pathological investigations).

FIG. 137 is an exploded diagrammatic representation of the host computing subsystem, of the FIG. 136, comprising an Opto-Magnetic Fingerprint (or OMF) Generator sub-module designed and implemented in accordance with at least some embodiments.

The host computing subsystem 13700 may comprise a processing unit 13702, a memory unit 13704 and an Input/Output (or I/O) unit 13706 respectively.

The host computing subsystem 13700, by virtue of its design and implementation, performs overall management of samples.

The processing unit 13702 may comprise an Arithmetic Logic Unit (or ALU) 13708, a Control Unit (or CU) 13710 and a Register Unit (or RU) 13712.

As shown in FIG. 137, the memory unit 13704 comprises a skin characterization module 13714.

In certain embodiments, the skin characterization module for characterization of samples via generation of unique spectral signatures from the digitally captured images of the samples and methods thereof are disclosed, in accordance with the principles of the invention. Specifically, in such embodiments, the skin characterization module utilizes the continuously captured digital images of the samples illuminated with white light both, non-angled and angled. More specifically, the skin characterization module takes into consideration the digital images in Red (R), Green (G) and Blue (B) (or RGB) system for purposes of analysis.

Further, as shown in FIG. 137, the skin characterization module 13714 includes a Fourier transform sub-module 13716, a spectral analyzer sub-module 13718 and an Opto-Magnetic Fingerprint Generator (or OMFG) sub-module 13720, respectively.

In certain embodiments, the Fourier transform sub-module 13716 is in essence a Discrete-Time Fourier Transform (or DTFT).

The term "DTFT", as used herein, refers to one of the specific forms of Fourier analysis. As such, it transforms one function into another, which is called the frequency domain representation, or simply, the "DTFT", of the original function, which is often a function in the time-domain. But, the DTFT requires an input function that is discrete. Sampling a continuous function, like a person's voice, often creates such inputs. The DTFT frequency-domain representation is always a periodic function. Since one period of the function contains all of the unique information, it is sometimes convenient to say that the DTFT is a transform to a "finite" frequency-domain (the length of one period), rather than to the entire real line.

DTFT 13716 converts time-domain digital signals into corresponding frequency-domain digital signals.

DTFT 13716 is coupled to the spectrum analyzer sub-module 13718.

As used herein, the term "spectrum analyzer" refers to a device used to examine the spectral composition of some electrical, acoustic, or optical waveform. It may also measure the power spectrum. In general, there are three types of spectrum analyzers, such as analog, digital and real-time spectrum analyzers. Firstly, an analog spectrum analyzer uses either a variable band-pass filter whose mid-frequency is automatically tuned (i.e. shifted, swept) through the range of frequencies of the spectrum to be measured or a super-heterodyne receiver, wherein the local oscillator is swept through a range of frequencies. Secondly, a digital spectrum analyzer computes the Discrete Fourier transform (or DFT), a mathematical process that transforms a waveform into the components of its frequency spectrum. Eventually, some spectrum analyzers, such as "real-time spectrum analyzers", use a hybrid technique where the incoming signal is first down-converted to a lower frequency using superheterodyne techniques and then analyzed using fast Fourier transformation (FFT) techniques.

In certain embodiments, the spectrum (or spectral) analyzer sub-module for analysis of digitally captured images of samples thereby facilitating analysis of the samples subjected to skin characterization is disclosed. Specifically, the spectrum (or spectral) analyzer sub-module in order to analyze the samples takes into consideration digital images of the samples in Red (R), Green (G) and Blue (B) (or RGB) system. In certain such embodiments, basic pixel data in Red (R) and Blue (B) channels for both white diffuse light (or W) and reflected polarized light (or P) is selected. In here, the algorithm for data analysis is based on chromaticity diagram called "Maxwell's triangle" and spectral convolution.

In certain specific embodiments, the digital images in Red (R), Green (G) and Blue (B) (or RGB) system are taken into consideration for purposes of spectral analysis. Specifically, basic pixel data in Red (R) and Blue (B) channels for white diffuse light (or W) and reflected polarized white light (or P) is selected. More specifically, the algorithm for data analysis is based on chromaticity diagram called "Maxwell's triangle" and spectral convolution operation, in accordance with a ratio of (R–B) & (W–P). Noticeably, the abbreviated designation implies that Red (R) minus Blue (B) wavelength of White light (W) and reflected Polarized light (P) are used in spectral convolution algorithm to calculate data for Opto-Magnetic Fingerprint (OMF) of matter both, organic and inorganic. Consequently, method and algorithm for creating unique spectral fingerprint are based on the convolution of RGB color channel spectral plots generated from digital images that capture single and multi-wavelength light-matter interaction for different paramagnetic materials, such as Al, Mn and Ti, diamagnetic materials, such as Cu, C and Zn, alloys, such as Pb1-xMnxTe, Biomolecules and biological tissues as paramagnetic/diamagnetic materials, such as skin, biological water, amniotic fluid, blood plasma and the like.

Further, incident white light can give different information about properties of thin layer of matter, such as skin surface, depending on the angle of light incidence. In use, when the incident white light is diffuse, the reflected white light is then composed of electrical and magnetic components, whereas diffuse incident light that is inclined under certain angle will produce reflected light which contains only electrical component of light.

As shown in FIG. 137, the spectrum analyzer sub-module 13718 may be coupled to the OMFG sub-module 13720.

OMFG sub-module 13720 includes a color histogram generator unit 13722, a spectral plot generator unit 13724 and a convolution unit 13726.

OMFG sub-module 13720, by virtue of its design and implementation, facilitates generation of unique spectral signatures from digitally captured images of skin samples. Specifically, the generated spectral signatures of skin samples facilitate detection of cervical and endometrial cancer based on Opto-Magnetic properties of light-test sample interaction.

Color histogram generator unit 13722, by virtue of its design, generates a normalized Red (R) and Blue (B) color channel histogram for each of the one or more images of the skin test samples.

The term "color histogram", as used in computer graphics and photography, refers to is a representation of the distribution of colors in an image, derived by counting the number of pixels of each of given set of color ranges in a typically two-dimensional (2D) or three-dimensional (3D) color space. A histogram is a standard statistical description of a distribution in terms of occurrence frequencies of different event classes; for color, the event classes are regions in color space. An image histogram of scalar pixel values is more commonly used in image processing than is a color histogram. The term "image histogram" refers to a type of histogram which acts as a graphical representation of the tonal distribution in a digital image. It plots the number of pixels for each tonal value. By looking at the histogram for a specific image a viewer is able to judge the entire tonal distribution at a glance.

Typically, color histograms are flexible constructs that can be built from images in various color spaces, whether RGB, rg chromaticity or any other color space of any dimension. A histogram of an image is produced first by discretization of the colors in the image into a number of bins, and counting the number of image pixels in each bin. For example, a Red-Blue chromaticity histogram can be formed by first normalizing color pixel values by dividing RGB values by R+G+B, then quantizing the normalized R and B coordinates into N bins each, where N=4, which might yield a 2D histogram that looks like this table:

Table 1 exhibits a tabular representation in connection with a 2D Red-Blue chromaticity histogram generated by first normalizing color pixel values by dividing RGB values by R+G+B, then quantizing the normalized R and B coordinates into N bins each, where N=4.

|   |         |      | R      |         |         |
|---|---------|------|--------|---------|---------|
|   |         | 0-63 | 64-127 | 128-191 | 192-255 |
| B | 0-63    | 43   | 78     | 18      | 0       |
|   | 64-127  | 45   | 67     | 33      | 2       |
|   | 128-191 | 127  | 58     | 25      | 8       |
|   | 192-255 | 140  | 47     | 47      | 13      |

As shown in FIG. 137, the color histogram generator unit 13722 may be coupled to the spectral plot generator unit 13724.

Spectral plot generator unit 13724 generates Red (R) and Blue (B) color channel spectral plots by correlating the normalized Red (R) and Blue (B) color channel histograms to a wavelength scale. In certain embodiments, a unit scale on the spectral signature is a difference of wavelength.

In general, color digital images are made of pixels and, in turn, pixels are made of combinations of primary colors. As used in the current context, the term "channel" refers to the grayscale image of the same size as a color image, made of just one of these primary colors. For instance, an image from a standard digital camera will have a red, green and blue channel. A grayscale image has just one channel. Further, an RGB image has three channels, namely Red (R), Green (G) and Blue (B). For example, if the RGB image is 24-bit then each channel has 8 bits, for R, G and B. Stated differently, the image is composed of three grayscale images, where each grayscale image can store discrete pixels with conventional brightness intensities between 0 and 255. Whereas, if the RGB image is 48-bit (i.e. very high resolution), each channel is made of 16-bit grayscale images.

The periodogram is an estimate of the spectral density of a signal. The term "spectral plot" refers to a smoothed version of the periodogram. Smoothing is performed to reduce the effect of measurement noise.

Convolution unit 13726 convolutes the Red (R) and Blue (B) color channel spectral plots by subtracting the spectral plot for the polarized optical electromagnetic signal from the non-polarized optical electromagnetic signal for each color to generate Red (R) and Blue (B) normalized, composite color channel spectral plots and subtracting the normalized, composite Blue (B) channel spectral plot from the normalized, composite Red (R) channel spectral plot thereby resulting in generation of a spectral signature for the skin test samples.

In certain embodiments, the spectral signature is analyzed for at least one of number of crests and troughs, amplitude, shape of peaks, intermediate structures and patterns. In certain such embodiments, the spectral signature is analysed for material composition, identification, purity and the like.

In certain other embodiments, the system configuration, discussed in conjunction with FIGS. 136 and 137, implement one or more processes facilitating estimation of sample type and properties (or characteristics) thereof to create a unique spectral signature.

FIG. 138 depicts a flow diagram delineating at least one process implemented by the system configuration of FIGS. 136 and 137 thereby facilitating estimation of skin test sample type and properties (or characteristics) thereof and creation of a unique spectral signature.

The process 13800 starts at stage 13802 and proceeds to stage 13804, wherein the process 300 comprises the phase of convolution of data associated with a first set of images of a skin sample captured by illuminating the sample with a white light (or unangled white light.) Noticeable here is the fact that the data associated with the first set of images of the skin sample illuminated with the white light (or unangled white light) may comprise one or more combinations of reflected and re-emitted angled and unangled white light.

At stage 13806, the process 13800 comprises the phase of convolution of data associated with a second set of images of the skin sample captured by illuminating the sample with an angled white light. It must be noted here that the data associated with the second set of images of the skin sample illuminated with the angled white light may comprise one or more combinations of reflected and re-emitted angled white light.

At stage 13808, the process 13800 comprises the phase of comparison of extrema (i.e. maxima and minima) (or extreme) positions of at least a pair of unique convolutions generated by convolution of data from the first set of images and second set of images.

At stage 13810, the process 13800 comprises the phase of determination of a distance between minimum and maximum (or extremum) intensity positions in convoluted Red (R) minus Blue (B) spectral plots from the pair of unique convolutions generated by convolution of data from the first set of images and second set of images to generate a numerical (or quantitative) skin sample type. The process 13800 ends at stage 13812.

In certain embodiments, the phase of comparison of extrema (i.e. maxima and minima) (or extreme) positions of at least a pair of unique convolutions comprises implementation of one or more sub-phases. Specifically, the one or more sub-phases include comparison of a first component Red (R) minus Blue (B) of unangled white light (or W) minus angled white light (or polarized white light or P) (i.e. (R–B) (W–P)) versus a second component Red (R) minus Blue (B) of unangled white light (or W) (i.e. (R–B) W). The two unique convolutions in unangled white light and angled (or polarized) white light further include a White Red component (WR), a White Blue component (WB), a reflected and/or re-emitted Polarized Blue component (PB) and a reflected and/or re-emitted Polarized Red component (PR). The two unique convolutions are based on a numerical value difference correlating to medical standards.

In certain alternative embodiments, the step of comparing extreme positions of at least two unique convolutions includes comparing a component (R–B) (W–P) for the reflected and/or re-emitted polarized light, and a component (R–B) W for the white light. Yet, in certain embodiments, the step of comparing extreme positions of at least two unique convolutions includes a spectral convolution scheme, wherein multiple combinations of subtraction of Blue (B) spectrum from Red (R), in white light and polarized white light are determined, wherein the spectral interval is expressed in a wavelength scale interval of 100 nanometers to 300 nanometers.

In certain specific circumstances, the investigation of human epidermal layers properties involves implementation of a combination of at least a pair of distinct methods, in accordance with the principles of the invention. By way of example, and in no way limiting the scope of the invention, a former method of the pair of distinct methods is the OMF; whereas the latter method is bioimpedance is complementary and compatible to the OMF. Specifically, the former method facilitates investigation of surface of matter, biological and non-biological (or organic and inorganic), and optical and magnetic properties of materials and tissues and thin layers thereof. More specifically, the OMF method is based on the difference between responses of the material illuminated with both right-angled white light (i.e. reflected light to sensor is diffuse) and with the same white light under Brewster angle (i.e. reflected light to sensor is polarized).

Still more specifically, the OMF method is based on electron properties of the matter (i.e. covalent bonds, hydrogen bonds, ion-electron interaction, van der Waals interaction) and its interaction with light, as disclosed in the JOURNAL MATERIALS SCIENCE FORUM, volume title and no. "RECENT DEVELOPMENTS IN ADVANCED MATERIALS AND PROCESSES" AND 518, edited by DRAGAN P. USKOKOVIC, SLOBODAN K. MILONJIC AND DEJAN I. RAKOVIC, in pages 491-496, Digital Object Identifier (or DOI) 10.4028/WWW.SCIENTIFIC.NET/MSF.518.491, cited as D J. KORUGA ET AL., 2006, MATERIALS SCIENCE FORUM, 518, 491, online since July, 2006, authored by D J. KORUGA, A. TOMIĆ, Z. RATKAJ, L. MATIJA. This method was originally developed for early skin cancer and melanoma detection by mySkin, Inc., USA and has been disclosed in U.S. Pat. App. No. 61/61,852, 2008, PCT/US2009/030347, Publication No: WO/2009/089292, Publication Date: Jul. 16, 2009 "SYSTEM AND METHOD FOR ANALYSIS OF LIGHT-MATTER INTERACTION BASED ON SPECTRAL CONVOLUTION" to KORUGA D J AND TOMIC A of mySkin, Inc. and US Pat. App. No. PCT/US2008/050438, Publication No: WO/2008/086311, Publication Date: Jul. 17, 2008 to BANDIC J, KORUGA D J, MEHENDALE R AND MARINKOVICH S of mySkin, Inc., the disclosure of which is incorporated herein by reference in its entirety. Thus, all remaining ins-and-outs in connection with the process of generating the spectral signature will not be further detailed herein. Further, the OMF method has been used for characterization of blood plasma, as disclosed in PAPIĆ-OBRADOVIĆ, M., KOJIĆ, D., MATIJA, L., ACTA PHYSICA POLONICA A, 117 (5), 782-784, 2010. Still further, this method has been used for characterization of contact lenses, as disclosed in STAMENKOVIĆ, D. KOJIĆ, D., MATIJA, L., MILJKOVIĆ, Y., BABIĆ, B., INT. J. MOD. PHYS B, 24(6-7), 825-834, 2010, and in characterization of water, as disclosed in KORUGA, D., MILJKOVIĆ, S., RIBAR, S., MATIJA, L., KOJIĆ, D., ACTA PHYSICA POLONICA A, 117 (5), 777-781, 2010. In such specific circumstances, the algorithm for data analysis is based on chromaticity diagram called "Maxwell's triangle" and spectral convolution operation according to ratio of (R–B)&(W–P). This is as disclosed in U.S. Pat. App. No. 61/61,852, 2008, PCT/US2009/030347, Publication No: WO/2009/089292, Publication Date: Jul. 16, 2009 "SYSTEM AND METHOD FOR ANALYSIS OF LIGHT-MATTER INTERACTION BASED ON SPECTRAL CONVOLUTION" to KORUGA D J AND TOMIC A of mySkin, Inc. For purposes of clarity and expediency, the abbreviated designation (R–B)&(W–P) implies Red minus Blue wavelength of White light and reflected Polarized light (based on Brewster angle) are used in spectral convolution algorithm to calculate data for Opto-Magnetic Fingerprint (or OMF) of the matter.

Further, in such experimental circumstances, bioimpedance measurement is been done by a suitable analyzer on one or more distinct frequencies in given, selected input voltage range using one or more electrodes. By way of example, and in no way limiting the scope of the invention, measurement is done by the BIA-1 (NanoLab, Serbia) analyzer on at least four distinct frequencies, i.e. 9, 30, 47 and 100 KHz, in the given, selected input voltage range from a minimum of approximately 1.5 V to a maximum of approximately 5.0 V (peak-to-peak), by at least a pair of electrodes possessing the following specifications: material is stainless steel; diameter is 10 mm and distance between electrode centers is 30 mm.

Still further, in such experimental circumstances, by way of example, and in no way limiting the scope of the invention, the thickness of removed skin layers on sticker plaster surface is investigated by Atomic Force Microscopy (or AFM)-(NanoProbe JEOL, Japan).

In certain circumstances, the investigation of human epidermal layers properties, corresponding to two distinct types of drinking waters, conducted over a sample set taken from 20 volunteers is disclosed. By way of example, and in no way limiting the scope of the invention, in such circumstances, the two distinct types of drinking waters have been hereinafter referred to as N-water (or normal tap water or normal water) and Z-water (or tap water), in that order. Still, by way of example, and in no way limiting the scope of the invention, in such circumstances, the Z-water possesses the following ingredient specifications: orthophosphates 4*(or four times) more, i.e. 0.64 mg/l, vis-à-vis allowed, i.e. 0.15 mg/l; residual chlorine 2*(or twice) more, i.e. 1.00 mg/l, vis-à-vis allowed, i.e. 0.5 mg/l; and iron 1.70*(or 1.70 times) more, i.e. 0.51 mg/l, vis-à-vis allowed, i.e. 0.3 mg/l. Specifically, in such circumstances, the sample set is sub-divided into one or more sample sub-sets, in accordance with the principles of the invention. By way of example, and in no way limiting the scope of the invention, the sample set is sub-divided into at a pair of sample sub-sets, namely a first and second sample sub-set. The first sample sub-set includes 15 out of 20 volunteers, who have been drinking or consuming the Z-water for years, whereas the second sample sub-set includes 5 out of 20 volunteers, who are drinking the N water.

In such experimental circumstances, characterization of skin surfaces of all the volunteers is disclosed, in accordance with the principles of the invention. Specifically, in a first given experimental circumstance, the inner arms and foreheads of all the volunteers included in the sample set are characterized using Opto-Magnetic Fingerprint (or OMF) and bioimpedance methods. In a second given experimental circumstance, the sample set was subjected to characterization of the first layer of the stratum corneum by OMF and bioimpedance subsequent to removal of all the impurities including, but not limited to, dust, surface oil, surface water, from surface skin by sticking plaster. In a third given experimental circumstance, the sample set was subjected to characterization of the first layer of the stratum *granulosum* by OMF and bioimpedance subsequent to removal of all the impurities including, but not limited to, dust, surface oil, surface water, from surface skin by sticking plaster. Further, in a fourth experimental circumstance, the sample set was subjected to characterization subsequent to removal of the first half portion of the stratum *granulosum*. Still further, in a fifth experimental circumstance, the sample set was subjected to characterization of water in lipid-water layers subsequent to removal of the second half portion of the stratum *granulosum*.

In similar experimental circumstances, from the day of commencement of the experimentation to the subsequent 6 weeks, the 10 out of 20 volunteers, who were drinking or consuming the Z-water, started to drink the N-water. In a sixth experimental circumstance, subsequent to completion of 8 weeks the sample set was subjected to characterization of epidermis in the same mode, as suggested earlier. In such experimental circumstance, 5 out of 20 subjects or volunteers, who were drinking the N-water, and 5 out of 20 subjects or volunteers, who were continuously drinking the Z-water, formed the control group. In such certain experimental circumstances, by way of example, and in no way limiting the scope of the invention, the sample set of 20 subjects or volunteers possesses the following specifications: age range from a minimum of approximately 11 years to a maximum of approximately 63 years; gender ratio in sample set 8 males is to 12 females; and skin types 2 and 3. Still, in such certain experimental circumstances, the sample set was subjected to following ambience specifications: relative humidity 48±0.2% and room temperature 22±0.3%, respectively.

FIG. 139 is a cross-sectional anatomical view of the epidermis with four main layers, basement membrane and other structures including, but not limited to, melanocyte, Langerhans cell, in accordance with the prior art and adapted therefrom.

As depicted in FIG. 139, the left margin reference numerals notation includes four distinct reference numerals indicating four distinct states in connection with epidermis and sub-layers thereof. For purpose of clarity and expediency, the four distinct reference numerals indicative of corresponding four distinct instances in connection with epidermis and layers thereof are hereinafter referred to as Layer "0"-skin surface with impurities, surface oiliness, surface moisture and first level of stratum corneum without water (about 6 μm), "1"—deeper part of stratum corneum with very small amount of water (about 5 μm), "2"—water in stratum corneum and the first water layers in stratum *granulosum* with significant amount of water (from 10 μm to 15 μm) and "3"—stratum *granulosum*, rich with water, i.e. about 20 μm, when the skin is in good condition.

FIGS. 140A-C depicts three distinct snapshots of epidermis of human skin, and layers thereof, juxtaposed to each other, in accordance with the prior art and adapted therefrom.

As shown in FIG. 140A, a first snapshot depicts a cross-sectional anatomical view of epidermis in which a square icon imposed thereupon indicates and emphasizes a selected portion of the stratum *granulosum* layer of the epidermis, and in which the square icon is contained.

Further, as shown in FIG. 140B, a second snapshot depicts a first level magnified view of the selected portion of the stratum *granulosum* layer comprising the square icon imposed on FIG. 140A.

Still further, as shown in FIG. 140C, a third snapshot depicts a second level magnified view of the selected portion of the stratum *granulosum* layer comprising one or more lipid layers and water therebetween.

Reiterating again, as depicted in FIG. 140C, the stratum *granulosum* layer holds water in water/lipid layers. By virtue of this, characterization of water as an independent substance is possible only in this part of the skin.

As observed in FIGS. 140A-C, the water layer possesses the following specifications: thickness of the water layer between a minimum of approximately 20 nm and a maximum of approximately 50 nm; state or phase is liquid crystalline or quasi-polymer and properties as liquid crystalline water.

In certain embodiments, it is observed that properties of skin confined to inner arm region of 5 out of 20 volunteers, who drank the N-water (or normal) water show similarity of convolution spectra for wavelength difference on one or more given, selected values. By way of example, and in no way limiting the scope of the invention, in such certain embodiments, the similarity of convolution spectra was found at 132 nm with symmetrical tolerance of 1.2 nm, i.e. 132±1.2 nm. However, for 5 out of 20 volunteers, who drank water the Z-water continuously, a peak was found at 140 nm with symmetrical tolerance of 1.2 nm, i.e. 140±1.2 nm. Still however, in 10 out of 20 volunteers, who switched to drinking the N-water from the Z-water for two months, there was peak at 135 nm with a symmetrical tolerance of 1.5 nm, i.e. on 135±1.5 nm. Further, it was found that the wavelength shift difference of volunteers, who drank the N-water and Z-water, was confined to a range from a minimum of approximately 5.6 nm to a maximum of approximately 10.4 nm. Thus, it is apparent that the volunteers who switched to drinking the N-water from the Z-water for two months were proximate to the volunteers drinking Z-water than in comparison to those drinking the N-water. This indicates that skin (i.e. dermis and subcutis) holds water longer than two months. In such certain embodiments, there is an assumption that the water in dermis of these volunteers is mixture of the N-water and Z-water and penetrates through basement membrane to epidermis. In certain experimental embodiments, based on the wavelength difference shift, tests can be conducted for determination of time the water stays in the human skin.

In such certain embodiments, one or more OMF diagrams obtained on implementation of the OMF method on digital images of skin layers, confined to the inner arm region, captured from one or more given, selected samples procured from one or more male subjects or volunteers, are disclosed in accordance with the principles of the invention. By way of example, and in no way limiting the scope of the invention, the OMF diagrams for one or more samples procured from one or more layers, discussed in conjunction with FIG. 139 and confined to inner arm region, of skin of a pair of male subjects or volunteers, aged 11 and 63, have been disclosed. In such certain embodiments, it is observed that there is difference of skin property for each epidermal layer. However, it is observed that peak on 132±1.5 nm wavelength difference exists in both cases involving the pair of male subjects or volunteers, aged 11 and 63. Still, however, a comparative analysis of the volunteers who switched to drinking the N-water from the Z-water for two months vis-à-vis the volunteers who drank at least one of the N-water and Z-water shows difference in peaks in an observation window interval ranging from a minimum of approximately 120 nm to a maximum of approximately 130 nm. In certain specific embodiments, the OMF diagrams were developed, studied and analyzed for one or more regions of the skin. For example, and by no way of limitation, the OMF diagrams were developed, studied and analyzed for a pair of regions of the skin, namely inner arm and forehead. It must be noted that more pronounced difference has been observed for forehead then inner arm. This is based on the assumption that the forehead has a more complex skin structure owing to the presence of sebaceous glands thereby rendering the skin moisturous and oilier.

FIG. 141A depicts a first plot of a typical spectral data (or OMF diagram) obtained on implementation of the OMF method on digital images of skin layers, confined to the inner arm region, captured from a given, selected first sample procured from a given, selected first male subject or volunteer aged 11 years, in accordance with certain embodiments of the invention.

As shown in FIG. 141A, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected first sample (or Layer "0" of skin, discussed in conjunction with FIG. 139 and confined to the inner arm region, in every day skin surface), analyzed and categorized as a first test case or Case 1(A), of the given, selected first subject or volunteer subjected to the skin characterization test.

As depicted in FIG. 141A, the first DI plot possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical X-axis includes a closed interval of Intensity Values ranging from a minimum of equal to −100 to a maximum of equal to +100 (n.a.u.*1000); analytical information is analysis of the first DI plot (or OMF Diagram) of the sample; subject or volunteer information is a given, selected first male subject or volunteer aged 11 years; test input sample is the given, selected first sample (or Layer "0" of skin, confined to the inner arm region, in every day skin surface) analyzed and categorized as Case 1(A) and operation is implementation of the OMF method on digital images of Layer "0" of skin, confined to the inner arm region, captured from the given, selected first sample procured from the given, selected first male subject or volunteer aged 11 years.

FIG. 141B depicts a second plot of a typical spectral data (or OMF diagram) obtained on implementation of the OMF method on digital images of the Layer "1" of skin, disclosed in conjunction with FIG. 139, and confined to the inner arm region, in which the digital images captured from a given, selected second sample procured from the given, selected first male subject or volunteer aged 11 years, in accordance with certain embodiments of the invention.

As shown in FIG. 141B, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected second sample (or Layer "1" of skin, confined to the inner arm region, on removal of impurities, surface water, surface oiliness and first stratum corneum cells), analyzed and categorized as a second test case or Case I(B), of the given, selected first subject or volunteer subjected to the skin characterization test.

As depicted in FIG. 141B, the second DI plot possesses the following specifications and associated analytical information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical X-axis includes a closed interval of Intensity Values ranging from a minimum of equal to −60 to a maximum of equal to +40 (n.a.u.*1000); analytical information is analysis of the second DI plot (or OMF Diagram) of the sample; subject or volunteer information is the given, selected first male subject or volunteer aged 11 years; test input sample is the given, selected second sample (or Layer "1" of skin, confined to the inner arm region, on removal of impurities, surface water, surface oiliness and first stratum corneum cells) analyzed and categorized as Case 1(B); operation is implementation of the OMF method on digital images of the given, selected second sample procured from the given, selected first male subject or volunteer aged 11 years.

FIG. 141C depicts a third plot of a typical spectral data (or OMF diagram) obtained on implementation of the OMF method on digital images captured from of a given, selected third sample procured from a third selected layer confined to the inner arm region, of skin of the given, selected first male subject or volunteer aged 11 years, in accordance with certain embodiments of the invention.

As shown in FIG. 141C, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected third sample (or Layer "2" of skin, confined to the inner arm region, on removal of stratum corneum), analyzed and categorized as a third test case or Case 1(C), of the given, selected first subject or volunteer subjected to the skin characterization test.

As depicted in FIG. 141C, the third DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −60 (n.a.u.*1000) to a maximum of equal to +40 (n.a.u.*1000) (i.e. [−60, +40]); analytical information is analysis of the third DI plot (or OMF Diagram) of the sample; subject or volunteer information is the given, selected first male subject or volunteer aged 11 years; test input sample is the given, selected third sample procured from the third selected layer (i.e. Layer "2", discussed in conjunction with FIG. 139) of skin in a third state (i.e. on removal of stratum corneum), and confined to the inner arm region of the given, selected first male subject or volunteer aged 11 years; test case nomenclature information is Case 1(B); operation is implementation of the OMF method on digital images of the given, selected third sample procured from the given, selected first male subject or volunteer aged 11 years.

FIG. 141D depicts a fourth plot of a typical spectral data (or OMF diagram) obtained on implementation of the OMF method on digital images captured from of a given, selected fourth sample procured from a fourth selected layer confined to the inner arm region of skin of the given, selected first male subject or volunteer aged 11 years, in accordance with certain embodiments of the invention.

As shown in FIG. 141D, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected fourth sample (or Layer "3" of skin, discussed in conjunction with FIG. 35, confined to the inner arm region, on removal of approximately 50% of the cells of stratum *granulosum*), analyzed and categorized as a fourth test case or Case 1(D), of the given, selected first subject or volunteer subjected to the skin characterization test.

In certain such embodiments, the fourth test case discloses implementation of the OMF method on digital images captured from the given, selected fourth sample procured from a fourth selected layer confined to the inner arm region and existing (or taken into consideration) in a given, selected fourth state of skin of the given, selected first male subject or volunteer aged 11 years. By way of example, and in no way limiting the scope of the invention, the fourth sample is the Layer "3", discussed in conjunction with FIG. 139, of skin in the fourth state (i.e. on removal of approximately 50% of cells of stratum *granulosum*), confined to the inner arm region of the given, selected first male subject or volunteer aged 11 years.

As depicted in FIG. 141D, the fourth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −40 (n.a.u.*1000) to a maximum of equal to +40 (n.a.u.*1000) (i.e. [−40, +40]); analytical information is analysis of the fourth DI plot (or OMF Diagram) of the sample; subject or volunteer information is the given, selected first male subject or volunteer aged 11 years; test input sample is the given, selected fourth sample procured from the fourth selected layer (i.e. Layer "3", discussed in conjunction with FIG. 139) of skin in the fourth state (i.e. on removal of approximately 50% of cells of stratum *granulosum*) confined to the inner arm region of the given, selected first male subject or volunteer aged 11 years; test case nomenclature information is Case 1(D); operation is implementation of the OMF method on digital images of the given, selected fourth sample procured from the given, selected first male subject or volunteer aged 11 years.

In general, the interaction of lipids and water are fundamental to all body tissues, but for skin it has special significance. Each water molecule is capable of hydrogen bonding with four neighboring water molecules. Further, water hydrogen bonds make network with the poplar head groups of lipids. Still further, the lipids of stratum corneum consist mainly of ceramides, cholesterol, and fatty acids. On the skin surface polar lipids are capable to form lamellar or hexagonal phases in the presence of excess water. A liquid ordered phase has both properties a gel phase and a liquid crystalline phase. The phase's mixture and properties of the skin layers depend on of many factors, but three are dominant, namely age, gender and skin type.

In certain specific embodiments, one or more test cases disclose implementation of the OMF method on digital images captured from given, selected one or more samples procured from given, selected one or more selected layers, confined to the inner arm region, and existing in given, selected one or more distinct states of the skin of a given, selected second male subject or volunteer aged 63 years.

FIG. 142A depicts a fifth plot of a typical spectral data (or OMF diagram) obtained on implementation of the OMF method on digital images captured from of a given, selected fifth sample procured from the given, selected first layer confined to the inner arm region of skin of the given, selected second male subject or volunteer aged 63 years, in accordance with certain embodiments of the invention.

As shown in FIG. 142A, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected fifth sample (or Layer "0" of every day skin surface confined to the inner arm region), analyzed and categorized as a fifth test case or Case 2(A), of the given, selected second subject or volunteer subjected to the skin characterization test.

In certain such embodiments, the fifth test case discloses implementation of the OMF method on digital images captured from the given, selected fifth sample procured from the given, selected first layer confined to the inner arm region and existing (or taken into consideration) in the given, selected first state of skin of the given, selected second male subject or volunteer aged 63 years. By way of example, and in no way limiting the scope of the invention, the fifth sample is the Layer "0", discussed in conjunction with FIG. 139, in the first state (i.e. every day skin surface), confined to the inner arm region of the given, selected second male subject or volunteer aged 63 years.

As depicted in FIG. 142A, the fifth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −50 (n.a.u.*1000) to a maximum of equal to +100 (n.a.u.*1000) (i.e. [−50, +100]); analytical information is analysis of the fifth DI plot (or OMF Diagram) of the sample; subject or volunteer information is the given, selected second male subject or volunteer aged 63 years; test input sample is the given, selected fifth sample procured from the first selected layer (i.e. Layer "0", discussed in conjunction with FIG. 139) in the first state (i.e. every day skin surface) confined to the inner arm region of the given, selected second male subject or volunteer aged 63 years; test case nomenclature information is Case 2(A); operation is implementation of the OMF method on digital images of the given, selected fifth sample procured from the given, selected second male subject or volunteer aged 63 years.

FIG. 142B depicts a sixth plot of a typical spectral data (or OMF diagram) obtained on implementation of the OMF method on digital images captured from of a given, selected sixth sample procured from the given, selected second layer confined to the inner arm region of skin of the given, selected second male subject or volunteer aged 63 years, in accordance with certain embodiments of the invention.

In certain such embodiments, a sixth test case discloses implementation of the OMF method on digital images captured from the given, selected sixth sample procured from the given, selected second layer confined to the inner arm region and existing (or taken into consideration) in the given, selected second state of skin of the given, selected second male subject or volunteer aged 63 years. By way of example, and in no way limiting the scope of the invention, the sixth sample is the Layer "1", discussed in conjunction with FIG. 139, in the second state (i.e. on removal of impurities, surface water, surface oiliness and first stratum corneum cells), confined to the inner arm region of the given, selected second male subject or volunteer aged 63 years.

As shown in FIG. 142B, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected sixth sample (or Layer "1" of skin on removal of impurities, surface water, surface oiliness and first stratum corneum cells, confined to the inner arm region), analyzed and categorized as the sixth test case or Case 2(B), of the given, selected second subject or volunteer subjected to the skin characterization test.

As depicted in FIG. 142B, the sixth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −100 (n.a.u.*1000) to a maximum of equal to +100 (n.a.u.*1000) (i.e. [−100, +100]); analytical information is analysis of the sixth DI plot (or OMF Diagram) of the sample; subject or volunteer information is the given, selected second male subject or volunteer aged 63 years; test input sample is the given, selected sixth sample procured from the first selected layer (i.e. Layer "1", discussed in conjunction with FIG. 139) in the second state (i.e. on removal of impurities, surface water, surface oiliness and first stratum corneum cells) confined to the inner arm region of the given, selected second male subject or volunteer aged 63 years; test case nomenclature information is Case 2(B); operation is implementation of the OMF method on digital images of the given, selected sixth sample procured from the given, selected second male subject or volunteer aged 63 years.

FIG. 142C depicts a seventh plot of a typical spectral data (or OMF diagram) obtained on implementation of the OMF method on digital images captured from of a given, selected seventh sample procured from the given, selected third layer confined to the inner arm region of skin of the given, selected second male subject or volunteer aged 63 years, in accordance with certain embodiments of the invention.

In certain such embodiments, a seventh test case discloses implementation of the OMF method on digital images captured from the given, selected seventh sample procured from the given, selected third layer confined to the inner arm region and existing (or taken into consideration) in the given, selected third state of skin of the given, selected second male subject or volunteer aged 63 years. By way of example, and in no way limiting the scope of the invention, the seventh sample is the Layer "2", discussed in conjunction with FIG. 139, in the third state (i.e. on removal of stratum corneum), confined to the inner arm region of the given, selected second male subject or volunteer aged 63 years.

As shown in FIG. 142C, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected seventh sample (or Layer "2" of skin on removal of stratum corneum, confined to the inner arm region) analyzed and categorized as Case 2(C) of the given, selected second subject or volunteer subjected to the skin characterization test.

As depicted in FIG. 142C, the seventh DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −100 (n.a.u.*1000) to a maximum of equal to +100 (n.a.u.*1000) (i.e. [−100, +100]); analytical information is analysis of the seventh DI plot (or OMF Diagram) of the sample; subject or volunteer information is the given, selected second male subject or volunteer aged 63 years; test input sample is the given, selected seventh sample procured from the third selected layer (i.e. Layer "2", discussed in conjunction with FIG. 139) in the third state (i.e. on removal of stratum corneum) confined to the inner arm region of the given, selected second male subject or volunteer aged 63 years; test case nomenclature information is Case 2(C); operation is implementation of the OMF method on digital images of the given, selected seventh sample procured from the given, selected second male subject or volunteer aged 63 years.

FIG. 142D depicts an eighth plot of a typical spectral data (or OMF diagram) obtained on implementation of the OMF method on digital images captured from of a given, selected eighth sample procured from the given, selected fourth layer confined to the inner arm region of skin of the given, selected second male subject or volunteer aged 63 years, in accordance with certain embodiments of the invention.

In certain such embodiments, an eighth test case discloses implementation of the OMF method on digital images captured from the given, selected eighth sample procured from the given, selected fourth layer confined to the inner arm region and existing (or taken into consideration) in the given, selected fourth state of skin of the given, selected second male subject or volunteer aged 63 years. By way of example, and in no way limiting the scope of the invention, the seventh sample is the Layer "3", discussed in conjunction with FIG. 139, in the fourth state (i.e. on removal of approximately 50% of the cells of stratum *granulosum*), confined to the inner arm region of the given, selected second male subject or volunteer aged 63 years.

As shown in FIG. 142D, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected eighth sample (or Layer "3" of skin on removal of approximately 50% of the cells of stratum *granulosum*, confined to the inner arm region) analyzed and categorized as Case 2(D) of the given, selected second subject or volunteer subjected to the skin characterization test.

As depicted in FIG. 142D, the eighth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −40 (n.a.u.*1000) to a maximum of equal to +40 (n.a.u.*1000) (i.e. [−40, +40]); analytical information is analysis of the eighth DI plot (or OMF Diagram) of the sample; subject or volunteer information is the given, selected second male subject or volunteer aged 63 years; test input sample is the given, selected eighth sample procured from the fourth selected layer (i.e. Layer "3", discussed in conjunction with FIG. 139) in the fourth state (i.e. on removal of approximately 50% of the cells of stratum *granulosum*) confined to the inner arm region of the given, selected second male subject or volunteer aged 63 years; test case nomenclature information is Case 2(D); operation is implementation of the OMF method on digital images of the given, selected eighth sample procured from the given, selected second male subject or volunteer aged 63 years.

FIG. 143A depicts a ninth plot of a typical spectral data (or OMF diagram) obtained on implementation of the OMF method on digital images captured from of a given, selected ninth sample procured from the given, selected first layer confined to the inner arm region of skin of the given, selected third male subject or volunteer aged 50 years, in accordance with certain embodiments of the invention.

In certain such embodiments, a ninth test case discloses implementation of the OMF method on digital images captured from the given, selected ninth sample procured from the given, selected first layer confined to the inner arm region and existing (or taken into consideration) in the given, selected first state of skin of the given, selected third male subject or volunteer aged 50 years. By way of example, and in no way limiting the scope of the invention, the ninth sample is the Layer "0", discussed in conjunction with FIG. 139, in the first state (i.e. every day skin surface), confined to the inner arm region of the given, selected third male subject or volunteer aged 50 years.

As shown in FIG. 143A, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected ninth sample (or Layer "0" of every day skin surface, confined to the inner arm region) analyzed and categorized as Case 3(A) of the given, selected third subject or volunteer subjected to the skin characterization test.

As depicted in FIG. 143A, the ninth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −100 (n.a.u.*1000) to a maximum of equal to +50 (n.a.u.*1000) (i.e. [−100, +50]); analytical information is analysis of the ninth DI plot (or OMF Diagram) of the sample; subject or volunteer information is the given, selected third male subject or volunteer aged 50 years; test input sample is the given, selected ninth sample procured from the first selected layer (i.e. Layer "0", discussed in conjunction with FIG. 139) in the first state (i.e. every day skin surface) confined to the inner arm region of the given, selected third male subject or volunteer aged 50 years; test case nomenclature information is Case 3(A); operation is implementation of the OMF method on digital images of the given, selected ninth sample procured from the given, selected third male subject or volunteer aged 50 years.

FIG. 143B depicts a tenth plot of a typical spectral data (or OMF diagram) obtained on implementation of the OMF method on digital images captured from of a given, selected tenth sample procured from the given, selected second layer confined to the inner arm region of skin of the given, selected third male subject or volunteer aged 50 years, in accordance with certain embodiments of the invention.

In certain such embodiments, a tenth test case discloses implementation of the OMF method on digital images captured from the given, selected tenth sample procured from the given, selected second layer confined to the inner arm region and existing (or taken into consideration) in the given, selected second state of skin of the given, selected third male subject or volunteer aged 50 years. By way of example, and in no way limiting the scope of the invention, the tenth sample is the Layer "1", discussed in conjunction with FIG. 139, in the second state (i.e. on removal of impurities, surface water, surface oiliness and first stratum corneum cells from skin), confined to the inner arm region of the given, selected third male subject or volunteer aged 50 years.

As shown in FIG. 143B, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected tenth sample (or Layer "1" on removal of impurities, surface water, surface oiliness and first stratum corneum cells from skin, confined to the inner arm region) analyzed and categorized as Case 3(B) of the given, selected third subject or volunteer subjected to the skin characterization test.

As depicted in FIG. 143B, the tenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −60 (n.a.u.*1000) to a maximum of equal to +40 (n.a.u.*1000) (i.e. [−60, +40]); analytical information is analysis of the tenth DI plot (or OMF Diagram) of the sample; subject or volunteer information is the given, selected third male subject or volunteer aged 50 years; test input sample is the given, selected tenth sample procured from the second selected layer (i.e. Layer "1", discussed in conjunction with FIG. 139) in the second state (i.e. on removal of impurities, surface water, surface oiliness and first stratum corneum cells from skin) of skin confined to the inner arm region of the given, selected third male subject or volunteer aged 50 years; test case nomenclature information is Case 3(B); operation is implementation of the OMF method on digital images of the given, selected tenth sample procured from the given, selected third male subject or volunteer aged 50 years.

FIG. 143C depicts an eleventh plot of a typical spectral data (or OMF diagram) obtained on implementation of the OMF method on digital images captured from of a given, selected eleventh sample procured from the given, selected third layer confined to the inner arm region of skin of the given, selected third male subject or volunteer aged 50 years, in accordance with certain embodiments of the invention.

In certain such embodiments, an eleventh test case discloses implementation of the OMF method on digital images captured from the given, selected eleventh sample procured from the given, selected third layer confined to the inner arm region and existing (or taken into consideration) in the given, selected third state of skin of the given, selected third male subject or volunteer aged 50 years. By way of example, and in no way limiting the scope of the invention, the eleventh sample is the Layer "2", discussed in conjunction with FIG. 139, in the third state (i.e. on removal of stratum corneum), confined to the inner arm region of the given, selected third male subject or volunteer aged 50 years.

As shown in FIG. 143C, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected eleventh sample (or Layer "2" on removal of stratum corneum from skin, confined to the inner arm region) analyzed and categorized as Case 3(C) of the given, selected third subject or volunteer subjected to the skin characterization test.

As depicted in FIG. 143C, the eleventh DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −60 (n.a.u.*1000) to a maximum of equal to +40 (n.a.u.*1000) (i.e. [−60, +40]); analytical information is analysis of the eleventh DI plot (or OMF Diagram) of the sample; subject or volunteer information is the given, selected third male subject or volunteer aged 50 years; test input sample is the given, selected eleventh sample procured from the third selected layer (i.e. Layer "2", discussed in conjunction with FIG. 139) in the third state (i.e. on removal of stratum corneum from skin) of skin confined to the inner arm region of the given, selected third male subject or volunteer aged 50 years; test case nomenclature information is Case 3(C); operation is implementation of the OMF method on digital images of the given, selected eleventh sample procured from the given, selected third male subject or volunteer aged 50 years.

FIG. 143D depicts a twelfth plot of a typical spectral data (or OMF diagram) obtained on implementation of the OMF method on digital images captured from of a given, selected twelfth sample procured from the given, selected fourth layer confined to the inner arm region of skin of the given, selected third male subject or volunteer aged 50 years, in accordance with certain embodiments of the invention.

In certain such embodiments, a twelfth test case discloses implementation of the OMF method on digital images captured from the given, selected twelfth sample procured from the given, selected fourth layer confined to the inner arm region and existing (or taken into consideration) in the given, selected fourth state of skin of the given, selected third male subject or volunteer aged 50 years. By way of example, and in no way limiting the scope of the invention, the twelfth sample is the Layer "3", discussed in conjunction with FIG. 139, in the fourth state (i.e. on removal of 50% of the cells of stratum *granulosum*), confined to the inner arm region of the given, selected third male subject or volunteer aged 50 years.

As shown in FIG. 143D, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected twelfth sample (or Layer "3" on removal of 50% of cells of stratum *granulosum* of skin, confined to the inner arm region) analyzed and categorized as Case 3(D) of the given, selected third subject or volunteer subjected to the skin characterization test.

As depicted in FIG. 143D, the twelfth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −60 (n.a.u.*1000) to a maximum of equal to +20 (n.a.u.*1000) (i.e. [−60, +20]); analytical information is analysis of the eleventh DI plot (or OMF Diagram) of the sample; subject or volunteer information is the given, selected third male subject or volunteer aged 50 years; test input sample is the given, selected twelfth sample procured from the fourth selected layer (i.e. Layer "3", discussed in conjunction with FIG. 139) in the fourth state (i.e. on removal of 50% of the cells stratum *granulosum* of skin) of skin confined to the inner arm region of the given, selected third male subject or volunteer aged 50 years; test case nomenclature information is Case 3(D); operation is implementation of the OMF method on digital images of the given, selected twelfth sample procured from the given, selected third male subject or volunteer aged 50 years.

FIG. 144A depicts a thirteenth plot of a typical spectral data (or OMF diagram) obtained on implementation of the OMF method on digital images captured from of a given, selected thirteenth sample procured from the given, selected first layer confined to the inner arm region of skin of the given, selected fourth male subject or volunteer aged 43 years, in accordance with certain embodiments of the invention.

In certain such embodiments, a thirteenth test case discloses implementation of the OMF method on digital images captured from the given, selected thirteenth sample procured from the given, selected first layer confined to the inner arm region and existing (or taken into consideration) in the given, selected first state of skin of the given, selected fourth male subject or volunteer aged 43 years. By way of example, and in no way limiting the scope of the invention, the thirteenth sample is the Layer "0", discussed in conjunction with FIG. 139, in the first state (i.e. every day skin surface), confined to the inner arm region of the given, selected fourth male subject or volunteer aged 43 years.

As shown in FIG. 144A, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected thirteenth sample (or Layer "0" every day surface of skin, confined to the inner arm region) analyzed and categorized as Case 4(A) of the given, selected third subject or volunteer subjected to the skin characterization test.

As depicted in FIG. 144A, the thirteenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −40 (n.a.u.*1000) to a maximum of equal to +40 (n.a.u.*1000) (i.e. [−40, +40]); analytical information is analysis of the thirteenth DI plot (or OMF Diagram) of the sample; subject or volunteer information is the given, selected fourth male subject or volunteer aged 43 years; test input sample is the given, selected thirteenth sample procured from the first selected layer (i.e. Layer "0", discussed in conjunction with FIG. 139) in the first state (i.e. every day surface of skin) of skin confined to the inner arm region of the given, selected fourth male subject or volunteer aged 43 years; test case nomenclature information is Case 4(A); operation is implementation of the OMF method on digital images of the given, selected thirteenth sample procured from the given, selected fourth male subject or volunteer aged 43 years.

FIG. 144B depicts a fourteenth plot of a typical spectral data (or OMF diagram) obtained on implementation of the OMF method on digital images captured from of a given, selected fourteenth sample procured from the given, selected second layer confined to the inner arm region of skin of the given, selected fourth male subject or volunteer aged 43 years, in accordance with certain embodiments of the invention.

In certain such embodiments, a fourteenth test case discloses implementation of the OMF method on digital images captured from the given, selected fourteenth sample procured from the given, selected second layer confined to the inner arm region and existing (or taken into consideration) in the given, selected second state of skin of the given, selected fourth male subject or volunteer aged 43 years. By way of example, and in no way limiting the scope of the invention, the fourteenth sample is the Layer "1", discussed in conjunction with FIG. 139, in the second state (i.e. on removal of impurities, surface water, surface oiliness and first stratum corneum cells), of skin confined to the inner arm region of the given, selected fourth male subject or volunteer aged 43 years.

As shown in FIG. 144B, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected fourteenth sample (or Layer "1" on removal of impurities, surface water, surface oiliness and first stratum corneum cells of skin, confined to the inner arm region) analyzed and categorized as Case 4(B) of the given, selected fourth subject or volunteer subjected to the skin characterization test.

As depicted in FIG. 144B, the fourteenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −40 (n.a.u.*1000) to a maximum of equal to +40 (n.a.u.*1000) (i.e. [−40, +40]); analytical information is analysis of the fourteenth DI plot (or OMF Diagram) of the sample; subject or volunteer information is the given, selected fourth male subject or volunteer aged 43 years; test input sample is the given, selected fourteenth sample procured from the second selected layer (i.e. Layer "1", discussed in conjunction with FIG. 139) in the second state (i.e. on removal of impurities, surface water, surface oiliness and first stratum corneum cells) of skin confined to the inner arm region of the given, selected fourth male subject or volunteer aged 43 years; test case nomenclature information is Case 4(B); operation is implementation of the OMF method on digital images of the given, selected fourteenth sample procured from the given, selected fourth male subject or volunteer aged 43 years.

FIG. 144C depicts a fifteenth plot of a typical spectral data (or OMF diagram) obtained on implementation of the OMF method on digital images captured from of a given, selected fifteenth sample procured from the given, selected third layer confined to the inner arm region of skin of the given, selected fourth male subject or volunteer aged 43 years, in accordance with certain embodiments of the invention.

In certain such embodiments, a fifteenth test case discloses implementation of the OMF method on digital images captured from the given, selected fifteenth sample procured from the given, selected third layer confined to the inner arm region and existing (or taken into consideration) in the given, selected third state of skin of the given, selected fourth male subject or volunteer aged 43 years. By way of example, and in no way limiting the scope of the invention, the fourteenth sample is the Layer "2", discussed in conjunction with FIG. 139, in the third state (i.e. on removal of stratum corneum), of skin confined to the inner arm region of the given, selected fourth male subject or volunteer aged 43 years.

As shown in FIG. 144C, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected fifteenth sample (or Layer "2" on removal of stratum corneum) analyzed and categorized as Case 4(C) of the given, selected fourth subject or volunteer subjected to the skin characterization test.

As depicted in FIG. 144C, the fifteenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −30 (n.a.u.*1000) to a maximum of equal to +20 (n.a.u.*1000) (i.e. [−30, +20]); analytical information is analysis of the fifteenth DI plot (or OMF Diagram) of the sample; subject or volunteer information is the given, selected fourth male subject or volunteer aged 43 years; test input sample is the given, selected fifteenth sample procured from the third selected layer (i.e. Layer "2", discussed in conjunction with FIG. 139) in the second state (i.e. on removal of stratum corneum) of skin confined to the inner arm region of the given, selected fourth male subject or volunteer aged 43 years; test case nomenclature information is Case 4(C); operation is implementation of the OMF method on digital images of the given, selected fifteenth sample procured from the given, selected fourth male subject or volunteer aged 43 years.

FIG. 144D depicts a sixteenth plot of a typical spectral data (or OMF diagram) obtained on implementation of the OMF method on digital images captured from of a given, selected sixteenth sample procured from the given, selected fourth layer confined to the inner arm region of skin of the given, selected fourth male subject or volunteer aged 43 years, in accordance with certain embodiments of the invention.

In certain such embodiments, a sixteenth test case discloses implementation of the OMF method on digital images captured from the given, selected sixteenth sample procured from the given, selected fourth layer confined to the inner arm region and existing (or taken into consideration) in the given, selected fourth state of skin of the given, selected fourth male subject or volunteer aged 43 years. By way of example, and in no way limiting the scope of the invention, the sixteenth sample is the Layer "3", discussed in conjunction with FIG. 139, in the fourth state (i.e. on removal of 50% of the cells of stratum *granulosum*), of skin confined to the inner arm region of the given, selected fourth male subject or volunteer aged 43 years.

As shown in FIG. 144D, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected sixteenth sample (or Layer "3" on removal of stratum corneum) analyzed and categorized as Case 4(D) of the given, selected fourth subject or volunteer subjected to the skin characterization test.

As depicted in FIG. 144D, the sixteenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −40 (n.a.u.*1000) to a maximum of equal to +40 (n.a.u.*1000) (i.e. [−40, +40]); analytical information is analysis of the sixteenth DI plot (or OMF Diagram) of the sample; subject or volunteer information is the given, selected fourth male subject or volunteer aged 43 years; test input sample is the given, selected sixteenth sample procured from the fourth selected layer (i.e. Layer "3", discussed in conjunction with FIG. 139) in the fourth state (i.e. on removal of 50% of the cells of stratum *granulosum*) of skin confined to the inner arm region of the given, selected fourth male subject or volunteer aged 43 years; test case nomenclature information is Case 4(D); operation is implementation of the OMF method on digital images of the given, selected sixteenth sample procured from the given, selected fourth male subject or volunteer aged 43 years.

In certain analysis embodiments, a comparative analysis of one or more test cases comprising one or more given, selected samples procured from at least one of a plurality of the given, selected layers, discussed in conjunction with FIG. 139, confined to the inner arm region of skin of the given, selected one or more male subjects or volunteers aged 11-63 years is disclosed, in accordance with the principles of the invention. By way of example, and in no way limiting the scope of the invention, in such analysis embodiments, the comparative analysis of four test samples procured from the given, selected third layer (i.e. Layer "2"), discussed in conjunction with FIG. 139, confined to the inner arm region of skin of the given, selected four male subjects or volunteers aged 11-63 years, namely the first male subject aged 11, second male subject aged 63, third male subject aged 50 and fourth male subject aged 43, in that order, is disclosed in accordance with the principles of the invention. Specifically, in the third layer (or Layer "2") the skin holds water in water-lipid layers difference was observed for all the aforementioned volunteers who drank or consumed both the N-water and Z-water, as depicted in FIGS. 146A-D.

FIG. 146A depicts a seventeenth plot of a typical spectral data (or OMF diagram) obtained on implementation of the OMF method on digital images captured from of a given, selected seventeenth sample procured from the given, selected third layer confined to the inner arm region of skin of the given, selected first male subject or volunteer aged 11 years, in accordance with certain embodiments of the invention.

In certain such embodiments, a seventeenth test case discloses implementation of the OMF method on digital images captured from the given, selected seventeenth sample procured from the given, selected third layer confined to the inner arm region and existing (or taken into consideration) in a given, selected fifth state of skin of the given, selected first male subject or volunteer aged 11 years. By way of example, and in no way limiting the scope of the invention, the seventeenth sample is the Layer "2", discussed in conjunction with FIG. 139, in the fifth state (i.e. on removal of 100% of stratum corneum and 20% of the cells of stratum *granulosum*), of skin confined to the inner arm region of the given, selected first male subject or volunteer aged 11 years.

As shown in FIG. 146A, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected seventeenth sample (or Layer "2" on removal of 100% of stratum corneum and 20% of the cells of stratum *granulosum*) analyzed and categorized as Case 5(A) of the given, selected first subject or volunteer subjected to the skin characterization test.

As depicted in FIG. 146A, the seventeenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −60 (n.a.u.*1000) to a maximum of equal to +40 (n.a.u.*1000) (i.e. [−60, +40]); analytical information is analysis of the seventeenth DI plot (or OMF Diagram) of the sample; subject or volunteer information is the given, selected first male subject or volunteer aged 11 years; test input sample is the given, selected seventeenth sample procured from the third selected layer (i.e. Layer "2", discussed in conjunction with FIG. 139) in the fifth state (i.e. on removal of 100% of stratum corneum and 20% of the cells of stratum *granulosum*) of skin confined to the inner arm region of the given, selected first male subject or volunteer aged 11 years, who consumed the N-water for all time (or continuously); test case nomenclature information is Case 5(A); operation is implementation of the OMF method on digital images of the given, selected seventeenth sample procured from the given, selected first male subject or volunteer aged 11 years; observation window interval is from a minimum of approximately 120 nm and a maximum of approximately 130 nm (or [120, 130]); number of upward (or positive) trending wavelength difference peaks (or extrema or maxima and minima) is 1 and identifier for the upward trending peak is first 14600A, in that order.

FIG. 146B depicts an eighteenth plot of a typical spectral data (or OMF diagram) obtained on implementation of the OMF method on digital images captured from of a given, selected eighteenth sample procured from the given, selected third layer confined to the inner arm region of skin of the given, selected second male subject or volunteer aged 63 years, in accordance with certain embodiments of the invention.

In certain such embodiments, an eighteenth test case discloses implementation of the OMF method on digital images captured from the given, selected eighteenth sample procured from the given, selected third layer confined to the inner arm region and existing in a given, selected fifth state of skin of the given, selected second male subject or volunteer aged 63 years. By way of example, and in no way limiting the scope of the invention, the eighteenth sample is the Layer "2", discussed in conjunction with FIG. 139, in the fifth state (i.e. on removal of 100% of stratum corneum and 20% of the cells of stratum *granulosum*), of skin confined to the inner arm region of the given, selected second male subject or volunteer aged 63 years.

As shown in FIG. 146B, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected eighteenth sample (or Layer "2" on removal of 100% of stratum corneum and 20% of the cells of stratum *granulosum*) analyzed and categorized as Case 5(B) of the given, selected second subject or volunteer subjected to the skin characterization test.

As depicted in FIG. 146B, the eighteenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to $-100$ (n.a.u.*1000) to a maximum of equal to $+100$ (n.a.u.*1000) (i.e. $[-100, +100]$); analytical information is analysis of the eighteenth DI plot (or OMF Diagram) of the sample; subject or volunteer information is the given, selected second male subject or volunteer aged 63 years; test input sample is the given, selected eighteenth sample procured from the third selected layer (i.e. Layer "2", discussed in conjunction with FIG. 139) in the fifth state (i.e. on removal of 100% of stratum corneum and 20% of the cells of stratum *granulosum*) of skin confined to the inner arm region of the given, selected second male subject or volunteer aged 63 years, who consumed the N-water for all time (or continually); test case nomenclature information is Case 5(B); operation is implementation of the OMF method on digital images of the given, selected seventeenth sample procured from the given, selected second male subject or volunteer aged 63 years; observation window interval is from a minimum of approximately 120 nm and a maximum of approximately 130 nm (or [120, 130]); number of upward (or positive) trending wavelength difference peaks (or extrema or maxima and minima) is 1 and identifier for the upward trending peak is second 14600B, in that order.

FIG. 146C depicts an nineteenth plot of a typical spectral data (or OMF diagram) obtained on implementation of the OMF method on digital images captured from of a given, selected nineteenth sample procured from the given, selected third layer confined to the inner arm region of skin of the given, selected third male subject or volunteer aged 50 years, in accordance with certain embodiments of the invention.

In certain such embodiments, a nineteenth test case discloses implementation of the OMF method on digital images captured from the given, selected eighteenth sample procured from the given, selected third layer confined to the inner arm region and existing in a given, selected fifth state of skin of the given, selected third male subject or volunteer aged 50 years. By way of example, and in no way limiting the scope of the invention, the eighteenth sample is the Layer "2", discussed in conjunction with FIG. 139, in the fifth state (i.e. on removal of 100% of stratum corneum and 20% of the cells of stratum *granulosum*), of skin confined to the inner arm region of the given, selected third male subject or volunteer aged 50 years.

As shown in FIG. 146C, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected nineteenth sample (or Layer "2" on removal of 100% of stratum corneum and 20% of the cells of stratum *granulosum*) analyzed and categorized as Case 5(C) of the given, selected third subject or volunteer subjected to the skin characterization test.

As depicted in FIG. 146C, the nineteenth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to $-60$ (n.a.u.*1000) to a maximum of equal to $+40$ (n.a.u.*1000) (i.e. $[-60, +40]$); analytical information is analysis of the nineteenth DI plot (or OMF Diagram) of the sample; subject or volunteer information is the given, selected third male subject or volunteer aged 50 years; test input sample is the given, selected nineteenth sample procured from the third selected layer (i.e. Layer "2", discussed in conjunction with FIG. 139) in the fifth state (i.e. on removal of 100% of stratum corneum and 20% of the cells of stratum *granulosum*) of skin confined to the inner arm region of the given, selected third male subject or volunteer aged 50 years, who changed from the Z-water to the N-water for two months; test case nomenclature information is Case 5(C); operation is implementation of the OMF method on digital images of the given, selected seventeenth sample procured from the given, selected third male subject or volunteer aged 50 years; observation window interval is from a minimum of approximately 120 nm and a maximum of approximately 130 nm (or [120, 130]); number of moderately (or partially) upward and downward trending wavelength difference peaks (or extrema or maxima and minima) is 1 and identifier for the upward trending peak is third 14600C, in that order.

FIG. 146D depicts a twentieth plot of a typical spectral data (or OMF diagram) obtained on implementation of the OMF method on digital images captured from of a given, selected twentieth sample procured from the given, selected third layer confined to the inner arm region of skin of the given, selected fourth male subject or volunteer aged 43 years, in accordance with certain embodiments of the invention.

In certain such embodiments, a twentieth test case discloses implementation of the OMF method on digital images captured from the given, selected twentieth sample procured from the given, selected third layer confined to the inner arm region and existing in a given, selected fifth state of skin of the given, selected fourth male subject or volunteer aged 43 years. By way of example, and in no way limiting the scope of the invention, the eighteenth sample is the Layer "2", discussed in conjunction with FIG. 139, in the fifth state (i.e. on removal of 100% of stratum corneum and 20% of the cells of stratum *granulosum*), of skin confined to the inner arm region of the given, selected fourth male subject or volunteer aged 43 years.

As shown in FIG. 146D, the 2D coordinate system is in essence a Wavelength Difference Versus Intensity plot (or DI plot or OMF diagram) obtained on plotting a plurality of DI ordered pairs. Each of the plurality of ordered pairs includes a Wavelength Difference value and a corresponding Intensity value. It must be noted here that the plurality of ordered pairs are obtained on processing the digital image of the sample, captured using diffuse white light and reflected polarized light, using the OMF method. Specifically, the OMF method implements the SCA and CAA to analyze the processed digital image of the sample. Further, the sample is the given, selected twentieth sample (or Layer "2" on removal of 100% of stratum corneum and 20% of the cells of stratum *granulosum*) analyzed and categorized as Case 5(D) of the given, selected fourth subject or volunteer subjected to the skin characterization test.

As depicted in FIG. 146D, the twentieth DI plot possesses the following specifications and associated analytical and sample information thereof: ordered (or DI) pair is (Wavelength Difference Value, Intensity Value); horizontal X-axis includes a closed interval of Wavelength Difference Values ranging from a minimum of equal to 100 nanometers (nm) to a maximum of equal to 200 nanometers (nm) (or [100, 200]); vertical Y-axis includes a closed interval of Intensity Values ranging from a minimum of equal to −30 (n.a.u.*1000) to a maximum of equal to +20 (n.a.u.*1000) (i.e. [−30, +20]); analytical information is analysis of the nineteenth DI plot (or OMF Diagram) of the sample; subject or volunteer information is the given, selected third male subject or volunteer aged 43 years; test input sample is the given, selected twentieth sample procured from the third selected layer (i.e. Layer "2", discussed in conjunction with FIG. 139) in the fifth state (i.e. on removal of 100% of stratum corneum and 20% of the cells of stratum *granulosum*) of skin confined to the inner arm region of the given, selected fourth male subject or volunteer aged 43 years, who is drinking the Z-water all the time (or continuously); test case nomenclature information is Case 5(D); operation is implementation of the OMF method on digital images of the given, selected twentieth sample procured from the given, selected fourth male subject or volunteer aged 43 years; observation window interval is from a minimum of approximately 120 nm and a maximum of approximately 130 nm (or [120, 130]); number of downward (or negative) trending wavelength difference peaks (or extrema or maxima and minima) is 1 and identifier for the upward trending peak is fourth 14600D, in that order.

Reiterating again, as shown and discussed in conjunction with FIGS. 146A-D, in such certain analysis embodiments, the comparative analysis of the four test samples procured from the given, selected third layer (i.e. Layer "2"), discussed in conjunction with FIG. 139, confined to the inner arm region of skin of the given, selected four male subjects or volunteers aged 11-63 years exhibits difference for one or more volunteers, who drank the N-type and Z-type waters. Specifically, as shown in FIGS. 146A-B, the pair of peaks of wavelength difference, namely 14600A and 14600B, in the observation window interval ranging from a minimum of approximately 120 nm and a maximum of approximately 130 nm (or [120, 130]) exhibits upward (or positive) trending wavelength difference peaks (or extrema or maxima and minima) in the seventeenth and eighteenth spectral data plots. More specifically, the seventeenth and eighteenth spectral data plots were obtained on implementation of the OMF method on digital images captured from the corresponding given, selected seventeenth and eighteenth samples procured from the given, selected third layer confined to the inner arm region of skin of the given, selected first and second male subjects or volunteers aged 11 and 63 years. Still, more specifically, the given, selected first and second male subjects or volunteers aged 11 and 63 years continually drank the N-water.

Further, as shown and discussed in conjunction with FIG. 146C, in such certain analysis embodiments, the peaks of wavelength difference in the observation window interval ranging from a minimum of approximately 120 nm and a maximum of approximately 130 nm (or [120, 130]) exhibits moderately (or partially) upward and downward trending wavelength difference peaks (or extrema or maxima and minima), namely 14600C and 14602C, in the nineteenth spectral data plot. More specifically, the nineteenth spectral data plot was obtained on implementation of the OMF method on digital images captured from the corresponding given, selected nineteenth sample procured from the given, selected third layer confined to the inner arm region of skin of the given, selected third subject or volunteer aged 50 years. Still, more specifically, the given, selected third subject or volunteer aged 50 years changed the type of drinking water for two months from the Z-water to the N-water.

Still further, as shown and discussed in conjunction with FIG. 146D, in such certain analysis embodiments, the peak of wavelength difference in the observation window interval ranging from a minimum of approximately 120 nm and a maximum of approximately 130 nm (or [120, 130]) exhibits downward (or negative) trending wavelength difference peak (or extrema or maxima and minima), namely 14600D, in the twentieth spectral data plot. More specifically, the twentieth spectral data plot was obtained on implementation of the OMF method on digital images captured from the corresponding given, selected twentieth sample procured from the given, selected third layer confined to the inner arm region of skin of the given, selected fourth subject or volunteer aged 43 years. Still, more specifically, the given, selected third subject or volunteer aged 43 years continually drank the Z-water.

Peak of wavelength difference between 120 nm and 130 nm goes up, as shown in FIGS. 143A-B, whereas peak goes up and than down for those volunteers who changed type of drinking water for two months from Z- to N-type, as shown in FIG. 143C. However, in case of volunteers who drank Z-type water all time (or throughout) peak goes down. This is shown in FIG. 142D. For the same group of drinking water (except for age 11) bioimpedance shows small difference for all volunteers for Layers "0" and "1", while for Layers "2" and "3" show significant difference for water type N and Z (Case 3—change drinking water from Z to N, and Case 4—all time drinking water Z).

Yet, in certain embodiments, a comparative analysis of samples procured from the first male volunteer aged 11 years vis-à-vis second aged 63 years based on bioimpedance measurements show difference of skin layers for young skin (i.e. skin of the first male volunteer aged 11) and old skin (i.e. skin of the second male volunteer aged 63). Specifically, the old skin (i.e. age 63) does not hold water in epidermis well. As shown in FIGS. 146A-B, a comparative analysis of samples procured from the first male volunteer aged 11 years vis-à-vis second aged 63 years shows a difference in stratum *granulosum* layer that is dramatically significant. Specifically, the young skin, age 11, holds water well in all epidermal layers. However, on skin surface, impedance is approximately the same for the young and old skin. Still however, the difference becomes obvious for stratum corneum, because this layer contents 8% of all water in epidermis. Eventually, these results indicate role of a single gel phase in stratum corneum, as disclosed in Norlen, L. J., Invest Dermatol. 117, 830-836, 2001. The gel phase domains could support barrier function, whereas the continuous liquid crystalline domain could provide the flexibility necessary for pliable skin, as disclosed in Bouwstra, J. A., J. Lipid Res., 42, 1759-1765, 2001.

Typically, an important function of the skin is protection against the loss of water. Transepidermal Water Loss (or TWL or TEWL) is process of passive diffusion through the skin. Specifically, the horny layer is the most important rate-limiting step for the transport of the water to the exterior. More specifically, the unique organization of the hydrophilic cells within the lipid, hydrophobic environment makes this 10- to 20 µm thick layer extremely efficient as a barrier.

Further, presently there is evidence that water amount in epidermis is reduced in aged individuals compared with TEWL values from mid-adulthood, as disclosed in Gilchrest, B. A., J. Am Acad. Dermatol., 21, 610–618, 1989. Thus, it was found that significant difference of water presence is in stratum *granulosum*, as seen in FIG. 12. With reference to FIG. 9, it can be seen that stratum corneum has also water-holding capacity (Layer 1: Case 1 and Case 2).

FIG. 147 depicts a graphical representation of bioimpedance versus skin layers obtained on implementation of bioimpedance measurements on one or more samples procured from corresponding one or more layers confined to the inner arm region of skin of the given, selected first and second male subjects aged 11 and 63 years, in accordance with certain embodiments of the invention.

In certain such embodiments, a twenty-first test case discloses implementation of the bioimpedance measurements on one or more samples procured from corresponding one or more layers confined to the inner arm region and existing in a given, selected sixth state of skin of the given, selected first and second male subjects aged 11 and 63 years. By way of example, and in no way limiting the scope of the invention, the twenty-first test case is based on one or more given, selected criterion, samples, layers and states thereof analogous to the one or more test cases discussed as the first, second, fifth and sixth test cases, namely Case 1(A), Case (1B), Case 2(A) and Case 2(B), in that order, delineated in conjunction with FIGS. 141A-B and 142A-B. Further, the one or more samples are the first and second layers, i.e. Layers "0" and "1", discussed in conjunction with FIG. 139, in the sixth state (i.e. on removal of 100% of stratum corneum and 30% of the cells of stratum *granulosum*), of skin confined to the inner arm region of the given, selected first and second male subjects or volunteers aged 11 and 63 years.

By way of example, and in no way limiting the scope of the invention, in such certain embodiments, the frequency selected for bioimpedance measurements is 100 KHz for the first and second layers, i.e. Layers "0" and "1", discussed in conjunction with FIG. 139, in the sixth state (i.e. on removal of 100% of stratum corneum and 30% of the cells of stratum *granulosum*) of skin confined to the inner arm region of the given, selected first and second male subjects or volunteers aged 11 and 63 years.

As shown in FIG. 147, the 2D coordinate system is in essence an Impedance Versus Skin Layer plot obtained on plotting a plurality of (Impedance, Skin Layer) ordered pairs. Each of the plurality of ordered pairs includes an Impedance value and a Skin Layer value. It must be noted here that the plurality of ordered pairs are obtained on implementation of bioimpedance measurements on the samples procured from the layers, discussed in conjunction with FIG. 139, of skin existing in the sixth state and confined to inner arm region of the first and second male subjects or volunteers aged 11 and 63 years. Further, the samples are procured from the layers, discussed in conjunction with FIG. 139, existing in the sixth state, i.e. on removal of 100% of stratum corneum and 30% of the cells of stratum *granulosum*, analyzed and categorized as Case 6 of the given, selected first and second male subjects or volunteers subjected to the skin characterization test.

As depicted in FIG. 147, the Impedance Versus Skin Layer plot possesses the following specifications and associated analytical and sample information thereof: ordered pair is (Impedance, Skin Layer); horizontal X-axis includes a set of discrete Skin Layer Values, namely "first layer or Layer "0"," "second layer or Layer "1"," "third layer or Layer "2"" and "fourth layer or "Layer "3"", discussed in conjunction with FIG. 35; vertical Y-axis includes a closed interval of Impedance Values ranging from a minimum of equal to +0 (Ohm) to a maximum of equal to +8000 (Ohm) (i.e. [−0, +8000]); analytical information is analysis of the Impedance Versus Skin Layer plot using the samples; subject or volunteer information is the given, selected first and second male subjects or volunteers aged 11 and 63 years; test input sample is the given, selected one or more samples procured from the all the layers (i.e. the "first layer or Layer "0"," "second layer or Layer "1"," "third layer or Layer "2"" and "fourth layer or "Layer "3"", discussed in conjunction with FIG. 139) in the sixth state (i.e. on removal of 100% of stratum corneum and 30% of the cells of stratum *granulosum*) of skin confined to the inner arm region of the given, selected first and second male subjects or volunteers aged 11 and 63 years; test case nomenclature information is Case 6; operation is implementation of the bioimpedance measurements on the given, selected samples procured from the given, selected first and second fourth male subjects or volunteers aged 11 and 63 years and frequency selected for bioimpedance measurements is 100 KHz, in that order.

Further, as shown in FIG. 147, a significant difference of bioimpedance is found out when complete stratum corneum and about 30% of cells of stratum *granulosum* were removed by adhesive bandage. This outcome is the same as found out by OMF spectra for region of wavelength difference, as discussed in conjunction with FIGS. 139 and 140. In general, old skin (age 63) does not hold water in epidermis well, and in particularly in stratum *granulosum* layer. However, young skin of age 11 is much better order and holds water well in all epidermal layers.

FIG. 145 depicts a three-dimensional (or 3-D) Atomic Force Microscopy (or AFM) image of skin on removal of the Layer "3", in accordance with certain embodiments of the invention.

Removed layer thickness for inner arm (i.e. Case 4(A)-(D)) is 4.92 µm (maximum thickness for layer 1 was 10.2 µm, while the min. was 4.2 µm for layer 0). Maximum removed thickness of all four layers for inner arm and forehead is 36.2 µm and 52.8 µm, while minimum is 30.4 µm and 43.6 µm, respectively.

Electrical Bioimpedance Monitoring is an emerging tool for biomedical research and medical practice. Electrical methods for measuring skin hydration have been studied for several decades and a low frequency susceptance method has proved to be the most appropriate. On the other hand, fractional calculus is not often used to model biological systems.

In general, the impedance of the skin is dominated by the stratum corneum at low frequencies. It has generally been stated that skin impedance is determined mainly by the stratum corneum at frequencies below 10 kHz and by the viable skin at higher frequencies. This may be dependent on one or more factors including, but not limited to, skin hydration, electrode size, and geometry. However, these factors may serve as a rough guideline. The Cole-Cole (Cole) equation has been found suitable for modeling most electrical measurements on biological tissue, including skin. However, the impact of the skin hydration by layers to bioelectrical properties is not fully tested.

Thus, in certain experimental embodiments, the underlying rationale behind the research and analysis, in accordance with the principles of the invention, is a generalized Cole equation. It is obtained by applying the new method in fractional calculus. In such embodiments, the fractional model presents the generalized continuous Cole model, which may predict structural-functional parameters as a lot of Cole relaxation times. These relaxation time constants correspond to structural-functional characteristics of the skin layers. The new continuous one-Cole model, disclosed in accordance with the principles of the invention, better describes electrical behavior of human skin. By way of example, and in no way limiting the scope of the invention, some of these features are dielectric properties of skin, fractality of structure, water content thereof etc.

In certain specific embodiments, usage and implementation of non-invasive applied techniques contribute to better characterization of any tissue or the appropriate biomaterial thereby facilitating a basis for the development of new technologies in various fields of Bioengineering.

In general, the Bioelectro-physical properties of human skin tissue, like most other soft tissues, exhibits electroviscoelastic behavior. In order to obtain complete information about the electroviscoelastic behavior of human skin, it is also necessary to have experimental data over a wide range of time scales.

Further, in operation, application of electricity from an external source outside the living organism facilitates measurement of bio-impedance. Still further, in order to analyze skin impedance effectively it is desirable to introduce the skin impedance model. In addition, the complex modulus concept is a powerful and widely used tool for characterizing the electroviscoelastic behavior of materials in the frequency domain. In certain specific embodiments, bioimpedance moduli are regarded as complex quantities, in accordance with the principles of the invention.

In the Bio Impedance Spectrometry (or BIS) technique, impedance measurements are done at each frequency and then plotted forming a circular arc. Using electrical engineering modeling mathematics, the points on a circular arc are transformed into an equivalent electrical model where the values correspond to specific compositional elements. Also, from mathematical point of view, the fractional integro-differential operators (or fractional calculus) are a generalization of integration and derivation to non-integer order (fractional) operators.

On the other hand, in certain embodiments, a given memory function equation, scaling relationships and structural-fractal behavior of biomaterials and a mathematical model based on fractional calculus are used for the physical interpretation of the Cole-Cole exponents. In addition, it is well-known, three expressions, such as Cole-Cole function, Cole-Davidson function and Havriliak-Negami function, for the impedance facilitates description of a wide range of experimental data.

In general, skin is usually observed as a simple structure. However, the equivalent electrical model of skin does not include tissue lamination. In certain specific embodiments, the skin structure is proposed as a more complex system comprising several layers, wherein each of the layers represents a simple structure. In such embodiments, the mathematical model of skin structure is obtained by applying fractional calculus, which describes series of structures via novel generalization of the Cole-Cole equation. In accordance with the proposed model and experimental data of the skin bioimpedance measurements, a more complex equivalent electrical circuit is predicted thereby facilitating definition of new mathematical parameters, which correspond to each individual layer.

In certain embodiments, methods for skin hydration assessment based on the utilization of bioimpedance and fractional calculus and systems and apparatuses facilitating implementation of such methods are disclosed. Stated differently, in certain such embodiments, systems and apparatuses for practicing the principles of the invention are disclosed. More specifically, the systems and apparatuses facilitate implementation of a method for skin hydration assessment based on the utilization of bioimpedance and fractional calculus with enhanced qualitative and quantitative parameters. Still more specifically, the systems and apparatuses facilitate implementation of a method for skin hydration assessment based on the utilization of bioimpedance and fractional calculus with enhanced qualitative and quantitative parameters, novel, enhanced and easy interpretability, enhanced and easy detectability, enhanced sensitivity, enhanced specificity, enhanced efficiency, greater accuracy, easily operable, rapid, economical, precise, timely and minute variation sensitive.

FIG. 148 is a block diagrammatic view of a system facilitating implementation of a process using a pair of electrodes for measurement of skin impedance, designed and implemented in accordance with certain embodiments of the invention.

System 14800 is in essence a Skin Impedance Assessment System (or SIAS). The SIAS 14800 includes a voltage generator subsystem 14802, an electrode subsystem 14804, an impedance measurement subsystem 14806 and a host computing subsystem 14808.

SIAS 14800, by virtue of its design and implementation, facilitates execution of a process based on utilization of bioimpedance and fractional calculus for skin hydration assessment. Specifically, the SIAS 14800 facilitates measurement of skin impedance through utilization of one or more electrodes in conjunction with constant amplitude sinusoidal voltage source.

Voltage generator subsystem 14802 may be one or more sinusoidal voltage generation sources.

Voltage generator subsystem 14802 may be adapted to generate sinusoidal voltage of constant amplitude.

As shown in the FIG. 148, in certain embodiments, the voltage generator subsystem 14802 may be coupled to the electrode subsystem 14804.

As shown in the FIG. 148, the electrode subsystem 14804 may in essence be a device used to develop contact with skin and conduct electrical signals thereof. In certain embodiments, the electrode subsystem 14804 captures continuous digital images of water samples. Specifically, in such embodiments, the sensor subsystem 14804 captures continuous digital images of the water samples illuminated with white light both, non-angled and angled. By way of, and by no way of limitation, the electrode subsystem 14804 may possess the following specifications: material is stainless steel; diameter is 2.0 cm; number of electrodes is 2; inter-electrode distance is 5.0 cm; electrode paste is EC33 skin resistance or conductance electrode paste.

As used in general, the term "Carbon-Paste Electrode (or CPE)" refers to electrodes made from a mixture of conducting graphite powder and a pasting liquid. These electrodes are simple to make and offer an easily renewable surface for electron exchange. Carbon paste electrodes belong to a special group of heterogeneous carbon electrodes. These electrodes are widely used mainly for voltammetric measurements; however, carbon paste-based sensors are also applicable in coulometry (both amperometry and potentiometry).

As shown in FIG. 148, the impedance measurement subsystem 14806 may be coupled to the voltage generator subsystem 14802, electrode subsystem 14804, and host computing subsystem 14808.

Further, as shown in FIG. 148, the impedance measurement subsystem 14806 may include a Frequency Response Analyzer (or FRA) 14806A and at least one of a Potentiostat (or Pstat) and a Galvanostat (or Gstat) 14806B respectively.

As used in general, the term "Galvanostat or Gstat" refers to a control and measuring device capable of keeping the current through an electrolytic cell in coulometric titrations constant, disregarding changes in the load itself. A synonym is "amperostat". Its main feature is nearly "infinite" (i.e. extremely high respect to common loads) internal resistance.

Likewise, the term "Potentiostat or Pstat" refers to the electronic hardware required to control a three-electrode cell and run most electroanalytical experiments. For example, bipotentiostat and polypotentiostat are potentiostats capable of controlling at least a pair of working electrodes.

In operation, the potentiostat system functions by maintaining the potential of the working electrode at a constant level with respect to the reference electrode by adjusting the current at an auxiliary electrode. It consists of an electric circuit, which is usually described in terms of simple Operational Amplifiers (or OPAMPS).

In certain embodiments, in operation, the impedance measurement subsystem 14806 measures the components of impedance and characteristic frequency of the skin in a given frequency range. In certain specific embodiments, the FRA 14806A and the Pstat/Gstat 14806B jointly measure the components of impedance and characteristic frequency of the skin in the given frequency range. In such embodiments, the FRA 14806A and the Pstat/Gstat 14806B jointly measure the components of impedance and characteristic frequency of the skin at a plurality of different frequencies between the given frequency range at a given applied voltage of a given amplitude supplied by the voltage generator subsystem 14802.

By way of example, and in no way limiting the scope of the invention, the impedance measurement subsystem 14806 may include the FRA 14806A, which is in essence a Solartron 1255, used in conjunction with the Pstat/Gstat 14806B, which is in essence a Solartron 1286.

In certain embodiments, the impedance measurement subsystem 14806 may possesses the following specifications: the FRA 14806A is the Solartron 1255; Pstat/Gstat 4306B is the Solartron 1286 Pstat/Gstat; operational configuration is the FRA 4306A is used in combination with the Pstat/Gstat 4306B; measurement input frequency range is 0.1 Hz to 100.0 KHz; number of distinct input frequencies in the measurement input frequency range is 61; amplitude of the applied voltage is 0.1 V.

In certain experimental embodiments, a mathematical model in connection with skin structure based on a generalized Cole equation, designed and implemented in accordance with the principles of the invention is disclosed. In certain such embodiments, the fractional mathematical model for the skin structure for use in skin hydration measurements is obtained by application of fractional calculus. Specifically, the fractional mathematical model provides for the generalized continuous Cole model, which may predict one or more structural-functional parameters as a lot of Cole relaxation times. Further, these relaxation time constants correspond to structural-functional characteristics of the skin layers. More specifically, the generalized continuous one-Cole model, disclosed here, provides an enhanced illustration of the electrical behavior of human skin. For example, some of the parameters illustrated in connection with the electrical behavior of human skin are the dielectric properties, fractality of structure, water content thereof etc.

In certain example embodiments, a continuous fractional derivative model in connection with a human skin is discussed, in accordance with the principles of the invention. In such embodiments, in light of the continuous fractional derivative model some basic outcomes in connection with bioimpedance of human skin are discussed. It must be noted here that the capacitive component of the polarization admittance is the proper electrical component to monitor the material as an insulator or semiconductor. Further, the electrical impedance method is used as a quantitative technique for evaluating changes in the skin. Still further, dielectric information, in general, may be presented in a number of equivalent ways but it is important to use the most appropriate form of presentation to suit particular requirements. By way of example and in no way limiting the scope of the invention, the continuous fractional derivative model in connection with bioimpedance of human skin has been disclosed in a book by A. K. Jonscher, entitled Universal Relaxation Law (published by Chelsea Dielectrics Press, in London, in 1996), the disclosure of which is partially incorporated herein by reference. Thus, all remaining ins-and-outs in connection with the continuous fractional derivative model in connection with bioimpedance of human skin will not be further detailed herein.

In such example embodiments, the following dielectric functions, namely the complex permittivity $\varepsilon^*(\omega)$ and the susceptibility $\chi^*(\omega)$, may be defined through the following Equation 1:

$$\chi^*(\omega)=[\varepsilon^*(\omega)-\varepsilon_\infty]/\varepsilon_0=\chi'(\omega)-j\chi''(\omega), j^2=-1 \quad \text{Equation 1,}$$

where $\varepsilon 0$ is the permittivity of free space, and $\varepsilon\infty$ is a suitable high-frequency permittivity contributing to the real and imaginary components of the polarization.

Based on the above defined dielectric functions, Debye, Cole-Cole, Cole-Davidson and Havriliak-Negami functions are presented in Equation 2 below:

$$\chi^*(\omega)|_D = \frac{\chi_0}{1+j\omega/\omega_p},$$
$$\chi^*(\omega)|_{C-C} = \frac{\chi_0}{1+(j\omega/\omega_p)^\alpha},$$
$$\chi^*(\omega)|_{C-D} = \frac{\chi_0}{(1+j\omega/\omega_p)^\nu},$$
$$\chi^*(\omega)|_{G-N} = \frac{\chi_0}{(1+(j\omega/\omega_p)^\alpha)^\nu},$$

Equation 2 where $\chi_0$ is constant, $\omega_p=1/\tau$ is the loss peak frequency and r denotes characteristic damped time $0<\alpha$, $\nu \le 1$.

Further, in such example embodiments, the experimental data show that the terms $\alpha$ and $\nu$ are strictly dependent on one or more qualitative and quantitative parameters, such as temperature, structure, composition and other controlled physical parameters, as disclosed in the book by A. K.

Jonscher, entitled Universal Relaxation Law (published by Chelsea Dielectrics Press, in London, in 1996). However, until recently the reasons underlying such dependencies on the aforementioned parameters have not been clear, as disclosed in the art in a book by B. K. P. Scaife, entitled Principles of Dielectrics (published by Oxford University Press, in Oxford, in 1989), the disclosure of which is partially incorporated herein by reference. In here, the α and v were discussed as the parameters of the distribution of the relaxation times or mentioned as broadening parameters without further discussion.

Still further, in such example embodiments, the for a given value α=1 in the Cole-Cole function the Debye function, as shown in Equation 2, can be obtained. Thus, the Cole-Cole equation described by means of permittivity [9]) is provided in Equation 3 below:

$$\varepsilon^* = \varepsilon_\infty + \frac{\varepsilon_S - \varepsilon_\infty}{1 + (j \cdot \omega \cdot \tau)^\alpha}, \qquad \text{Equation 3}$$

where $\varepsilon_s$ is the static permittivity of material. This has been disclosed in the art in a book by Markus Haschka and Volker Krebs, entitled A Direct Approximation of Fractional Cole-Cole Systems by Ordinary First-order Processes in Advances in Fractional Calculus Theoretical Developments and Applications in Physics and Engineering, edited by J. Sabatier, O. P. Agrawal and J. A. Tenreiro Machado, Springer, 2007, 257-270, the disclosure of which is partially incorporated herein by reference.

Further, the Cole impedance model is introduced in final form by introducing a Constant Phase Element (or CPE), as disclosed in the art in a non-patent literature by Cole K. S., entitled Permeability and Impermeability of Cell Membranes for Ions, Cold Spring Harbor Symposium, Quant. Biol. 1940, 8, 110–122, the disclosure of which is partially incorporated herein by reference.

FIG. 149 depicts an equivalent circuit Cole model for calculation of the electrical impedance of the skin, in accordance with the prior art and adapted therefrom.

In certain example embodiments, a continuous fractional derivative model in connection with a human skin is discussed, in accordance with the principles of the invention. In such embodiments, in light of the continuous fractional derivative model some basic outcomes in connection with bioimpedance of human skin are discussed. It must be noted here that the capacitive component of the polarization admittance is the proper electrical component to monitor the material as an insulator or semiconductor. Further, the electrical impedance method is used as a quantitative technique for evaluating changes in the skin. Still further, dielectric information, in general, may be presented in a number of equivalent ways but it is important to use the most appropriate form of presentation to suit particular requirements. By way of example and in no way limiting the scope of the invention, the continuous fractional derivative model in connection with bioimpedance of human skin has been disclosed in a book by A. K. Jonscher, entitled Universal Relaxation Law (published by Chelsea Dielectrics Press, in London, in 1996), the disclosure of which is partially incorporated herein by reference. Thus, all remaining ins-and-outs in connection with the continuous fractional derivative model in connection with bioimpedance of human skin will not be further detailed herein.

In such example embodiments, the following dielectric functions, namely the complex permittivity $\varepsilon^*(\omega)$ and the susceptibility $\chi^*(\omega)$, may be defined through the following Equation 1:

$$\chi^*(\omega) = [\varepsilon^*(\omega) - \varepsilon_\infty]/\varepsilon_0 = \chi'(\omega) - j\chi''(\omega), \ j^2 = -1 \qquad \text{Equation 1,}$$

where ε0 is the permittivity of free space, and ε∞ is a suitable high-frequency permittivity contributing to the real and imaginary components of the polarization.

Based on the above defined dielectric functions, Debye, Cole-Cole, Cole-Davidson and Havriliak-Negami functions are presented in Equation 2 below:

$$\begin{aligned}\chi^*(\omega)|_D &= \frac{\chi_0}{1 + j\omega/\omega_p},\\ \chi^*(\omega)|_{C-C} &= \frac{\chi_0}{1 + (j\omega/\omega_p)^\alpha},\\ \chi^*(\omega)|_{C-D} &= \frac{\chi_0}{(1 + j\omega/\omega_p)^\nu},\\ \chi^*(\omega)|_{G-N} &= \frac{\chi_0}{(1 + (j\omega/\omega_p)^\alpha)^\nu},\end{aligned} \qquad \text{Equation 2}$$

where $\chi_0$ is constant, $\omega_p = 1/\tau$ is the loss peak frequency and τ denotes characteristic damped time $0 < \alpha, \nu \le 1$.

Further, in such example embodiments, the experimental data show that the terms α and v are strictly dependent on one or more qualitative and quantitative parameters, such as temperature, structure, composition and other controlled physical parameters, as disclosed in the book by A. K. Jonscher, entitled Universal Relaxation Law (published by Chelsea Dielectrics Press, in London, in 1996). However, until recently the reasons underlying such dependencies on the aforementioned parameters have not been clear, as disclosed in the art in a book by B. K. P. Scaife, entitled Principles of Dielectrics (published by Oxford University Press, in Oxford, in 1989), the disclosure of which is partially incorporated herein by reference. In here, the α and v were discussed as the parameters of the distribution of the relaxation times or mentioned as broadening parameters without further discussion.

Still further, in such example embodiments, the for a given value α=1 in the Cole-Cole function the Debye function, as shown in Equation 2, can be obtained. Thus, the Cole-Cole equation described by means of permittivity [9]) is provided in Equation 3 below:

$$\varepsilon^* = \varepsilon_\infty + \frac{\varepsilon_S - \varepsilon_\infty}{1 + (j \cdot \omega \cdot \tau)^\alpha}, \qquad \text{Equation 3}$$

where $\varepsilon_s$ is the static permittivity of material. This has been disclosed in the art in a book by Markus Haschka and Volker Krebs, entitled A Direct Approximation of Fractional Cole-Cole Systems by Ordinary First-order Processes in Advances in Fractional Calculus Theoretical Developments and Applications in Physics and Engineering, edited by J. Sabatier, O. P. Agrawal and J. A. Tenreiro Machado, Springer, 2007, 257-270, the disclosure of which is partially incorporated herein by reference.

Further, the Cole impedance model is introduced in final form by introducing a Constant Phase Element (or CPE), as disclosed in the art in a non-patent literature by Cole K. S., entitled Permeability and Impermeability of Cell Membranes for Ions, Cold Spring Harbor Symposium, Quant.

Biol. 1940, 8, 110–122, the disclosure of which is partially incorporated herein by reference.

FIG. 149 depicts an equivalent circuit Cole mathematical model for calculation of the electrical impedance of the skin, partly in accordance with the prior art and adapted therefrom.

In certain prior art embodiments, a circuit for modeling the skin are disclosed. In such prior art embodiments, design and implementation of the circuit is disclosed in accordance with the non-patent literature by Sverre Grimnes and Orjan G. Martinsen, entitled "Bioimpedance and Bioelectricity Basics", Second edition 2008 Elsevier Ltd. and by Martinsen O. G., Grimnes S., entitled "On using single frequency electrical measurements for skin hydration assessment", Innov. Techn. Biol. Med. Vol 19 no 5, 395-399, 1998, the disclosures of which are incorporated herein by reference, in entirety.

In certain embodiments, usage and implementation of the aforementioned circuit for modeling the skin, discussed in the aforementioned prior art and adapted therefrom, in accordance with the principles of the invention is disclosed.

In such embodiments, Equation 4 below describes the electric Cole circuit:

$$Z_\alpha(\omega) = R_\infty + \frac{R_0 - R_\infty}{1 + (j \cdot \omega \cdot \tau)^\alpha} \qquad \text{Equation 4}$$

where $R_0$ denotes a low-frequency resistor and $R\infty$ is a high-frequency resistor.

As disclosed in the art in a non-patent literature by R. L. Magin, entitled Fractional Calculus In Bioengineering, Part 1, Critic. Rev. in Biomed. Eng. 32 (1, 2) (2004), no. 105, 193 pp., the disclosure of which is partially incorporated herein by reference. Specifically, as shown in FIG. 149 of the art above, the CPE is disclosed in the equivalent fractional circuit diagrams.

In certain specific embodiments, one or more mathematical models in connection with human skin based on a fractional approach, designed and implemented in accordance with the principles of the invention are disclosed. In such embodiments, the design and implementation of a generalized continuous Cole-Cole model is disclosed.

In general, the idea of fractional calculus has been known since the development of the regular calculus. But, it is only in the last few decades that scientists and engineers have realized that such fractional differential equations provide a natural framework for the discussion of various kinds of questions modeled by fractional differential equations and fractional integrals, i.e. they provide more accurate models of systems under consideration. Further, fractional derivatives provide an excellent instrument for the description of memory and hereditary properties of various materials and processes, as disclosed in the art in non-patent literature by Podlubny I., entitled "Fractional Differential Equations" Academic Press, San Diego, 1999 and R. Hilfer, entitled "Applications of Fractional Calculus in Physics", World Scientific Publishing, Company, Singapore, 2000, the disclosures of which are incorporated herein by reference.

As disclosed in the aforementioned literature, in use, the differential and integral operators are generalized into one fundamental $_{t_0}D_t^\alpha$ operator, which is known as fractional calculus. Further, the fundamental $_{t_0}D_t^\alpha$ operator is represented by the following Equation 5:

$$_{t_0}D_t^\alpha = \begin{cases} \frac{d^\alpha}{dt^\alpha} & \Re(\alpha) > 0, \\ 1 & \Re(\alpha) = 0, \\ \int_{t_0}^t (d\tau)^{-\alpha} & \Re(\alpha) < 0. \end{cases} \qquad \text{Equation 5}$$

Still further, taking into consideration the left Riemann-Liouville integral of suitable f(t) of fractional order α which is represented by the following Equation 6:

$$_{t_0}^{RL}I_t^\alpha f(t) \stackrel{d}{=} \frac{1}{\Gamma(\alpha)} \int_{t_0}^t (t-t')^{\alpha-1} f(t')\,dt'. \qquad \text{Equation 6}$$

where Γ(.) is the Euler's gamma function. In certain scenarios involving initial moments or instances, $t_0 = -\infty$ usually refers to integral as a left Weyl fractional integral of order $\alpha \in (0,1]$. In addition, left Riemann-Liouville and Caputo derivative of ƒ(t) of order α, are represented by the following pair of Equations 7 and 8:

$$_{t_0}^{RL}D_t^\alpha f(t) \equiv \frac{d}{dt}\left(_{t_0}^{RL}I_t^{1-\alpha} f(t)\right) \stackrel{d}{=} \frac{1}{\Gamma(1-\alpha)} \frac{d}{dt} \int_{t_0}^t (t-t')^{-\alpha} f(t')\,dt'. \qquad \text{Equation 7}$$

$$_{t_0}^{RL}D_t^\alpha f(t) \equiv \frac{d}{dt}\left(_{t_0}^{RL}I_t^{1-\alpha} f(t)\right) \stackrel{d}{=} \frac{1}{\Gamma(1-\alpha)} \frac{d}{dt} \int_{t_0}^t (t-t')^{-\alpha} f(t')\,dt'. \qquad \text{Equation 8}$$

In certain circumstances involving the aforementioned embodiment, for a given value $t_0 = -\infty$, the Equation 8 represents a left Weyl fractional derivative (in turn, Riemann-Liouville-Weyl and Caputo-Weyl derivative). Besides, linearity and derivative of the constant is zero, a left Caputo-Weyl fractional derivative has following characteristics, as disclosed in the art R. Hilfer, entitled "Applications of Fractional Calculus in Physics", World Scientific Pub Co, Singapore, 2000, the disclosure of which is incorporated herein by reference.

The aforementioned characteristics may be represented a pair of equations, namely Equation 9 and 10, as under:

$$_{-\infty}^{CW}D_t^\alpha \exp(pt) = (p)^\alpha \exp(pt),\ Re(p) \geq 0 \qquad \text{Equation 9}$$

$$_{-\infty}^{CW}D_t^0 f(t) = _{-\infty}^{RLW}I_t^0 f(t) = f(t). \qquad \text{Equation 10}$$

Also, the initial conditions problems of fractional differential equations, which were compared to the given fractional derivatives, were considered in light of a non-patent literature by Ortigueira M. D. and Coito F. J., entitled Initial Conditions: What Are We Talking About?, discussed in 2008 in Third IFAC workshop on fractional differentiation, Ankara, Turkey, the disclosure of which is incorporated herein by reference. In line with recent work, if the input or output of the system is known as per the aforementioned case, it is possible to calculate physically acceptable initialization function.

As used in mathematics, the "Riemann-Liouville integral" associates with a real function ƒ: R→R another function Iαƒ of the same kind for each value of the parameter α>0. The integral is a manner of generalization of the repeated antiderivative of ƒ in the sense that for positive integer values of α, Iαƒ is an iterated antiderivative of ƒ of order α. The operator agrees with the Euler transform, after Leonhard Euler, when applied to analytic functions. It was generalized to arbitrary dimensions by Marcel Riesz, who introduced the Riesz potential.

In certain embodiments involving single frequency electrical circuits in Bioelectrical Impedance Spectroscopy (or BIS), the Cole equation determines behaviour of the biological tissue. This has been disclosed in the non-patent literature by D. M. Fereira, C. S. Silva and M. N. Souza, entitled "Electrical Impedance Model for Evaluation of Skin Irritation in Rabbits and Humans", 2007, Skin research and technology 13, 259-267, the disclosure of which is incorporated herein by reference, and especially for some points of the human skin, as disclosed in Prokhorova, T. E., Zaldivar Lelo de Larrea, G., in 2000, In Vivo Electrical Characteristics of Human Skin, including at Biological Active Points, Med. Biol. Eng. Comput., 38, 507-511, the disclosure of which is also incorporated herein by reference. In such embodiments, the parameters of impedance are obtained from an electrical impedance system based on current response to a voltage step excitation. In certain circumstances involving relaxation in the electric circuit consisting of parallel connected resistor R and Constant Phase Element (or CPE), the suitable fractional differential equation is represented by and discussed in conjunction with the following Equation 11 below:

$$C_\alpha \cdot {}_0^C D_t^\alpha V(t) + V(t)/R = 0, \; V(0) = V_0, \; \sqrt[\alpha]{RC_\alpha} = \tau_\alpha.$$  Equation 11 where voltage on CPE element was marked with V (t) and V (0) represents given initial condition. The solution is given represented by the following Equation 12 below:

In such circumstances, the solution to the fractional differential Equation 11 is represented by the following Equation 12 below:

$$V(t) = V_0 \sum_{k=0}^{\infty} \frac{(-(t/\tau_\alpha)^\alpha)^k}{\Gamma(k\alpha + 1)} = V_0 \cdot E_\alpha(-(t/\tau_\alpha)^\alpha)$$  Equation 12 where $E\alpha(t)$ denotes Mittag-Leffler's function. In here, the time relaxation constant $\tau_\alpha$ describes the electrical and dielectric properties of material. In certain scenarios, the complex alternating-oscillating voltage is supplied to the same electric circuit in the shape of $V(t)=V_0 \cdot \exp(j(\omega t + \theta))$ and Weyl derivative is used, wherein $V_0$ is the voltage amplitude, $\omega$ is the source frequency and $\theta$ is the phase angle between the voltage and the current. In such circumstances, the time dependency of the electric current of amplitude $i_0$ is introduced as $i(t)=i_0 \cdot \exp(j\omega t)$ thereby resulting in the following pair of Equations 13:

$$i(t) = C_\alpha \cdot {}_{-\infty}^{CW} D_t^\alpha V(t) + V(t)/R,$$  Equations 13

$$i_0 = V_0(C_\alpha \cdot (j \cdot \omega)^\alpha + 1/R)e^{j\theta} = \frac{V_0 e^{j\theta}}{\underline{Z}},$$

where $\underline{Z} = \underline{Z}(\omega)$ is a complex impedance of the system. In certain scenarios, by introducing the sign "∥" for the parallel connection of complex resistance the following pair of Equations 14 is written:

$$\underline{Z} = R \| C_\alpha \cdot (j \cdot \omega)^\alpha = R/((j \tau_\alpha \cdot \omega)^\alpha + 1)$$

$$\underline{Z} = |\underline{Z}| \cdot e^{j\theta}, \; \cos \theta = R/|\underline{Z}|.$$  Equations 14

As used in mathematics, the "Mittag-Leffler's function" $E\alpha, \beta$ refers to a special function, a complex function which depends on two complex parameters $\alpha$ and $\beta$. It may be defined by the following series when the real part of $\alpha$ is strictly positive:

$$E_{\alpha,\beta}(z) = \sum_{k=0}^{\infty} \frac{z^k}{\Gamma(\alpha k + \beta)}.$$

In this case, the series converges for all values of the argument z, so the Mittag-Leffler's function is an entire function. For $\alpha > 0$, the Mittag-Leffler function $E\alpha, 1$ is en entire function of order $1/\alpha$, and is in some sense the simplest entire function of its order.

As discussed in conjunction with Equation 4, the electric Cole circuit influenced by the aforementioned alternating voltage essentially models the system consisting of orderly connection of resistance $R\infty$ and reduced Cole element $(R_0 - R\infty) \| C\alpha \cdot (j\omega)\alpha$. In certain proposed embodiments, generalization of the Cole model in connection with the prior art is suggested, in accordance with the principles of the invention. In such proposed embodiments, the basic suppositions behind this generalization are that there are neither inductive resistances, nor active or nonlinear elements, serially or parallely connected. In certain scenarios involving such proposed embodiments, from the electrical standpoint the skin is considered as serially, continually many connected non-interactive, linear, reduced Cole elements $R\alpha \| C\alpha(j\omega)\alpha$ and one $R\infty$. This is discussed in conjunction with FIG. 153. In here, resistance $R_\alpha$ is presented as $R\alpha = p(\alpha) \cdot (R0 - R\infty)$ and characterizes each individual reduced Cole element, wherein $p(\alpha)$ is a real function. In such proposed embodiments, the equivalent total impedance Z of the new electric circuit is given by the Equation 15 below:

$$\underline{Z} = R_\infty + \int_{0+}^{1} \frac{p(\alpha) \cdot (R_0 - R_\infty) \cdot d\alpha}{1 + (j \cdot \omega \cdot \tau_\alpha)^\alpha}$$  Equation 15

Equation 15 is the continuous Cole generalization equation, where $\tau_\alpha$, $0 < \alpha \le 1$ are corresponding time constants, which, in contrast to the Equation 11, are independent quantities in relation to the resistance and CPE, as disclosed in Sverre Grimnes and Orjan G. Martinsen, entitled "Bioimpedance and Bioelectricity Basics", Second edition 2008 Elsevier Ltd., pp 312-313. In certain scenarios, if $\tau_\alpha$ are dependent quantities $((\tau_\alpha)^\alpha = p(\alpha) \cdot (R_0 - R_\infty) \cdot C_\alpha)$. In certain scenarios involving the proposed embodiments, the cases $\alpha \ne 1$ correspond to the analogous fractional processes in skin.

In certain computational embodiments, Equation 15 corresponds to the application of continually many derivatives, which have not been distributed. In context of such computational embodiments, the application of the concept of distributed derivatives on oscillating movement is found, as disclosed in Atanackovic et al., 2005. In certain scenarios, for a given, selected criteria $(R_0 - R_\infty) \to \infty$ and $(\tau_\alpha)^\alpha = p(\alpha) \cdot (R_0 - R_\infty) \cdot C_\alpha$ ($\tau_\alpha$ are dependent quantities), the following Equation 16 is taken into consideration:

$$Z = R_\infty + \int_{0+}^{1} \frac{d\alpha}{C_\alpha \cdot (j \cdot \omega)^\alpha},$$  Equation 16

Equation 16 corresponds to distributed Caputo-Weyl derivatives which generalizes Equation 14 thereby resulting in the following pair of Equations 17:

$$i(t) = V(t)/R + {}_{-\infty}^{DCW}D_t^\alpha(V(t)) =$$ Equations 17

$$= V(t)/R + \int_{0+}^{1} C\alpha \cdot ({}_{-\infty}^{CW}D_t^\alpha(V(t)))\,d\alpha.$$

In certain scenarios involving the proposed embodiments, based on $R_0 - R_\infty \neq \infty$ or $(\tau_\alpha)^\alpha \neq (\alpha)\cdot(R_0-R_\infty)\cdot C_\alpha$, one generalization of distributed Caputo-Weyl derivatives is described. On the other hand, in certain scenarios, if $p(\alpha)$ is represented by the following Equation 18:

$$p(\alpha) = \sum_{i=1}^{n} p(\alpha_i) \cdot \delta(\alpha - \alpha_i),\ 0 < \alpha_i \le 1 \quad \text{Equation 18}$$

In such scenarios, Equation 15 changes to Equation 19 below:

$$Z = R_\infty + (R_0 - R_\infty)\sum_{i=1}^{n}\frac{p(\alpha_i)}{1+(j\cdot\omega\cdot\tau_{\alpha_i})^{\alpha_i}} \quad \text{Equation 19}$$

Equation 19 represents discrete series of Cole elements. On the other hand, discrete sum by Cole-Cole dielectric elements for modeling human biological tissues is discussed in a non-patent literature Kang, K., Chu, X., Dilmaghani, R. and Ghavami, M., (2007), entitled "Low-complexity Cole-Cole expression for modelling human biological tissues in (FD)2TD method", Electronics Letters, Vol 43 Issue 3, 210-216. Therefore, Equation 15 is a continuous generalization of discrete Cole model.

In certain proposed embodiments, a continuous one-Cole-Cole mathematical model is disclosed in accordance with the principles of the invention. In such proposed embodiments, the rationale behind achievement of one or more equations in connection with one-Cole mathematical model is discussed hereafter. Based on the fact that a discrete one-cole model, represented by Equation 18, corresponds to a delta function, in order to test the adequacy of this model approximation of a single parameter of the delta function is introduced. This gives the basic equations of the continuous one-Cole-Cole model.

In certain embodiments, one-Cole element is considered for $(\tau = \tau_\alpha)$ represented by a pair of Equations 20 below:

$$Z_\alpha(\omega) = R_\infty + \frac{R_0 - R_\infty}{(1+(j\cdot\omega\cdot\tau)^\alpha)} \quad \text{Equations 20}$$

$$= R_\infty + (R_0 - R_\infty)\cdot\int_{0+}^{1}\frac{p(\beta)\cdot\delta(\beta-\alpha)\cdot d\beta}{1+(j\cdot\omega\cdot\tau_\beta)^\beta}$$

In certain such embodiments, the following approximation of δ-functions associated interval measure a that contains the point α is defined and represented by the Equation 21 below:

$$\delta_\sigma(\beta - \alpha) = \frac{1}{\sigma},\ \sigma > 0,\ \beta \in U_\alpha(\sigma) \subset (0,1) \quad \text{Equation 21}$$

Further, the following relation represented by the Equation 22 is satisfied.

$$\delta(\beta - \alpha) = \lim_{\sigma \to 0}\delta_\sigma(\beta - \alpha) \quad \text{Equation 22}$$

Still further, for small changes in $p(\beta)$ and $\tau_\beta$ in the interval, they are replaced with values of $p(\alpha) \approx 1$ and $\tau_\alpha = \tau$, thereby resulting in pair of Equations 23:

$$\int_{0+}^{1}\frac{p(\beta)\cdot\delta(\beta-\alpha)\cdot d\beta}{1+(j\cdot\omega\cdot\tau_\beta)^\beta} \approx \frac{1}{\sigma}\cdot\int_{U_\alpha(\sigma)}\frac{p(\alpha)\cdot d\beta}{1+(j\cdot\omega\cdot\tau)^\beta} = \quad \text{Equations 23}$$

$$\frac{1}{\sigma}\cdot\int_{U_\alpha(\sigma)}\frac{d\beta}{1+(j\cdot\omega\cdot\tau)^\beta}$$

Eventually, the last integral is represented by the following Equation 24:

$$\frac{1}{\sigma}\cdot\int_{U_\alpha(\sigma)}\frac{d\beta}{1+(j\cdot\omega\cdot\tau)^\beta} = \frac{1}{\sigma}\cdot\left(\beta - \frac{\ln(1+(j\cdot\omega\cdot\tau)^\beta)}{\ln(j\cdot\omega\cdot\tau)}\right)\bigg|_{U_\alpha(\sigma)} \quad \text{Equation 24}$$

In such embodiments, based on the assumption represented by the following Equation 25:

$$U_\alpha(\sigma) = \left(\alpha - \frac{\sigma}{2},\ \alpha + \frac{\sigma}{2}\right) \quad \text{Equation 25}$$

Substitution of the value of Equation 25 in Equation 24 results in Equation below:

$$\frac{1}{\sigma}\cdot\int_{U_\alpha(\sigma)}\frac{d\beta}{1+(j\cdot\omega\cdot\tau)^\beta} = 1 - \frac{\ln\left(\frac{1+(j\cdot\omega\cdot\tau)^{\alpha+\frac{\sigma}{2}}}{1+(j\cdot\omega\cdot\tau)^{\alpha-\frac{\sigma}{2}}}\right)}{\sigma\cdot\ln(j\cdot\omega\cdot\tau)} \quad \text{Equation 26}$$

Taking into consideration Equations 20 and 26 the following Equation 27 is obtained:

$$Z_{\alpha\sigma}(\omega) = R_\infty + (R_0 - R_\infty)\cdot\left(1 - \frac{\ln\left(\frac{1+(j\cdot\omega\cdot\tau)^{\alpha+\frac{\sigma}{2}}}{1+(j\cdot\omega\cdot\tau)^{\alpha-\frac{\sigma}{2}}}\right)}{\sigma\cdot\ln(j\cdot\omega\cdot\tau)}\right) \quad \text{Equation 27}$$

In such embodiments, valid control relationship is represented by the following Equation 28:

$$Z_\alpha(\omega) = \lim_{\sigma \to 0} Z_{\alpha\sigma}(\omega) \quad \text{Equation 28}$$

Further, Equation 28 is adapted for fitting and is represented by the Equation 29:

$$Z_{\alpha\sigma}(\omega) = m(1) + m(2)\cdot\left(1 - \frac{\ln\left(\frac{1+(j\cdot\omega\cdot m(3))^{m(4)+\frac{m(5)}{2}}}{1+(j\cdot\omega\cdot m(3))^{m(4)-\frac{m(5)}{2}}}\right)}{m(5)\cdot\ln(j\cdot\omega\cdot m(3))}\right) \quad \text{Equation 29}$$

Where values $m(1)=R_\infty$, $m(2)=R_0-R_\infty$, $m(3)=\tau$, $M(4)=\alpha$, $m(5)=\sigma$ are fitting parameters. Equation 29 is the approximation of generalized Cole model compared to a Cole element and it will continue to fitting. The expected value of σ should be a few percent (3-4%) of α. Also, for smaller values of σ from a border all the other parameters should be approximately equal to the corresponding parameters for one-Cole model. For larger values of σ from the border, the values of other parameters should be correct. Fitting method used herein, in the Matlab programming environment are well known Levenberg-Marquardt non-linear least squares algorithms L2 ($L_2$-norm)-further marked with LM and L1 ($L_1$-norm) robustfit, bisquare-method. In here, are not included weithing squares, increasing the error to a few percent of the value parameters.

FIG. 150 depicts a plot for bioimpedance of human skin for a voltage amplitude 0.1V and diameter of electrodes is 2 cm.

FIG. 151 depicts a plot for a robust fit one-Cole model, "bisquare"-method, designed and implemented in accordance with certain embodiments of the invention.

FIG. 152 depicts a plot for Levenberg-Marquardt nonlinear least squares fit one-Cole model, in accordance with certain embodiments of the invention.

FIG. 153 depicts a plot for Levenberg-Marquardt nonlinear least squares fit one-Cole and continuous one-Cole model for $\zeta=0.20$, "log-log"-plot.

In combined embodiments, methods and systems with enhanced qualitative and quantitative parameters for imaging, analyzing, assessing and characterizing organic and inorganic materials thereby facilitating printing of organs are disclosed, in accordance with the principles of the invention. Specifically, combined systems with enhanced qualitative and quantitative parameters for facilitating organ (or bio) printing comprising involvement of Opto-Magnetic properties of interaction between electromagnetic radiation and matter and methods thereof are disclosed, in accordance with the principles of the invention. More specifically, design and implementation of a combined system with enhanced qualitative and quantitative parameters for facilitating organ (or bio) printing comprising implementation of Opto-Magnetic properties of light-matter interaction and methods thereof are disclosed, in accordance with the principles of the invention. Still more specifically, the combined system with enhanced qualitative and quantitative parameters, such as easy integrability, early or premature detectability, practitioner capability, subjectivity or knowledge independent diagnosability, enhanced sensitivity, enhanced specificity, enhanced efficiency, greater accuracy, easily operability, rapid, economical, precise, timely and minute variation sensitivity, for facilitating organ (or bio) printing comprises implementation of an Opto-Magnetic method for imaging, analyzing, assessing and characterizing organic and inorganic materials based on Opto-Magnetic properties of light-matter interaction. In such combined embodiments, implementation and usage of the Opto-Magnetic method for imaging, analyzing, assessing and characterizing organic and inorganic materials based on Opto-Magnetic properties of light-matter interaction facilitates printing of organs.

FIG. 154 is a block diagrammatic view of a system facilitating organ (or bio) printing deployed in conjunction with the system configuration of FIGS. 129A-B and 130A-F, designed and implemented in accordance with certain embodiments of the invention;

System 15400 is in essence an Organ Bio-Printing System (or OBPS or Bio-Printer). The OBPS 15400 includes an illumination subsystem 15402, an imaging subsystem 15404, a printer head assembly 15406, one or more cartridges 15408 and a host computing subsystem 15410.

In general, there are two main design standpoints in inkjet head design, namely fixed- and disposable head.

Further, the fixed-head design provides an inbuilt print head (often referred to as a Gaither Head) that is designed to last for the life of the printer. The idea is that because the head need not be replaced every time the ink runs out, consumable costs can be made lower and the head itself can be more precise than a cheap disposable one, typically requiring no calibration. On the other hand, if a fixed head is damaged, obtaining a replacement head can become expensive if removing and replacing the head is even possible. If the printer's head cannot be removed, the printer itself will then need to be replaced.

Still further, the disposable head design uses a print head, which is supplied as a part of a replaceable ink cartridge. Every time a cartridge is exhausted, the entire cartridge and print head are replaced with a new one. This adds to the cost of consumables and makes it more difficult to manufacture a high-precision head at a reasonable cost, but also means that a damaged print head is only a minor problem: the user can simply buy a new cartridge.

OBPS 15400, by virtue of its design and implementation, facilitates organ (or bio) printing comprising implementation and usage of an Opto-Magnetic method based on interaction between electromagnetic radiation and matter, for instance light-matter interaction. Specifically, the Opto-Magnetic process employs apparatuses for generation of unique spectral signatures from digitally captured images of skin thereby facilitating analysis, assessment and characterization of the samples based on Opto-Magnetic properties of light-skin matter interaction.

As used in general, the term "3D scanner" refers to a device that analyzes a real-world object or environment to collect data on its shape and possibly its appearance (i.e. color). The collected data can then be used to construct digital, three-dimensional models useful for a wide variety of applications. These devices are used extensively by the entertainment industry in the production of movies and video games. Other common applications of this technology include industrial design, orthotics and prosthetics, reverse engineering and prototyping, quality control/inspection and documentation of cultural artifacts.

In certain applications, laser scanning describes a method where a surface is sampled or scanned using laser technology. Several areas of application exist that mainly differ in the power of the lasers that are used, and in the results of the scanning process. Lasers with low power are used when the scanned surface doesn't have to be influenced, e.g. when it has to be digitized. Confocal or 3D laser scanning are methods to get information about the scanned surface.

Depending on the power of the laser, its influence on a working piece differs: lower power values are used for laser engraving, where material is partially removed by the laser. With higher powers the material becomes fluid and laser welding can be realized, or if the power is high enough to remove the material completely, then laser cutting can be performed.

In certain working embodiments involving laser scanning, in use the host computing subsystem implements a scan management module (not shown here explicitly). The scan management module controls scanning. A scanner card, coupled to the scan management module running on the host computing subsystem, captures or receives vector data. The scanner card converts the captured vector data to movement information. The scanner card transmits the movement information to a scan head. The pair of mirrors of the scan head deflects the laser beam in a given Two-Dimensional (or 2D) plane, i.e. X-Y plane or X and Y-coordinates. In specific working embodiments, a specific optic facilitates realization of a third dimension, i.e. Z-coordinate. The specific optic moves the focal point of the laser beam along the depth direction, i.e. Z-axis.

In certain specific embodiments, in operation, the third dimension is needed for some special applications like the rapid prototyping where an object is built up layer by layer or for in-glass-marking where the laser has to influence the material at specific positions within it. For these cases, it is important that the laser has as small a focal point as possible.

Scan head (not shown here explicitly) consists of a pair of mirrors.

Positional data in the form of coordinates of the ends of line segments, points, text position, etc.

As used in general, the term "thermographic camera or infrared sensor" refers to a device that forms an image using infrared radiation, similar to a common camera that forms an image using visible light. Instead of the 450-750 nanometer range of the visible light camera, infrared cameras operate in wavelengths as long as 14,000 nm (14 μm).

Reiterating again, as discussed in conjunction with FIG. 154, the illumination subsystem 15402 may be one or more electromagnetic radiation sources. In certain specific embodiments, the Illumination subsystem 15402 may be a set of Light Emitting Diodes (LEDs).

Illumination subsystem 15402 may be adapted to emit polarized and unpolarized electromagnetic signals. The polarized electromagnetic signal is angled white light and unpolarized electromagnetic signal is non-angled white light.

As shown in the FIG. 154, in certain embodiments, the illumination subsystem 102 may be coupled to the sensor subsystem 15404.

As shown in the FIG. 154, the sensor subsystem 15404 may in essence be a device that converts optical images (or optical signals) to electric signals. In certain embodiments, the sensor subsystem 15404 captures continuous digital images of skin. Specifically, in such embodiments, the sensor subsystem 15404 captures continuous digital images of the skin illuminated with white light both, non-angled and angled. By way of, and by no way of limitation, the sensor subsystem 15404 may be anyone selected from a group consisting of an Infrared sensor, Complementary Metal-Oxide-Semiconductor (CMOS) image sensor, Charged Coupled Device (CCD) image sensor, and the like.

Again, as shown in FIG. 154, the sensor subsystem 15404 may be coupled to the host computing subsystem 15406.

For example, and in no way limiting the scope of the invention, in certain embodiments the sensor subsystem 15404 may be selected on the basis of the following specifications: color is color or monochrome; optical format; horizontal pixels X vertical pixels; pixel size; one or more performance parameters, such as maximum frame rate, data rate, maximum power dissipation, quantum efficiency, dynamic range and supply voltage; output; one or more features, such as integrated Analog-to-Digital Converter (ADC) and microlenses; and environment, such as operating temperature.

As used in general, the term "ink cartridge or inkjet cartridge" refers to a replaceable component of an inkjet printer that contains the ink (and sometimes the print head itself) that is spread on paper during printing. Each ink cartridge contains one or more partitioned ink reservoirs; certain manufacturers also add electronic contacts and a chip that communicates with the printer.

Typically, two separate cartridges are inserted into a printer, namely first containing black ink and second with each of the three primary colors. Alternatively, each primary color may have a dedicated cartridge.

Coagulation is a complex process by which blood forms clots. It is an important part of hemostasis (the cessation of blood loss from a damaged vessel), wherein a platelet and fibrin-containing clot to stop bleeding and begin repair of the damaged vessel covers a damaged blood vessel wall. Disorders of coagulation can lead to an increased risk of bleeding (hemorrhage) or obstructive clotting (thrombosis).

Coagulation is highly conserved throughout biology; in all mammals, coagulation involves both a cellular (platelet) and a protein (coagulation factor) component. The system in humans has been the most extensively researched and is therefore the best understood.

Coagulation begins almost instantly after an injury to the blood vessel has damaged the endothelium (lining of the vessel). Exposure of the blood to proteins such as tissue factor initiates changes to blood platelets and the plasma protein fibrinogen, a clotting factor. Platelets immediately form a plug at the site of injury; this is called primary hemostasis. Secondary hemostasis occurs simultaneously: Proteins in the blood plasma, called coagulation factors or clotting factors, respond in a complex cascade to form fibrin strands, which strengthen the platelet plug.

In certain specific embodiments, the printer head assembly comprises one or more print heads, in accordance with the principles of the invention. By way of example, and in no way limiting the scope of the invention, the printer head assembly X06 consists of a pair of print heads. By way of example, for purposes of clarity and expediency, the pair of print heads has been hereinafter referred as first and second print head, in that order.

In such embodiments, the first print head comprises skin cells, a coagulant, and collagen, in accordance with the principles of the invention. On the other hand, in such embodiments, the second print head comprises one or more blood coagulants.

As used in general, the term "epoxy or polyepoxide" refers to thermosetting polymer formed from reaction of an epoxide "resin" with polyamine "hardener". Epoxy has a wide range of applications, including fiber-reinforced plastic materials and general-purpose adhesives. Epoxy adhesives are a major part of the class of adhesives called "structural adhesives" or "engineering adhesives" (that includes polyurethane, acrylic, cyanoacrylate, and other chemistries.)

In certain specific embodiments, an analysis of Three-Dimensional Organ Bio Printing for generation of skin vis-à-vis activation of two-part epoxy glues on mixing forms a basis for analogy thereof.

In such embodiments, in use the first print head (or chamber) supplies a combination of skin cells, a coagulant, and collagen whereas the second print head (or chamber) supplies one or more blood coagulants. The printer head assembly mixes the combination of skin cells, a coagulant, and collagen and one or more blood coagulants to form fibrin. The printer head assembly covers the fibrin layer with keratinocyte skin cells.

As used in general, the term "fibrin or Factor Ia" refers to a fibrous protein involved in the clotting of blood, and is non-globular. It is a fibrillar protein that is polymerised to form a "mesh" that forms a hemostatic plug or clot (in conjunction with platelets) over a wound site.

Further, the term "fibrin scaffold" refers to a network of protein that holds together and supports a variety of living tissues. It is produced naturally by the body after injury, but also can be engineered as a tissue substitute to speed healing. The scaffold consists of naturally occurring biomaterials composed of a cross-linked fibrin network and has a broad use in biomedical applications.

Bruises can have medicolegal significance such that the age of a bruise may be an important issue. One potential solution involves use of colorimetry or reflectance spectrophotometry to objectively estimate the age of bruises. In such solution, reflectance spectrophotometric scans are obtained from bruises using a Cary 100 Bio Spectrophotometer fitted with a fibre-optic reflectance probe. Specifically, measurements are taken from the bruise and a control area. Application-specific software is used to calculate the first derivative at 490 and 480 nm wavelengths. The proportion of oxygenated hemoglobin is calculated using an isobestic point method and yet application-specific software is used to convert the scan data into colorimetry data.

In addition, one or more data factors including, but not limited to, subject age, subject sex, degree of trauma, bruise size, skin color, body build, depth of bruise, associated the age of a bruise are recorded.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware.

The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device, may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

All documents referenced herein are hereby incorporated by reference.

The invention is intended to cover all equivalent embodiments, and is limited only by the appended claims. Various other embodiments are possible within the spirit and scope of the invention. While the invention may be susceptible to various modifications and alternative forms, the specific embodiments have been shown by way of example in the drawings and have been described in detail herein. The aforementioned specific embodiments are meant to be for explanatory purposes only, and not intended to delimit the scope of the invention. Rather, the invention is to cover all modifications, equivalents, and alternatives falling within the spirit and scope of the invention as defined by the following appended claims.

What is claimed is:

1. A method for characterizing an epidermis of a person, the method comprising:
    subjecting a first sublayer of the epidermis of the person to optomagnetic fingerprinting, yielding first wavelength difference-intensity data to characterize the first sublayer;
    subjecting a second sublayer of the epidermis of the person to optomagnetic fingerprinting, yielding second wavelength difference-intensity data to characterize the second sublayer;
    comparing the first wavelength difference-intensity data to wavelength difference-intensity data of other persons from the first sublayer of the epidermis of the other persons;
    comparing the second wavelength difference-intensity data to wavelength difference-intensity data of other persons from the second sublayer of the epidermis of the other persons; and
    determining at least one of an age and a state of hydration of the person using the steps of comparing.

2. The method of claim 1, wherein the first sublayer comprises a skin surface of a stratum corneum of the epidermis of the person.

3. The method of claim 1, wherein the second sublayer is selected from the group consisting of: a non-surface layer of the stratum corneum, layer 1; a watery layer comprising water from the stratum corneum and at least one water layer from a stratum *granulosum* of the person, layer 2; and the stratum *granulosum* of the person, layer 3.

4. The method of claim 3, wherein the second sublayer comprises layer 2, reached by removal of the stratum corneum and a portion of the cells of the stratum *granulosum*.

5. The method of claim 1, wherein optomagnetic fingerprinting comprises:
    taking a first image of the first sublayer with non-polarized light;
    taking a second image of the first sublayer with polarized light;
    generating a normalized red color channel histogram for the first image;
    generating a normalized blue color channel histogram for the first image;
    generating a normalized red color channel histogram for the second image;
    generating a normalized blue color channel histogram for the second image;
    generating red color channel spectral plots of the normalized red color channel histograms for the first and second images;
    generating blue color channel spectral plots of the normalized blue color channel histograms for the first and second images;
    subtracting the spectral plot for the blue color channel for the second image from the spectral plot for the red color channel for the second image to form a red-minus-blue polarized spectral plot (R–B) (P);
    subtracting the spectral plot for the blue color channel for the first image from the spectral plot for the red color channel for the first image to form a red-minus-blue non-polarized spectral plot (R–B) (W); and
    plotting wavelength difference versus intensity for the red-minus-blue polarized spectral plot and the red-minus-blue non-polarized spectral plot to form a red-minus-blue non-polarized/polarized spectral plot (R–B) (W–P) for the epidermis of the person.

6. The method of claim 1, further comprising:
    testing at least one of the first sublayer and the second sublayer for bioimpedance;
    comparing the bioimpedance of the first sublayer or the second sublayer to a bioimpedance level of other persons; and
    characterizing the person by an age or a hydration level based on the bioimpedance of the first sublayer or the second sublayer.

7. The method of claim 1, wherein the bioimpedance of the first sublayer is lower for a younger person than the bioimpedance of the first layer for an older person.

8. The method of claim 1, wherein the first sublayer and the second sublayer are adjacent one another and are in a location selected from the group consisting of an inner arm and a forehead region of a skin surface of the person.

* * * * *